(12) United States Patent
Fatheree et al.

(10) Patent No.: US 12,234,225 B2
(45) Date of Patent: *Feb. 25, 2025

(54) IL-17 LIGANDS AND USES THEREOF

(71) Applicant: DiCE Alpha, Inc., Indianapolis, IN (US)

(72) Inventors: Paul R. Fatheree, San Francisco, CA (US); Martin S. Linsell, San Mateo, CA (US); John R. Jacobsen, San Mateo, CA (US); Wouter Van Der Linden, Menlo Park, CA (US); Timothy J. Church, San Mateo, CA (US); Claudio Aquino, Newark, CA (US); Margot Paulick, San Carlos, CA (US)

(73) Assignee: DICE ALPHA, INC., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/866,227

(22) Filed: Jul. 15, 2022

(65) Prior Publication Data

US 2023/0053746 A1    Feb. 23, 2023

Related U.S. Application Data

(63) Continuation of application No. 16/783,268, filed on Feb. 6, 2020, now Pat. No. 11,447,468.
(Continued)

(51) Int. Cl.
*A61P 37/00* (2006.01)
*C07D 241/04* (2006.01)
(Continued)

(52) U.S. Cl.
CPC ............ *C07D 403/12* (2013.01); *A61P 37/00* (2018.01); *C07D 241/04* (2013.01);
(Continued)

(58) Field of Classification Search
CPC .. C07D 403/12; C07D 241/04; C07D 401/12; C07D 403/14; C07D 413/12;
(Continued)

(56) References Cited

U.S. PATENT DOCUMENTS 3,536,809 A    10/1970   Applezweig et al.
3,598,123 A    8/1971    Zaffaroni
(Continued)

FOREIGN PATENT DOCUMENTS

CN    105980353 A    9/2016
CN    108473429 A    8/2018
(Continued)

OTHER PUBLICATIONS

Harvard Health, "A Deeper Look at Psoriasis." Harvard Health, Nov. 1, 2018, https://www.health.harvard.edu/diseases-and-conditions/a-deeper-look-at-psoriasis (Year: 2018).*
(Continued)

*Primary Examiner* — Clinton A Brooks
*Assistant Examiner* — Kyle Nottingham
(74) *Attorney, Agent, or Firm* — Dan L. Wood

(57) ABSTRACT

Provided herein are novel ligands and pharmaceutical compositions thereof which modulate IL-17A. Also provided are methods for preparing the IL-17A modulators. Such compounds may be useful in the treatment and/or prevention of, for example, inflammation, cancer or autoimmune disease.

20 Claims, 32 Drawing Sheets

Related U.S. Application Data

(60) Provisional application No. 62/901,249, filed on Sep. 16, 2019, provisional application No. 62/801,870, filed on Feb. 6, 2019.

(51) Int. Cl.
  *C07D 401/12* (2006.01)
  *C07D 403/12* (2006.01)
  *C07D 403/14* (2006.01)
  *C07D 413/12* (2006.01)
  *C07D 455/02* (2006.01)
  *C07D 471/04* (2006.01)

(52) U.S. Cl.
  CPC .......... *C07D 401/12* (2013.01); *C07D 403/14* (2013.01); *C07D 413/12* (2013.01); *C07D 455/02* (2013.01); *C07D 471/04* (2013.01)

(58) Field of Classification Search
  CPC .. C07D 455/02; C07D 471/04; C07D 279/12; C07D 401/06; C07D 405/12; C07D 409/12; C07D 409/14; C07D 413/14; C07D 417/12; C07D 487/04; C07D 487/08; C07D 493/04; C07D 513/04; C07D 231/38; A61P 35/00; A61P 37/00
  See application file for complete search history.

(56) References Cited

U.S. PATENT DOCUMENTS

| | | |
|---|---|---|
| 3,710,795 A | 1/1973 | Higuchi et al. |
| 3,845,770 A | 11/1974 | Theeuwes et al. |
| 3,916,899 A | 11/1975 | Theeuwes et al. |
| RE28,819 E | 5/1976 | Thompson |
| 4,008,719 A | 2/1977 | Theeuwes et al. |
| 4,044,126 A | 8/1977 | Cook et al. |
| 4,328,245 A | 5/1982 | Yu et al. |
| 4,358,603 A | 11/1982 | Yu |
| 4,364,923 A | 12/1982 | Cook et al. |
| 4,409,239 A | 10/1983 | Yu |
| 4,410,545 A | 10/1983 | Yu et al. |
| 4,414,209 A | 11/1983 | Cook et al. |
| 4,522,811 A | 6/1985 | Eppstein et al. |
| 5,033,252 A | 7/1991 | Carter |
| 5,052,558 A | 10/1991 | Carter |
| 5,059,595 A | 10/1991 | Le Grazie |
| 5,073,543 A | 12/1991 | Marshall et al. |
| 5,120,548 A | 6/1992 | McClelland et al. |
| 5,323,907 A | 6/1994 | Kalvelage |
| 5,354,556 A | 10/1994 | Sparks et al. |
| 5,591,767 A | 1/1997 | Mohr et al. |
| 5,639,476 A | 6/1997 | Oshlack et al. |
| 5,639,480 A | 6/1997 | Bodmer et al. |
| 5,674,533 A | 10/1997 | Santus et al. |
| 5,709,874 A | 1/1998 | Hanson et al. |
| 5,733,566 A | 3/1998 | Lewis |
| 5,739,108 A | 4/1998 | Mitchell |
| 5,759,542 A | 6/1998 | Gurewich |
| 5,840,674 A | 11/1998 | Yatvin et al. |
| 5,860,957 A | 1/1999 | Jacobsen et al. |
| 5,891,474 A | 4/1999 | Busetti et al. |
| 5,900,252 A | 5/1999 | Calanchi et al. |
| 5,922,356 A | 7/1999 | Koseki et al. |
| 5,948,433 A | 9/1999 | Burton et al. |
| 5,972,366 A | 10/1999 | Haynes et al. |
| 5,972,891 A | 10/1999 | Kamei et al. |
| 5,980,945 A | 11/1999 | Ruiz |
| 5,983,134 A | 11/1999 | Ostrow |
| 5,985,307 A | 11/1999 | Hanson et al. |
| 5,985,317 A | 11/1999 | Venkateshwaran et al. |
| 5,993,855 A | 11/1999 | Yoshimoto et al. |
| 6,004,534 A | 12/1999 | Langer et al. |
| 6,010,715 A | 1/2000 | Wick et al. |
| 6,024,975 A | 2/2000 | D'Angelo et al. |
| 6,039,975 A | 3/2000 | Shah et al. |
| 6,045,830 A | 4/2000 | Igari et al. |
| 6,048,736 A | 4/2000 | Kosak |
| 6,060,082 A | 5/2000 | Chen et al. |
| 6,071,495 A | 6/2000 | Unger et al. |
| 6,087,324 A | 7/2000 | Igari et al. |
| 6,113,943 A | 9/2000 | Okada et al. |
| 6,120,751 A | 9/2000 | Unger |
| 6,131,570 A | 10/2000 | Schuster et al. |
| 6,139,865 A | 10/2000 | Friend et al. |
| 6,167,301 A | 12/2000 | Flower et al. |
| 6,197,350 B1 | 3/2001 | Yamagata et al. |
| 6,248,363 B1 | 6/2001 | Patel et al. |
| 6,253,872 B1 | 7/2001 | Neumann |
| 6,256,533 B1 | 7/2001 | Yuzhakov et al. |
| 6,261,595 B1 | 7/2001 | Stanley et al. |
| 6,264,970 B1 | 7/2001 | Hata et al. |
| 6,267,981 B1 | 7/2001 | Okamoto et al. |
| 6,267,983 B1 | 7/2001 | Fujii et al. |
| 6,271,359 B1 | 8/2001 | Norris et al. |
| 6,274,552 B1 | 8/2001 | Tamarkin et al. |
| 6,316,652 B1 | 11/2001 | Steliou |
| 6,376,461 B1 | 4/2002 | Igari et al. |
| 6,419,961 B1 | 7/2002 | Igari et al. |
| 6,589,548 B1 | 7/2003 | Oh et al. |
| 6,613,358 B2 | 9/2003 | Randolph et al. |
| 6,699,500 B2 | 3/2004 | Okada et al. |
| 6,740,634 B1 | 5/2004 | Saikawa et al. |
| 11,274,094 B2 | 3/2022 | Fatheree et al. |
| 11,447,468 B2 | 9/2022 | Fatheree et al. |
| 2006/0270730 A1 | 11/2006 | Katopodis |
| 2015/0005319 A1 | 1/2015 | Taylor et al. |
| 2017/0107240 A1 | 4/2017 | Yamamoto et al. |
| 2021/0101886 A1 | 4/2021 | Fatheree et al. |
| 2022/0235038 A1 | 7/2022 | Fatheree et al. |
| 2023/0141212 A1 | 5/2023 | Fatheree et al. |
| 2023/0145481 A1 | 5/2023 | Fatheree et al. |

FOREIGN PATENT DOCUMENTS

| | | |
|---|---|---|
| CN | 110072848 A | 7/2019 |
| CN | 113874080 A | 12/2021 |
| WO | WO-2005025506 A2 | 3/2005 |
| WO | WO-2013116682 A1 | 8/2013 |
| WO | WO-2014066726 A2 | 5/2014 |
| WO | WO-2020120141 A1 | 6/2020 |
| WO | WO-2020163554 A1 | 8/2020 |
| WO | WO-2021055376 A1 | 3/2021 |

OTHER PUBLICATIONS

Batta et al, "IL-17 and -23 Inhibitors for the Treatment of Psoriasis." EMJ Allergy Immunol Allergy & Immunology 2023, Dec. 2023 (Year: 2023).*
Espada et al, "A Binding Site on IL-17A for Inhibitory Macrocycles Revealed by Hydrogen/Deuterium Exchange Mass Spectrometry." Journal of Medicinal Chemistry, vol. 59, No. 5, Mar. 2016, pp. 2255-2260 (Year: 2016).*
2013RN 1469885-68-4, registry database compound (2013).
Alexander et al. CAPLUS 2014:717295 (2014).
Appel et al. Analysis of IL-17(+) cells in facet joints of patients with spondyloarthritis suggests that the innate immune pathway might be of greater relevance than the Th17-mediated adaptive immune response Arthritis Res Therap 13:R95 (2011-).
Brittain Polymorphism in Pharmaceutical Solids, (Brittain, H. ed.), Marcel Dekker, Inc. New York, (1999). Chapter 6, pp. 205-208.
Buchwald et al. Long-term, continuous intravenous heparin administration by an implantable infusion pump in ambulatory patients with recurrent venous thrombosis. Surgery 88:507-516 (1980).
Dudler et al. Effect of interleukin 17 on proteoglycan degradation in murine knee joints. Ann Rheum Dis 59:529-32 (2000).
Fingl et al. Chapter 1: General Principles. In: The Pharmacological basis of therapeutics (pp. 1-46) (1975).
Gaffen. Biology of recently discovered cytokines: interleukin-17—a unique inflammatory cytokine with roles in bone biology and arthritis. Arthritis Res Therapy 6:240-247 (2004).

(56) References Cited

OTHER PUBLICATIONS

Gaffen. Structure and signalling in the IL-17 receptor family. Nature Rev Immunol 9:556-567 (2009).
Goodson. Chapter 6: Dental Applications. Medical Applications of Controlled Release 2:115-138 (1984).
Guillory. Chapter 5: Generation of Polymorphs, Hydrates, Solvates, and Amorphous Solids. Polymorphism in Pharmaceutical Solids pp. 183-226 (Brittain, H.G., ed., 1999).
Jens. Chapter 12: Preformulation. Drug Stability: Principles & Practice, 2d. Ed., Marcel Dekker, NY, NY, 1995, pp. 361-385.
Ji et al. Th17 cells: positive or negative role in tumor? Cancer Immunol Immunother 59:979-987 (2010).
Langer. New methods of drug delivery. Science 249:1527-1533 (1990).
Lubberts et al. IL-1-independent role of IL-17 in synovial inflammation and joint destruction during collagen-induced arthritis. J Immunol 167:1004-1013 (2001).
Matthews. Professor Paul Matthews talks 'big data' within multiple sclerosis. Neurodegener Dis Manag 5:101-104 (2015).
Matusevicius et al. Interleukin-17 mRNA expression in blood and CSF mononuclear cells is augmented in multiple sclerosis. Mult Scler 5(2):101-4 (1999).
Nakae et al. Suppression of immune induction of collagen-induced arthritis in IL-17-deficient mice. J Immunol 171:6173-6177 (2003).
PCT/US2020/016925 International Search Report and Written Opinion dated Apr. 17, 2020.
PCT/US2020/050924 International Search Report and Written Opinion dated Oct. 21, 2020.
Prabhala et al. Elevated IL-17 produced by Th17 cells promotes myeloma cell growth and inhibits immune function in multiple myeloma. Blood 115(26):5385-5392 (2010).
Saudek et al. A preliminary trial of the programmable implantable medication system for insulin delivery. N. Engl. J. Med. 321:574 (1989).
Sefton. Implantable pumps. Crit Rev Biomed Eng 14(3):201-240 (1987).
Spriggs et al. Interleukin-17 and its receptor. J Clin Immunol 17:366-369 (1997).
U.S. Appl. No. 16/783,268 Office Action dated Oct. 12, 2021.
U.S. Appl. No. 17/118,947 Office Action dated Apr. 16, 2021.
Van Bezooijen et al. Interleukin 17 synergises with tumour necrosis factor alpha to induce cartilage destruction in vitro. Ann Rheum Dis 61:870-876 (2002).
Zhang et al. Increased intratumoral IL-17-producing cells correlate with poor survival in hepatocellular carcinoma patients. J Hepatol 50:980-89 (2009).
U.S. Appl. No. 18/090,275 Office Action dated Mar. 17, 2023.
U.S. Appl. No. 18/090,319 Office Action dated Mar. 17, 2023.

* cited by examiner 218-220, 228-230, 233-234, 240-296, 389, 390,
393, 394, 397, 399, 404, 405, 418 and 419.

341-346, 348-375 and 392

IL-17 LIGANDS AND USES THEREOF

CROSS-REFERENCE TO RELATED APPLICATIONS

This application is a continuation of U.S. application Ser. No. 16/783,268, filed Feb. 6, 2020, which claims priority to U.S. Provisional Application No. 62/801,870, filed Feb. 6, 2019, and U.S. Provisional Application No. 62/901,249, filed Sep. 16, 2019, the entire contents of each of which are incorporated herein by reference.

FIELD

Provided herein are novel ligands and pharmaceutical compositions thereof which modulate IL-17A. Also provided are methods for preparing the IL-17A modulators. Such compounds may be useful, for example, in the treatment and/or prevention of inflammation, cancer or autoimmune disease.

BACKGROUND

Interleukin-17A ("IL-17A"), is a pro-inflammatory cytokine, which is a glycoprotein with a molecular weight of 17,000 daltons (Spriggs et al., J Clin Immunol, 17: 366-369 (1997)) that stimulates secretion of various other cytokines in a variety of cell types. For example, IL-17A induces IL-6, IL-8, G-CSF, TNF-α, IL-1β, PGE2, and IFN-γ, as well as numerous chemokines and other effectors (Gaffen, Arthritis Research & Therapy 6: 240-247 (2004)).

IL-17A is expressed by Th17 cells, which are involved in the pathology of inflammation and autoimmunity and also by CD8+ T cells, γδ cells, NK cells, NKT cells, macrophages and dendritic cells. IL-17A and Th17 are also necessary for defense against various microbes despite their involvement in inflammation and autoimmune disorders. IL-17A can form homodimers or heterodimers with its family member, IL-17F. IL-17A binds to both IL-17 RA and IL-17 RC to mediate signaling. IL-17A, signaling through its receptor, activates the NF-κB transcription factor, as well as various MAPKs (Gaffen, S L, Nature Rev Immunol. 9: 556-567 (2009)).

IL-17A can act in cooperation with other inflammatory cytokines such as TNF-α, IFN-γ, and IL-1β to mediate pro-inflammatory effects (Gaffen, Arthritis Research & Therapy 6: 240-247 (2004)). Increased levels of IL-17A have been implicated in numerous diseases, including, but not limited to, rheumatoid arthritis (RA), bone erosion, intraperitoneal abscesses, inflammatory bowel disease, allograft rejection, psoriasis, angiogenesis, atherosclerosis, asthma, and multiple sclerosis.

IL-17A and IL-17A-producing Th17 cells have also recently been implicated in certain cancers (Ji and Zhang, Cancer Immunol Immunother 59: 979-987 (2010)). For example, IL-17-expressing Th17 cells were shown to be involved in multiple myeloma (Prabhala et al., Blood, online DOI 10.1182/blood-2009-10-246660, Apr. 15 (2010)) and to correlate with poor prognosis in patients with hepatocellular carcinoma (HCC) (Zhang et al., J Hepatology 50: 980-89 (2009)).

Clearly modulation of IL-17A has important therapeutic implications. However, despite its therapeutic importance relatively few examples of small molecule modulators of IL-17A are known. Accordingly, there is a need for the development of small molecule modulators of IL-17A.

SUMMARY

The present invention satisfies this and other needs providing novel IL-17A modulators. In one aspect, a compound of structural Formula (I) is provided:

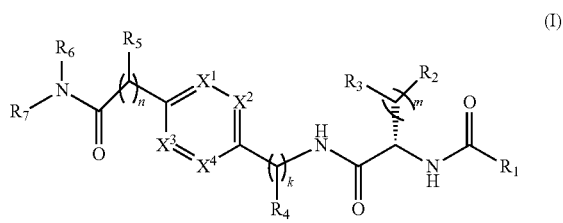

or a pharmaceutically acceptable salt, solvate or hydrate thereof where $R_1$ is alkyl, substituted alkyl, aryl, substituted aryl, heteroaryl, substituted heteroaryl, arylalkyl, substituted arylalkyl, heteroarylalkyl, substituted heteroarylalkyl —$OR_8$ or —$NR_9R_{10}$ or an F pocket substituent; $R_2$ is alkyl, substituted alkyl, cycloheteroalkyl, substituted cycloheteroalkyl, aryl, substituted aryl, fused cycloalkylaryl, substituted fused cycloalkylaryl, heteroaryl, substituted heteroaryl or a D pocket substituent; each $R_3$ is independently hydrogen, ($C_1$-$C_7$) alkyl, ($C_1$-$C_7$) substituted alkyl or —$OR_{32}$; m is 0, 1 or 2; each $R_4$ is independently hydrogen, ($C_1$-$C_7$) alkyl, ($C_1$-$C_7$) substituted alkyl, cycloalkyldiyl, substituted cycloalkyldiyl, heterocycloalkyldiyl or substituted heterocycloalkyldiyl; k is 0 or 1; $X^1$, $X^2$, $X^3$ and $X^4$ are independently —N— or —$CR_{11}$— provided that no more than two of $X^1$, $X^2$, $X^3$ and $X^4$ are nitrogen; each $R_5$ is independently hydrogen, ($C_1$-$C_7$) alkyl, ($C_1$-$C_7$) substituted alkyl, ($C_1$-$C_7$) cycloheteroalkyl, ($C_1$-$C_7$) substituted cycloheteroalkyl, cycloalkyldiyl, substituted cycloalkyldiyl, heterocycloalkyldiyl, substituted heterocycloalkyldiyl, —$NR_{12}R_{13}$, —$NR_{14}C(O)R_{15}$, —$NHSO_2R^{31}$, OH or a B pocket substituents; $R_6$ is hydrogen or alkyl; $R_7$ is cycloheteroalkyl, substituted cycloheteroalkyl, —$(CHR_{16})_oR_{17}$ or —$(CHR_{18})_pR_{19}$ or $R_6$ and $R_7$ taken together with the nitrogen atom to which they are attached form piperazine, substituted piperazine, cycloheteroalkyl or substituted cycloheteroalkyl,

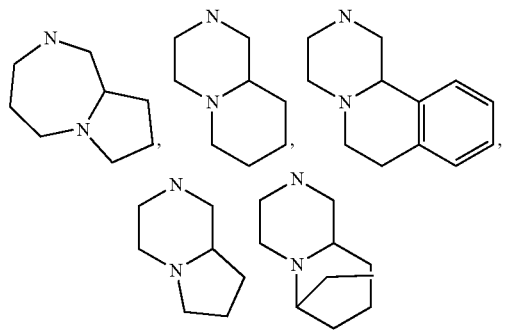

or an A pocket substituent; $R_8$ is ($C_1$-$C_7$) alkyl, ($C_1$-$C_7$) substituted alkyl, aryl, substituted aryl, heteroaryl or substituted heteroaryl; each $R_{11}$ is independently hydrogen, alkyl, substituted alkyl, —$OR_{20}$, —$NR_{21}R_{22}$, halo, —CN, —$CO_2R_{23}$, —$CONR_{24}R_{25}$ or —$SR_{26}$; n is 1, 2 or 3; o is 1, 2 or 3; p is 1, 2 or 3, each $R_{16}$ is independently hydrogen, ($C_1$-$C_7$) alkyl or ($C_1$-$C_7$) substituted alkyl; $R_{17}$ is

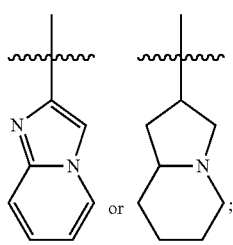

each $R_{18}$ is independently hydrogen, $(C_1-C_7)$ alkyl or $(C_1-C_7)$ substituted alkyl; $R_{19}$ is —$NR_{27}R_{28}$; $R_{27}$ and $R_{28}$ together with the nitrogen atom to which they are attached form a cycloheteroalkyl or substituted cycloheteroalkyl ring or

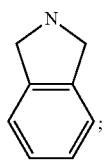

and $R_9$, $R_{10}$, $R_{12}$-$R_{15}$, $R_{18}$-$R_{26}$ and $R^{30}$-$R^{32}$ are independently hydrogen, alkyl, substituted alkyl, heteroalkyl, substituted heteroalkyl, aryl, substituted aryl, heteroaryl or substituted heteroaryl or alternatively, independently, $R_9$ and $R_{10}$, $R_{21}$ and $R_{22}$ and $R_{24}$ and $R_{25}$ together with atom to which they are attached form a cycloalkyl, substituted cycloalkyl, cycloheteroalkyl or substituted cycloheteroalkyl ring; and $R_{28}$ is hydrogen or alkyl.

Also provided are derivatives, including esters, enol ethers, enol esters, solvates, metabolites and prodrugs of the compounds described herein. Further provided are pharmaceutical compositions, which include the compounds provided herein and a pharmaceutically acceptable vehicle.

Methods of treating, preventing, or ameliorating symptoms of medical disorders such as, for example, inflammation, cancer or autoimmune disease are also provided herein. In practicing the methods, therapeutically effective amounts of the compounds or pharmaceutical compositions thereof are administered to a patient.

Methods of modulating IL-17A with the compounds and compositions described herein are also provided herein. In practicing the methods, therapeutically effective amounts of the compounds or pharmaceutical compositions are administered to a subject.

Methods of modulating the IL-17A receptor with the compounds and compositions described herein are also provided herein. In practicing the methods, therapeutically effective amounts of the compounds or pharmaceutical compositions are administered to a subject.

DETAILED DESCRIPTION

Definitions

Figure 1:
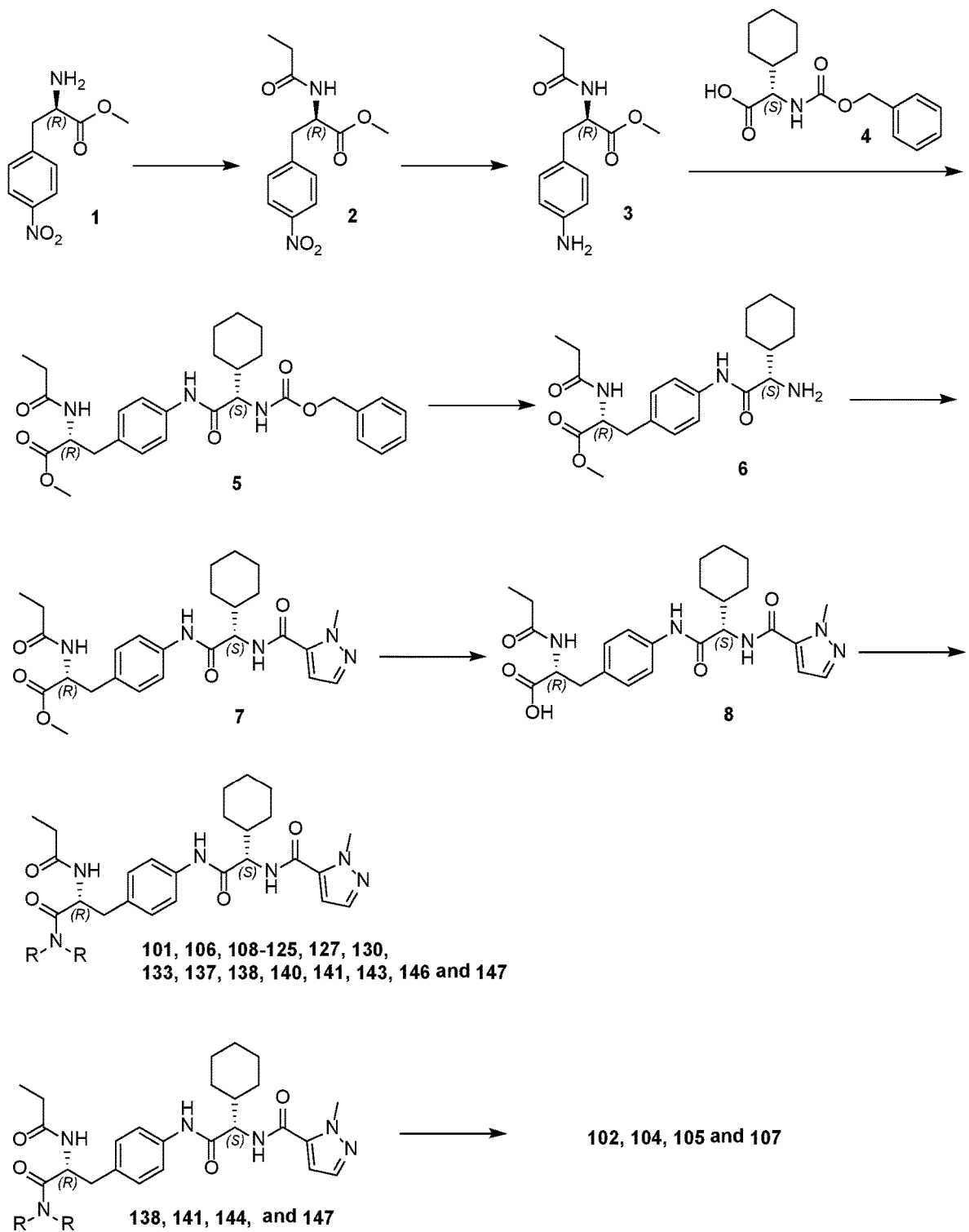
FIG. 1 describes a synthetic scheme which may be used to prepare compounds 101, 102, 104-125, 127, 130, 133, 137, 138, 140, 141, 143, 144, 146 and 147.

Unless defined otherwise, all technical and scientific terms used herein have the same meaning as is commonly understood by one of ordinary skill in the art to which this invention belongs. If a plurality of definitions for a term exist herein, those in this section prevail unless stated otherwise.

As used herein, and unless otherwise specified, the terms "about" and "approximately," when used in connection with a property with a numeric value or range of values indicate that the value or range of values may deviate to an extent deemed reasonable to one of ordinary skill in the art while still describing the particular property. Specifically, the terms "about" and "approximately," when used in this context, indicate that the numeric value or range of values may vary by 5%, 4%, 3%, 2%, 1%, 0.9%, 0.8%, 0.7%, 0.6%, 0.5%, 0.4%, 0.3%, 0.2% or 0.1% of the recited value or range of values.

"A-pocket substituent" as defined herein refers to the groups depicted below:

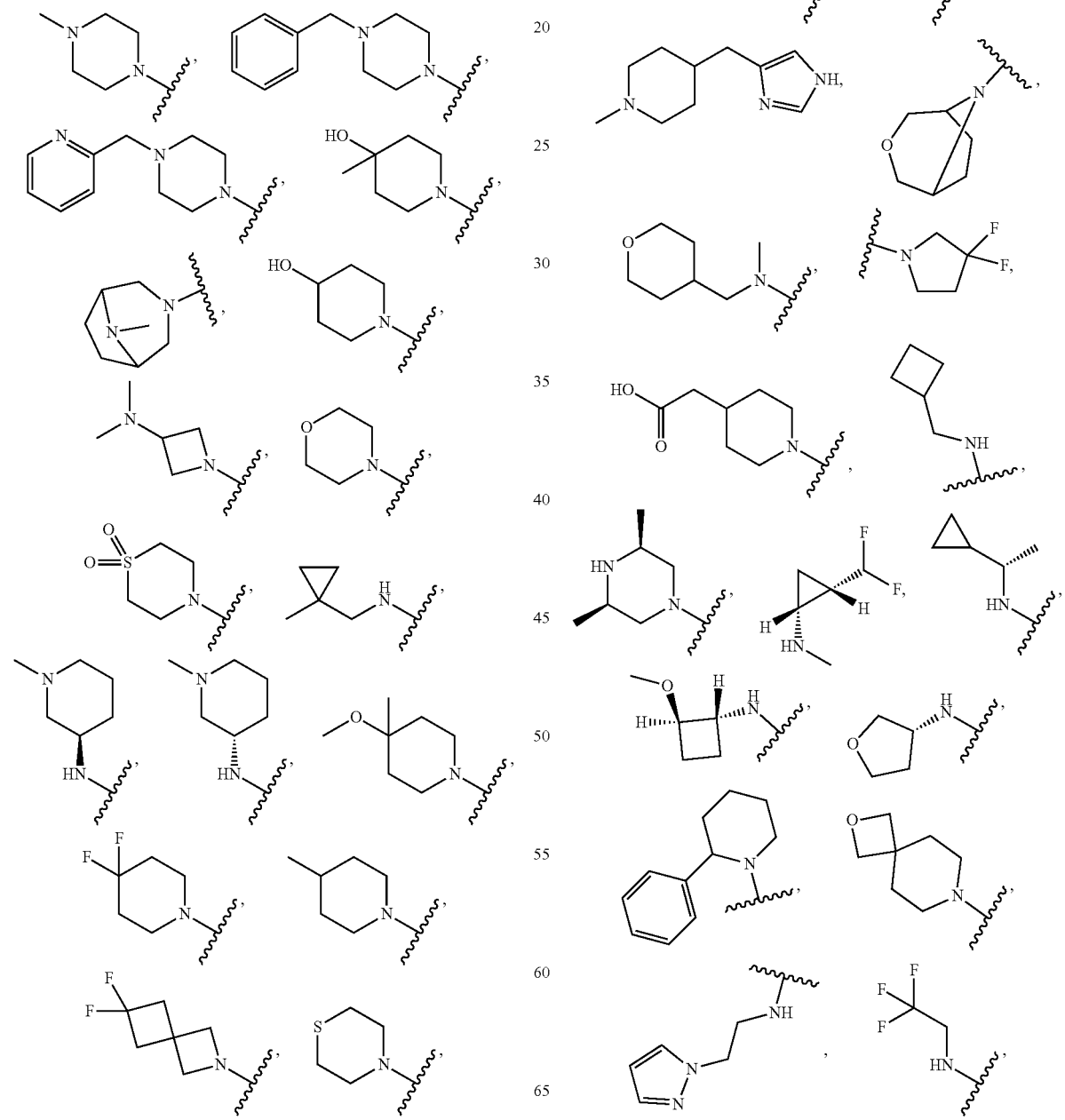

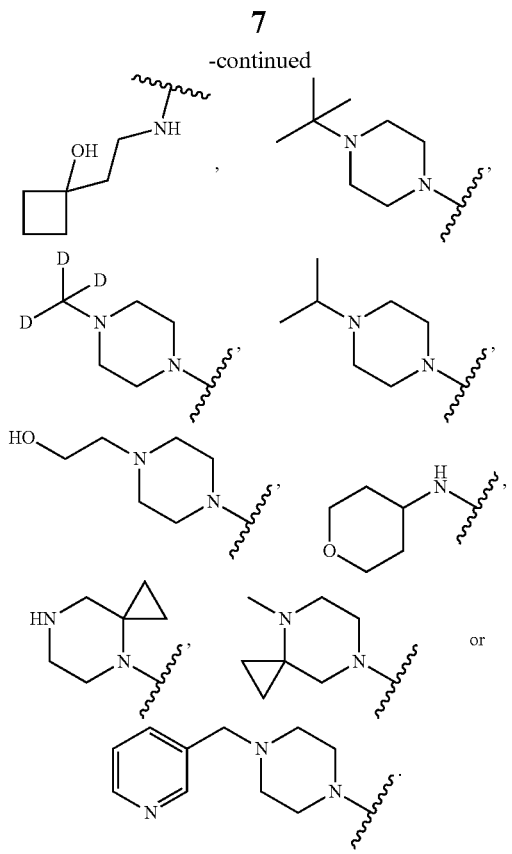
"B-pocket substituent" as defined herein refers to the groups depicted below:
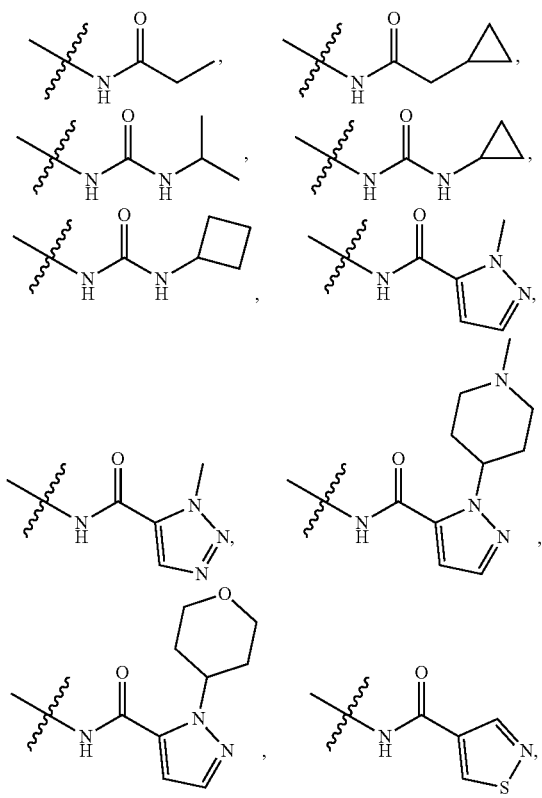
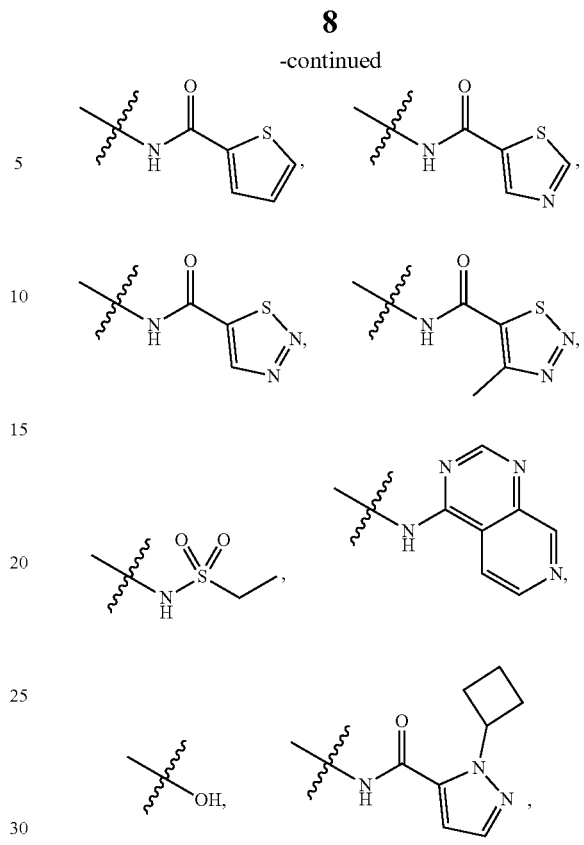
"D-pocket substituent" as defined herein refers to the groups depicted below:
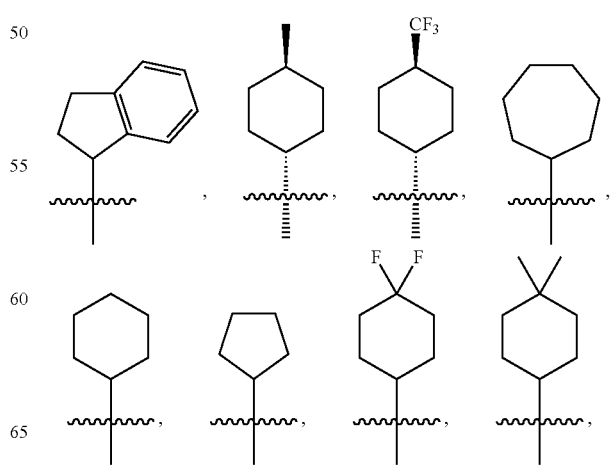

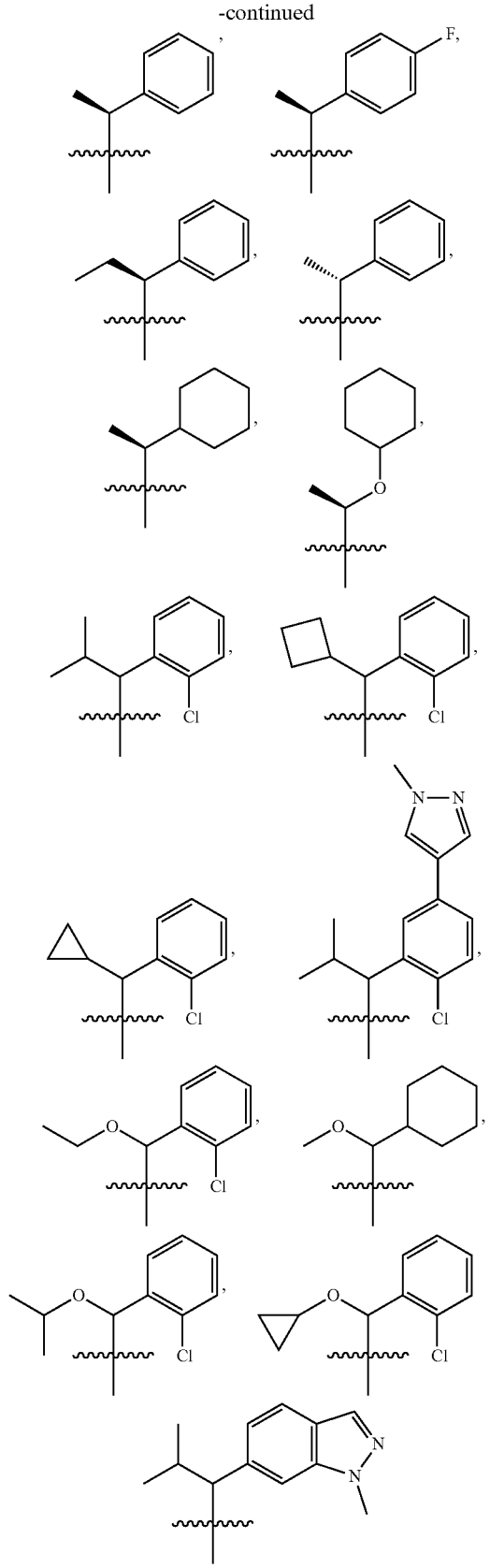
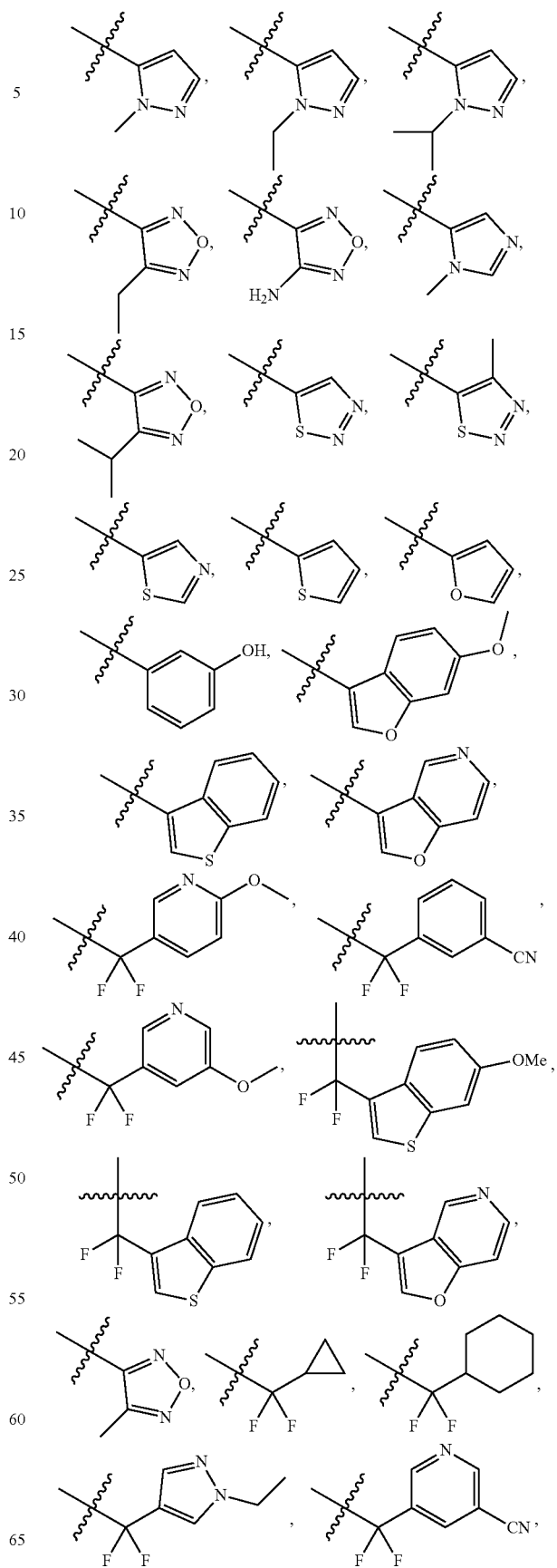
"F-pocket substituent" as defined herein refers to one of the groups depicted below:

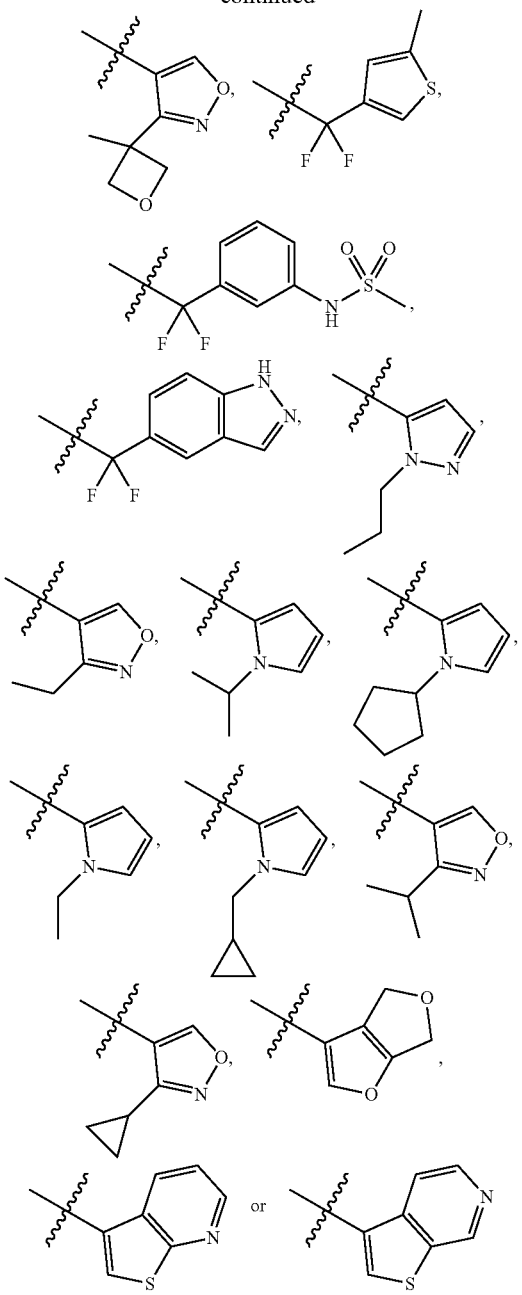

"Alkyl," by itself or as part of another substituent, refers to a saturated or unsaturated, branched, straight-chain or cyclic monovalent hydrocarbon radical derived by the removal of one hydrogen atom from a single carbon atom of a parent alkane, alkene or alkyne. Typical alkyl groups include, but are not limited to, methyl; ethyls such as ethanyl, ethenyl, ethynyl; propyls such as propan-1-yl, propan-2-yl, cyclopropan-1-yl, prop-1-en-1-yl, prop-1-en-2-yl, prop-2-en-1-yl (allyl), cycloprop-1-en-1-yl; cycloprop-2-en-1-yl, prop-1-yn-1-yl, prop-2-yn-1-yl, etc.; butyls such as butan-1-yl, butan-2-yl, 2-methyl-propan-1-yl, 2-methyl-propan-2-yl, cyclobutan-1-yl, but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, but-1-yn-1-yl, but-1-yn-3-yl, but-3-yn-1-yl, etc.; and the like. The term "alkyl" is specifically intended to include groups having any degree or level of saturation, i.e., groups having exclusively single carbon-carbon bonds, groups having one or more double carbon-carbon bonds, groups having one or more triple carbon-carbon bonds and groups having mixtures of single, double and triple carbon-carbon bonds. Where a specific level of saturation is intended, the expressions "alkanyl," "alkenyl," and "alkynyl" are used. In some embodiments, an alkyl group comprises from 1 to 20 carbon atoms ($C_1$-$C_{20}$ alkyl). In other embodiments, an alkyl group comprises from 1 to 10 carbon atoms ($C_1$-$C_{10}$ alkyl). In still other embodiments, an alkyl group comprises from 1 to 6 carbon atoms ($C_1$-$C_6$ alkyl). The term 'cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Alkanyl," by itself or as part of another substituent, refers to a saturated branched, straight-chain or cyclic alkyl radical derived by the removal of one hydrogen atom from a single carbon atom of a parent alkane. Typical alkanyl groups include, but are not limited to, methanyl; ethanyl; propanyls such as propan-1-yl, propan-2-yl (isopropyl), cyclopropan-1-yl, etc.; butanyls such as butan-1-yl, butan-2-yl (sec-butyl), 2-methyl-propan-1-yl (isobutyl), 2-methyl-propan-2-yl (t-butyl), cyclobutan-1-yl, etc.; and the like.

"Alkenyl," by itself or as part of another substituent, refers to an unsaturated branched, straight-chain or cyclic alkyl radical having at least one carbon-carbon double bond derived by the removal of one hydrogen atom from a single carbon atom of a parent alkene. The group may be in either the cis or trans conformation about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl, etc.; and the like.

"Alkynyl," by itself or as part of another substituent refers to an unsaturated branched, straight-chain or cyclic alkyl radical having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl, etc.; butynyls such as but-1-yn-1-yl, but-1-yn-3-yl, but-3-yn-1-yl, etc.; and the like.

"Alkyldiyl" by itself or as part of another substituent, refers to a saturated or unsaturated, branched, straight-chain or cyclic divalent hydrocarbon group derived by the removal of one hydrogen atom from each of two different carbon atoms of a parent alkane, alkene or alkyne, or by the removal of two hydrogen atoms from a single carbon atom of a parent alkane, alkene or alkyne. The two monovalent radical centers or each valency of the divalent radical center can form bonds with the same or different atoms. Typical alkyldiyl groups include, but are not limited to methandiyl; ethyldiyls such as ethan-1,1-diyl, ethan-1,2-diyl, ethen-1,1-diyl, ethen-1,2-diyl; propyldiyls such as propan-1,1-diyl, propan-1,2-diyl, propan-2,2-diyl, propan-1,3-diyl, cyclopropan-1,1-diyl, cyclopropan-1,2-diyl, prop-1-en-1,1-diyl, prop-1-en-1,2-diyl, prop-2-en-1,2-diyl, prop-1-en-1,3-diyl, cycloprop-1-en-1,2-diyl, cycloprop-2-en-1,2-diyl, cycloprop-2-en-1,1-diyl, prop-1-yn-1,3-diyl, etc.; butyldiyls such as, butan-1,1-diyl, butan-1,2-diyl, butan-1,3-diyl, butan-1,4-diyl, butan-2,2-diyl, 2-methyl-propan-1,1-diyl, 2-methyl-propan-1,2-diyl, cyclobutan-1,1-diyl; cyclobutan-1,2-diyl, cyclobutan-1,3-diyl, but-1-en-1,1-diyl, but-1-en-1,2-diyl, but-1-en-1,3-diyl, but-1-en-1,4-diyl, 2-methyl-prop-1-en-1,1-diyl, 2-methanylidene-propan-1,1-diyl, buta-1,3-dien-1,1-diyl, buta-1,3-dien-1,2-diyl, buta-1,3-dien-1,3-diyl, buta-1,3-dien-1,4-diyl, cyclobut-1-en-1,2-diyl, cyclobut-1-en-1,3-diyl, cyclobut-2-en-1,2-diyl, cyclobuta-1,3-dien-1,2-diyl, cyclobuta-1,3-dien-1,3-diyl, but-1-yn-1,3-diyl, but-1-yn-1,4-diyl, buta-1,3-diyn-1,4-diyl, etc.; and the like. Where specific levels of saturation are intended, the nomenclature alkanyldiyl, alkenyldiyl and/or alkynyldiyl is used. In some embodiments, the alkyldiyl group is $(C_1-C_{20})$ alkyldiyl. In other embodiments, the alkyldiyl group is $(C_1-C_{10})$ alkyldiyl. In still other embodiments, the alkyldiyl group is $(C_1-C_6)$ alkyldiyl. In some embodiments, saturated acyclic alkanyldiyl groups in which the radical centers are at the terminal carbons, e.g., methandiyl (methano); ethan-1,2-diyl (ethano); propan-1,3-diyl (propano); butan-1,4diyl (butano); and the like are preferred.

"Aryl," by itself or as part of another substituent, refers to a monovalent aromatic hydrocarbon group derived by the removal of one hydrogen atom from a single carbon atom of a parent aromatic ring system, as defined herein. Typical aryl groups include, but are not limited to, groups derived from aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like. In some embodiments, an aryl group comprises from 6 to 20 carbon atoms ($C_6-C_{20}$ aryl). In other embodiments, an aryl group comprises from 6 to 15 carbon atoms ($C_6-C_{15}$ aryl). In still other embodiments, an aryl group comprises from 6 to 15 carbon atoms ($C_6-C_{10}$ aryl).

"Arylalkyl," by itself or as part of another substituent, refers to an acyclic alkyl group in which one of the hydrogen atoms bonded to a carbon atom, typically a terminal or $sp^3$ carbon atom, is replaced with an aryl group as, as defined herein. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like. Where specific alkyl moieties are intended, the nomenclature arylalkanyl, arylalkenyl and/or arylalkynyl is used. In some embodiments, an arylalkyl group is ($C_6-C_{30}$) arylalkyl, e.g., the alkanyl, alkenyl or alkynyl moiety of the arylalkyl group is ($C_1-C_{10}$) alkyl and the aryl moiety is ($C_6-C_{20}$) aryl. In other embodiments, an arylalkyl group is ($C_6-C_{20}$) arylalkyl, e.g., the alkanyl, alkenyl or alkynyl moiety of the arylalkyl group is ($C_1-C_8$) alkyl and the aryl moiety is ($C_6-C_{12}$) aryl. In still other embodiments, an arylalkyl group is ($C_6-C_{15}$) arylalkyl, e.g., the alkanyl, alkenyl or alkynyl moiety of the arylalkyl group is ($C_1-C_5$) alkyl and the aryl moiety is ($C_6-C_{10}$) aryl.

"Cycloalkyl," by itself or as part of another substituent, refers to a saturated or unsaturated cyclic monovalent hydrocarbon radical derived by the removal of one hydrogen atom from a single carbon atom of a parent cycloalkane or cycloalkene. Typical cycloalkyl groups include, but are not limited to, cyclopropyl, cyclobutyl, cyclopentyl cycopentenyl; etc.; and the like. Where a specific level of saturation is intended, the expressions "cycloalkanyl," and "cycloalkenyl," are used. In some embodiments, a cycloalkyl group comprises from 1 to 20 carbon atoms ($C_1-C_{15}$ alkyl). In other embodiments, a cycloalkyl group comprises from 1 to 10 carbon atoms ($C_1-C_{10}$ alkyl). In still other embodiments, a cycloaklyl group comprises from 1 to 8 carbon atoms ($C_1-C_8$ alkyl). The term 'cyclic monovalent hydrocarbon radical" also includes multicyclic hydrocarbon ring systems having a single radical and between 3 and 12 carbon atoms. Exemplary multicyclic cycloalkyl rings include, for example, norbornyl, pinyl, and adamantyl.

"Cycloalkyldiyl," by itself or as part of another substituent, refers to cyclic vicinal diradical. Examples include, for example

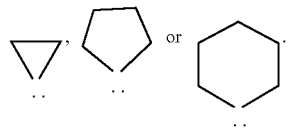

"Cycloheteroalkyl," by itself or as part of another substituent, refers to a cycloalkyl group as defined herein in which one or more one or more of the carbon atoms (and optionally any associated hydrogen atoms), are each, independently of one another, replaced with the same or different heteroatoms or heteroatomic groups as defined in "heteroalkyl" below.

"Fusedcycloalkylaryl," by itself or as part of another substituent, refers to a radical where a cycloalkyl radical as defined herein is fused to an aryl group. Examples include, for example, 1-indanyl, 2-indanyl, 1-tetrahydronapthalene or 2-tetrahydronapthalene.

"Compounds," refers to compounds encompassed by structural formulae disclosed herein and includes any specific compounds within these formulae whose structure is disclosed herein. Compounds may be identified either by their chemical structure and/or chemical name. The chemical structure is determinative of the identity of the compound. The compounds described herein may contain one or more chiral centers and/or double bonds and therefore, may exist as stereoisomers, such as double-bond isomers (i.e., geometric isomers), enantiomers or diastereomers. Accordingly, the chemical structures depicted herein encompass the stereoisomerically pure form depicted in the structure (e.g., geometrically pure, enantiomerically pure or diastereomerically pure). The chemical structures depicted herein also encompass the enantiomeric and stereoisomeric derivatives of the compound depicted. Enantiomeric and stereoisomeric mixtures can be resolved into their component enantiomers or stereoisomers using separation techniques or chiral synthesis techniques well known to the skilled artisan. The compounds may also exist in several tautomeric forms including the enol form, the keto form and mixtures thereof. Accordingly, the chemical structures depicted herein encompass all possible tautomeric forms of the illustrated compounds. The compounds described also include isotopically labeled compounds where one or more atoms have an atomic mass different from the atomic mass conventionally found in nature. Examples of isotopes that may be incorporated into the compounds disclosed herein include, but are not limited to, $^2H$, $^3H$, $^{11}C$, $^{13}C$, $^{14}C$, $^{15}N$, $^{18}O$, $^{17}O$, etc. Compounds may exist in unsolvated forms as well as solvated forms, including hydrated forms. In general, compounds may be hydrated or solvated. Certain compounds may exist in multiple crystalline or amorphous forms. In general, all physical forms are equivalent for the uses contemplated herein and are intended to be within the scope of the present disclosure. Further, it should be understood, when partial structures of the compounds are illustrated, that brackets indicate the point of attachment of the partial structure to the rest of the molecule.

"Halo," by itself or as part of another substituent refers to a radical —F, —Cl, —Br or —I.

"Heteroalkyl," "Heteroalkanyl," "Heteroalkenyl" and "Heteroalkynyl," by themselves or as part of other substituents, refer to alkyl, alkanyl, alkenyl and alkynyl groups, respectively, in which one or more of the carbon atoms (and optionally any associated hydrogen atoms), are each, independently of one another, replaced with the same or different heteroatoms or heteroatomic groups. Typical heteroatoms or heteroatomic groups which can replace the carbon atoms include, but are not limited to, —O—, —S—, —N—, —Si—, —NH—, —S(O)—, —S(O)$_2$—, —S(O)NH—, —S(O)$_2$NH— and the like and combinations thereof. The heteroatoms or heteroatomic groups may be placed at any interior position of the alkyl, alkenyl or alkynyl groups. Typical heteroatomic groups which can be included in these groups include, but are not limited to, —O—, —S—, —O—O—, —S—S—, —O—S—, —NR$^{501}$R$^{502}$, =N—N=, —N=N—, —N=N—NR$^{503}$R$^{504}$, —PR$^{505}$—, —P(O)$_2$—, —POR$^{506}$—, —O—P(O)$_2$—, —SO—, —SO$_2$—, —SnR$^{507}$R$^{508}$ and the like, where R$^{501}$, R$^{502}$, R$^{503}$, R$^{504}$, R$^{505}$, R$^{506}$, R$^{307}$ and R$^{508}$ are independently hydrogen, alkyl, substituted alkyl, aryl, substituted aryl, arylalkyl, substituted arylalkyl, heteroalkyl, substituted heteroalkyl, heteroaryl, substituted heteroaryl, heteroarylalkyl or substituted heteroarylalkyl.

"Heteroaryl," by itself or as part of another substituent, refers to a monovalent heteroaromatic radical derived by the removal of one hydrogen atom from a single atom of a parent heteroaromatic ring systems, as defined herein. Typical heteroaryl groups include, but are not limited to, groups derived from acridine, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene, and the like. In some embodiments, the heteroaryl group comprises from to 20 ring atoms (5-20 membered heteroaryl). In other embodiments, the heteroaryl group comprises from 5 to 10 ring atoms (5-10 membered heteroaryl). Exemplary heteroaryl groups include those derived from furan, thiophene, pyrrole, benzothiophene, benzofuran, benzimidazole, indole, pyridine, pyrazole, quinoline, imidazole, oxazole, isoxazole and pyrazine.

"Heteroarylalkyl," by itself or as part of another substituent refers to an acyclic alkyl group in which one of the hydrogen atoms bonded to a carbon atom, typically a terminal or sp$^a$ carbon atom, is replaced with a heteroaryl group. Where specific alkyl moieties are intended, the nomenclature heteroarylalkanyl, heteroarylalkenyl and/or heteroarylalkynyl is used. In some embodiments, the heteroarylalkyl group is a 6-21 membered heteroarylalkyl, e.g., the alkanyl, alkenyl or alkynyl moiety of the heteroarylalkyl is (C$_1$-C$_6$) alkyl and the heteroaryl moiety is a 5-15-membered heteroaryl. In other embodiments, the heteroarylalkyl is a 6-13 membered heteroarylalkyl, e.g., the alkanyl, alkenyl or alkynyl moiety is (C$_1$-C$_3$) alkyl and the heteroaryl moiety is a 5-10 membered heteroaryl.

"Heterocycloalkyldiyl," by itself or as part of another substituent, refers to a cycloalkyldiyl group as defined herein where one or more of the carbon atoms has been replace by a heteroatom. Examples include, for example

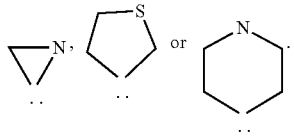

"Hydrates," refers to incorporation of water into to the crystal lattice of a compound described herein, in stoichiometric proportions, resulting in the formation of an adduct. Methods of making hydrates include, but are not limited to, storage in an atmosphere containing water vapor, dosage forms that include water, or routine pharmaceutical processing steps such as, for example, crystallization (i.e., from water or mixed aqueous solvents), lyophilization, wet granulation, aqueous film coating, or spray drying. Hydrates may also be formed, under certain circumstances, from crystalline solvates upon exposure to water vapor, or upon suspension of the anhydrous material in water. Hydrates may also crystallize in more than one form resulting in hydrate polymorphism. See e.g., (Guillory, K., Chapter 5, pp. 202205 in *Polymorphism in Pharmaceutical Solids*, (Brittain, H. ed.), Marcel Dekker, Inc., New York, NY, 1999). The above methods for preparing hydrates are well within the ambit of those of skill in the art, are completely conventional and do not require any experimentation beyond what is typical in the art. Hydrates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of hydrates such as, for example, HOLODIAG, Pharmaparc II, Voie de l'Innovation, 27 100 Val de Reuil, France (http://www.holodiag.com).

"Parent Aromatic Ring System," refers to an unsaturated cyclic or polycyclic ring system having a conjugated π electron system. Specifically included within the definition of "parent aromatic ring system" are fused ring systems in which one or more of the rings are aromatic and one or more of the rings are saturated or unsaturated, such as, for example, fluorene, indane, indene, phenalene, etc. Typical parent aromatic ring systems include, but are not limited to, aceanthrylene, acenaphthylene, acephenanthrylene, anthracene, azulene, benzene, chrysene, coronene, fluoranthene, fluorene, hexacene, hexaphene, hexalene, as-indacene, s-indacene, indane, indene, naphthalene, octacene, octaphene, octalene, ovalene, penta-2,4-diene, pentacene, pentalene, pentaphene, perylene, phenalene, phenanthrene, picene, pleiadene, pyrene, pyranthrene, rubicene, triphenylene, trinaphthalene and the like.

"Parent Heteroaromatic Ring System," refers to a parent aromatic ring system in which one or more carbon atoms (and optionally any associated hydrogen atoms) are each independently replaced with the same or different heteroatom. Typical heteroatoms to replace the carbon atoms include, but are not limited to, N, P, O, S, Si, etc. Specifically included within the definition of "parent heteroaromatic ring system" are fused ring systems in which one or more of the rings are aromatic and one or more of the rings are saturated or unsaturated, such as, for example, benzodioxan, benzofuran, chromane, chromene, indole, indoline, xanthene, etc. Typical parent heteroaromatic ring systems include, but are not limited to, arsindole, carbazole, β-carboline, chromane, chromene, cinnoline, furan, imidazole, indazole, indole, indoline, indolizine, isobenzofuran, isochromene, isoindole, isoindoline, isoquinoline, isothiazole, isoxazole, naphthyridine, oxadiazole, oxazole, perimidine, phenanthridine, phenanthroline, phenazine, phthalazine, pteridine, purine, pyran, pyrazine, pyrazole, pyridazine, pyridine, pyrimidine, pyrrole, pyrrolizine, quinazoline, quinoline, quinolizine, quinoxaline, tetrazole, thiadiazole, thiazole, thiophene, triazole, xanthene and the like.

"Pharmaceutically acceptable salt," refers to a salt of a compound, which possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl) benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound is replaced by a metal ion, e.g., an alkali metal ion, an alkaline earth ion, or an aluminum ion; or coordinates with an organic base such as ethanolamine, diethanolamine, triethanolamine, N-methylglucamine and the like.

"Preventing," or "prevention," refers to a reduction in risk of acquiring a disease or disorder (i.e., causing at least one of the clinical symptoms of the disease not to develop in a patient that may be exposed to or predisposed to the disease but does not yet experience or display symptoms of the disease). The application of a therapeutic for preventing or prevention of a disease or disorder is known as 'prophylaxis.' In some embodiments, the compounds provided herein provide superior prophylaxis because of lower long term side effects over long time periods.

"Protecting group," refers to a grouping of atoms that when attached to a reactive functional group in a molecule masks, reduces or prevents reactivity of the functional group during chemical synthesis. Examples of protecting groups can be found in Green et al., "Protective Groups in Organic Chemistry", (Wiley, 2$^{nd}$ ed. 1991) and Harrison et al., "Compendium of Synthetic Organic Methods", Vols. 1-8 (John Wiley and Sons, 1971-1996). Representative amino protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethylsilyl-ethanesulfonyl ("SES"), trityl and substituted trityl groups, allyloxycarbonyl, 9-fluorenylmethyloxycarbonyl ("FMOC"), nitro-veratryloxycarbonyl ("NVOC") and the like. Representative hydroxy protecting groups include, but are not limited to, those where the hydroxy group is either acylated or alkylated such as benzyl, and trityl ethers as well as alkyl ethers, tetrahydropyranyl ethers, trialkylsilyl ethers and allyl ethers.

"Solvates," refers to incorporation of solvents into to the crystal lattice of a compound described herein, in stoichiometric proportions, resulting in the formation of an adduct. Methods of making solvates include, but are not limited to, storage in an atmosphere containing a solvent, dosage forms that include the solvent, or routine pharmaceutical processing steps such as, for example, crystallization (i.e., from solvent or mixed solvents) vapor diffusion, etc. Solvates may also be formed, under certain circumstances, from other crystalline solvates or hydrates upon exposure to the solvent or upon suspension material in solvent. Solvates may crystallize in more than one form resulting in solvate polymorphism. See e.g., (Guillory, K., Chapter 5, pp. 205208 in *Polymorphism in Pharmaceutical Solids*, (Brittain, H. ed.), Marcel Dekker, Inc., New York, NY, 1999)). The above methods for preparing solvates are well within the ambit of those of skill in the art, are completely conventional do not require any experimentation beyond what is typical in the art. Solvates may be characterized and/or analyzed by methods well known to those of skill in the art such as, for example, single crystal X-ray diffraction, X-ray powder diffraction, polarizing optical microscopy, thermal microscopy, thermogravimetry, differential thermal analysis, differential scanning calorimetry, IR spectroscopy, Raman spectroscopy and NMR spectroscopy. (Brittain, H., Chapter 6, pp. 205208 in *Polymorphism in Pharmaceutical Solids*, (Brittain, H. ed.), Marcel Dekker, Inc. New York, 1999). In addition, many commercial companies routine offer services that include preparation and/or characterization of solvates such as, for example, HOLODIAG, Pharmaparc II, Voie de l'Innovation, 27 100 Val de Reuil, France (http://www.holodiag.com).

"Substituted," when used to modify a specified group or radical, means that one or more hydrogen atoms of the specified group or radical are each, independently of one another, replaced with the same or different substituent(s). Substituent groups useful for substituting saturated carbon atoms in the specified group or radical include $-R^a$, halo, $-O^-$, $=O$, $-OR^b$, $-SR^b$, $-S=S$, $-NR^cR^c$, $=NR^b$, $=N-OR^b$, trihalomethyl, $-CF_3$, $-CN$, $-OCN$, $-SCN$, $-NO$, $-NO_2$, $-N=OR^b$, $-N-NR^cR^c$, $-NR^bS(O)_2R^b$, $=N_2$, $-N_3$, $-S(O)_2R^b$, $-S(O)_2NR^bR^b$, $-S(O)_2O^b$, $-S(O)_2OR^b$, $-OS(O)_2R^b$, $-OS(O)_2O^-$, $-OS(O)_2OR^b$, $-OS(O)_2NR^cNR^c$, $-P(O)(O^-)_2$, $-P(O)(OR^b)(O^-)$, $-P(O)(OR^b)(OR^b)$, $-C(O)R^b$, $-C(O)NR^b-OR^b-C(S)R^b$, $-C(NR^b)R^b$, $-C(O)O C(O)OR^b$, $-C(S)OR^b$, $-C(O)NR^cR^c$, $-C(NR^b)NR^cR^c$, $-OC(O)R^b$, $-OC(S)R^b$, $-OC(O)O^-$, $-OC(O)OR^b$, $-OC(O)NR^cR^c$, $-OC(NCN)NR^cR_c$, $-OC(S)OR^b$, $-NR^bC(O)R^b$, $-NR^bC(S)R^b$, $-NR^bC(O)O^-$, $-NR^bC(O)OR^b$, $-NR^bC(NCN)OR^b$, $-NR^bS(O)_2NR^cR^c$, $-NR^bC(S)OR^b$, $-NR^bC(O)NR^cR^c$, $-NR^bC(S)NR^cR^c$, $-NR^bC(S)NR^bC(O)R^a$, $-NR^bS(O)_2OR^b$, $-NR^bS(O)_2R^b$, $-NR^bC(NCN)NR^cR^c$, $-NR^bC(NR^b)R^b$ and $-NR^bC(NR^b)NR^cR^c$, where each $R^a$ is independently alkyl, substituted alkyl, aryl, substituted aryl, heteroaryl or substituted heteroaryl; each $R^b$ is independently hydrogen, $R^a$, heteroalkyl, substituted heteroalkyl, arylalkyl, substituted arylalkyl, heteroarylalkyl or substituted heteroarylalkyl; and each $R^c$ is independently $R^b$ or alternatively, the two $R^c$s taken together with the nitrogen atom to which they are bonded form a 4-, 5-, 6- or 7 membered-cycloheteroalkyl, substituted cycloheteroalkyl or a cycloheteroalkyl fused with an aryl group which may optionally include from 1 to 4 of the same or different additional heteroatoms selected from the group consisting of O, N and S. As specific examples, —NR$^c$R$^c$ is meant to include —NH$_2$, —NH-alkyl, N-pyrrolidinyl and N-morpholinyl. In other embodiments, substituent groups useful for substituting saturated carbon atoms in the specified group or radical include R$^a$, halo, —OR$^b$, —NR$^c$R$^c$, trihalomethyl, —CN, —NR$^b$S(O)$_2$R$^b$, —C(O)R$^b$, —C(O)NR$^b$—OR$^b$, —C(O)NR$^c$R$^c$, —OC(O)R$^b$, —OC(O)OR$^b$, —OS(O)$_2$NR$^c$NR$^c$, —OC(O)NR$^c$R$^c$, and —NR$^b$C(O)OR$^b$, where each R$^a$ is independently alkyl, aryl, heteroaryl, each R$^b$ is independently hydrogen, R$^a$, heteroalkyl, arylalkyl, heteroarylalkyl; and each R$^c$ is independently R$^b$ or alternatively, the two R$^c$s taken together with the nitrogen atom to which they are bonded form a 4-, 5-, 6 or -7 membered-cycloheteroalkyl ring.

Substituent groups useful for substituting unsaturated carbon atoms in the specified group or radical include, but are not limited to, —R$^a$, halo, —O$^-$, —OR$^b$, —SR$^b$, —S$^-$, —NR$^c$R$^c$, trihalomethyl, —CF$_3$, —CN, —OCN, —SCN, —NO, —NO$_2$, —N$_3$, —S(O)$_2$O$^-$, —S(O)$_2$OR$^b$, —OS(O)$_2$R$^b$, —OS(O)$_2$OR$^b$, —OS(O)$_2$O$^-$, —P(O)(O$^-$)$_2$, —P(O)(OR$^b$)(O$^-$), —P(O)(OR$^b$)(OR$^b$), —C(O)R$^b$, —C(S)R$^b$, —C(NR$^b$)R$^b$, —C(O)O$^-$, —C(O)OR$^b$, —C(S)OR$^b$, —C(O)NR$^c$R$^c$, —C(NR$^b$)NR$^c$R$^c$, —OC(O)R$^b$, —OC(S) R$^b$, —OC(O)O$^-$, —OC(O)OR$^b$, —OC(S)OR$^b$, —OC(O)NR$^c$R$^c$, —OS(O)$_2$NR$^c$NR$^c$, —NR$^b$C(O)R$^b$, —NR$^b$C(S)R$^b$, —NR$^b$C(O)O$^-$, —NR$^b$C(O)OR$^b$, —NR$^b$S(O)$_2$OR$^a$, —NR$^b$S(O)$_2$R$^a$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined. In other embodiments, substituent groups useful for substituting unsaturated carbon atoms in the specified group or radical include —R$^a$, halo, —OR$^b$, —SR$^b$, —NR$^c$R$^c$, trihalomethyl, —CN, —S(O)$_2$OR$^b$, —C(O)R$^b$, —C(O)OR$^b$, —C(O)NR$^c$R$^c$, —OC(O)R$^b$, —OC(O)OR$^b$, —OS(O)$_2$NR$^c$ NR$^c$, —NR$^b$C(O)R$^b$ and —NR$^b$C(O)OR$^b$, where R$^a$, R$^b$ and R$^c$ are as previously defined.

Substituent groups useful for substituting nitrogen atoms in heteroalkyl and cycloheteroalkyl groups include, but are not limited to, —R$^a$, —O$^-$, —OR$^b$, —SR$^b$, —S$^-$, trihalomethyl, —CF$_3$, —CN, —NO, —NO$_2$, —S(O)$_2$R$^b$, —S(O)$_2$O$^-$, —S(O)$_2$OR$^b$, —OS(O)$_2$R$^b$, —OS(O)$_2$O$^-$, —OS(O)$_2$OR$^b$, —P(O)(O$^-$)$_2$, —P(O)(OR$^b$)(O), —P(O)(OR$^b$)(OR$^b$), —C(O)R$^b$, —C(S)R$^b$, —C(NR$^b$)R$^b$, —C(O)OR$^b$, —C(S)OR$^b$, —C(O)NR$^c$R$^c$, —C(NR$^b$)NR$^c$R$^c$, —OC(O)R$^b$, —OC(S)R$^b$, —OC(O)OR$^b$, —OC(S)OR$^b$, —NR$^b$C(O)R$^b$, —NR$^b$C(S)R$^b$, —NR$^b$C(O)OR$^b$, —NR$^b$C(S)OR$^b$, —NR$^b$C(O)NR$^c$R$^c$, —NR$^b$C(NR$^b$)R$^b$ and —NR$^b$C(NR$^b$)NR$^c$R$^c$, where R$^a$, R$^b$ and R$^c$ are as previously defined. In some embodiments, substituent groups useful for substituting nitrogen atoms in heteroalkyl and cycloheteroalkyl groups include, R$^a$, halo, —OR$^b$, —NR$^c$R$^c$, trihalomethyl, —CN, —S(O)$_2$OR$^b$, —OS(O)$_2$R$^b$, —OS(O)$_2$OR$^b$, —C(O)R$^b$, —C(NR$^b$)R$^b$, —C(O)OR$^b$, —C(O)NR$^c$R$^c$, —OC(O)R$^b$, —OC(O)OR$^b$, —OS(O)$_2$NR$^c$NR$^c$, —NR$^b$C(O)R$^b$ and —NR$^b$C(O)OR$^b$, where R$^a$, R$^b$ and R$^c$ are as previously defined.

Substituent groups from the above lists useful for substituting other specified groups or atoms will be apparent to those of skill in the art.

The substituents used to substitute a specified group can be further substituted, typically with one or more of the same or different groups selected from the various groups specified above.

"Subject," "individual," or "patient," is used interchangeably herein and refers to a vertebrate, preferably a mammal. Mammals include, but are not limited to, murines, rodents, simians, humans, farm animals, sport animals and pets.

"Treating," or "treatment," of any disease or disorder refers, in some embodiments, to ameliorating the disease or disorder (i.e., arresting or reducing the development of the disease or at least one of the clinical symptoms thereof). Treatment may also be considered to include preemptive or prophylactic administration to ameliorate, arrest or prevent the development of the disease or at least one of the clinical symptoms. In a further feature the treatment rendered has lower potential for long-term side effects over multiple years. In other embodiments "treating" or "treatment" refers to ameliorating at least one physical parameter, which may not be discernible by the patient. In yet other embodiments, "treating" or "treatment" refers to inhibiting the disease or disorder, either physically, (e.g., stabilization of a discernible symptom), physiologically, (e.g., stabilization of a physical parameter) or both. In yet other embodiments, "treating" or "treatment" refers to delaying the onset of the disease or disorder.

"Therapeutically effective amount," means the amount of a compound that, when administered to a patient for treating a disease, is sufficient to treat the disease. The "therapeutically effective amount" will vary depending on the compound, the disease and its severity and the age, weight, adsorption, distribution, metabolism and excretion etc., of the patient to be treated.

"Vehicle," refers to a diluent, excipient or carrier with which a compound is administered to a subject. In some embodiments, the vehicle is pharmaceutically acceptable.

Compounds

The present invention provides novel IL-17A ligands useful in the treatment of various medical conditions where such ligands mediate the negative effects of the condition. Such conditions include, for example, inflammation, cancer or autoimmune disease.

In one aspect, a compound of structural Formula (I) is provided:

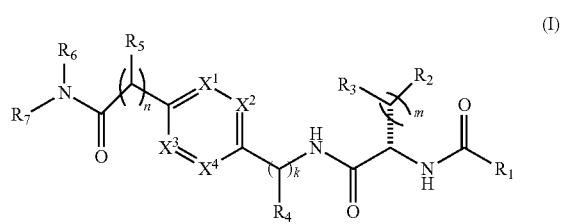

(I)

or a pharmaceutically acceptable salt, solvate or hydrate thereof where R$_1$ is alkyl, substituted alkyl, aryl, substituted aryl, heteroaryl, substituted heteroaryl, arylalkyl, substituted arylalkyl, heteroarylalkyl, substituted heteroarylalkyl —OR$_8$ or —NR$_9$R$_{10}$ or an F pocket substituent; R$_2$ is alkyl, substituted alkyl, cycloheteroalkyl, substituted cycloheteroalkyl, aryl, substituted aryl, fused cycloalkylaryl, substituted fused cycloalkylaryl, heteroaryl, substituted heteroaryl or a D pocket substituent; each R$_3$ is independently hydrogen, (C$_1$-C$_7$) alkyl, (C$_1$-C$_7$) substituted alkyl or —OR$_{32}$; m is 0, 1 or 2; each R$_4$ is independently hydrogen, (C$_1$-C$_7$) alkyl, (C$_1$-C$_7$) substituted alkyl, cycloalkyldiyl, substituted cycloalkyldiyl, heterocycloalkyldiyl or substituted heterocycloalkyldiyl; k is 0 or 1; X$^1$, X$^2$, X$^3$ and X$^4$ are independently —N— or —CR$_{11}$— provided that no more than two of X$^1$, X$^2$, X$^3$ and X$^4$ are nitrogen; each R$_5$ is independently hydrogen, (C$_1$-C$_7$) alkyl, (C$_1$-C$_7$) substituted alkyl, (C$_1$-C$_7$)

cycloheteroalkyl, (C$_1$-C$_7$) substituted cycloheteroalkyl, cycloalkyldiyl, substituted cycloalkyldiyl, heterocycloalkyldiyl, substituted heterocycloalkyldiyl, —NR$_{12}$R$_{13}$, —NR$_{14}$C(O)R$_{15}$, —NHSO$_2$R$^{31}$, OH or a B pocket substituents; R$_6$ is hydrogen or alkyl; R$_7$ is cycloheteroalkyl, substituted cycloheteroalkyl, —(CHR$_{16}$)$_o$R$_{17}$ or —(CHR$_{18}$)$_p$R$_{19}$ or R$_6$ and R$_7$ taken together with the nitrogen atom to which they are attached form piperazine, substituted piperazine, cycloheteroalkyl or substituted cycloheteroalkyl,

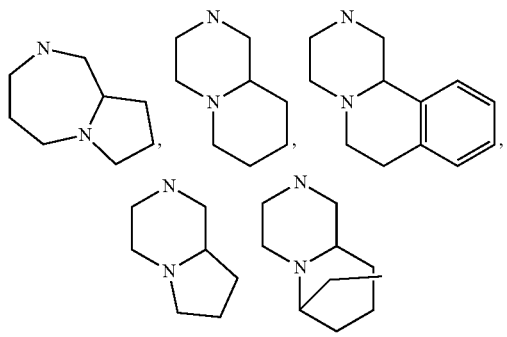

or an A pocket substituent; R$_8$ is (C$_1$-C$_7$) alkyl, (C$_1$-C$_7$) substituted alkyl, aryl, substituted aryl, heteroaryl or substituted heteroaryl; each R$_{11}$ is independently hydrogen, alkyl, substituted alkyl, —OR$_{20}$, —NR$_{21}$R$_{22}$, halo, —CN, —CO$_2$R$_{23}$, —CONR$_{24}$R$_{25}$ or —SR$_{26}$; n is 1, 2 or 3; o is 1, 2 or 3; p is 1, 2 or 3; each R$_{16}$ is independently hydrogen, (C$_1$-C$_7$) alkyl or (C$_1$-C$_7$) substituted alkyl; R$_{17}$ is

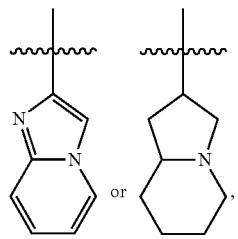

each R$_{18}$ is independently hydrogen, (C$_1$-C$_7$) alkyl or (C$_1$-C$_7$) substituted alkyl; R$_{19}$ is —NR$_{27}$R$_{28}$; R$_{27}$ and R$_{28}$ together with the nitrogen atom to which they are attached form a cycloheteroalkyl or substituted cycloheteroalkyl ring or

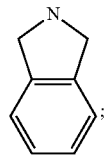

and R$_9$, R$_{10}$, R$_{12}$-R$_{15}$, R$_{18}$-R$_{26}$ and R$^{30}$-R$^{21}$ are independently hydrogen, alkyl, substituted alkyl, heteroalkyl, substituted heteroalkyl, aryl, substituted aryl, heteroaryl or substituted heteroaryl or alternatively, independently, R$_9$ and R$_{10}$, R$_{21}$ and R$_{22}$ and R$_{24}$ and R$_{25}$ together with atom to which they are attached form a cycloalkyl, substituted cycloalkyl, cycloheteroalkyl or substituted cycloheteroalkyl ring; and R$_{28}$ is hydrogen or alkyl.

In some embodiments, n is 2 and k is 1. In other embodiments, n is 1 and k is 1. In still other embodiments, n is 2 and k is 0. In still other embodiments, n is 1 and k is 0.

In some of the above embodiments, R$_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl. In other embodiments, R$_1$ is substituted phenyl, 5-membered heteroaryl, substituted 5-membered heteroaryl, —CF$_2$R$_{29}$ where R$_{29}$ is aryl, substituted aryl, heteroaryl or substituted heteroaryl. In still other embodiments, R$_1$ is substituted phenyl, oxadiazole, substituted oxadiazole, pyrazole, substituted pyrazole, thiophene, substituted thiophene, furan, substituted furan, thiazole, substituted thiazole, pyrrole, substituted pyrrole, oxazole, substituted oxazole, isoxazole, substituted isoxazole, thiadiazole, substituted thiadiazole, tetrazole or substituted tetrazole, triazole or substituted triazole, —CF$_2$R$_{29}$ where R$_{29}$ is cycloalkyl, substituted cycloalkyl, phenyl, substituted phenyl, pyridyl, substituted pyridyl, thiazole or substituted thiazole. In still other embodiments, R$_1$ is

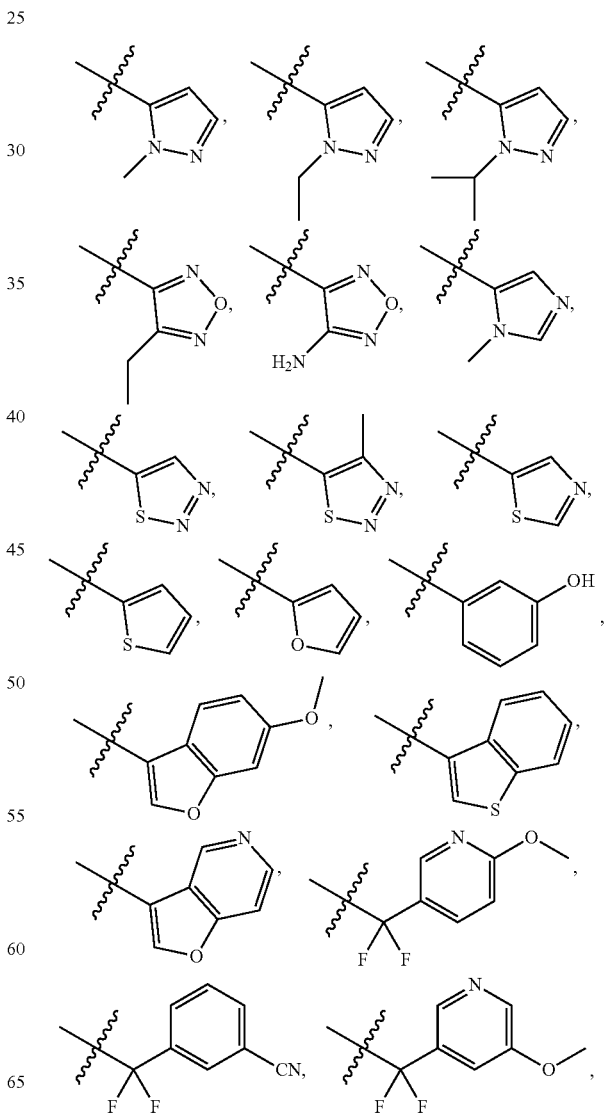

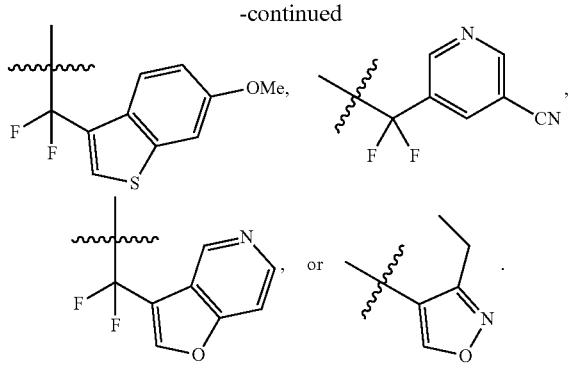

In still other embodiments, $R_1$ is an F pocket substituent.

In still other embodiments, $R_1$ is $—CF_2R_{29}$ where $R_{29}$ is cycloalkyl, substituted cycloalkyl, phenyl, substituted phenyl, pyridyl, substituted pyridyl, thiazole or substituted thiazole. In still other embodiments, $R_{29}$ is

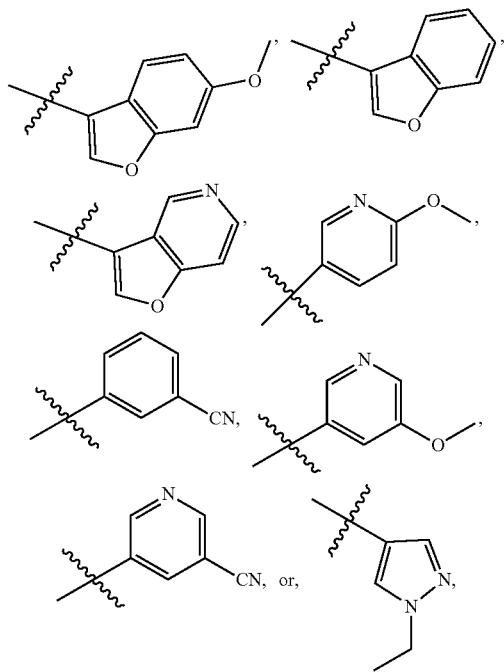

In some embodiments, $R_2$ is cycloalkyl, substituted alkyl, aryl, substituted aryl, heteroaryl, substituted heteroaryl, 1-indanyl, 2-indanyl, 1-tetrahydronapthyl 2-tetrahydronapthyl, 4-methylcyclohexyl, $(—CH_2(R_3))—O$-cycloalkyl) or $—CH(R_3)$phenyl optionally substituted. In other embodiments, $R_2$ is cycloalkyl, aryl, heteroaryl, 1-indanyl, 2-indanyl, 1-tetrahydronapthyl, 2-tetrahydronapthyl, $—CH(R_3)$phenyl. In still other embodiments, $R_2$ is cycloalkyl, 1-indanyl, 2-indanyl, 1-tetrahydronapthyl, 2-tetrahydronapthyl, 4-methylcyclohexyl, $—CH(R_3)$phenyl, optionally substituted phenyl, or $—OR_{30}$ where $R_{30}$ is alkyl, aryl or substituted aryl. In still other embodiments, $R_2$ is cyclohexyl, cycloheptyl, cyclooctyl, cyclopentyl, 1-indanyl, 2-indanyl, 1-tetrahydronapthyl, 2-tetrahydronapthyl, 4-methylcyclohexyl, $(—CH_2(R_3)—O$-cycloalkyl) or $—CH(R_3)$phenyl optionally substituted or when m is 1 or greater, phenyl, substituted o-chlorophenyl or p-fluorophenyl, or $—OR_{30}$ wherein $R_{30}$ is t-butyl, cyclohexyl or phenyl. In still other embodiments, $R_2$ is a D pocket substituent.

In some embodiments, each $R_3$ is independently hydrogen or $(C_1-C_4)$ alkyl.

In some embodiments, each $R_4$ is independently hydrogen, $(C_1-C_4)$ alkyl, cycloalkyldiyl or heterocycloalkyldiyl. In some embodiments, each $R_4$ is independently hydrogen or $(C_1-C_4)$ alkyl.

In some embodiments, each $R_5$ is independently hydrogen, $(C_1-C_4)$ alkyl, cycloalkyldiyl, heterocycloalkyldiyl $—NR_{12}R_{13}$ or $—NR_{14}C(O)R_{15}$. In some embodiments, each $R_5$ is independently hydrogen, $(C_1-C_4)$ alkyl or $—NR_{14}C(O)R_{15}$. In some embodiments, $R_5$ is a B pocket substituent.

In some of the above embodiments, only 1 of $X^1$, $X^2$, $X^3$ and $X^4$ are nitrogen.

In some embodiments, $R_7$ is cycloheteroalkyl, substituted cycloheteroalkyl, $—(CHR_{16})_oR_{17}$ or $—(CHR_{18})_pR_{19}$. In other embodiments, each $R_{1b}$ is independently hydrogen or $(C_1-C_4)$ alkyl. In still other embodiments, each $R_{18}$ is independently hydrogen or $(C_1-C_4)$ alkyl.

In some embodiments, $R_6$ and $R_7$ taken together with the nitrogen atom to which they are attached form a piperazine or substituted piperazine ring, a cycloheteroalkyl or substituted cycloheteroalkyl ring or

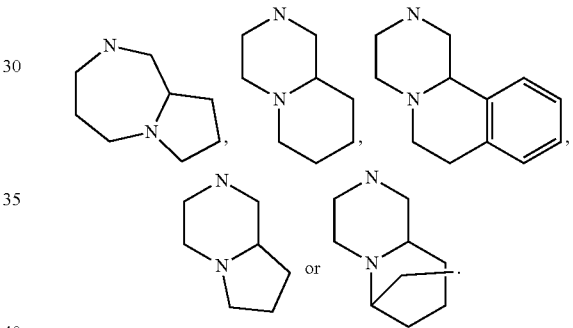

In other embodiments, $R_6$ and $R_7$ taken together with the nitrogen atom to which they are attached form an A pocket substituent.

In some of the above embodiments, $R_8$ is $(C_1-C_4)$ alkyl, aryl or heteroaryl.

In some of the above embodiments, $R_{11}$ is hydrogen, fluoro or $(C_1-C_4)$ alkyl In some of the above embodiments, $R_{25}$ and $R_{26}$ together with the nitrogen atom to which they are attached form a cycloheteroalkyl or substituted cycloheteroalkyl ring.

In some of the above embodiments, $R_9$, $R_{10}$, $R_{12}$-$R_{15}$ and $R_{18}$-$R_{26}$ are independently hydrogen, alkyl, heteroalkyl, aryl or heteroaryl or alternatively, independently, $R_9$ and $R_{10}$, $R_{21}$ and $R_{22}$ and $R_{24}$ and $R_{25}$ together with atom to which they are attached form a cycloalkyl, cycloheteroalkyl ring. In other of the above embodiments, $R_9$, $R_{10}$, $R_{12}$-$R_{15}$ and $R_{18}$-$R_{26}$ are independently hydrogen or $(C_1-C_4)$ alkyl or alternatively, independently, $R_9$ and $R_{10}$, $R_{21}$ and $R_{22}$ and $R_{24}$ and $R_{25}$ together with atom to which they are attached form a cyclohexyl, piperidinyl or morpholinyl ring.

In some embodiments, $R_6$ and $R_7$ taken together with the nitrogen atom to which they are attached are a pocket substituent, $R_1$ is an F pocket substituent, $R_2$ is a D pocket substituent and $R_5$ is a B pocket substituent. In other embodiments, $R_6$ and $R_7$ taken together with the nitrogen atom to which they are attached are an A pocket substituent, $R_1$ is an F pocket substituent and $R_5$ is a B pocket substituent. In still other embodiments, $R_6$ and $R_7$ taken together with the nitrogen atom to which they are attached are an A pocket substituent, $R_1$ is an F pocket substituent and $R_2$ is a D pocket substituent. In still other embodiments, $R_6$ and $R_7$ taken together with the nitrogen atom to which they are attached are an A pocket substituent, $R_2$ is a D pocket substituent and $R_5$ is a B pocket substituent. In still other embodiments, $R_1$ is an F pocket substituent, $R_2$ is a D pocket substituent and $R_5$ is a B pocket substituent. In still other embodiments, $R_1$ is an F pocket substituent, and $R_5$ is a B pocket substituent. In still other embodiments, $R_1$ is an F pocket substituent and $R_2$ is a D pocket substituent. In still other embodiments, $R_2$ is a D pocket substituent and $R_5$ is a B pocket substituent.

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, (C$_1$-C$_4$) alkyl, cycloalkyldiyl, heterocycloalkyldiyl, —NR$_{12}$R$_{13}$ or —NR$_{14}$C(O)R$_{15}$, $R_7$ is cycloheteroalkyl, substituted cycloheteroalkyl, —(CHR$_{16}$)$_o$R$_{17}$ or —(CHR$_{18}$)$_p$R$_{19}$, each $R_{16}$ is independently hydrogen or (C$_1$-C$_4$) alkyl, each $R_{18}$ is independently hydrogen or (C$_1$-C$_4$) alkyl, $R_{11}$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is a F-pocket substituent, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, (C$_1$-C$_4$) alkyl, cycloalkyldiyl, heterocycloalkyldiyl, —NR$_{12}$R$_{13}$ or —NR$_{14}$C(O)R$_{15}$, $R_7$ is cycloheteroalkyl, substituted cycloheteroalkyl, —(CHR$_{16}$)$_o$R$_{17}$ or —(CHR$_{18}$)$_p$R$_{19}$, each $R_{16}$ is independently hydrogen or (C$_1$-C$_4$) alkyl, each $R_{18}$ is independently hydrogen or (C$_1$-C$_4$) alkyl, $R_{11}$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is a d-pocket substituent, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, (C$_1$-C$_4$) alkyl, cycloalkyldiyl, heterocycloalkyldiyl, —NR$_{12}$R$_{13}$ or —NR$_{14}$C(O)R$_{15}$, $R_7$ is cycloheteroalkyl, substituted cycloheteroalkyl, —(CHR$_{16}$)$_o$R$_{17}$ or —(CHR$_{18}$)$_p$R$_{19}$, each Rib is independently hydrogen or (C$_1$-C$_4$) alkyl, each Rig is independently hydrogen or (C$_1$-C$_4$) alkyl, $R_H$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently a B pocket substituents, $R_7$ is cycloheteroalkyl, substituted cycloheteroalkyl, —(CHR$_{16}$)$_o$R$_{17}$ or —(CHR$_{18}$)$_p$R$_{19}$, each $R_{16}$ is independently hydrogen or (C$_1$-C$_4$) alkyl, each Rig is independently hydrogen or (C$_1$-C$_4$) alkyl, $R_{11}$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, (C$_1$-C$_4$) alkyl, cycloalkyldiyl, heterocycloalkyldiyl, —NR$_{12}$R$_{13}$ or —NR$_{14}$C(O)R$_{15}$, $R_7$ is cycloheteroalkyl, substituted cycloheteroalkyl, —(CHR$_{16}$)$_o$R$_{17}$ or —(CHR$_{18}$)$_p$R$_{19}$, each $R_{16}$ is independently hydrogen or (C$_1$-C$_4$) alkyl, each $R_{18}$ is independently hydrogen or (C$_1$-C$_4$) alkyl, $R_{11}$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is substituted phenyl, 5-membered heteroaryl or substituted 5-membered heteroaryl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, (C$_1$-C$_4$) alkyl, cycloalkyldiyl, heterocycloalkyldiyl, —NR$_{12}$R$_{13}$ or —NR$_{14}$C(O)R$_{15}$, $R_7$ is cycloheteroalkyl, substituted cycloheteroalkyl, —(CHR$_{16}$)$_o$R$_{17}$ or —(CHR$_{18}$)$_p$R$_{19}$, each Rib is independently hydrogen or (C$_1$-C$_4$) alkyl, each Rig is independently hydrogen or (C$_1$-C$_4$) alkyl, $R_H$ is hydrogen, fluoro or (C$_1$-C$_4$) alkyl and $R_{12}$-$R_{15}$ are independently hydrogen or (C$_1$-C$_4$) alkyl.

In some embodiments, $R_1$ is substituted phenyl, oxadiazole, substituted oxadiazole, pyrazole, substituted pyrazole, thiophene, substituted thiophene, furan, substituted furan, thiazole, substituted thiazole, pyrrole, substituted pyrrole, oxazole, substituted oxazole, isoxazole, substituted isoxazole, thiadiazole, substituted thiadiazole, tetrazole or substituted tetrazole, triazole or substituted triazole, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl, each $R_4$ is independently hydrogen, (C$_1$-C$_4$) alkyl, cycloalkyldiyl or heterocycloalkyldiyl; only 1 of $X^1$, $X^2$, $X^3$ and $X^4$ are nitrogen; each $R_5$ is independently hydrogen, ($C_1$-$C_4$) alkyl, cycloalkyldiyl, heterocycloalkyldiyl, —$NR_{12}R_{13}$ or —$NR_{14}C(O)R_{15}$, $R_7$ is cycloheteroalkyl, substituted cycloheteroalkyl, —$(CHR_{16})_oR_{17}$ or —$(CHR_{18})_pR_{19}$, each $R_{16}$ is independently hydrogen or ($C_1$-$C_4$) alkyl, each $R_{18}$ is independently hydrogen or ($C_1$-$C_4$) alkyl, $R_{11}$ is hydrogen, fluoro or ($C_1$-$C_4$) alkyl and $R_{12}$-$R_{15}$ are independently hydrogen or ($C_1$-$C_4$) alkyl.

In some embodiments, $R_1$ is

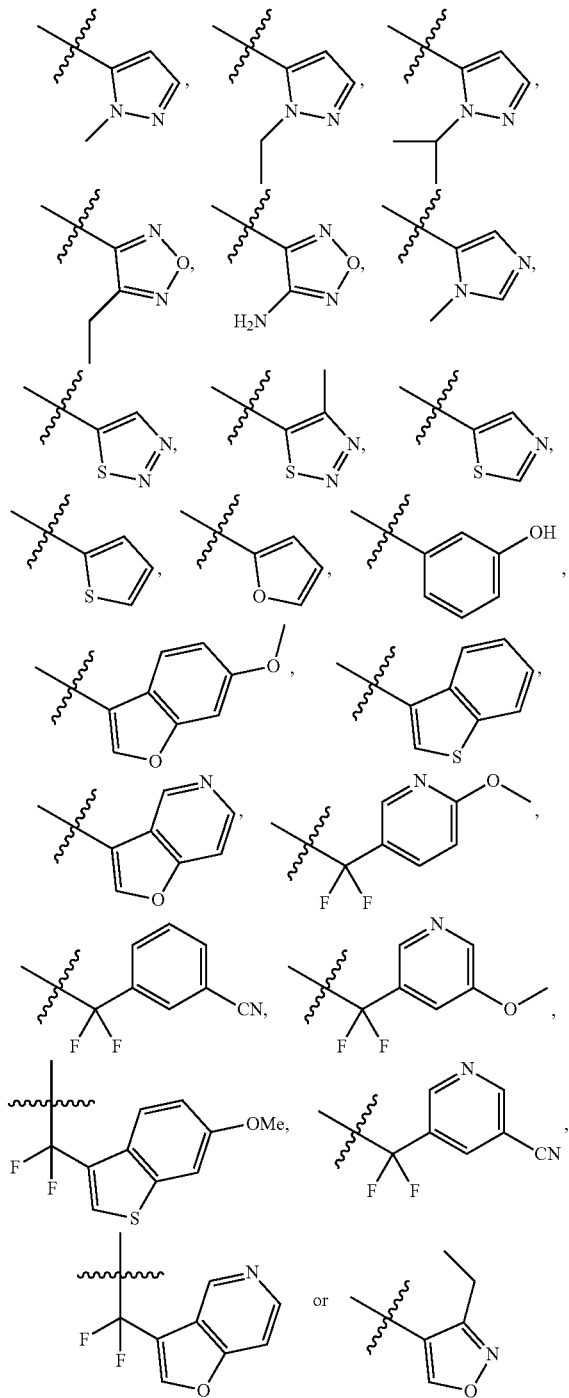

or an A pocket substituent, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—$CH_2(R_3)$—O-cycloalkyl) or —$CH(R_3)$phenyl optionally substituted, each $R_3$ is independently hydrogen or ($C_1$-$C_4$) alkyl, each $R_4$ is independently hydrogen, ($C_1$-$C_4$) alkyl, cycloalkyldiyl or heterocycloalkyldiyl; only 1 of $X^1$, $X^2$, $X^3$ and $X^4$ are nitrogen; each $R_5$ is independently hydrogen, ($C_1$-$C_4$) alkyl, cycloalkyldiyl, heterocycloalkyldiyl, —$NR_{12}R_{13}$ or —$NR_{14}C(O)R_{15}$, $R_7$ is cycloheteroalkyl, substituted cycloheteroalkyl, —$(CHR_{16})_oR_{17}$ or —$(CHR_{18})_pR_{19}$, each $R_{16}$ is independently hydrogen or ($C_1$-$C_4$) alkyl, each $R_{18}$ is independently hydrogen or ($C_1$-$C_4$) alkyl, $R_{11}$ is hydrogen, fluoro or ($C_1$-$C_4$) alkyl and $R_{12}$-$R_{15}$ are independently hydrogen or ($C_1$-$C_4$) alkyl.

In some embodiments, $R_1$ is —$CF_2R_{29}$ where $R_{29}$ is phenyl, substituted phenyl, pyridyl, substituted pyridyl, thiazole or substituted thiazole, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—$CH_2(R_3)$—O-cycloalkyl) or —$CH(R_3)$phenyl optionally substituted, each $R_3$ is independently hydrogen or ($C_1$-$C_4$) alkyl, each $R_4$ is independently hydrogen, ($C_1$-$C_4$) alkyl, cycloalkyldiyl or heterocycloalkyldiyl; only 1 of $X^1$, $X^2$, $X^3$ and $X^4$ are nitrogen; each $R_5$ is independently hydrogen, ($C_1$-$C_4$) alkyl, cycloalkyldiyl, heterocycloalkyldiyl, —$NR_{12}R_{13}$ or —$NR_{14}C(O)R_{15}$, $R_7$ is cycloheteroalkyl, substituted cycloheteroalkyl, —$(CHR_{16})_oR_{17}$ or —$(CHR_{18})_pR_{19}$, each $R_{16}$ is independently hydrogen or ($C_1$—$C_4$) alkyl, each $R_{18}$ is independently hydrogen or ($C_1$-$C_4$) alkyl, $R_{11}$ is hydrogen, fluoro or ($C_1$-$C_4$) alkyl and $R_{12}$-$R_{15}$ are independently hydrogen or ($C_1$-$C_4$) alkyl.

In still other embodiments, $R_1$ is —$CF_2R_{29}$ where $R_{29}$ is

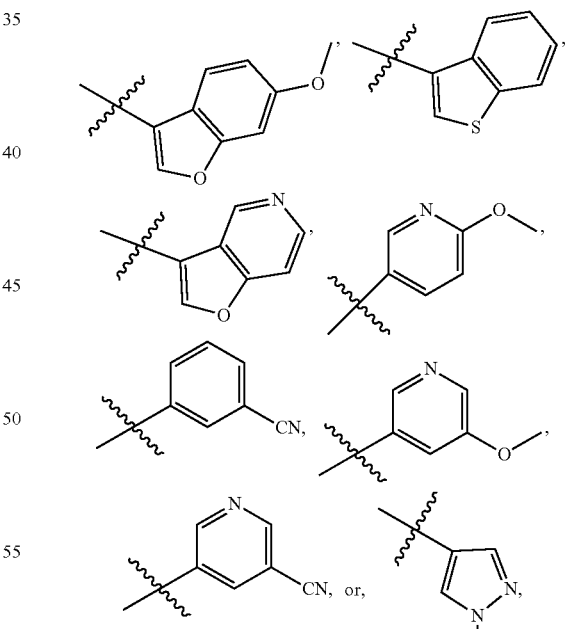

$R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl 4-methylcyclohexyl, (—$CH_2(R_3)$—O— cycloalkyl) or —$CH(R_3)$phenyl optionally substituted, each $R_3$ is independently hydrogen or ($C_1$-$C_4$) alkyl, each $R_4$ is independently hydrogen, ($C_1$-$C_4$)

alkyl, cycloalkyldiyl or heterocycloalkyldiyl; only 1 of $X^1$, $X^2$, $X^3$ and $X^4$ are nitrogen; each $R_5$ is independently hydrogen, $(C_1-C_4)$ alkyl, cycloalkyldiyl, heterocycloalkyldiyl, $-NR_{12}R_{13}$ or $-NR_{14}C(O)R_{15}$, $R_7$ is cycloheteroalkyl, substituted cycloheteroalkyl, $-(CHR_{16})_oR_{17}$ or $-(CHR_{18})_pR_{19}$, each $R_{16}$ is independently hydrogen or $(C_1-C_4)$ alkyl, each Rig is independently hydrogen or $(C_1-C_4)$ alkyl, $R_{11}$ is hydrogen, fluoro or $(C_1-C_4)$ alkyl and $R_{12}-R_{15}$ are independently hydrogen or $(C_1-C_4)$ alkyl.

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl 4-methylcyclohexyl, ($-CH_2(R_3)-O$-cycloalkyl) or $-CH(R_3)$phenyl optionally substituted, each $R_3$ is independently hydrogen or $(C_1-C_4)$ alkyl; each $R_4$ is independently hydrogen, $(C_1-C_4)$ alkyl, cycloalkyldiyl or heterocycloalkyldiyl, only 1 of $X^1$, $X^2$, $X^3$ and $X^4$ are nitrogen, each $R_5$ is independently hydrogen, $(C_1-C_4)$ alkyl, cycloalkyldiyl, heterocycloalkyldiyl, $-NR_{12}R_{13}$, $-NR_{14}C(O)R_{15}$, $R_{11}$ is hydrogen, fluoro or $(C_1-C_4)$ alkyl, $R_{12}-R_{15}$ are independently hydrogen or $(C_1-C_4)$ alkyl and $R_6$ and $R_7$ taken together with the nitrogen atom to which they are attached form a piperazine or substituted piperazine ring, a cycloheteroalkyl or substituted cycloheteroalkyl ring or

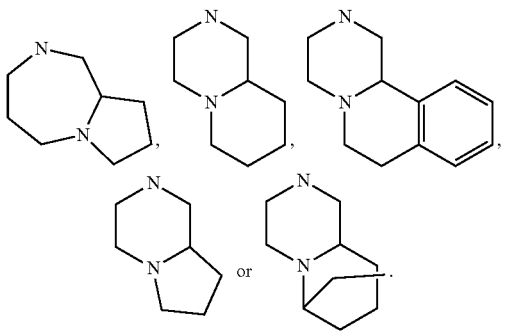

In some embodiments, $R_1$ an A pocket substituent, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl 4-methylcyclohexyl, ($-CH_2(R_3)-O$-cycloalkyl) or $-CH(R_3)$phenyl optionally substituted, each $R_3$ is independently hydrogen or $(C_1-C_4)$ alkyl; each $R_4$ is independently hydrogen, $(C_1-C_4)$ alkyl, cycloalkyldiyl or heterocycloalkyldiyl, only 1 of $X^1$, $X^2$, $X^3$ and $X^4$ are nitrogen, each $R_5$ is independently hydrogen, $(C_1-C_4)$ alkyl, cycloalkyldiyl, heterocycloalkyldiyl, $-NR_{12}R_{13}$, $-NR_{14}C(O)R_{15}$, $R_{11}$ is hydrogen, fluoro or $(C_1-C_4)$ alkyl, $R_{12}-R_{15}$ are independently hydrogen or $(C_1-C_4)$ alkyl and $R_6$ and $R_7$ taken together with the nitrogen atom to which they are attached form a piperazine or substituted piperazine ring, a cycloheteroalkyl or substituted cycloheteroalkyl ring or

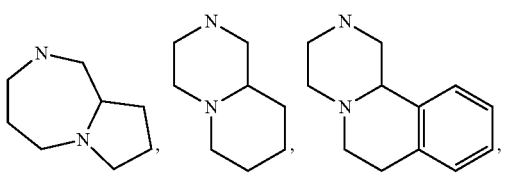

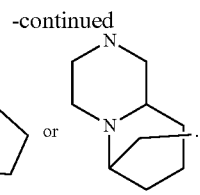

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is a D pocket substituents, each $R_3$ is independently hydrogen or $(C_1-C_4)$ alkyl; each $R_4$ is independently hydrogen, $(C_1-C_4)$ alkyl, cycloalkyldiyl or heterocycloalkyldiyl, only 1 of $X^1$, $X^2$, $X^3$ and $X^4$ are nitrogen, each $R_5$ is independently hydrogen, $(C_1-C_4)$ alkyl, cycloalkyldiyl, heterocycloalkyldiyl, $-NR_{12}R_{13}$, $-NR_{14}C(O)R_{15}$, $R_{11}$ is hydrogen, fluoro or $(C_1-C_4)$ alkyl, $R_{12}-R_{15}$ are independently hydrogen or $(C_1-C_4)$ alkyl and $R_6$ and $R_7$ taken together with the nitrogen atom to which they are attached form a piperazine or substituted piperazine ring, a cycloheteroalkyl or substituted cycloheteroalkyl ring or

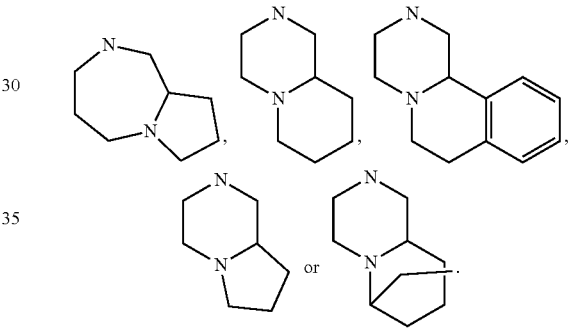

In some embodiments, $R_1$ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, ($-CH_2(R_3)-O$-cycloalkyl) or $-CH(R_3)$phenyl optionally substituted, each $R_3$ is independently hydrogen or $(C_1-C_4)$ alkyl; each $R_4$ is independently hydrogen, $(C_1-C_4)$ alkyl, cycloalkyldiyl or heterocycloalkyldiyl, only 1 of $X^1$, $X^2$, $X^3$ and $X^4$ are nitrogen, each $R_5$ is independently a B-pocket substituents, $R_{11}$ is hydrogen, fluoro or $(C_1-C_4)$ alkyl, $R_{12}-R_{15}$ are independently hydrogen or $(C_1-C_4)$ alkyl and $R_6$ and $R_7$ taken together with the nitrogen atom to which they are attached form a piperazine or substituted piperazine ring, a cycloheteroalkyl or substituted cycloheteroalkyl ring or

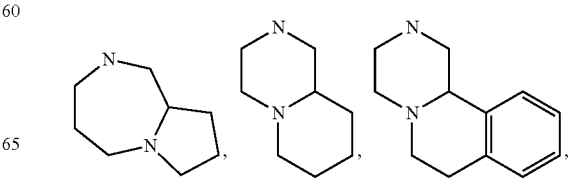

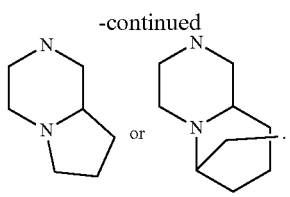

In some embodiments, R₁ is heteroarylalkyl, substituted heteroarylalkyl, phenyl, substituted phenyl, phenylalkyl, substituted phenylalkyl, heteroaryl, substituted heteroaryl, heteroarylalkyl or substituted heteroarylalkyl, R₂ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH₂(R₃)—O-cycloalkyl) or —CH(R₃)phenyl optionally substituted, each R₃ is independently hydrogen or (C₁-C₄) alkyl; each R₄ is independently hydrogen, (C₁-C₄) alkyl, cycloalkyldiyl or heterocycloalkyldiyl, only 1 of X¹, X², X³ and X⁴ are nitrogen, each R₅ is independently hydrogen, (C₁-C₄) alkyl, cycloalkyldiyl, heterocycloalkyldiyl, —NR₁₂R₁₃, —NR₁₄C(O)R₁₅, R₁₁ is hydrogen, fluoro or (C₁-C₄) alkyl, R₁₂-R₁₅ are independently hydrogen or (C₁-C₄) alkyl and R₆ and R₇ taken together with the nitrogen atom to which they are attached form an A pocket substituent.

In some embodiments, R₁ is substituted phenyl, 5-membered heteroaryl or substituted 5-membered heteroaryl, R₂ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH₂(R₃)—O-cycloalkyl) or —CH(R₃)phenyl optionally substituted, each R₃ is independently hydrogen or (C₁-C₄) alkyl; each R₄ is independently hydrogen, (C₁-C₄) alkyl, cycloalkyldiyl or heterocycloalkyldiyl, only 1 of X¹, X², X³ and X⁴ are nitrogen, each R₅ is independently hydrogen, (C₁-C₄) alkyl, cycloalkyldiyl, heterocycloalkyldiyl, —NR₁₂R₁₃, —NR₁₄C(O)R₁₅, R₁₁ is hydrogen, fluoro or (C₁-C₄) alkyl, R₁₂-R₁₅ are independently hydrogen or (C₁-C₄) alkyl and R₆ and R₇ taken together with the nitrogen atom to which they are attached form a piperazine or substituted piperazine ring, a cyclohetero alkyl or substituted cyclohetero alkyl ring or

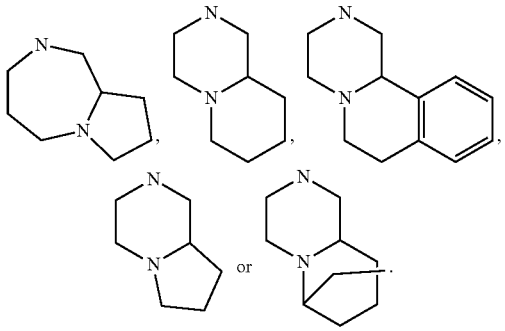

In some embodiments, R₁ is substituted phenyl, oxadiazole, substituted oxadiazole, pyrazole, substituted pyrazole, thiophene, substituted thiophene, furan, substituted furan, thiazole, substituted thiazole, pyrrole, substituted pyrrole, oxazole, substituted oxazole, isoxazole, substituted isoxazole, thiadiazole, substituted thiadiazole, tetrazole or substituted tetrazole, triazole or substituted triazole, R₂ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH₂(R₃)—O-cycloalkyl) or —CH(R₃)phenyl optionally substituted, each R₃ is independently hydrogen or (C₁-C₄) alkyl; each R₄ is independently hydrogen, (C₁-C₄) alkyl, cycloalkyldiyl or heterocycloalkyldiyl, only 1 of X¹, X², X³ and X⁴ are nitrogen, each R₅ is independently hydrogen, (C₁-C₄) alkyl, cycloalkyldiyl, heterocycloalkyldiyl, —NR₁₂R₁₃, —NR₁₄C(O)R₁₅, R₁₁ is hydrogen, fluoro or (C₁-C₄) alkyl, R₁₂-R₁₅ are independently hydrogen or (C₁-C₄) alkyl and R₆ and R₇ taken together with the nitrogen atom to which they are attached form a cyclohetero alkyl or substituted cyclohetero alkyl ring or

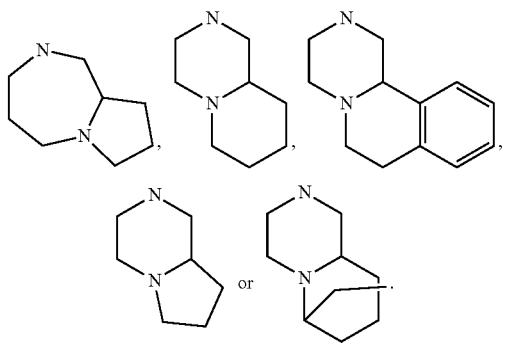

In some embodiments, R₁ is

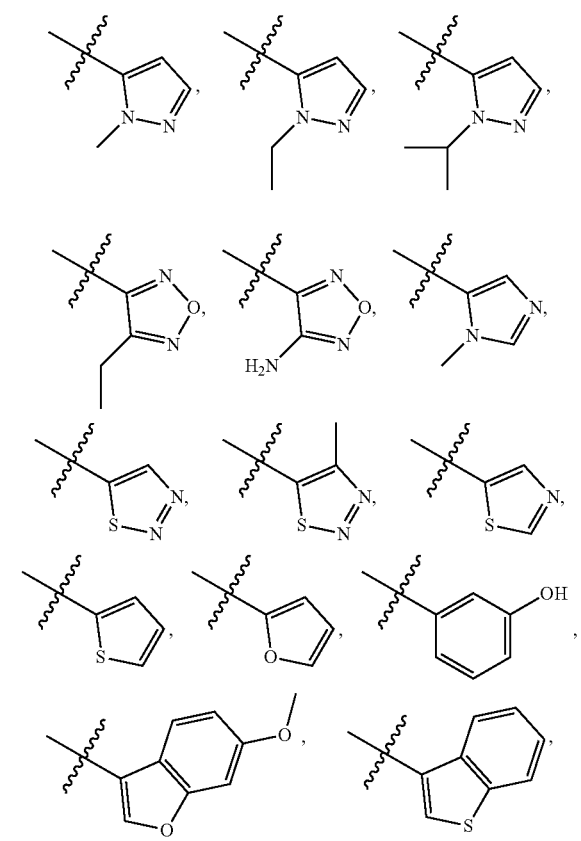

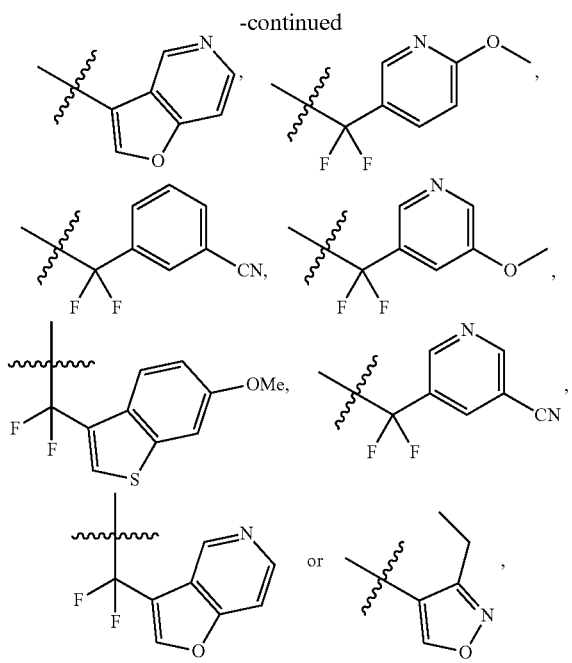

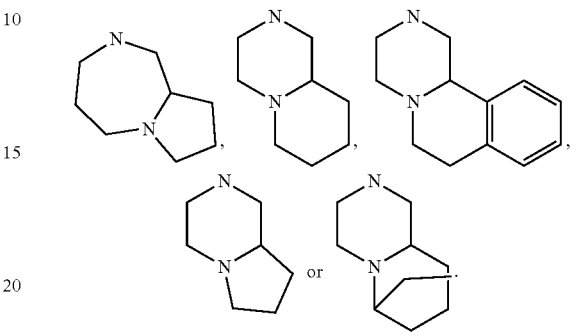

$R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl; each $R_4$ is independently hydrogen, (C$_1$-C$_4$) alkyl, cycloalkyldiyl or heterocycloalkyldiyl, only 1 of $X^1$, $X^2$, $X^3$ and $X^4$ are nitrogen, each $R_5$ is independently hydrogen, (C$_1$-C$_4$) alkyl, cycloalkyldiyl, heterocycloalkyldiyl, —NR$_{12}$R$_{13}$, —NR$_{14}$C(O)R$_{15}$, is hydrogen, fluoro or (C$_1$-C$_4$) alkyl, R$_{12}$-R$_{15}$ are independently hydrogen or (C$_1$-C$_4$) alkyl and $R_6$ and $R_7$ taken together with the nitrogen atom to which they are attached form a piperazine or substituted piperazine ring or a cycloheteroalkyl or substituted cycloheteroalkyl ring or

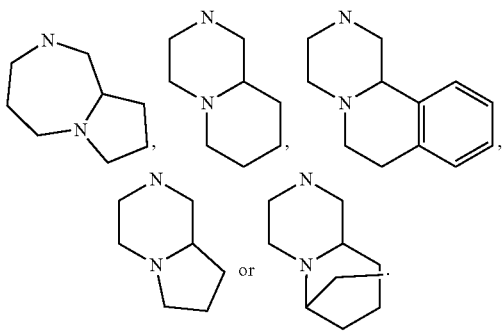

In some embodiments, $R_1$ is CF$_2$R$_{29}$ where R$_{29}$ is phenyl, substituted phenyl, pyridyl, substituted pyridyl, thiazole or substituted thiazole, $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl; each $R_4$ is independently hydrogen, (C$_1$-C$_4$) alkyl, cycloalkyldiyl or heterocycloalkyldiyl, only 1 of $X^1$, $X^2$, $X^3$ and $X^4$ are nitrogen, each $R_5$ is independently hydrogen, (C$_1$-C$_4$) alkyl, cycloalkyldiyl, heterocycloalkyldiyl, —NR$_{12}$R$_{13}$, —NR$_{14}$C(O)R$_{15}$, R$_{11}$ is hydrogen, fluoro or (C$_1$-C$_4$) alkyl, R$_{12}$-R$_{15}$ are independently hydrogen or (C$_1$-C$_4$) alkyl and $R_6$ and $R_7$ taken together with the nitrogen atom to which they are attached form a cycloheteroalkyl or substituted cycloheteroalkyl ring or

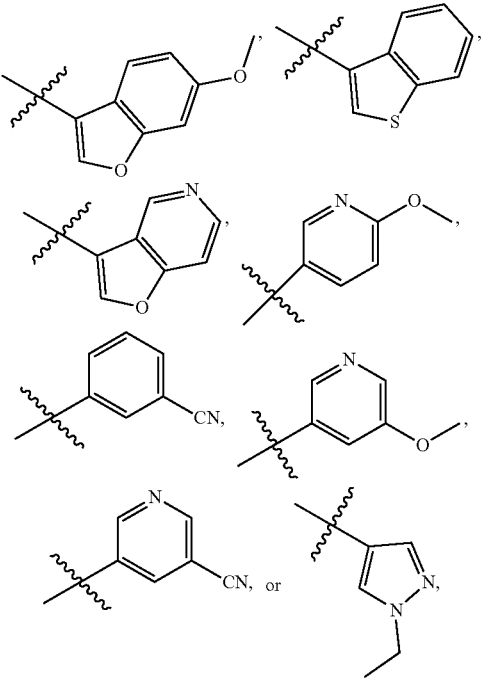

In some embodiments, $R_1$ is CF$_2$R$_{29}$ where R$_{29}$ is $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl, 4-methylcyclohexyl, (—CH$_2$(R$_3$)—O-cycloalkyl) or —CH(R$_3$)phenyl optionally substituted, each $R_3$ is independently hydrogen or (C$_1$-C$_4$) alkyl; each $R_4$ is independently hydrogen, (C$_1$-C$_4$) alkyl, cycloalkyldiyl or heterocycloalkyldiyl, only 1 of $X^1$, $X^2$, $X^3$ and $X^4$ are nitrogen, each $R_5$ is independently hydrogen, (C$_1$-C$_4$) alkyl, cycloalkyldiyl, heterocycloalkyldiyl, —NR$_{12}$R$_{13}$, —NR$_{14}$C(O)R$_{15}$, R$_{11}$ is hydrogen, fluoro or (C$_1$-C$_4$) alkyl, R$_{12}$-R$_{15}$ are independently hydrogen or (C$_1$-C$_4$) alkyl and $R_6$ and $R_7$ taken together with the nitrogen atom to which they are attached form a cycloheteroalkyl or substituted cycloheteroalkyl ring or

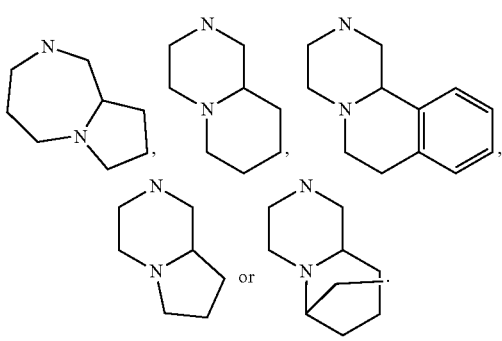

In some of the above embodiments, m is 0.

In some embodiments, a compound of structural Formula (II) is provided:

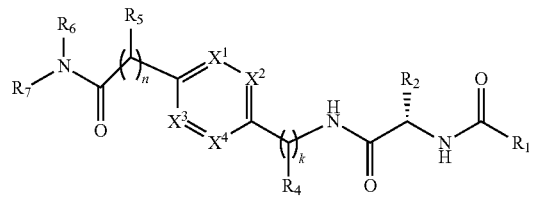

(II)

or a pharmaceutically acceptable salt, solvate or hydrate thereof wherein $R_1$, $R_2$, $R_4$, $X_1$, $X_2$, $X_3$, $X_4$, k, n, $R_5$, $R_6$ and $R_7$ are as defined above.

In some embodiments, a compound of structural Formula (III) is provided:

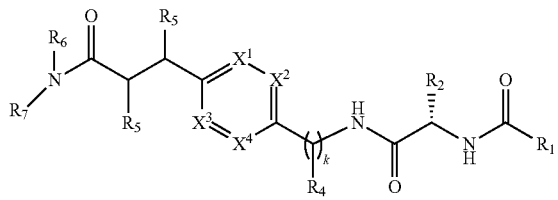

(III)

or a pharmaceutically acceptable salt, solvate or hydrate thereof wherein $R_1$, $R_2$, $R_4$, $X_1$, $X_2$, $X_3$, $X_4$, k, $R_5$, $R_6$ and $R_7$ are as defined above.

In some embodiments, a compound of structural Formula (IV) is provided:

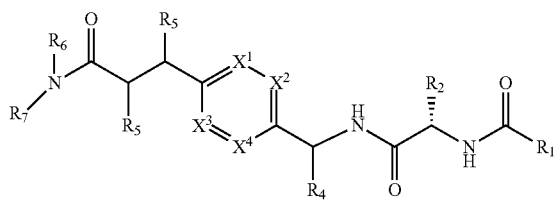

(IV)

or a pharmaceutically acceptable salt, solvate or hydrate thereof wherein $R_1$, $R_2$, $R_4$, $X_1$, $X_2$, $X_3$, $X_4$, $R_5$, $R_6$ and $R_7$ are as defined above.

In some embodiments, a compound of structural Formula (V) is provided:

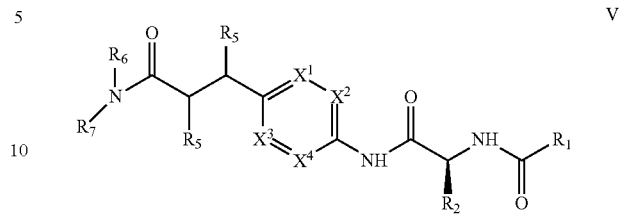

V or a pharmaceutically acceptable salt, solvate or hydrate thereof wherein $R_1$, $R_2$, $R_4$, $X_1$, $X_2$, $X_3$, $X_4$, $R_5$, $R_6$ and $R_7$ are as defined above.

In some embodiments, a compound of structural Formula (VI) is provided:

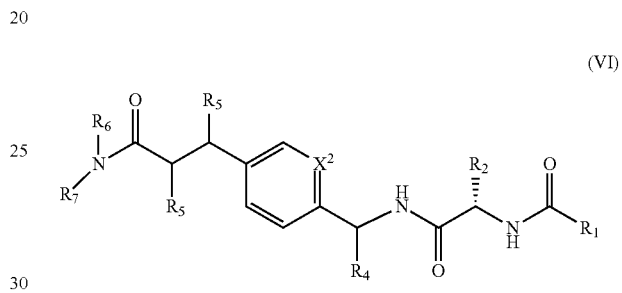

(VI)

or a pharmaceutically acceptable salt, solvate or hydrate thereof wherein $R_1$, $R_2$, $R_4$, $X_2$, $R_5$, $R_6$ and $R_7$ are as defined above.

In some embodiments, a compound of structural Formula (VII) is provided:

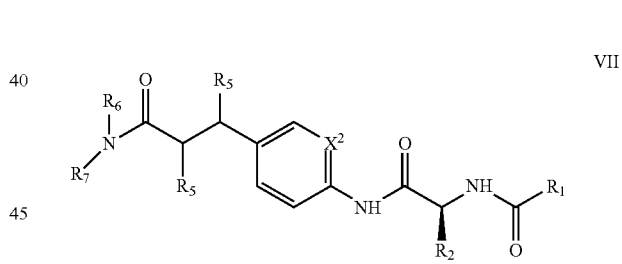

VII or a pharmaceutically acceptable salt, solvate or hydrate thereof wherein $R_1$, $R_2$, $X_2$, $R_5$, $R_6$ and $R_7$ are as defined above.

In some embodiments of compounds of Formula (II), $R_1$ is arylalkyl, substituted arylalkyl, heteroaryl, substituted heteroaryl, heteroarylalkyl or substituted heteroarylalkyl; $R_2$ is cycloalkyl or substituted cycloalkyl, $R_4$ is independently hydrogen or $(C_1$-$C_4)$ alkyl; $X^1$, $X^4$, $X^3$ and $X^2$ are —CH— or —CF—; n is 2, each $R_5$ is independently hydrogen, $(C_1$-$C_7)$ alkyl or —$NR_{14}C(O)R_{15}$; $R_6$ and $R_7$ taken together with the nitrogen atom to which they are attached form a cycloheteroalkyl or substituted cycloheteroalkyl ring, $R_{14}$ is hydrogen; and $R_{15}$ is alkyl, substituted alkyl, heteroaryl or substituted heteroaryl.

In some embodiments of compounds of Formula (III), $R_1$ is arylalkyl, substituted arylalkyl, heteroaryl, substituted heteroaryl, heteroarylalkyl, or substituted heteroarylalkyl; $R_2$ is cycloalkyl or substituted cycloalkyl; $R_4$ is independently hydrogen or $(C_1$-$C_4)$ alkyl; $X^1$, $X^4$, $X^3$ and $X^2$ are —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In some embodiments of compounds of Formula (IV), $R_1$ is arylalkyl, substituted arylalkyl, heteroaryl, substituted heteroaryl, heteroarylalkyl, or substituted heteroarylalkyl; $R_2$ is cycloalkyl or substituted cycloalkyl; $R_4$ is independently hydrogen or $(C_1-C_4)$ alkyl; $X^1$, $X^4$, $X^3$ and $X^2$ are —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In some embodiments of compounds of Formula (V), $R_1$ is arylalkyl, substituted arylalkyl, heteroaryl, substituted heteroaryl, heteroarylalkyl or substituted heteroarylalkyl; $R_2$ is cycloalkyl or substituted cycloalkyl; $X^1$, $X^4$, $X^3$ and $X^2$ are —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring, $R_{14}$ is hydrogen; and $R_{15}$ is alkyl, substituted alkyl, heteroaryl or substituted heteroaryl.

In some embodiments of compounds of Formula (VI), $R_1$ is arylalkyl, substituted arylalkyl, heteroaryl, substituted heteroaryl, heteroarylalkyl or substituted heteroarylalkyl; $R_2$ is cycloalkyl or substituted cycloalkyl; $X^1$, $X^4$, $X^3$ and $X^2$ are —CH— or —CF—; $R_4$ is independently hydrogen or $(C_1-C_4)$ alkyl; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In some embodiments of compounds of Formula (VII), $R_1$ is heteroaryl or substituted heteroaryl; $R_2$ is cycloalkyl or substituted cycloalkyl; $X^2$ are —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In other embodiments of compounds of Formula (VII), $R_1$ is substituted heteroaryl; $R_2$ is cycloalkyl or substituted cycloalkyl; $X^2$ is —CF—; each $R_5$ is independently $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl or heteroaryl.

In still other embodiments of compounds of Formula (VII), $R_1$ is

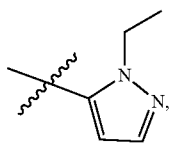 [SMILES: *c1ccnn1CC]

$R_2$ is cycloalkyl or substituted cycloalkyl; $X^2$ is —CF—, each $R_5$ is independently $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring, $R_{14}$ is hydrogen; and $R_{15}$ is alkyl or heteroaryl.

In still other embodiments of compounds of Formula (VII), $R_1$ is heteroaryl or substituted heteroaryl; $R_2$ is cyclohexyl, cycloheptyl or 4-methyl cyclohexyl; $X^2$ is —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl; $R_2$ is cyclohexyl, cycloheptyl or 4-methyl cyclohexyl; $X^2$ is —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In still other embodiments of compounds of Formula (VII), $R_1$ is

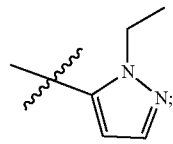 [SMILES: *c1ccnn1CC]

$R_2$ is cyclohexyl, cycloheptyl or 4-methyl cyclohexyl; $X^2$ is —CH— or —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In still other embodiments of compounds of Formula (VII), $R_1$ is heteroaryl or substituted heteroaryl; $R_2$ is cyclohexyl, cycloheptyl or 4-methyl cyclohexyl; $X^2$ is —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl; $R_2$ is cyclohexyl, cycloheptyl or 4-methyl cyclohexyl; $X^2$ is —CF—; each $R_5$ is independently hydrogen, $(C_1-C_7)$ alkyl or —$NR_{14}C(O)R_{15}$; $R_6$ and $R_7$ taken together with the nitrogen atom to which they are attached form a cycloheteroalkyl or substituted cycloheteroalkyl ring; $R_{14}$ is hydrogen; and $R_{15}$ is alkyl, substituted alkyl, heteroaryl or substituted heteroaryl.

In still other embodiments of compounds of Formula (VII), $R_1$ is

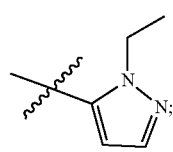 [SMILES: *c1ccnn1CC]

R$_2$ is cyclohexyl, cycloheptyl or 4-methyl cyclohexyl; X$^2$ is —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is heteroaryl or substituted heteroaryl; R$_2$ is cycloheptyl or 4-methyl cyclohexyl; X$^2$ is —CH— or —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is substituted heteroaryl; R$_2$ is cycloheptyl or 4-methyl cyclohexyl; X$^2$ is —CH— or —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is

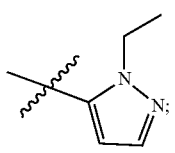

R$_2$ is cycloheptyl or 4-methyl cyclohexyl; X$^2$ is —CH— or —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is heteroaryl or substituted heteroaryl; R$_2$ is cycloheptyl or 4-methyl cyclohexyl; X$^2$ is —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is substituted heteroaryl; R$_2$ is cycloheptyl or 4-methyl cyclohexyl; X$^2$ is —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is

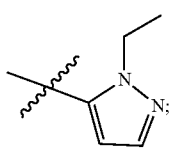

R$_2$ is cycloheptyl or 4-methyl cyclohexyl; X$^2$ is —CF—; each R$_5$ is independently hydrogen, (C$_1$-C$_7$) alkyl or —NR$_{14}$C(O)R$_{15}$; R$_6$ and R$_7$ taken together with the nitrogen atom to which they are attached form a cycloheteroalkyl or substituted cycloheteroalkyl ring; R$_{14}$ is hydrogen; and R$_{15}$ is alkyl, substituted alkyl, heteroaryl or substituted heteroaryl.

In still other embodiments of compounds of Formula (VII), R$_1$ is heteroaryl or substituted heteroaryl; R$_2$ is cycloalkyl or substituted cycloalkyl; X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), R$_1$ is substituted heteroaryl; R$_2$ is cycloalkyl or substituted cycloalkyl; X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), R$_1$ is

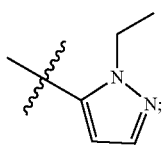 [SMILES: *c1ccnn1CC]

R$_2$ is cycloalkyl or substituted cycloalkyl, X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), R$_1$ is heteroaryl or substituted heteroaryl; R$_2$ is cyclohexyl, cycloheptyl or 4-methyl cyclohexyl; X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), R$_1$ is substituted heteroaryl, R$_2$ is cyclohexyl, cycloheptyl or 4-methyl cyclohexyl, X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), R$_1$ is

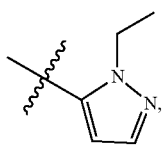 [SMILES: *c1ccnn1CC]

R$_2$ is cyclohexyl, cycloheptyl or 4-methyl cyclohexyl, X$^2$ is —CF—; each R$_5$ is independently hydrogen, methyl or —CO(NH)CH$_2$CH$_3$ and R$_6$ and R$_7$ taken together with the nitrogen atom to which they are attached form a cycloheteroalkyl or substituted cycloheteroalkyl ring.

In still other embodiments of compounds of Formula (VII), $R_1$ is heteroaryl or substituted heteroaryl, $R_2$ is cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is substituted heteroaryl, $R_2$ is cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is

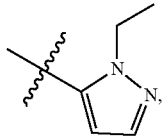 [SMILES: *c1ccnn1CC]

$R_2$ is cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is heteroaryl or substituted heteroaryl, $R_2$ is cyclohexyl, cycloheptyl or 4-methyl cyclohexyl, $X^2$ is —CF— or —CH—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is substituted heteroaryl, $R_2$ is cyclohexyl, cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is

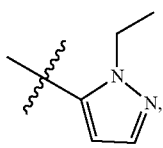 [SMILES: *c1ccnn1CC]

$R_2$ is cyclohexyl, cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is heteroaryl or substituted heteroaryl, $R_2$ is cycloheptyl or 4-methyl cyclohexyl, $X^2$ is —CF—; each $R_5$ is independently is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is substituted heteroaryl, $R_2$ is cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is

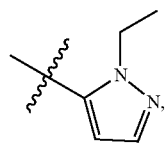 [SMILES: *c1ccnn1CC]

$R_2$ is cycloheptyl or 4-methyl cyclohexyl, $X^2$ is —CF—; each $R_5$ is independently hydrogen, methyl or —CO(NH)CH$_2$CH$_3$ and $R_6$ and $R_7$ taken together with the nitrogen atom to which they are attached form a cycloheteroalkyl or substituted cycloheteroalkyl ring.

In still other embodiments of compounds of Formula (VII), $R_1$ is heteroaryl or substituted heteroaryl; $R_2$ is cycloalkyl or substituted cycloalkyl, $X^2$ is —CF— or —CH—; each $R_5$ is independently hydrogen, (C$_1$-C$_7$) alkyl or —NR$_{14}$C(O)R$_{15}$; $R_6$ and $R_7$ taken together are

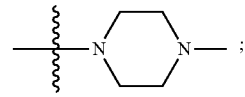

$R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl; $R_2$ is cycloalkyl or substituted cycloalkyl, $X^2$ is —CF—; each $R_5$ is independently (C$_1$-C$_7$) alkyl or —NR$_{14}$C(O)R$_{15}$, $R_6$ and $R_7$ taken together are

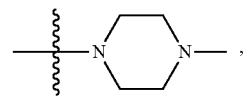

$R_{14}$ is hydrogen; and $R_{15}$ is alkyl or heteroaryl.

In still other embodiments of compounds of Formula (VII), $R_1$ is

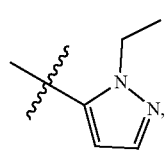 [SMILES: *c1ccnn1CC]

$R_2$ is cycloalkyl or substituted cycloalkyl, $X^2$ is —CF—, each $R_5$ is independently (C$_1$-C$_7$) alkyl or —NR$_{14}$C(O)R$_{15}$, $R_6$ and $R_7$ taken together are

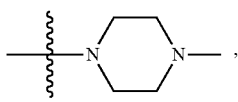

$R_{14}$ is hydrogen; and $R_{15}$ is alkyl or heteroaryl.

In still other embodiments of compounds of Formula (VII), $R_1$ is heteroaryl or substituted heteroaryl, $R_2$ is cyclohexyl, cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

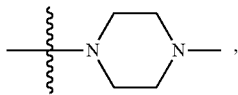

$R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl, $R_2$ is cyclohexyl, cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

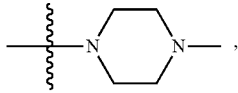

$R_{14}$ is hydrogen; and $R_{15}$ is alkyl, substituted alkyl, heteroaryl or substituted heteroaryl.

In still other embodiments of compounds of Formula (VII), $R_1$ is

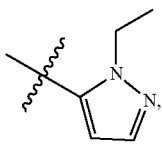 [SMILES: *c1ccnn1CC]

$R_2$ is cyclohexyl, cycloheptyl or 4-methyl cyclohexyl, $X^2$ is —CF—; each $R_5$ is independently hydrogen, $(C_1-C_7)$ alkyl or —NR$_{14}$C(O)R$_{15}$; and $R_6$ taken together are

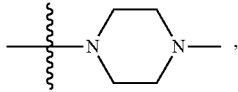

$R_{14}$ is hydrogen; and $R_{15}$ is alkyl, substituted alkyl, heteroaryl or substituted heteroaryl.

In still other embodiments of compounds of Formula (VII), $R_1$ is heteroaryl or substituted heteroaryl, $R_2$ is cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

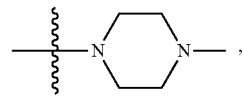

$R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl, $R_2$ is cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

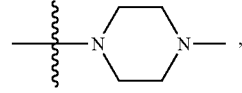

$R_{14}$ is hydrogen; and $R_{15}$ is alkyl, substituted alkyl, heteroaryl or substituted heteroaryl.

In other embodiments of compounds of Formula (VII), $R_1$ is

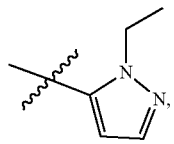 [SMILES: *c1ccnn1CC]

$R_2$ is cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

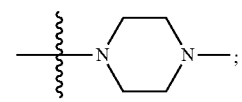

$R_{14}$ is hydrogen; and $R_{15}$ is alkyl, substituted alkyl, heteroaryl or substituted heteroaryl.

In other embodiments of compounds of Formula (VII), $R_1$ is heteroaryl or substituted heteroaryl, $R_2$ is cyclohexyl, cycloheptyl or 4-methyl cyclohexyl, $X^2$ is —CF— or —CH—; each $R_5$ is independently hydrogen, $(C_1-C_7)$ alkyl or —NR$_{14}$C(O)R$_{15}$; $R_6$ and $R_7$ taken together are

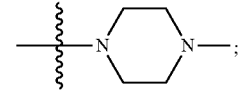 [SMILES: *N1CCN(C)CC1]

$R_{14}$ is hydrogen; and $R_{14}$ is alkyl, substituted alkyl, heteroaryl or substituted heteroaryl.

In still other embodiments of compounds of Formula (VII), $R_1$ is substituted heteroaryl, $R_2$ is cyclohexyl, cycloheptyl or 4-methyl cyclohexyl, $X^2$ is —CF—; each $R_5$ is independently hydrogen, $(C_1-C_7)$ alkyl or —NR$_{14}$C(O)R$_{15}$; $R_6$ and $R_7$ taken together are

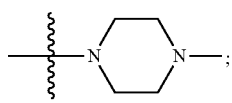 [SMILES: *N1CCN(C)CC1]

$R_{14}$ is hydrogen; and $R_{15}$ is alkyl, substituted alkyl, heteroaryl or substituted heteroaryl.

In other embodiments of compounds of Formula (VII), $R_1$ is

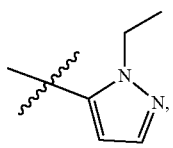

$R_2$ is cyclohexyl, cycloheptyl or 4-methyl cyclohexyl, $X^2$ is —CF—; each $R_5$ is independently hydrogen, $(C_1-C_7)$ alkyl or —$NR_{14}C(O)R_{15}$; $R_6$ and $R_7$ taken together are

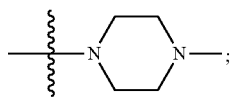 [SMILES: *N1CCN(C)CC1]

$R_{14}$ is hydrogen; and $R_{15}$ is alkyl, substituted alkyl, heteroaryl or substituted heteroaryl.

In other embodiments of compounds of Formula (VII), $R_1$ is heteroaryl or substituted heteroaryl, $R_2$ is cycloheptyl or 4-methyl cyclohexyl, $X^2$ is —CF—; each $R_5$ is independently hydrogen, $(C_1-C_7)$ alkyl or —$NR_{14}C(O)R_{15}$; $R_6$ and $R_7$ taken together are

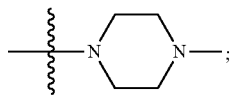 [SMILES: *N1CCN(C)CC1]

$R_{14}$ is hydrogen; and $R_{15}$ is alkyl, substituted alkyl, heteroaryl or substituted heteroaryl.

In still other embodiments of compounds of Formula (VII), $R_1$ is substituted heteroaryl, $R_2$ is cycloheptyl or 4-methyl cyclohexyl, $X^2$ is —CF—; each $R_5$ is independently hydrogen, $(C_1-C_7)$ alkyl or —$NR_{14}C(O)R_{15}$; $R_6$ and $R_7$ taken together are

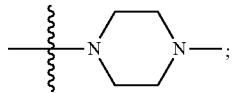

$R_{14}$ is hydrogen; and $R_{15}$ is alkyl, substituted alkyl, heteroaryl or substituted heteroaryl.

In other embodiments of compounds of Formula (VII), $R_1$ is

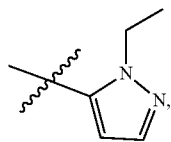 [SMILES: *c1ccnn1CC]

$R_2$ is cycloheptyl or 4-methyl cyclohexyl, $X^2$ is —CF—; each $R_5$ is independently hydrogen, $(C_1-C_7)$ alkyl or —$NR_{14}C(O)R_{15}$; $R_6$ and $R_7$ taken together are

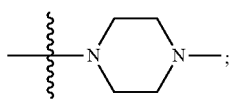 [SMILES: *N1CCN(C)CC1]

$R_{14}$ is hydrogen; and $R_{15}$ is alkyl, substituted alkyl, heteroaryl or substituted heteroaryl.

In still other embodiments of compounds of Formula (VII), $X^2$ is —CF—. In still other embodiments of compounds of Formula (VII), each $R_5$ is independently hydrogen, methyl or —CO(NH)CH$_2$CH$_3$. In still other embodiments of compounds of Formula (VII), one $R_5$ is methyl and the other $R_5$ is —CO(NH)CH$_2$CH$_3$. In still other embodiments of compounds of Formula (VII), $R_6$ and $R_7$ taken together are

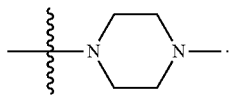

In some embodiments of compounds of Formula (VII), $R_1$ is

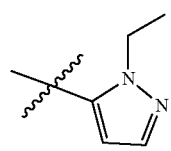 [SMILES: *c1ccnn1CC]

and $R_2$ is cyclohexyl, cycloheptyl or 4-methyl cyclohexyl. In other embodiments of compounds of Formula (VII), $R_1$ is

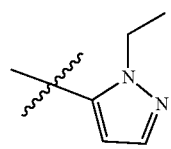 [SMILES: *c1ccnn1CC]

and $R_2$ is cycloheptyl or 4-methyl cyclohexyl. In still other embodiments of compounds of Formula (VII), $R_1$ is

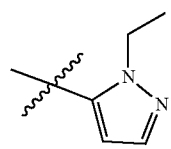 [SMILES: *c1ccnn1CC]

and $X^2$ is —CF—. In still other embodiments of compounds of Formula (VII), $R_1$ is

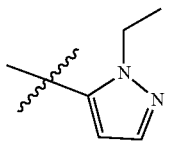 [SMILES: *c1ccnn1CC]

each $R_5$ is methyl or —CO(NH)CH$_2$CH$_3$. In still other embodiments of compounds of Formula (VII), $R_1$ is

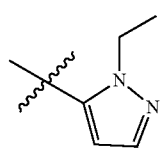 [SMILES: *c1ccnn1CC]

and $R_6$ and $R_7$ taken together are

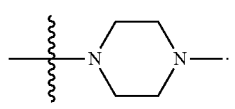

In some embodiments of compounds of Formula (VII), $R_2$ is cyclohexyl, cycloheptyl or 4-methyl cyclohexyl and $X^2$ is —CF—. In other embodiments of compounds of Formula (VII), $R_2$ is cycloheptyl or 4-methyl cyclohexyl and $X^2$ is —CF—. In still other embodiments of compounds of Formula (VII), $R_2$ is cyclohexyl, cycloheptyl or 4-methyl cyclohexyl and each $R_5$ is methyl or —CO(NH)CH$_2$CH$_3$. In still other embodiments of compounds of Formula (VII), $R_2$ is cycloheptyl or 4-methyl cyclohexyl and each $R_5$ is methyl or —CO(NH)CH$_2$CH$_3$. In still other embodiments of compounds of Formula (VII), $R_2$ is cyclohexyl, cycloheptyl or 4-methyl cyclohexyl and $R_6$ and $R_7$ taken together are

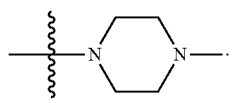

In still other embodiments of compounds of Formula (VII), $R_2$ is cycloheptyl or 4-methyl cyclohexyl and $R_6$ and $R_7$ taken together are

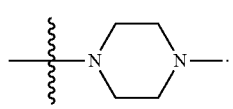

In some embodiments of compounds of Formula (VII), $X^2$ is —CF—; and each $R_5$ is methyl or —CO(NH)CH$_2$CH$_3$. In other embodiments of compounds of Formula (VII), $X^2$ is —CF—; and $R_6$ and $R_7$ taken together are

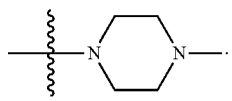

In still other embodiments of compounds of Formula (VII), $R_5$ is methyl or —CO(NH)CH$_2$CH$_3$ and $R_6$ and $R_7$ taken together are

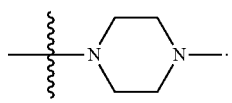

In some embodiments of compounds of Formulae (I)—(VII), $R_1$ is

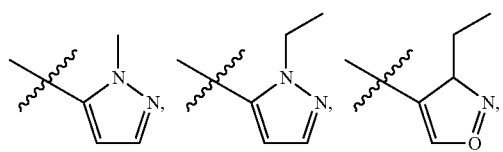
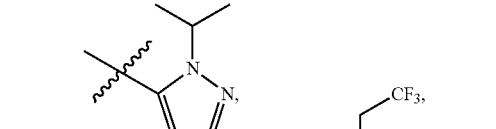
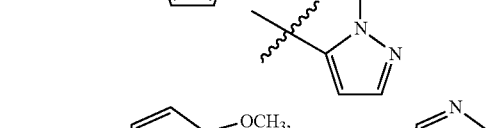
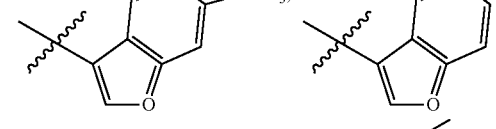
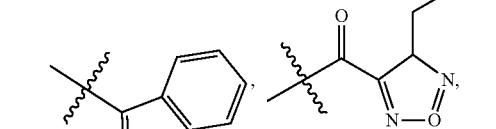
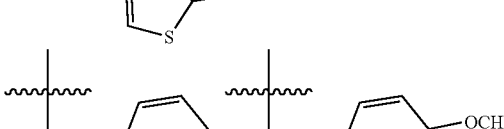
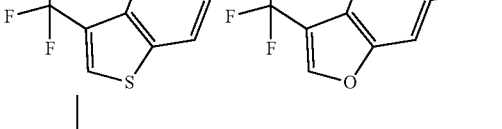
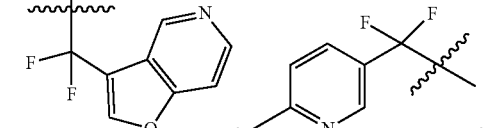
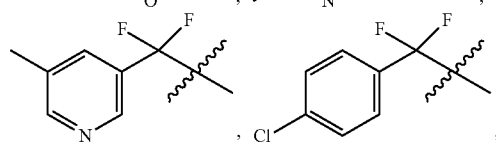

-continued
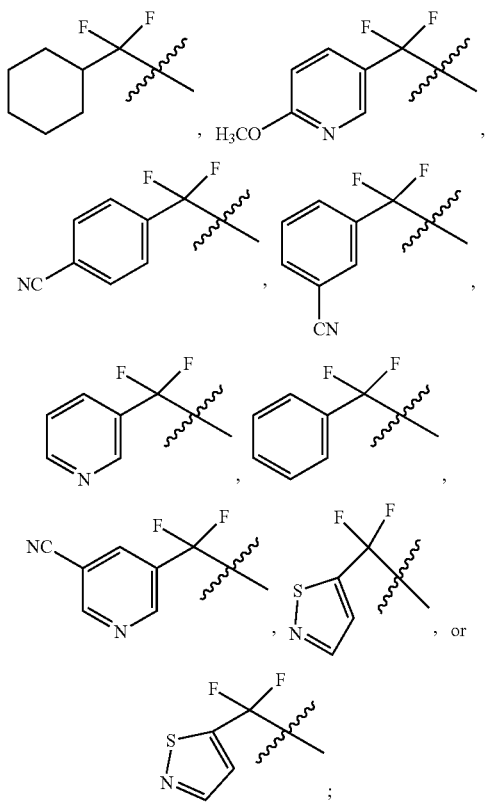
R$_2$ is cyclopentyl, cyclohexyl, cycloheptyl, 4-methyl cyclohexyl, —CH$_2$-cyclohexyl, —C(CH$_3$)H-cyclohexyl, —CH$_2$CH$_2$-cyclohexyl, 2-indanyl, 1-indanyl, 4,4-dimethyl cyclohexyl, 4,4-difluorocyclohexyl, 4-methylcyclohexyl or
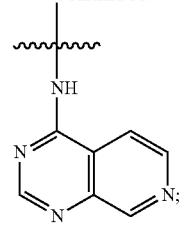
X$^2$ is —CH—, or —CF—, R$_5$ is —OH, NHC(O)CH$_2$CH$_3$, —NHC(O)CH(CH$_3$)CH$_3$, NHC(O)CH(C$_2$H$_5$)CH$_3$,
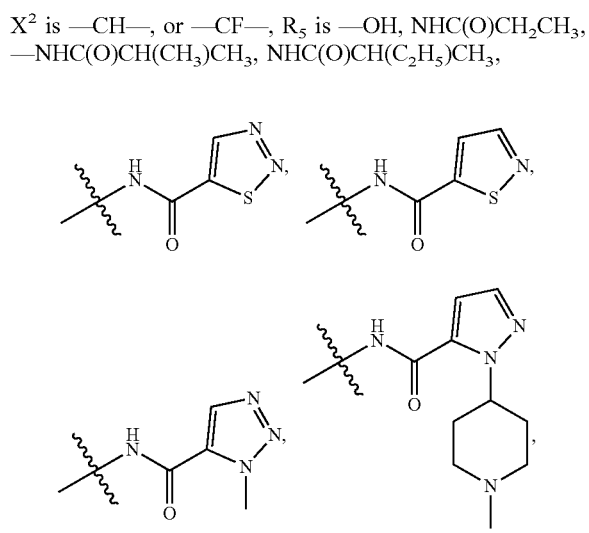
-continued
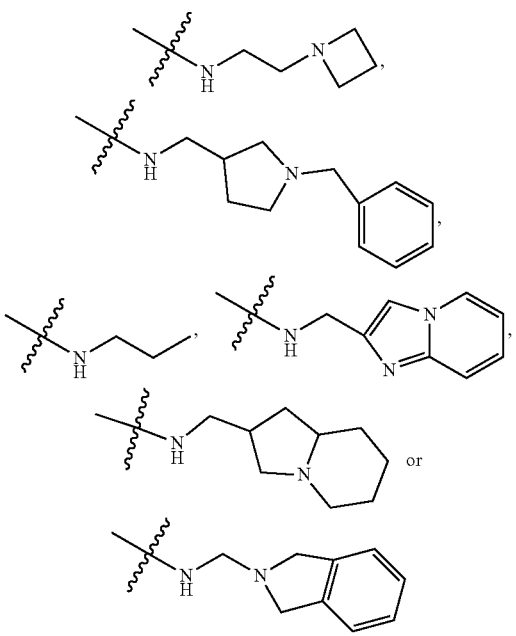
R$_6$ is hydrogen and R$_7$ is
or R$_6$ and R$_7$ taken together are

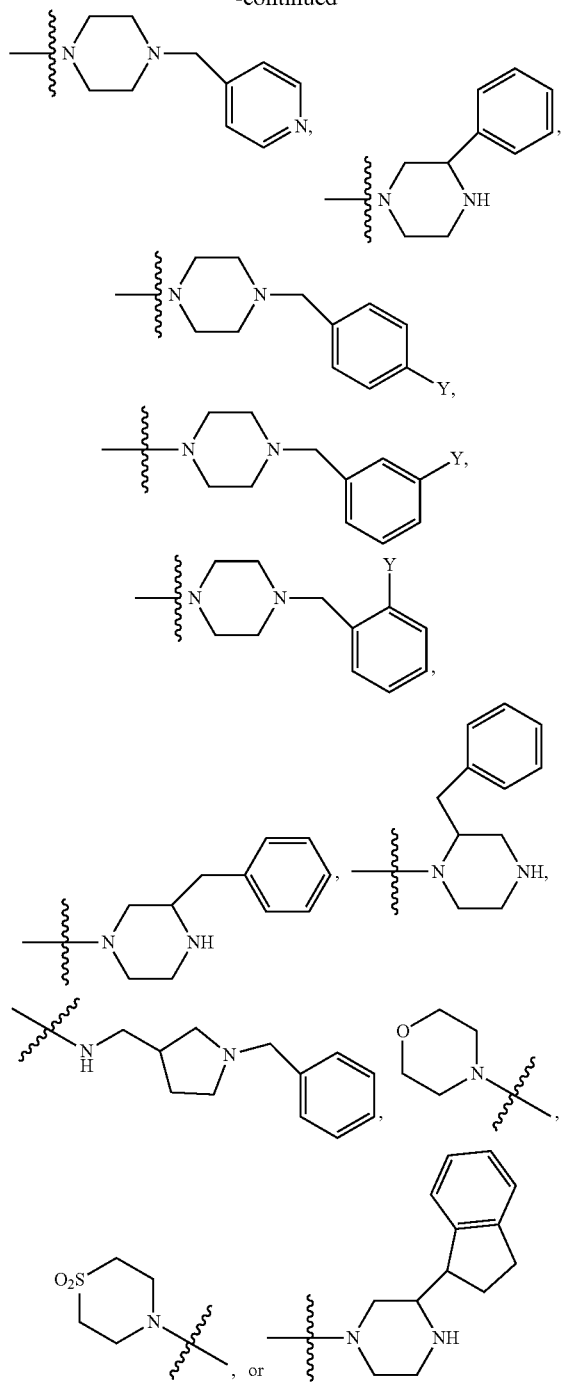

where X is —CH₃, -Ph, 1-indanyl, —CH₂cyclohexyl, —CH₂cyclopropyl and Y is —CH₃, —Cl, —CN or —H. In other embodiments of compounds of Formulae (I)—(VII) R₁ is

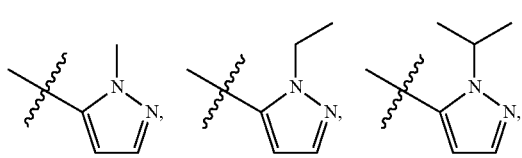

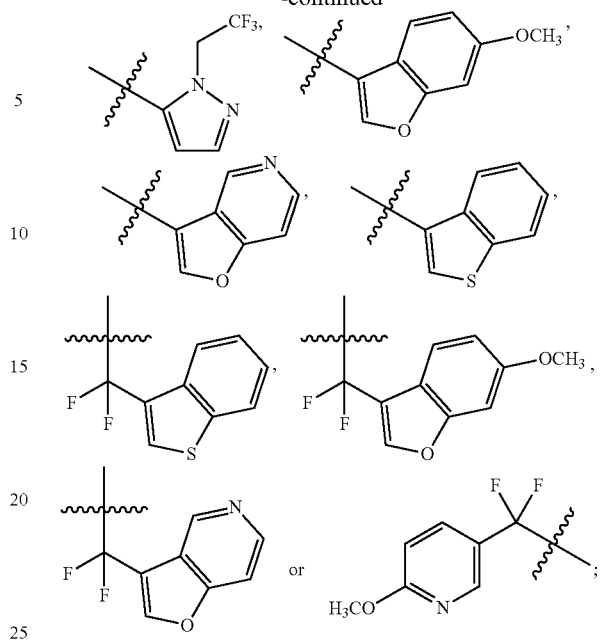

$R_2$ is cyclohexyl, cycloheptyl, 4,4-difluorocyclohexyl or 4-methylcyclohexyl; $X^2$ is —CF— or —CH—, $R_5$ is —NHC(O)CH₂CH₃, —NHC(O)CH(CH₃)CH₃, NHC(O)CH(C₂H₅)CH₃ or

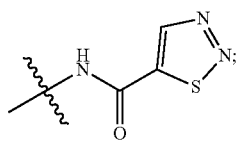 [SMILES: *NC(=O)c1cnns1]

and $R_6$ and $R_7$ taken together are

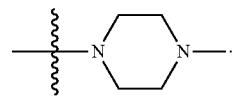

In some of the above embodiments, substituent groups useful for substituting saturated carbon atoms in the specified group or radical include $R^a$, halo, —OR$^b$, —NR$^c$R$^c$, trihalomethyl, —CN, —NR$^b$S(O)₂R$^b$, —C(O)R$^b$, —C(O)NR$^b$—OR$^b$, —C(O)OR$^b$, —C(O)NR$^c$R$^c$, —OC(O)R$^b$, —OC(O)OR$^b$, —OS(O)₂NR$^c$NR$^c$, —OC(O)NR$^c$R$^c$, and —NR$^b$C(O)OR$^b$, substituent groups useful for substituting unsaturated carbon atoms in the specified group or radical include —R$^a$, halo, —OR$^b$, —SR$^b$, —NR$^c$R$^c$, trihalomethyl, —CN, —S(O)₂OR$^b$, —C(O)R$^b$, —C(O)OR$^b$, —C(O)NR$^c$R$^c$, —OC(O)R$^b$, —OC(O)OR$^b$, —OS(O)₂NR$^c$NR$^c$, —NR$^b$C(O)R$^b$ and —NR$^b$C(O)OR$^b$ and substituent groups useful for substituting nitrogen atoms in heteroalkyl and cycloheteroalkyl groups include, R$^a$, halo, —OR$^b$, —NR$^c$R$^c$, trihalomethyl, —CN, —S(O)₂R$^b$, —OS(O)₂R$^b$, —OS(O)₂OR$^b$, —C(O)R$^b$, —C(NR$^b$)R$^b$, —C(O)OR$^b$, —C(O)NR$^c$R$^c$, —OC(O)R$^b$, —OC(O)OR$^b$, —OS(O)₂NR$^c$NR$^c$, —NR$^b$C(O)R$^b$ and —NR$^b$C(O)OR$^b$, where each R$^a$ is independently alkyl, aryl, heteroaryl, each R$^b$ is independently hydrogen, R$^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6- or 7-membered cycloheteroalkyl ring. In other of the above embodiments, substituent groups useful for substituting saturated carbon atoms in the specified group or radical include $R^a$, halo, —$OR^b$, —$NR^cR^c$, trihalomethyl, —$C(O)R^b$, —$C(O)OR^b$, —$C(O)NR^cR^c$, —$OC(O)R^b$, —$OC(O)OR^b$, —$OC(O)NR^cR^c$, and —$NR^bC(O)OR^b$, substituent groups useful for substituting unsaturated carbon atoms in the specified group or radical include —$R^a$, halo, —$OR^b$, —$NR^cR^c$, trihalomethyl, —CN, —$C(O)R^b$, —$C(O)OR^b$, —$C(O)NR^cR^c$, —$OC(O)R^b$, —$OC(O)OR^b$, —$NR^bC(O)R^b$ and —$NR^bC(O)OR^b$ and substituent groups useful for substituting nitrogen atoms in heteroalkyl and cycloheteroalkyl groups include, $R^a$, halo, —$OR^b$, —$NR^cR^c$, trihalomethyl, —CN, —$C(O)R^b$, —$C(NR^b)R^b$, —$C(O)OR^b$, —$C(O)NR^cR^c$, —$OC(O)R^b$, —$OC(O)OR^b$, —$NR^bC(O)R^b$ and —$NR^bC(O)OR^b$, where each $R^a$ is independently alkyl, aryl, heteroaryl, each $R^b$ is independently hydrogen, $R^a$, heteroalkyl, arylalkyl, heteroarylalkyl; and each $R^c$ is independently $R^b$ or alternatively, the two $R^c$s taken together with the nitrogen atom to which they are bonded form a 4-, 5-, 6- or 7-membered cycloheteroalkyl ring. In still other of the above embodiments, substituent groups useful for substituting saturated carbon atoms in the specified group or radical include $R^a$, halo, —$OR^b$, trihalomethyl, —$C(O)R^b$, —$C(O)OR^b$, —$OC(O)R^b$, —$OC(O)OR^b$ and —$NR^bC(O)OR^b$ substituent groups useful for substituting unsaturated carbon atoms in the specified group or radical include —$R^a$, halo, —$OR^b$, trihalomethyl, —CN, —$C(O)R^b$, —$C(O)OR^b$, —$OC(O)R^b$, —$OC(O)OR^b$ and —$NR^bC(O)OR^b$ where each $R^a$ is independently alkyl, each $R^b$ is independently hydrogen or $R^a$.

Table 1 illustrates compound of structural formula (I).

TABLE 1

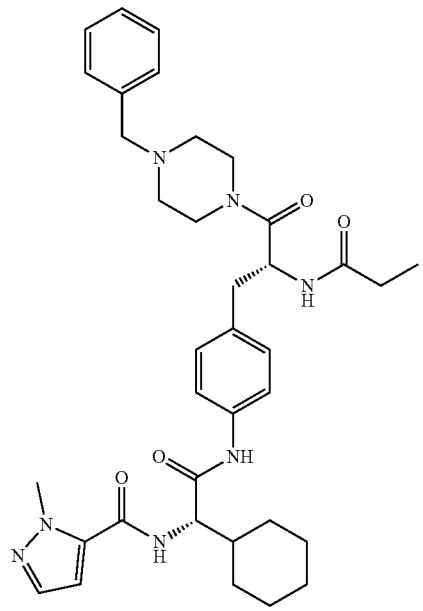 [SMILES: CCC(=O)N[C@H](Cc1ccc(NC(=O)[C@@H](NC(=O)c2ccnn2C)C2CCCCC2)cc1)C(=O)N1CCN(Cc2ccccc2)CC1]

100

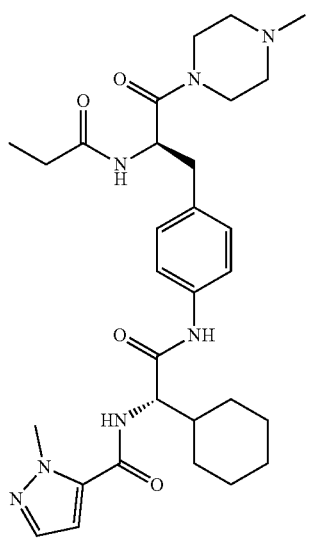 [SMILES: CCC(=O)N[C@H](Cc1ccc(NC(=O)[C@@H](NC(=O)c2ccnn2C)C2CCCCC2)cc1)C(=O)N1CCN(C)CC1]

101

TABLE 1-continued
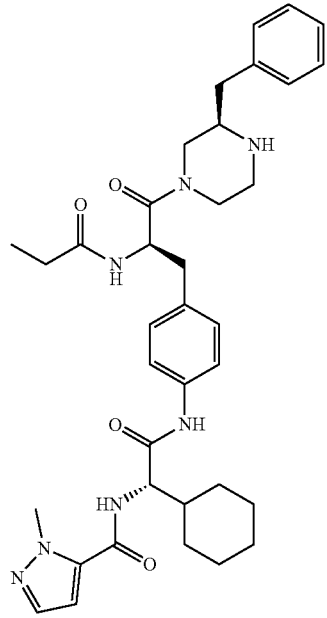 [SMILES: CCC(=O)N[C@H](Cc1ccc(NC(=O)[C@@H](NC(=O)c2ccnn2C)C2CCCCC2)cc1)C(=O)N1CCN[C@H](Cc2ccccc2)C1]
102
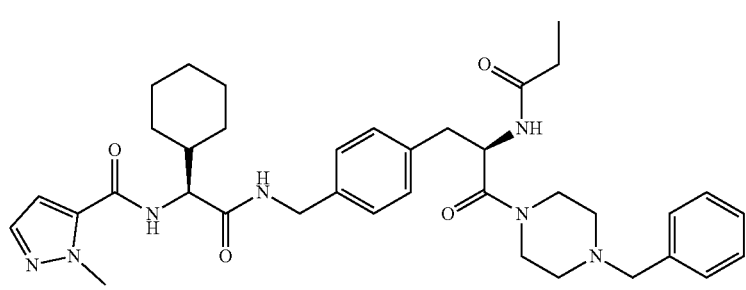 [SMILES: CCC(=O)N[C@H](Cc1ccc(CNC(=O)[C@@H](NC(=O)c2ccnn2C)C2CCCCC2)cc1)C(=O)N1CCN(Cc2ccccc2)CC1]
103
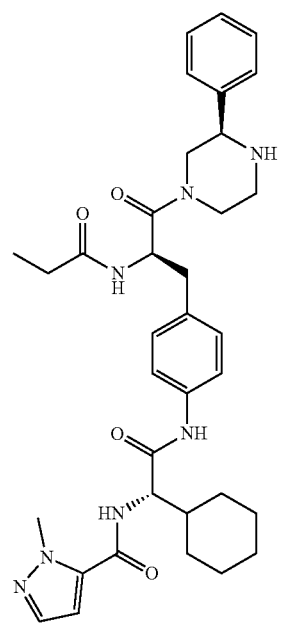 [SMILES: CCC(=O)N[C@H](Cc1ccc(NC(=O)[C@@H](NC(=O)c2ccnn2C)C2CCCCC2)cc1)C(=O)N1CCN[C@H](c2ccccc2)C1]
104

TABLE 1-continued
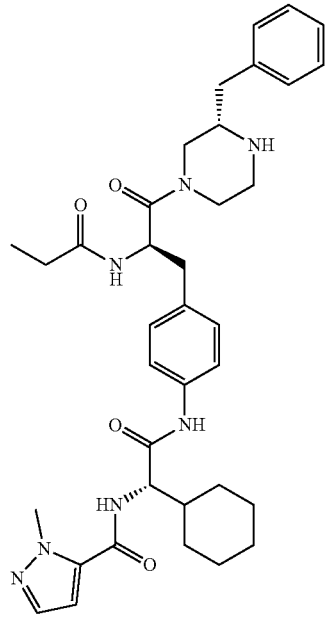 [SMILES: CCC(=O)N[C@H](Cc1ccc(NC(=O)[C@@H](NC(=O)c2ccnn2C)C2CCCCC2)cc1)C(=O)N1CCN[C@@H](Cc2ccccc2)C1]
105
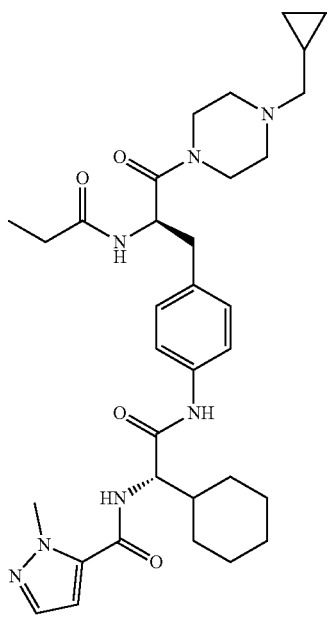 [SMILES: CCC(=O)N[C@H](Cc1ccc(NC(=O)[C@@H](NC(=O)c2ccnn2C)C2CCCCC2)cc1)C(=O)N1CCN(CC2CC2)CC1]
106

TABLE 1-continued
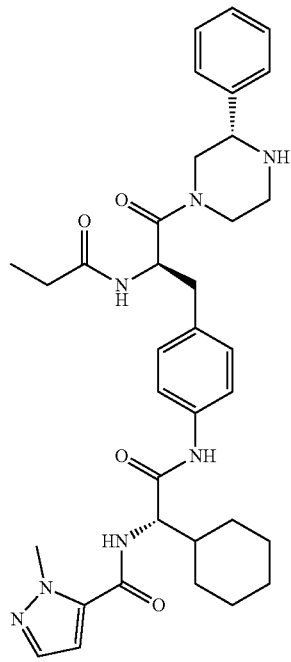 [SMILES: CCC(=O)N[C@H](Cc1ccc(NC(=O)[C@@H](NC(=O)c2ccnn2C)C2CCCCC2)cc1)C(=O)N1CCN[C@@H](c2ccccc2)C1]
107
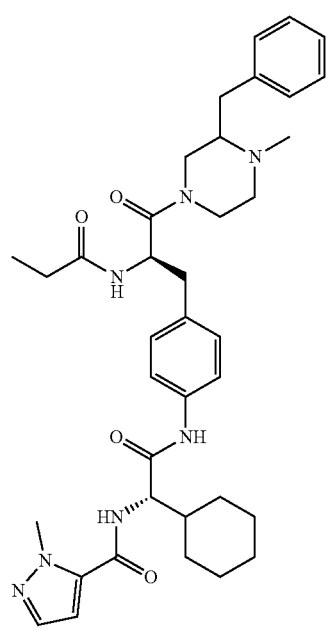 [SMILES: CCC(=O)N[C@H](Cc1ccc(NC(=O)[C@@H](NC(=O)c2ccnn2C)C2CCCCC2)cc1)C(=O)N1CCN(C)C(Cc2ccccc2)C1]
108

TABLE 1-continued
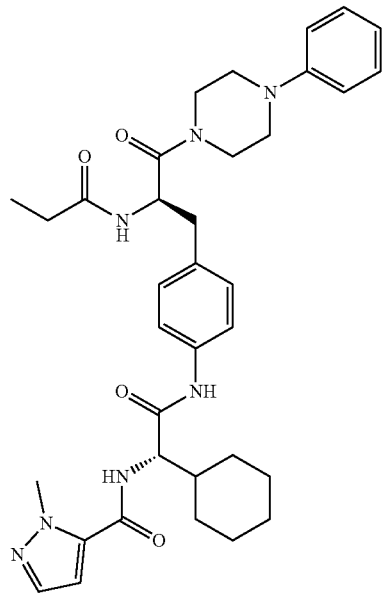 [SMILES: CCC(=O)N[C@H](Cc1ccc(NC(=O)[C@@H](NC(=O)c2ccnn2C)C2CCCCC2)cc1)C(=O)N1CCN(c2ccccc2)CC1]
109
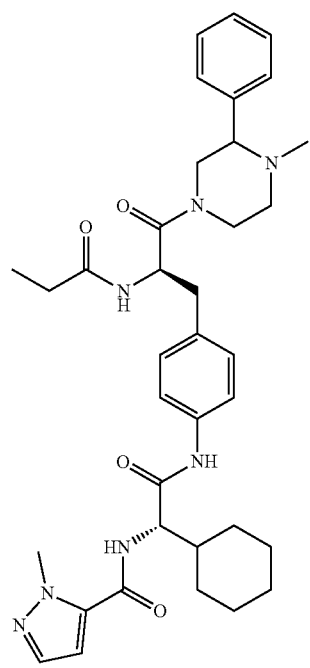 [SMILES: CCC(=O)N[C@H](Cc1ccc(NC(=O)[C@@H](NC(=O)c2ccnn2C)C2CCCCC2)cc1)C(=O)N1CCN(C)C(c2ccccc2)C1]
110

TABLE 1-continued
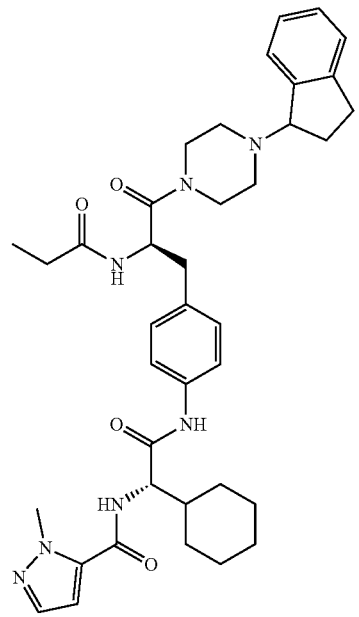 [SMILES: CCC(=O)N[C@H](Cc1ccc(NC(=O)[C@@H](NC(=O)c2ccnn2C)C2CCCCC2)cc1)C(=O)N1CCN(C2CCc3ccccc32)CC1]
111
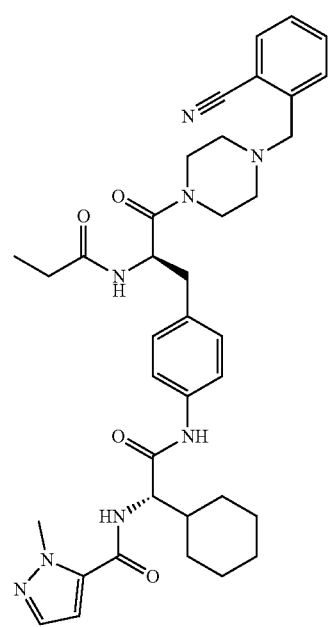 [SMILES: CCC(=O)N[C@H](Cc1ccc(NC(=O)[C@@H](NC(=O)c2ccnn2C)C2CCCCC2)cc1)C(=O)N1CCN(Cc2ccccc2C#N)CC1]
112

TABLE 1-continued
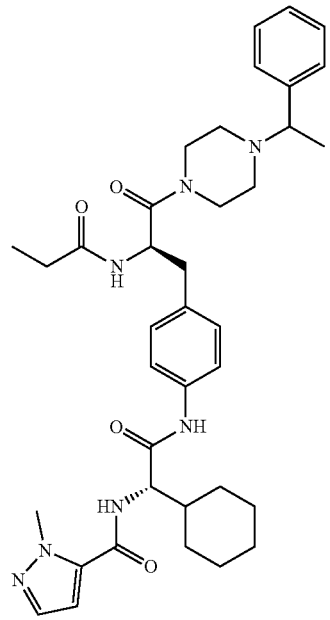 [SMILES: CCC(=O)N[C@H](Cc1ccc(NC(=O)[C@@H](NC(=O)c2ccnn2C)C2CCCCC2)cc1)C(=O)N1CCN(C(C)c2ccccc2)CC1]
113
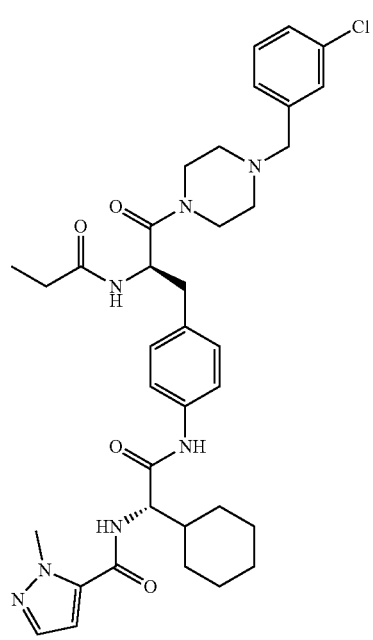 [SMILES: CCC(=O)N[C@H](Cc1ccc(NC(=O)[C@@H](NC(=O)c2ccnn2C)C2CCCCC2)cc1)C(=O)N1CCN(Cc2cccc(Cl)c2)CC1]
114

TABLE 1-continued
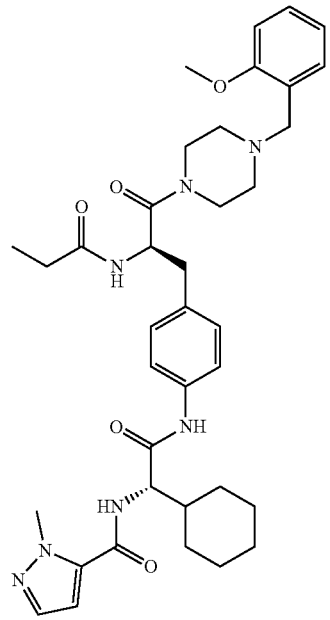 [SMILES: CCC(=O)N[C@H](Cc1ccc(NC(=O)[C@@H](NC(=O)c2ccnn2C)C2CCCCC2)cc1)C(=O)N1CCN(Cc2ccccc2OC)CC1]
115
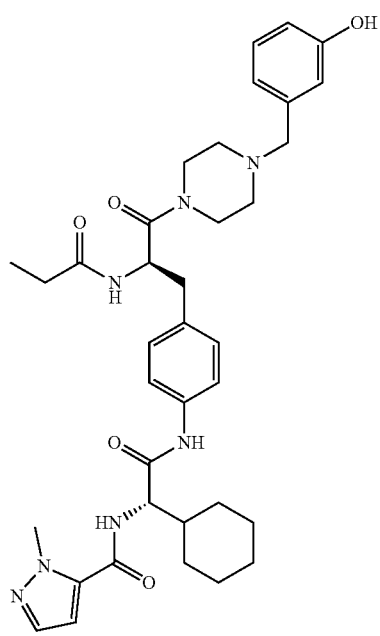 [SMILES: CCC(=O)N[C@H](Cc1ccc(NC(=O)[C@@H](NC(=O)c2ccnn2C)C2CCCCC2)cc1)C(=O)N1CCN(Cc2cccc(O)c2)CC1]
116

TABLE 1-continued
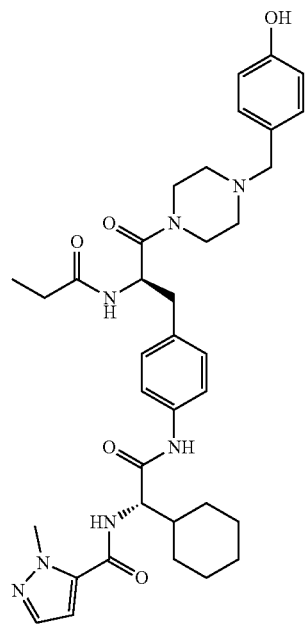 [SMILES: CCC(=O)N[C@H](Cc1ccc(NC(=O)[C@@H](NC(=O)c2ccnn2C)C2CCCCC2)cc1)C(=O)N1CCN(Cc2ccc(O)cc2)CC1]
117
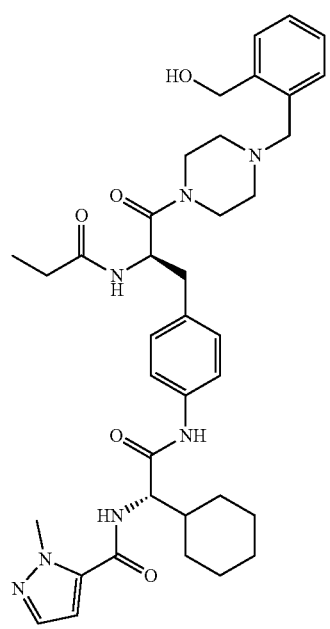 [SMILES: CCC(=O)N[C@H](Cc1ccc(NC(=O)[C@@H](NC(=O)c2ccnn2C)C2CCCCC2)cc1)C(=O)N1CCN(Cc2ccccc2CO)CC1]
118

TABLE 1-continued
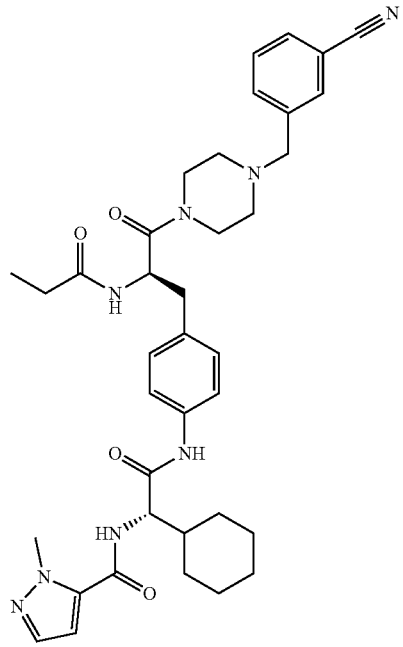 [SMILES: CCC(=O)N[C@H](Cc1ccc(NC(=O)[C@@H](NC(=O)c2ccnn2C)C2CCCCC2)cc1)C(=O)N1CCN(Cc2cccc(C#N)c2)CC1]
119
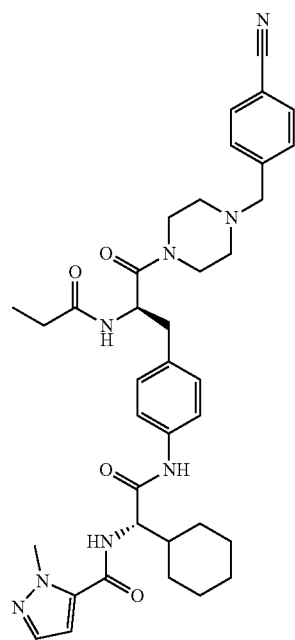 [SMILES: CCC(=O)N[C@H](Cc1ccc(NC(=O)[C@@H](NC(=O)c2ccnn2C)C2CCCCC2)cc1)C(=O)N1CCN(Cc2ccc(C#N)cc2)CC1]
120

TABLE 1-continued
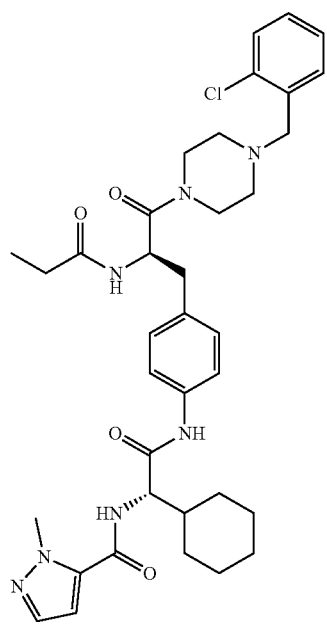 [SMILES: CCC(=O)N[C@H](Cc1ccc(NC(=O)[C@@H](NC(=O)c2ccnn2C)C2CCCCC2)cc1)C(=O)N1CCN(Cc2ccccc2Cl)CC1]
121
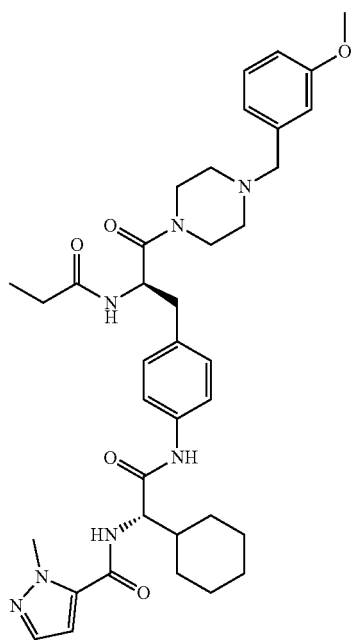 [SMILES: CCC(=O)N[C@H](Cc1ccc(NC(=O)[C@@H](NC(=O)c2ccnn2C)C2CCCCC2)cc1)C(=O)N1CCN(Cc2cccc(OC)c2)CC1]
122

TABLE 1-continued
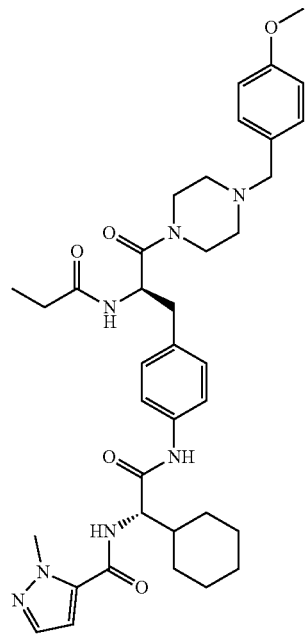 [SMILES: CCC(=O)N[C@H](Cc1ccc(NC(=O)[C@@H](NC(=O)c2ccnn2C)C2CCCCC2)cc1)C(=O)N1CCN(Cc2ccc(OC)cc2)CC1]
123
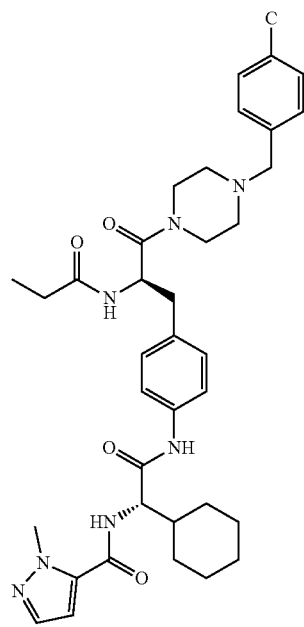 [SMILES: CCC(=O)N[C@H](Cc1ccc(NC(=O)[C@@H](NC(=O)c2ccnn2C)C2CCCCC2)cc1)C(=O)N1CCN(Cc2ccc(C)cc2)CC1]
124

TABLE 1-continued
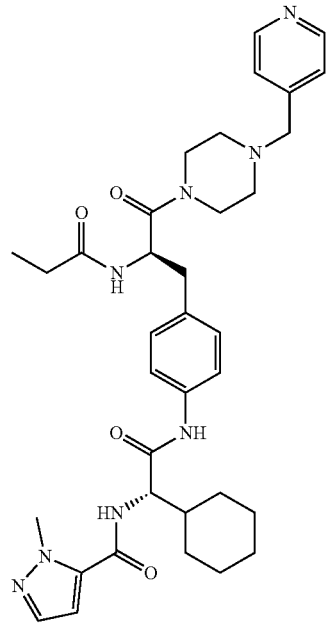 [SMILES: CCC(=O)N[C@H](Cc1ccc(NC(=O)[C@@H](NC(=O)c2ccnn2C)C2CCCCC2)cc1)C(=O)N1CCN(Cc2ccncc2)CC1]
125
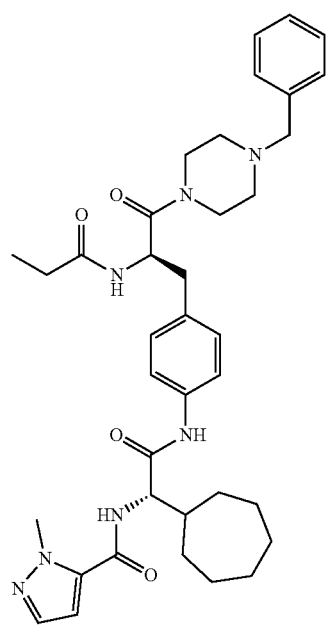 [SMILES: CCC(=O)N[C@H](Cc1ccc(NC(=O)[C@@H](NC(=O)c2ccnn2C)C2CCCCCC2)cc1)C(=O)N1CCN(Cc2ccccc2)CC1]
126

TABLE 1-continued
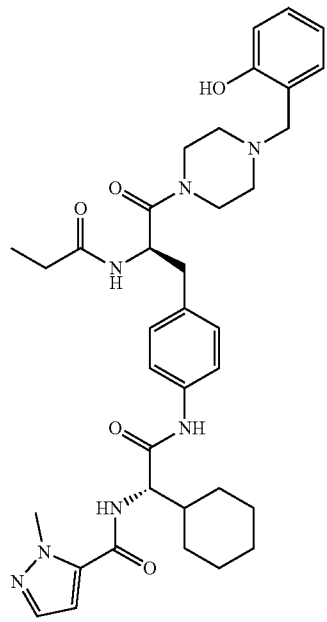 [SMILES: CCC(=O)N[C@H](Cc1ccc(NC(=O)[C@@H](NC(=O)c2ccnn2C)C2CCCCC2)cc1)C(=O)N1CCN(Cc2ccccc2O)CC1]
127
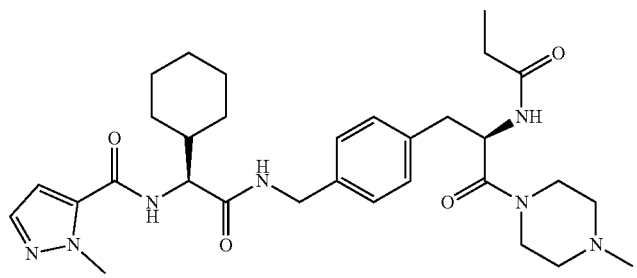 [SMILES: CCC(=O)N[C@H](Cc1ccc(CNC(=O)[C@@H](NC(=O)c2ccnn2C)C2CCCCC2)cc1)C(=O)N1CCN(C)CC1]
128
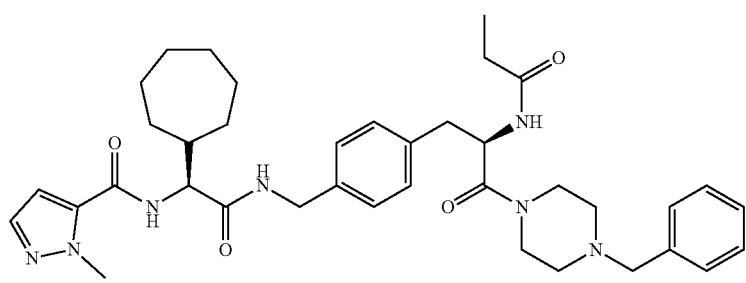 [SMILES: CCC(=O)N[C@H](Cc1ccc(CNC(=O)[C@@H](NC(=O)c2ccnn2C)C2CCCCCC2)cc1)C(=O)N1CCN(Cc2ccccc2)CC1]
129

TABLE 1-continued
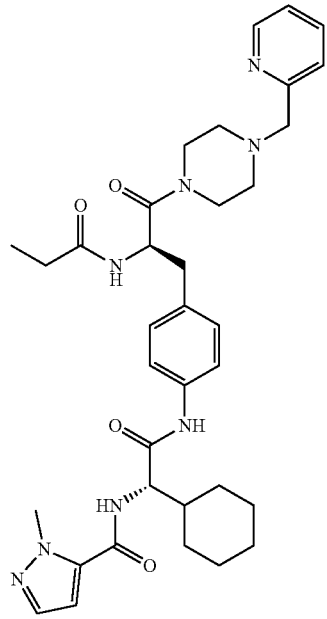 [SMILES: CCC(=O)N[C@H](Cc1ccc(NC(=O)[C@@H](NC(=O)c2ccnn2C)C2CCCCC2)cc1)C(=O)N1CCN(Cc2ccccn2)CC1]
130
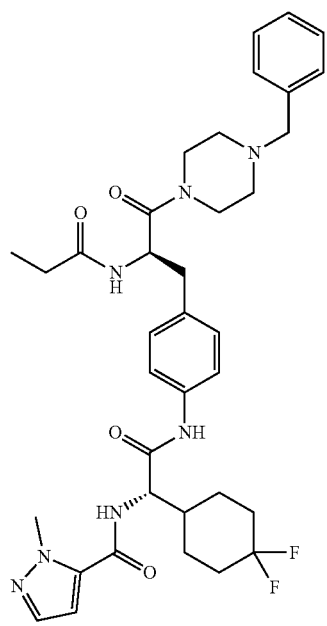 [SMILES: CCC(=O)N[C@H](Cc1ccc(NC(=O)[C@@H](NC(=O)c2ccnn2C)C2CCC(F)(F)CC2)cc1)C(=O)N1CCN(Cc2ccccc2)CC1]
131

TABLE 1-continued
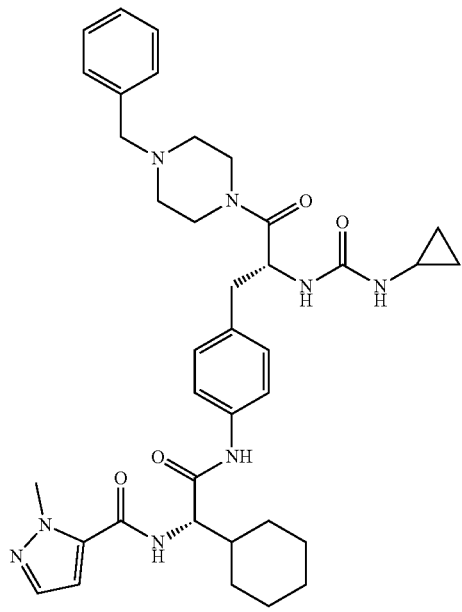 [SMILES: Cn1nccc1C(=O)N[C@H](C(=O)Nc1ccc(C[C@@H](NC(=O)NC2CC2)C(=O)N2CCN(Cc3ccccc3)CC2)cc1)C1CCCCC1]
132
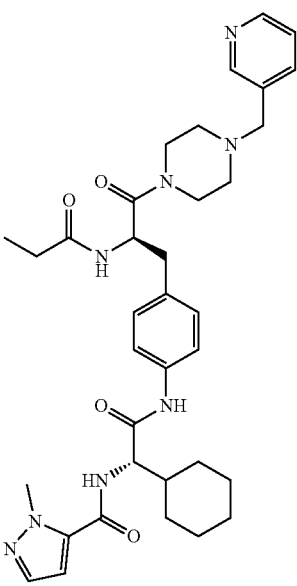 [SMILES: CCC(=O)N[C@H](Cc1ccc(NC(=O)[C@@H](NC(=O)c2ccnn2C)C2CCCCC2)cc1)C(=O)N1CCN(Cc2cccnc2)CC1]
133
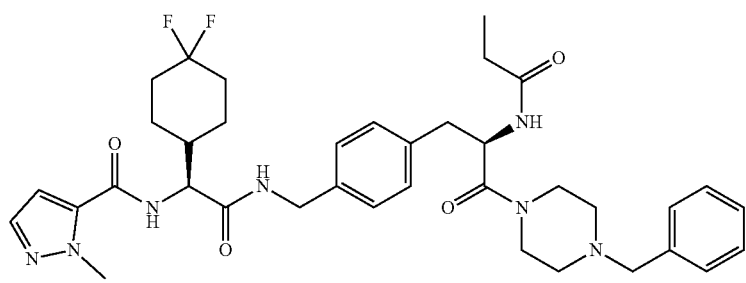 [SMILES: CCC(=O)N[C@H](Cc1ccc(CNC(=O)[C@@H](NC(=O)c2ccnn2C)C2CCC(F)(F)CC2)cc1)C(=O)N1CCN(Cc2ccccc2)CC1]
134

TABLE 1-continued
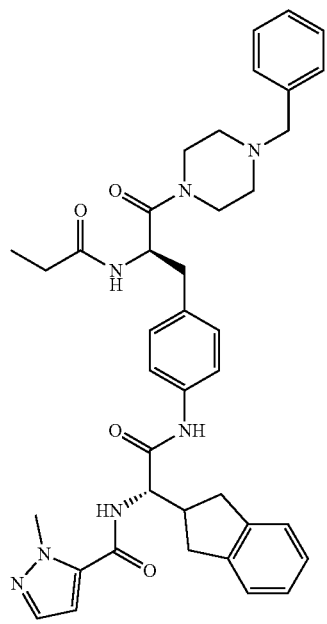 [SMILES: CCC(=O)N[C@H](Cc1ccc(NC(=O)[C@@H](NC(=O)c2ccnn2C)C2Cc3ccccc3C2)cc1)C(=O)N1CCN(Cc2ccccc2)CC1]
135
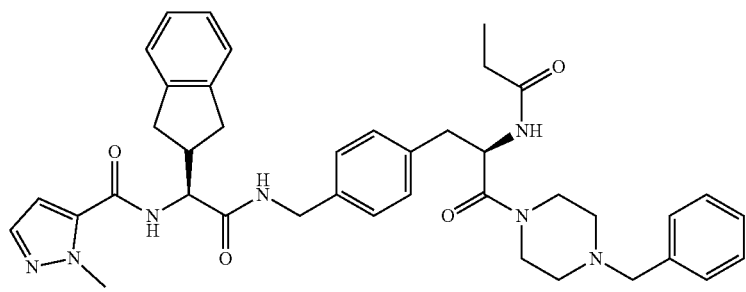 [SMILES: CCC(=O)N[C@H](Cc1ccc(CNC(=O)[C@@H](NC(=O)c2ccnn2C)C2Cc3ccccc3C2)cc1)C(=O)N1CCN(Cc2ccccc2)CC1]
136
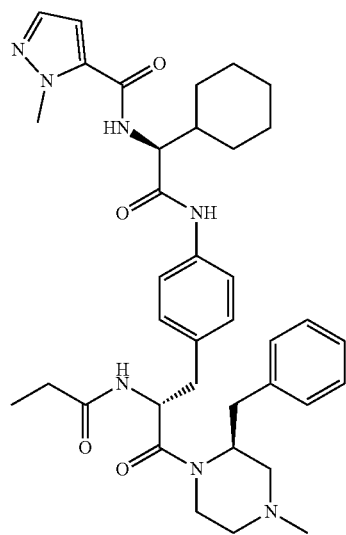 [SMILES: CCC(=O)N[C@H](Cc1ccc(NC(=O)[C@@H](NC(=O)c2ccnn2C)C2CCCCC2)cc1)C(=O)N1CCN(C)C[C@@H]1Cc1ccccc1]
137

TABLE 1-continued
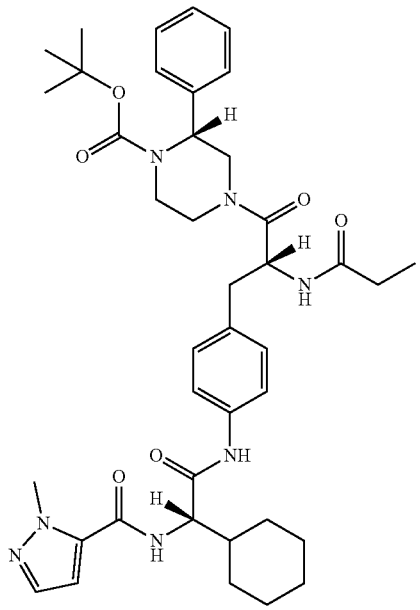 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@H](c2ccccc2)C1]
138
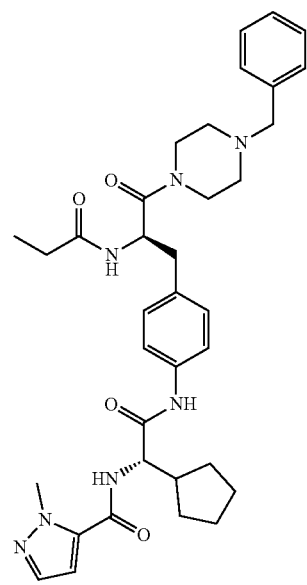 [SMILES: CCC(=O)N[C@H](Cc1ccc(NC(=O)[C@@H](NC(=O)c2ccnn2C)C2CCCC2)cc1)C(=O)N1CCN(Cc2ccccc2)CC1]
139

TABLE 1-continued
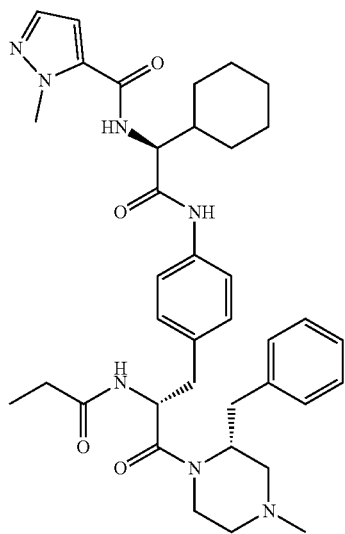 [SMILES: CCC(=O)N[C@H](Cc1ccc(NC(=O)[C@@H](NC(=O)c2ccnn2C)C2CCCCC2)cc1)C(=O)N1CCN(C)C[C@H]1Cc1ccccc1]
140
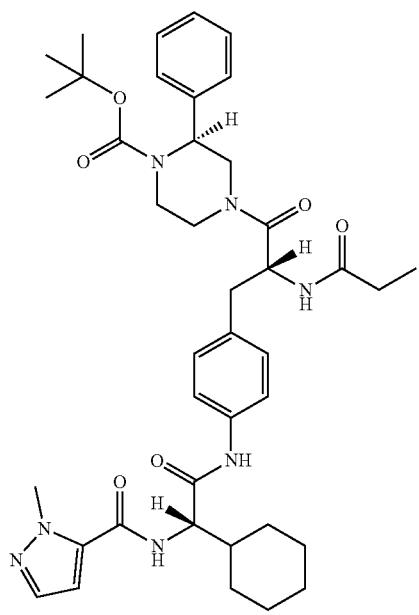 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@@H](c2ccccc2)C1]
141
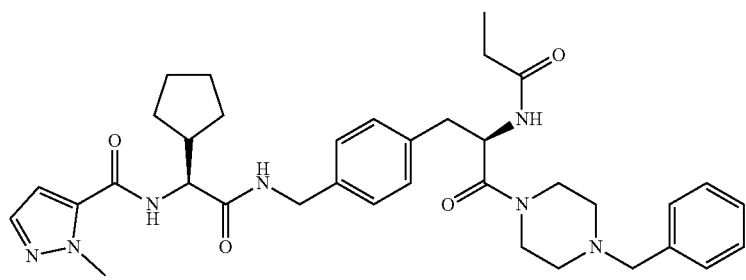 [SMILES: CCC(=O)N[C@H](Cc1ccc(CNC(=O)[C@@H](NC(=O)c2ccnn2C)C2CCCC2)cc1)C(=O)N1CCN(Cc2ccccc2)CC1]
142

TABLE 1-continued
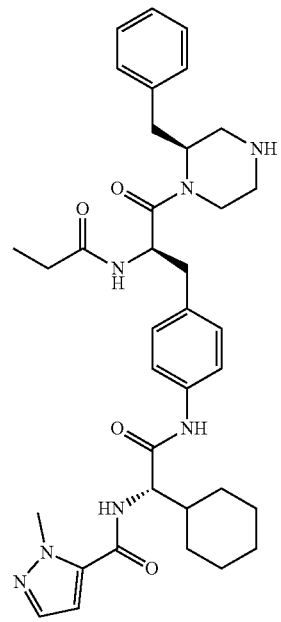 [SMILES: CCC(=O)N[C@H](Cc1ccc(NC(=O)[C@@H](NC(=O)c2ccnn2C)C2CCCCC2)cc1)C(=O)N1CCNC[C@@H]1Cc1ccccc1]
143
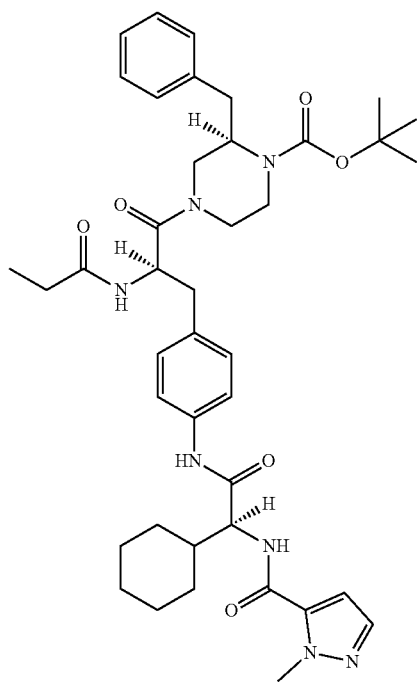 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@H](Cc2ccccc2)C1]
144

TABLE 1-continued
145
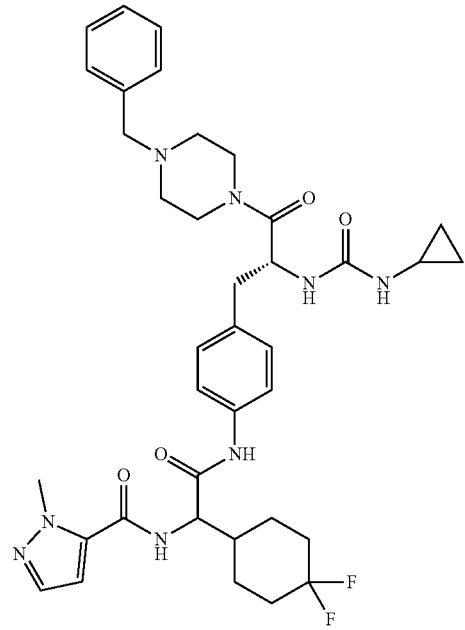 [SMILES: Cn1nccc1C(=O)NC(C(=O)Nc1ccc(C[C@@H](NC(=O)NC2CC2)C(=O)N2CCN(Cc3ccccc3)CC2)cc1)C1CCC(F)(F)CC1]
146
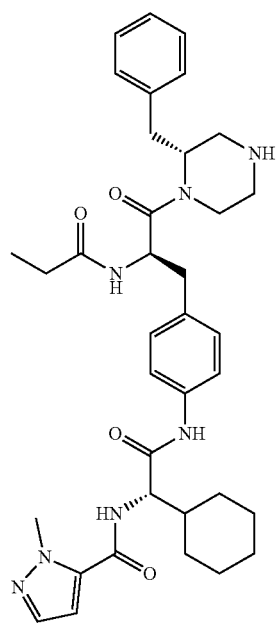 [SMILES: CCC(=O)N[C@H](Cc1ccc(NC(=O)[C@@H](NC(=O)c2ccnn2C)C2CCCCC2)cc1)C(=O)N1CCNC[C@H]1Cc1ccccc1]

TABLE 1-continued
147
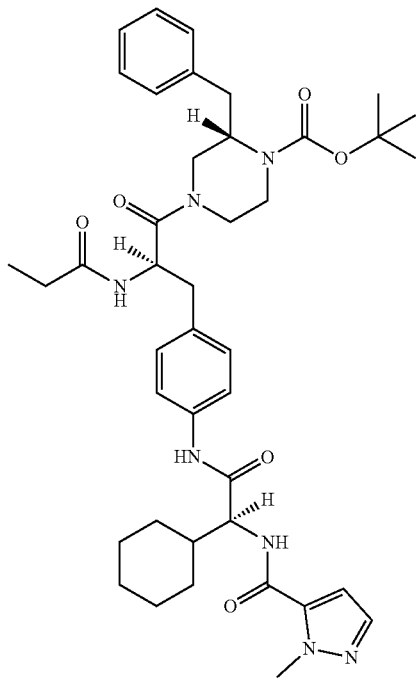 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@@H](Cc2ccccc2)C1]
148
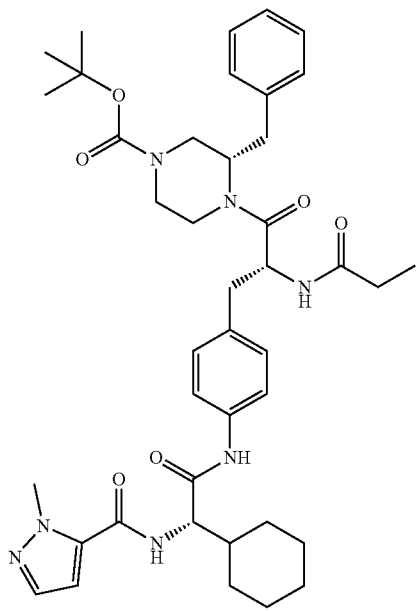 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)C[C@@H]1Cc1ccccc1]
149
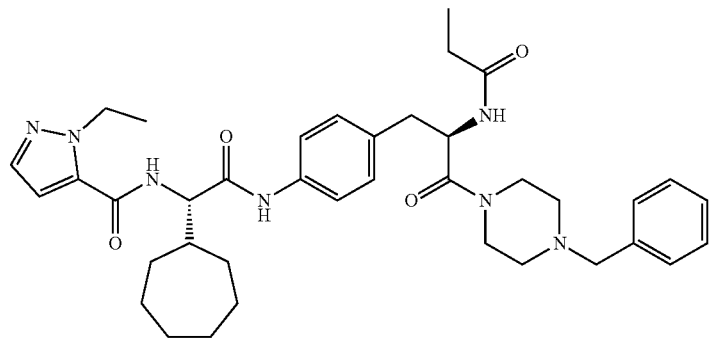 [SMILES: CCC(=O)N[C@H](Cc1ccc(NC(=O)[C@@H](NC(=O)c2ccnn2CC)C2CCCCCC2)cc1)C(=O)N1CCN(Cc2ccccc2)CC1]

TABLE 1-continued
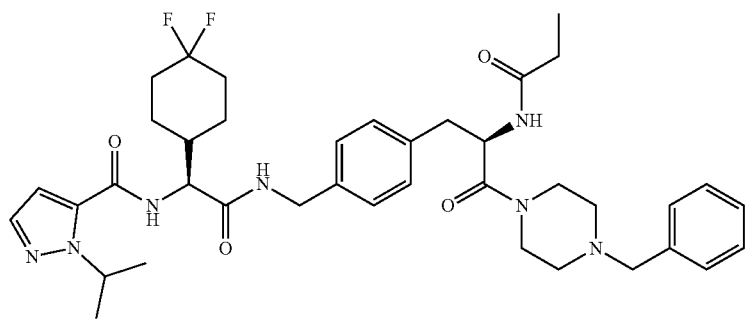 [SMILES: CCC(=O)N[C@H](Cc1ccc(CNC(=O)[C@@H](NC(=O)c2ccnn2C(C)C)C2CCC(F)(F)CC2)cc1)C(=O)N1CCN(Cc2ccccc2)CC1]
150
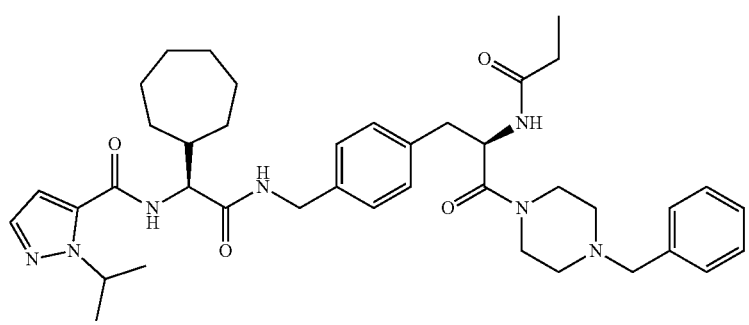 [SMILES: CCC(=O)N[C@H](Cc1ccc(CNC(=O)[C@@H](NC(=O)c2ccnn2C(C)C)C2CCCCCC2)cc1)C(=O)N1CCN(Cc2ccccc2)CC1]
151
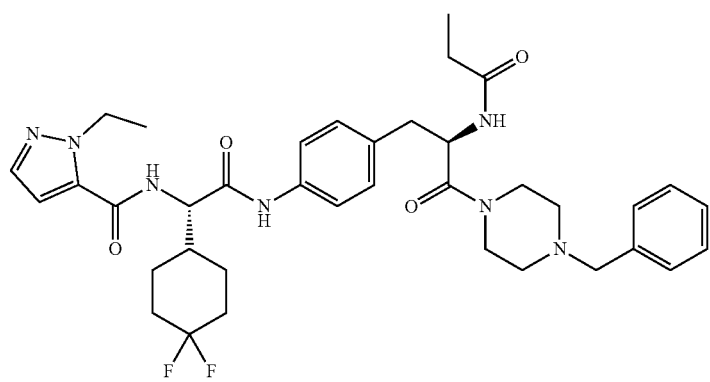 [SMILES: CCC(=O)N[C@H](Cc1ccc(NC(=O)[C@@H](NC(=O)c2ccnn2CC)C2CCC(F)(F)CC2)cc1)C(=O)N1CCN(Cc2ccccc2)CC1]
152
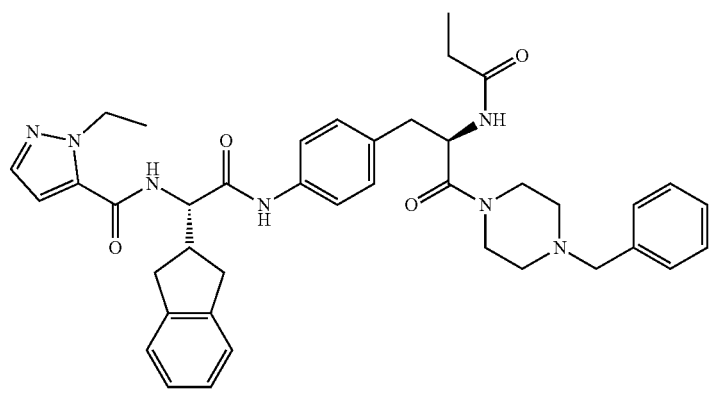 [SMILES: CCC(=O)N[C@H](Cc1ccc(NC(=O)[C@@H](NC(=O)c2ccnn2CC)C2Cc3ccccc3C2)cc1)C(=O)N1CCN(Cc2ccccc2)CC1]
153

TABLE 1-continued
| | |
|---|---|
| 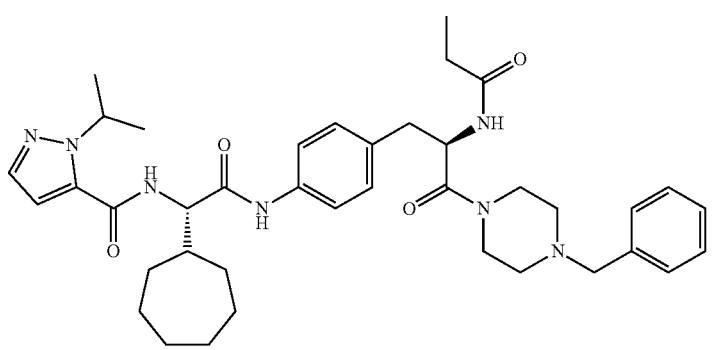 [SMILES: CCC(=O)N[C@H](Cc1ccc(NC(=O)[C@@H](NC(=O)c2ccnn2C(C)C)C2CCCCCC2)cc1)C(=O)N1CCN(Cc2ccccc2)CC1] | 154 |
| 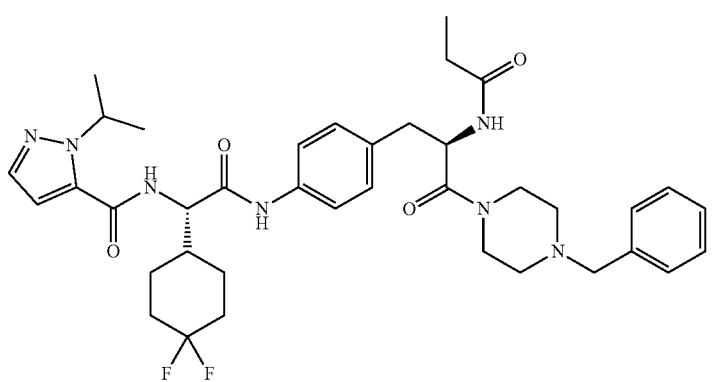 [SMILES: CCC(=O)N[C@H](Cc1ccc(NC(=O)[C@@H](NC(=O)c2ccnn2C(C)C)C2CCC(F)(F)CC2)cc1)C(=O)N1CCN(Cc2ccccc2)CC1] | 155 |
| 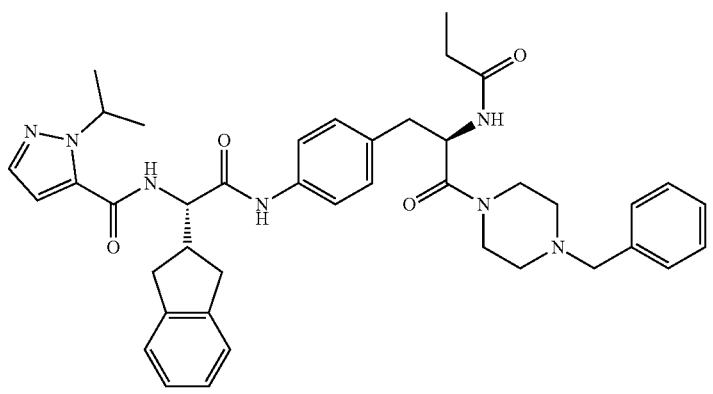 [SMILES: CCC(=O)N[C@H](Cc1ccc(NC(=O)[C@@H](NC(=O)c2ccnn2C(C)C)C2Cc3ccccc3C2)cc1)C(=O)N1CCN(Cc2ccccc2)CC1] | 156 |
| 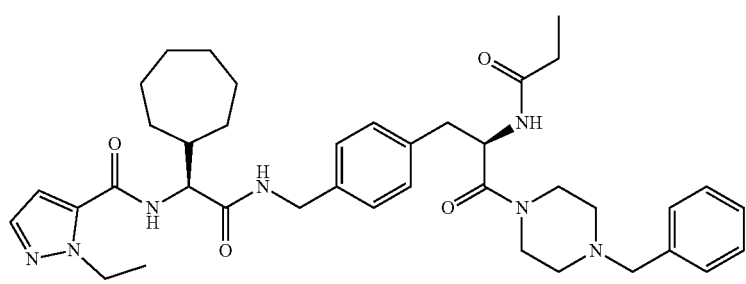 [SMILES: CCC(=O)N[C@H](Cc1ccc(CNC(=O)[C@@H](NC(=O)c2ccnn2CC)C2CCCCCC2)cc1)C(=O)N1CCN(Cc2ccccc2)CC1] | 157 |

TABLE 1-continued
| | |
|---|---|
| 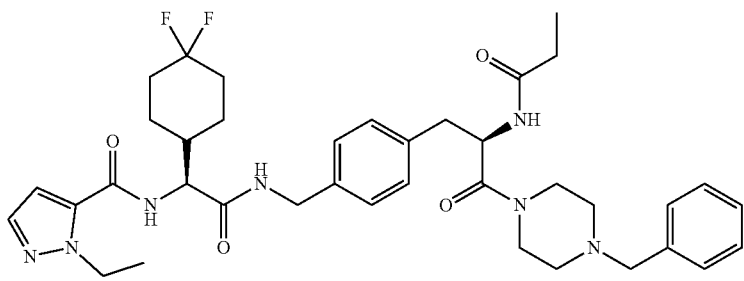 [SMILES: CCC(=O)N[C@H](Cc1ccc(CNC(=O)[C@@H](NC(=O)c2ccnn2CC)C2CCC(F)(F)CC2)cc1)C(=O)N1CCN(Cc2ccccc2)CC1] | 158 |
| 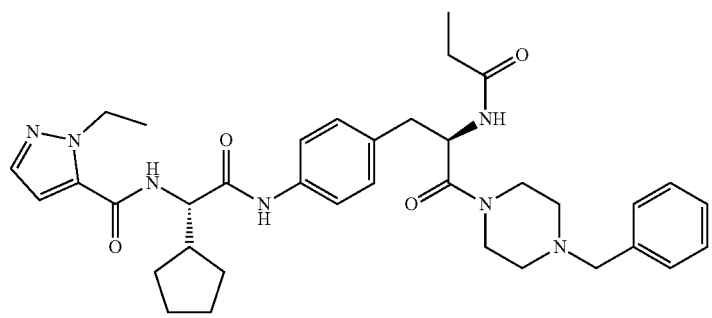 [SMILES: CCC(=O)N[C@H](Cc1ccc(NC(=O)[C@@H](NC(=O)c2ccnn2CC)C2CCCC2)cc1)C(=O)N1CCN(Cc2ccccc2)CC1] | 159 |
| 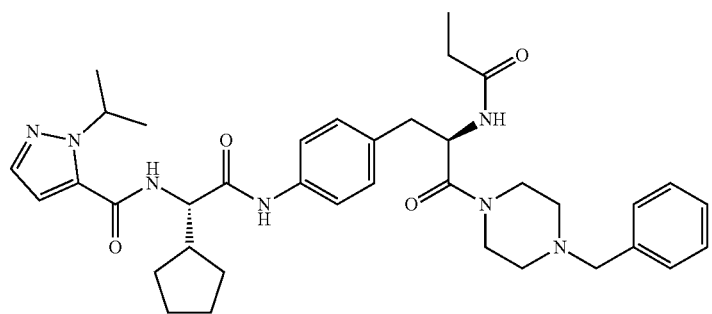 [SMILES: CCC(=O)N[C@H](Cc1ccc(NC(=O)[C@@H](NC(=O)c2ccnn2C(C)C)C2CCCC2)cc1)C(=O)N1CCN(Cc2ccccc2)CC1] | 160 |
| 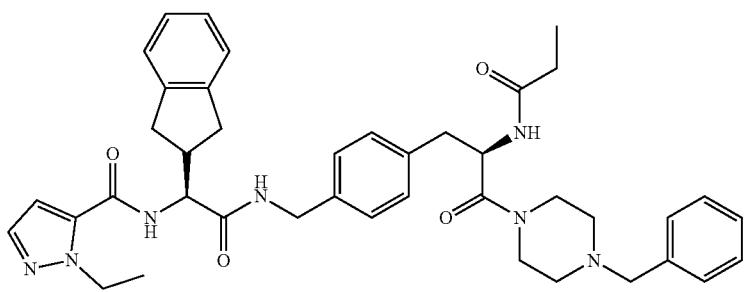 [SMILES: CCC(=O)N[C@H](Cc1ccc(CNC(=O)[C@@H](NC(=O)c2ccnn2CC)C2Cc3ccccc3C2)cc1)C(=O)N1CCN(Cc2ccccc2)CC1] | 161 |
| 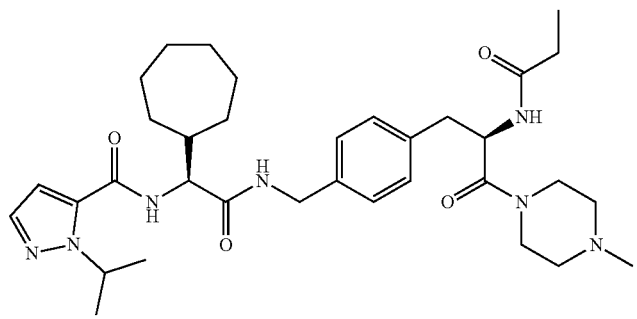 [SMILES: CCC(=O)N[C@H](Cc1ccc(CNC(=O)[C@@H](NC(=O)c2ccnn2C(C)C)C2CCCCCC2)cc1)C(=O)N1CCN(C)CC1] | 162 |

TABLE 1-continued
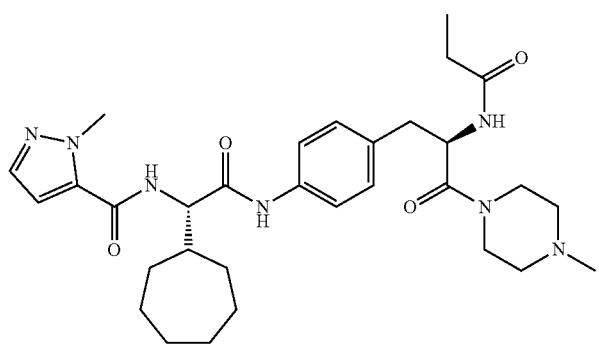 [SMILES: CCC(=O)N[C@H](Cc1ccc(NC(=O)[C@@H](NC(=O)c2ccnn2C)C2CCCCCC2)cc1)C(=O)N1CCN(C)CC1]
163
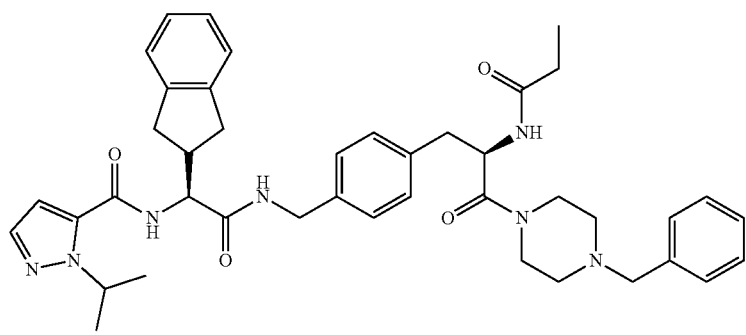 [SMILES: CCC(=O)N[C@H](Cc1ccc(CNC(=O)[C@@H](NC(=O)c2ccnn2C(C)C)C2Cc3ccccc3C2)cc1)C(=O)N1CCN(Cc2ccccc2)CC1]
164
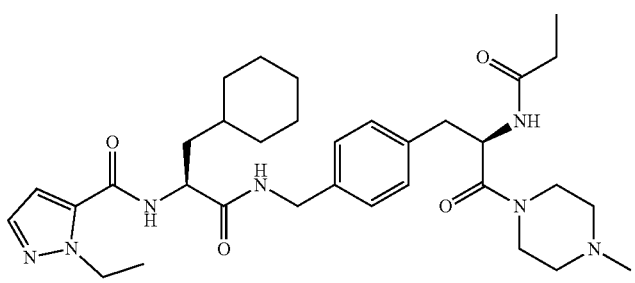 [SMILES: CCC(=O)N[C@H](Cc1ccc(CNC(=O)[C@H](CC2CCCCC2)NC(=O)c2ccnn2CC)cc1)C(=O)N1CCN(C)CC1]
165
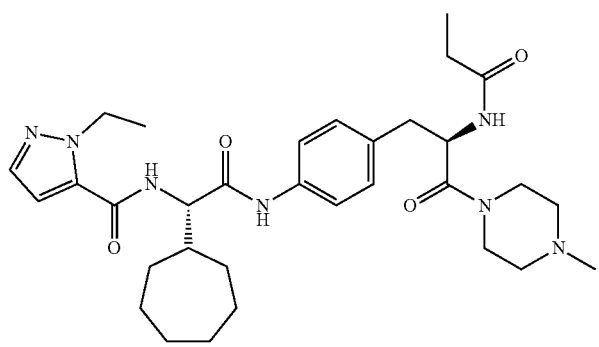 [SMILES: CCC(=O)N[C@H](Cc1ccc(NC(=O)[C@@H](NC(=O)c2ccnn2CC)C2CCCCCC2)cc1)C(=O)N1CCN(C)CC1]
166
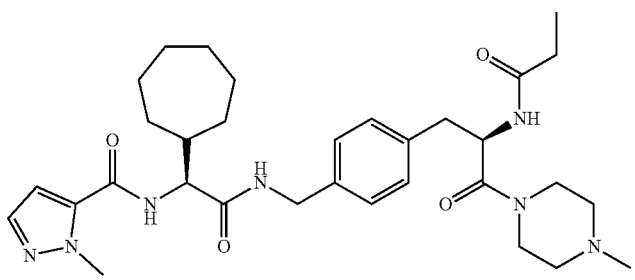
167

TABLE 1-continued
| | |
|---|---|
| 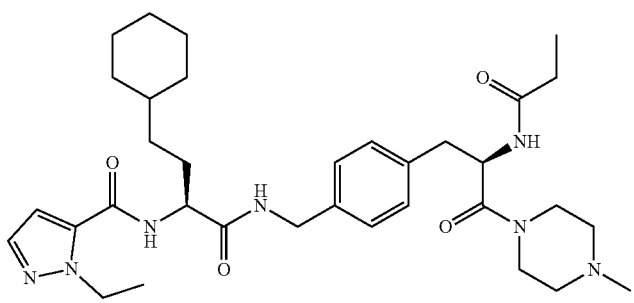 [SMILES: CCC(=O)N[C@H](Cc1ccc(CNC(=O)[C@H](CCC2CCCCC2)NC(=O)c2ccnn2CC)cc1)C(=O)N1CCN(C)CC1] | 168 |
| 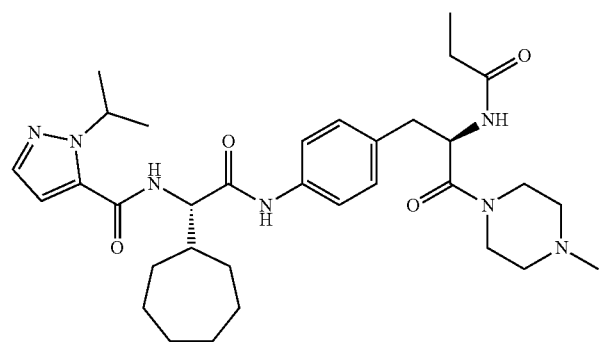 [SMILES: CCC(=O)N[C@H](Cc1ccc(NC(=O)[C@@H](NC(=O)c2ccnn2C(C)C)C2CCCCCC2)cc1)C(=O)N1CCN(C)CC1] | 169 |
| 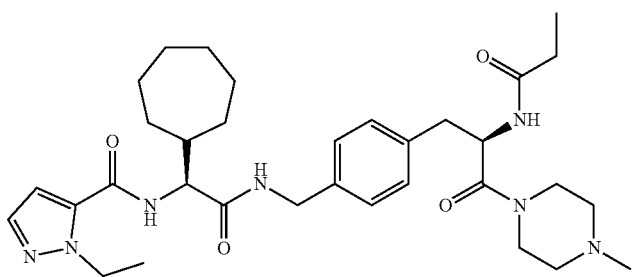 [SMILES: CCC(=O)N[C@H](Cc1ccc(CNC(=O)[C@@H](NC(=O)c2ccnn2CC)C2CCCCCC2)cc1)C(=O)N1CCN(C)CC1] | 170 |
| 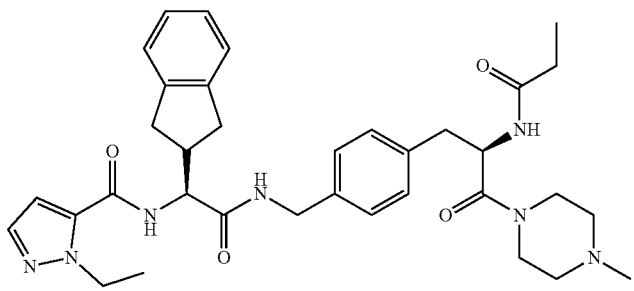 [SMILES: CCC(=O)N[C@H](Cc1ccc(CNC(=O)[C@@H](NC(=O)c2ccnn2CC)C2Cc3ccccc3C2)cc1)C(=O)N1CCN(C)CC1] | 171 |

TABLE 1-continued
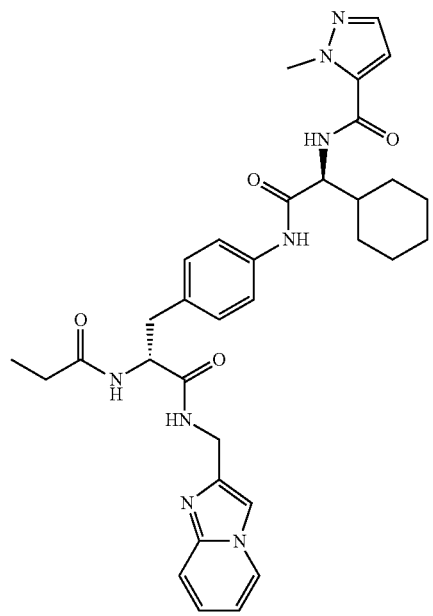 [SMILES: CCC(=O)N[C@H](Cc1ccc(NC(=O)[C@@H](NC(=O)c2ccnn2C)C2CCCCC2)cc1)C(=O)NCc1cn2ccccc2n1]
172
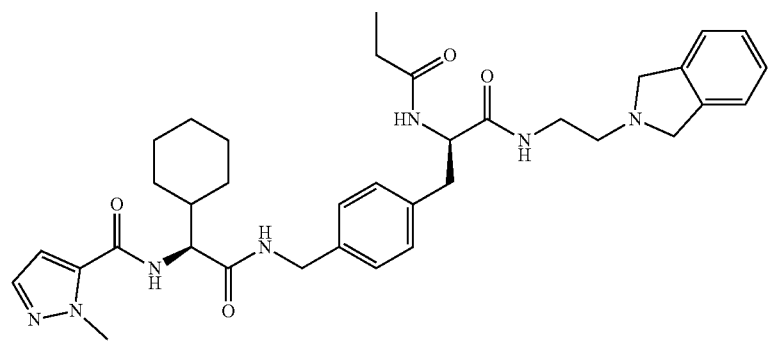 [SMILES: CCC(=O)N[C@H](Cc1ccc(CNC(=O)[C@@H](NC(=O)c2ccnn2C)C2CCCCC2)cc1)C(=O)NCCN1Cc2ccccc2C1]
173
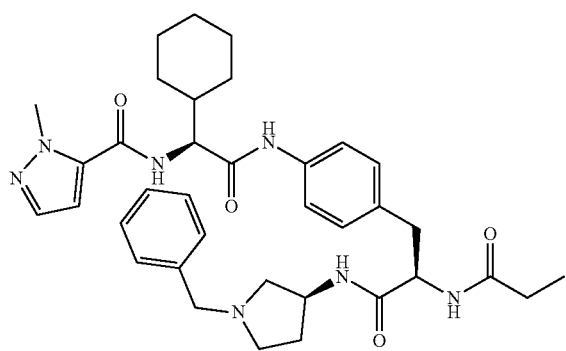 [SMILES: CCC(=O)N[C@H](Cc1ccc(NC(=O)[C@@H](NC(=O)c2ccnn2C)C2CCCCC2)cc1)C(=O)N[C@H]1CCN(Cc2ccccc2)C1]
174

TABLE 1-continued
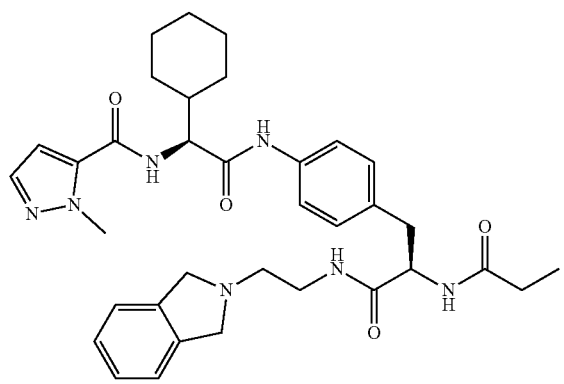 [SMILES: CCC(=O)N[C@H](Cc1ccc(NC(=O)[C@@H](NC(=O)c2ccnn2C)C2CCCCC2)cc1)C(=O)NCCN1Cc2ccccc2C1]
175
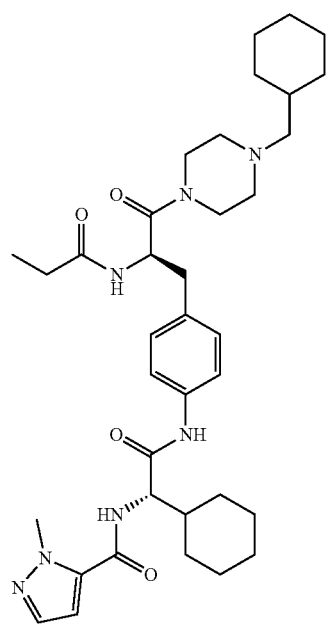 [SMILES: CCC(=O)N[C@H](Cc1ccc(NC(=O)[C@@H](NC(=O)c2ccnn2C)C2CCCCC2)cc1)C(=O)N1CCN(CC2CCCCC2)CC1]
176
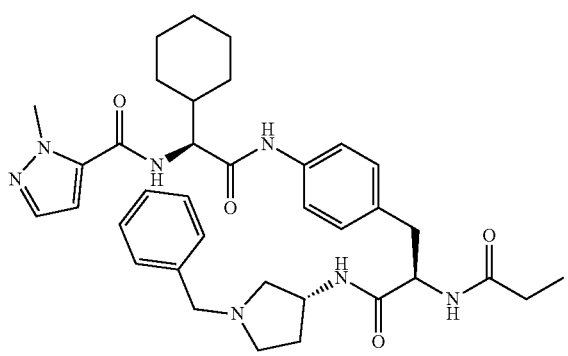 [SMILES: CCC(=O)N[C@H](Cc1ccc(NC(=O)[C@@H](NC(=O)c2ccnn2C)C2CCCCC2)cc1)C(=O)N[C@@H]1CCN(Cc2ccccc2)C1]
177

TABLE 1-continued
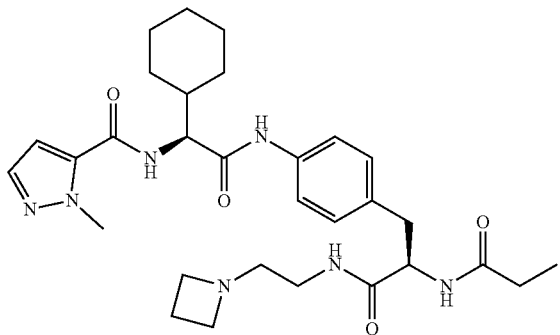 [SMILES: CCC(=O)N[C@H](Cc1ccc(NC(=O)[C@@H](NC(=O)c2ccnn2C)C2CCCCC2)cc1)C(=O)NCCN1CCC1]
178
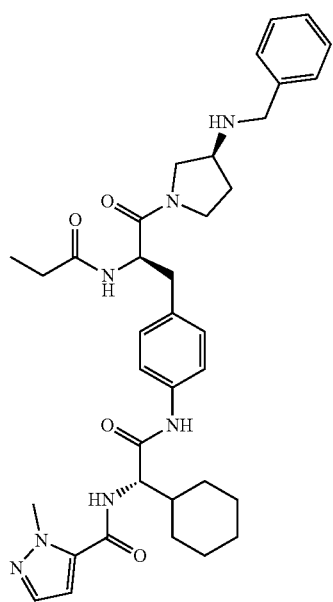 [SMILES: CCC(=O)N[C@H](Cc1ccc(NC(=O)[C@@H](NC(=O)c2ccnn2C)C2CCCCC2)cc1)C(=O)N1CC[C@H](NCc2ccccc2)C1]
179
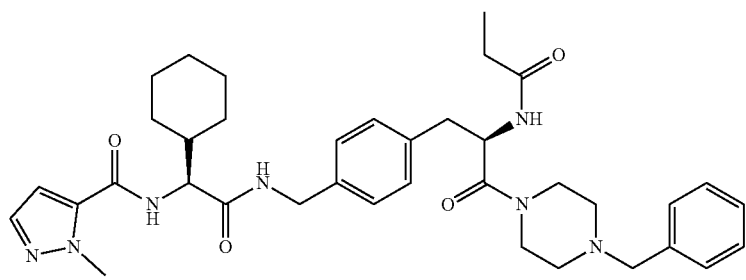 [SMILES: CCC(=O)N[C@H](Cc1ccc(CNC(=O)[C@@H](NC(=O)c2ccnn2C)C2CCCCC2)cc1)C(=O)N1CCN(Cc2ccccc2)CC1]
180
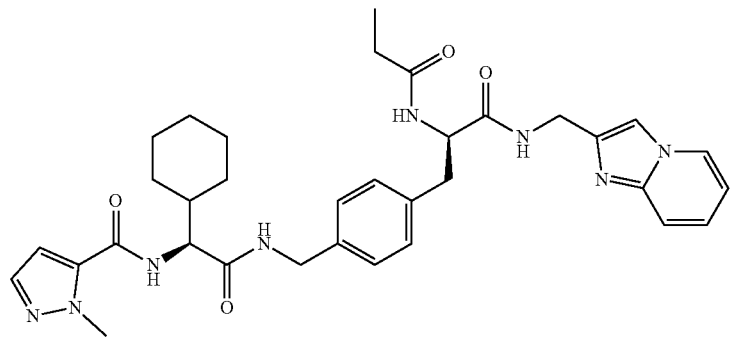 [SMILES: CCC(=O)N[C@H](Cc1ccc(CNC(=O)[C@@H](NC(=O)c2ccnn2C)C2CCCCC2)cc1)C(=O)NCc1cn2ccccc2n1]
181

TABLE 1-continued
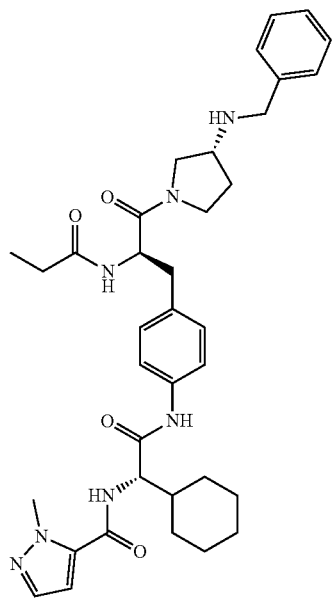 [SMILES: CCC(=O)N[C@H](Cc1ccc(NC(=O)[C@@H](NC(=O)c2ccnn2C)C2CCCCC2)cc1)C(=O)N1CC[C@@H](NCc2ccccc2)C1]
182
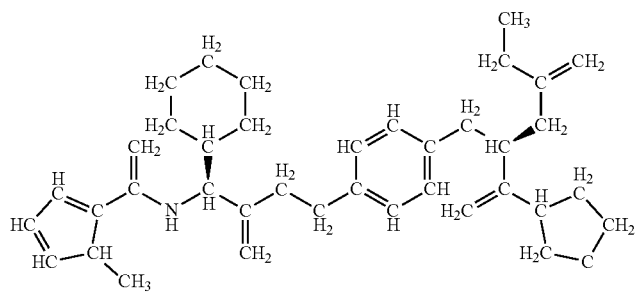 [SMILES: C=C(CC)C[C@H](Cc1ccc(CCC(=C)[C@@H](NC(=C)C2=CC=CC2C)C2CCCCC2)cc1)C(=C)C1CCCC1]
183
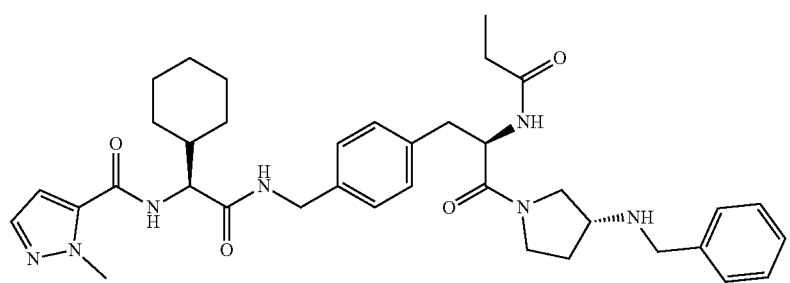 [SMILES: CCC(=O)N[C@H](Cc1ccc(CNC(=O)[C@@H](NC(=O)c2ccnn2C)C2CCCCC2)cc1)C(=O)N1CC[C@@H](NCc2ccccc2)C1]
184

TABLE 1-continued
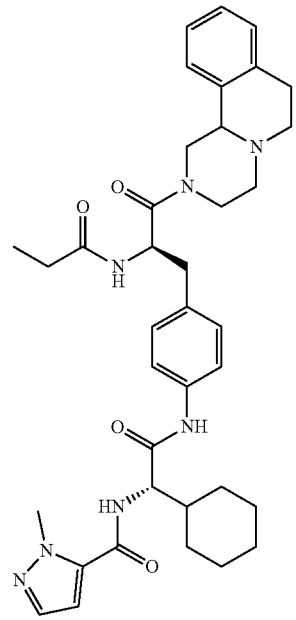 [SMILES: CCC(=O)N[C@H](Cc1ccc(NC(=O)[C@@H](NC(=O)c2ccnn2C)C2CCCCC2)cc1)C(=O)N1CCN2CCc3ccccc3C2C1]
185
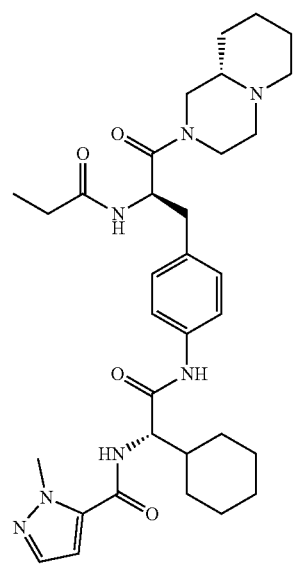 [SMILES: CCC(=O)N[C@H](Cc1ccc(NC(=O)[C@@H](NC(=O)c2ccnn2C)C2CCCCC2)cc1)C(=O)N1CCN2CCCC[C@H]2C1]
186

TABLE 1-continued
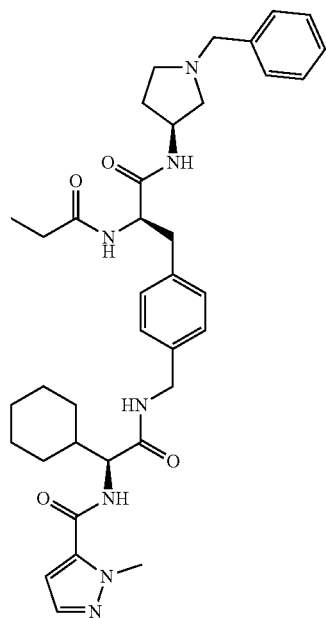 [SMILES: CCC(=O)N[C@H](Cc1ccc(CNC(=O)[C@@H](NC(=O)c2ccnn2C)C2CCCCC2)cc1)C(=O)N[C@H]1CCN(Cc2ccccc2)C1]
187
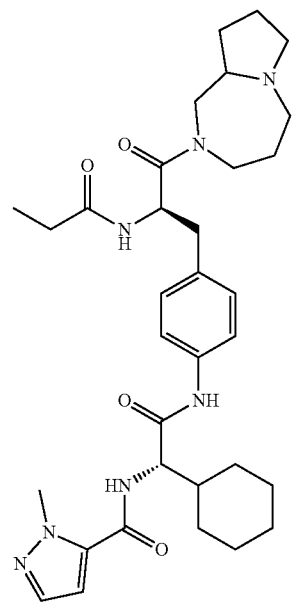 [SMILES: CCC(=O)N[C@H](Cc1ccc(NC(=O)[C@@H](NC(=O)c2ccnn2C)C2CCCCC2)cc1)C(=O)N1CCCN2CCCC2C1]
188

TABLE 1-continued
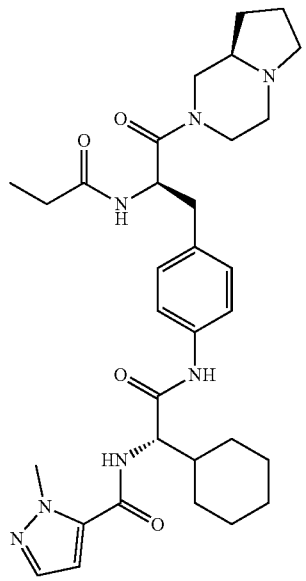 [SMILES: CCC(=O)N[C@H](Cc1ccc(NC(=O)[C@@H](NC(=O)c2ccnn2C)C2CCCCC2)cc1)C(=O)N1CCN2CCC[C@@H]2C1]
189
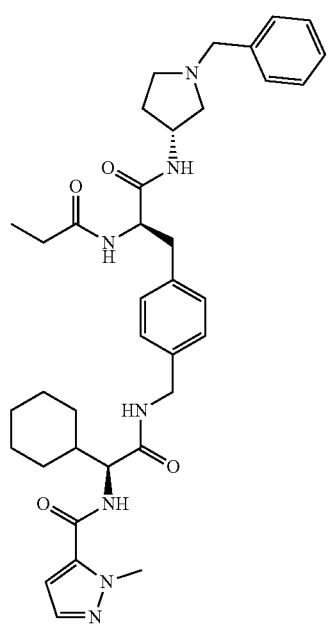 [SMILES: CCC(=O)N[C@H](Cc1ccc(CNC(=O)[C@@H](NC(=O)c2ccnn2C)C2CCCCC2)cc1)C(=O)N[C@@H]1CCN(Cc2ccccc2)C1]
190

TABLE 1-continued
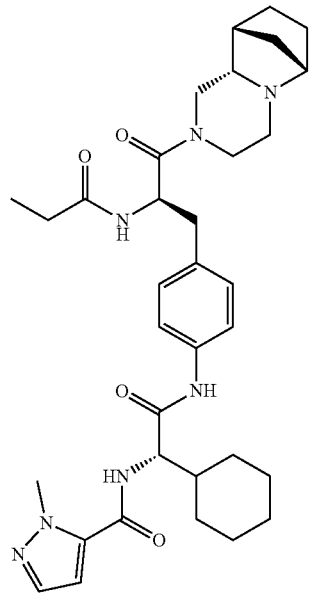 [SMILES: CCC(=O)N[C@H](Cc1ccc(NC(=O)[C@@H](NC(=O)c2ccnn2C)C2CCCCC2)cc1)C(=O)N1CCN2[C@H]3CC[C@H](C3)[C@H]2C1]
191
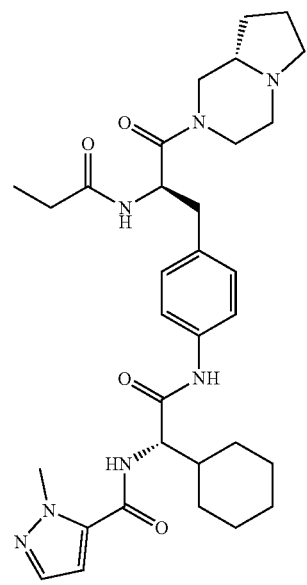 [SMILES: CCC(=O)N[C@H](Cc1ccc(NC(=O)[C@@H](NC(=O)c2ccnn2C)C2CCCCC2)cc1)C(=O)N1CCN2CCC[C@H]2C1]
192

TABLE 1-continued
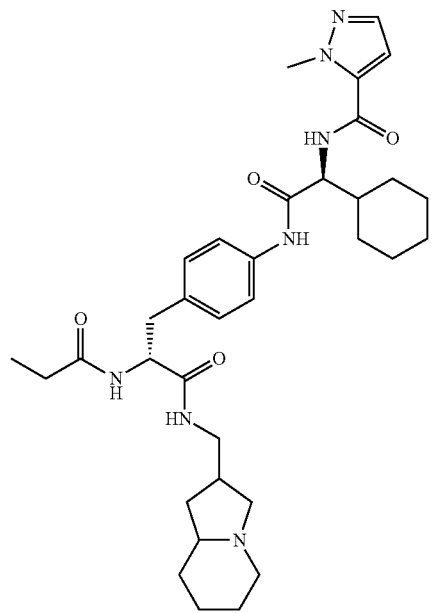 [SMILES: CCC(=O)N[C@H](Cc1ccc(NC(=O)[C@@H](NC(=O)c2ccnn2C)C2CCCCC2)cc1)C(=O)NCC1CC2CCCCN2C1]
193
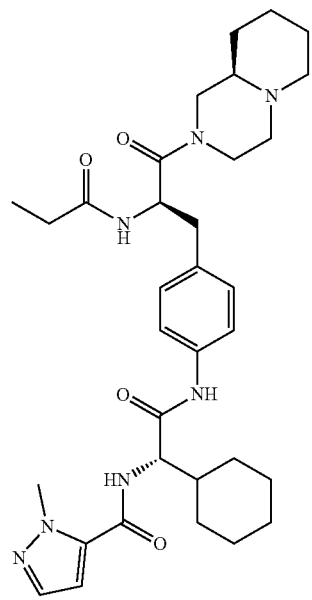
194
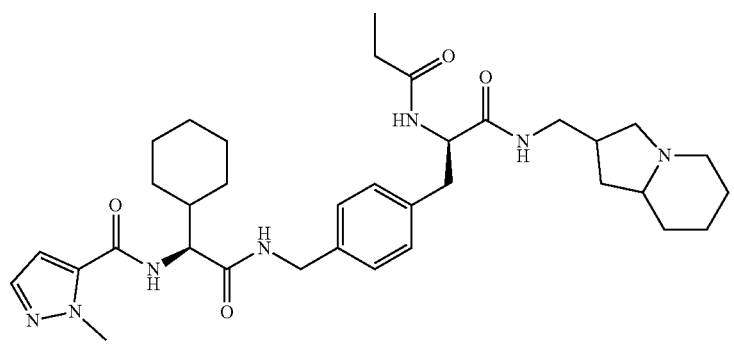 [SMILES: CCC(=O)N[C@H](Cc1ccc(CNC(=O)[C@@H](NC(=O)c2ccnn2C)C2CCCCC2)cc1)C(=O)NCC1CC2CCCCN2C1]
195

TABLE 1-continued
| | |
|---|---|
| 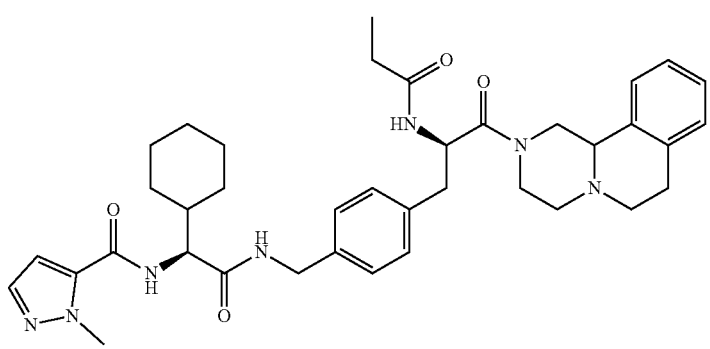 [SMILES: CCC(=O)N[C@H](Cc1ccc(CNC(=O)[C@@H](NC(=O)c2ccnn2C)C2CCCCC2)cc1)C(=O)N1CCN2CCc3ccccc3C2C1] | 196 |
| 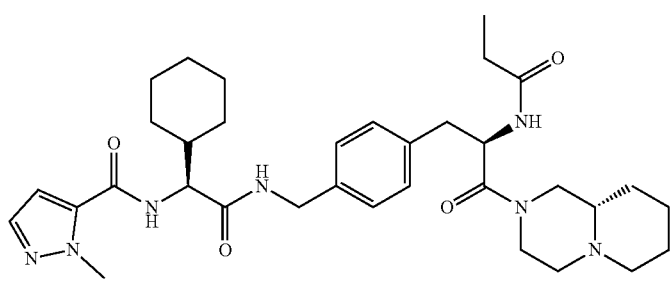 [SMILES: CCC(=O)N[C@H](Cc1ccc(CNC(=O)[C@@H](NC(=O)c2ccnn2C)C2CCCCC2)cc1)C(=O)N1CCN2CCCC[C@H]2C1] | 197 |
| 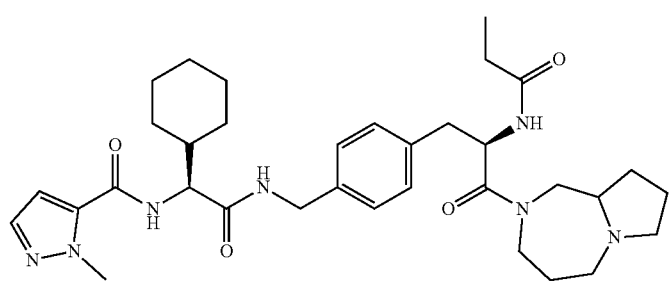 [SMILES: CCC(=O)N[C@H](Cc1ccc(CNC(=O)[C@@H](NC(=O)c2ccnn2C)C2CCCCC2)cc1)C(=O)N1CCCN2CCCC2C1] | 198 |
| 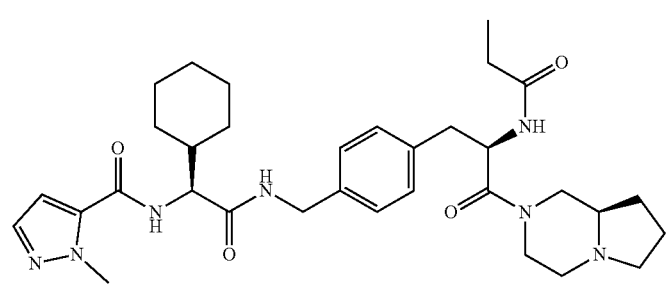 [SMILES: CCC(=O)N[C@H](Cc1ccc(CNC(=O)[C@@H](NC(=O)c2ccnn2C)C2CCCCC2)cc1)C(=O)N1CCN2CCC[C@@H]2C1] | 199 |
| 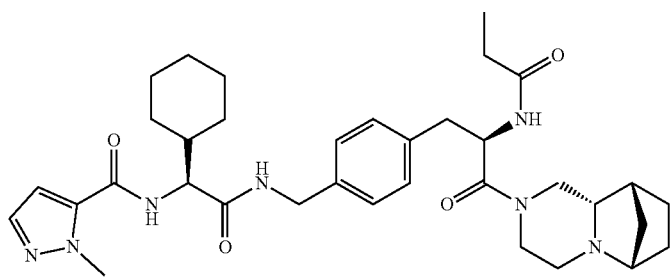 [SMILES: CCC(=O)N[C@H](Cc1ccc(CNC(=O)[C@@H](NC(=O)c2ccnn2C)C2CCCCC2)cc1)C(=O)N1CCN2[C@H]3CC[C@H](C3)[C@H]2C1] | 200 |

TABLE 1-continued
| | |
|---|---|
| 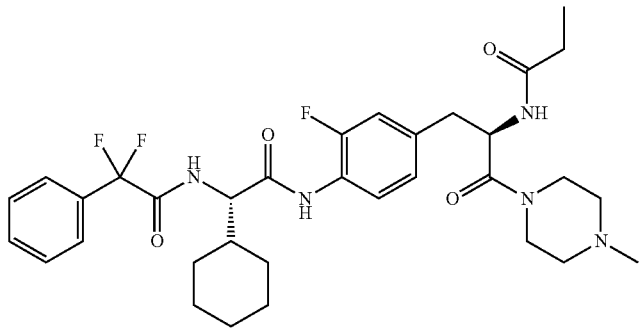 [SMILES: CCC(=O)N[C@H](Cc1ccc(NC(=O)[C@@H](NC(=O)C(F)(F)c2ccccc2)C2CCCCC2)c(F)c1)C(=O)N1CCN(C)CC1] | 201 |
| 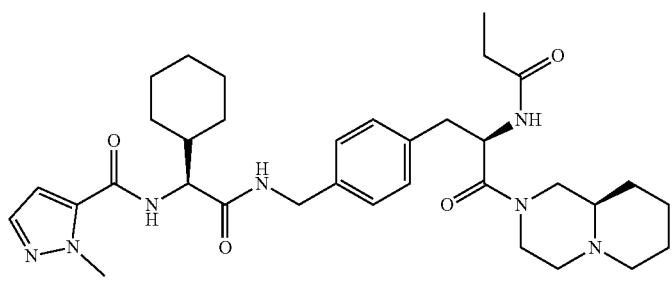 [SMILES: CCC(=O)N[C@H](Cc1ccc(CNC(=O)[C@@H](NC(=O)c2ccnn2C)C2CCCCC2)cc1)C(=O)N1CCN2CCCC[C@@H]2C1] | 202 |
| 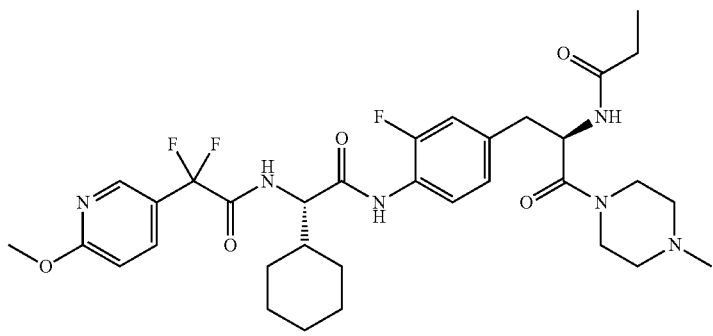 | 203 |
| 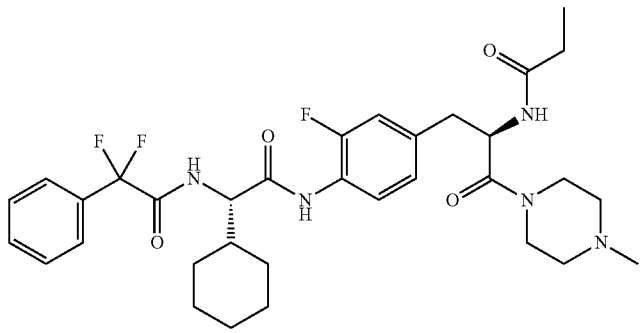 [SMILES: CCC(=O)N[C@H](Cc1ccc(NC(=O)[C@@H](NC(=O)C(F)(F)c2ccccc2)C2CCCCC2)c(F)c1)C(=O)N1CCN(C)CC1] | 204 |
| 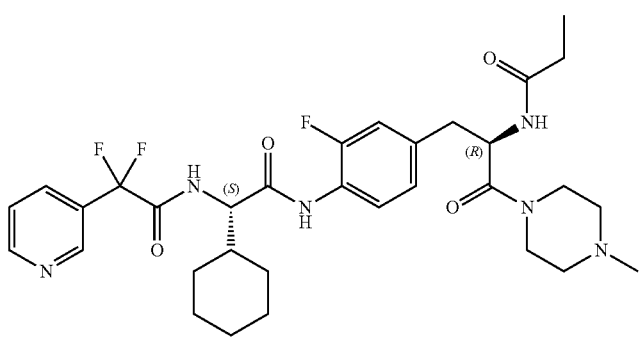 | 205 |

TABLE 1-continued
206
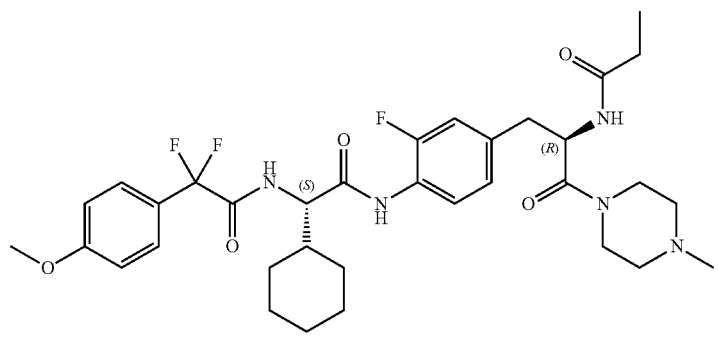
207
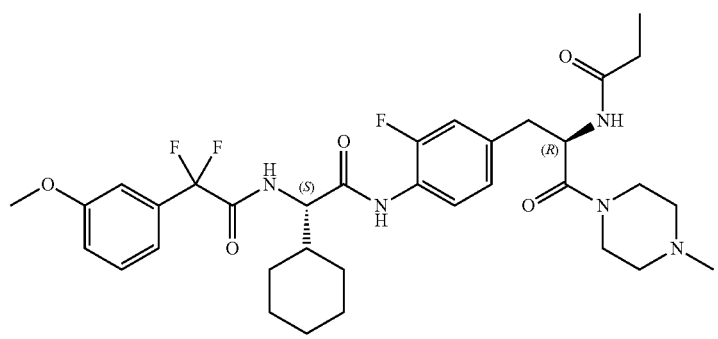
208
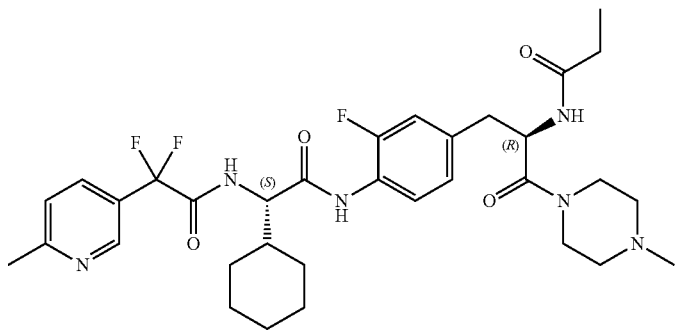
209
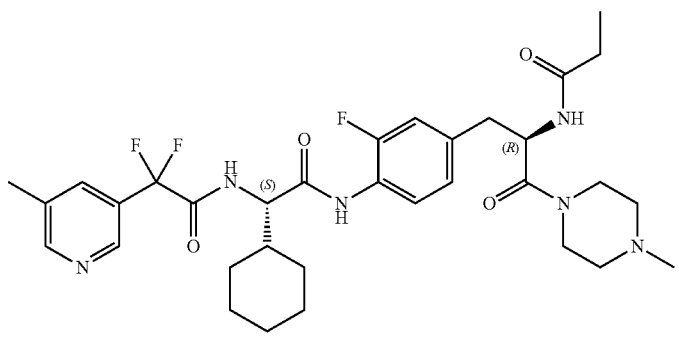

TABLE 1-continued
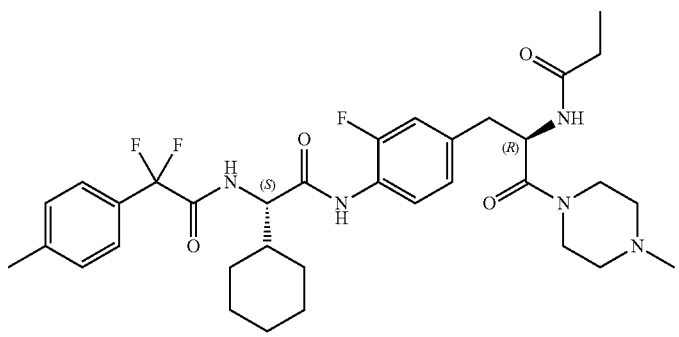
210
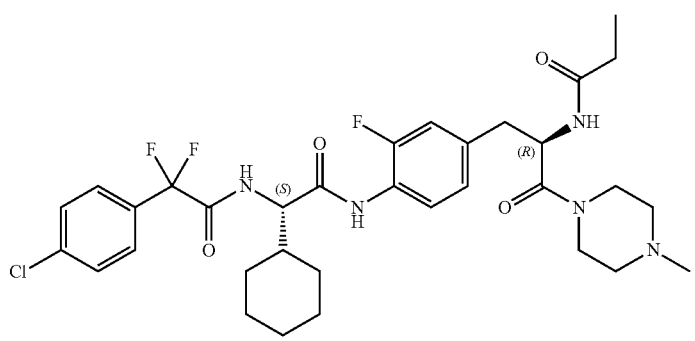
211
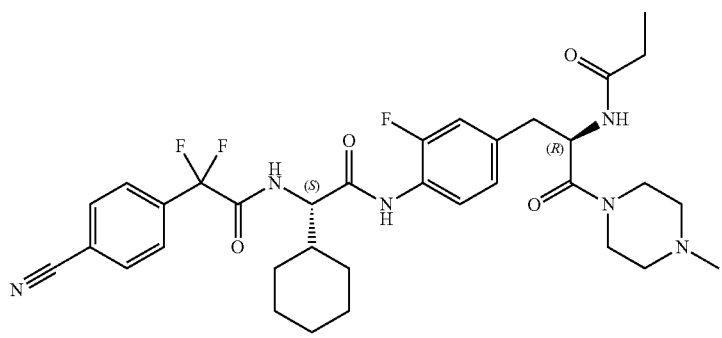
212
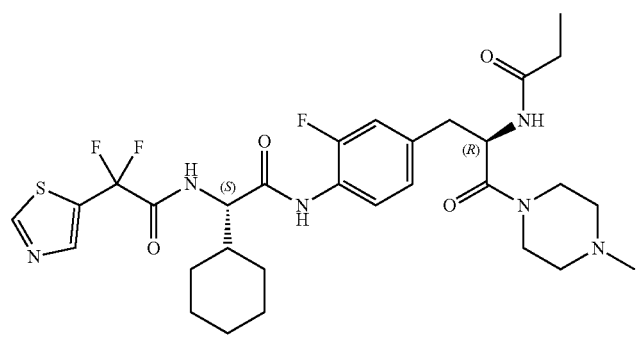
213

TABLE 1-continued
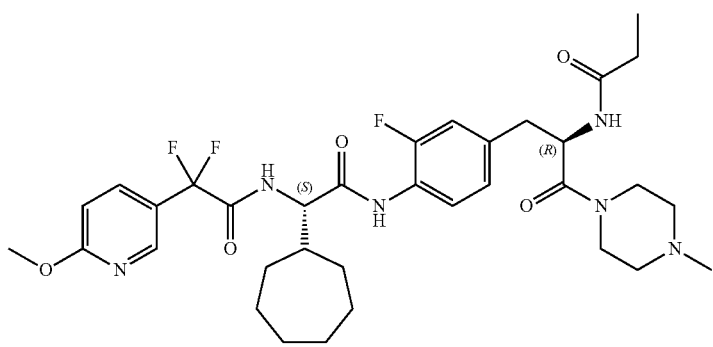
214
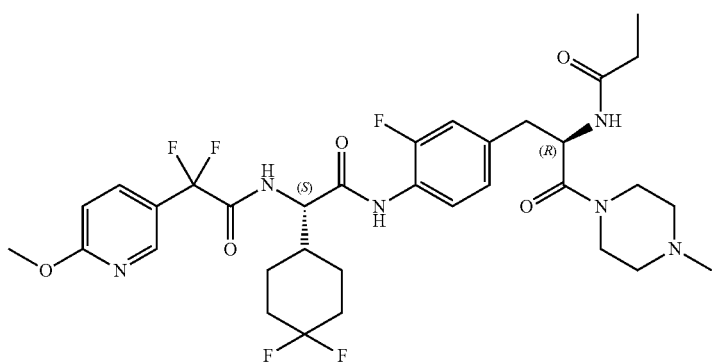
215
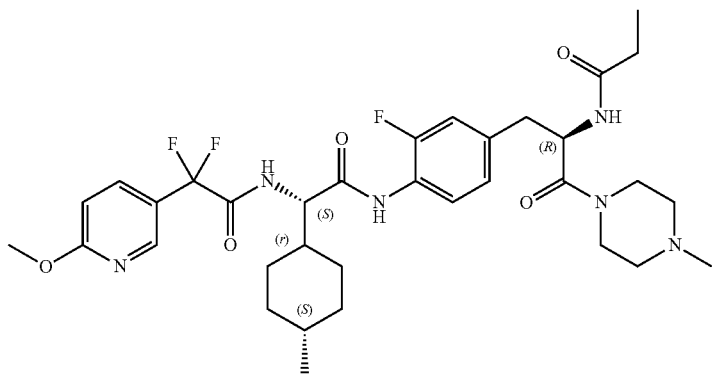
216
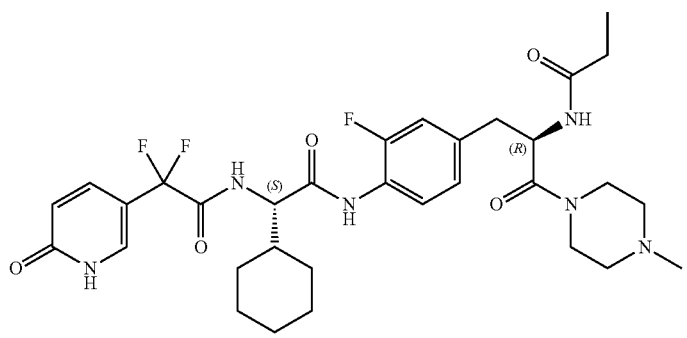
217

TABLE 1-continued
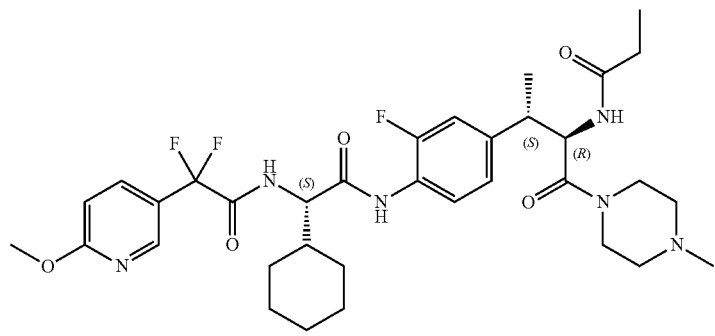
218
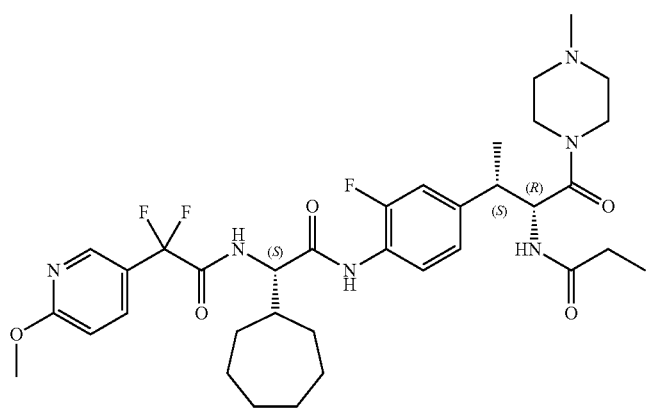
219
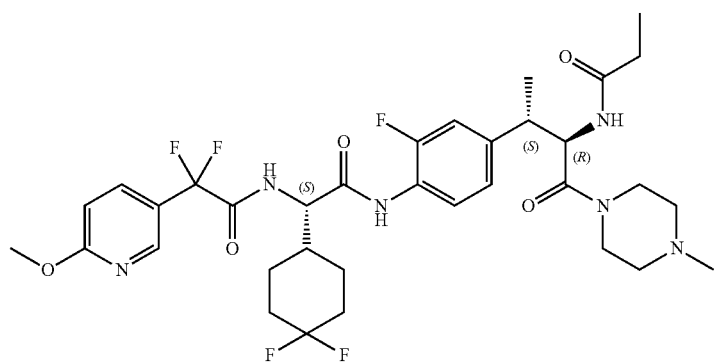
220
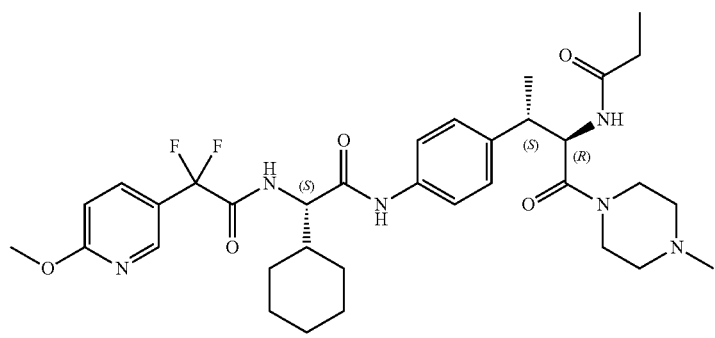
221

TABLE 1-continued
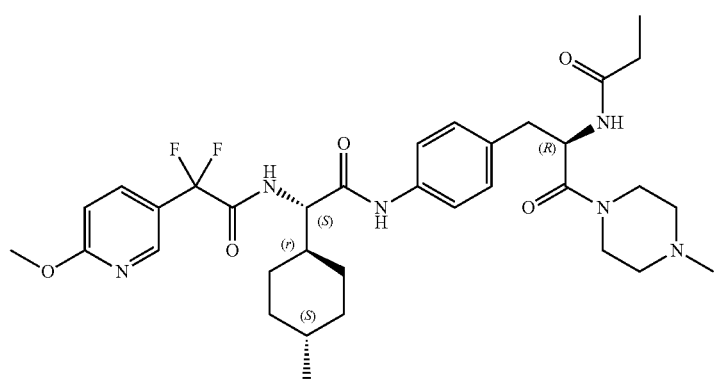
222
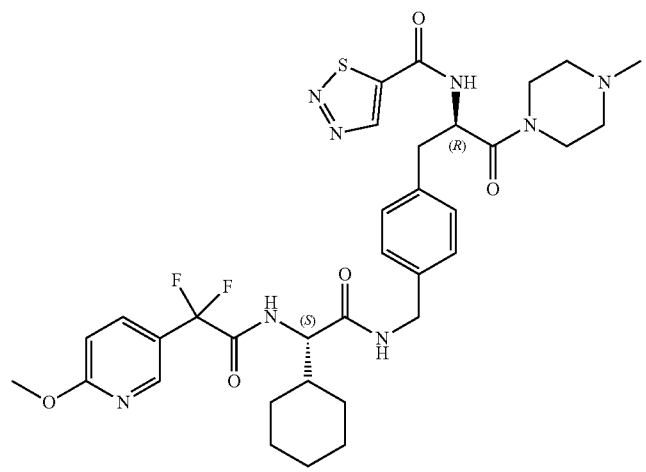
223
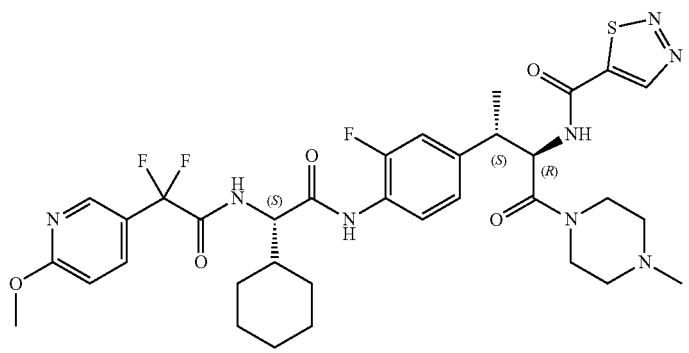
224
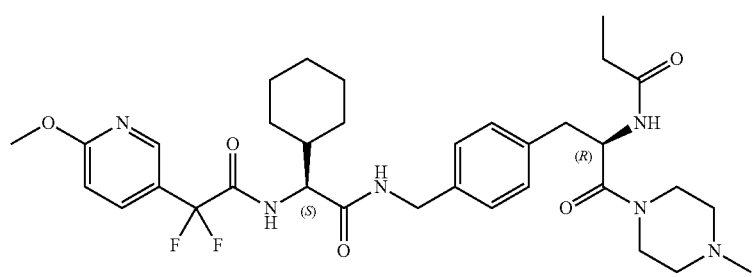
225

TABLE 1-continued
226
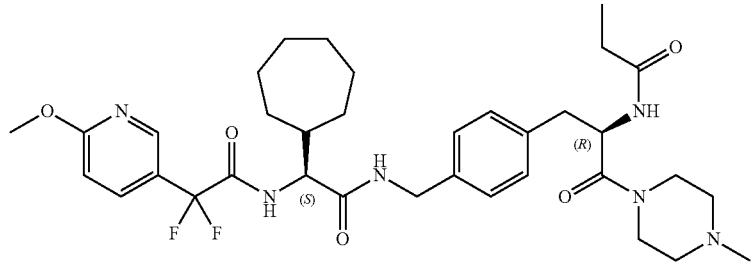
227
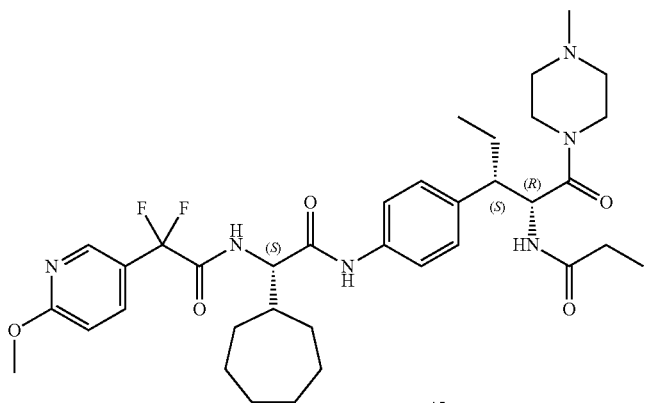
228
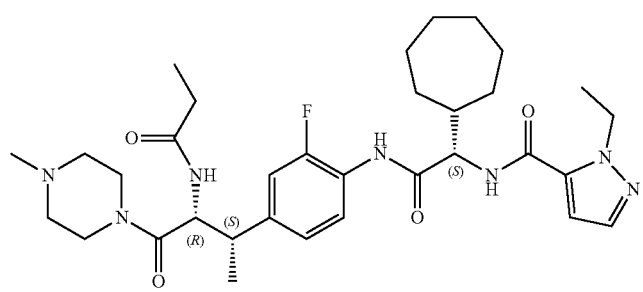
229
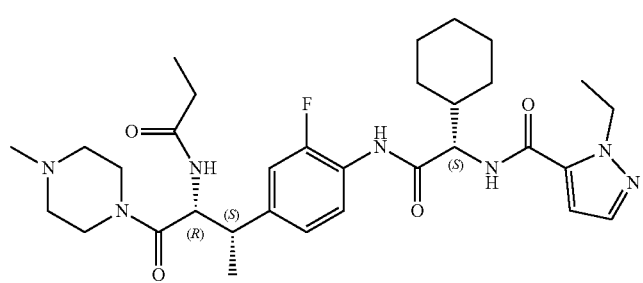
230
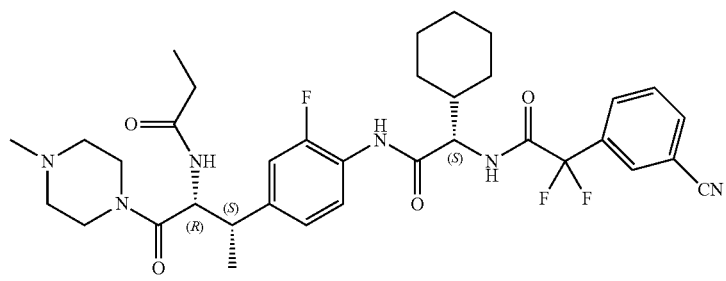

TABLE 1-continued
| | |
|---|---|
| 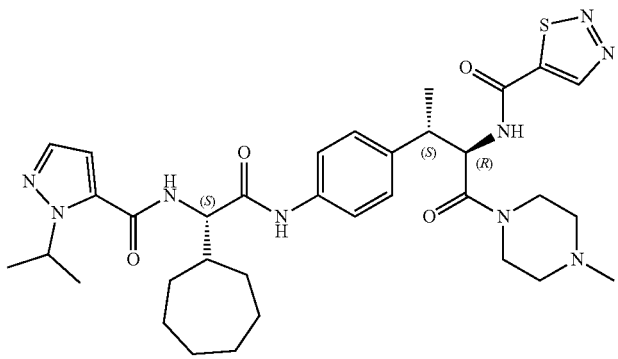 | 231 |
| 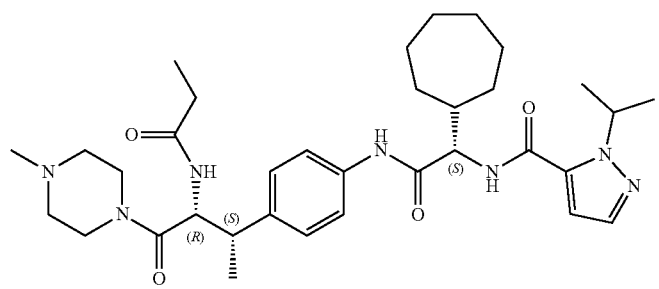 | 232 |
| 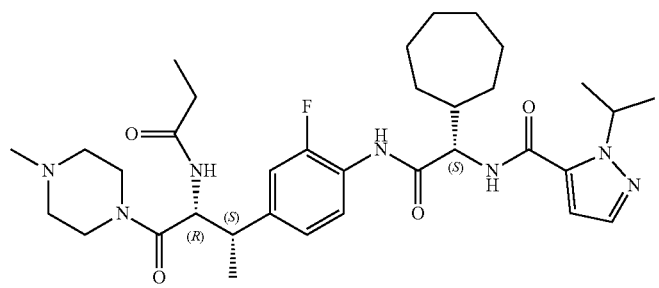 | 233 |
| 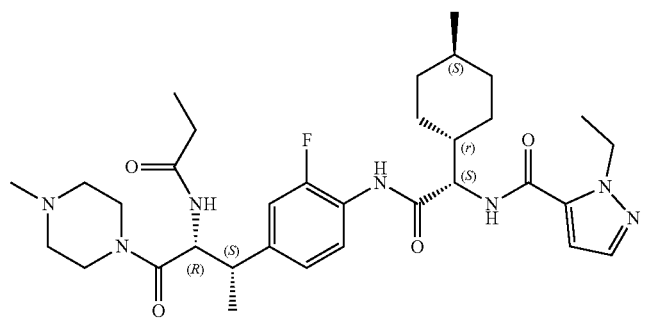 | 234 |
| 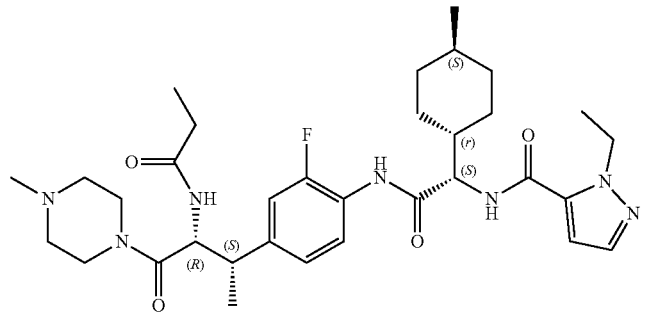 | 235 |

TABLE 1-continued
236
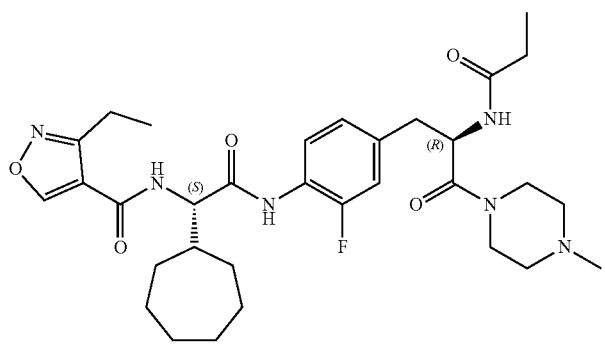
237
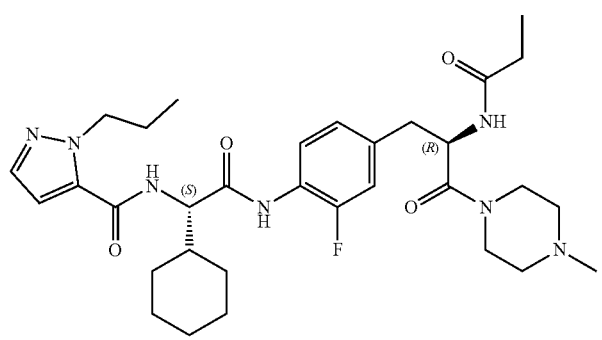
238
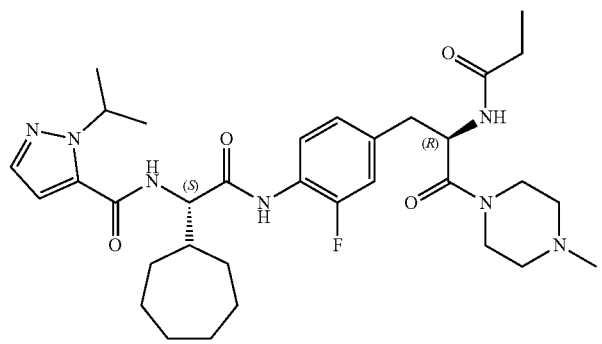
239
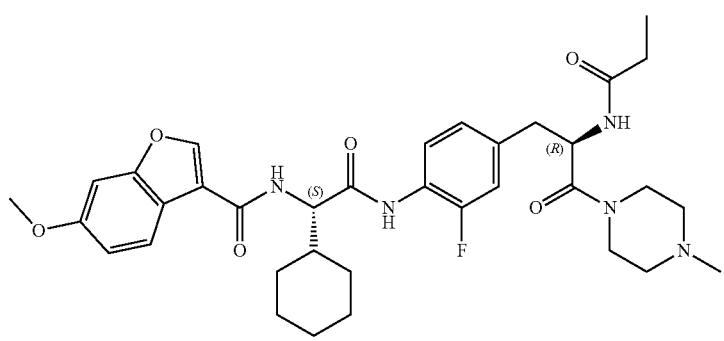

TABLE 1-continued
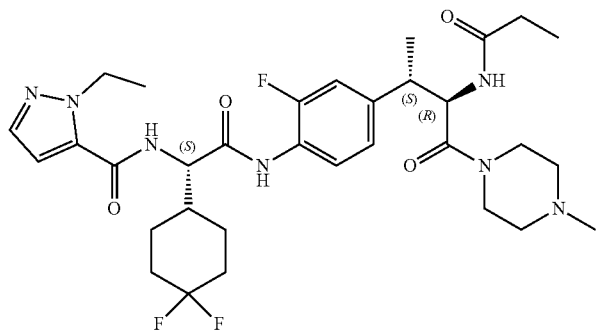
240
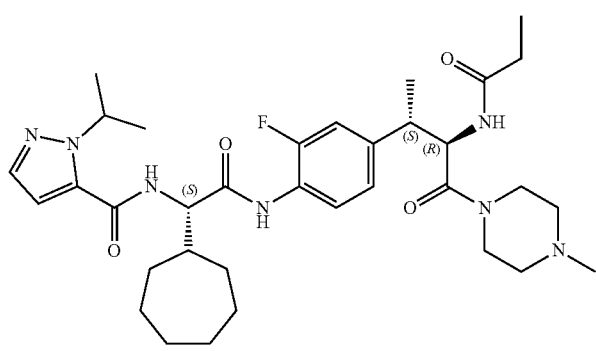
241
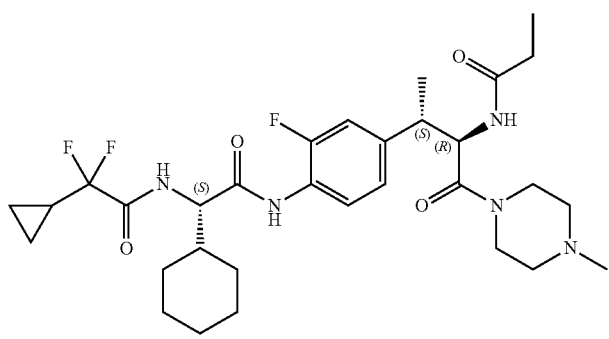
242
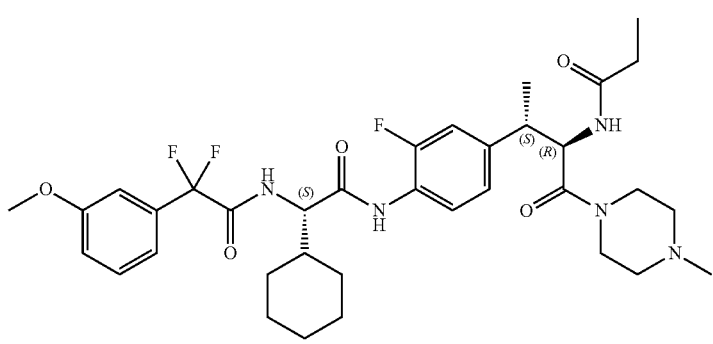
243

TABLE 1-continued
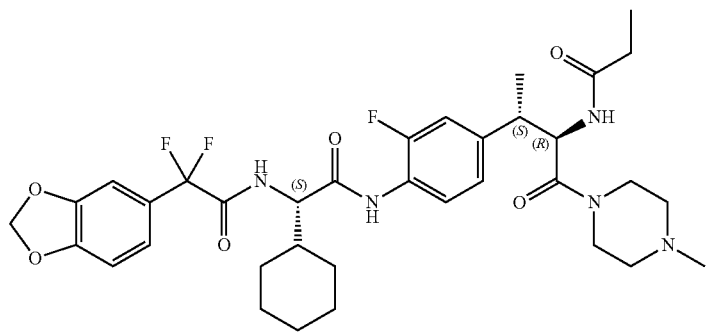
244
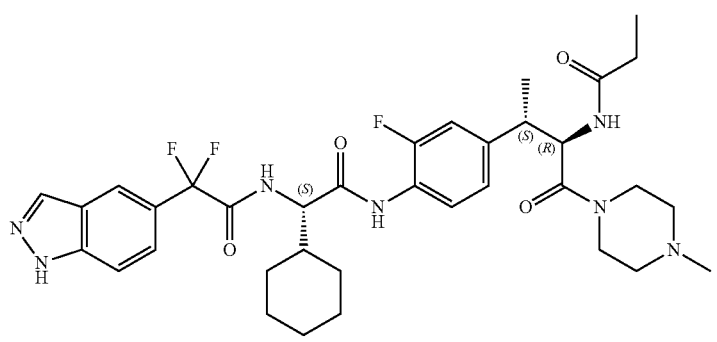
245
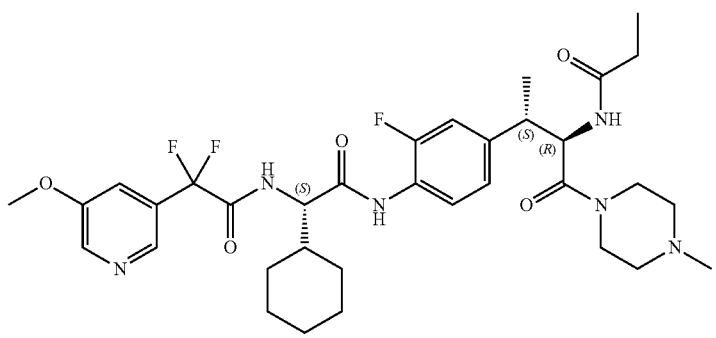
246
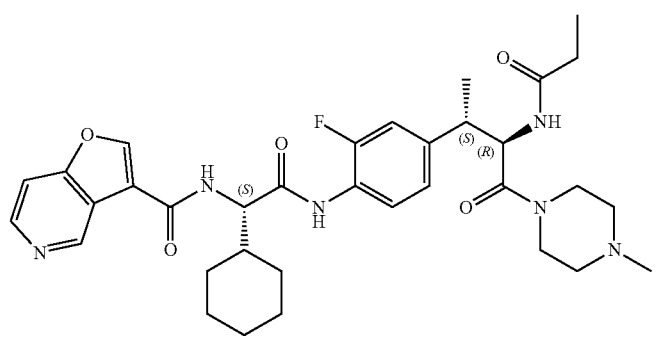
247

TABLE 1-continued
| | |
|---|---|
| 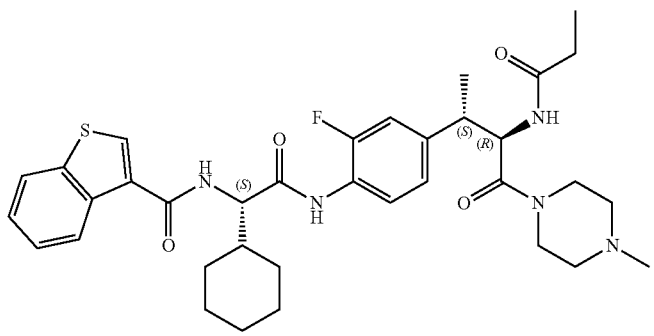 | 248 |
| 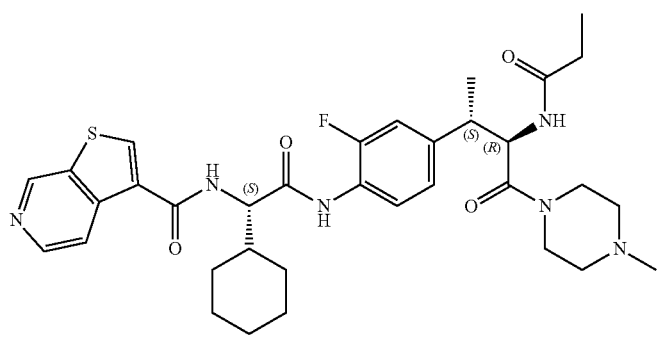 | 249 |
| 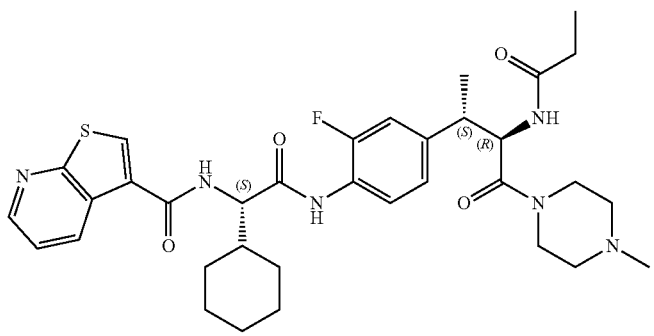 | 250 |
| 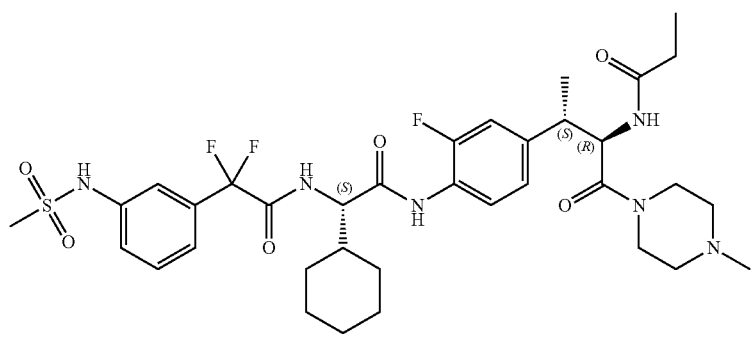 | 251 |

TABLE 1-continued
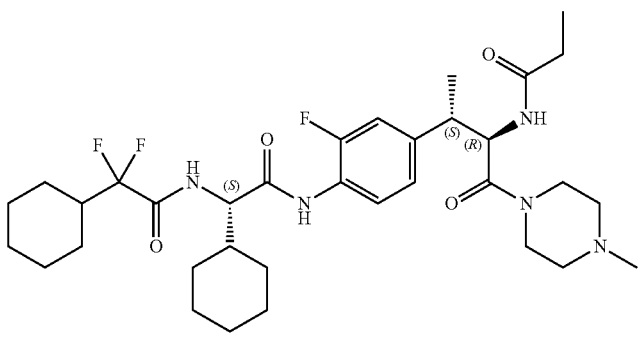
252
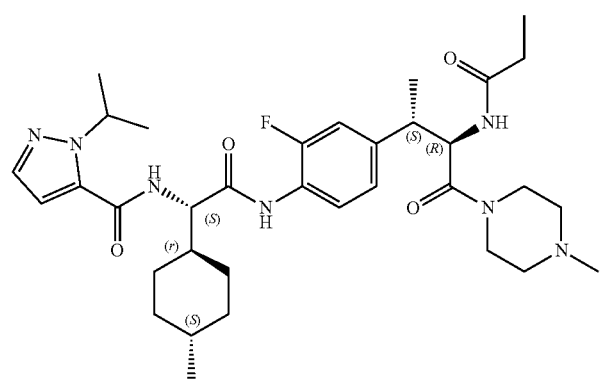
253
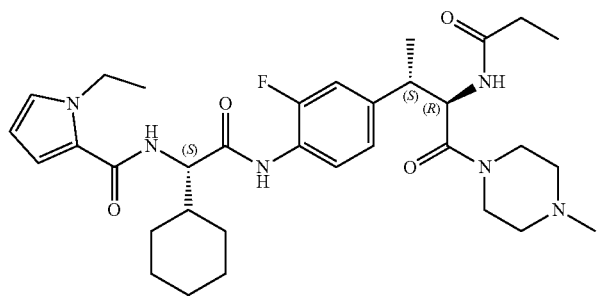
254
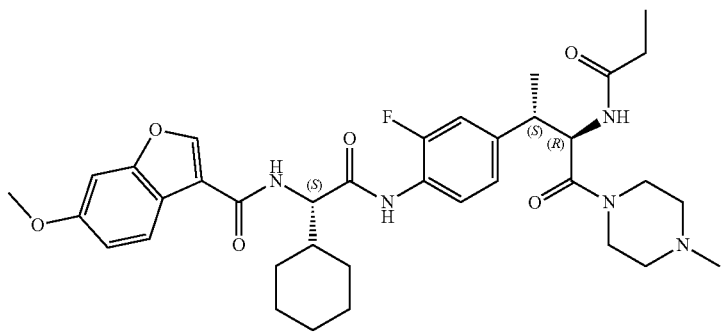
255
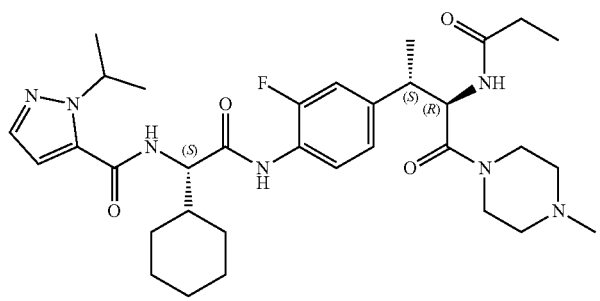
256

TABLE 1-continued
257
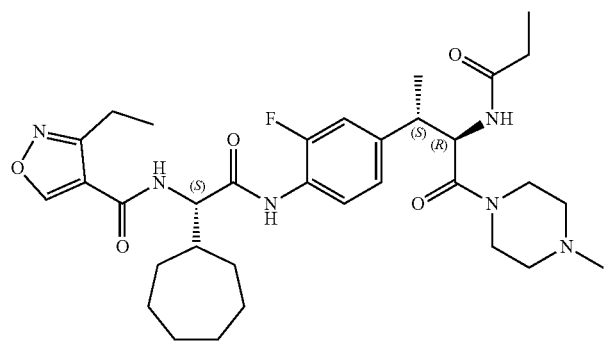
258
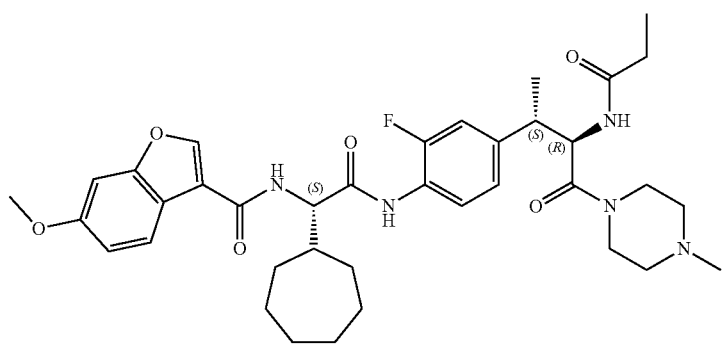
259
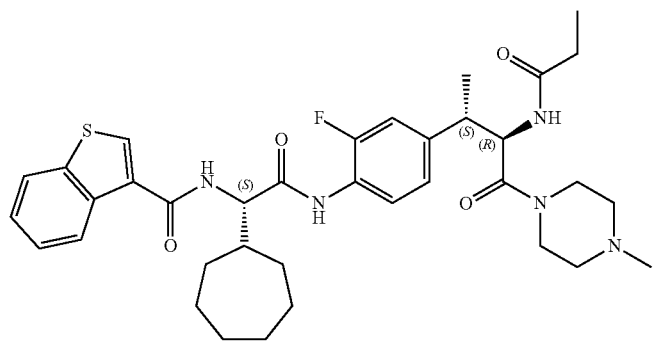
260
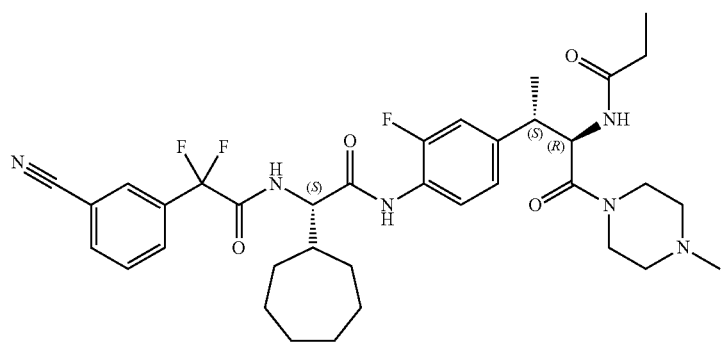

TABLE 1-continued
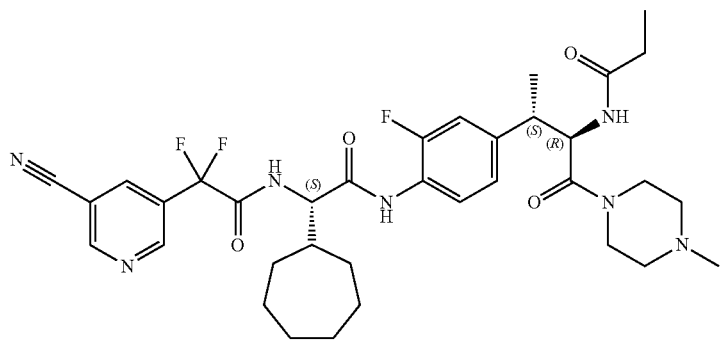
261
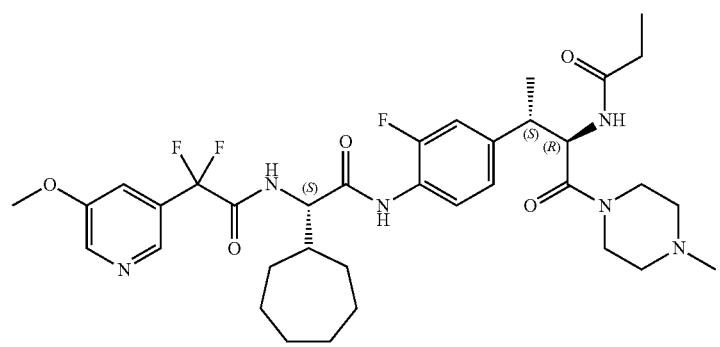
262
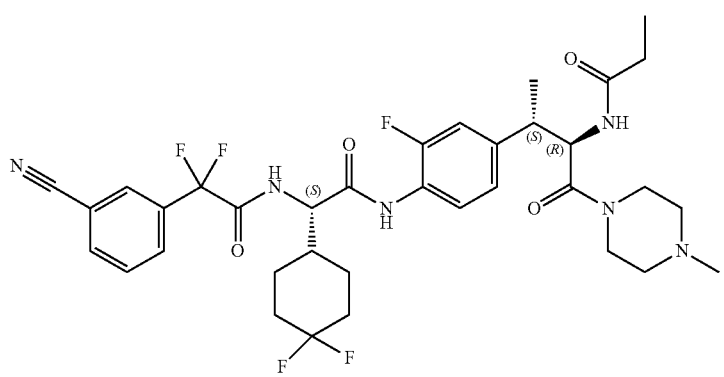
263
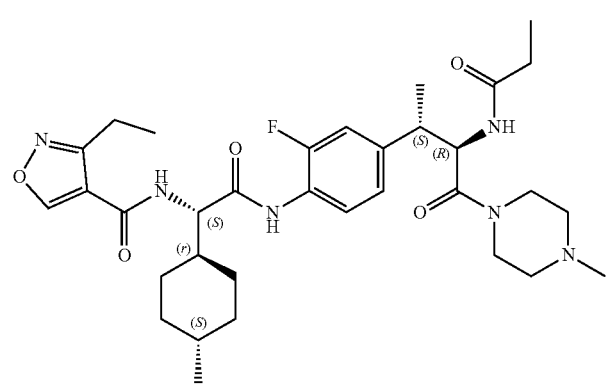
264

TABLE 1-continued
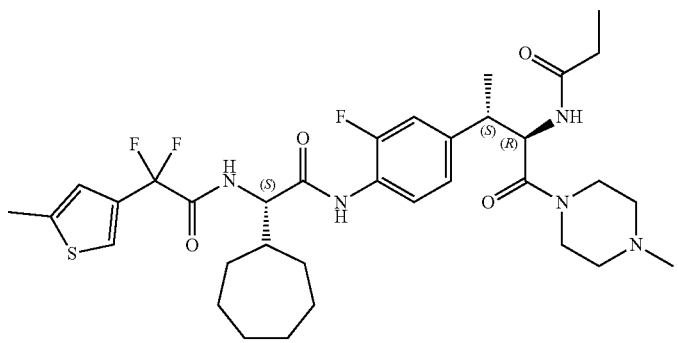
265
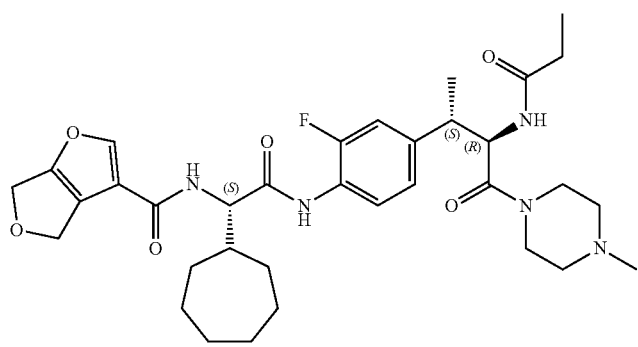
266
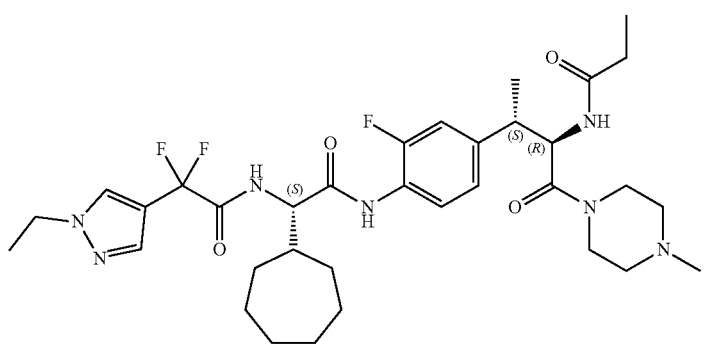
267
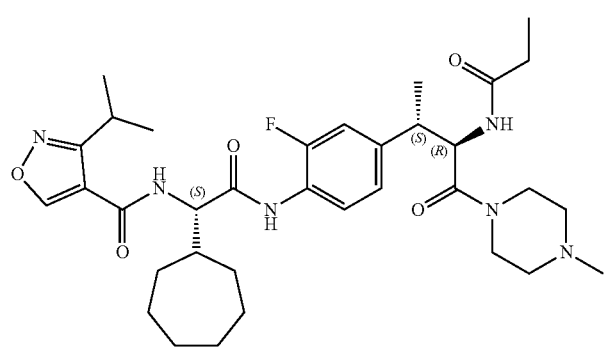
268

TABLE 1-continued
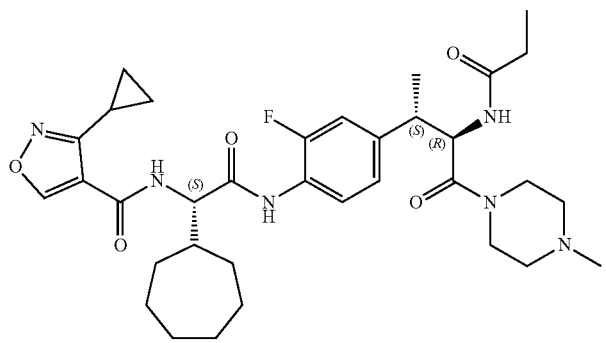
269
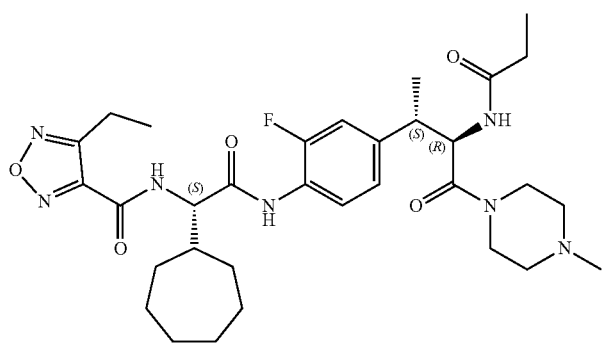
270
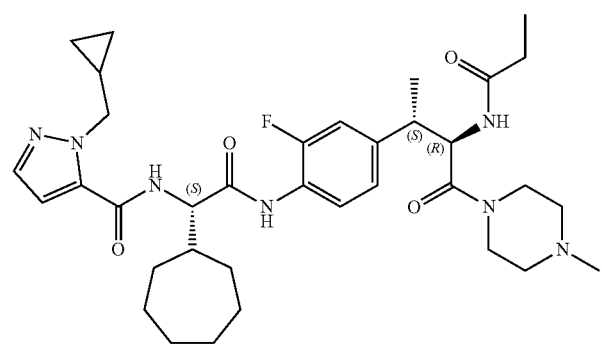
271
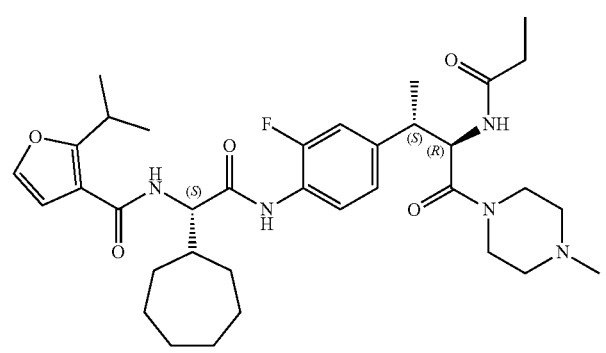
272

TABLE 1-continued
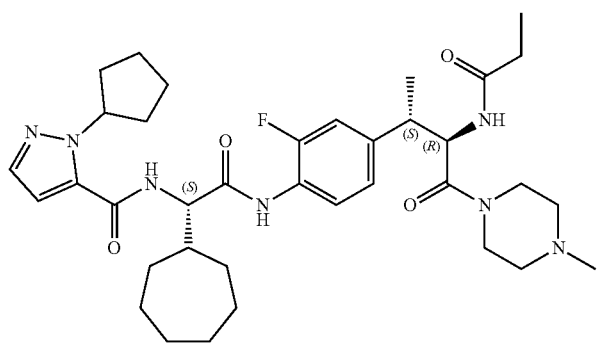
273
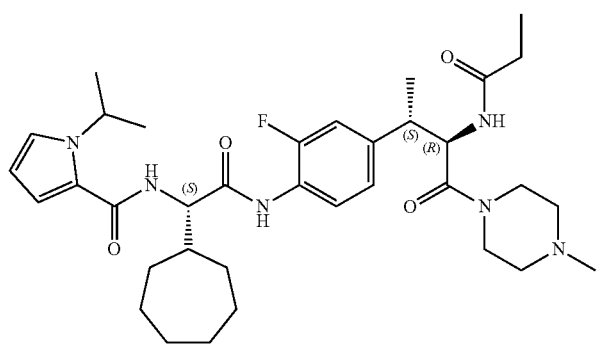
274
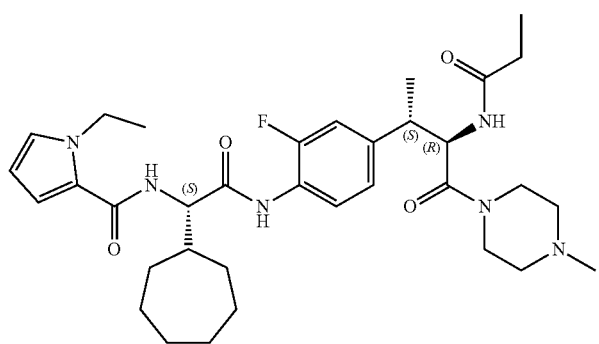
275
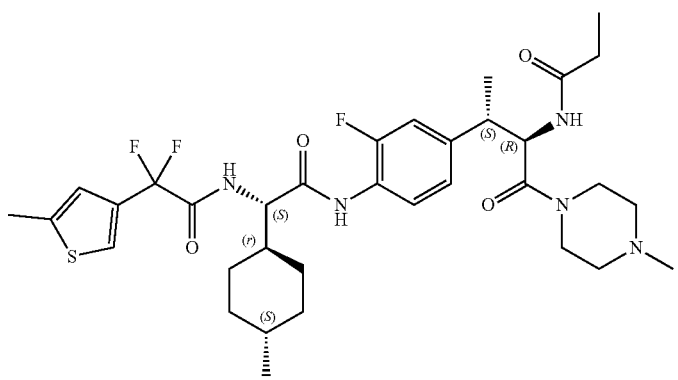
276

TABLE 1-continued
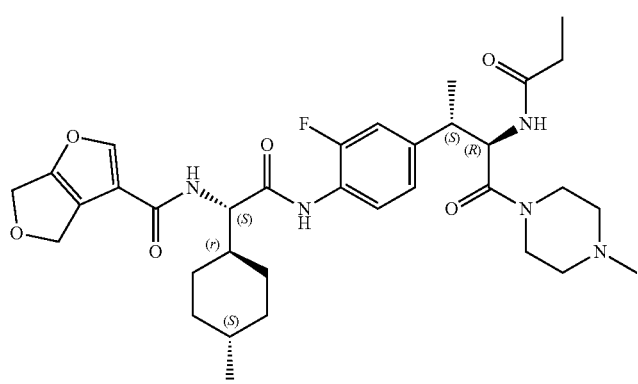
277
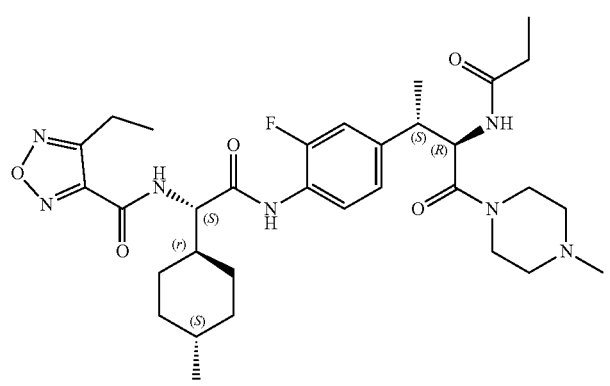
278
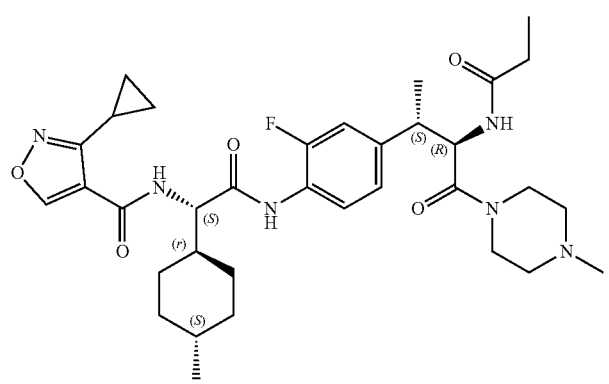
279
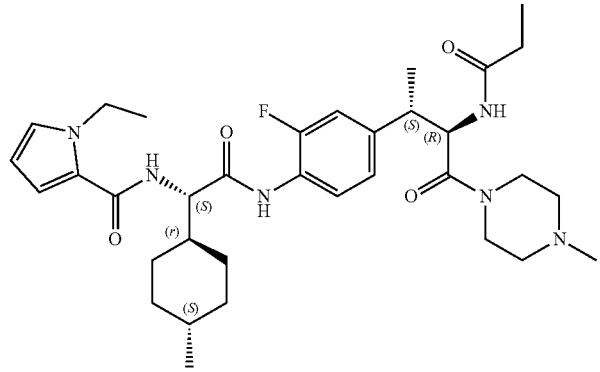
280

TABLE 1-continued
281
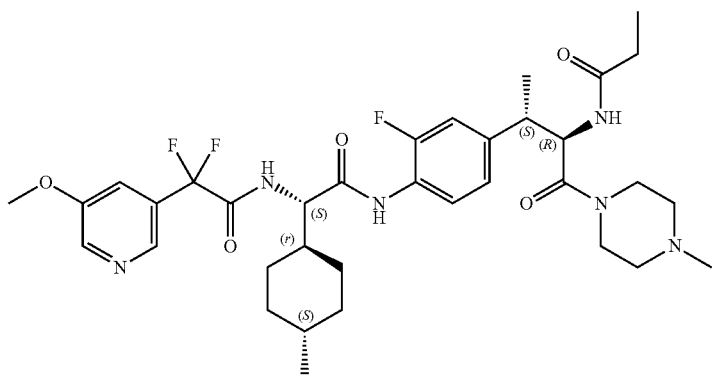
282
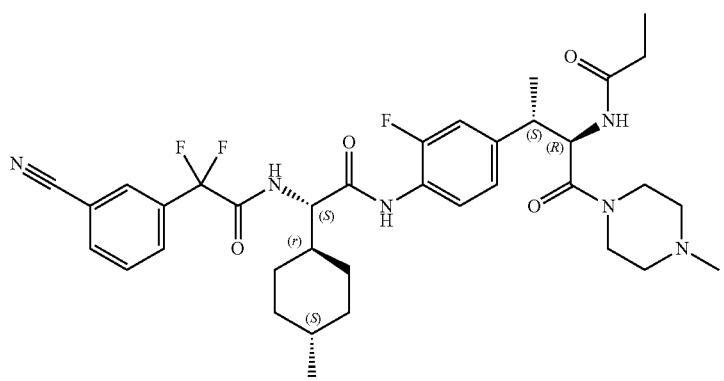
283
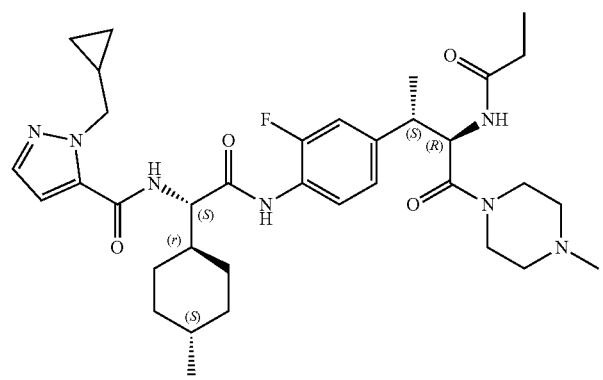
284
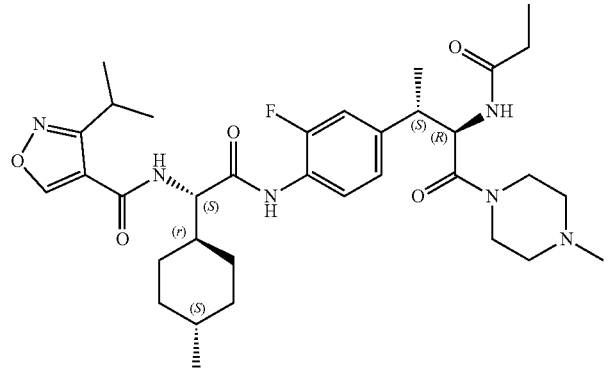

TABLE 1-continued
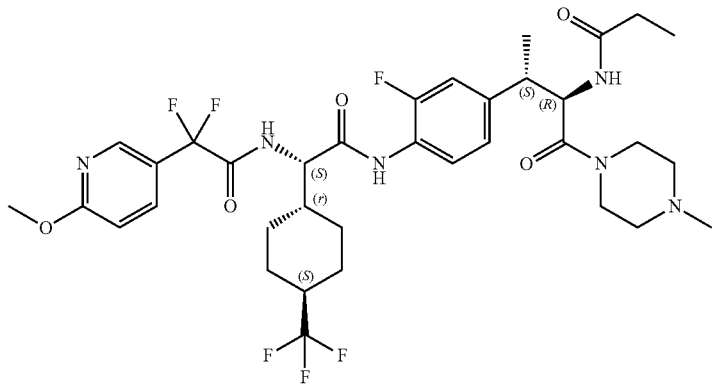
285
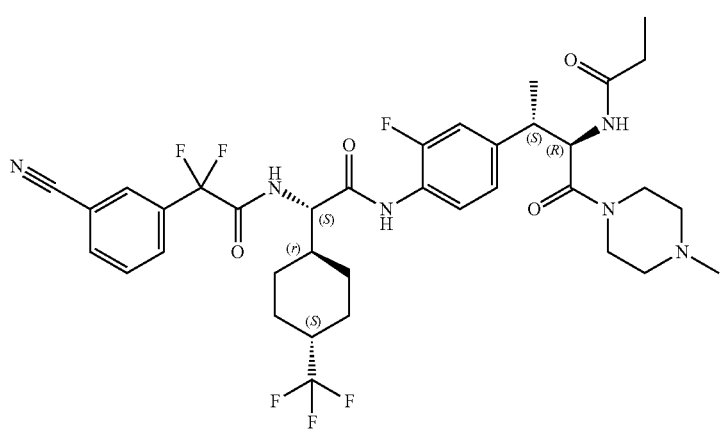
286
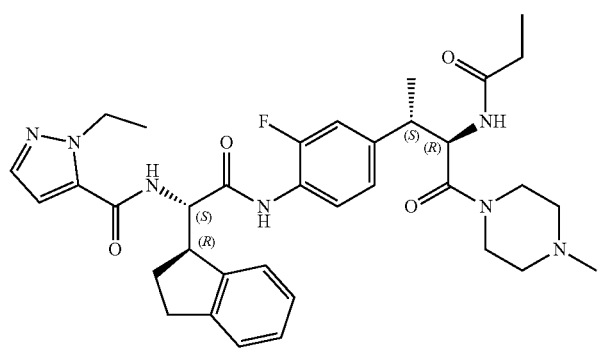
287
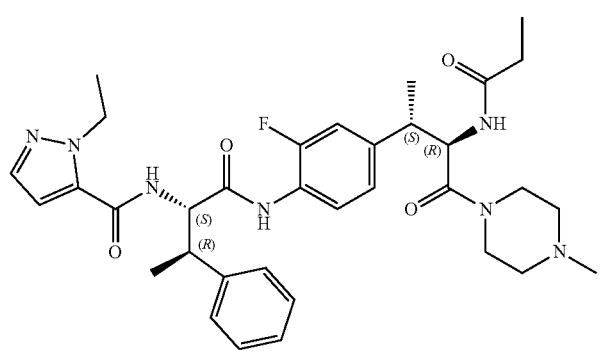
288

TABLE 1-continued
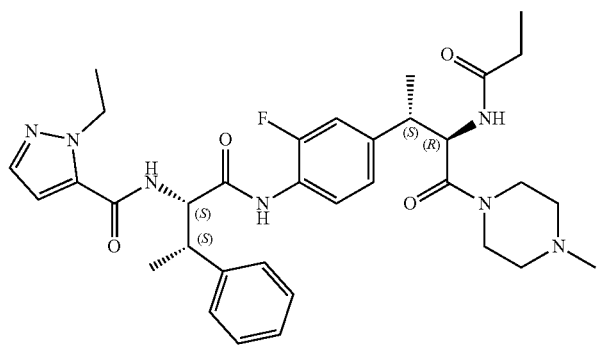
289
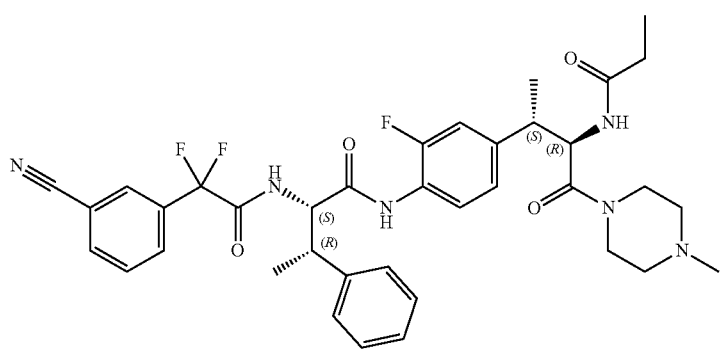
290
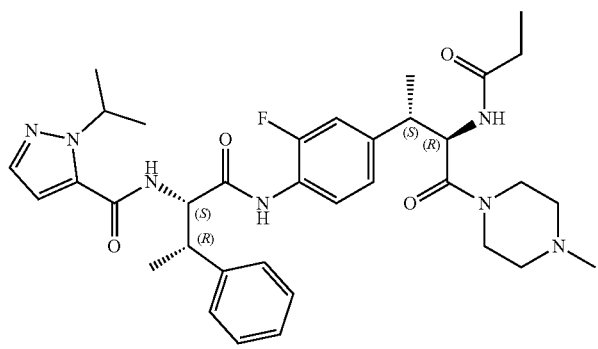
291
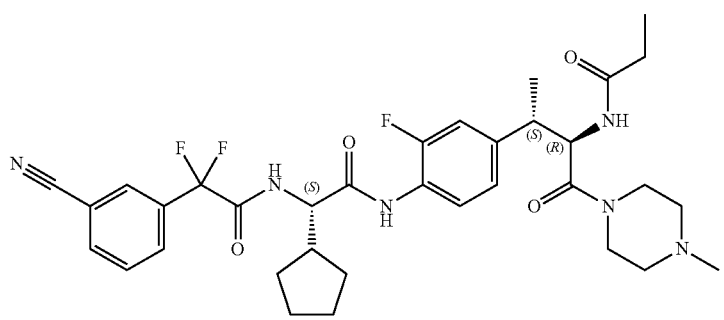
292

TABLE 1-continued
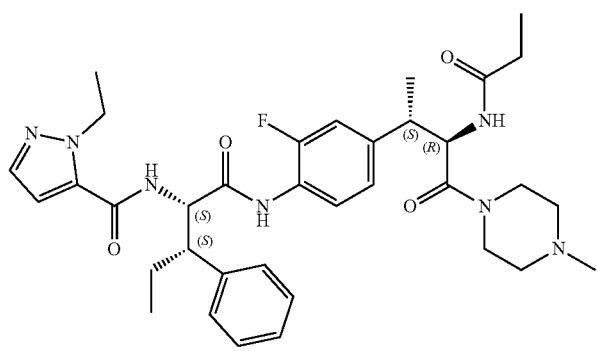
293
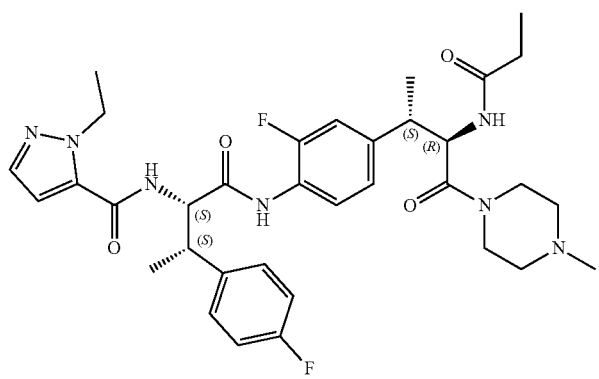
294
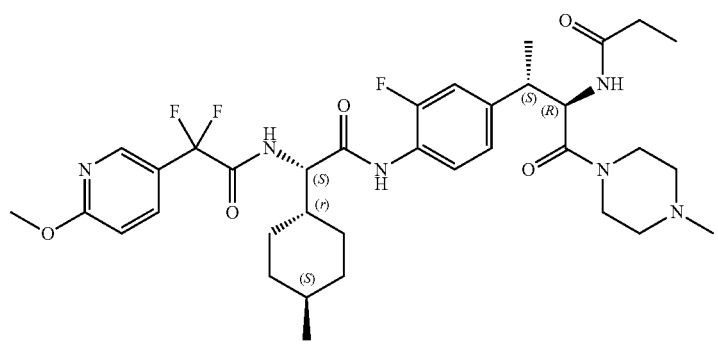
295
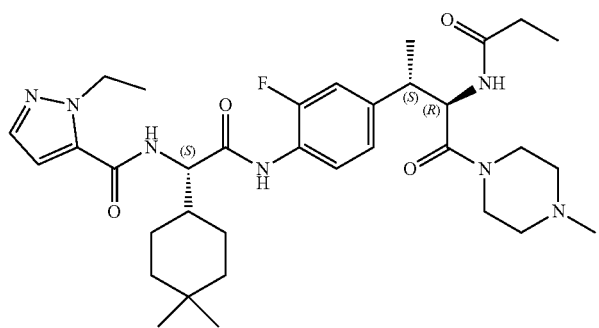
296

TABLE 1-continued
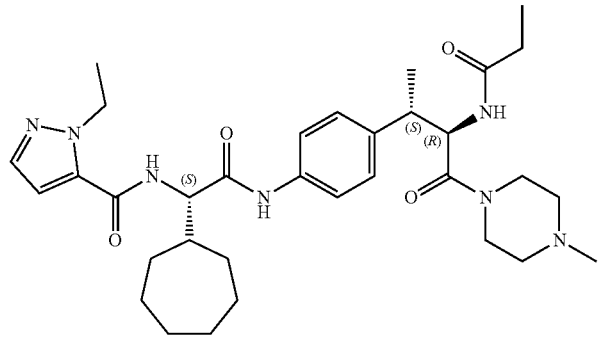
297
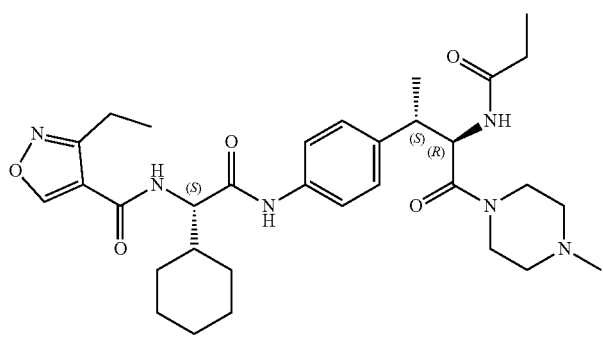
298
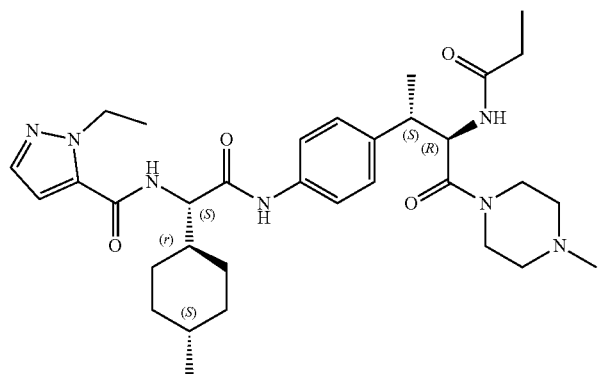
299
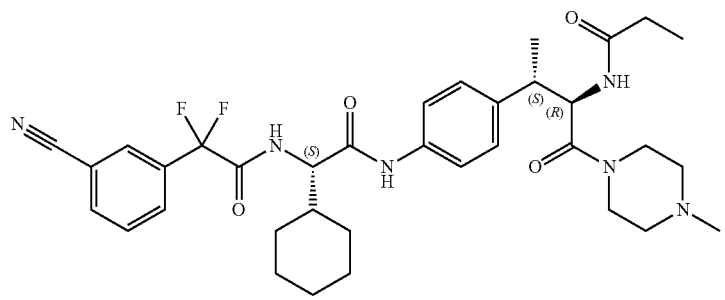
300

TABLE 1-continued

| | |
|---|---|
| [Chemical structure] | 301 |
| [Chemical structure] | 302 |
| [Chemical structure] | 303 |
| [Chemical structure] | 304 |

TABLE 1-continued
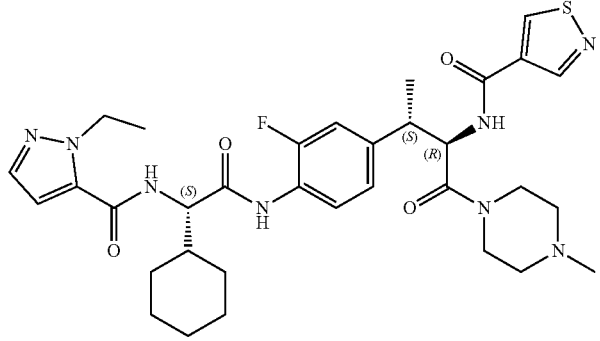
305
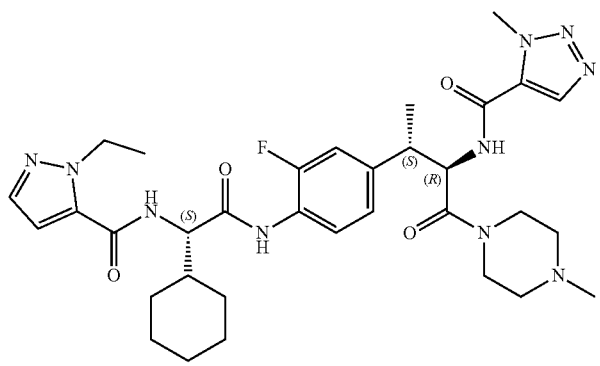
306
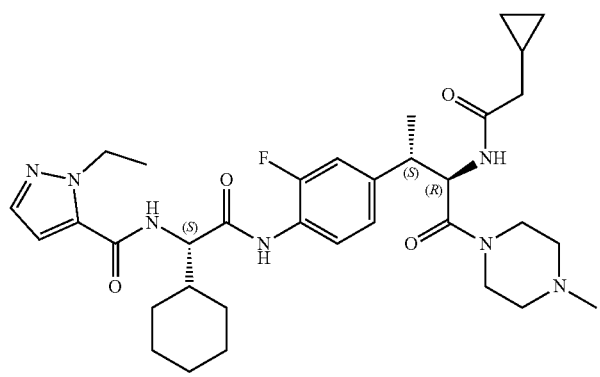
307
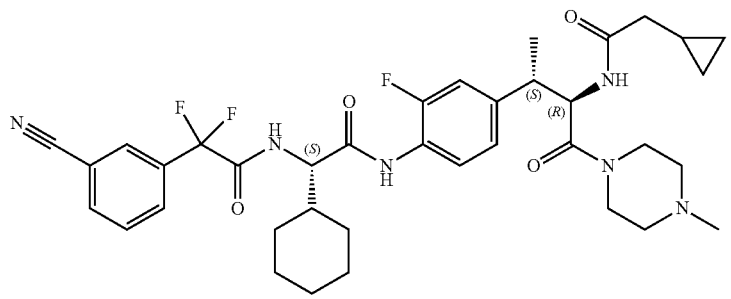
308

TABLE 1-continued

| | |
|---|---|
| (chemical structure) | 309 |
| (chemical structure) | 310 |
| (chemical structure) | 311 |
| (chemical structure) | 312 |

TABLE 1-continued
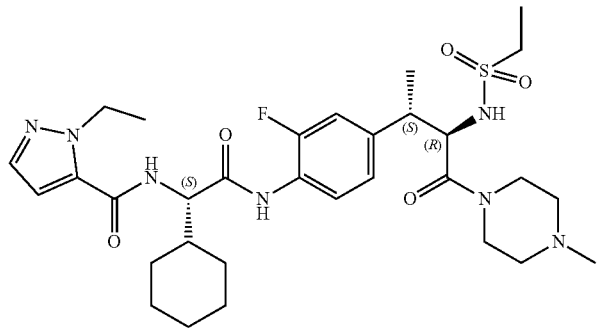
313
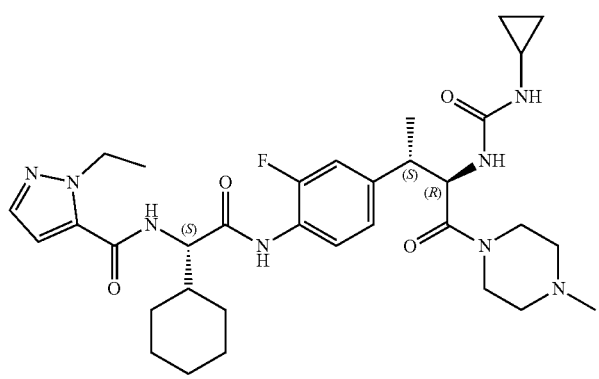
314
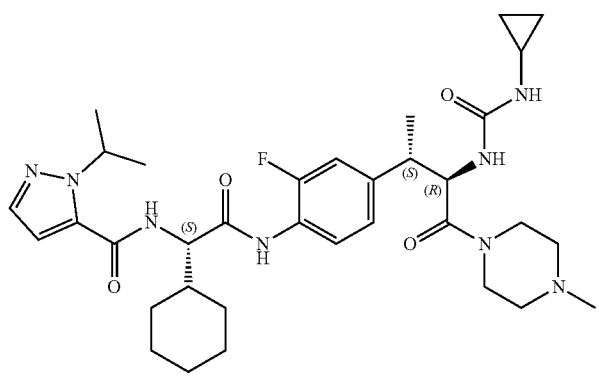
315
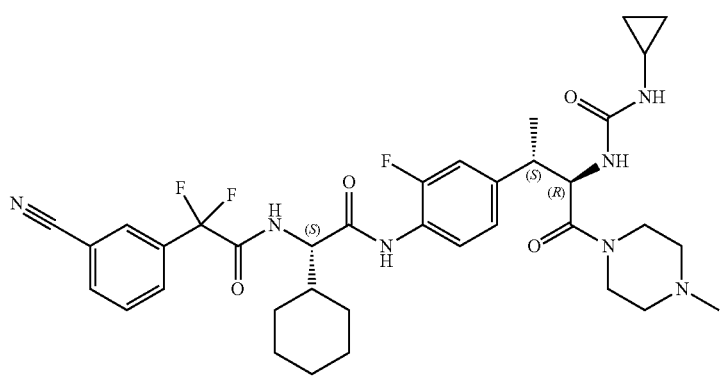
316

TABLE 1-continued
| | |
|---|---|
| 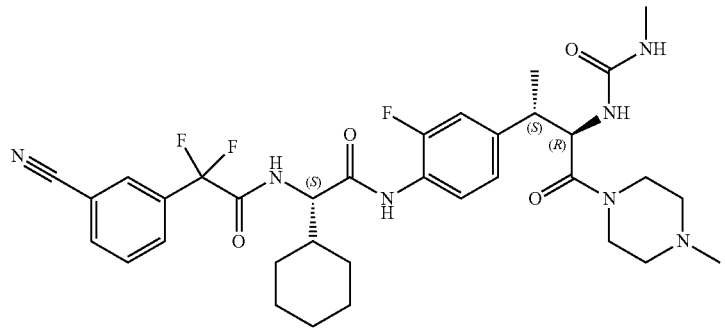 | 317 |
| 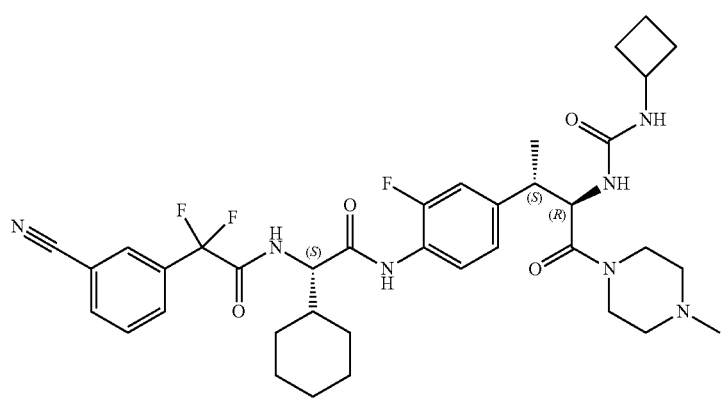 | 318 |
| 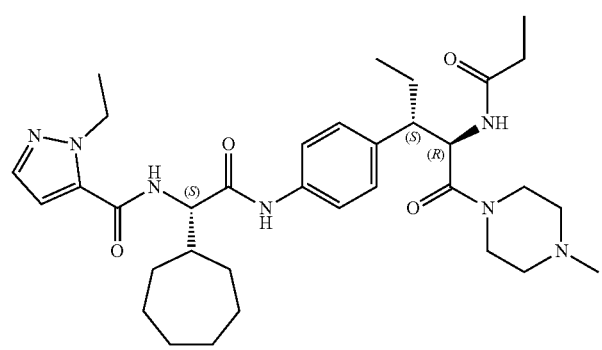 | 319 |
| 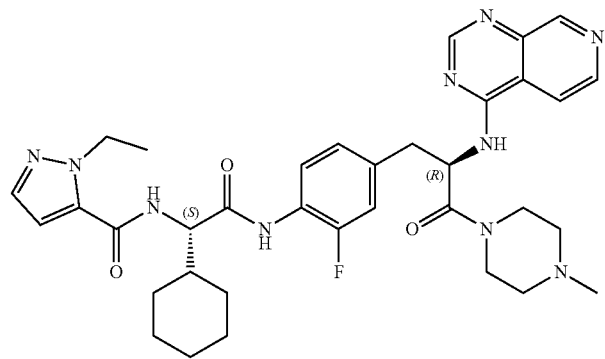 | 320 |

TABLE 1-continued
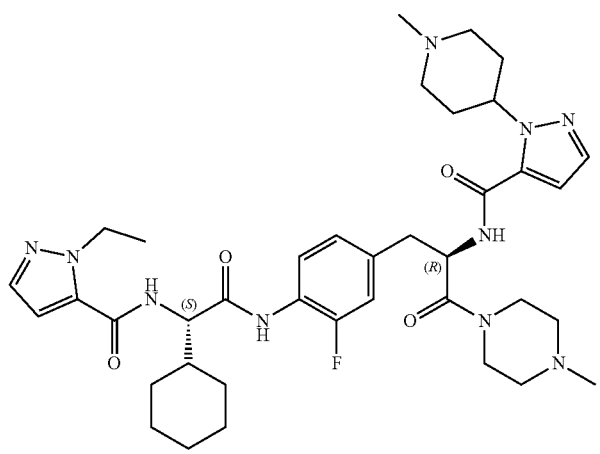
321
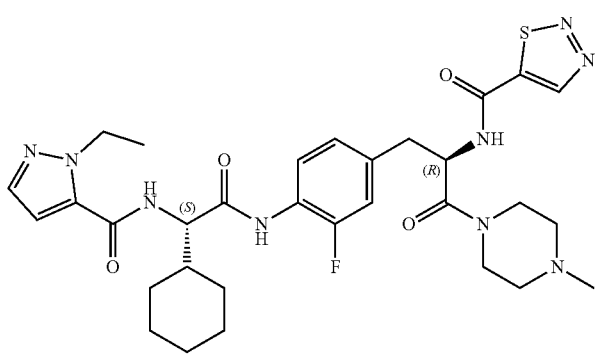
322
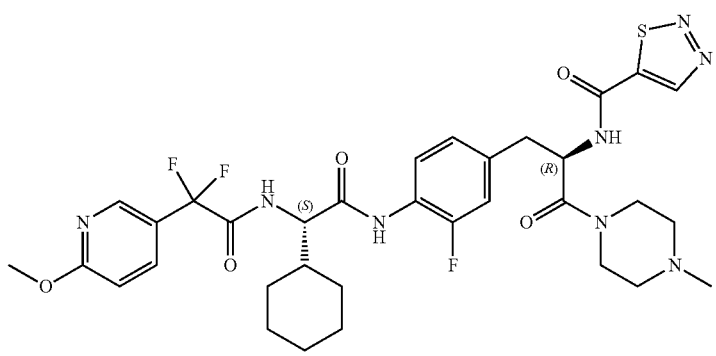
323
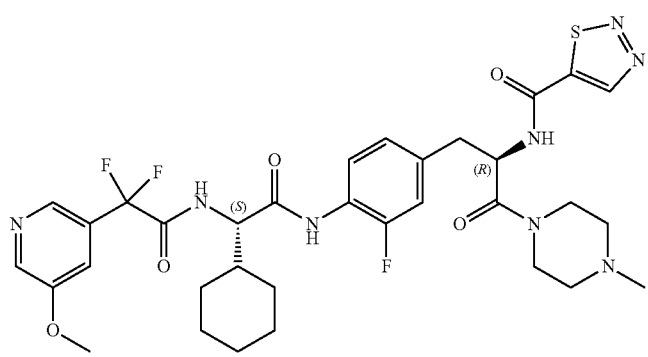
324

TABLE 1-continued
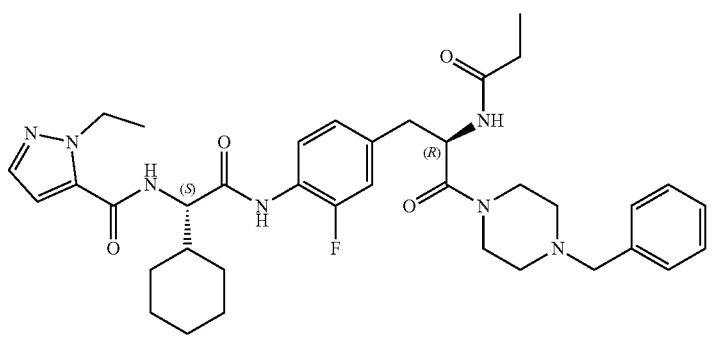
325
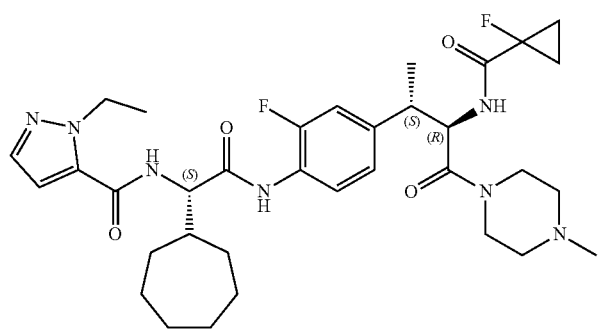
326
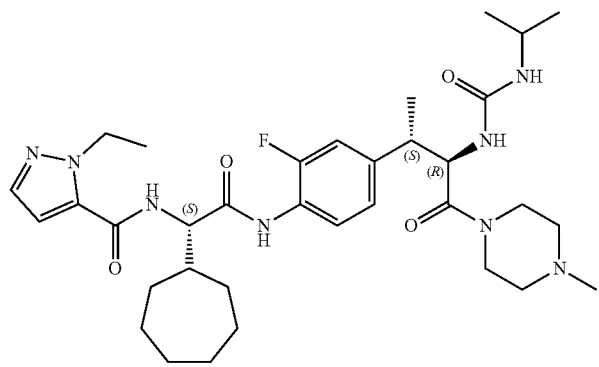
327
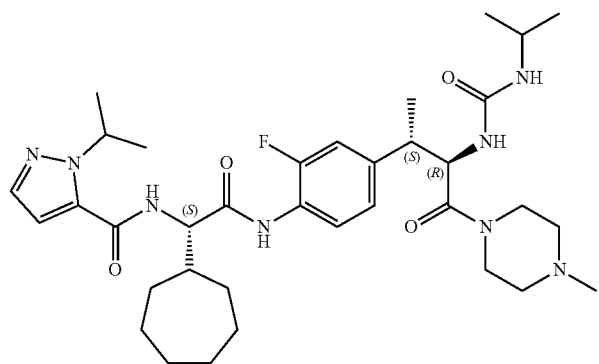
328

TABLE 1-continued
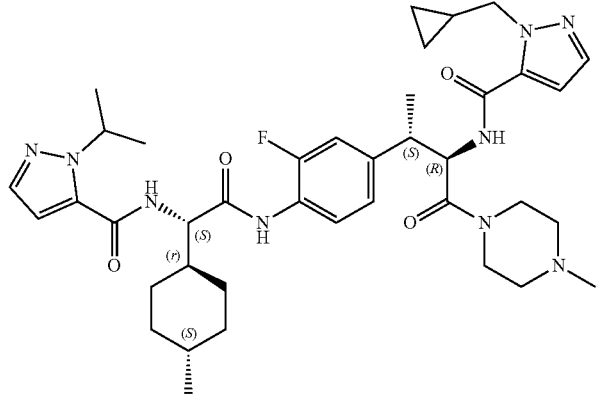
329
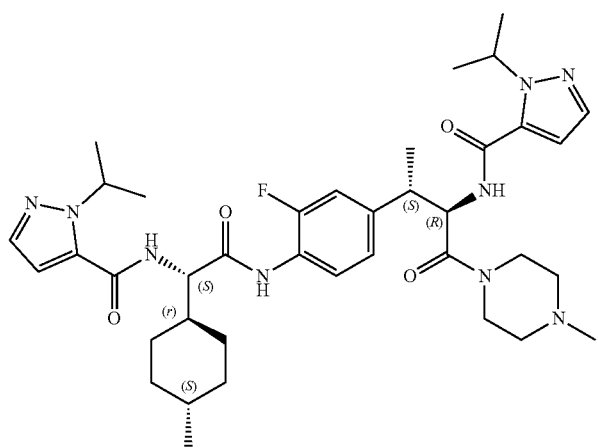
330
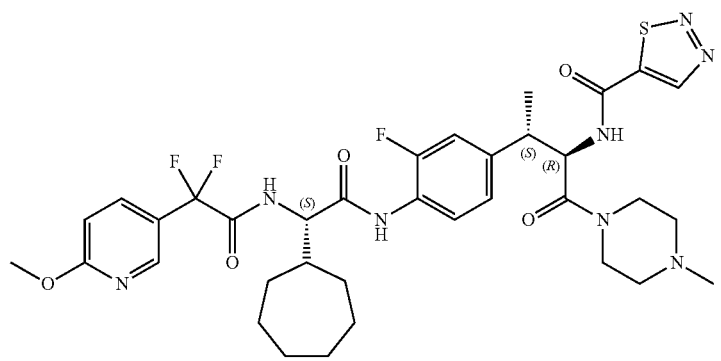
331
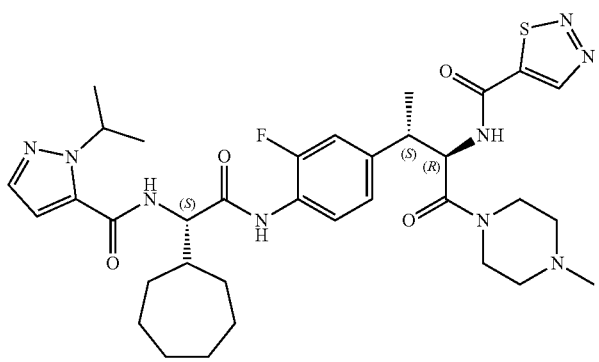
332

TABLE 1-continued
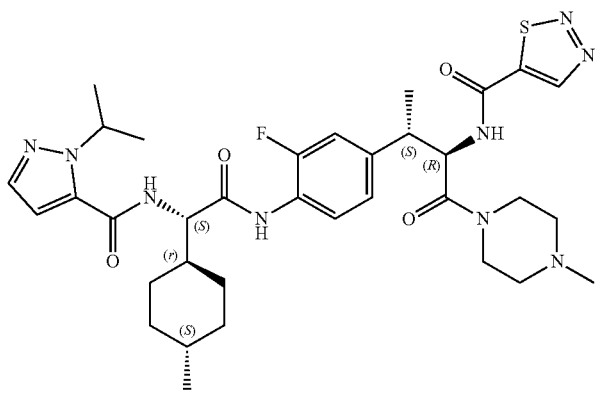 333
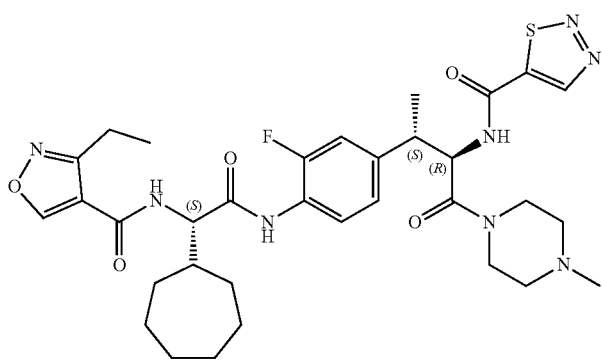 334
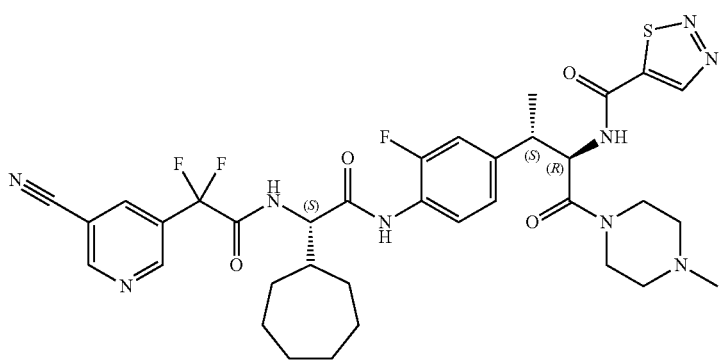 335
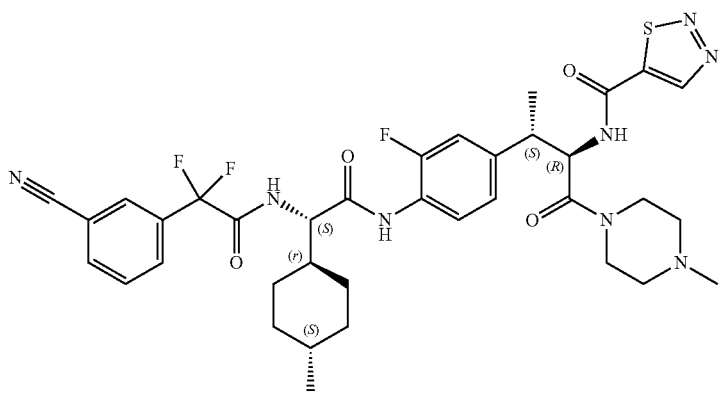 336

TABLE 1-continued
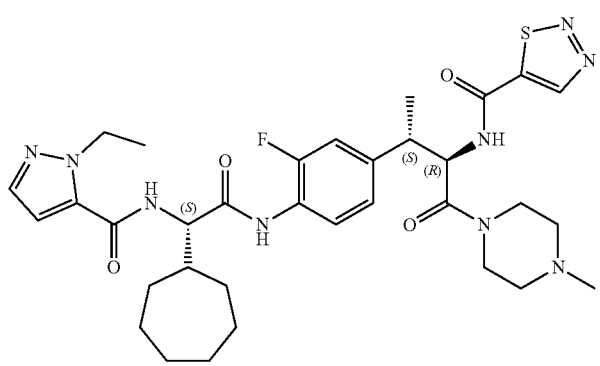
337
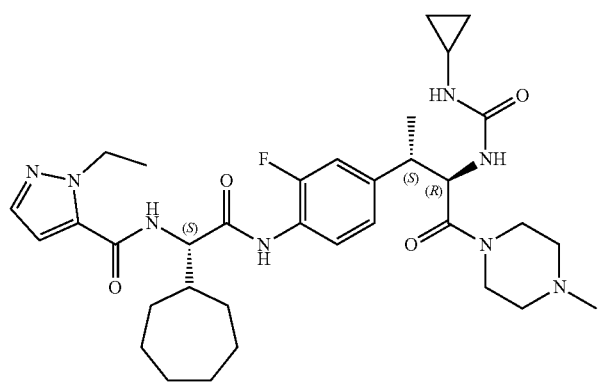
338
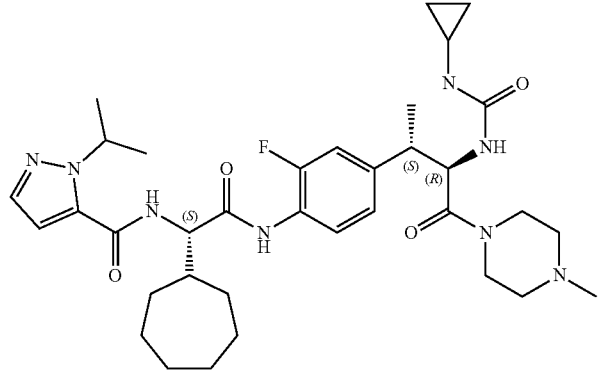
339
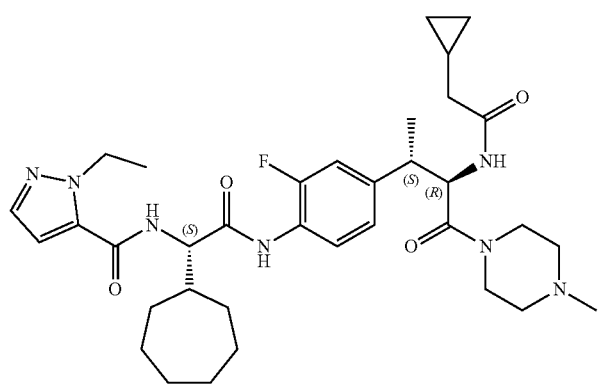
340

TABLE 1-continued
341
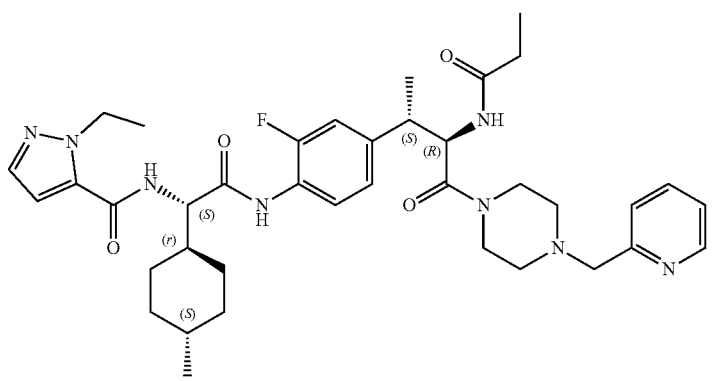
342
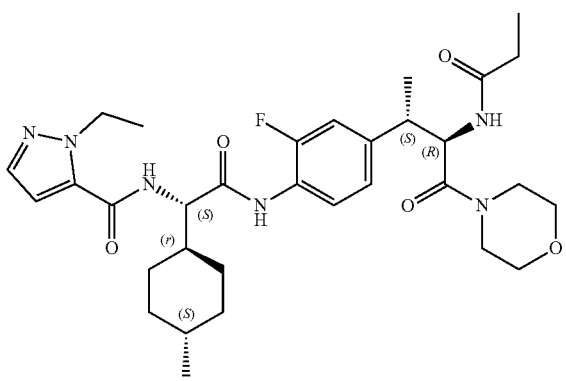
343
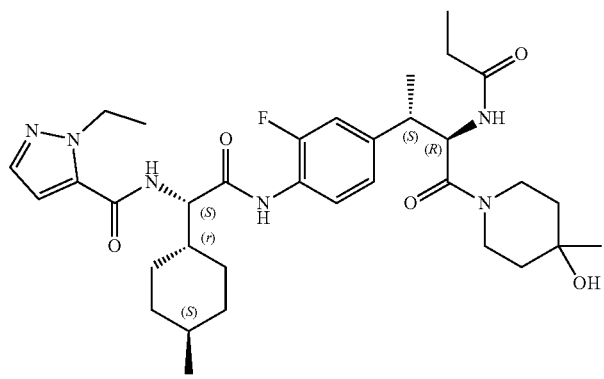
344
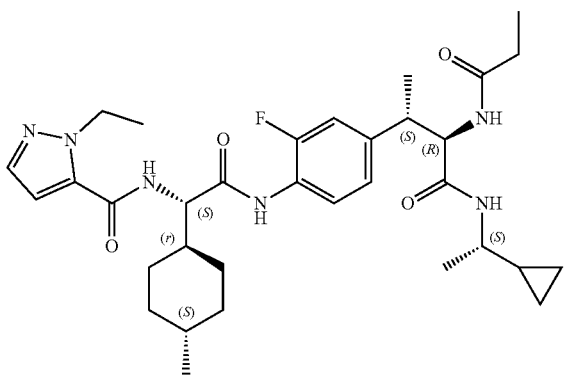

TABLE 1-continued
345
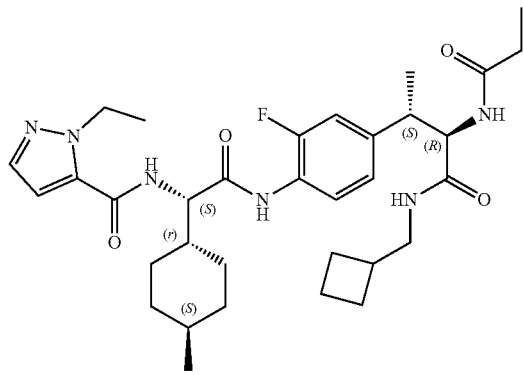
346
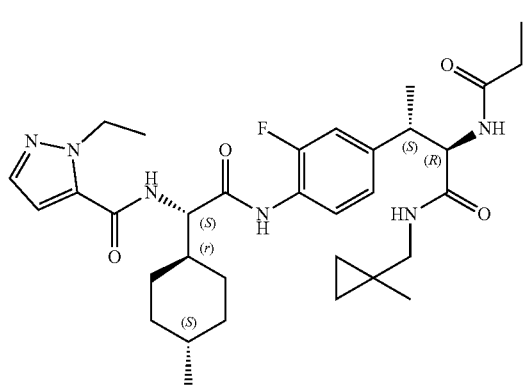
347
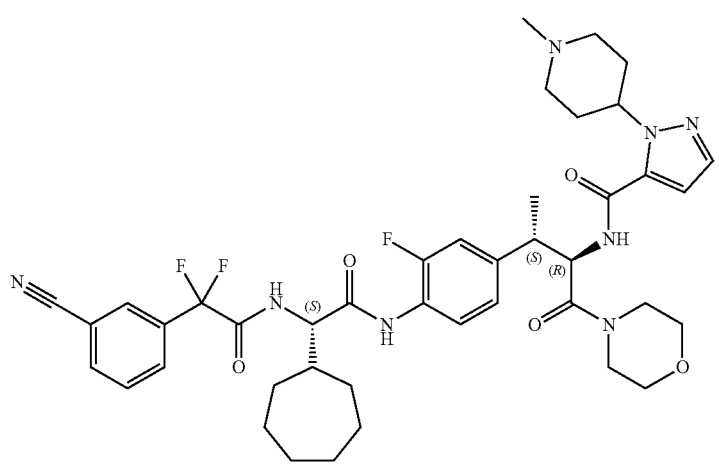
348
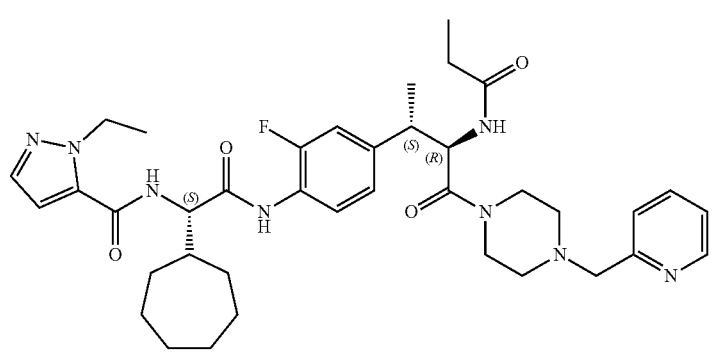

TABLE 1-continued
349
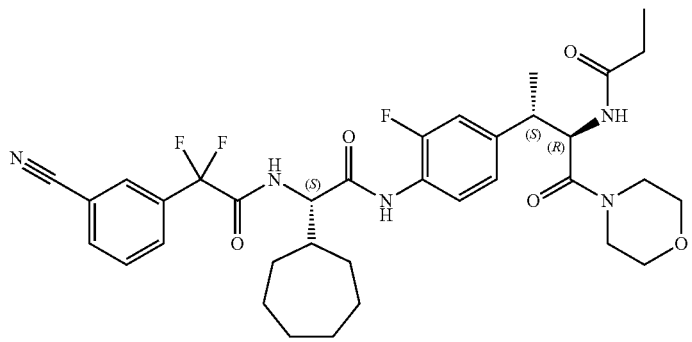
350
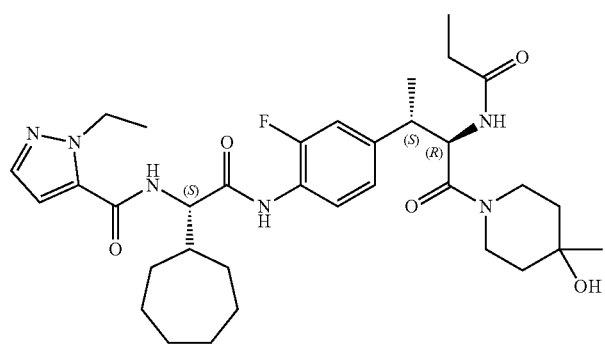
351
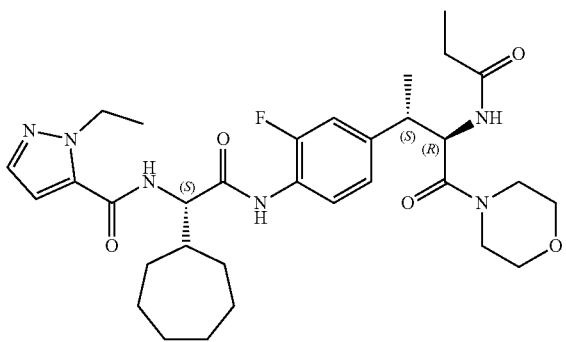
352
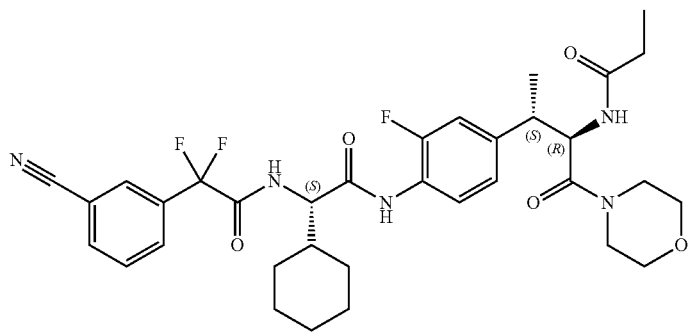

TABLE 1-continued
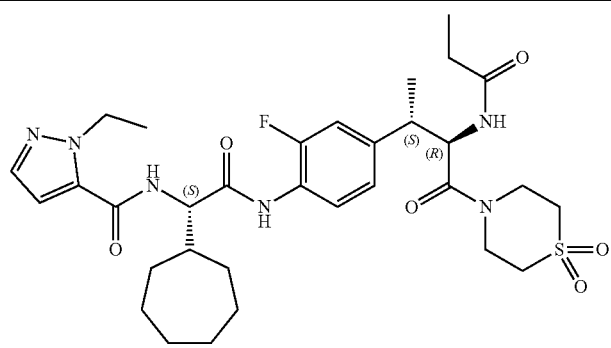
353
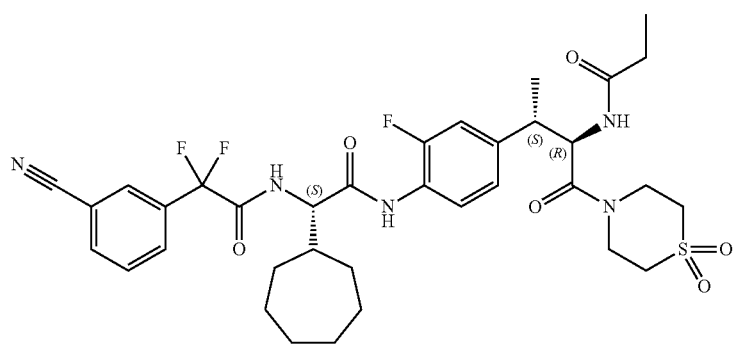
354
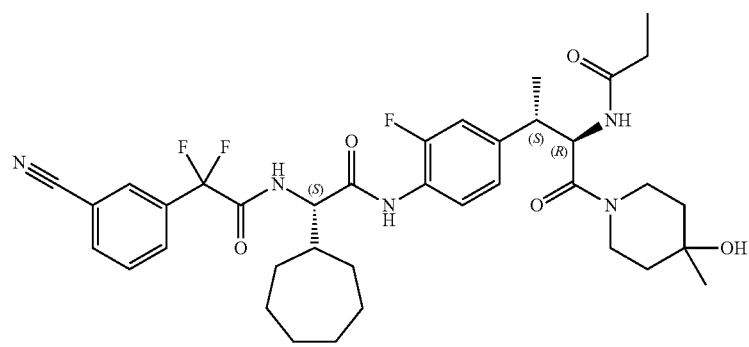
355
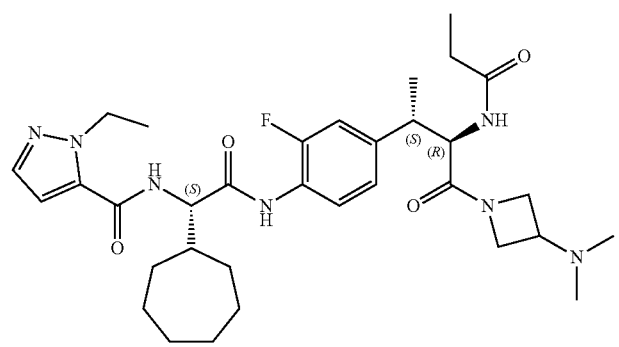
356

TABLE 1-continued
357
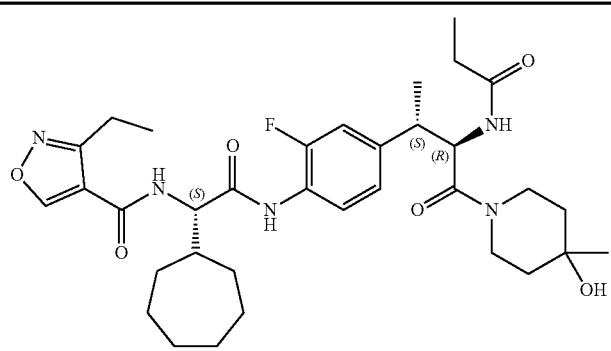
358
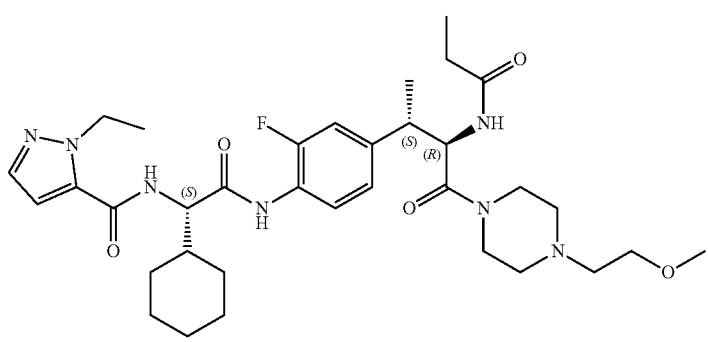
359
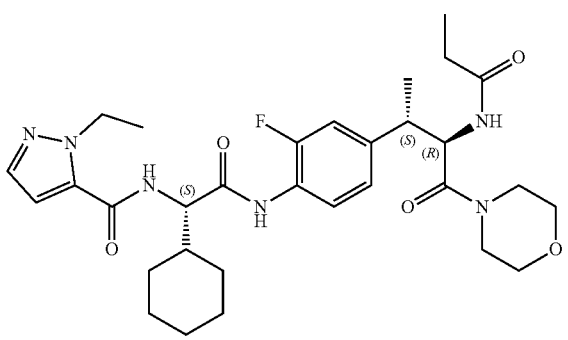
360
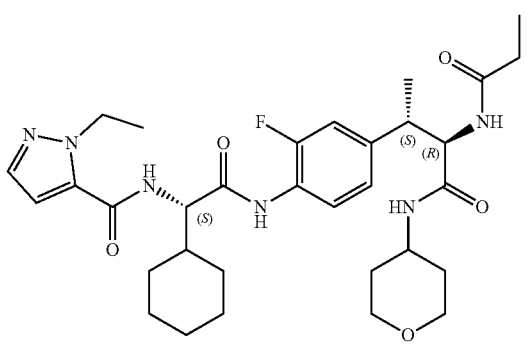

TABLE 1-continued
361
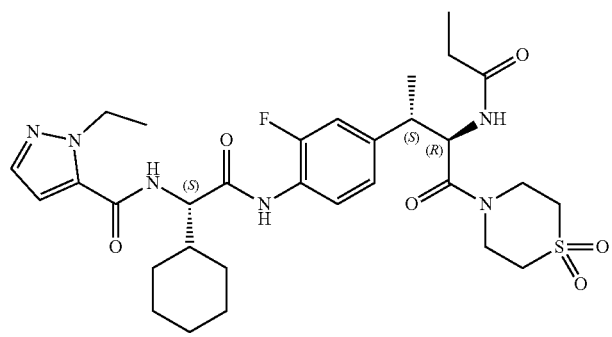
362
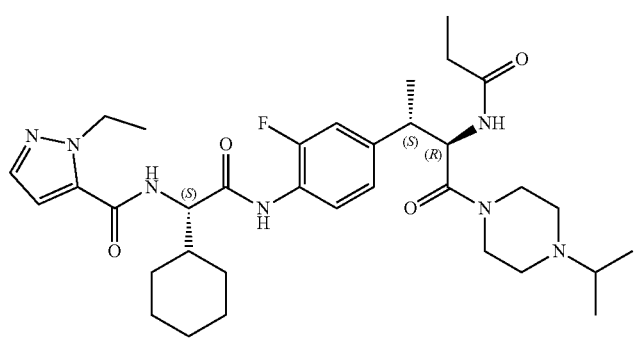
363
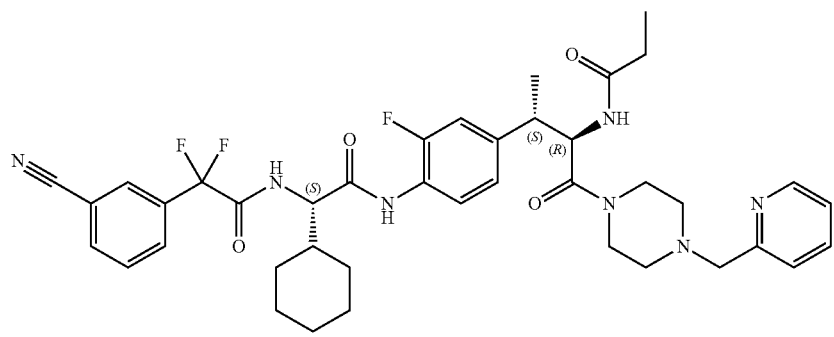
364
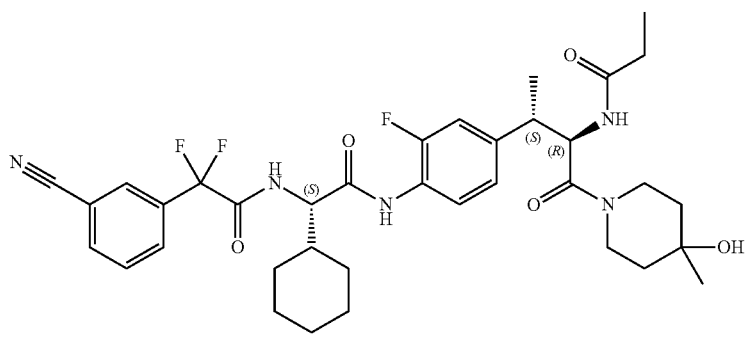

TABLE 1-continued
365
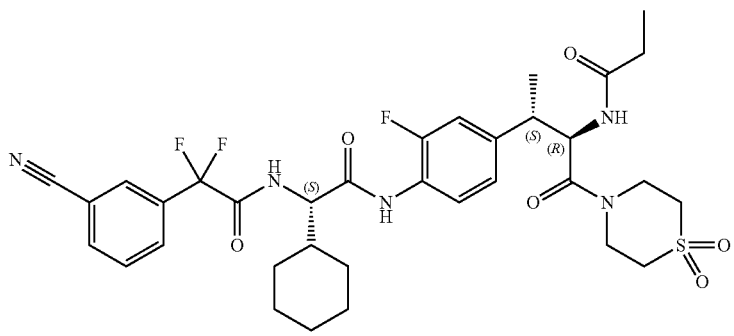
366
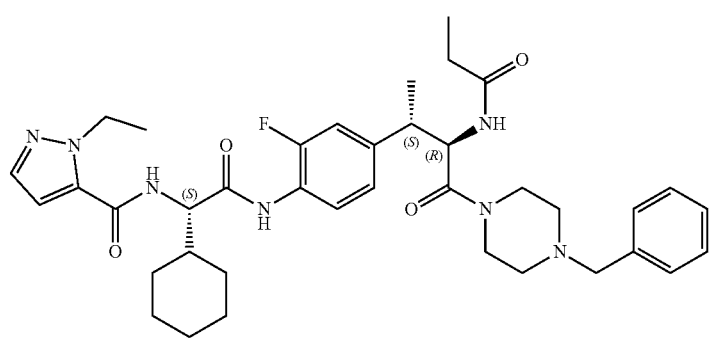
367
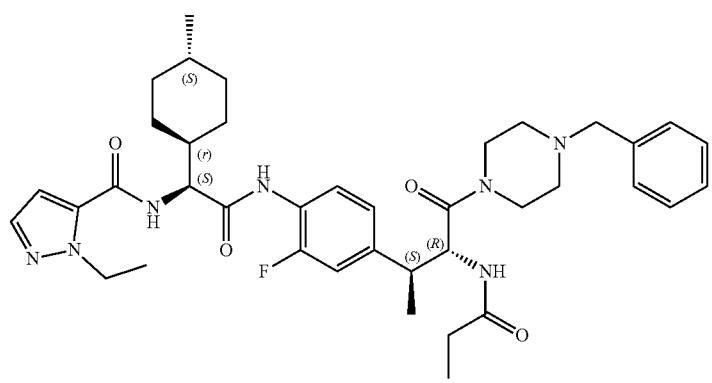
368
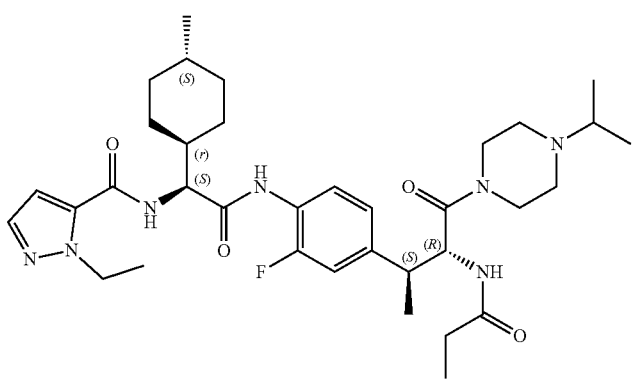

TABLE 1-continued
| | |
|---|---|
| 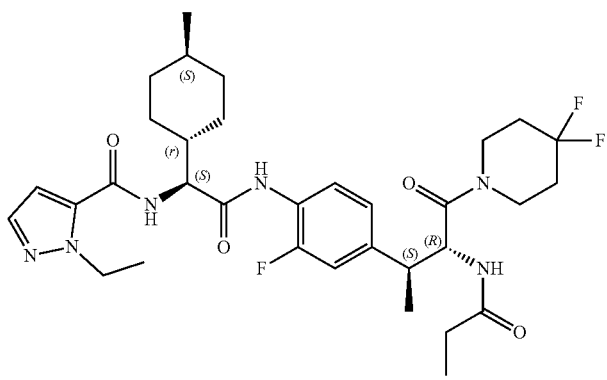 | 369 |
| 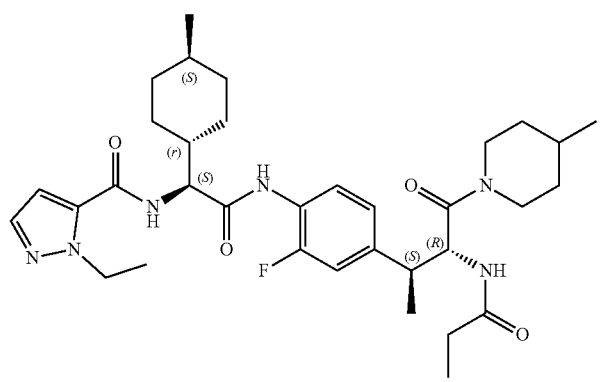 | 370 |
| 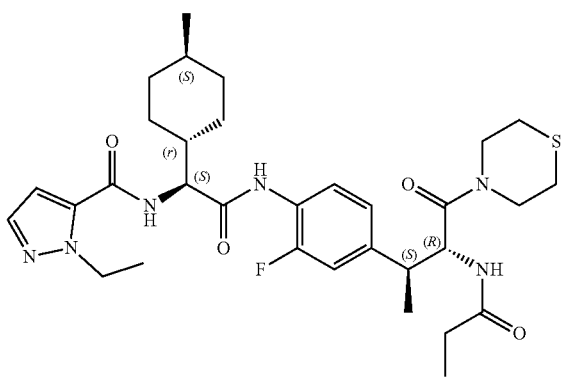 | 371 |
| 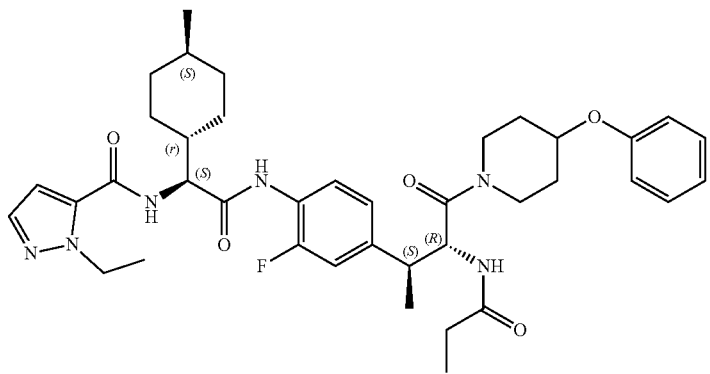 | 372 |

TABLE 1-continued
| | |
|---|---|
| 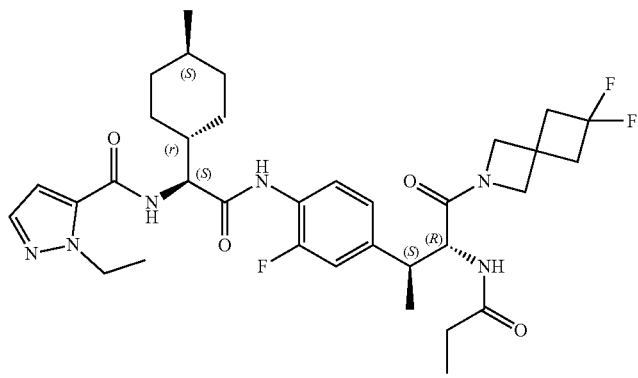 | 373 |
| 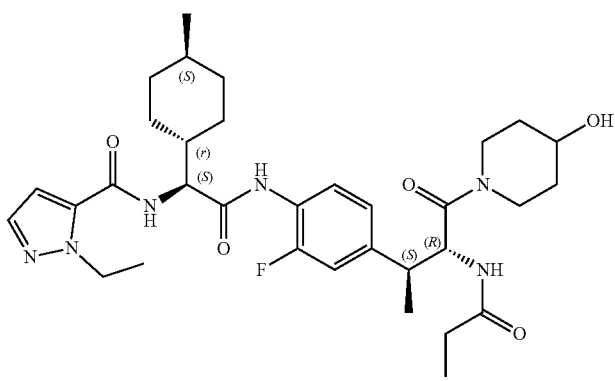 | 374 |
| 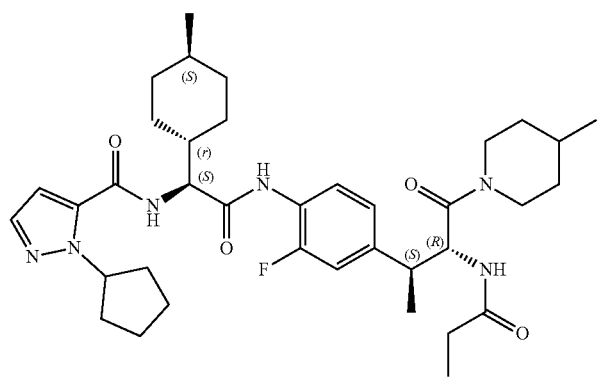 | 375 |
| 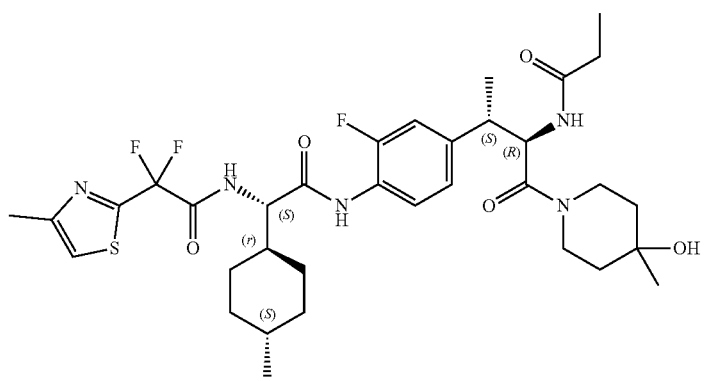 | 376 |

TABLE 1-continued
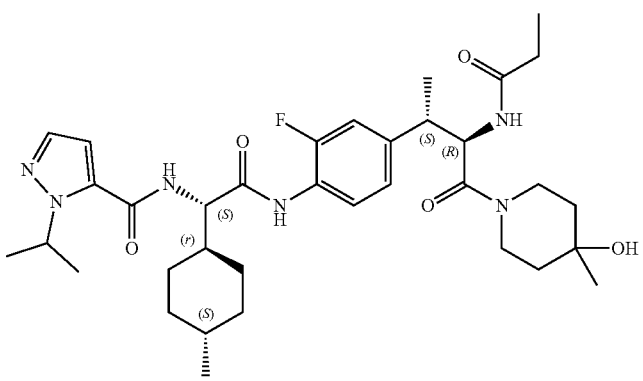
377
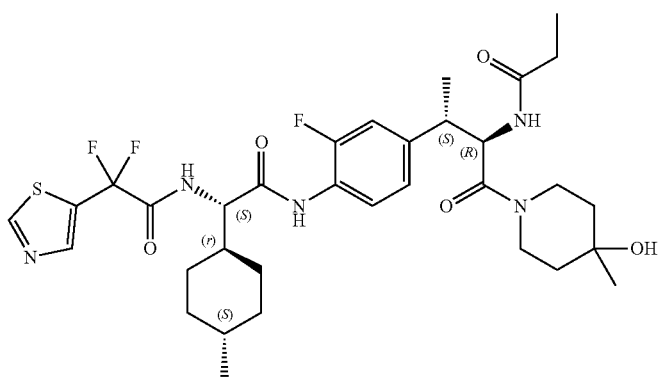
378
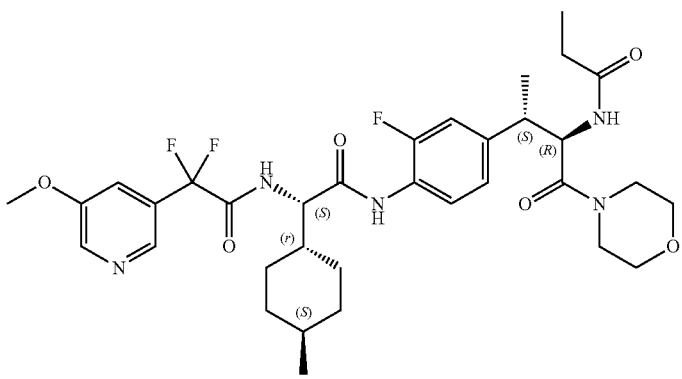
379
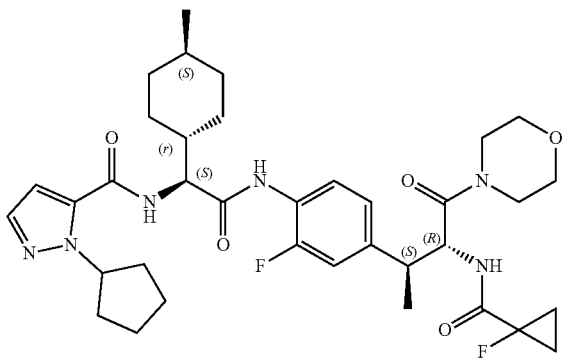
380

TABLE 1-continued
| | |
|---|---|
| 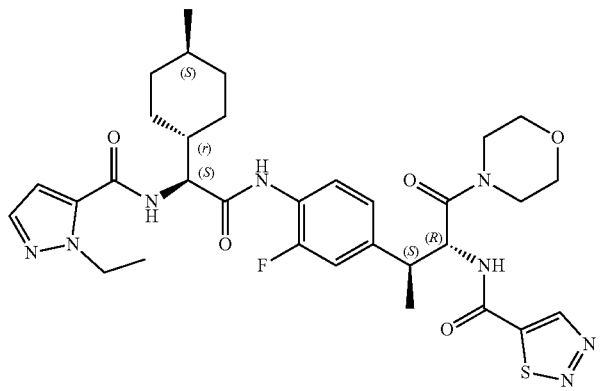 | 381 |
| 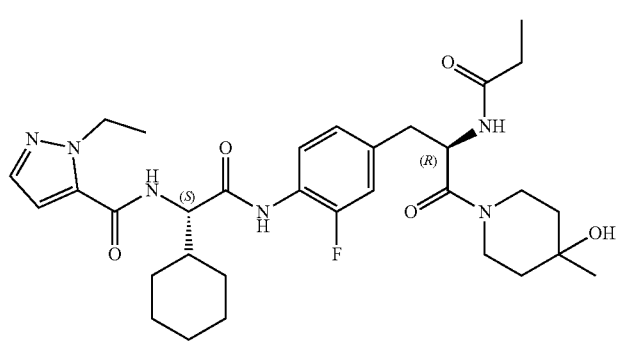 | 382 |
| 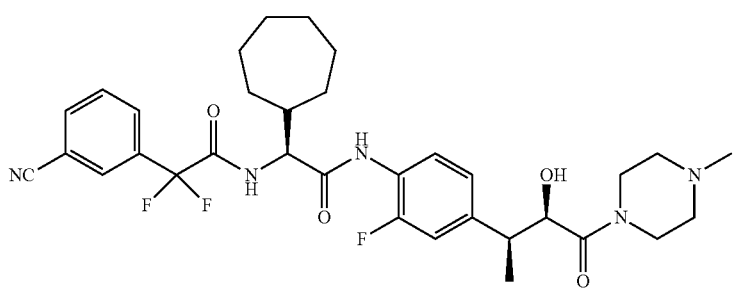 [SMILES: C[C@@H](c1ccc(NC(=O)[C@@H](NC(=O)C(F)(F)c2cccc(C#N)c2)C2CCCCCC2)c(F)c1)[C@@H](O)C(=O)N1CCN(C)CC1] | 383 |
| 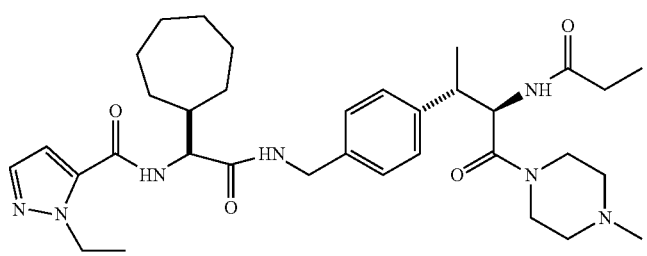 [SMILES: CCC(=O)N[C@@H](C(=O)N1CCN(C)CC1)[C@@H](C)c1ccc(CNC(=O)[C@@H](NC(=O)c2ccnn2CC)C2CCCCCC2)cc1] | 384 |
| 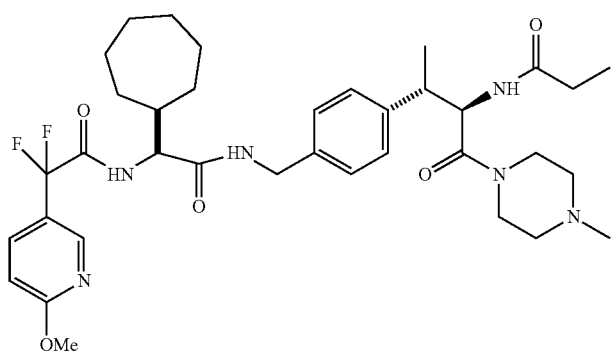 [SMILES: CCC(=O)N[C@@H](C(=O)N1CCN(C)CC1)[C@@H](C)c1ccc(CNC(=O)[C@@H](NC(=O)C(F)(F)c2ccc(OC)nc2)C2CCCCCC2)cc1] | 385 |

TABLE 1-continued
| | |
|---|---|
| 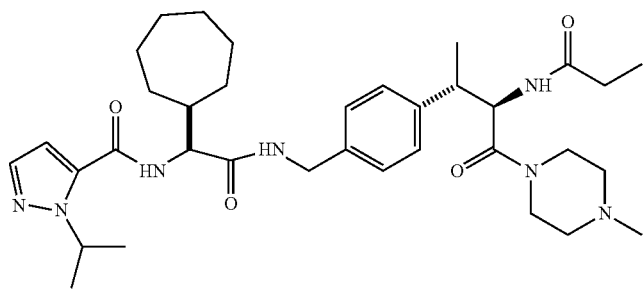 [SMILES: CCC(=O)N[C@@H](C(=O)N1CCN(C)CC1)[C@@H](C)c1ccc(CNC(=O)[C@@H](NC(=O)c2ccnn2C(C)C)C2CCCCCC2)cc1] | 386 |
| 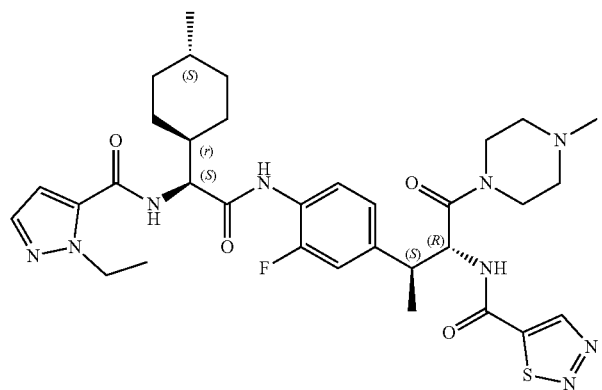 | 388 |
| 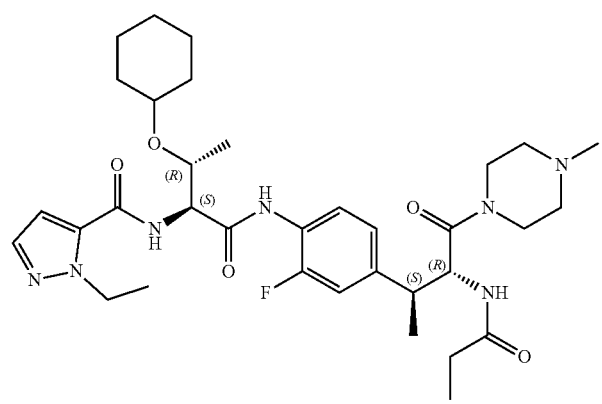 | 389 |
| 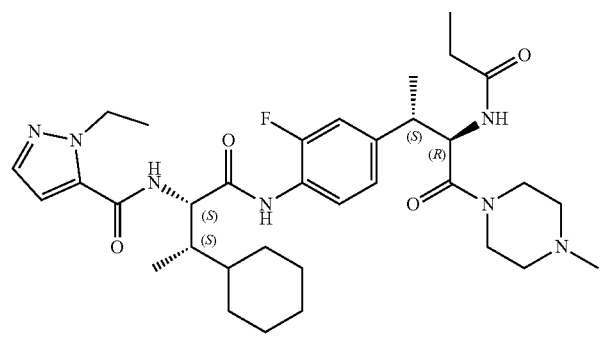 | 390 |

TABLE 1-continued
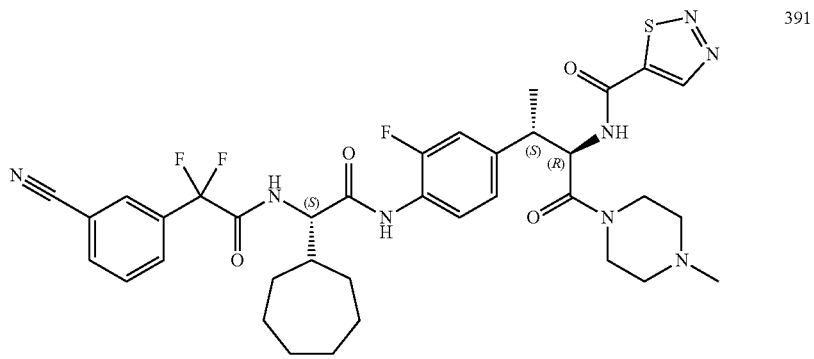
391
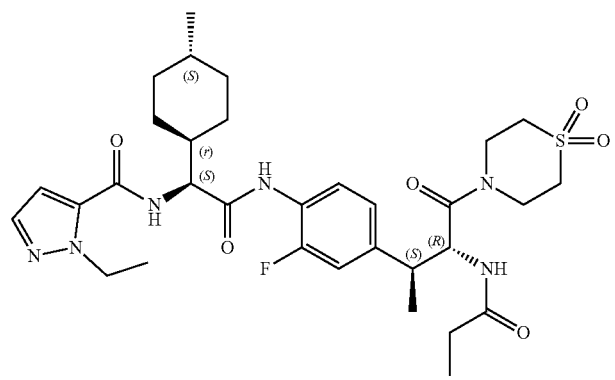
392
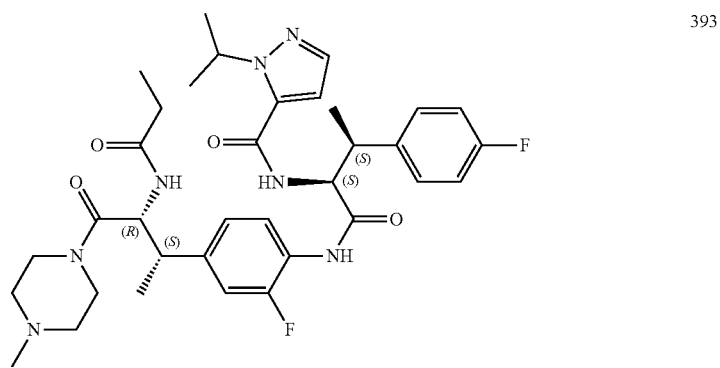
393
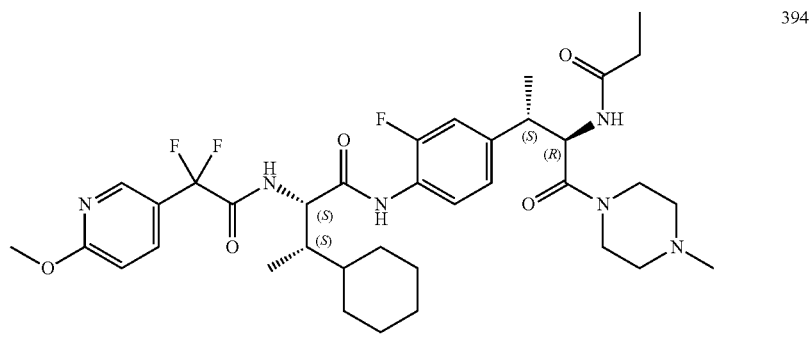
394

TABLE 1-continued
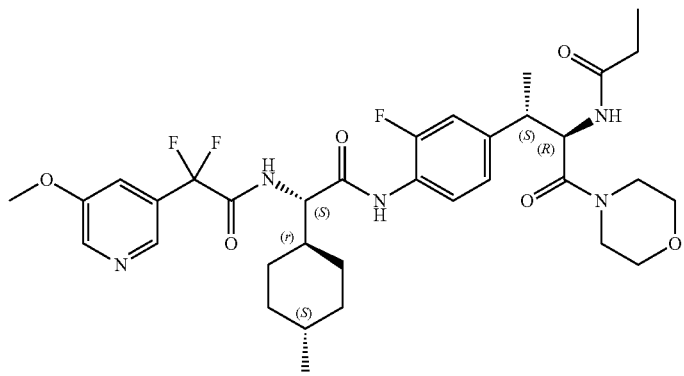
395
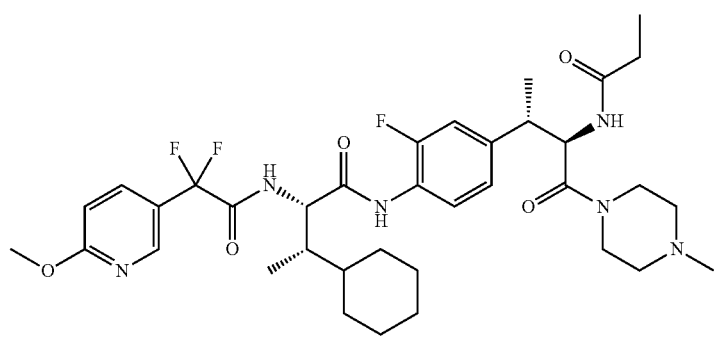
396
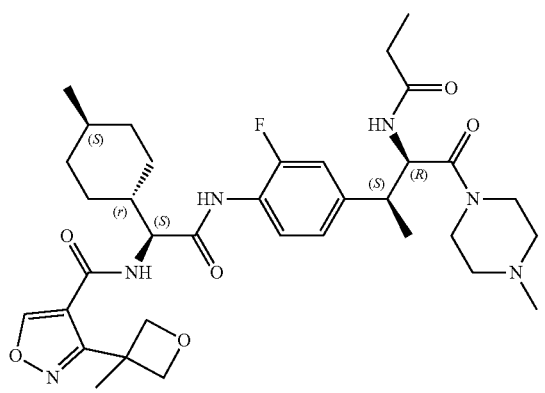
397
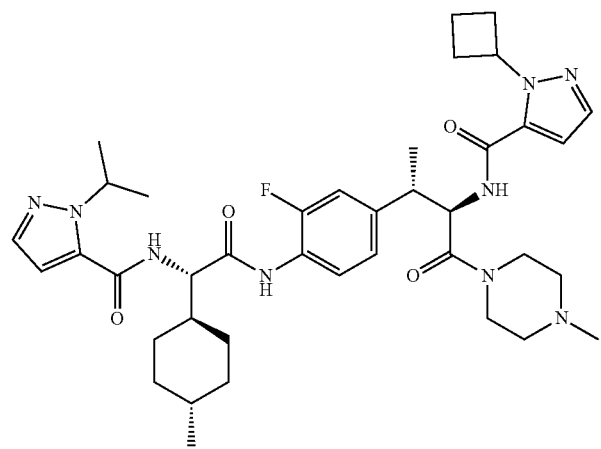 [SMILES: CC(C)n1nccc1C(=O)N[C@H](C(=O)Nc1ccc([C@H](C)[C@@H](NC(=O)c2ccnn2C2CCC2)C(=O)N2CCN(C)CC2)cc1F)[C@H]1CC[C@H](C)CC1]
398

TABLE 1-continued
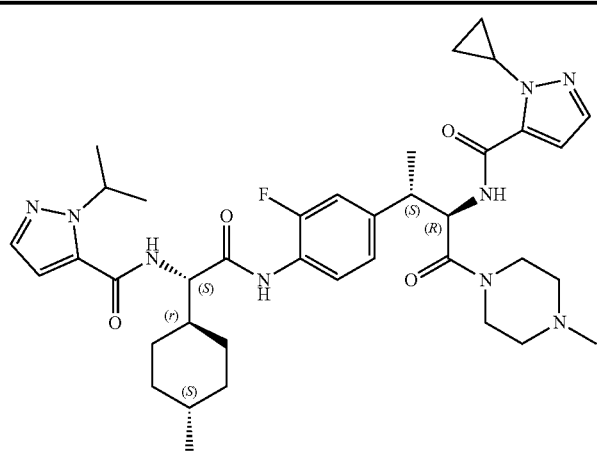
399
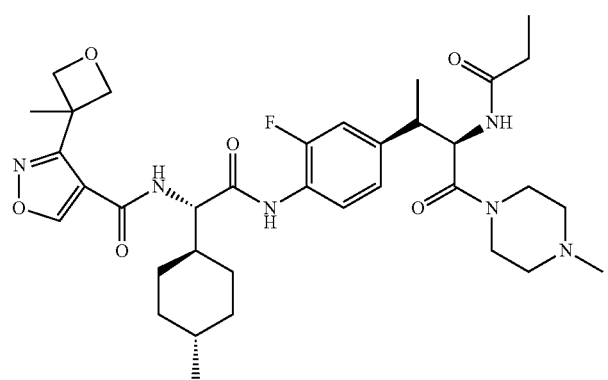
400
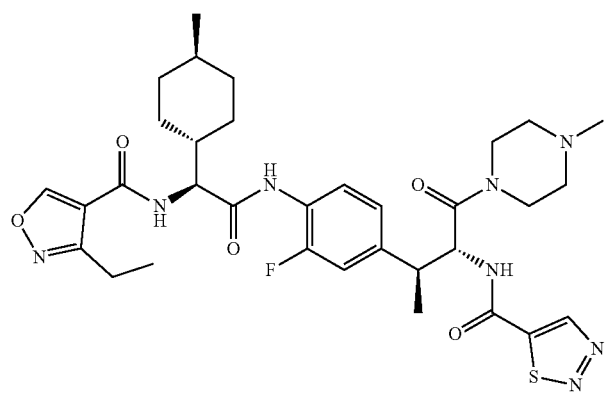 [SMILES: CCc1nocc1C(=O)N[C@H](C(=O)Nc1ccc([C@H](C)[C@@H](NC(=O)c2cnns2)C(=O)N2CCN(C)CC2)cc1F)[C@H]1CC[C@H](C)CC1]
402
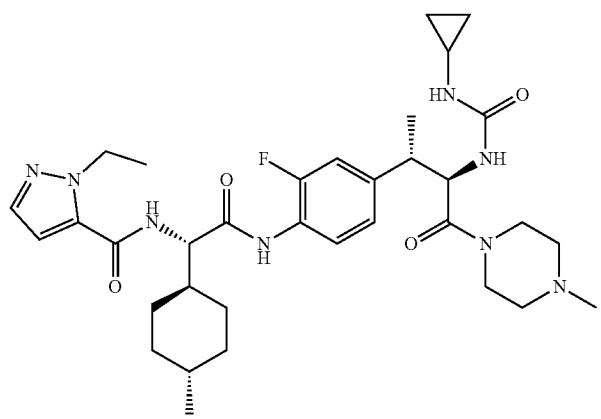 [SMILES: CCn1nccc1C(=O)N[C@H](C(=O)Nc1ccc([C@H](C)[C@@H](NC(=O)NC2CC2)C(=O)N2CCN(C)CC2)cc1F)[C@H]1CC[C@H](C)CC1]
404

TABLE 1-continued
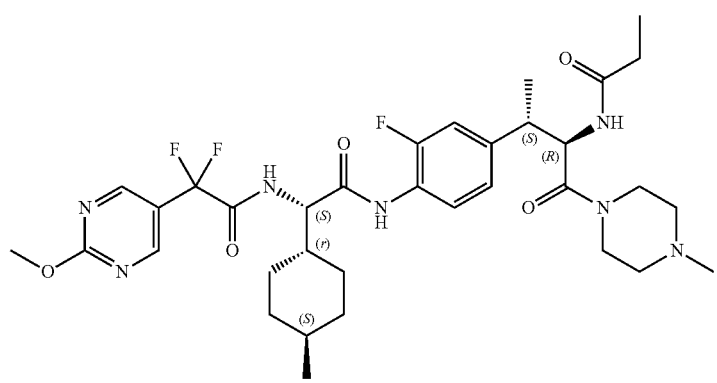
405
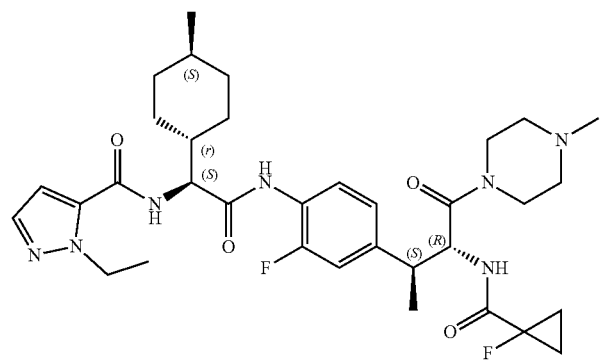
406
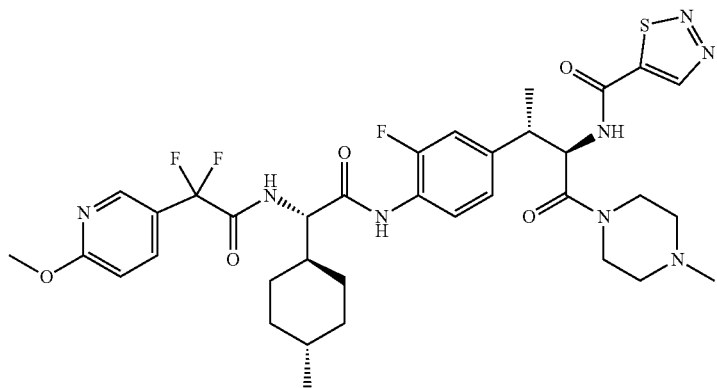
407
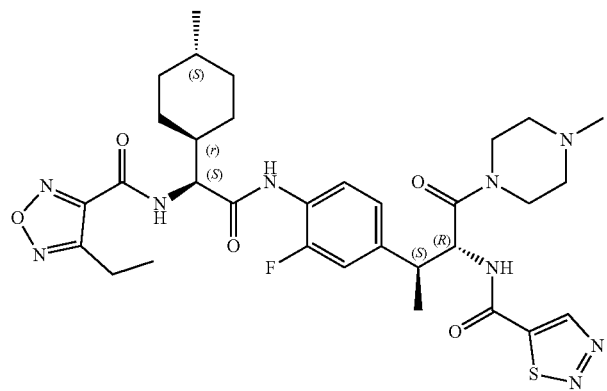
408

TABLE 1-continued
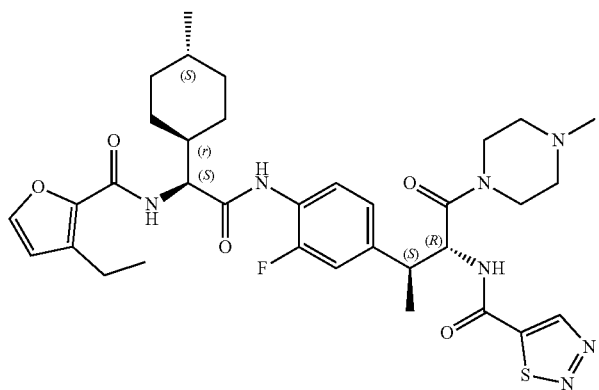
409
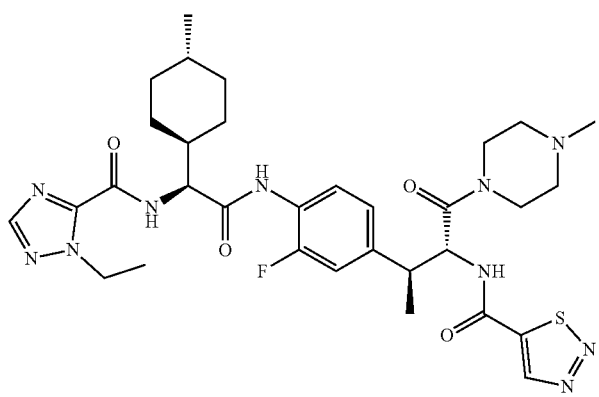 [SMILES: CCn1ncnc1C(=O)N[C@H](C(=O)Nc1ccc([C@H](C)[C@@H](NC(=O)c2cnns2)C(=O)N2CCN(C)CC2)cc1F)[C@H]1CC[C@H](C)CC1]
410
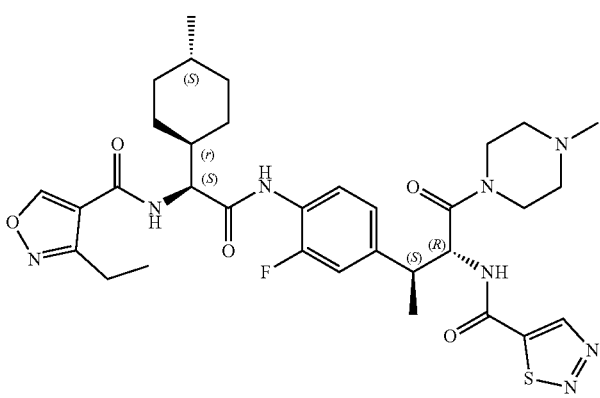
414
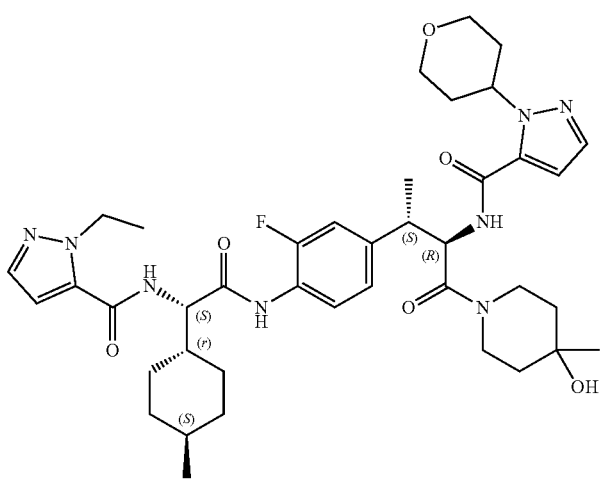
417

TABLE 1-continued

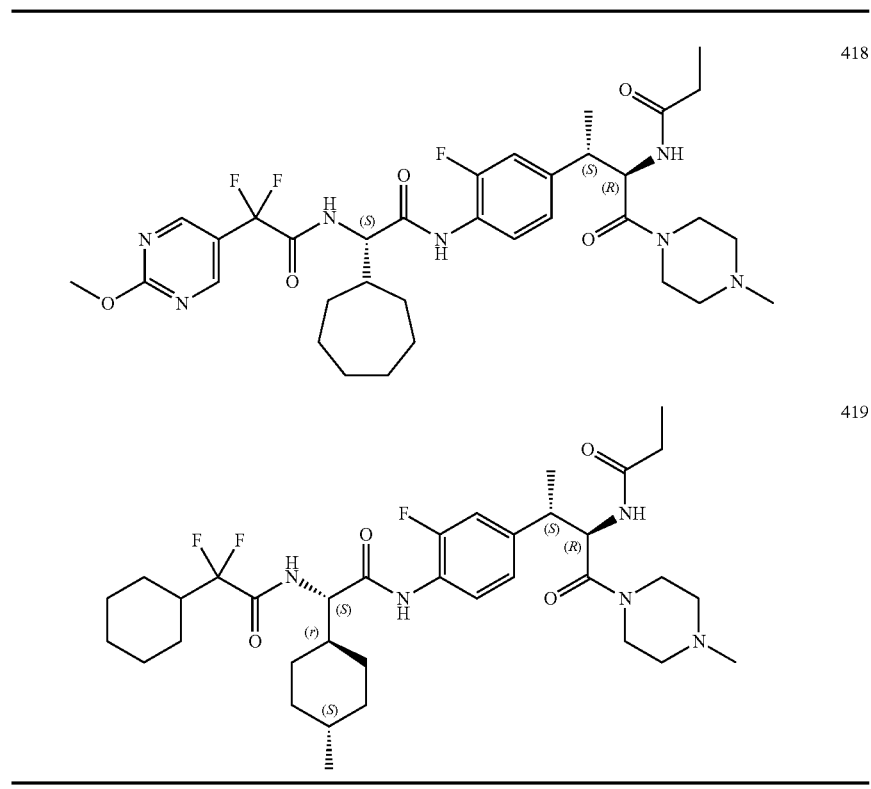

Preparation of the Compounds

FIGS. 1-32 illustrate exemplary synthetic routes to compounds of structural formula (I). Those of skill in the art are aware that the compounds of Formula (I) may be prepared by any number of synthetic methods. Accordingly, the methods presented in FIGS. 1-32 for the synthesis of compounds of formula (I) are illustrative rather than comprehensive.

FIG. 1 illustrates synthetic schemes used to prepare compounds 101, 102, 104-125, 127, 130, 133, 137, 138, 140, 141, 143, 144, 146 and 147. Referring to FIG. 1, amino ester 1 is acylated (propionic acid (1.2 eq., HATU (1.5 eq.), DIPEA (4 eq.) in DMF at ambient temperature for 1 h) to provide amide ester 2 in 100% yield. Reduction of the nitro group under standard conditions ($H_2$, Pd/C (20 mol %), EtOH, 4 h) provides amine 3 in 100% yield. Reaction with protected cyclohexyl glycine 4 ((1.2 eq.), HATU (1.5 eq.), DIPEA (3 eq.), DMF) at ambient temperature for 1 h provided protected amino acid 5 in 94% yield. Removal of the benzyl protecting group was accomplished under standard conditions ($H_2$, Pd/C (20 mol %), 1M HCl (1.03 eq) EtOH, 18 h) to provide the free amine 6 which was then acylated (1-methyl pyrazole carboxylic acid (1.2 eq., HATU (1.5 eq.), DIPEA (3 eq.), DMF) at ambient temperature for 1 h) to provide 7 in 77% yield. Ester hydrolysis (1M LiOH in water (3.0 eq.)) provided key intermediate 8 in 99% yield. Free acid 8 was then reacted with various amines to provide amides 101, 106, 108-125, 127, 130, 133, 137, 138, 140, 141, 143, 144, 146 and 147. Compounds 138, 141, 144 and 147 were treated with acid to provided compounds 102, 104, 105 and 107.

Figure 2:
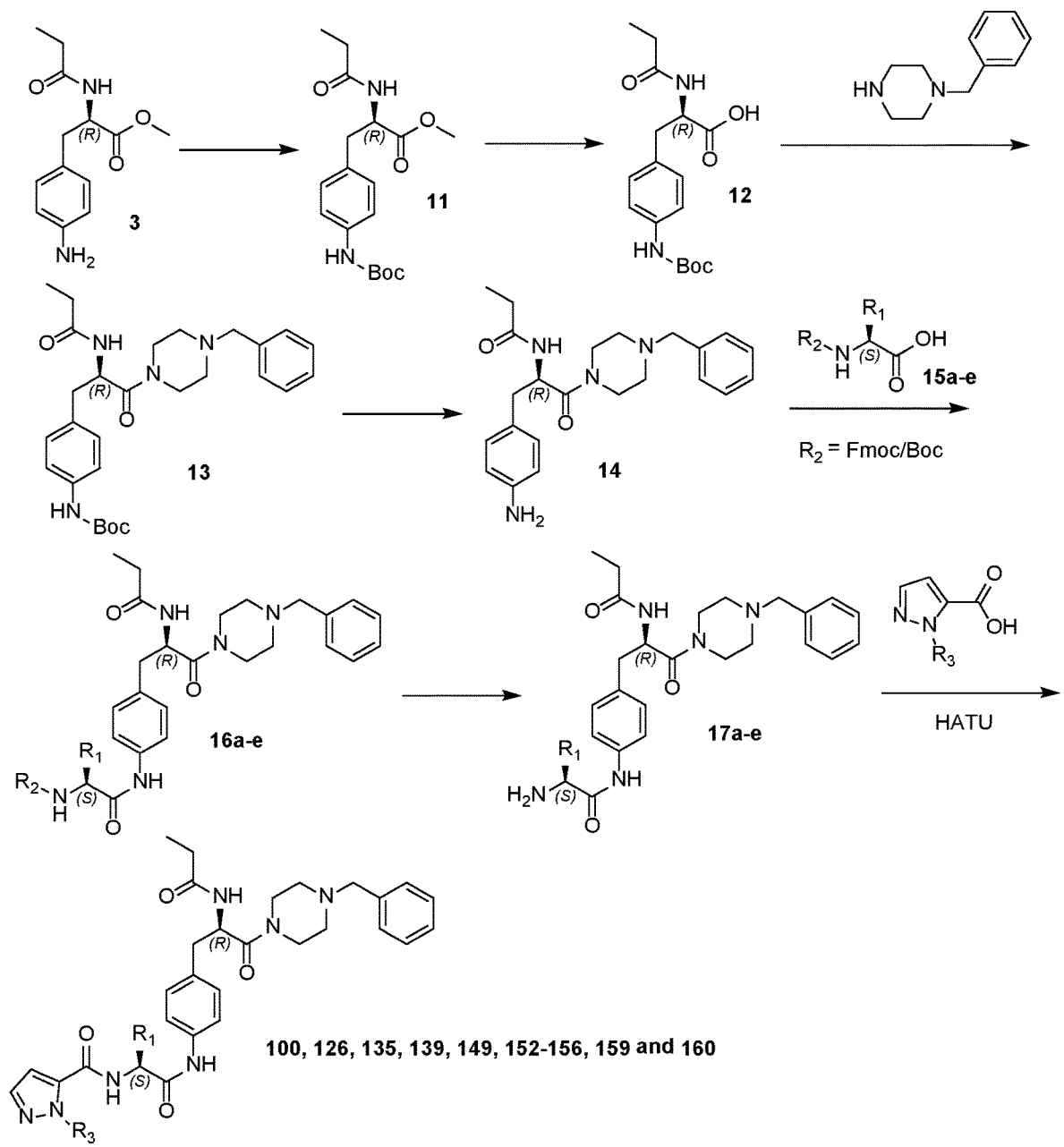
FIG. 2 illustrates a synthetic scheme used to prepare compounds 100, 126, 135, 139, 149, 152-156, 159 and 160.

FIG. 2 illustrates a synthetic scheme used to prepare compounds 100, 126, 135, 139, 149, 152-156, 159 and 160. Referring to FIG. 2, compound 3, prepared as described above, was protected ($Boc_2O$ (1.1 eq.), DIPEA (3.0 eq.), DCM, 0° C. to RT, 72 h) to provide BOC derivative 11 in 58% yield. Ester hydrolysis (1M LiOH in water (1.2 eq.), THF, MeOH, RT, 1 h) provided lithium salt 12 in 100% yield, which was then converted (N-benzyl piperazine (1.2 eq.), HATU (1.5 eq.), DIPEA (4 eq.), RT, 1 h, DMF) to piperazine 13 in 91% yield. The BOC group was removed (TFA, RT, 2 h) to provide arylamine 14 in 78% yield which was then acylated with FMOC or BOC amino acid 15a-e. Removal of the amine protecting group followed by acylation of the free amine 17a-e (1H-pyrazole-5-carboxylic acid derivatives (1.2 eq.), HATU (1.5 eq.), DIPEA (4 eq.), RT, 1 h, DMF) provided compounds 100, 126, 135, 139, 149, 152-156, 159 and 160. Examples 44-71 describe preparation of the above compounds.

Figure 3:
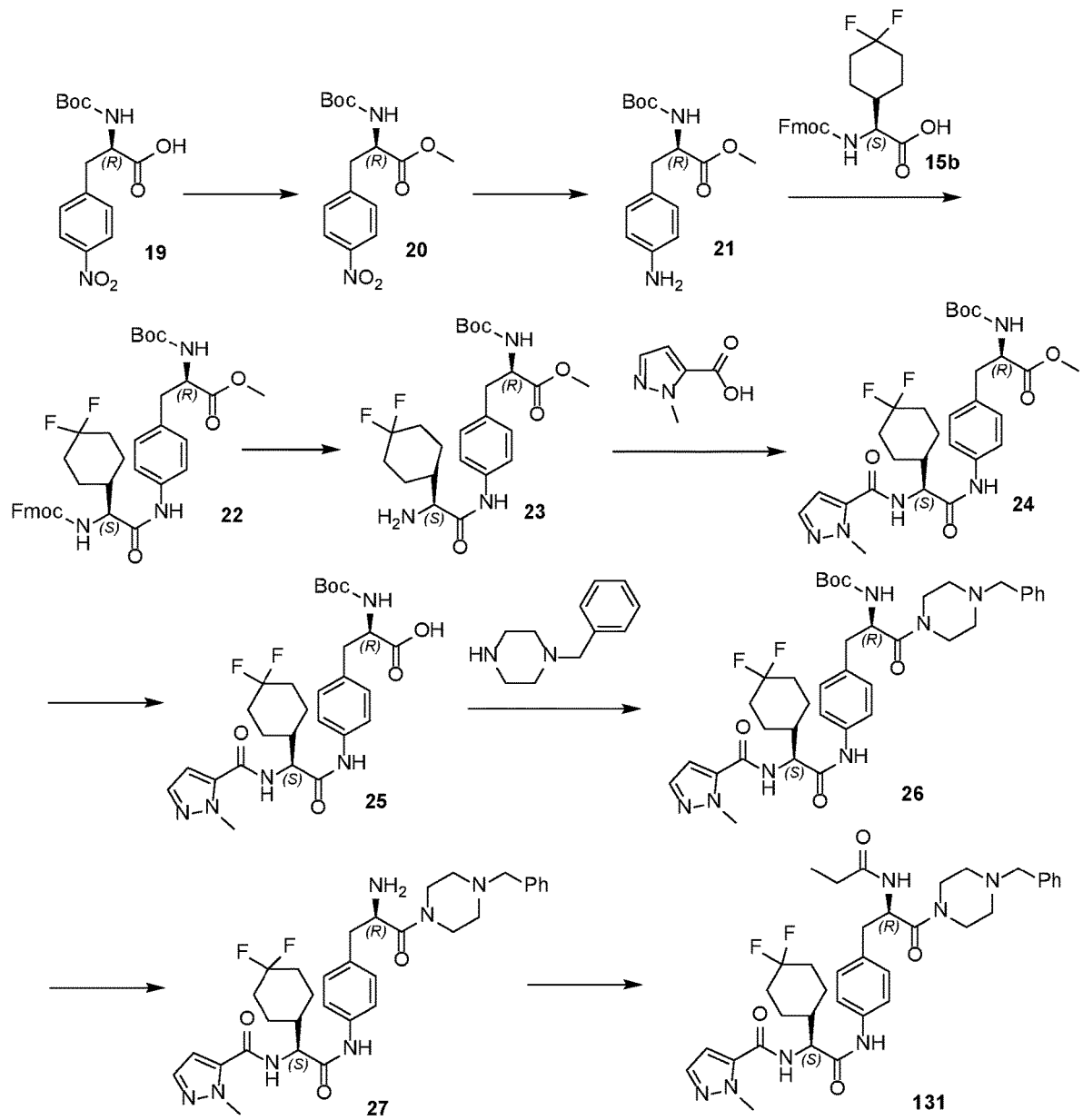
FIG. 3 illustrates a synthetic scheme used to prepare compound 131.

FIG. 3 illustrates a synthetic scheme used to prepare compound 131. Referring to FIG. 3, compound 19, a commercially available amino acid, is esterified (MeI (5.0 eq.), $NaHCO_3$ (2.0 eq.), DMF, 0° C. to RT, 18 h) to yield methyl ester 20 in 87% yield. Reduction of the nitro group was accomplished under standard conditions ($H_2$, Pd/C (20 mol %), EtOH, THF, RT, 4 h) to provide arylamine 21 in 91% yield which was acylated with an FMOC 4-difluorocyclohexylglycine (15 (1.2 eq.), HATU (1.5 eq.), DIPEA (3 eq.), RT, 1 h) to provide amide 22 in in 63% yield. Removal of the FMOC group under standard conditions (piperidine (20.0 eq.), DMF, RT, 1 h) yielded free amine 23 in 65% yield which was acylated (1-methyl-1H-pyrazole-5-carboxylic acid (1.2 eq.), HATU (1.5 eq.), DIPEA (4 eq.), RT, 1 h, DMF) to provide pyrazole 24 in 100% yield. Ester hydrolysis (1M LiOH in water (1.2 eq.), THF, MeOH, RT, 1 h) provided free acid 25 in 100% yield which was then converted (N-benzyl piperazine (1.2 eq.), HATU (1.5 eq.), DIPEA (4 eq.), RT, 1 h, DMF) to piperazine 26 in 100% yield. Removal of the BOC protecting group (TFA, RT, 2 h) gave the free amine 27 in 100% yield which was then acylated (propionic acid (1.2 eq.), HATU (1.5 eq.), DIPEA (3.0 eq.), DMF, RT, 1 h) to provide 131.

Figure 4:
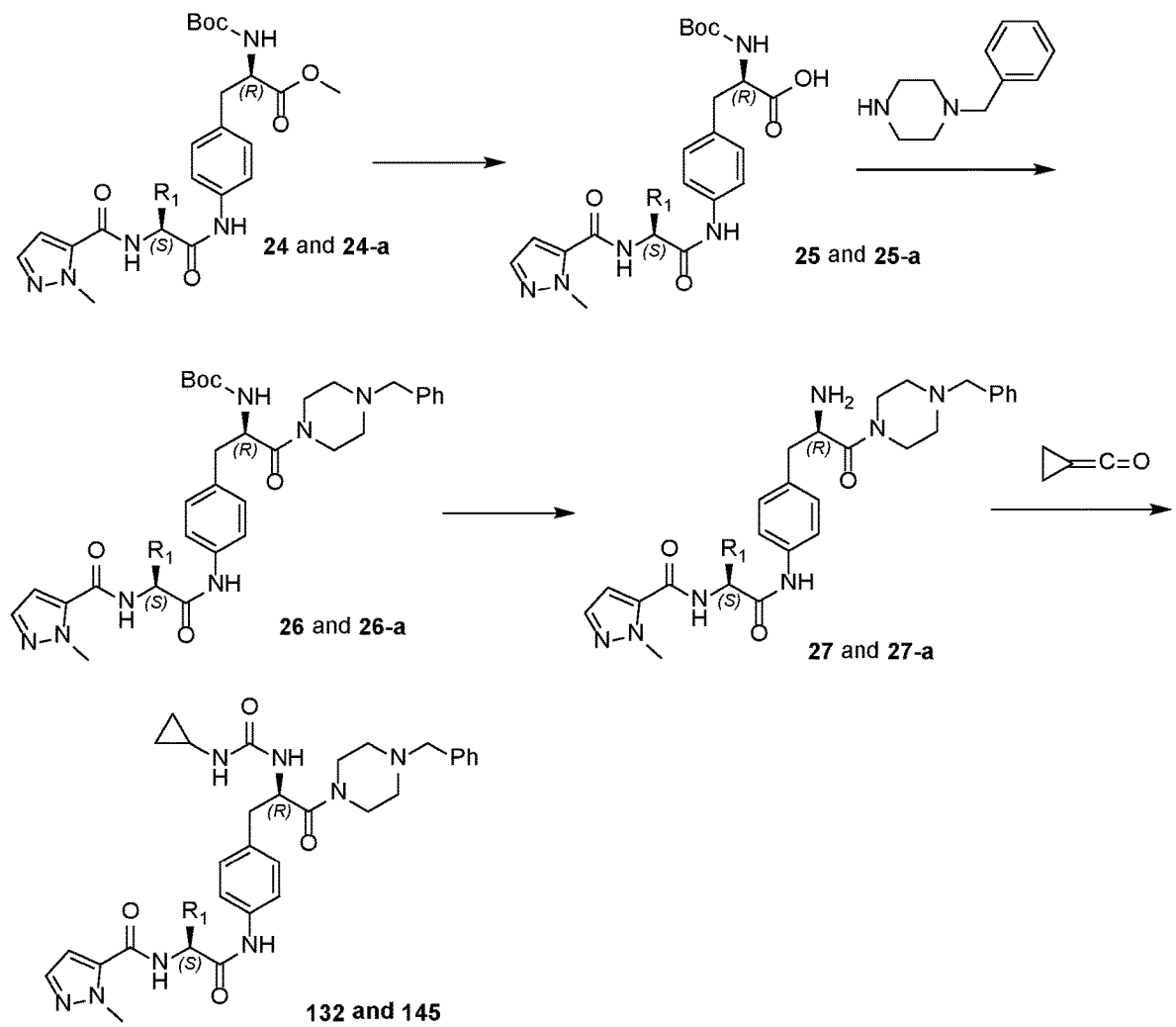
FIG. 4 illustrates a synthetic scheme used to prepare compound 132 and 145.

FIG. 4 illustrates a synthetic scheme used to prepare compound 132 and 145. Referring to FIG. 4, hydrolysis of compounds 24 and 24-a, (24-a is made by a method analogous to the preparation of 24 except that FMOC-cyclohexyl glycine is used to acylate compound 20 in Scheme 3), (1M LiOH in water (1.2 eq.), THF, MeOH, RT, 1 h) provided free acid 25 and 25-a in 58-100% yield, which was then converted (N-benzyl piperazine (1.2 eq.), HATU (1.5 eq.), DIPEA (4 eq.), RT, 1 h, DMF) to piperazine 26 and 26-a in 89-100% yield. Removal of the BOC group (TFA, RT, 2 h) gave the free amine 27 and 27-a in 100% yield, which was acylated (isocyanatocyclopropane, 1.5 eq., DIPEA (3.0 eq.), DMF, RT, 1 h) to provide 132 and 145 in 17% and 58% yield, respectively.

Figure 5:
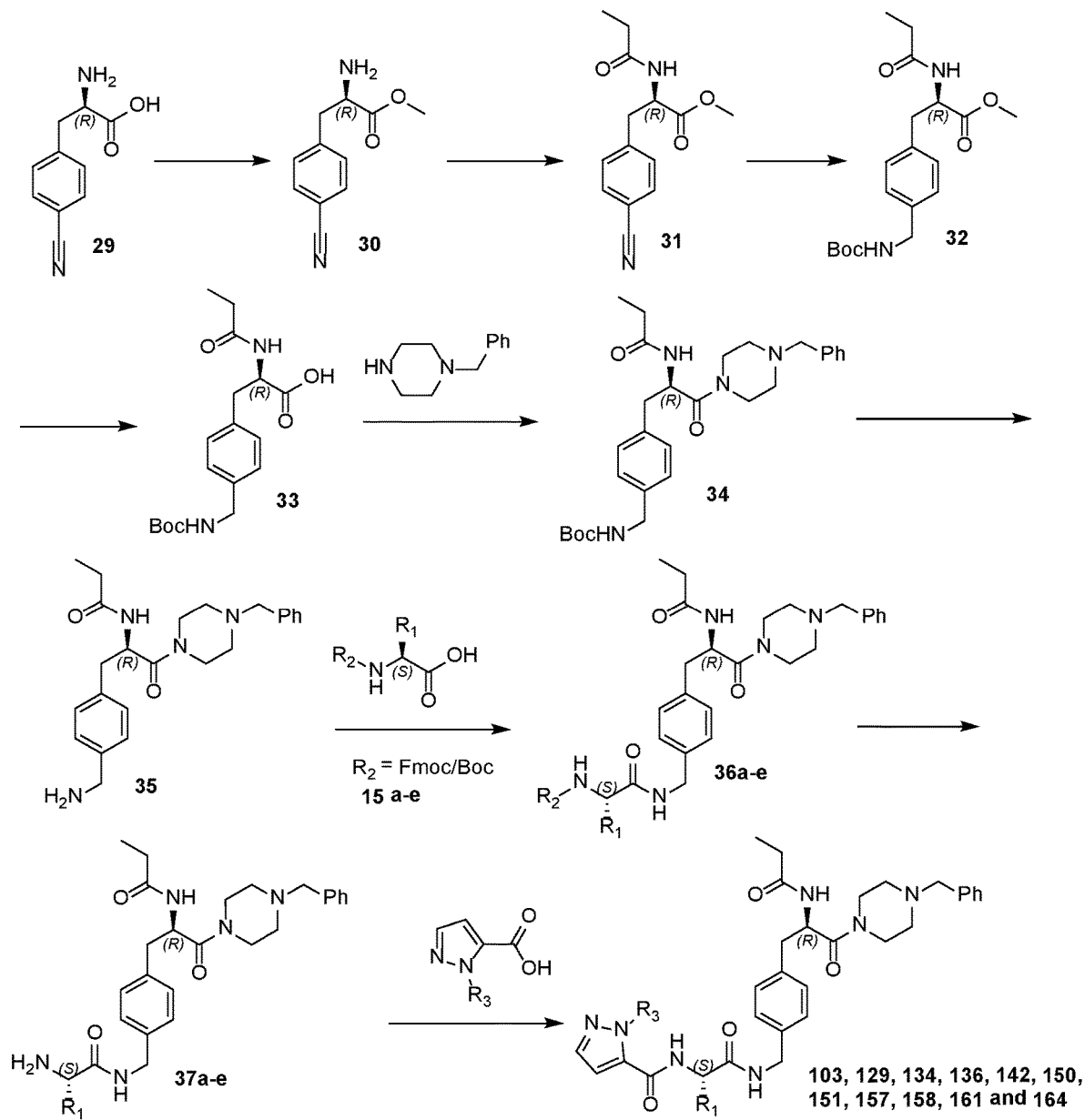
FIG. 5 illustrates a synthetic scheme used to prepare compounds 103, 129, 134, 136, 142, 150, 151, 157, 158, 161 and 164.

FIG. 5 illustrates a synthetic scheme used to prepare compounds 103, 129, 134, 136, 142, 150, 151, 157, 158, 161 and 164. Referring to FIG. 5, amino acid 29, is esterified ($SOCl_2$ (5.0 eq.), MeOH, 0° C. to RT, 18 h) to provide methyl ester 30 in 92% yield. The amino group is acylated (propionic acid (1.2 eq.), HATU (1.5 eq.), DIPEA (3.0 eq.), DMF, RT, 1 h), to provide amide 31 in 100% yield. Reduction of the aromatic nitrile with in-situ capture of the amino product ($NiCl_2.6H_2O$ (0.1 eq.), $Boc_2O$ (2.0 eq.), $NaBH_4$ (7.0 eq.), MeOH, −20° C. to RT, 2 h) provides the protected benzyl amine 32 in 62% yield. Hydrolysis of methyl ester (1M LiOH in water (1.2 eq.), THF, MeOH, RT, 1 h) in provides the free acid 33 in 100% yield which is then acylated (N-benzyl piperazine (1.2 eq.), HATU (1.5 eq.), DIPEA (4 eq.), RT, 1 h, DMF) to yield piperazine 34 in 82% yield. Removal of the BOC group (TFA, RT, 2 h) provides benzyl amine 35 in 82% yield which is then acylated with protected amino acids 15a-e (15a-e (1.2 eq.), HATU (1.5 eq.), DIPEA (3 eq.), RT, 1 h) to provide amides 36a-e in 62-95% yield. Removal of the BOC protecting group with acid (TFA, RT, 2 h) provided 37 in 28% to 100% yield. Removal of the FMOC group with base (piperidine, DMF, RT, 0.5 h) provided 37 in 37% to 64% yield. Acylation of the amine (1-methyl-1H-pyrazole-5-carboxylic acid, 1-ethyl-1H-pyrazole-5-carboxylic acid (1.2 eq.), HATU (1.5 eq.), DIPEA (4 eq.), DMF, RT, 1 h or 1-isopropyl-1H-pyrazole-5-carboxylic acid) provides 103, 129, 134, 136, 142, 150, 151, 157, 158, 161 and 164.

Figure 6:
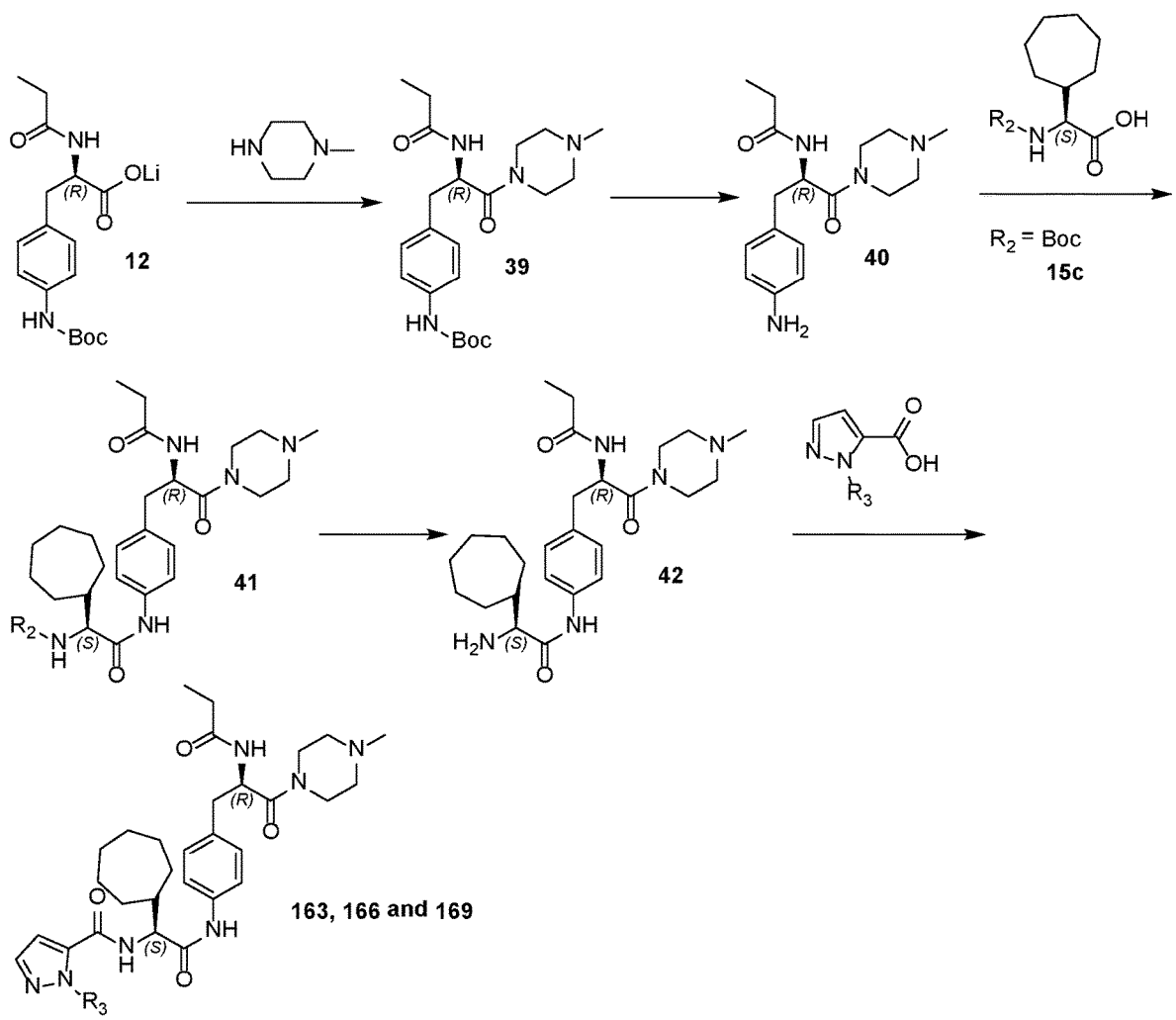
FIG. 6 illustrates a synthetic scheme used to prepare compounds 163, 166 and 169.

FIG. 6 illustrates a synthetic scheme used to prepare compounds 163, 166 and 169. Referring to FIG. 6, compound 12 is converted (N-methyl piperazine (1.05 eq.), HATU (1.2 eq.), DIPEA (2.5 eq.), RT, 1 h, DMF) to piperazine 39 in 70% yield. The Boc group is removed (TFA, RT, 2 h) to yield aryl amine 40 in 46% yield, which is then acylated with protected amine acid (15c (1.2 eq.), HATU (1.5 eq.), DIPEA (3 eq.), RT, DMF, 1 h) to provide amide 41. The protecting group was removed to yield free amine 42 which was then acylated (1-methyl-1H-pyrazole-5-carboxylic acid, 1-ethyl-1H-pyrazole-5-carboxylic acid (1.2 eq.), HATU (1.5 eq.), DIPEA (4 eq.), DMF, RT, 1 h or 1-isopropyl-1H-pyrazole-5-carboxylic acid) to provide 163, 166 and 169.

Figure 7:
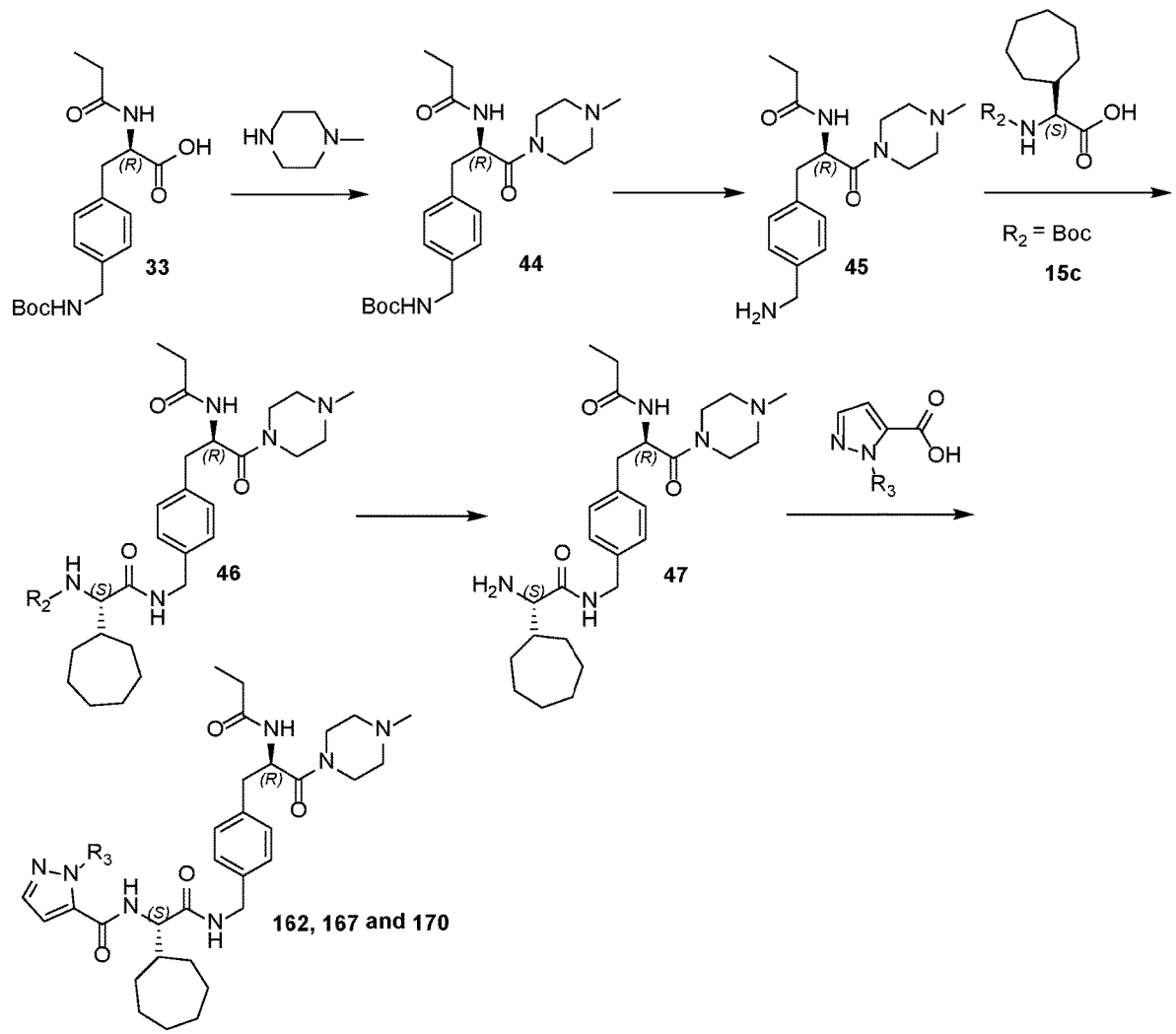
FIG. 7 illustrates a synthetic scheme used to prepare compounds 162, 167 and 170.

FIG. 7 illustrates a synthetic scheme used to prepare compounds 162, 167 and 170. Referring to FIG. 7, compound 33 is converted (N-methyl piperazine (1.2 eq.), HATU (1.5 eq.), DIPEA (3.0 eq.), RT, 1 h, DMF) to piperazine 44 in 57% yield. The Boc group is removed (TFA, RT, 1 h) to yield benzylamine 45 in 63% yield, which is then acylated with protected amine acid (15c (1.2 eq.), HATU (1.5 eq.), DIPEA (3 eq.), RT, DMF, 1 h) to provide amide 46. The protecting group was removed to yield free amine 47 which was then acylated (1-methyl-1H-pyrazole-5-carboxylic acid, 1-ethyl-1H-pyrazole-5-carboxylic acid (1.2 eq.), HATU (1.5 eq.), DIPEA (4 eq.), DMF, RT, 1 h or 1-isopropyl-1H-pyrazole-5-carboxylic acid) to provide 162, 167 and 170.

The synthesis of compounds 172-202 via solid phase methods is described in Examples 135-142.

Figure 8:
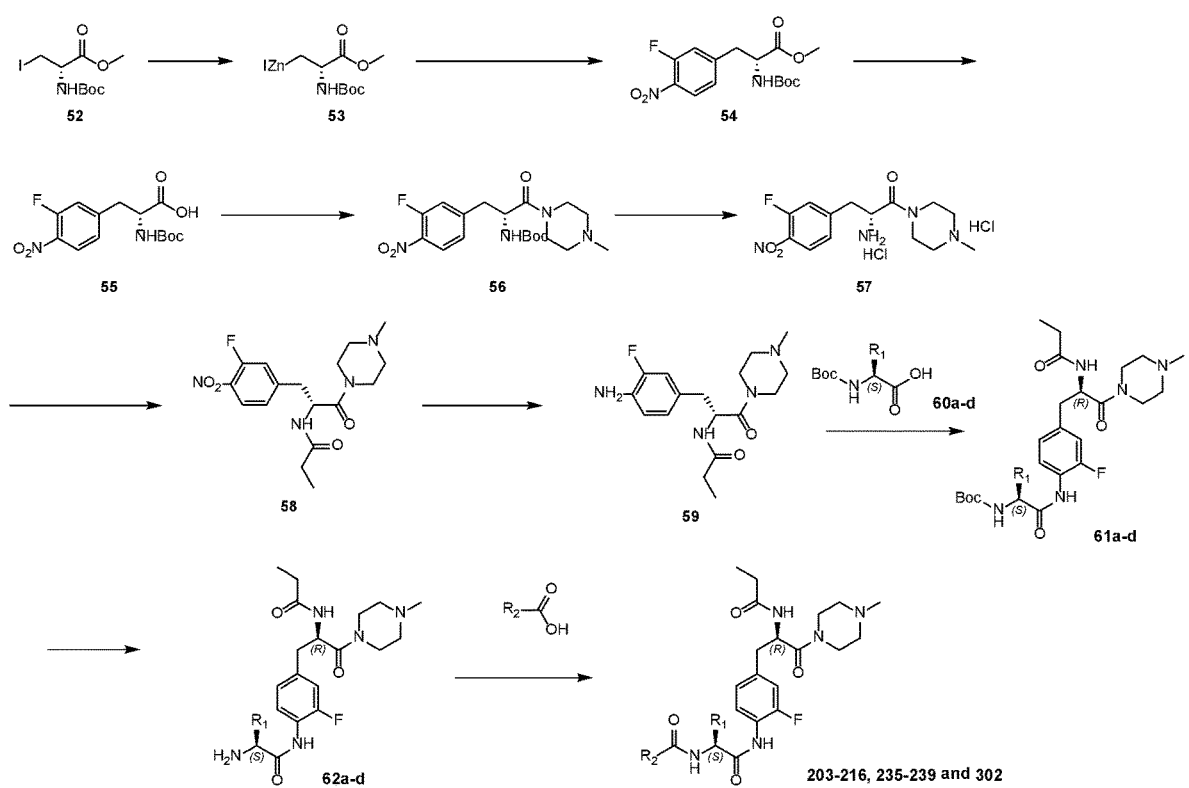
FIG. 8 illustrates a synthetic scheme used to prepare compounds 203-216, 235-239 and 302.

FIG. 8 illustrates a synthetic scheme used to prepare compounds 203-216, 235-239, and 302. Referring to FIG. 8, compound 52 was treated with Zn and $I_2$ in DMF to provide the iodozinc intermediate 53 which was reacted in situ with 2-fluoro-4-bromo nitrobenzene in the presence of a palladium catalyst and SPhos to provide amino ester 54. Hydrolysis provided carboxylic acid 55 (LiOH, THE-$H_2O$) which was then converted to amide 56. The Boc group was removed (HCl/dioxane, DCM) to yield 57 and the amine was then acylated ($Et_2CO$, TEA, DCM) to provide 58. Reduction of the nitro group (Raney Ni, $H_2$, MeOH) provided key intermediate 59 which was then acylated with protected amino acids 60a-d ((1.2 eq.), HATU (1.5-2.0 eq.), DIPEA (4.0-8.0 eq.), RT, 1 h, DMF) to yield 61a-d. Removal of the Boc group (TFA, DCM, RT, 0.5 h) provided free amines 62a-d which were then acylated with a variety of carboxylic acids ((1.2 eq.), HATU (1.5 eq.), DIPEA (3.0-8.0 eq.), RT, 1 h, DMF) to yield compounds 203-216, 235-239 and 302

Figure 9:
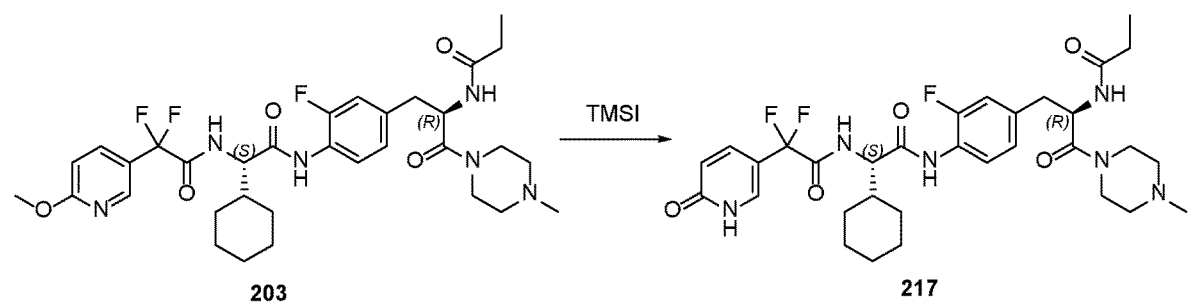
FIG. 9 illustrates a synthetic scheme used to prepare compound 217.

FIG. 9 illustrates a synthetic scheme used to prepare compound 217. Referring to FIG. 9, compound 203 was treated with TMSI in DCM to yield compound 217.

Figure 10:
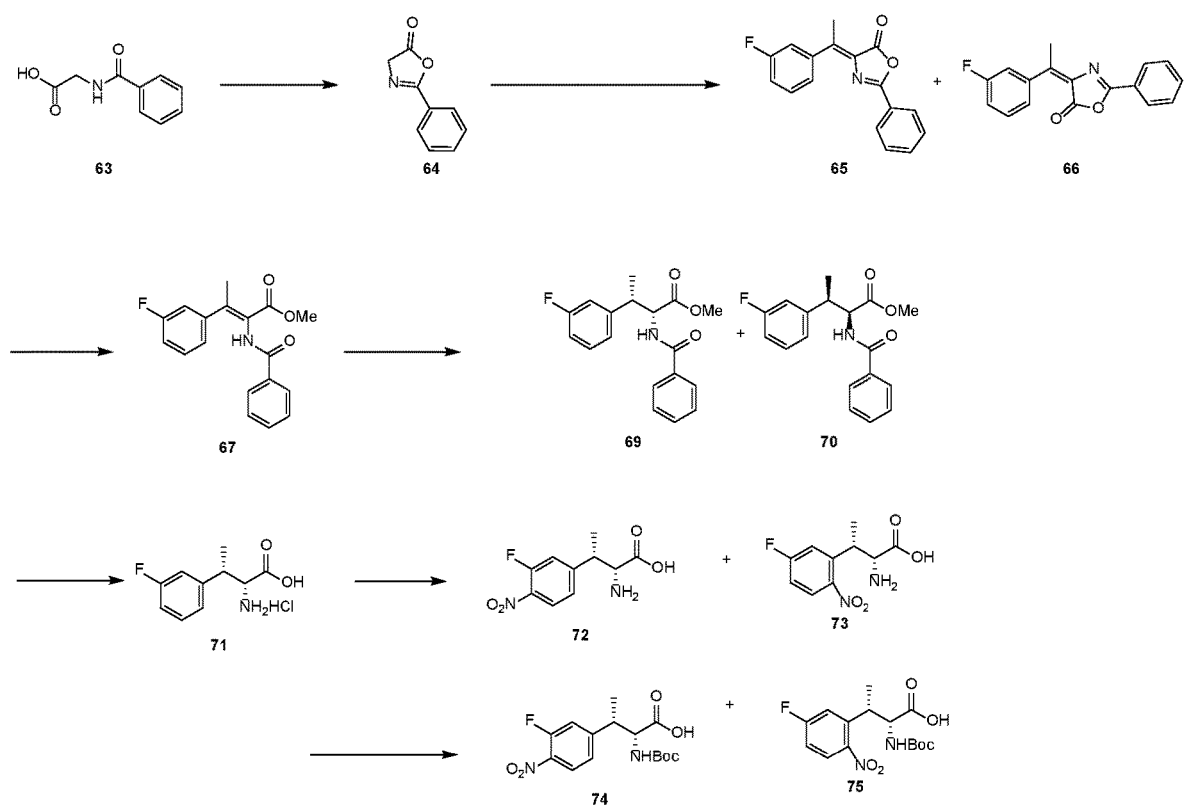
FIG. 10 illustrates a synthetic scheme used to prepare intermediate 74.

FIG. 10 illustrates a synthetic scheme used to prepare intermediate 74. Referring to FIG. 10, compound 63 was cyclized (EDCI, DCM) to provide imino lactam 64. Aldol condensation ($TiCl_4$, DCM, THF) with 3-fluoroacetophenone provided a mixture of aldol adducts 65 and 66. The aldol adducts were separated to provide regioisomer 65 which was then hydrolyzed (MeONa, MeOH) to provide ester 67. Hydrogenation of 67 (Pd/C $H_2$, MeOH) yielded a racemic mixture of 69 and 70, which were resolved to provide isolated ester 69. Hydrolysis of the amide 69 (AcOH/HCl) provided amine hydrochloride 71 which was then nitrated (HNO3, $H_2SO_4$) to yield the free amine regioisomers 72 and 73. Protection of the amine with the Boc group and separation of the regioisomers provided the desired intermediate 74 in pure form.

Figure 11:
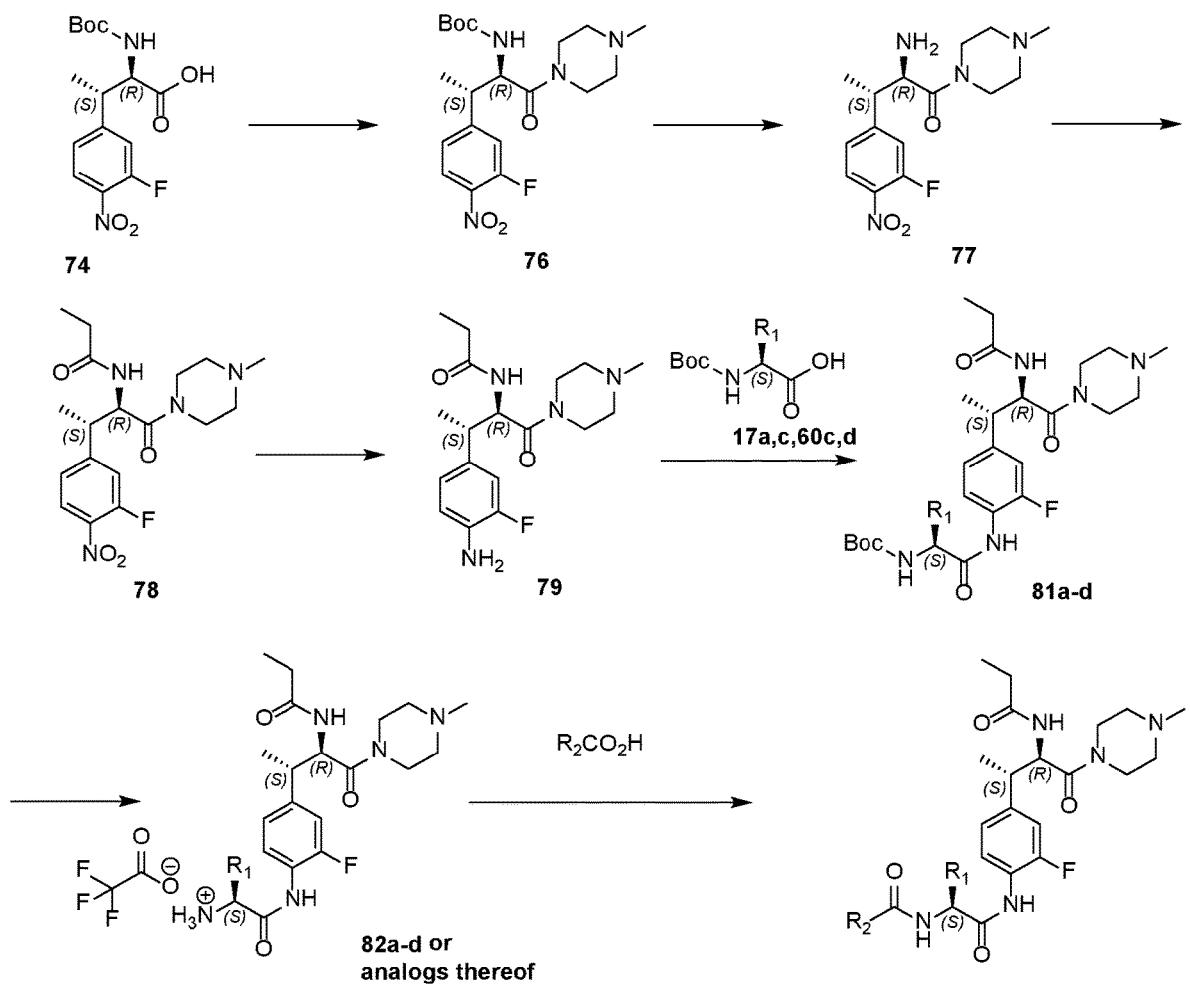
FIG. 11 illustrates a synthetic scheme used to prepare compounds 218-220, 228-230, 233-234, 240-296, 389, 390, 393, 394, 397, 399, 404, 405, 418 and 419.

FIG. 11 illustrates a synthetic scheme used to prepare compounds 218-220, 228-230, 233-234, 240-296, 389, 390, 393, 394, 397, 399, 404, 405, 418 and 419. Referring to FIG. 11, key intermediate 74 was converted to amide 76 (N-methyl piperazine (1.2 eq.) HATU (1.5 eq.), DIPEA (5.0 eq.), DMF, RT, 1 h) which after deprotection (TFA, DCM, RT, 1 h) provided free amine 77. Acylation of the amine provided the propionamide derivative 78 (propionic anhydride (1.2 eq.), DIPEA (1.2 eq.), DMF, RT, 1 h) which was reduced to provide the arylamine 79 ($H_2$, Pd/C (20 mol %), EtOH, THF, RT, 18 h). Acylation of the arylamine 79 with acids 80a-d ((1.2 eq.), HATU (1.5 eq.), DIPEA (3.0 eq.), DMF, RT, 1 h) provided compounds 81a-d which were then deprotected (TFA, DCM, RT, 1 h) and acylated with a variety of acids ((1.2 eq.), HATU (1.5 eq.), DIPEA (3.0 eq.), DMF, RT, 1 h) to provide compounds 218-220, 228-230, 233-234, 240-296, 389, 390, 393, 394, 397, 399, 404, 405, 418 and 419.

Figure 12:
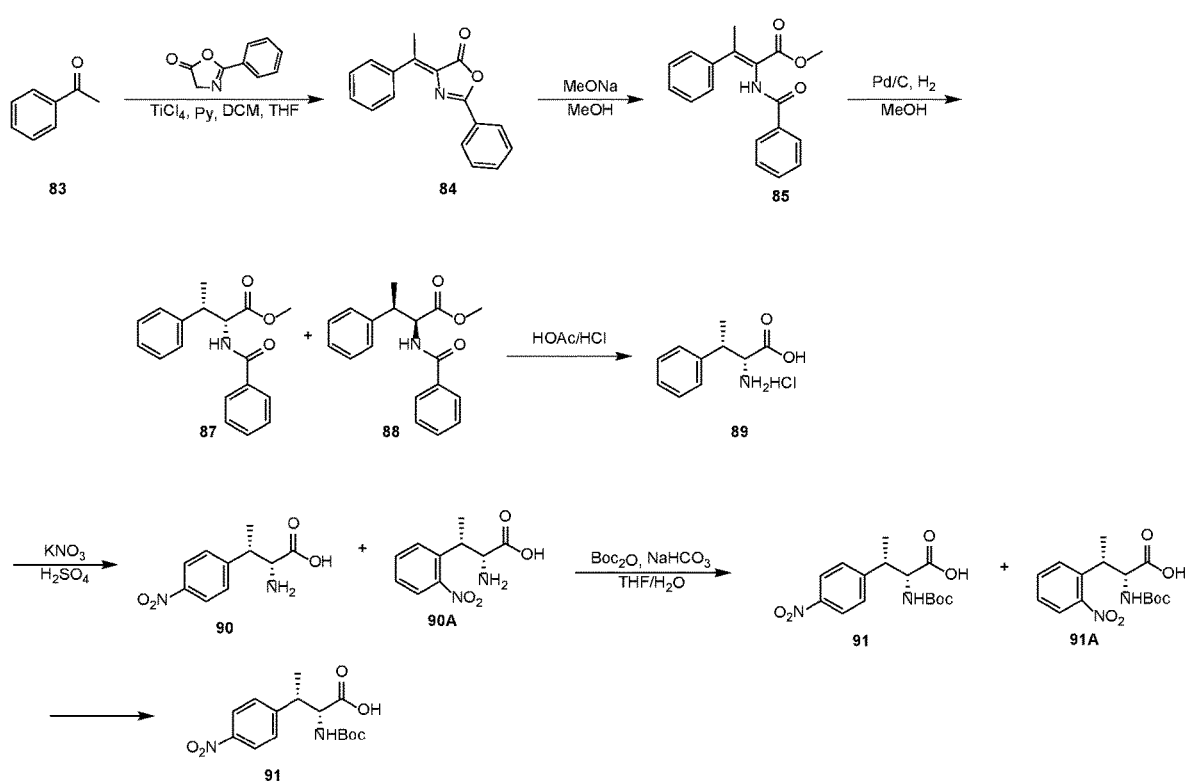
FIG. 12 illustrates a synthetic scheme used to prepare key intermediate 91.

FIG. 12 illustrates a synthetic scheme used to prepare intermediate 91. Referring to FIG. 12, Aldol condensation between acetophenone 83 and the iminolactone (TiCl$_4$, pyridine and DCM and THF) provided the aldol adduct 84 which was then hydrolyzed (MeONa, MeOH) to provide the unsaturated compound 85, which was separated from its regioisomer (not shown). Hydrogenation (Pd/C, H$_2$, MeOH) provided a mixture of isomers 87 and 88 which were separated to provide the desired isomer 87. Hydrolysis (AcOH/HCl) of 87 provided amine hydrochloride 89 which was then converted to a mixture of nitro regioisomers (KNO$_3$, H$_2$SO$_4$) 90 and 90A, protected (Boc$_2$O, NaHCO$_3$, THF/H$_2$O) and separated to provide key intermediate 91.

Figure 13:
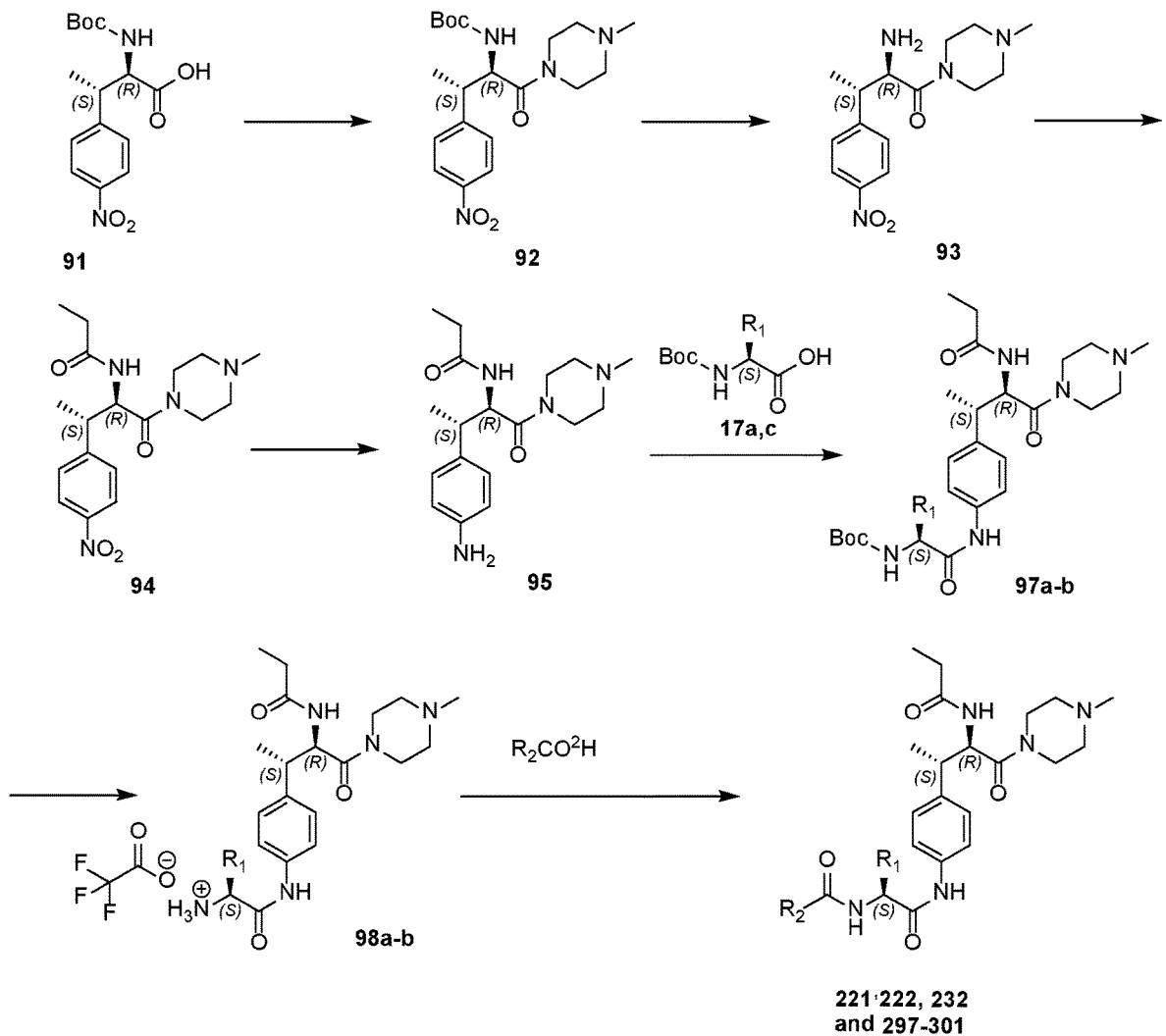
FIG. 13 illustrates a synthetic scheme used to prepare compounds 221, 222, 232 and 297-301.

FIG. 13 illustrates a synthetic scheme used to prepare compounds 221, 222, 232 and 297-301. Referring to FIG. 13, key intermediate 91 was converted to amide 92 (N-methyl piperazine (1.2 eq.) HATU (1.5 eq.), DIPEA (5.0 eq.), DMF, RT, 1 h) which after deprotection (TFA, DCM, RT, 1 h) provided free amine 93. Acylation of the amine provided the propionamide derivative 94 (propionic anhydride (1.2 eq.), DIPEA (1.2 eq.), DMF, RT, 1 h) which was reduced to yield the arylamine 95 (H$_2$, Pd/C (20 mol %), EtOH, THF, RT, 18 h). Acylation of the arylamine 95 with acids 96a-b ((1.2 eq.), HATU (1.5 eq.), DIPEA (3.0 eq.), DMF, RT, 1 h), provided amides 97a-b, which were then deprotected (TFA, DCM, RT, 1 h) and acylated with different acids ((1.2 eq.), HATU (1.5 eq.), DIPEA (3.0 eq.), DMF, RT, 1 h) to provide compounds 221, 222, 232 and 297-301.

Figure 14:
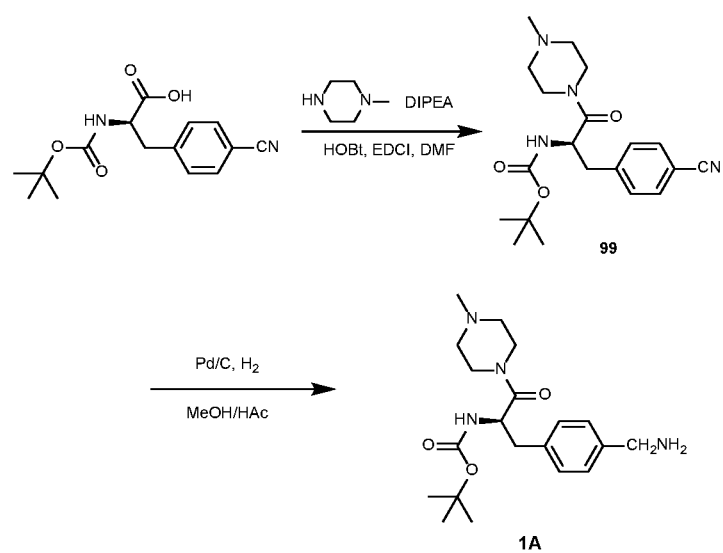
FIG. 14 illustrates a synthetic scheme used to prepare key intermediate 1A.

FIG. 14 illustrates a synthetic scheme used to prepare intermediate 1A. Referring to FIG. 14, protected amino acid 99, made by acylation of methyl piperidine with the commercially available protected amino acid, was reduced (Pd/C Hz, MeOH/AcOH) to provide key intermediate 1A.

Figure 15:
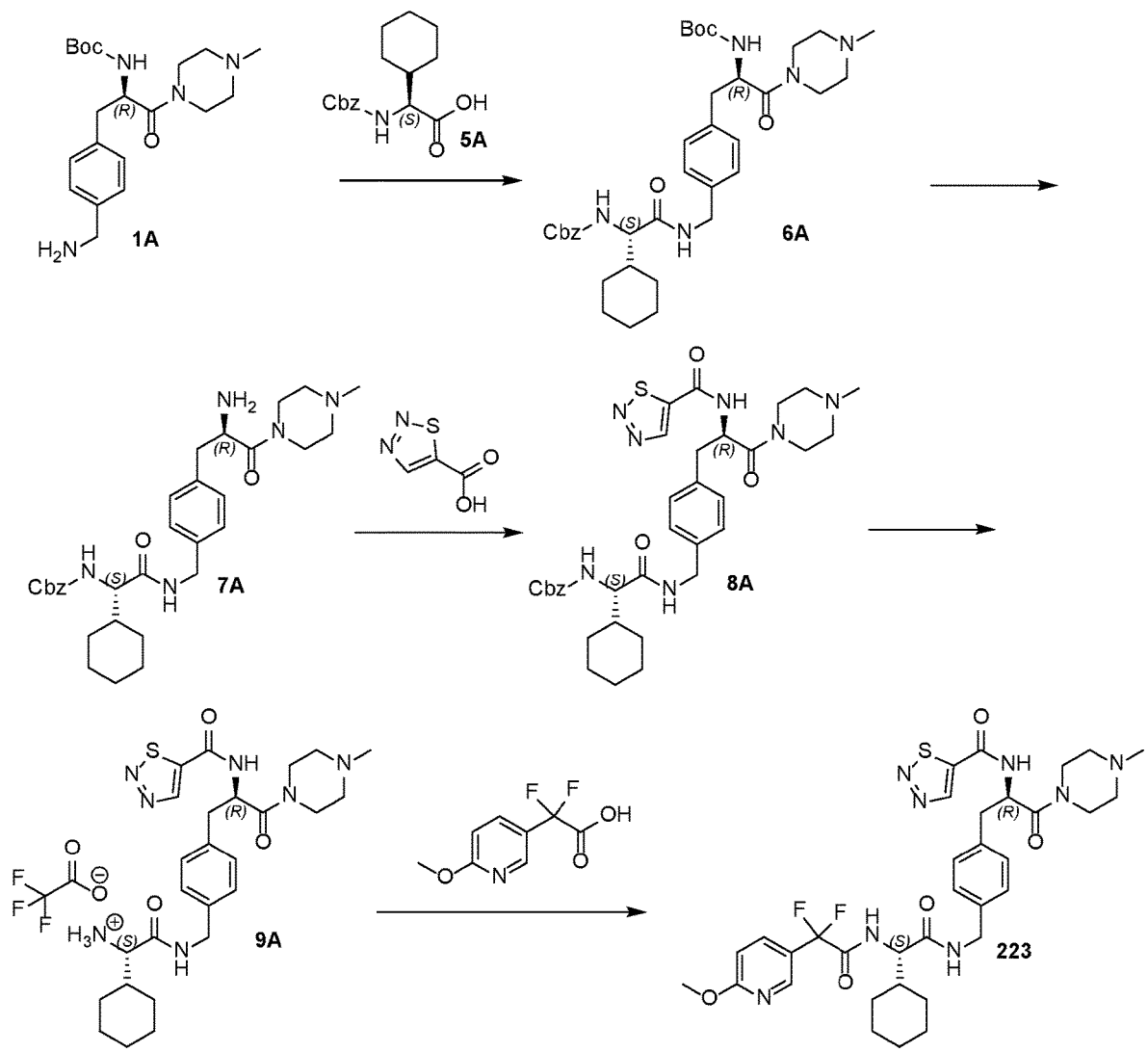
FIG. 15 illustrates a synthetic scheme used to prepare compound 223.

FIG. 15 illustrates a synthetic scheme used to prepare compound 223. Referring to FIG. 15, Key intermediate 1A was acylated (1A (1.0 eq.), 5A (1.5 eq.), T3P (2.5 eq.), DIPEA (6.0 eq.), THF, RT, 1 h) to provide 6A and then deprotected (TFA, DCM, RT, 1 h) to yield amine 7A. Acylation of 7A (1,2,3-thiadiazole-5-carboxylic acid (1.5 eq.), T3P (2.5 eq.), DIPEA (6.0 eq.), THF, RT, 18 h) provided amide 8A which was then deprotected (TFA, (2.0 mL), 100° C. for 3 h) to yield 9A. Acylation of the free amine (2,2-difluoro-2-(6-methoxypyridin-3-yl)acetic acid (1.2 eq.), HATU (1.5 eq.), DIPEA (12.0 eq.), DMF, RT, 1 h) then provided compound 223.

Figure 16:
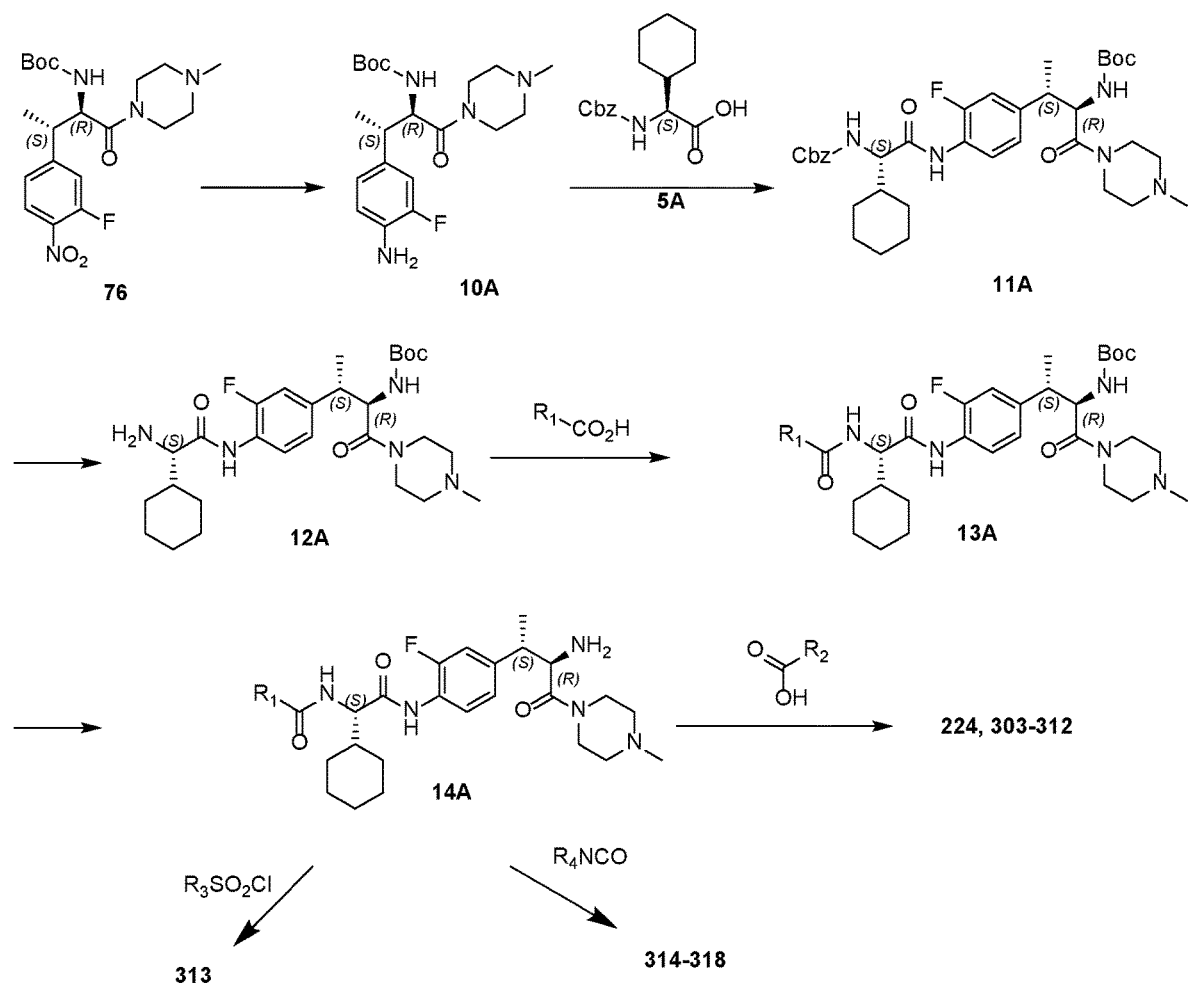
FIG. 16 illustrates a synthetic scheme used to prepare compound 224 and 303-318.

FIG. 16 illustrates a synthetic scheme used to prepare compound 224 and 303-318. Referring to FIG. 16, key intermediate 76 was reduced (Hz, Pd(OH)$_2$/C (1.0 eq.), THF, RT, 18 h) to provide 10A which was acylated (2.8 eq.), HATU (3.8 eq.), COMU (1.5 eq.), DIPEA (16.9 eq.), DMF, RT, 18 h) to yield 11A. Deprotection of 11A (H$_2$, Pd(OH)$_2$/C (1.27 eq.), THF, RT, 2 h) provided 12A which was acylated (HATU (1.5 eq.), DIPEA (4.0 eq.), DMF, RT, 1 h) with 2-difluoro-2-(6-methoxypyridin-3-yl)acetic acid to yield 13A. Deprotection (TFA, DCM, RT, 2 h) of 13A provided the amine 14A which was then acylated to provide 224 and 302-312, sulfonated to provide sulfonamide 313 or converted to ureas 314-318 by reaction with an isocyanate.

Figure 17:
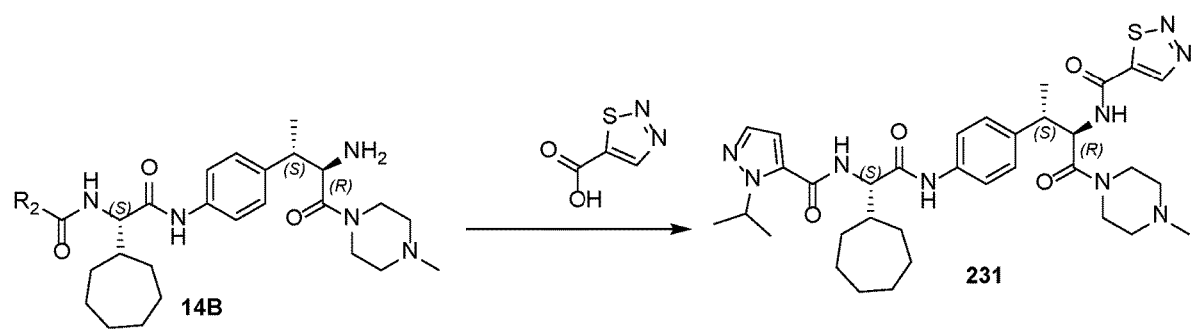
FIG. 17 illustrates a synthetic scheme used to prepare compound 231.

FIG. 17 illustrates a synthetic scheme used to prepare compound 231. Referring to FIG. 17, The amine 14B, which was made by a procedure analogous to that used to prepare amine 14A in scheme 16, was acylated (1,2,3-thiadiazole-5-carboxylic acid (1.2 eq.), HATU (1.5 eq.), DIPEA (3.0 eq.), DMF, RT, 1 h) to provide 231.

Figure 18:
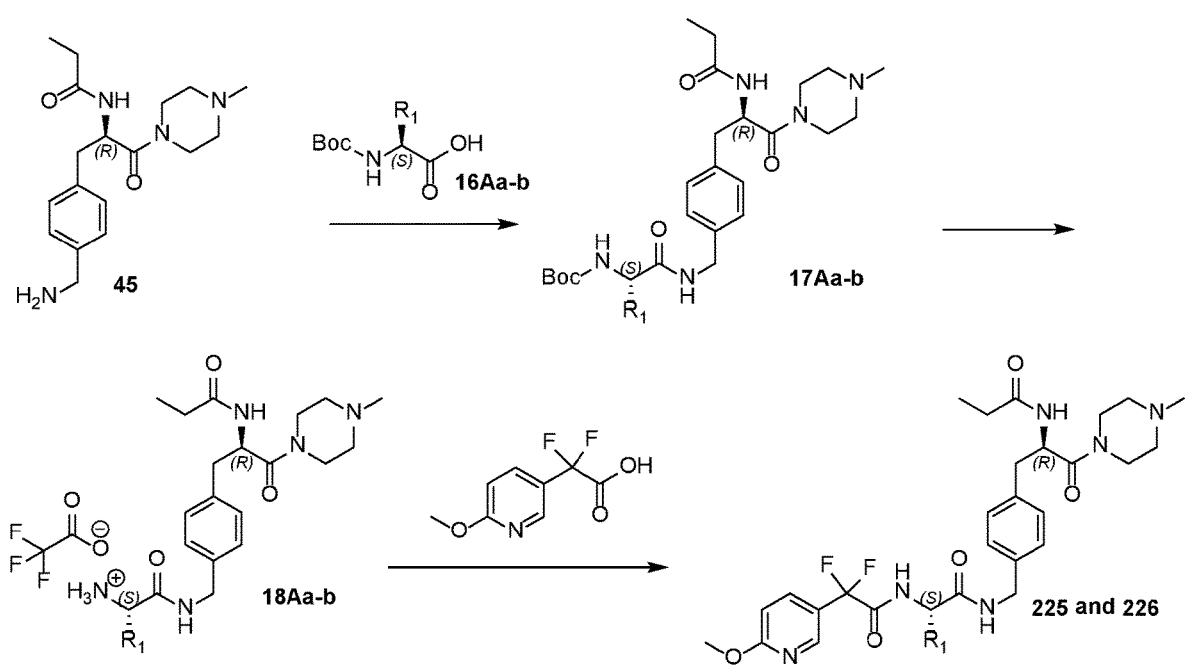
FIG. 18 illustrates a synthetic scheme used to prepare compounds 225 and 226.

FIG. 18 illustrates a synthetic scheme used to prepare compounds 225 and 226. Referring to FIG. 18, compound 45 was acylated (16Aa-b (1.5 eq.), T$_3$P (2.0 eq.), DIPEA (4.0-8.0 eq.), RT, 1 h, THF) to provide 17Aa-b, which was then deprotected (TFA, DCM, RT, 0.5 h) to yield 18Aa-b.

Acylation of free amine 18Aa-b (2,2-difluoro-2-(6-methoxypyridin-3-yl)acetic acid (1.2 eq.), HATU (1.5 eq.), DIPEA (3.0-8.0 eq.), RT, 1 h, DMF) provided 225 and 226.

Figure 19:
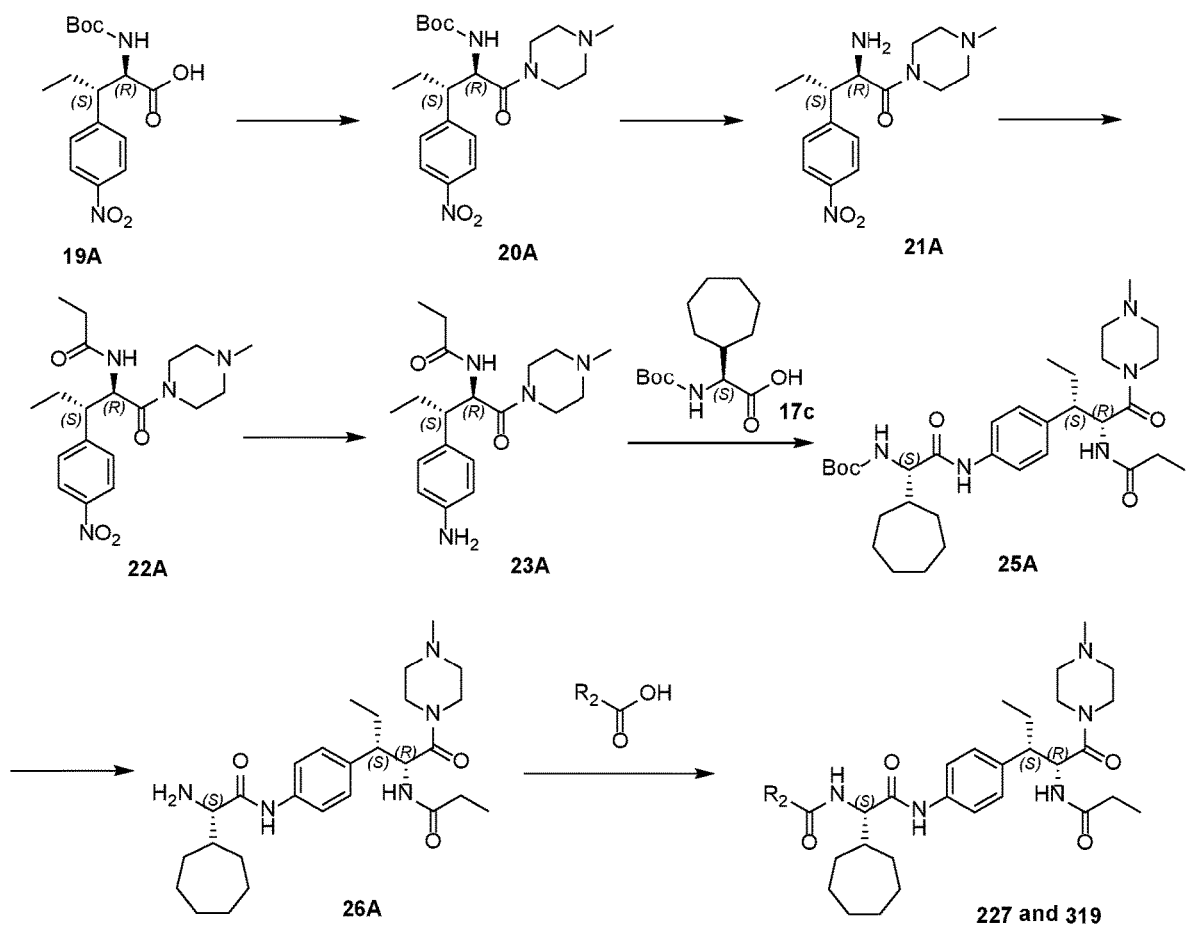
FIG. 19 illustrates a synthetic scheme used to prepare compound 227 and 319.

FIG. 19 illustrates a synthetic scheme used to prepare compound 227 and 319. Referring to FIG. 19, starting material 19A which was made by the procedure shown in FIG. 21 was converted (N-methyl piperazine (1.2 eq.) HATU (1.5 eq.), DIPEA (5.0 eq.), DMF, RT, 1 h) to 20A which was then deprotected (TFA, DCM, RT, 20 min) to yield 21A. Acylation of 21A (propionic anhydride (1.2 eq.), DIPEA (3.0 eq.), DMF, RT, 1 h) provided propionamide 22A which was then reduced (H$_2$, Pd/C (35 mol %), EtOH, THF, RT, 18 h) to provide arylamine 23A. Acylation of 23A with 24A (17c (1.2 eq.), HATU (1.5 eq.), DIPEA (8.0 eq.), DMF, RT, 1 h) provided 25A which was deprotected (TFA, DCM, RT, 0.5 h) to yield 26A. Acylation of 26A with carboxylic acids provided 227 and 319.

Figure 20:
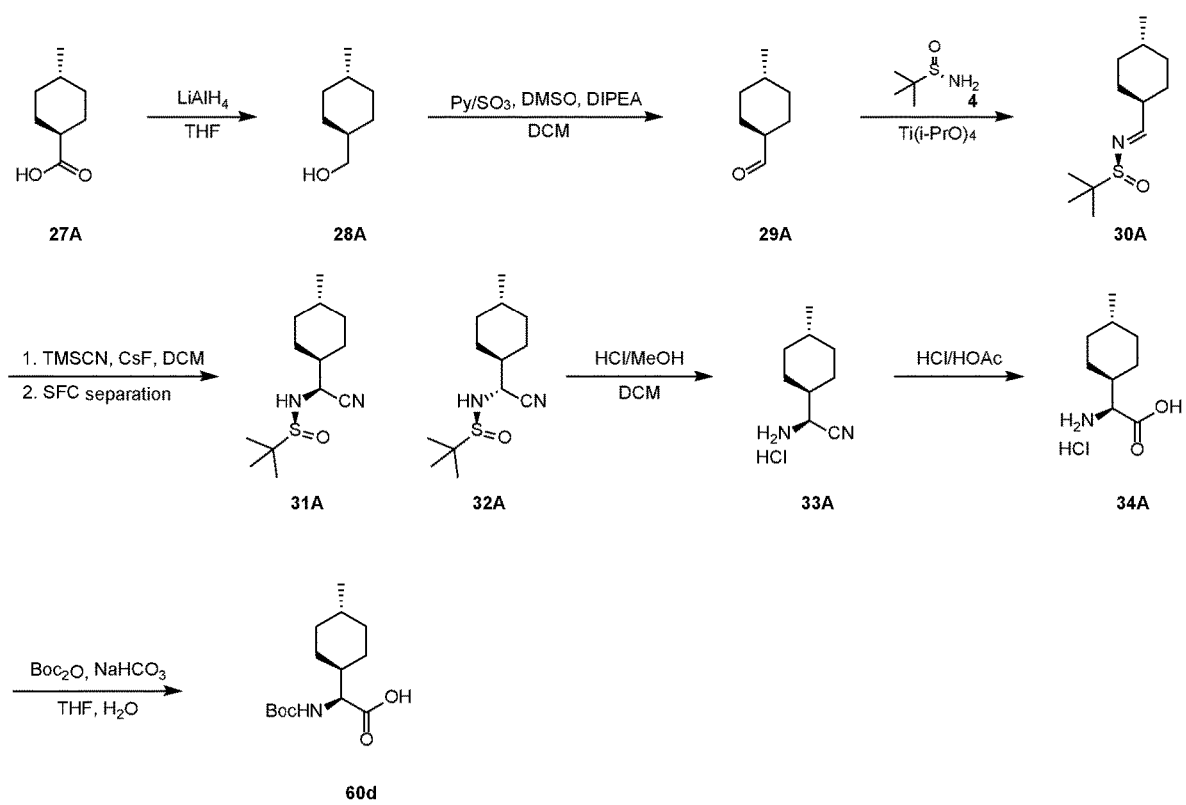
FIG. 20 illustrates a synthetic scheme used to prepare key intermediate 60d.

FIG. 20 illustrates a synthetic scheme used to prepare key intermediate 60d. Referring to FIG. 20, commercially available carboxylic acid 27A is reduced to alcohol 28A which is then oxidized to the aldehyde 29A. Aldehyde 29A is converted to the iminosulfonamide 30A, which is reduced to provide a mixture of sulfonamide stereoisomers 31A and 32A, which are separated to provide desired isomer 31A. The sulfonamide 31A is hydrolyzed and the free amino group protected as the BOC derivative to provide intermediate 60d.

Figure 21:
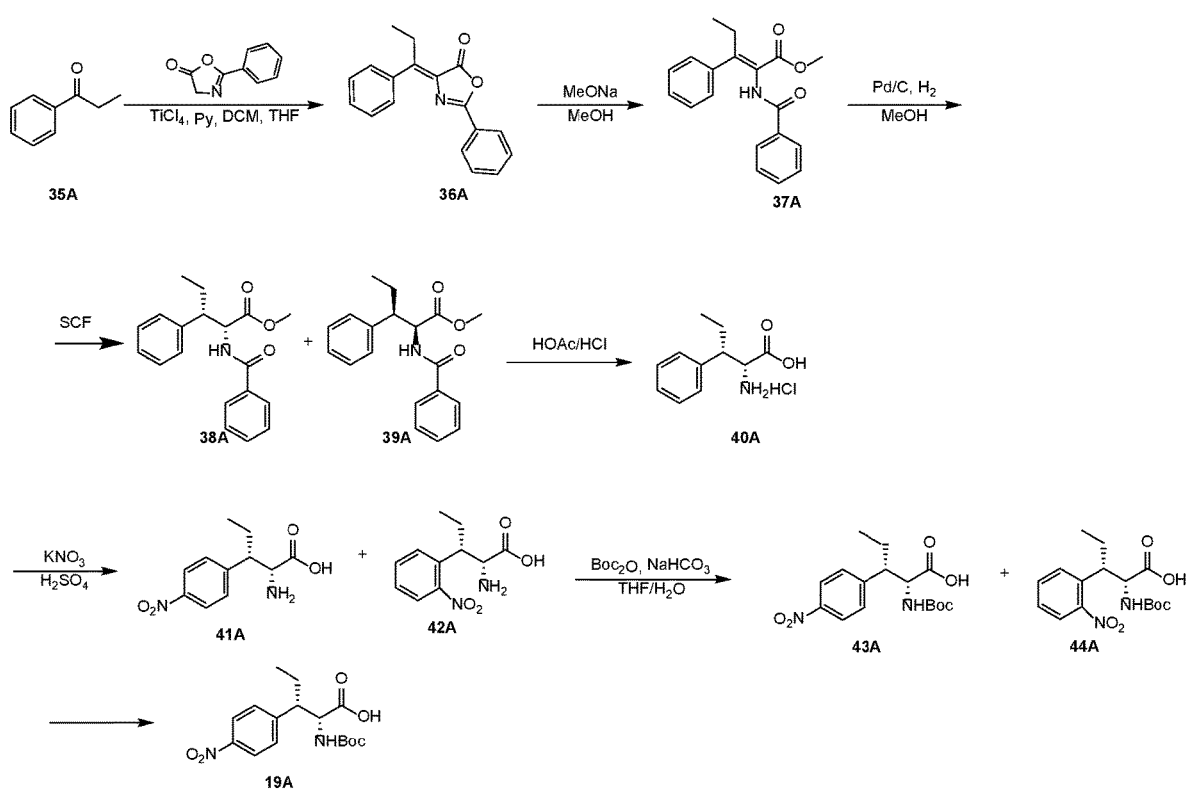
FIG. 21 illustrates a synthetic scheme used to prepare key intermediate 19A.

FIG. 21 illustrates a synthetic scheme used to prepare intermediate 19A. Referring to FIG. 21, aldol condensation between ethylketone 35A and the iminolactone (TiCl$_4$, pyridine and DCM and THF) provided the aldol adduct 36A which was then hydrolyzed (MeONa, MeOH) to provide the unsaturated compound 37A, which was separated from its regioisomer (not shown). Hydrogenation (Pd/C, H$_2$, MeOH) provided a mixture of isomers 38A and 38B which were separated to provide the desired isomer 38A. Hydrolysis (AcOH/HCl) of 38A provided amine hydrochloride 40A which was then converted to a mixture of nitro regioisomers (KNO$_3$, H$_2$SO$_4$) 41A and 42A, protected (Boc$_2$O, NaHCO$_3$, THF/H$_2$O) and separated to provide key intermediate 19A.

Figure 22:
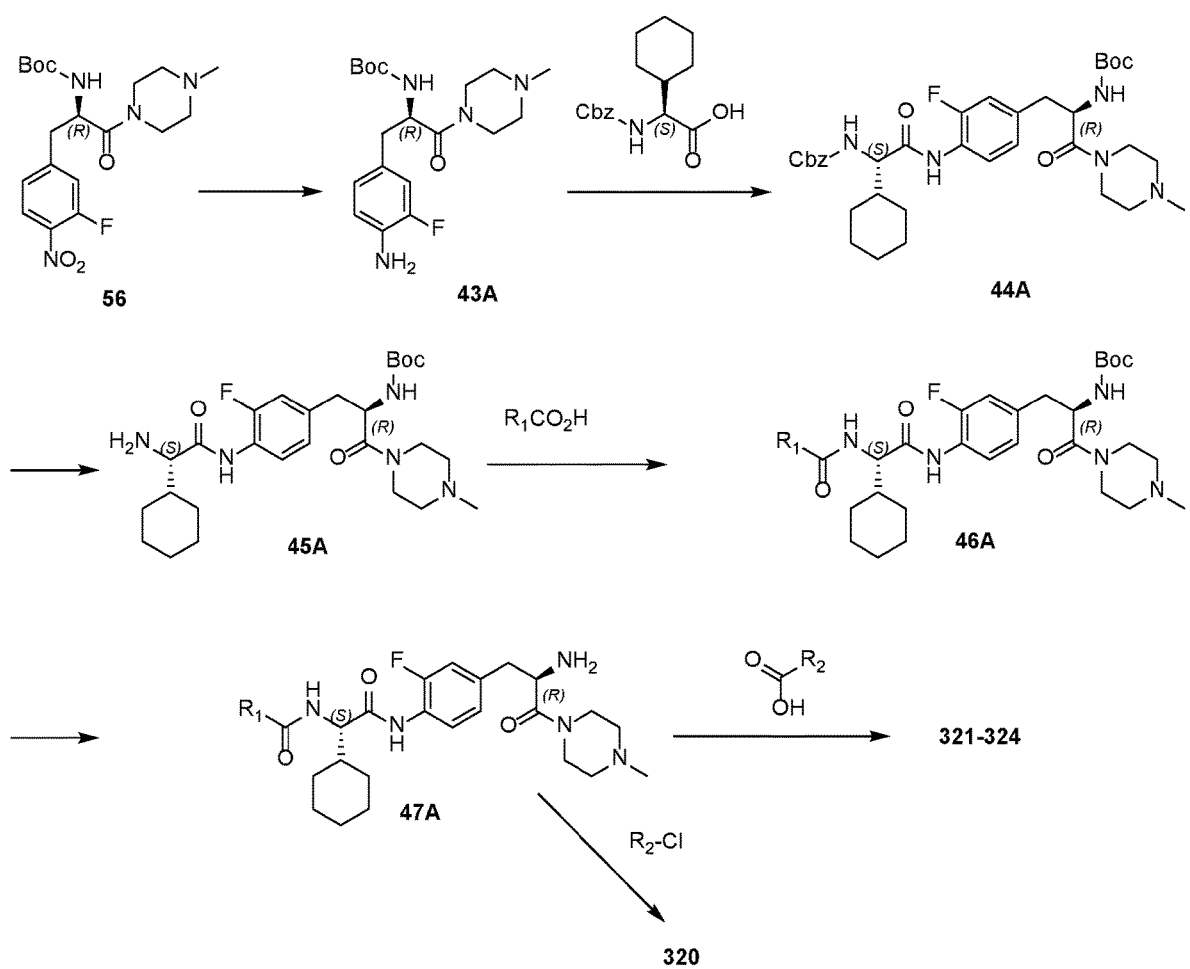
FIG. 22 illustrates a synthetic scheme used to prepare compounds 320-324.

FIG. 22 illustrates a synthetic scheme used to prepare compounds 320-324. Referring to FIG. 22, 56 was reduced to provide the arylamine 43A, which was reacted with CBZ-cyclohexylglycine to yield the amide 44A which was then reduced to yield the free amine 45A. Acylation of the free amine with a variety of acids provided 46A, which was then deprotected under standard conditions and the amino group acylated with a variety of acids to yield compounds 320-324.

Figure 23:
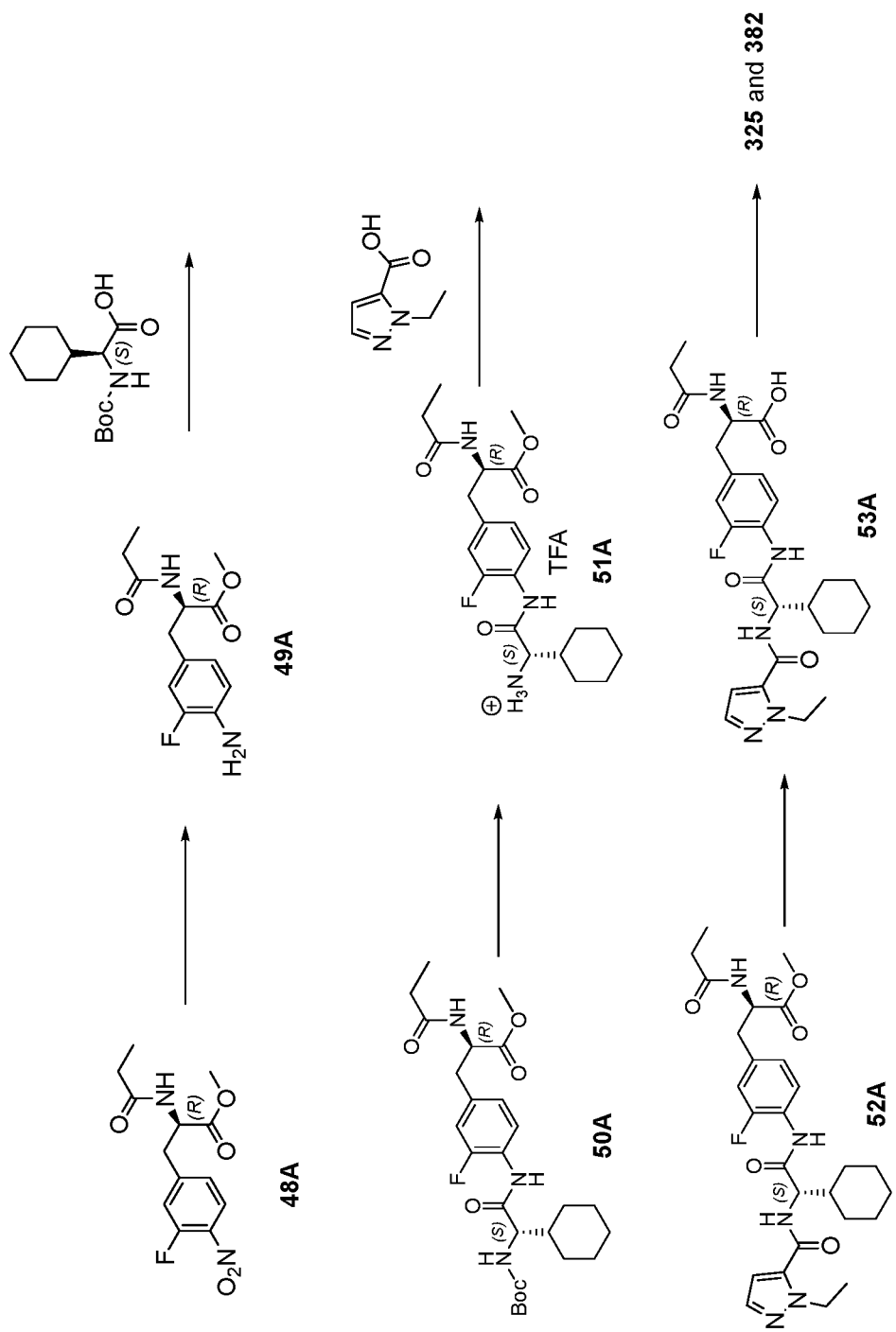
FIG. 23 illustrates a synthetic scheme used to prepare compounds 325 and 382.

FIG. 23 illustrates a synthetic scheme used to prepare compounds 325 and 382. Referring now to FIG. 23, aryl nitro compound 48A, which can be made from compound 55 by those of skill in the art is reduced to yield aryl amine 49A which is acylated with BOC-cyclohexylglycine to provide 50A, which is then deprotected to yield free amine 51A. Acylation of the free amine 51A with the depicted carboxylic acid provides amide 52A. Hydrolysis of the ester group of 52A followed reaction with various amines provide compounds 325 and 382.

Figure 24:
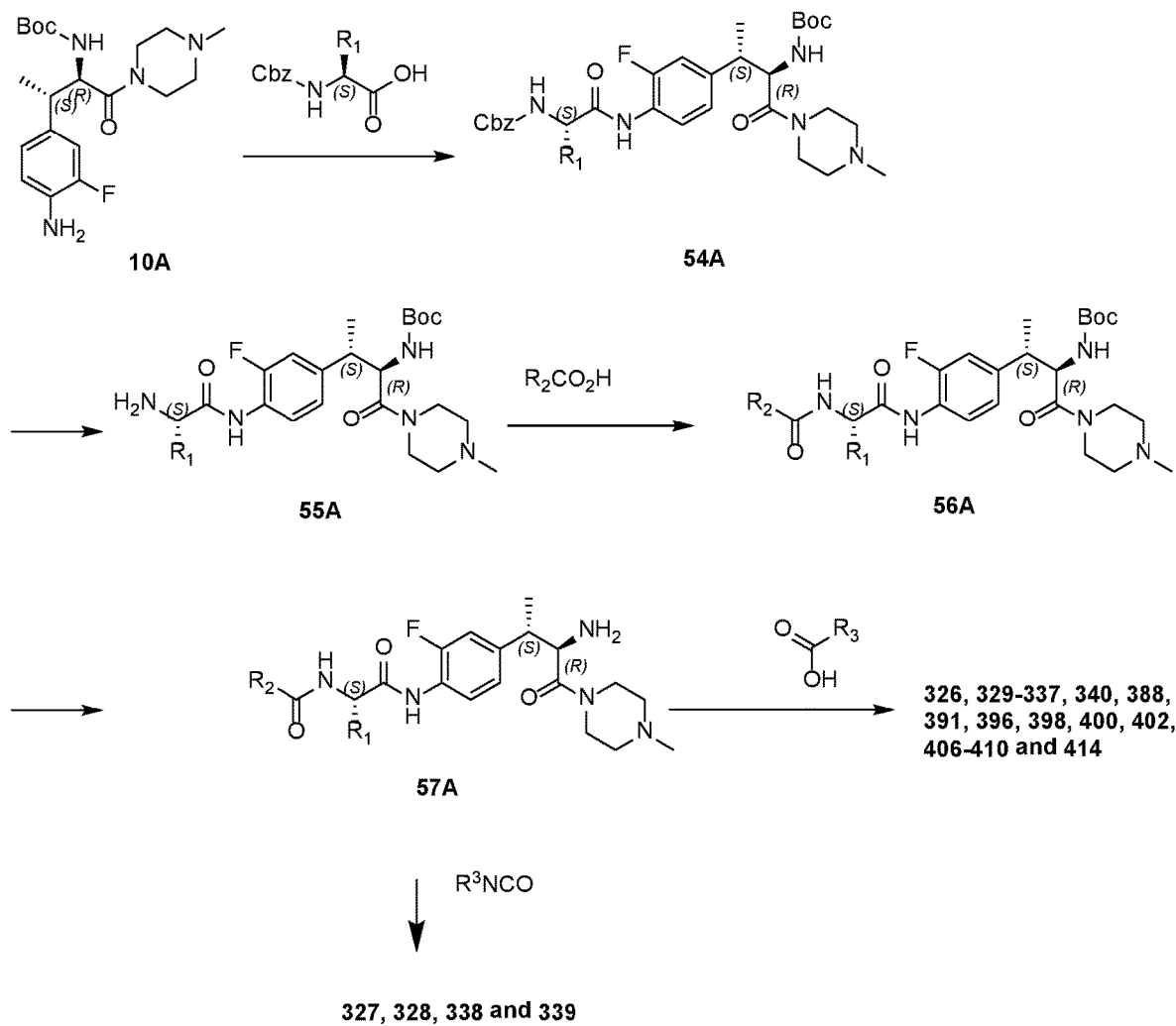
FIG. 24 illustrates a synthetic scheme used to prepare compounds 326-340, 388, 391, 396, 398, 400, 406-410 and 414.

FIG. 24 illustrates a synthetic scheme used to prepare compounds 326-340, 388, 391, 396, 398, 400, 406-410 and 414. Referring now to FIG. 24, the previously prepared aniline 10A is acylated with a CBZ protected glycine derivative to yield 54A. The CBZ group is removed by reduction to provide free amine 55A which is acylated to yield the triamide 56A. Removal of the BOC group under standard conditions yields the amine 57A which is either acylated with various carboxylic acids to yield 326-340, 388, 391, 396, 398, 400, 406-410 and 414 or carbamylated to provide ureas 327, 328, 338 and 339.

Figure 25:
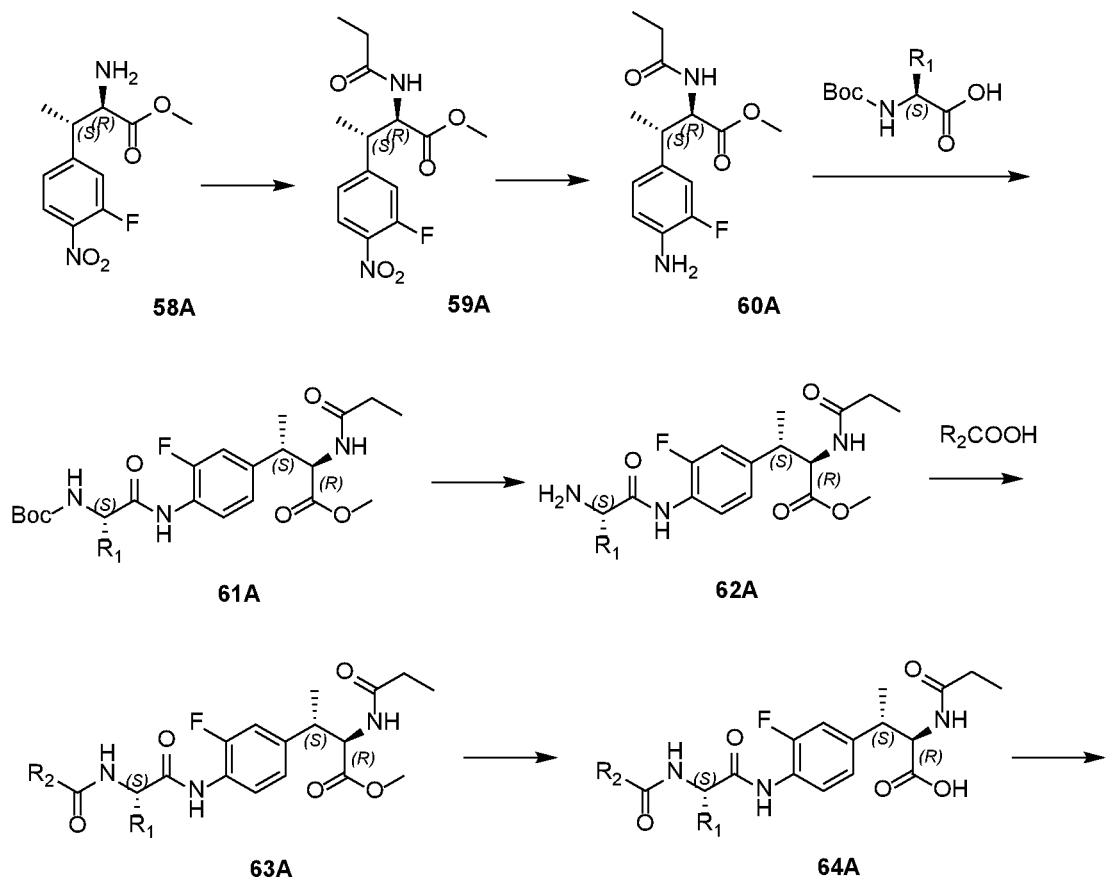
FIG. 25 illustrates a synthetic scheme used to prepare compounds 341-346, 348-375 and 392.

FIG. 25 illustrates a synthetic scheme used to prepare compounds 341-346, 348-375 and 392. Referring now to FIG. 25, aryl nitro compound 58A, which can be made from 74 is acylated to provide 59A, which is then reduced to yield the free aryl amine 60A. Acylation of the aromatic amine 60A provides diamide ester 61A whose terminal amine is deprotected and then acylated with various carboxylic acids to yield triamide ester 63A. Hydrolysis of the ester and reaction with various amines provides compounds 341-346, 348-375, and 392.

Figure 26:
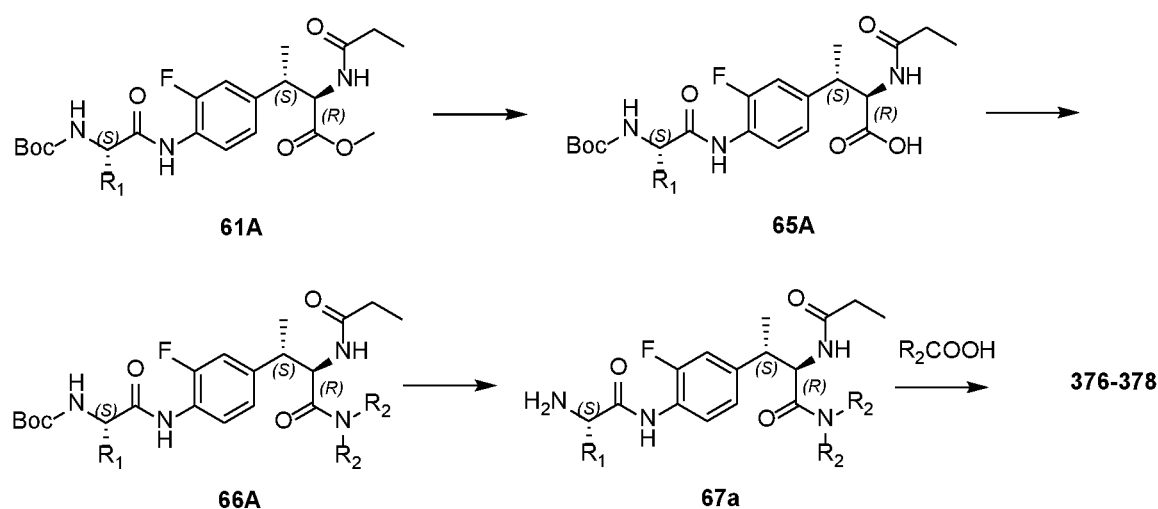
FIG. 26 illustrates a synthetic scheme used to prepare compounds 376-378.

FIG. 26 illustrates a synthetic scheme used to prepare compounds 376-378. Referring now to FIG. 26, hydrolysis of the diamide ester 61A provides the carboxylic acid 65A which is then reacted with various amines to provide compound 66A. Removal of the BOC group and acylation of the free amine 67A provides compounds 376-378.

Figure 27:
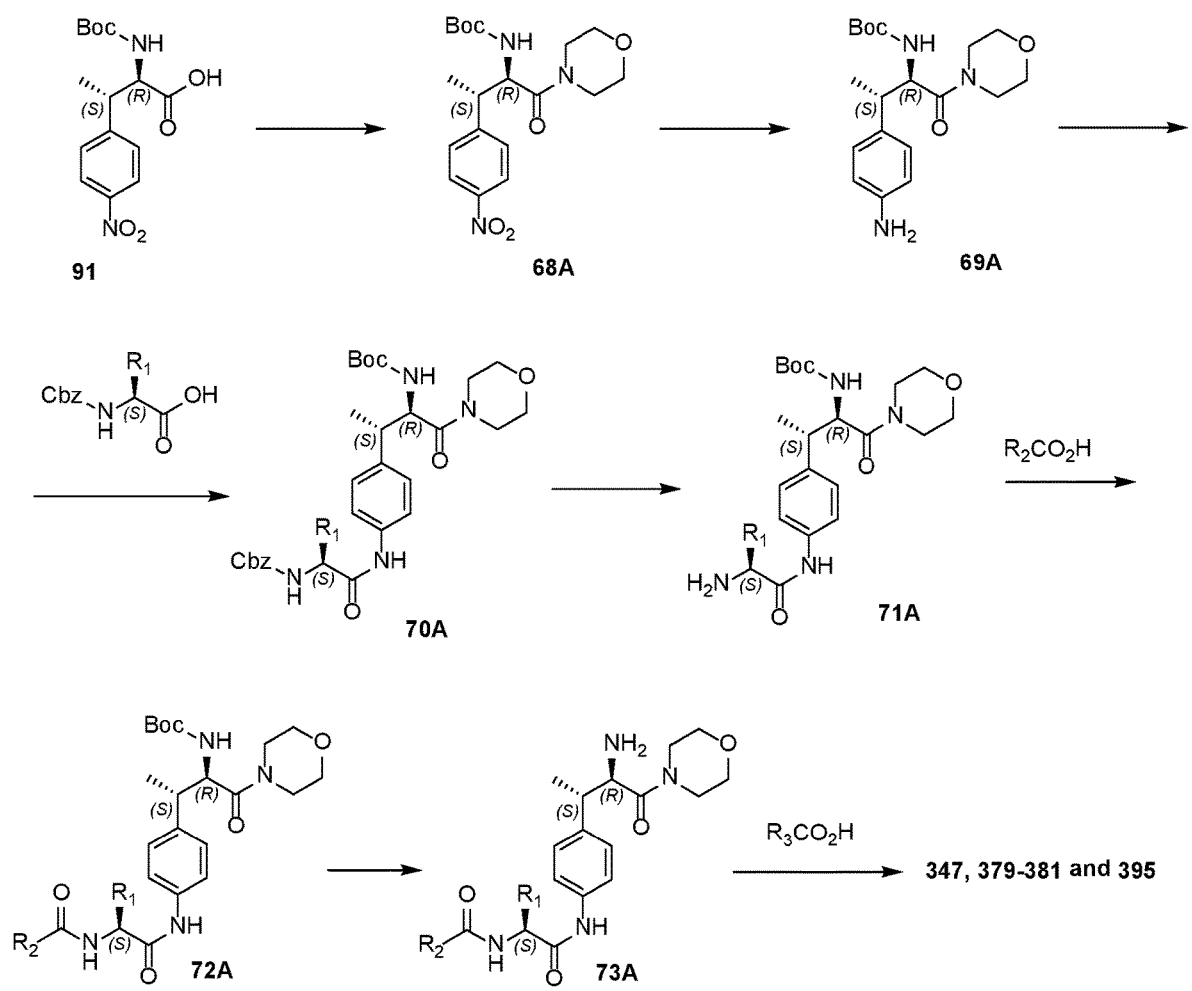
FIG. 27 illustrates a synthetic scheme used to prepare compounds 347, 379-381 and 395.

FIG. 27 illustrates a synthetic scheme used to prepare compounds 347, 379-381 and 395. Referring now to FIG. 27, compound 91 is converted to the morpholine amide 68A and then the aryl nitro group is reduced to yield 69A. Condensation with a CBZ protected glycine derivative provided diamide 70A. Removal of the CBZ group provides free amine 71A which is acylated with various carboxylic acids to yield the triamide 72A. Removal of the BOC group followed by acylation of free amine 73A yields 347, 379-381 and 395.

Figure 28:
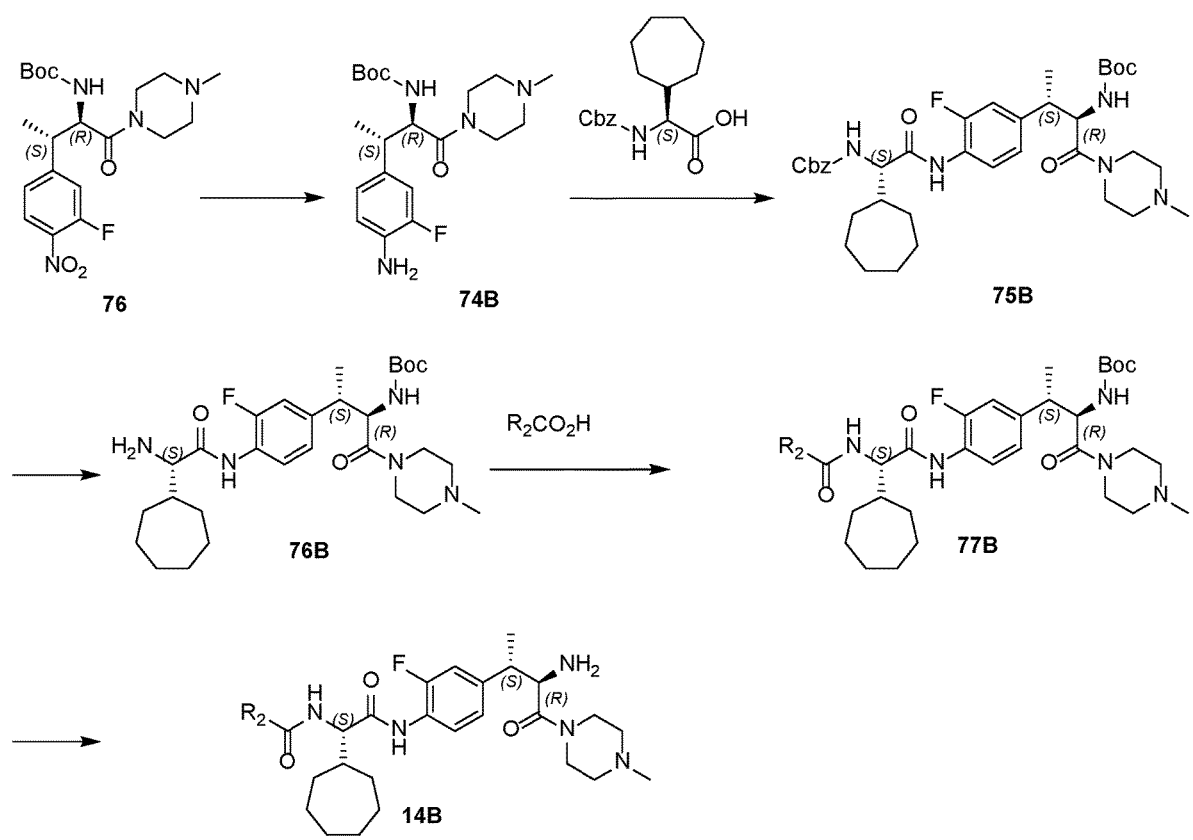
FIG. 28 illustrates a synthetic scheme used to prepare intermediate 14B.

FIG. 28 illustrates a synthetic scheme used to prepare compounds intermediate 14B. Referring now to FIG. 28, compound 76 is reduced to provide arylamine 74B which is acylated with CBZ-cycloheptylglycine to yield the differentially protected diamine 75B. Selective removal of the CBZ group yield the free amine 76B, which is reacted with various carboxylic acids to yield 77B. Removal of the BOC group provides intermediate 14B.

Figure 29:
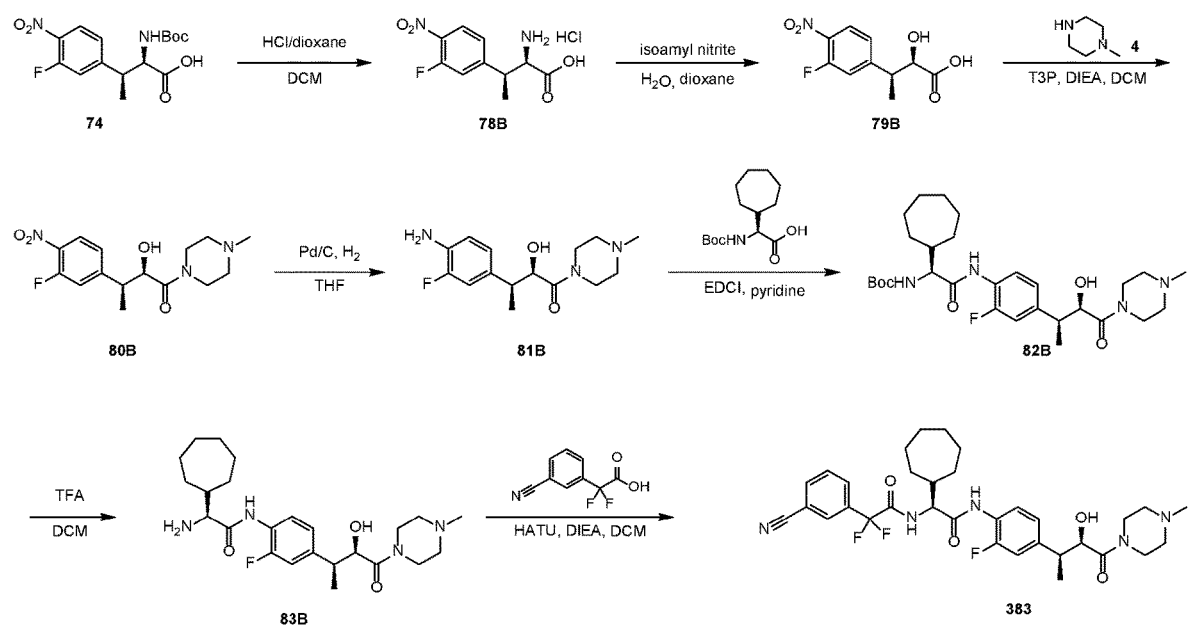
FIG. 29 illustrates a synthetic scheme used to prepare intermediate 383.

FIG. 29 illustrates a synthetic scheme used to prepare intermediate 383. Referring now to FIG. 29, compound 74 is deprotected to provide the amino acid 78B which is then hydroxylated at the alpha carbon to provide the alpha hydroxy acid 79B. Amide bond formation provides the amide 80B which is reduced to yield the arylamine 81B. Acylation with protected cycloheptylglycine provides 82B which is then deprotected under standard conditions to yield the free amine 83B. Finally, acylation with the difluoro acid provides 383.

Figure 30:
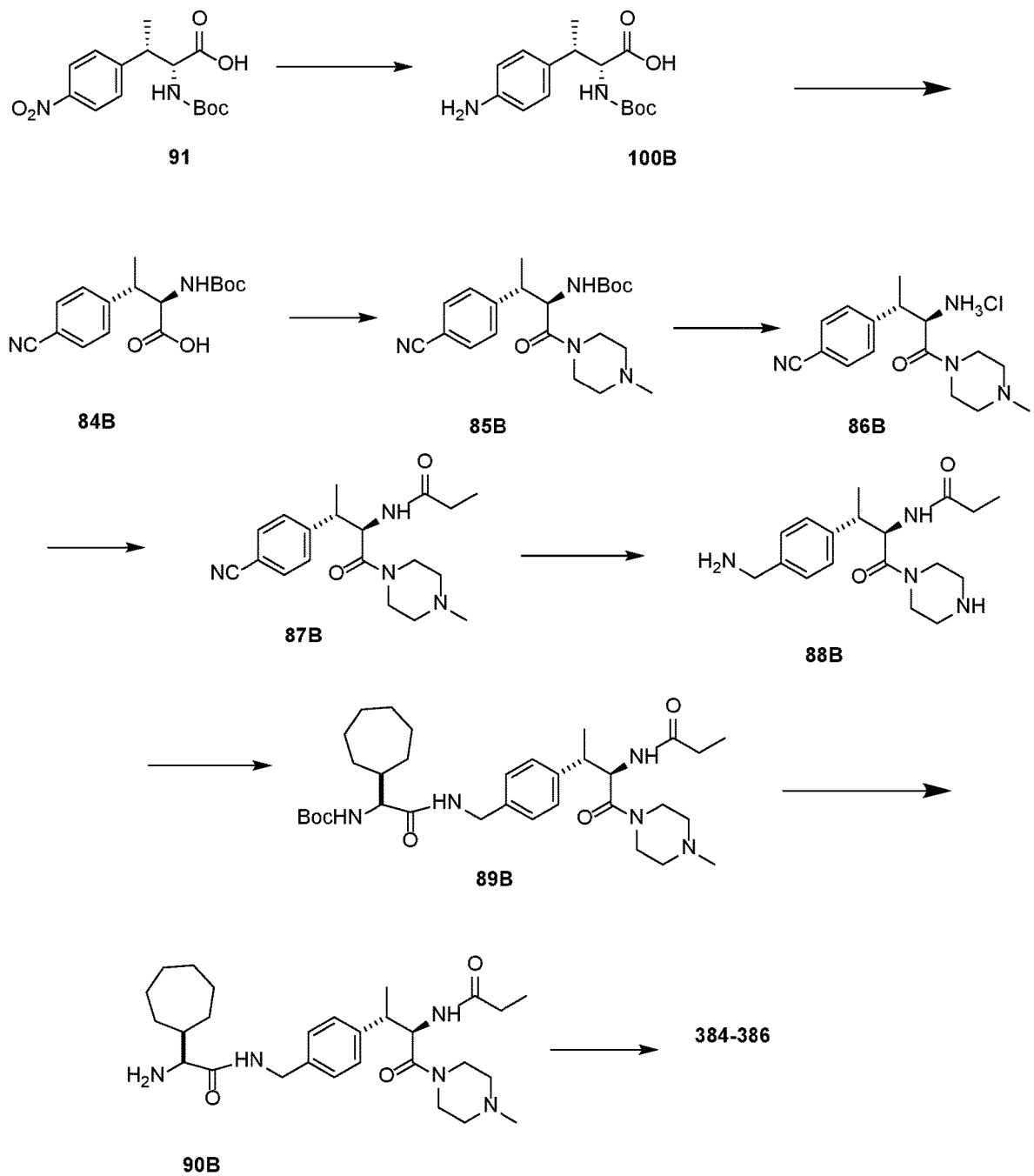
FIG. 30 illustrates a synthetic scheme used to prepare compounds 384-386.

FIG. 30 illustrates a synthetic scheme used to prepare compounds 384-386. Compound 91 is reduced under standard conditions to provide arylamine 100B, which is converted via Sandmeyer reaction to nitrile 84B. Protected amino acid 84B is converted to amine 85B, which is then deprotected to provide amine salt 86B which is acylated to provide bisamide 87B. Reduction of the nitrile group provides 88B, which is acylated with protected cycloheptylglycine to yield 89B. Finally, acylation with the various carboxylic acids provides 384-386.

Figure 31:
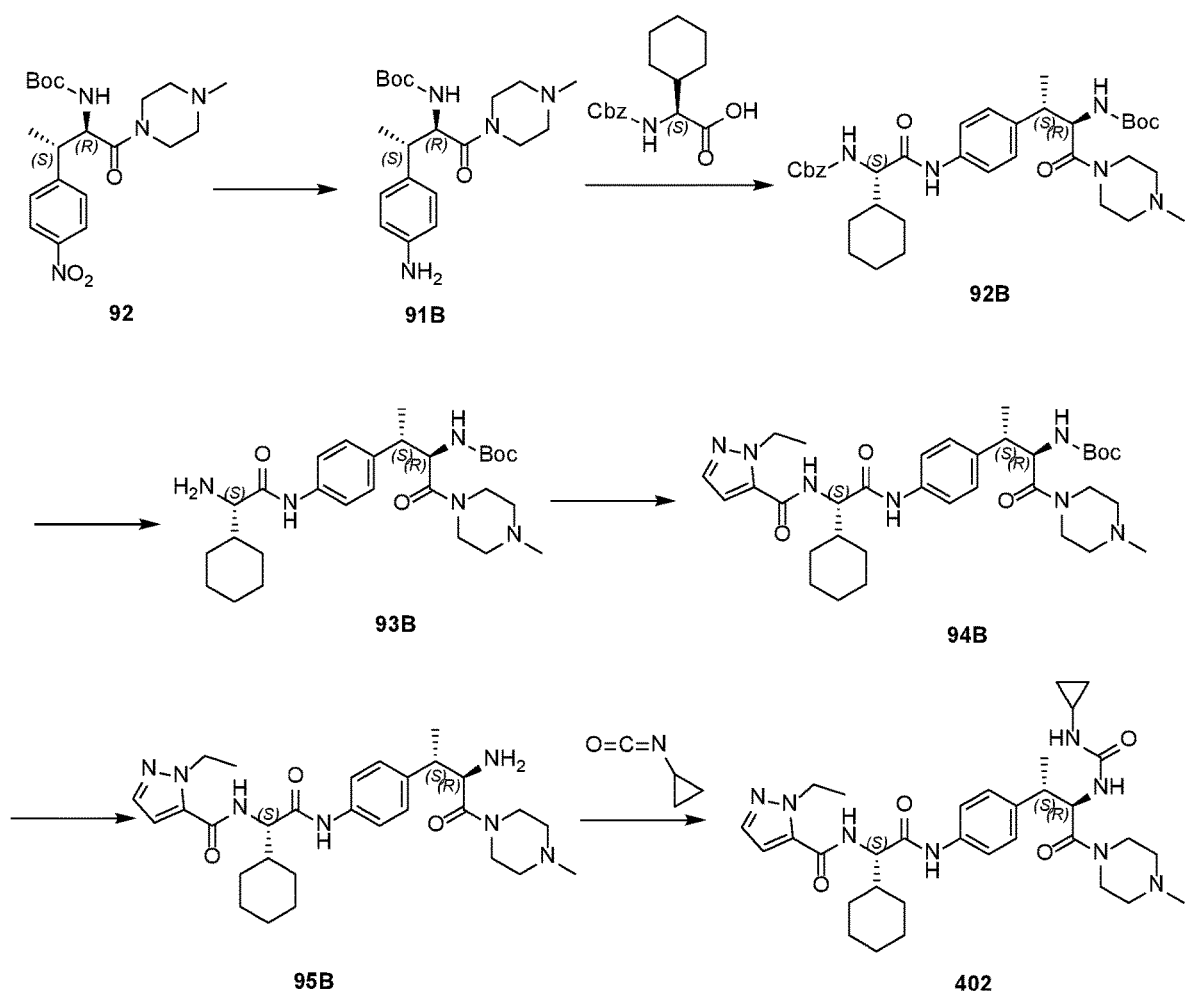
FIG. 31 illustrates a synthetic scheme used to prepare compounds 402.

FIG. 31 illustrates a synthetic scheme used to prepare compounds 402. Compound 92 is reduced to aryl amine 91B which is acylated CBZ-cyclohexylglycine to yield protected diamide 92B. Removal of the CBZ group via reduction yielded free amine 93B which was acylated to provide the amide 94B. Removal of the Boc group followed by reaction with cyclopropyl isocyanate provided compound 402.

Figure 32:
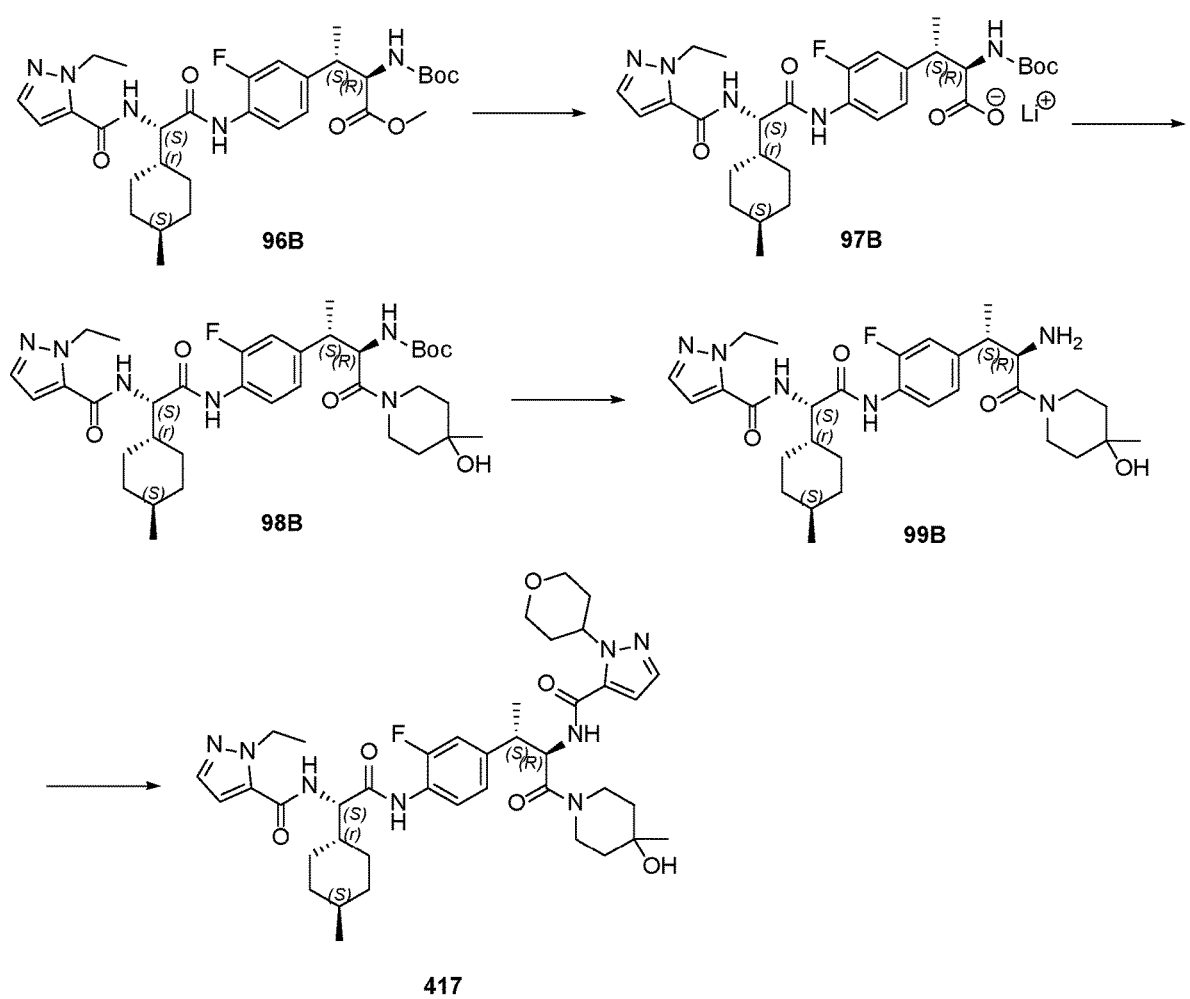
FIG. 32 illustrates a synthetic scheme used to prepare compound 417.

FIG. 32 illustrates a synthetic scheme used to prepare compound 417. Compound 96B, which may be prepared from compound 74 by those of skill in the art is hydrolyzed to yield the lithium salt 97B which is converted to amide 98B under standard amide bond forming conditions. Removal of the Boc group provides amine 99B, which is converted to compound 417 by acylation.

Compositions and Methods of Administration

The compositions provided herein contain therapeutically effective amounts of one or more of the compounds provided herein that are useful in the prevention, treatment, or amelioration of one or more of the symptoms of diseases or disorders described herein and a vehicle. Vehicles suitable for administration of the compounds provided herein include any such carriers known to those skilled in the art to be suitable for the particular mode of administration. In addition, the compounds may be formulated as the sole active ingredient in the composition or may be combined with other active ingredients.

The compositions contain one or more compounds provided herein. The compounds are, in some embodiments, formulated into suitable preparations such as solutions, suspensions, tablets, dispersible tablets, pills, capsules, powders, sustained release formulations or elixirs, for oral administration or in sterile solutions or suspensions for parenteral administration, as well as topical administration, transdermal administration and oral inhalation via nebulizers, pressurized metered dose inhalers and dry powder inhalers. In some embodiments, the compounds described above are formulated into compositions using techniques and procedures well known in the art (see, e.g., Ansel, Introduction to Pharmaceutical Dosage Forms, Seventh Edition (1999)).

In the compositions, effective concentrations of one or more compounds or derivatives thereof is (are) mixed with a suitable vehicle. The compounds may be derivatized as the corresponding salts, esters, enol ethers or esters, acetals, ketals, orthoesters, hemiacetals, hemiketals, acids, bases, solvates, ion-pairs, hydrates or prodrugs prior to formulation, as described above. The concentrations of the compounds in the compositions are effective for delivery of an amount, upon administration that treats, leads to prevention, or amelioration of one or more of the symptoms of diseases or disorders described herein. In some embodiments, the compositions are formulated for single dosage administration. To formulate a composition, the weight fraction of a compound is dissolved, suspended, dispersed or otherwise mixed in a selected vehicle at an effective concentration such that the treated condition is relieved, prevented, or one or more symptoms are ameliorated.

The active compound is included in the vehicle in an amount sufficient to exert a therapeutically useful effect in the absence of undesirable side effects on the patient treated. The therapeutically effective concentration may be predicted empirically by testing the compounds in in vitro and in vivo systems well known to those of skill in the art and then extrapolated therefrom for dosages for humans. Human doses are then typically fine-tuned in clinical trials and titrated to response.

The concentration of active compound in the composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders as described herein.

In instances in which the compounds exhibit insufficient solubility, methods for solubilizing compounds may be used such as use of liposomes, prodrugs, complexation/chelation, nanoparticles, or emulsions or tertiary templating. Such methods are known to those of skill in this art, and include, but are not limited to, using co-solvents, such as dimethylsulfoxide (DMSO), using surfactants or surface modifiers, such as TWEEN®, complexing agents such as cyclodextrin or dissolution by enhanced ionization (i.e. dissolving in aqueous sodium bicarbonate). Derivatives of the compounds, such as prodrugs of the compounds may also be used in formulating effective compositions.

Upon mixing or addition of the compound(s), the resulting mixture may be a solution, suspension, emulsion or the like. The form of the resulting mixture depends upon a number of factors, including the intended mode of administration and the solubility of the compound in the selected vehicle. The effective concentration is sufficient for ameliorating the symptoms of the disease, disorder or condition treated and may be empirically determined.

The compositions are provided for administration to humans and animals in indication appropriate dosage forms, such as dry powder inhalers (DPIs), pressurized metered dose inhalers (pMDIs), nebulizers, tablets, capsules, pills, sublingual tapes/bioerodible strips, tablets or capsules, powders, granules, lozenges, lotions, salves, suppositories, fast melts, transdermal patches or other transdermal application devices/preparations, sterile parenteral solutions or suspensions, and oral solutions or suspensions, and oil-water emulsions containing suitable quantities of the compounds or derivatives thereof. The therapeutically active compounds and derivatives thereof are, in some embodiments, formulated and administered in unit-dosage forms or multiple-dosage forms. Unit-dose forms as used herein refer to physically discrete units suitable for human and animal subjects and packaged individually as is known in the art. Each unit-dose contains a predetermined quantity of the therapeutically active compound sufficient to produce the desired therapeutic effect, in association with the required vehicle. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

Liquid compositions can, for example, be prepared by dissolving, dispersing, or otherwise mixing an active compound as defined above and optional adjuvants in a vehicle, such as, for example, water, saline, aqueous dextrose, glycerol, glycols, ethanol, and the like, to thereby form a solution or suspension, colloidal dispersion, emulsion or liposomal formulation. If desired, the composition to be administered may also contain minor amounts of nontoxic auxiliary substances such as wetting agents, emulsifying agents, solubilizing agents, pH buffering agents and the like, for example, acetate, sodium citrate, cyclodextrin derivatives, sorbitan monolaurate, triethanolamine sodium acetate, triethanolamine oleate, and other such agents.

Actual methods of preparing such dosage forms are known, or will be apparent, to those skilled in this art; for example, see Remington's Pharmaceutical Sciences, Mack Publishing Company, Easton, Pa., 15th Edition, 1975 or later editions thereof.

Dosage forms or compositions containing active ingredient in the range of 0.005% to 100% with the balance made up from vehicle or carrier may be prepared. Methods for preparation of these compositions are known to those skilled in the art. The contemplated compositions may contain 0.001%-100% active ingredient, in one embodiment 0.1-95%, in another embodiment 0.4-10%.

In certain embodiments, the compositions are lactose-free compositions containing excipients that are well known in the art and are listed, for example, in the *U.S. Pharmacopeia* (USP) 25-NF20 (2002). In general, lactose-free compositions contain active ingredients, a binder/filler, and a lubricant in compatible amounts. Particular lactose-free dosage forms contain active ingredients, microcrystalline cellulose, pre-gelatinized starch, and magnesium stearate.

Further provided are anhydrous compositions and dosage forms comprising active ingredients, since water can facilitate the degradation of some compounds. For example, the addition of water (e.g., 5%) is widely accepted as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous compositions and dosage forms provided herein can be prepared using anhydrous or low moisture containing ingredients and low moisture or low humidity conditions.

An anhydrous composition should be prepared and stored such that its anhydrous nature is maintained. Accordingly, anhydrous compositions are generally packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Oral dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms such as for example, capsules or tablets. The tablets, pills, capsules, troches and the like can contain one or more of the following ingredients, or compounds of a similar nature: a binder; a lubricant; a diluent; a glidant; a disintegrating agent; a coloring agent; a sweetening agent; a flavoring agent; a wetting agent; an enteric coating; a film coating agent and modified release agent. Examples of binders include microcrystalline cellulose, methyl paraben, polyalkyleneoxides, gum tragacanth, glucose solution, acacia mucilage, gelatin solution, molasses, polyvinylpyrrolidine, povidone, crospovidones, sucrose and starch and starch derivatives. Lubricants include talc, starch, magnesium/calcium stearate, lycopodium and stearic acid. Diluents include, for example, lactose, sucrose, trehalose, lysine, leucine, lecithin, starch, kaolin, salt, mannitol and dicalcium phosphate. Glidants include, but are not limited to, colloidal silicon dioxide. Disintegrating agents include crosscarmellose sodium, sodium starch glycolate, alginic acid, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate and advanced coloring or anti-forgery color/opalescent additives known to those skilled in the art. Sweetening agents include sucrose, lactose, mannitol and artificial sweetening agents such as saccharin and any number of spray dried flavors. Flavoring agents include natural flavors extracted from plants such as fruits and synthetic blends of compounds which produce a pleasant sensation or mask unpleasant taste, such as, but not limited to peppermint and methyl salicylate. Wetting agents include propylene glycol monostearate, sorbitan monooleate, diethylene glycol monolaurate and polyoxyethylene lauryl ether. Enteric-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate. Modified release agents include polymers such as the Eudragit® series and cellulose esters.

The compound, or derivative thereof, can be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, $H_2$ blockers, and diuretics. The active ingredient is a compound or derivative thereof as described herein. Higher concentrations, up to about 98% by weight of the active ingredient may be included.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Vehicles used in elixirs include solvents. Syrups are concentrated aqueous solutions of a sugar, for example, sucrose, and may contain a preservative. An emulsion is a two-phase system in which one liquid is dispersed in the form of small globules throughout another liquid. Carriers used in emulsions are non-aqueous liquids, emulsifying agents and preservatives. Suspensions use suspending agents and preservatives. Acceptable substances used in non-effervescent granules, to be reconstituted into a liquid oral dosage form, include diluents, sweeteners and wetting agents. Acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic acid, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic acids include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example, propylene carbonate, vegetable oils or triglycerides, is in some embodiments encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a liquid vehicle, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. RE28,819 and 4,358,603. Briefly, such formulations include, but are not limited to, those containing a compound provided herein, a dialkylated mono- or polyalkylene glycol, including, but not limited to, 1,2-dimethoxyethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including an acetal. Alcohols used in these formulations are any water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

Parenteral administration, in some embodiments characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. The injectables, solutions and emulsions also contain one or more excipients. Suitable excipients are, for example, water, saline, dextrose, glycerol or ethanol. In addition, if desired, the compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Vehicles used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcellulose, hydroxypropyl methylcellulose and polyvinylpyrrolidone. Emulsifying agents include Polysorbate 80 (Tween® 80). A sequestering or chelating agent of metal ions includes EDTA. Carriers also include ethyl alcohol, polyethylene glycol and propylene glycol for water miscible vehicles; and sodium hydroxide, hydrochloric acid, citric acid or lactic acid for pH adjustment.

The concentration of compound is adjusted so that an injection provides an effective amount to produce the desired pharmacological effect. The exact dose depends on the age, weight, body surface area and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. In some embodiments, a therapeutically effective dosage is formulated to contain a concentration of at least about 0.01% w/w up to about 90% w/w or more, in certain embodiments more than 0.1% w/w of the active compound to the treated tissue(s).

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 and 6,740,634. Such dosage forms can be used to provide slow or controlled-release of one or more active ingredients using, for example, hydroxypropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein.

All controlled-release products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

In certain embodiments, the agent may be administered using intravenous infusion, an implantable osmotic pump, a transdermal patch, liposomes, or other modes of administration. In some embodiments, a pump may be used (see, Sefton, CRC Crit. Ref. Biomed. Eng. 14:201 (1987); Buchwald et al., Surgery 88:507 (1980); Saudek et al., N. Engl. J. Med. 321:574 (1989)). In other embodiments, polymeric materials can be used. In other embodiments, a controlled release system can be placed in proximity of the therapeutic target, i.e., thus requiring only a fraction of the systemic dose (see, e.g., Goodson, Medical Applications of Controlled Release, vol. 2, pp. 115-138 (1984)). In some embodiments, a controlled release device is introduced into a subject in proximity of the site of inappropriate immune activation or a tumor. Other controlled release systems are discussed in the review by Langer (Science 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient contained in such parenteral compositions is highly dependent on the specific nature thereof, as well as the needs of the subject.

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a derivative thereof, in a suitable solvent. The solvent may contain an excipient which improves the stability or other pharmacological component of the powder or reconstituted solution, prepared from the powder. Excipients that may be used include, but are not limited to, an antioxidant, a buffer and a bulking agent. In some embodiments, the excipient is selected from dextrose, sorbitol, fructose, corn syrup, xylitol, glycerin, glucose, sucrose and other suitable agent. The solvent may contain a buffer, such as citrate, sodium or potassium phosphate or other such buffer known to those of skill in the art at, at about neutral pH. Subsequent sterile filtration of the solution followed by lyophilization under standard conditions known to those of skill in the art provides the desired formulation. In some embodiments, the resulting solution will be apportioned into vials for lyophilization. Each vial will contain a single dosage or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, the lyophilized powder is added to sterile water or other suitable carrier. The precise amount depends upon the selected compound. Such amount can be empirically determined.

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will, in some embodiments, have mass median geometric diameters of less than 5 microns, in other embodiments less than 10 microns.

Oral inhalation formulations of the compounds or derivatives suitable for inhalation include metered dose inhalers, dry powder inhalers and liquid preparations for administration from a nebulizer or metered dose liquid dispensing system. For both metered dose inhalers and dry powder inhalers, a crystalline form of the compounds or derivatives is the preferred physical form of the drug to confer longer product stability.

In addition to particle size reduction methods known to those skilled in the art, crystalline particles of the compounds or derivatives can be generated using supercritical fluid processing which offers significant advantages in the production of such particles for inhalation delivery by producing respirable particles of the desired size in a single step. (e.g., International Publication No. WO2005/025506). A controlled particle size for the microcrystals can be selected to ensure that a significant fraction of the compounds or derivatives is deposited in the lung. In some embodiments, these particles have a mass median aerodynamic diameter of about 0.1 to about 10 microns, in other embodiments, about 1 to about 5 microns and still other embodiments, about 1.2 to about 3 microns.

Inert and non-flammable HFA propellants are selected from HFA 134a (1,1,1,2-tetrafluoroethane) and HFA 227e (1,1,1,2,3,3,3-heptafluoropropane) and provided either alone or as a ratio to match the density of crystal particles of the compounds or derivatives. A ratio is also selected to ensure that the product suspension avoids detrimental sedimentation or cream (which can precipitate irreversible agglomeration) and instead promote a loosely flocculated system, which is easily dispersed when shaken. Loosely fluctuated systems are well regarded to provide optimal stability for pMDI canisters. As a result of the formulation's properties, the formulation contained no ethanol and no surfactants/stabilizing agents.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other excipients can also be administered.

For nasal administration, the preparation may contain an esterified phosphonate compound dissolved or suspended in a liquid carrier, in particular, an aqueous carrier, for aerosol application. The carrier may contain solubilizing or suspending agents such as propylene glycol, surfactants, absorption enhancers such as lecithin or cyclodextrin, or preservatives.

Solutions, particularly those intended for ophthalmic use, may be formulated as 0.01%-10% isotonic solutions, pH about 5-7.4, with appropriate salts.

Other routes of administration, such as transdermal patches, including iontophoretic and electrophoretic devices, and rectal administration, are also contemplated herein.

Transdermal patches, including iontophoretic and electrophoretic devices, are well known to those of skill in the art. For example, such patches are disclosed in U.S. Pat. Nos. 6,267,983, 6,261,595, 6,256,533, 6,167,301, 6,024,975, 6,010715, 5,985,317, 5,983,134, 5,948,433 and 5,860,957.

For example, dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The weight of a rectal suppository, in one embodiment, is about 2 to 3 gm. Tablets and capsules for rectal administration are manufactured using the same substance and by the same methods as for formulations for oral administration.

The compounds provided herein, or derivatives thereof, may also be formulated to be targeted to a particular tissue, receptor, or other area of the body of the subject to be treated. Many such targeting methods are well known to those of skill in the art. All such targeting methods are contemplated herein for use in the instant compositions. For non-limiting examples of targeting methods, see, e.g., U.S. Pat. Nos. 6,316,652, 6,274,552, 6,271,359, 6,253,872, 6,139,865, 6,131,570, 6,120,751, 6,071,495, 6,060,082, 6,048,736, 6,039,975, 6,004,534, 5,985,307, 5,972,366, 5,900,252, 5,840,674, 5,759,542 and 5,709,874.

In some embodiments, liposomal suspensions, including tissue-targeted liposomes, such as tumor-targeted liposomes, may also be suitable as carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down phosphatidyl choline and phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The compounds or derivatives may be packaged as articles of manufacture containing packaging material, a compound or derivative thereof provided herein, which is effective for treatment, prevention or amelioration of one or more symptoms of the diseases or disorders, supra, within the packaging material, and a label that indicates that the compound or composition or derivative thereof, is used for the treatment, prevention or amelioration of one or more symptoms of the diseases or disorders, supra.

The articles of manufacture provided herein contain packaging materials. Packaging materials for use in packaging products are well known to those of skill in the art. See, e.g., U.S. Pat. Nos. 5,323,907, 5,052,558 and 5,033,252. Examples of packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder described herein.

Dosages

For use to treat or prevent infectious disease, the compounds described herein, or pharmaceutical compositions thereof, are administered or applied in a therapeutically effective amount. In human therapeutics, the physician will determine the dosage regimen that is most appropriate according to a preventive or curative treatment and according to the age, weight, stage of the disease and other factors specific to the subject to be treated. The amount of active ingredient in the formulations provided herein, which will be effective in the prevention or treatment of an infectious disease will vary with the nature and severity of the disease or condition, and the route by which the active ingredient is administered. The frequency and dosage will also vary according to factors specific for each subject depending on the specific therapy (e.g., therapeutic or prophylactic agents) administered, the severity of the infection, the route of administration, as well as age, body, weight, response, and the past medical history of the subject.

Exemplary doses of a formulation include milligram or microgram amounts of the active compound per kilogram of subject (e.g., from about 1 microgram per kilogram to about 50 milligrams per kilogram, from about 10 micrograms per kilogram to about 30 milligrams per kilogram, from about 100 micrograms per kilogram to about 10 milligrams per kilogram, or from about 100 micrograms per kilogram to about 5 milligrams per kilogram).

In some embodiments, a therapeutically effective dosage should produce a serum concentration of active ingredient of from about 0.001 ng/ml to about 50-200 µg/ml. The compositions, in other embodiments, should provide a dosage of from about 0.0001 mg to about 70 mg of compound per kilogram of body weight per day. Dosage unit forms are prepared to provide from about 0.01 mg, 0.1 mg or 1 mg to about 500 mg, 1000 mg or 5000 mg, and in some embodiments from about 10 mg to about 500 mg of the active ingredient or a combination of essential ingredients per dosage unit form.

The active ingredient may be administered at once or may be divided into a number of smaller doses to be administered at intervals of time. It is understood that the precise dosage and duration of treatment is a function of the disease being treated and may be determined empirically using known testing protocols or by extrapolation from in vivo or in vitro test data or subsequent clinical testing. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions and that the concentration ranges set forth herein are exemplary only and are not intended to limit the scope or practice of the claimed compositions.

It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with subject response.

For systemic administration, a therapeutically effective dose can be estimated initially from in vitro assays. For example, a dose can be formulated in animal models to achieve a circulating concentration range that includes the $IC_{50}$ as determined in cell culture (i.e., the concentration of test compound that is lethal to 50% of a cell culture), or the $IC_{100}$ as determined in cell culture (i.e., the concentration of compound that is lethal to 100% of a cell culture). Such information can be used to more accurately determine useful doses in humans.

Initial dosages can also be estimated from in vivo data (e.g., animal models) using techniques that are well known in the art. One of ordinary skill in the art can readily optimize administration to humans based on animal data.

Alternatively, initial dosages can be determined from the dosages administered of known agents by comparing the $IC_{50}$, MIC and/or $I_{100}$ of the specific compound disclosed herein with that of a known agent and adjusting the initial dosages accordingly. The optimal dosage may be obtained from these initial values by routine optimization In cases of local administration or selective uptake, the effective local concentration compound used may not be related to plasma concentration. One of skill in the art will be able to optimize therapeutically effective local dosages without undue experimentation.

Ideally, a therapeutically effective dose of the compounds described herein will provide therapeutic benefit without causing substantial toxicity. Toxicity of compounds can be determined using standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Compounds which exhibit high therapeutic indices are preferred. The data obtained from these cell culture assays and animal studies can be used in formulating a dosage range that is not toxic for use in subjects. The dosage of the compounds described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition (See, e.g., Fingl et al., 1975, In: *The Pharmacological Basis of Therapeutics*, Ch. 1, p. 1).

The therapy may be repeated intermittently. In certain embodiments, administration of the same formulation provided herein may be repeated and the administrations may be separated by at least 1 day, 2 days, 3 days, 5 days, 10 days, 15 days, 30 days, 45 days, 2 months, 75 days, 3 months, or 6 months. In other embodiments, administrations may be separated by Methods of Use of the Compounds and Compositions The compounds and compositions described herein can be used in a wide variety of applications to treat or preventing disease or condition that is mediated directly or indirectly by IL-17A. Such diseases include inflammatory diseases and conditions, proliferative diseases (e.g., cancer), autoimmune diseases and other disease described herein. The methods generally involve administering therapeutically effective amounts of compounds disclosed herein or a pharmaceutical composition thereof to the subject.

Increased levels of IL-17A have been associated with several conditions including airway inflammation, rheumatoid arthritis (RA), osteoarthritis, bone erosion intraperitoneal abscesses and adhesions, inflammatory bowel disorder (IBD), allograft rejection, psoriasis, psoriatic arthritis, ankylosing spondylitis, certain types of cancer, angiogenesis, atherosclerosis and multiple sclerosis (MS). Both IL-17A and IL-17R are upregulated in the synovial tissue of RA patients. IL-17A exerts its role in pathogenesis of RA through IL-1-β and TNF-α dependent and independent pathways. IL-17A stimulates secretion of other cytokines and chemokines, e.g., TNF-α, IL-1β, IL-6, IL-8 and Gro-α. IL-17A directly contributes to disease progression in RA. Injection of IL-17A into the mouse knee promotes joint destruction independently of IL-1β activity (Ann Rheum Dis 2000, 59.529-32). Anti-IL-1β antibody has no effect on IL-17A induced inflammation and joint damage (J Immunol 2001, 167:1004-1013). In an SCW-induced murine arthritis model. IL-17A induced inflammatory cell infiltration and proteoglycan depletion in wild-type and IL-1β knockout and TNF-α knockout mice. IL-17A knockout mice are phenotypically normal in the absence of antigenic challenge but have markedly reduced arthritis following type II collagen immunization (J Immunol 2003, 171:6173-6177). Increased levels of IL-17A-secreting cells have also been observed in the facet joints of patients suffering from ankylosing spondylitis (H Appel et al., Arthritis Res Therap 2011, 13:R95).

Multiple sclerosis is an autoimmune disease characterized by central nervous system (CNS) inflammation with damage to the myelin sheath surrounding axons. A hallmark of MS is that T cells infiltrate into the CNS. Higher numbers of IL-17A mRNA-expressing blood mono-nuclear cells (MNC) are detected during MS clinical exacerbation compared to remission (Multiple Sclerosis, 5.101-104, 1999). Furthermore, experimental autoimmune encephalomyelitis ("EAE"), a preclinical animal model for MS is significantly suppressed in IL-17A knockout mice.

In some embodiments, a method for the treatment or prevention of a condition including, but not limited to, airway inflammation, ankylosing spondylitis, asthma. RA (including juvenile RA), osteoarthritis, bone erosion, intra-peritoneal abscesses and adhesions, IBD, Crohn's disease, allograft rejection, psoriasis, psoriatic arthritis, certain types of cancer, angiogenesis, atherosclerosis and MS, as well as other inflammatory disorders, conditions, diseases or states including without limit: erythematosus, response to allergen exposure, *Helicobacter pylori* associated gastritis, bronchial asthma, allograft rejection (e.g., renal), systemic lupus erythematosus and lupus nephritis is provided.

In other embodiments, a method for the treatment or prevention of a condition including, but not limited to, Behcet's disease, ulcerative colitis, Wegener's granulomatosis, sarcoidosis, systemic sclerosis, insulin-dependent diabetes mellitus, septic shock syndrome, Alzheimer's disease, an inflammatory eye disease, and uveitis is provided.

In still another aspect, a method of treating a patient suffering from a disease or condition associated with elevated levels of IL-17A comprising the steps of: a) determining whether the patient has an elevated level of one or more IL-17A-induced chemokine or effector; and b) if the patient does have an elevated level of the one or more IL-17A chemokine or effector, administering to the patient an effective amount of a compound of Formula I for a time sufficient to treat the disease or condition is provided. The IL-17A chemokine or effector may be one or more of IL-6, IL-8, G-CSF, TNF-α, IL-1β, PGE2 or IFN-γ.

Methods for determining the levels of IL-17A or any of its chemokines or effectors in a patient are well-known in the art. Typically, a tissue or biological fluid sample is obtained from the patient and is subject to ELISA with commercially available antibodies or kits (e.g., Quantikine IL-17A ELISA; R&D Systems, Minneapolis, MN, USA). Commercially available antibodies and kits are available for IL-6, IL-8, G-CSF, TNF-α, IL-1β, PGE2, and IFN-γ.

Combination Therapy

The compounds and compositions disclosed herein may also be used in combination with one or more other active ingredients. In certain embodiments, the compounds may be administered in combination, or sequentially, with another therapeutic agent. Such other therapeutic agents include those known for treatment, prevention, or amelioration one or more symptoms associated with, for example inflammation, cancer or autoimmune disease.

Accordingly, in certain instances, co-administering a therapeutically effective amount of an anti-inflammatory agent is contemplated. The anti-inflammatory agent may be a salicylate, diclofenac, aceclofenac, acemetacin, alclofenac, bromfenac, etodolac, indometacin, nabumetone, oxametacin, proglumetacin, sulindac, tolmetin, piroxicam, droxicam, lornoxicam, meloxicam, tenoxicam, ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, phenylbutazone, sulfinpyrazone, celecoxib, etoricoxib, lumiracoxib, parecoxib, rofecoxib, valdecoxib, prednisone, methylprednisolone, hydrocortisone, or budesonide.

In other instance, co-administering a therapeutically effective amount of an agent for treating multiple sclerosis is contemplated. In certain instances, the agent for treating multiple sclerosis may be interferon beta-2, interferon beta-1, glatiramer, natalizumab, or mitoxantrone.

It should be understood that any suitable combination of the compounds and pharmaceutical compositions provided herein with one or more of the above therapeutic agents and optionally one or more further pharmacologically active substances are considered to be within the scope of the present disclosure. In some embodiments, the compounds and pharmaceutical compositions provided herein are administered prior to or subsequent to the one or more additional active ingredients.

All publications and patents cited herein are incorporated by reference in their entirety.

The following examples are provided for illustrative purposes only and are not intended to limit the scope of the invention.

EXAMPLES

Example 1: Methyl (2R)-3-(4-nitrophenyl)-2-propanamidopropanoate (2)

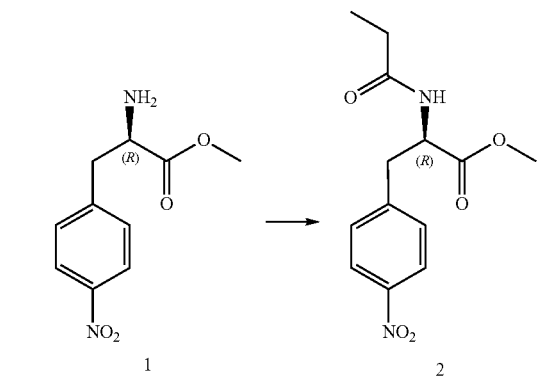

To a solution of propionic acid (6.9 mL, 92.1 mmol, 1.2 eq.) in DMF (120 mL) was added HATU (43.8 g, 115 mmol, 1.5 eq.) and DIPEA (26.7 mL, 153 mmol, 2.0 eq). The resulting mixture was stirred at RT for 10 min. and then a solution of methyl (2R)-2-amino-3-(4-nitrophenyl)propanoate hydrochloride 1 (20.0 g, 76.7 mmol, 1.0 eq,) and DIPEA (26.7 mL, 153 mmol, 2.0 eq) in DMF (80.0 mL) was added. The resulting mixture was stirred at RT under a $N_2$ atmosphere for 1 h. The mixture was diluted with aq. sat. $NaHCO_3$ solution (2 L) and then extracted with EtOAc (2×500 mL). The organic layer was washed with ice cold brine (2×1 L), dried over $Na_2SO_4$ then concentrated to afford 2 as a light brown solid (21.5 g, 100%). $^1$H NMR (400 MHz, DMSO-d6) δ 8.32 (d, J=8.0 Hz, 1H), 8.20-8.12 (m, 2H), 7.55-7.47 (m, 2H), 4.56 (ddd, J=9.7, 8.0, 5.3 Hz, 1H), 3.63 (s, 3H), 3.17 (td, J=13.7, 6.3 Hz, 1H), 3.03 (dd, J=13.7, 9.8 Hz, 1H), 2.71 (d, J=17.0 Hz, 1H), 2.05 (qd, J=7.6, 1.4 Hz, 2H), 1.25 (q, J=7.3, 6.6 Hz, 3H), 0.90 (t, J=7.6 Hz, 3H). UPLC-MS (basic 2 min): Rt=0.91 min; m/z=281.0 for [M+H]⁺.

Example 2: Methyl (2R)-3-(4-aminophenyl)-2-propanamidopropanoate (3)

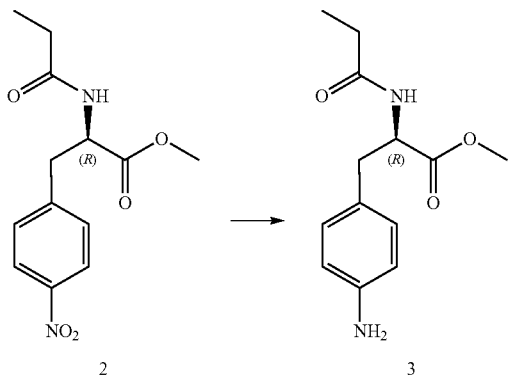

To a degassed solution of 2 (21.5 g, 76.7 mmol, 1.0 eq) in EtOH (383.5 mL) and THF (383.5 mL) was added Pd/C (1.63 g, 15.3 mmol, 0.20 eq). The mixture was degassed for another 20 minutes and then evacuated under vacuum before introducing a hydrogen balloon. The resulting mixture was stirred at RT for 4 h. The mixture was filtered through a pad of celite which was washed with THF (50 mL) and EtOH (50 mL). The solution was concentrated to dryness to afford 3 as a yellow oil (19.1 g, 100%). ¹H NMR (400 MHz, DMSO-d6) δ 8.15 (d, J=7.7 Hz, 1H), 6.88-6.80 (m, 2H), 6.50-6.42 (m, 2H), (4.90 br s, 2H), 4.40-4.26 (m, 2H), 3.58 (s, 3H), 2.81 (dd, J=13.8, 5.8 Hz, 1H), 2.76-2.64 (m, 2H), 2.07 (q, J=7.6 Hz, 2H), 0.93 (t, J=7.6 Hz, 3H). UPLC-MS (basic 2 min): Rt=0.76 min; m/z=251.1 for [M+H]⁺.

Example 3: (R)-methyl 3-(4-((S)-2-(benzyloxycarbonylamino)-2-cyclohexylacetamido)phenyl)-2-propionamidopropanoate (5)

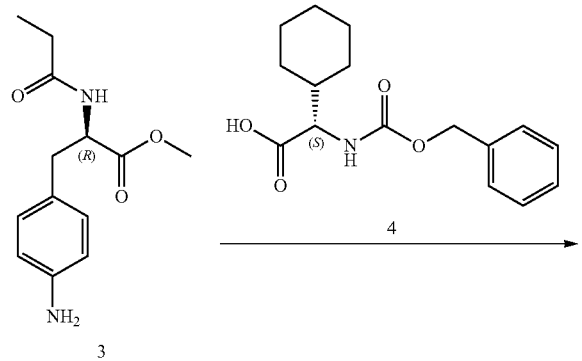

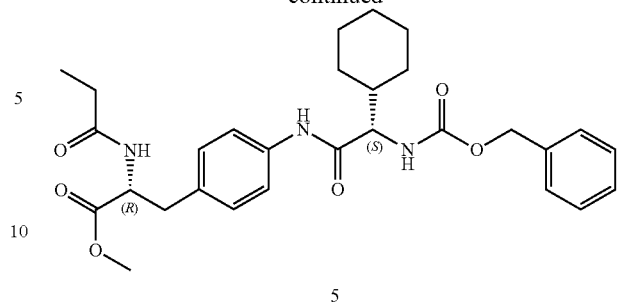

To a solution of Z-Chg-OH 4 (0.816 g, 2.80 mmol, 1.2 eq.) in DMF (12.0 mL) was added HATU (1.34 g, 3.51 mmol, 1.5 eq.) and DIPEA (1.22 mL, 7.02 mmol, 3.0 eq) and then stirred at RT for 10 min. A solution of 3 (0.585 g, 2.34 mmol, 1.0 eq,) in DMF (10.0 mL) was added and the resulting mixture was stirred at RT for 1 h. The mixture was concentrated to dryness and the residue triturated with EtOAc/heptane (9:1) to afford 5 as a white solid (1.10 g, 94%). ¹H NMR (400 MHz, DMSO-d6) δ 10.01 (s, 1H), 8.78-8.09 (m, 2H), 7.55-7.27 (m, 8H), 7.13 (d, J=8.1 Hz, 2H), 5.03 (s, 2H), 4.43 (td, J=8.6, 5.6 Hz, 1H), 4.00 (t, J=8.3 Hz, 1H), 3.61 (s, 3H), 3.16-3.07 (m, 1H), 2.96 (dd, J=13.8, 5.6 Hz, 1H), 2.83 (dd, J=13.8, 9.2 Hz, 1H), 2.07 (q, J=7.6 Hz, 2H), 1.76-1.51 (m, 4H), 1.17-0.99 (m, 5H), 0.92 (t, J=7.6 Hz, 3H). UPLC-MS (basic 2 min): rt=1.14 min; m/z=541.3 for [M+H]⁺.

Example 4: (R)-methyl 3-(4-((S)-2-amino-2-cyclohexylacetamido)phenyl)-2-propionamidopropanoate (6)

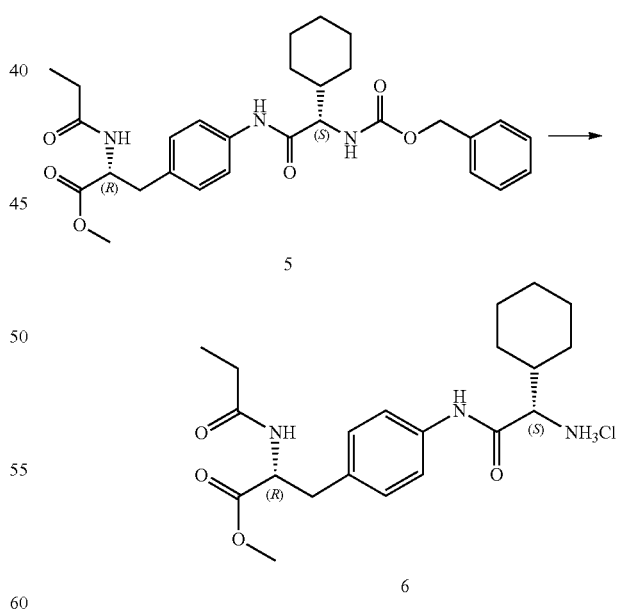

To a degassed suspension of 5 (11.65 g, 22.3 mmol, 1.0 eq.) in EtOH (580 mL) and THF (580 mL) was added Pd(OH)₂/C (2.33 g, 20 mol %) and 1M aq. solution of HCl (23.1 mL, 1.03 eq.). The mixture was degassed for another 20 minutes and then evacuated under vacuum before introducing a hydrogen balloon. The resulting mixture was stirred at room temperature for 18 h. The mixture was filtered through a pad of celite which was washed with EtOH (500 mL) and THF (500 mL). The solution was concentrated to dryness to afford a residue which was triturated with MTBE (20 mL) to afford 6 as a white solid (9.42 g, 100%). ¹H NMR (400 MHz, DMSO-d6) δ 10.77 (s, 1H), 8.31 (dd, J=35.0, 6.4 Hz, 4H), 7.64-7.48 (m, 2H), 7.19 (d, J=8.3 Hz, 2H), 4.43 (m, 1H), 3.83 (t, J=5.7 Hz, 1H), 3.60 (s, 3H), 2.98 (dd, J=13.7, 5.5 Hz, 1H), 2.91-2.79 (m, 1H), 2.71 (d, J=16.9 Hz, 1H), 2.07 (q, J=7.6 Hz, 2H), 1.74-1.58 (m, 4H), 1.21-1.00 (m, 5H), 0.91 (t, J=7.6 Hz, 3H). UPLC-MS (basic 2 min): rt=0.97 min; m/z=390.1 for [M+H]⁺.

Example 5: (R)-methyl 3-(4-((S)-2-cyclohexyl-2-(1-methyl-1H-pyrazole-5-carboxamido)acetamido)phenyl)-2-propionamidopropanoate (7)

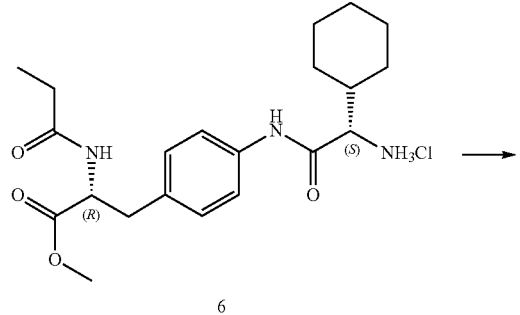

6

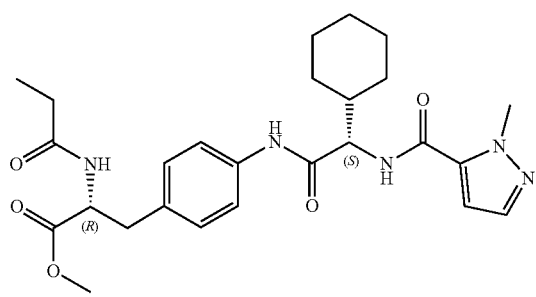

7

To a solution of 1-methyl-1H-pyrazole-5-carboxylic acid (3.35 g, 26.5 mmol, 1.2 eq.) in DMF (200 mL) was added HATU (12.6 g, 33.2 mmol, 1.5 eq.) and DIPEA (15.4 mL, 88.4 mmol, 4.0 eq) and then stirred at RT for 10 min. A solution of 6 (9.42 g, 22.1 mmol, 1.0 eq,) in DMF (180 mL) was added and the resulting mixture was stirred at RT for 1 h. The mixture was concentrated to dryness and the residue triturated with Et₂O/MeCN (4:1) to afford 7 as a white solid (8.50 g, 77%). ¹H NMR (400 MHz, DMSO-d6) δ 10.19 (s, 1H), 8.51 (d, J=8.3 Hz, 1H), 8.22 (d, J=7.9 Hz, 1H), 7.60-7.41 (m, 3H), 7.22-6.99 (m, 3H), 4.44-4.42 (m, 2H), 4.03 (s, 3H), 3.60 (s, 3H), 3.13 (s, 1H), 3.00-2.78 (m, 2H), 2.07 (q, J=7.5 Hz, 2H), 1.89-1.54 (m, 6H), 1.16 (s, 3H), 1.05-0.85 (m, 4H). UPLC-MS (basic 2 min): rt=1.02 min; m/z=498.1 for [M+H]⁺.

Example 6: (2R)-3-{4-[(2S)-2-cyclohexyl-2-[(1-methyl-1H-pyrazol-5-yl)formamido]acetamido]phenyl}-2-propanamidopropanoic acid (8)

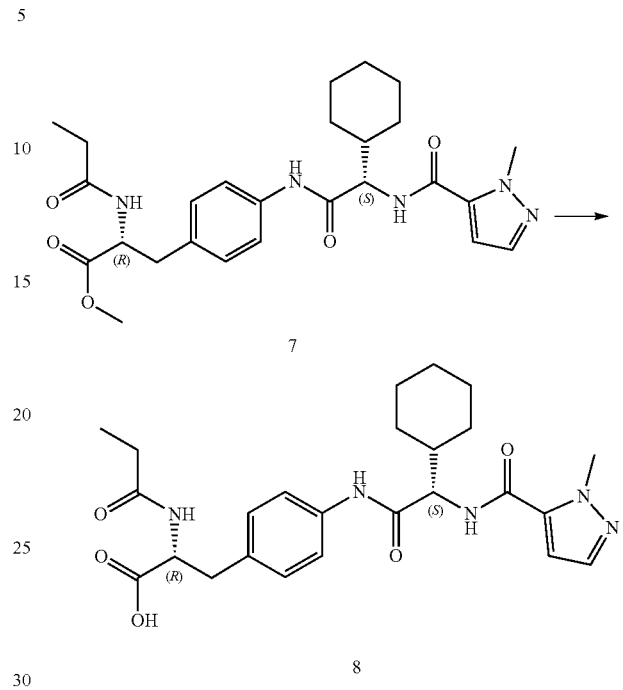

To a suspension of 7 (8.50 g, 17.1 mmol, 1.0 eq.) in THF (215 mL) and MeOH (51 mL) was added 1M LiOH solution (51.3 mL, 51.3 mmol, 3.0 eq.). The resulting mixture was stirred at room temperature for 1 h and then concentrated to dryness. The residue was suspended in water (400 mL) and then acidified with conc. HCl (pH=1.0). The resulting precipitate was filtered under vacuum and washed with Et₂O (3×100 mL) to afford 8 as a white solid (8.22 g, 99%). ¹H NMR (400 MHz, DMSO-d6) δ 12.66 (s, 1H), 10.16 (s, 1H), 8.49 (d, J=8.2 Hz, 1H), 8.06 (d, J=8.1 Hz, 1H), 7.71-7.36 (m, 3H), 7.27-6.96 (m, 3H), 4.49-4.23 (m, 2H), 4.03 (s, 3H), 2.98 (dd, J=13.8, 5.0 Hz, 1H), 2.79 (dd, J=13.8, 9.5 Hz, 1H), 2.06 (q, J=7.5 Hz, 2H), 1.91-1.52 (m, 5H), 1.46-0.95 (m, 5H), 0.91 (t, J=7.6 Hz, 3H). UPLC-MS (basic 2 min): rt=0.74 min; m/z=484.1 for [M+H]⁺.

Example 7: General Procedure A for the Synthesis of 101, 106, 108-125, 127, 130, 133, 137, 138, 140, 141, 143, 144, 146 and 147

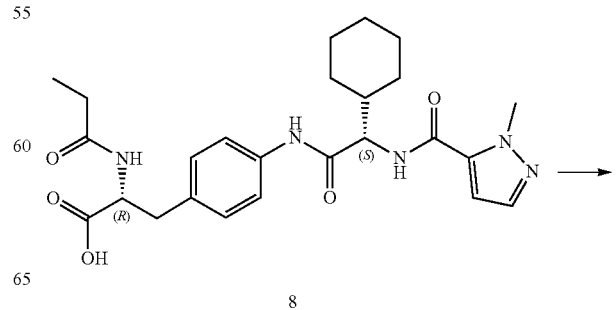

8

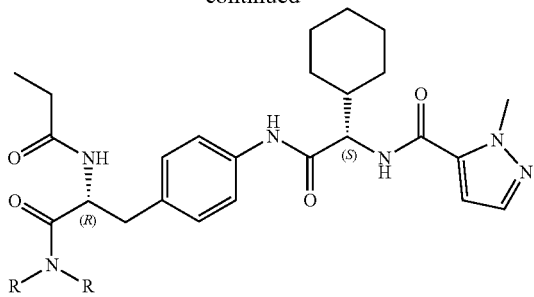

101, 106, 108-125, 127, 130,
133, 137, 138, 140, 141, 143,
144, 146 and 147

To a solution of (2R)-3-{4-[(2S)-2-cyclohexyl-2-[(1-methyl-1H-pyrazol-5-yl)formamido]acetamido]phenyl}-2-propanamidopropanoic acid 8 (1.0 eq.) in DMF (0.05M) was added HATU (1.5 eq.) and DIPEA (3.0 eq.) and the resulting mixture was stirred at RT for 10 minutes. The required amine (1.5 eq.) was added and the reaction mixture was stirred at RT for 1 h. The reaction mixture was concentrated to dryness to afford a residue which was purified via reverse phase column chromatography on a 120 g C18 cartridge eluting with a 5-95% H$_2$O:MeCN eluent (0.1% ammonia) to afford 101, 106, 108-125, 127, 130, 133, 137, 138, 140, 141, 143, 144, 146 and 147.

Example 8: N—((S)-1-cyclohexyl-2-(4-((R)-3-(4-(cyclopropylmethyl)piperazin-1-yl)-3-oxo-2-propionamidopropyl)phenylamino)-2-oxoethyl)-1-methyl-1H-pyrazole-5-carboxamide (106)

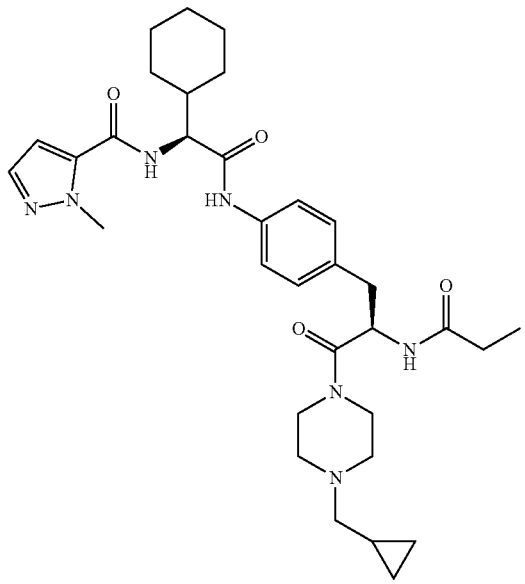 [SMILES: CCC(=O)N[C@H](Cc1ccc(NC(=O)[C@@H](NC(=O)c2ccnn2C)C2CCCCC2)cc1)C(=O)N1CCN(CC2CC2)CC1]

Following General Procedure A, 8 (0.038 g, 0.079 mmol, 1.0 eq.) was reacted with 1-(cyclopropylmethyl)piperazine (0.013 g, 0.094 mmol, 1.2 eq.), HATU (0.045 g, 0.119 mmol, 1.5 eq.) and DIPEA (0.04 mL, 0.237 mmol, 3.0 eq.) in DMF (2 mL) to afford, after flash column chromatography, 106 (9.8 mg) as a white solid. $^1$H NMR (400 MHz, DMSO-d6) δ 10.13 (s, 1H), 8.46 (d, J=8.3 Hz, 1H), 8.17 (d, J=8.3 Hz, 1H), 7.52 (d, J=8.4 Hz, 2H), 7.46 (d, J=2.0 Hz, 1H), 7.13 (d, J=8.3 Hz, 2H), 7.07 (d, J=2.1 Hz, 1H), 4.88 (q, J=7.6 Hz, 1H), 4.40 (t, J=8.6 Hz, 1H), 4.10 (q, J=5.3 Hz, 2H), 4.03 (s, 3H), 3.18 (d, J=5.1 Hz, 8H), 2.86 (dd, J=13.2, 7.5 Hz, 1H), 2.75-2.67 (m, 1H), 2.28 (s, 2H), 2.06 (q, J=7.6 Hz, 3H), 1.91-1.51 (m, 4H), 1.44-0.97 (m, 4H), 0.92 (t, J=7.6 Hz, 3H), 0.74 (s, 1H), 0.45-0.35 (m, 2H) −0.10-0.00 (m, 2H). UPLC-MS (basic 2 min): rt=1.01 min; m/z=606.5 for [M+H]$^+$.

Example 9: N-[(2R)-3-{4-[(2S)-2-cyclohexyl-2-[(1-methyl-1H-pyrazol-5-yl)formamido]acetamido]phenyl}-1-oxo-1-(4-phenylpiperazin-1-yl)propan-2-yl] propanamide (109)

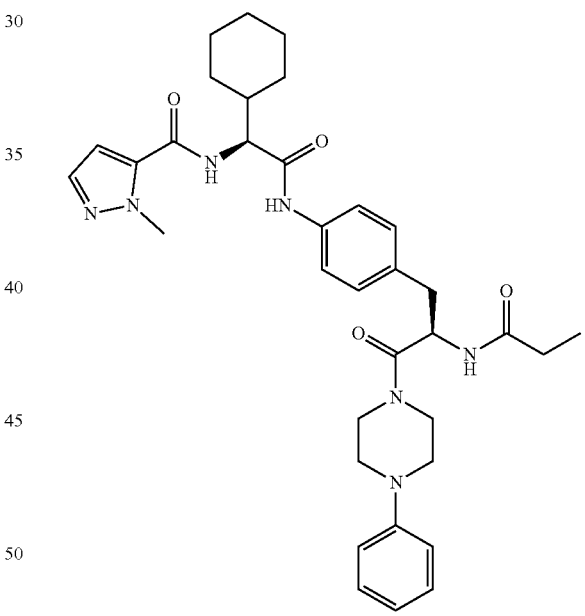

Following General Procedure A, 8 (0.050 g, 0.103 mmol, 1.0 eq.) was reacted with 1-phenylpiperazine (0.020 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 109 (41.3 mg) as a white solid. UPLC-MS (basic 2 min): rt=1.10 min; m/z=628.3 for [M+H]$^+$.

Example 10: N—((S)-1-cyclohexyl-2-(4-((R)-3-(4-methylpiperazin-1-yl)-3-oxo-2-propionamidopropyl)phenylamino)-2-oxoethyl)-1-methyl-1H-pyrazole-5-carboxamide (101)

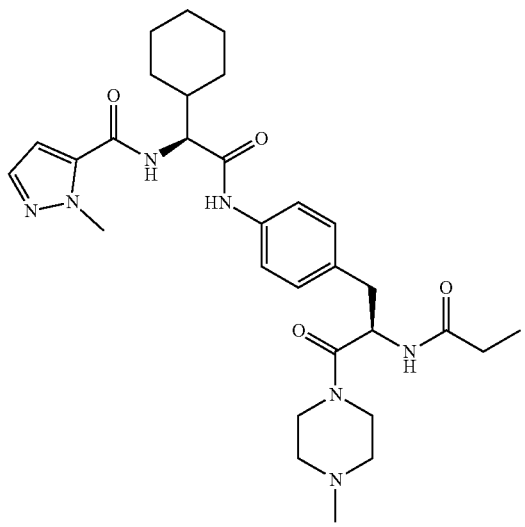 [SMILES: CCC(=O)N[C@H](Cc1ccc(NC(=O)[C@@H](NC(=O)c2ccnn2C)C2CCCCC2)cc1)C(=O)N1CCN(C)CC1]

Following General Procedure A, 8 (0.050 g, 0.103 mmol, 1.0 eq.) was reacted with 1-methylpiperazine (0.012 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 101 (28.4 mg) as a white solid. UPLC-MS (basic 2 min): rt=0.96 min; m/z=566.2 for [M+H]$^+$.

Example 11: (R)-tert-butyl 4-((R)-3-(4-((S)-2-cyclohexyl-2-(1-methyl-1H-pyrazole-5-carboxamido)acetamido)phenyl)-2-propionamidopropanoyl)-2-phenylpiperazine-1-carboxylate (138)

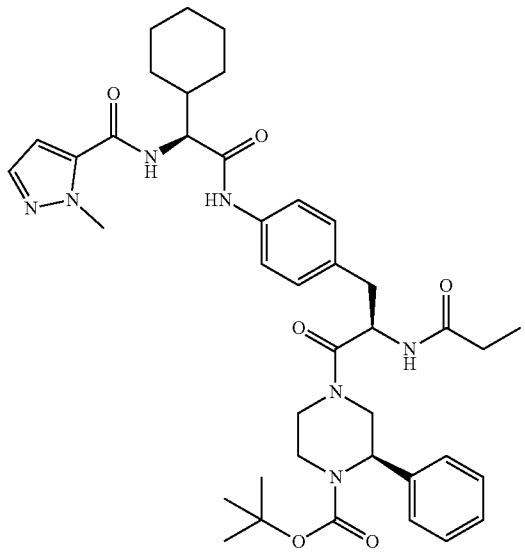 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@H](c2ccccc2)C1]

Following General Procedure A, 8 (0.100 g, 0.206 mmol, 1.0 eq.) was reacted with (R)-1-Boc-2-phenylpiperazine (0.065 g, 0.248 mmol, 1.2 eq.), HATU (0.118 g, 0.310 mmol, 1.5 eq.) and DIPEA (0.1 mL, 0.618 mmol, 3.0 eq.) in DMF (4 mL) to afford, after flash column chromatography, 138 (240 mg) as a white solid.

Example 12: (S)-tert-butyl 4-((R)-3-(4-((S)-2-cyclohexyl-2-(1-methyl-1H-pyrazole-5-carboxamido)acetamido)phenyl)-2-propionamidopropanoyl)-2-phenylpiperazine-1-carboxylate (141)

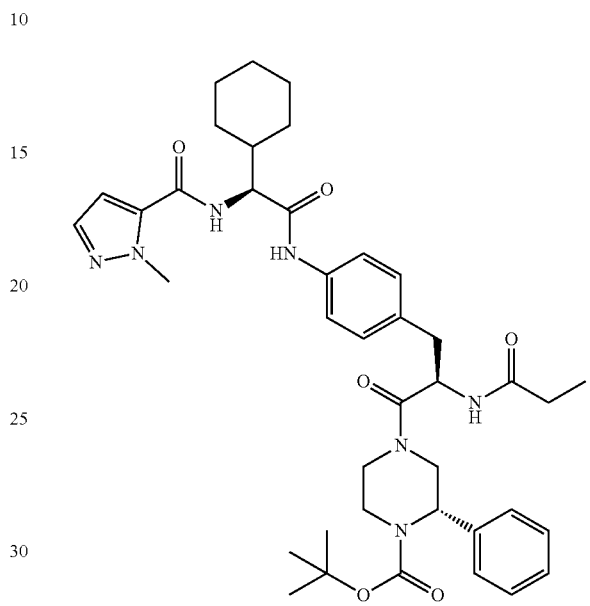

Following General Procedure A, 8 (0.100 g, 0.206 mmol, 1.0 eq.) was reacted with (S)-1-Boc-2-phenylpiperazine (0.065 g, 0.248 mmol, 1.2 eq.), HATU (0.118 g, 0.310 mmol, 1.5 eq.) and DIPEA (0.1 mL, 0.618 mmol, 3.0 eq.) in DMF (4 mL) to afford, after flash column chromatography, 141 (115 mg) as a white solid. UPLC-MS (basic 2 min): rt=1.18 min; m/z=728.4 for [M+H]$^+$.

Example 13: N-((1S)-1-cyclohexyl-2-(4-((2R)-3-(4-methyl-3-phenylpiperazin-1-yl)-3-oxo-2-propionamidopropyl)phenylamino)-2-oxoethyl)-1-methyl-1H-pyrazole-5-carboxamide (110)

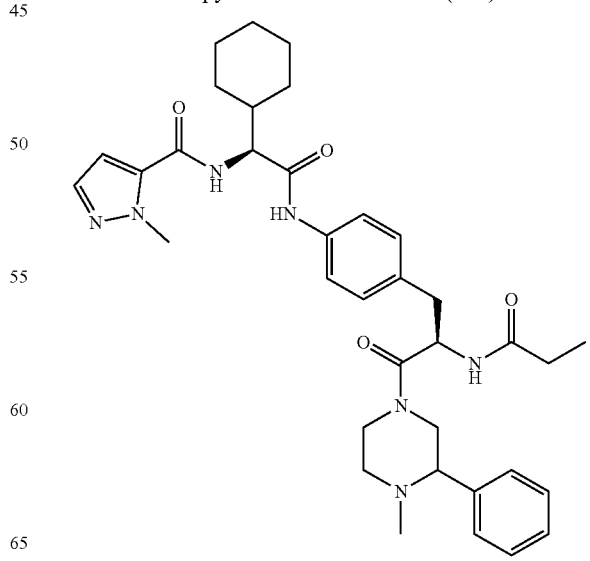

Following General Procedure A, 8 (0.050 g, 0.103 mmol, 1.0 eq.) was reacted with 1-methyl-2-phenylpiperazine (0.022 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 110 (33.9 mg) as a white solid. UPLC-MS (basic 2 min): rt=1.07 min; m/z=642.3 for [M+H]$^+$.

Example 14: tert-butyl (2R)-2-benzyl-4-[(2R)-3-{4-[(2S)-2-cyclohexyl-2-[(1-methyl-1H-pyrazol-5-yl)formamido]acetamido]phenyl}-2-propanamidopropanoyl]piperazine-1-carboxylate (144)

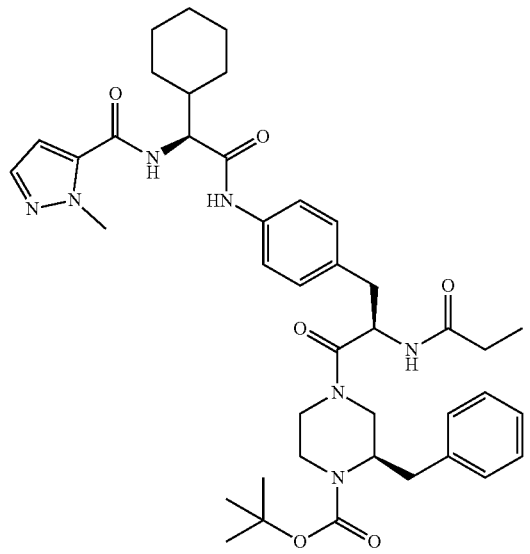 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@H](Cc2ccccc2)C1]

Following General Procedure A, 8 (0.100 g, 0.206 mmol, 1.0 eq.) was reacted with (R)-1-Boc-2-Benzylpiperazine (0.068 g, 0.248 mmol, 1.2 eq.), HATU (0.118 g, 0.310 mmol, 1.5 eq.) and DIPEA (0.10 mL, 0.618 mmol, 3.0 eq.) in DMF (4 mL) to afford, after flash column chromatography, 144 (121.8 mg) as a white solid. UPLC-MS (basic 2 min): rt=1.20 min; m/z=742.6 for [M+H]$^+$.

Example 15: tert-butyl (2S)-2-benzyl-4-[(2R)-3-{4-[(2S)-2-cyclohexyl-2-[(1-methyl-1H-pyrazol-5-yl)formamido]acetamido]phenyl}-2-propanamidopropanoyl]piperazine-1-carboxylate (147)

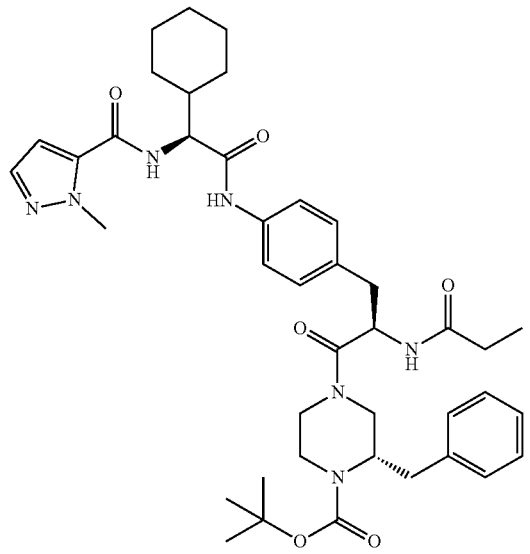 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)[C@@H](Cc2ccccc2)C1]

Following General Procedure A, 8 (0.100 g, 0.206 mmol, 1.0 eq.) was reacted with (S)-1-Boc-2-Benzylpiperazine (0.068 g, 0.248 mmol, 1.2 eq.), HATU (0.118 g, 0.310 mmol, 1.5 eq.) and DIPEA (0.10 mL, 0.618 mmol, 3.0 eq.) in DMF (4 mL) to afford, after flash column chromatography, 147 (110.5 mg) as a white solid. UPLC-MS (basic 2 min): rt=1.20 min; m/z=742.6 for [M+H]$^+$.

Example 16: N-((1S)-2-(4-((2R)-3-(3-benzyl-4-methylpiperazin-1-yl)-3-oxo-2-propionamidopropyl)phenylamino)-1-cyclohexyl-2-oxoethyl)-1-methyl-1H-pyrazole-5-carboxamide (108)

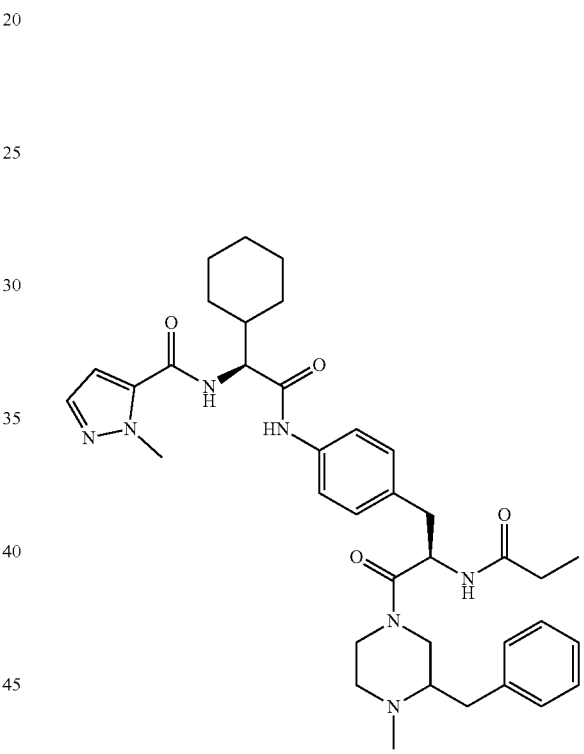

Following General Procedure A, 8 (0.050 g, 0.103 mmol, 1.0 eq.) was reacted with 2-benzyl-1-methylpiperazine (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 108 (31.0) as a white solid. UPLC-MS (basic 2 min): rt=1.07 min; m/z=656.3 for [M+H]$^+$.

Example 17: N-((1S)-1-cyclohexyl-2-(4-((2R)-3-(4-(2,3-dihydro-1H-inden-1-yl)piperazin-1-yl)-3-oxo-2-propionamidopropyl)phenylamino)-2-oxoethyl)-1-methyl-1H-pyrazole-5-carboxamide (111)

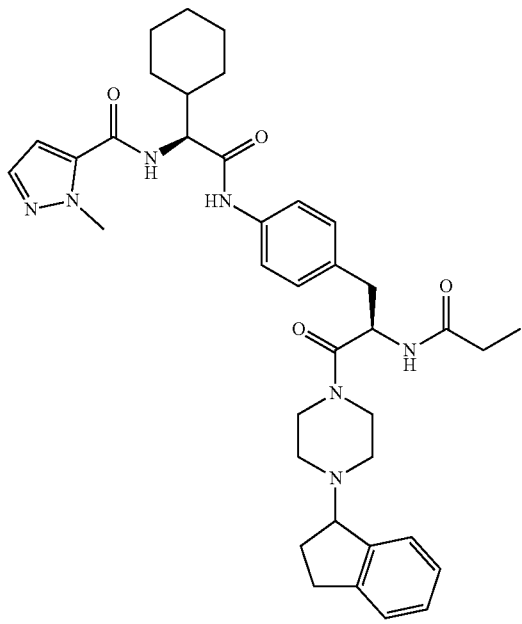 [SMILES: CCC(=O)N[C@H](Cc1ccc(NC(=O)[C@@H](NC(=O)c2ccnn2C)C2CCCCC2)cc1)C(=O)N1CCN(C2CCc3ccccc32)CC1]

Following General Procedure A, 8 (0.050 g, 0.103 mmol, 1.0 eq.) was reacted with 1-indan-1-yl-piperazine (0.025 g, 0.124 mmol, 1.2 eq.), HATU (0.059 g, 0.155 mmol, 1.5 eq.) and DIPEA (0.05 mL, 0.310 mmol, 3.0 eq.) in DMF (2 mL) to afford, after reverse phase column chromatography, 111 (6.4 mg) as a white solid. UPLC-MS (basic 2 min): rt=1.12 min; m/z=668.4 for [M+H]⁺.

Example 18: N—((S)-2-(4-((R)-3-(4-(2-cyanobenzyl)piperazin-1-yl)-3-oxo-2-propionamidopropyl)phenylamino)-1-cyclohexyl-2-oxoethyl)-1-methyl-1H-pyrazole-5-carboxamide (112)

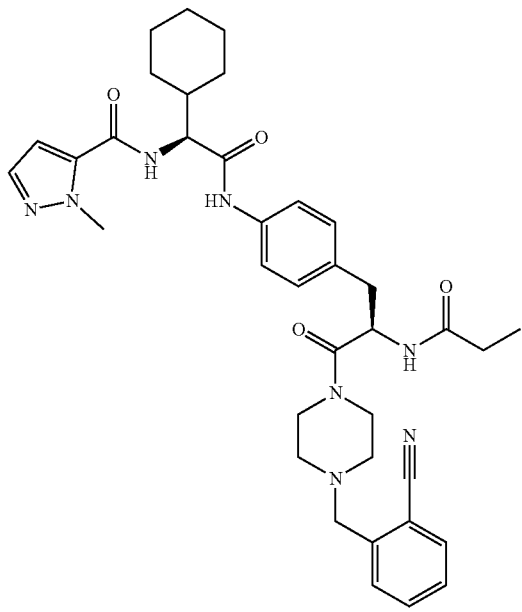 [SMILES: CCC(=O)N[C@H](Cc1ccc(NC(=O)[C@@H](NC(=O)c2ccnn2C)C2CCCCC2)cc1)C(=O)N1CCN(Cc2ccccc2C#N)CC1]

Following General Procedure A, 8 (0.050 g, 0.103 mmol, 1.0 eq.) was reacted with 1-(2-cyanobenzyl)piperazine (0.025 g, 0.124 mmol, 1.0 eq.), HATU (0.059 g, 1.5 mmol, 1.5 eq.) and DIPEA (0.05 mL, 0.309 mmol, 3.0 eq.) in DMF (2 mL) to afford, after flash column chromatography, 112 (18.5 mg) as a white solid. UPLC-MS (basic 5 min): rt=2.43 min; m/z=667.3 for [M+H]⁺.

Example 19: N—((S)-1-cyclohexyl-2-(4-((R)-3-(4-(2-methoxybenzyl)piperazin-1-yl)-3-oxo-2-propionamidopropyl)phenylamino)-2-oxoethyl)-1-methyl-1H-pyrazole-5-carboxamide (115)

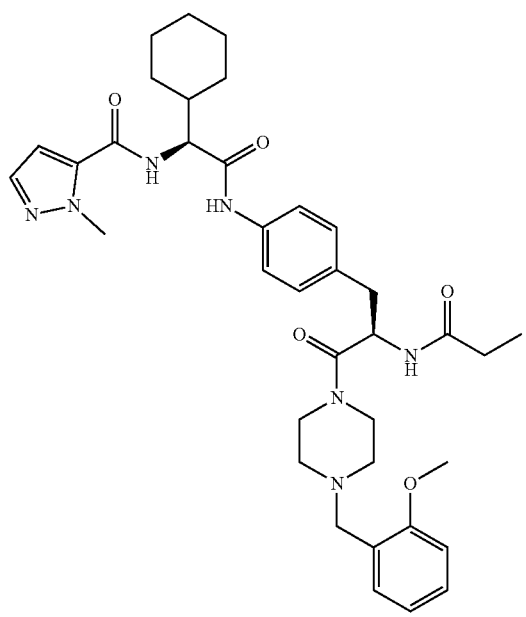 [SMILES: CCC(=O)N[C@H](Cc1ccc(NC(=O)[C@@H](NC(=O)c2ccnn2C)C2CCCCC2)cc1)C(=O)N1CCN(Cc2ccccc2OC)CC1]

Following General Procedure A, 8 (0.050 g, 0.103 mmol, 1.0 eq.) was reacted with 1-(2-methoxybenzyl)piperazine (0.020 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 115 (136 mg) as a white solid. UPLC-MS (basic 2 min): rt=1.09 min; m/z=672.3 for [M+H]⁺.

Example 20: N—((S)-1-cyclohexyl-2-(4-((R)-3-(4-(2-(hydroxymethyl)benzyl)piperazin-1-yl)-3-oxo-2-propionamidopropyl)phenylamino)-2-oxoethyl)-1-methyl-1H-pyrazole-5-carboxamide (118)

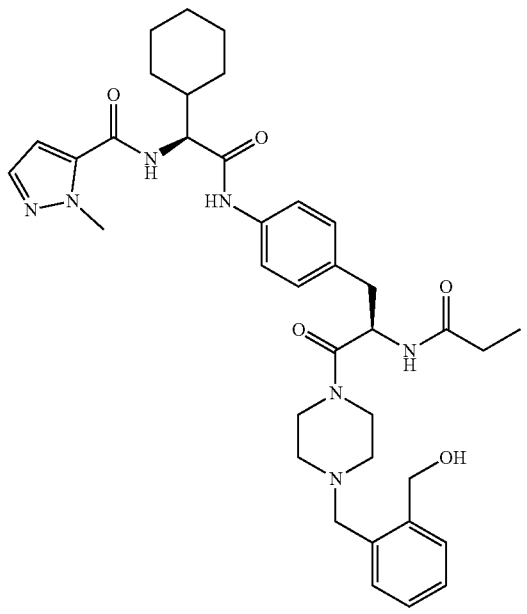 [SMILES: CCC(=O)N[C@H](Cc1ccc(NC(=O)[C@@H](NC(=O)c2ccnn2C)C2CCCCC2)cc1)C(=O)N1CCN(Cc2ccccc2CO)CC1]

Following General Procedure A, 8 (0.050 g, 0.103 mmol, 1.0 eq.) was reacted with [2-(piperazin-1-ylmethyl)phenyl]methanol (0.026 g, 0.124 mmol, 1.2 eq.), HATU (0.059 g, 1.55 mmol, 1.5 eq.) and DIPEA (0.05 mL, 0.309 mmol, 3.0 eq.) in DMF (2 mL) to afford, after reverse phase column chromatography, 118 (18.8 mg) as a white solid. UPLC-MS (basic 5 min): rt=2.43 min; m/z=672.3 for [M+H]$^+$.

Example 21: N—((S)-2-(4-((R)-3-(4-(2-chlorobenzyl)piperazin-1-yl)-3-oxo-2-propionamidopropyl)phenylamino)-1-cyclohexyl-2-oxoethyl)-1-methyl-1H-pyrazole-5-carboxamide (121)

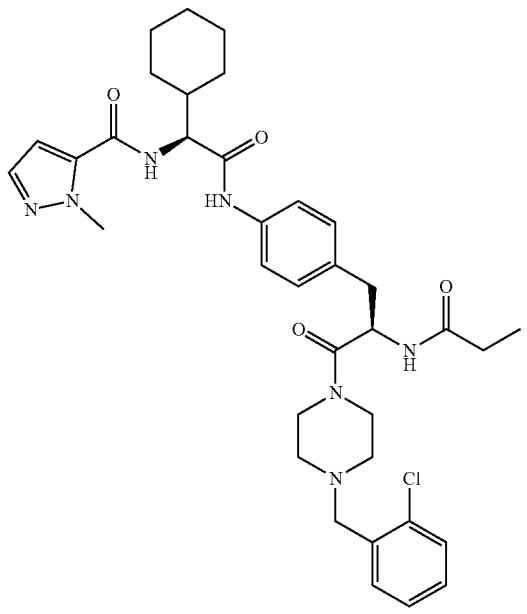 [SMILES: CCC(=O)N[C@H](Cc1ccc(NC(=O)[C@@H](NC(=O)c2ccnn2C)C2CCCCC2)cc1)C(=O)N1CCN(Cc2ccccc2Cl)CC1]

Following General Procedure A, 8 (0.050 g, 0.103 mmol, 1.0 eq.) was reacted with 2-chlorobenzylpiperazine (0.026 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 121 (17.6 mg) as a white solid. UPLC-MS (basic 5 min): rt=2.47 min; m/z=676.2 for [M+H]$^+$.

Example 22: N-((1S)-1-cyclohexyl-2-oxo-2-(4-((2R)-3-oxo-3-(4-(1-phenylethyl)piperazin-1-yl)-2-propionamidopropyl)phenylamino)ethyl)-1-methyl-1H-pyrazole-5-carboxamide (113)

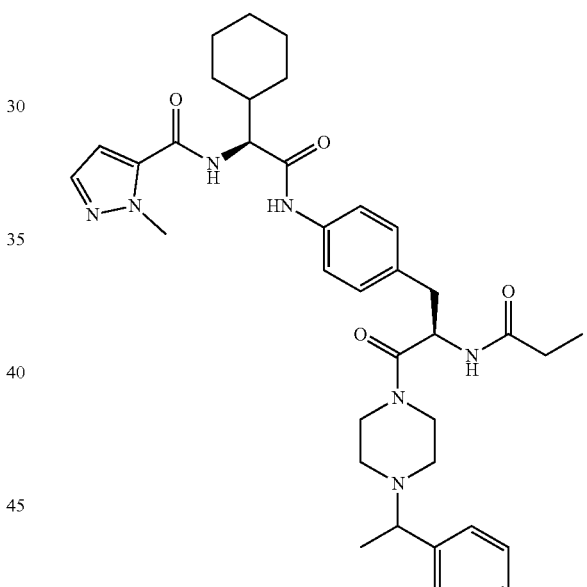

Following General Procedure A, 8 (0.057 g, 0.118 mmol, 1.0 eq.) was reacted with 1-(1-phenylethyl)piperazine (0.027 g, 0.141 mmol, 1.2 eq.), HATU (0.067 g, 0.177 mmol, 1.5 eq.) and DIPEA (0.66 mL, 0.354 mmol, 3.0 eq.) in DMF (2 mL) to afford, after flash column chromatography, 113 (3.8 mg) as a white solid. UPLC-MS (basic 5 min): rt=2.49 min; m/z=656.6 for [M+H]$^+$.

Example 23: N—((S)-1-cyclohexyl-2-(4-((R)-3-(4-(3-hydroxybenzyl)piperazin-1-yl)-3-oxo-2-propionamidopropyl)phenylamino)-2-oxoethyl)-1-methyl-1H-pyrazole-5-carboxamide (116)

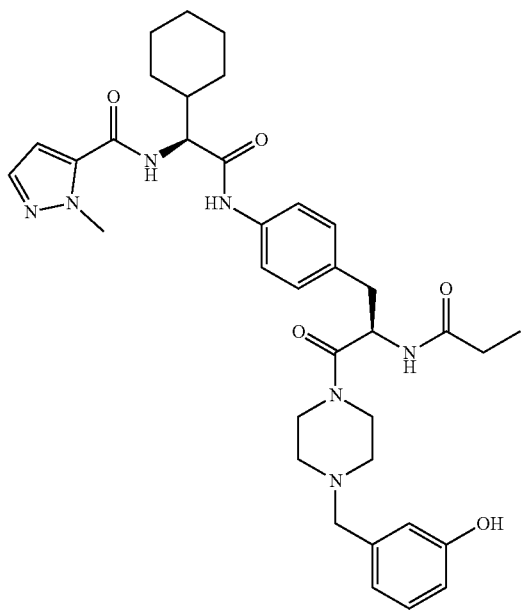 [SMILES: CCC(=O)N[C@H](Cc1ccc(NC(=O)[C@@H](NC(=O)c2ccnn2C)C2CCCCC2)cc1)C(=O)N1CCN(Cc2cccc(O)c2)CC1]

Following General Procedure A, 8 (0.050 g, 0.103 mmol, 1.0 eq.) was reacted with 3-(piperazin-1-ylmethyl)phenol (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 116 (10.0) as a white solid. UPLC-MS (basic 5 min): rt=2.38 min; m/z=658.3 for [M+H]$^+$.

Example 24: N—((S)-2-(4-((R)-3-(4-(3-cyanobenzyl)piperazin-1-yl)-3-oxo-2-propionamidopropyl)phenylamino)-1-cyclohexyl-2-oxoethyl)-1-methyl-1H-pyrazole-5-carboxamide (119)

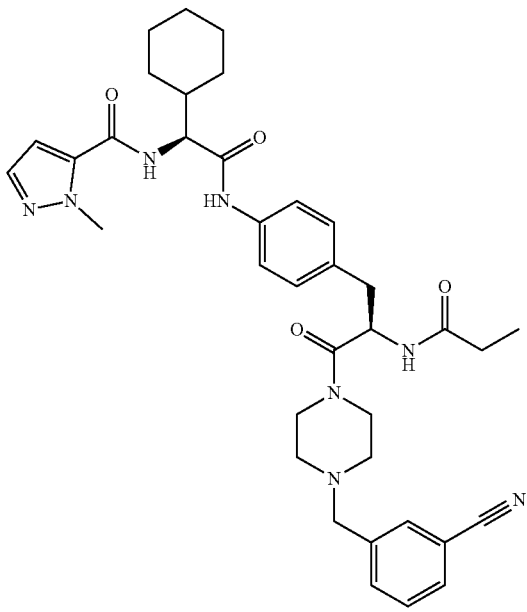 [SMILES: CCC(=O)N[C@H](Cc1ccc(NC(=O)[C@@H](NC(=O)c2ccnn2C)C2CCCCC2)cc1)C(=O)N1CCN(Cc2cccc(C#N)c2)CC1]

Following General Procedure A, 8 (0.050 g, 0.103 mmol, 1.0 eq.) was reacted with 1-(3-cyanobenzyl)piperazine (0.025 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 119 (23.8 mg) as a white solid.

Example 25: N—((S)-1-cyclohexyl-2-(4-((R)-3-(4-(3-methoxybenzyl)piperazin-1-yl)-3-oxo-2-propionamidopropyl)phenylamino)-2-oxoethyl)-1-methyl-1H-pyrazole-5-carboxamide (122)

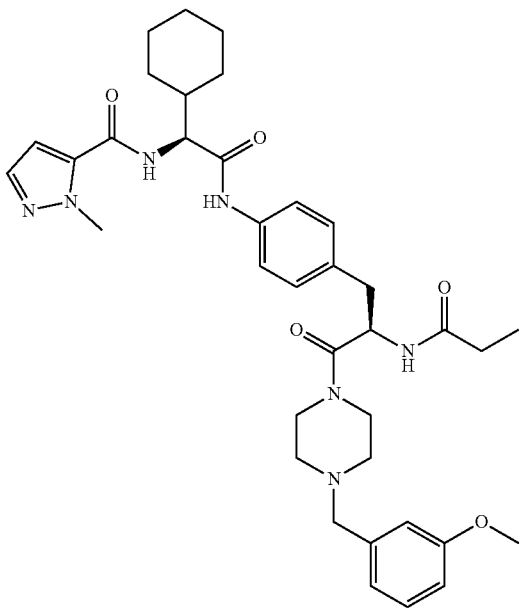 [SMILES: CCC(=O)N[C@H](Cc1ccc(NC(=O)[C@@H](NC(=O)c2ccnn2C)C2CCCCC2)cc1)C(=O)N1CCN(Cc2cccc(OC)c2)CC1]

Following General Procedure A, 8 (0.050 g, 0.103 mmol, 1.0 eq.) was reacted with 1-(3-methoxybenzyl)piperazine (0.025 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 122 (24.4 mg) as a white solid. UPLC-MS (basic 5 min): rt=2.49 min; m/z=672.3 for [M+H]$^+$.

Example 26: N—((S)-2-(4-((R)-3-(4-(3-chlorobenzyl)piperazin-1-yl)-3-oxo-2-propionamidopropyl)phenylamino)-1-cyclohexyl-2-oxoethyl)-1-methyl-1H-pyrazole-5-carboxamide (114)

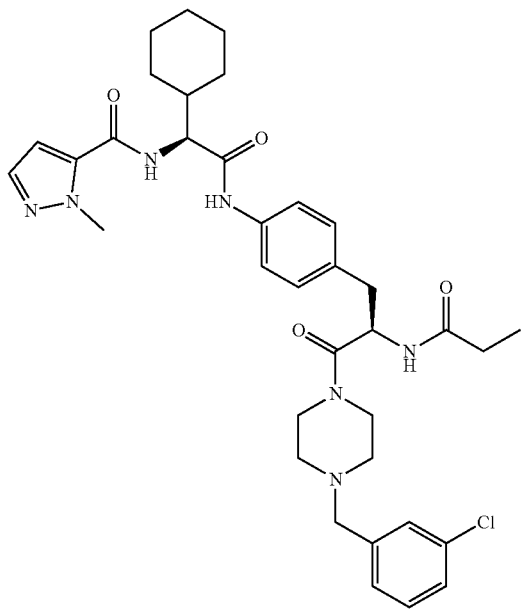 [SMILES: CCC(=O)N[C@H](Cc1ccc(NC(=O)[C@@H](NC(=O)c2ccnn2C)C2CCCCC2)cc1)C(=O)N1CCN(Cc2cccc(Cl)c2)CC1]

Following General Procedure A, 8 (0.050 g, 0.103 mmol, 1.0 eq.) was reacted with 1-(3-chlorobenzyl)piperazine (0.027 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 114 (14.8 mg) as a white solid. UPLC-MS (basic 2 min): rt=2.55 min; m/z=676.2 for [M+H]$^+$.

Example 27: N—((S)-1-cyclohexyl-2-(4-((R)-3-(4-(4-hydroxybenzyl)piperazin-1-yl)-3-oxo-2-propionamidopropyl)phenylamino)-2-oxoethyl)-1-methyl-1H-pyrazole-5-carboxamide (117)

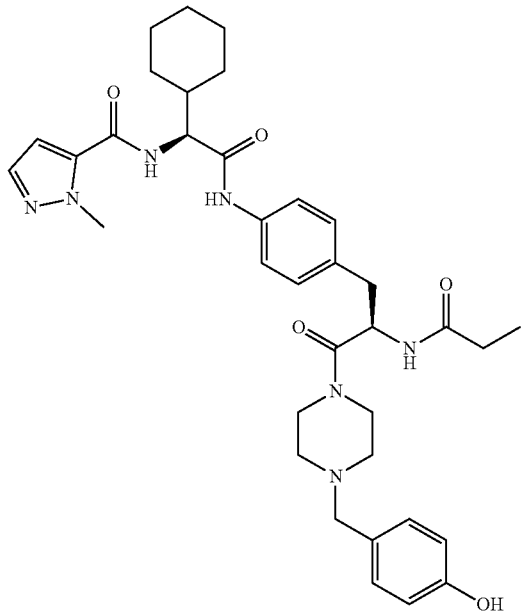 [SMILES: CCC(=O)N[C@H](Cc1ccc(NC(=O)[C@@H](NC(=O)c2ccnn2C)C2CCCCC2)cc1)C(=O)N1CCN(Cc2ccc(O)cc2)CC1]

Following General Procedure A, 8 (0.050 g, 0.103 mmol, 1.0 eq.) was reacted with 4-((piperazin-1-yl)methyl)phenol (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 117 (14.4 mg) as a white solid. UPLC-MS (basic 5 min): rt=2.36 min; m/z=658.4 for [M+H]$^+$.

Example 28: N—((S)-2-(4-((R)-3-(4-(4-cyanobenzyl)piperazin-1-yl)-3-oxo-2-propionamidopropyl)phenylamino)-1-cyclohexyl-2-oxoethyl)-1-methyl-1H-pyrazole-5-carboxamide (120)

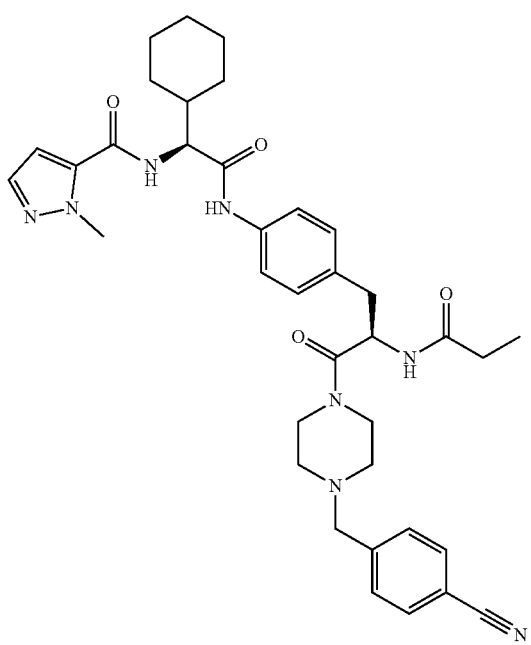 [SMILES: CCC(=O)N[C@H](Cc1ccc(NC(=O)[C@@H](NC(=O)c2ccnn2C)C2CCCCC2)cc1)C(=O)N1CCN(Cc2ccc(C#N)cc2)CC1]

Following General Procedure A, 8 (0.050 g, 0.103 mmol, 1.0 eq.) was reacted with 1-(4-cyanobenzyl)piperazine (0.025 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 120 (13.4 mg) as a white solid. UPLC-MS (basic 5 min): rt=2.45 min; m/z=667.3 for [M+H]$^+$.

Example 29: N—((S)-1-cyclohexyl-2-(4-((R)-3-(4-(4-methoxybenzyl)piperazin-1-yl)-3-oxo-2-propionamidopropyl)phenylamino)-2-oxoethyl)-1-methyl-1H-pyrazole-5-carboxamide (123)

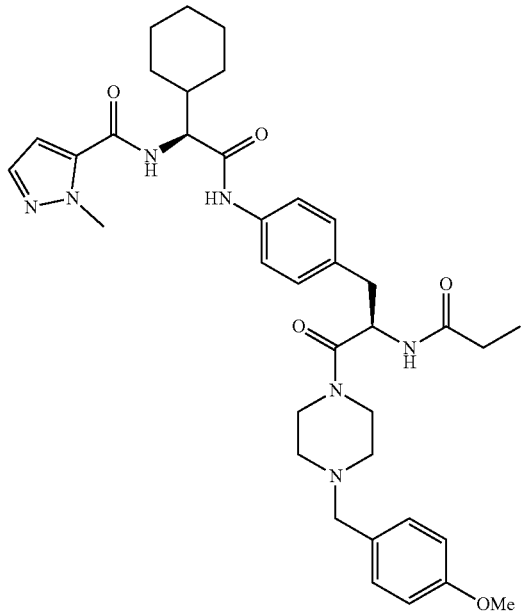 [SMILES: CCC(=O)N[C@H](Cc1ccc(NC(=O)[C@@H](NC(=O)c2ccnn2C)C2CCCCC2)cc1)C(=O)N1CCN(Cc2ccc(OC)cc2)CC1]

Following General Procedure A, 8 (0.050 g, 0.103 mmol, 1.0 eq.) was reacted with 1-(4-methoxybenzyl)piperazine (0.026 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 123 (14.5 mg) as a white solid. UPLC-MS (basic 5 min): rt=2.48 min; m/z=672.3 for [M+H]$^+$.

Example 30: N—((S)-2-(4-((R)-3-(4-(4-chlorobenzyl)piperazin-1-yl)-3-oxo-2-propionamidopropyl)phenylamino)-1-cyclohexyl-2-oxoethyl)-1-methyl-1H-pyrazole-5-carboxamide (124)

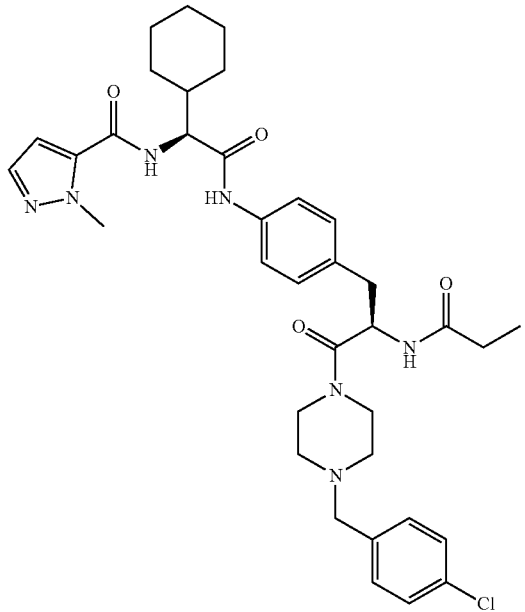 [SMILES: CCC(=O)N[C@H](Cc1ccc(NC(=O)[C@@H](NC(=O)c2ccnn2C)C2CCCCC2)cc1)C(=O)N1CCN(Cc2ccc(Cl)cc2)CC1]

Following General Procedure A, 8 (0.050 g, 0.103 mmol, 1.0 eq.) was reacted with 1-(4-chlorobenzyl)piperazine (0.026 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 124 (16.5 mg) as a white solid. UPLC-MS (basic 5 min): rt=2.56 min; m/z=676.3 for [M+H]$^+$.

Example 31: N-[(2R)-3-{4-[(2S)-2-cyclohexyl-2-[(1-methyl-1H-pyrazol-5-yl)formamido]acetamido]phenyl}-1-{4-[(2-hydroxyphenyl)methyl]piperazin-1-yl}-1-oxopropan-2-yl]propanamide (127)

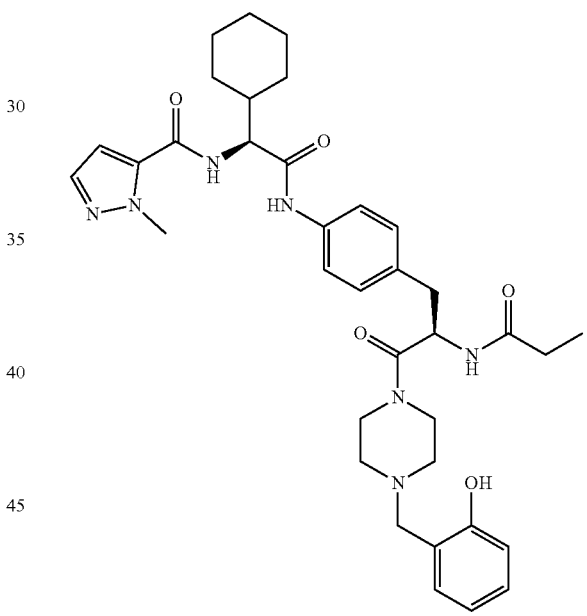

Following General Procedure A, 8 (0.050 g, 0.103 mmol, 1.0 eq.) was reacted with 2-[(piperidin-4-yl)methyl]phenol (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 127 (32.5 mg) as a white solid. UPLC-MS (basic 5 min): rt=2.81 min; m/z=658.6 for [M+H]$^+$.

Example 32: N—((S)-1-cyclohexyl-2-oxo-2-(4-((R)-3-oxo-2-propionamido-3-(4-(pyridin-2-ylmethyl)piperazin-1-yl)propyl)phenylamino)ethyl)-1-methyl-1H-pyrazole-5-carboxamide (130)

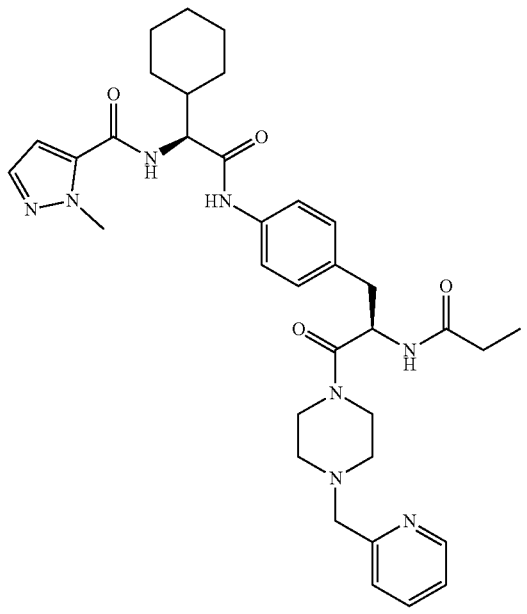

Following General Procedure A, 8 (0.050 g, 0.103 mmol, 1.0 eq.) was reacted with 2-[(piperazin-1-yl)methyl]pyridine (0.026 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 130 (17.3 mg) as a white solid. UPLC-MS (basic 5 min): rt=2.34 min; m/z=643.3 for [M+H]$^+$.

Example 33: N—((S)-1-cyclohexyl-2-oxo-2-(4-((R)-3-oxo-2-propionamido-3-(4-(pyridin-3-ylmethyl)piperazin-1-yl)propyl)phenylamino)ethyl)-1-methyl-1H-pyrazole-5-carboxamide (133)

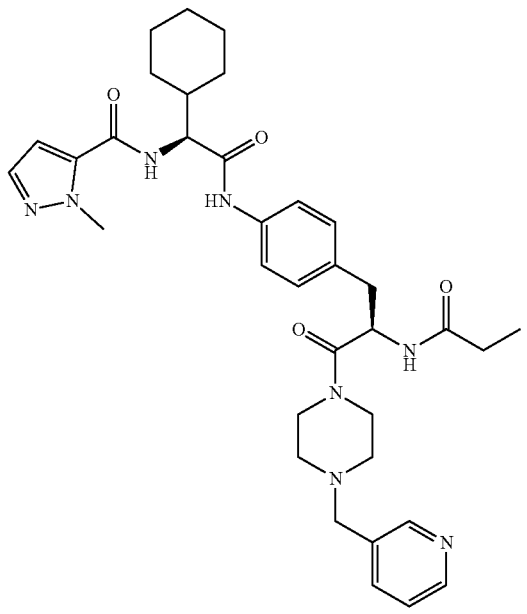

Following General Procedure A, 8 (0.050 g, 0.103 mmol, 1.0 eq.) was reacted with 3-[(piperazin-1-yl)methyl]pyridine (0.022 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 133 (32.4) as a white solid. UPLC-MS (basic 2 min): rt=0.96 min; m/z=643.3 for [M+H]$^+$.

Example 34: N—((S)-1-cyclohexyl-2-oxo-2-(4-((R)-3-oxo-2-propionamido-3-(4-(pyridin-4-ylmethyl)piperazin-1-yl)propyl)phenylamino)ethyl)-1-methyl-1H-pyrazole-5-carboxamide (125)

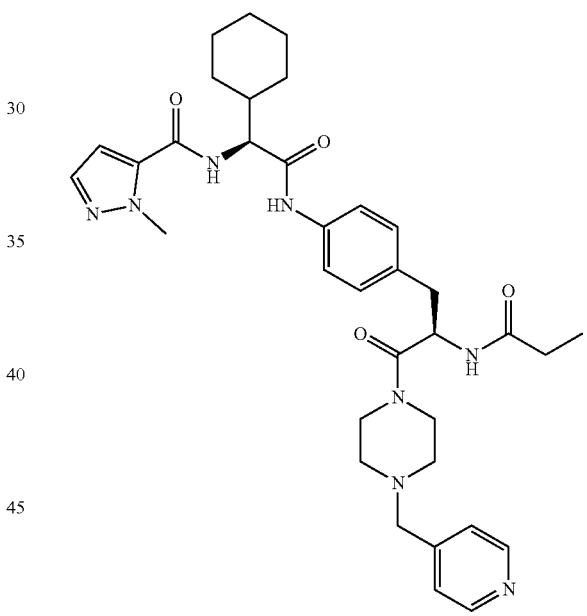

Following General Procedure A, 8 (0.066 g, 0.136 mmol, 1.0 eq.) was reacted with 4-[(piperazin-1-yl)methyl]pyridine (0.029 g, 0.163 mmol, 1.2 eq.), HATU (0.078 g, 0.204 mmol, 1.5 eq.) and DIPEA (0.07 mL, 0.408 mmol, 3.0 eq.) in DMF (2 mL) to afford, after reverse phase column chromatography, 125 (36.2 mg) as a white solid. UPLC-MS (basic 5 min): rt=2.20 min; m/z=643.3 for [M+H]$^+$.

Example 35: N-[(2R)-1-[(2S)-2-benzyl-4-methylpiperazin-1-yl]-3-{4-[(2S)-2-cyclohexyl-2-[(1-methyl-1H-pyrazol-5-yl)formamido]acetamido]phenyl}-1-oxopropan-2-yl]propanamide (137)

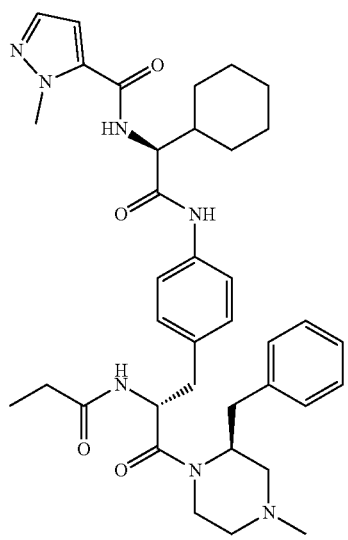 [SMILES: CCC(=O)N[C@H](Cc1ccc(NC(=O)[C@@H](NC(=O)c2ccnn2C)C2CCCCC2)cc1)C(=O)N1CCN(C)C[C@@H]1Cc1ccccc1]

Following General Procedure A, 8 (0.050 g, 0.103 mmol, 1.0 eq.) was reacted with (3R)-(3S)-benzyl-1-methylpiperazine (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 137 (16.6 mg) as a white solid. UPLC-MS (basic 5 min): rt=3.11 min; m/z=656.6 for [M+H]$^+$.

Example 36: N-[(2R)-1-[(2R)-2-benzyl-4-methylpiperazin-1-yl]-3-{4-[(2S)-2-cyclohexyl-2-[(1-methyl-1H-pyrazol-5-yl)formamido]acetamido]phenyl}-1-oxopropan-2-yl]propanamide (140)

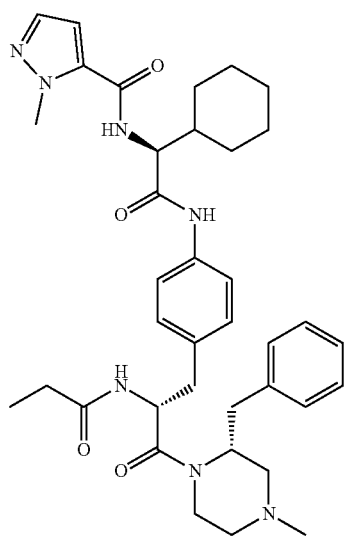 [SMILES: CCC(=O)N[C@H](Cc1ccc(NC(=O)[C@@H](NC(=O)c2ccnn2C)C2CCCCC2)cc1)C(=O)N1CCN(C)C[C@H]1Cc1ccccc1]

Following General Procedure A, 8 (0.050 g, 0.103 mmol, 1.0 eq.) was reacted with (3S)-(3R)-benzyl-1-methylpiperazine (0.024 g, 0.124 mmol, 1.2 eq.), HATU (0.059 g, 0.155 mmol, 1.5 eq.) and DIPEA (0.05 mL, 0.309 mmol, 3.0 eq.) in DMF (2 mL) to afford, after reverse phase column chromatography, 140 (9.0) as a white solid. UPLC-MS (basic 5 min): rt=3.12 min; m/z=656.6 for [M+H]$^+$.

Example 37: tert-butyl (R)-2-benzyl-4-((R)-3-(4-((S)-2-cyclohexyl-2-(1-methyl-1H-pyrazole-5-carboxamido)acetamido)phenyl)-2-propionamidopropanoyl)piperazine-1-carboxylate (144)

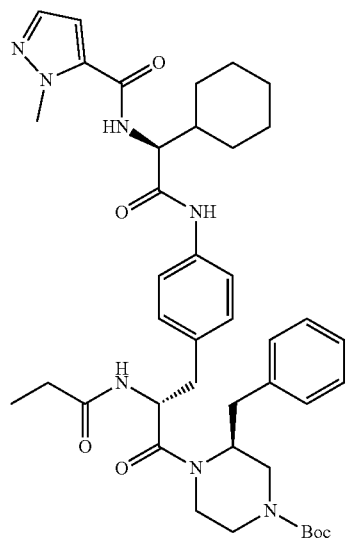 [SMILES: CCC(=O)N[C@H](Cc1ccc(NC(=O)[C@@H](NC(=O)c2ccnn2C)C2CCCCC2)cc1)C(=O)N1CCN(C(=O)OC(C)(C)C)C[C@@H]1Cc1ccccc1]

Following General Procedure A, 8 (0.150 g, 0.310 mmol, 1.0 eq.) was reacted with tert-butyl (3S)-3-benzylpiperazine-1-carboxylate (0.103 g, 0.372 mmol, 1.2 eq.), HATU (0.177 g, 0.465 mmol, 1.5 eq.) and DIPEA (0.16 mL, 0.930 mmol, 3.0 eq.) in DMF (6 mL) to afford, after reverse phase column chromatography, 144 (123.6 mg) as a white solid. UPLC-MS (basic 2 min): rt=1.21 min; m/z=742.3 for [M+H]$^+$.

Example 38: tert-butyl (S)-2-benzyl-4-((R)-3-(4-((S)-2-cyclohexyl-2-(1-methyl-1H-pyrazole-5-carboxamido)acetamido)phenyl)-2-propionamidopropanoyl)piperazine-1-carboxylate (147)

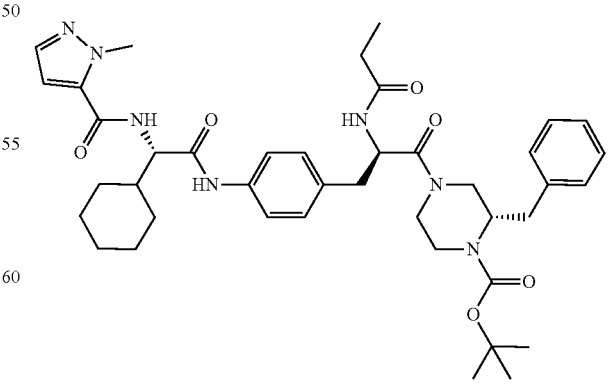

Following General Procedure A, 8 (0.200 g, 0.414 mmol, 1.0 eq.) was reacted with tert-butyl (3R)-3-benzylpiperazine-1-carboxylate (0.137 g, 0.496 mmol, 1.2 eq.), HATU (0.236 g, 0.620 mmol, 1.5 eq.) and DIPEA (0.22 mL, 1.24 mmol, 3.0 eq.) in DMF (8 mL) to afford, after reverse phase column chromatography, 147 (171.5 mg) as a white solid. UPLC-MS (basic 2 min): rt=1.21 min; m/z=742.3 for [M+H]$^+$.

Example 39: General Procedure B for the Synthesis of 102, 104, 105 and 107

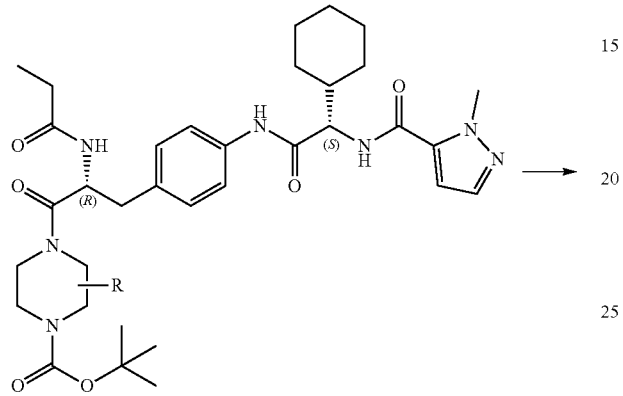

Example 40: N—((S)-1-cyclohexyl-2-oxo-2-(4-((R)-3-oxo-3-((R)-3-phenylpiperazin-1-yl)-2-propionamidopropyl)phenylamino)ethyl)-1-methyl-1H-pyrazole-5-carboxamide (104)

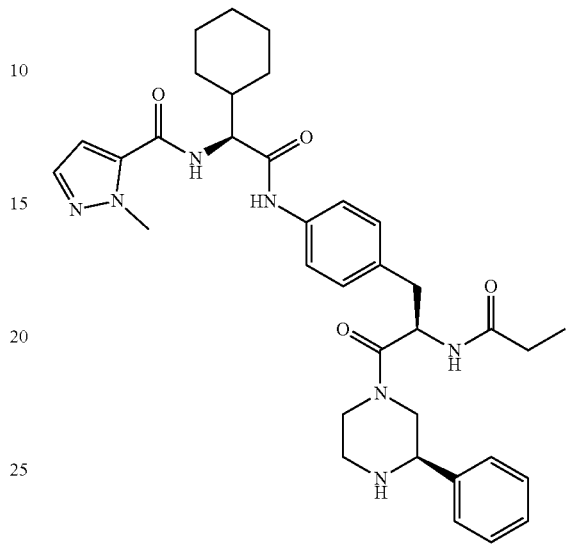

Following General Procedure B, 138 (0.115 g, 0.158 mmol, 1.0 eq.) was reacted with 4N HCl in Dioxane (0.6 mL) in DCM (0.6 mL) to afford, after reverse phase column chromatography, 104 (27.0 mg) as a white solid. UPLC-MS (basic 2 min): rt=1.03 min; m/z=628.3 for [M+H]$^+$.

Example 41: N—((S)-1-cyclohexyl-2-oxo-2-(4-((R)-3-oxo-3-((S)-3-phenylpiperazin-1-yl)-2-propionamidopropyl)phenylamino)ethyl)-1-methyl-1H-pyrazole-5-carboxamide (107)

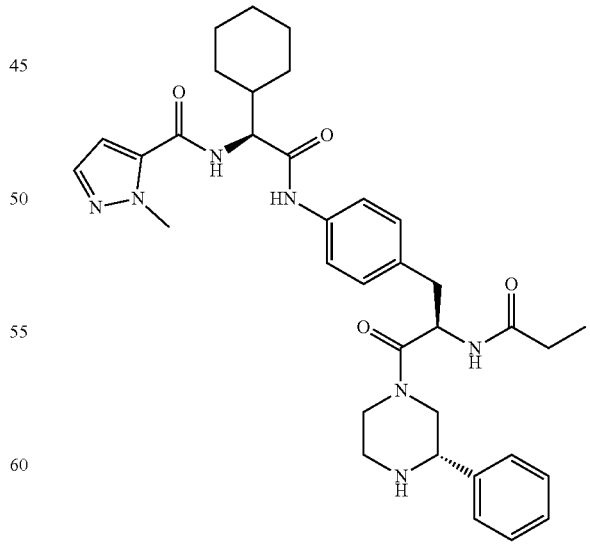

To a solution of 138 or 141 or 144 or 147 (1.0 eq.) in DCM (5 volumes) was added 4N HCl in dioxane (5 volumes) and the resulting mixture was stirred at RT for 30 minutes. The reaction mixture was concentrated to dryness to afford a residue which was purified via reverse phase column chromatography on a 120 g C18 cartridge eluting with a 5-95% H$_2$O:MeCN eluent (0.1% ammonia) to afford 102 or 104 or 105 or 107, respectively.

Following General Procedure B, 141 (0.231 g, 0.317 mmol, 1.0 eq.) was reacted with 4N HCl in Dioxane (1.15 mL) in DCM (4.6 mL) to afford, after reverse phase column chromatography, 107 (32.4 mg) as a white solid. UPLC-MS (basic 2 min): rt=1.02 min; m/z=628.3 for [M+H]⁺.

Example 42: N-[(2R)-1-[(3R)-3-benzylpiperazin-1-yl]-3-{4-[(2S)-2-cyclohexyl-2-[(1-methyl-1H-pyrazol-5-yl)formamido]acetamido]phenyl}-1-oxopropan-2-yl]propanamide hydrochloride (102)

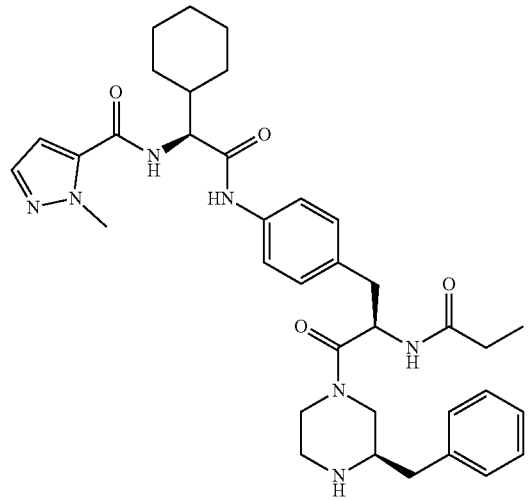 [SMILES: CCC(=O)N[C@H](Cc1ccc(NC(=O)[C@@H](NC(=O)c2ccnn2C)C2CCCCC2)cc1)C(=O)N1CCN[C@H](Cc2ccccc2)C1]

Following General Procedure B, 144 (0.104 g, 0.317 mmol, 1.0 eq.) was reacted with 4N HCl in Dioxane (0.52 mL) in DCM (2 mL) to afford, after reverse phase column chromatography, 102 (32.3 mg) as a white solid. UPLC-MS (basic 2 min): rt=1.03 min; m/z=642.5 for [M+H]⁺.

Example 43: N-[(2R)-1-[(3S)-3-benzylpiperazin-1-yl]-3-{4-[(2S)-2-cyclohexyl-2-[(1-methyl-1H-pyrazol-5-yl)formamido]acetamido]phenyl}-1-oxopropan-2-yl]propanamide hydrochloride (105)

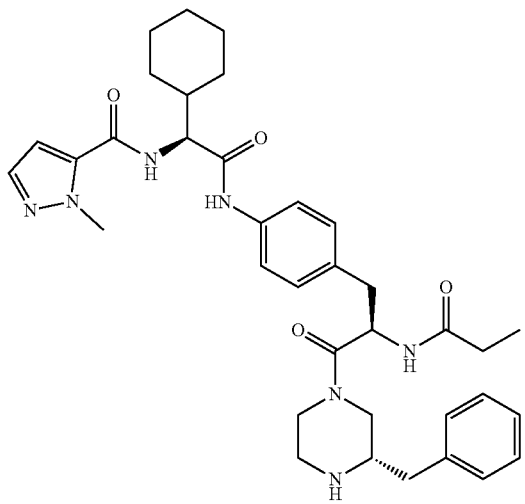 [SMILES: CCC(=O)N[C@H](Cc1ccc(NC(=O)[C@@H](NC(=O)c2ccnn2C)C2CCCCC2)cc1)C(=O)N1CCN[C@@H](Cc2ccccc2)C1]

Following General Procedure B, 147 (0.097 g, 0.130 mmol, 1.0 eq.) was reacted with 4N HCl in Dioxane (0.49 mL) in DCM (2 mL) to afford, after 105 (32.3 mg) as a white solid. UPLC-MS (basic 2 min): rt=1.03 min; m/z=642.5 for [M+H]⁺.

Example 44: Methyl (2R)-3-(4-{[(tert-butoxy)carbonyl]amino}phenyl)-2-propanamidopropanoate) (11)

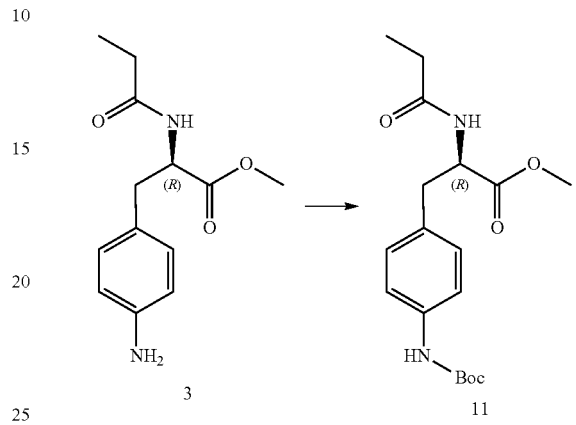

To a solution of ethyl (2R)-3-(4-aminophenyl)-2-propanamidopropanoate 3 (19.1 g, 76.3 mmol, 1.0 eq.) in DCM (150 mL) was added di-tert-butyl dicarbonate (18.3 g, 83.9 mmol, 1.1 eq.) and DIPEA (39.9 mL, 229 mmol, 3.0 eq.) at 0° C. The resulting mixture was stirred at 0° C. for 1 h and then stirred at RT for 72 h. The reaction mixture was diluted with aq. sat. NaHCO₃ solution (250 mL) and the organic layer separated and washed with brine (250 mL) before drying over sodium sulfate and concentrating to dryness. The residue was purified by flash column chromatography (Silica, 0-100% EtOAc, isohexane) to afford 11 as a white solid (15.5 g, 58%). ¹H NMR (400 MHz, DMSO-d6) δ 9.25 (s, 1H), 8.18 (d, J=7.8 Hz, 1H), 7.35 (d, J=8.2 Hz, 2H), 7.12-7.04 (m, 2H), 4.40 (ddd, J=9.2, 7.8, 5.6 Hz, 1H), 3.59 (s, 3H), 3.18 (d, J=5.3 Hz, 1H), 2.93 (dd, J=13.8, 5.6 Hz, 1H), 2.80 (dd, J=13.8, 9.2 Hz, 1H), 2.07 (qd, J=7.6, 1.1 Hz, 2H), 1.47 (s, 9H), 0.92 (t, J=7.6 Hz, 3H). UPLC-MS (basic 2 min): Rt=1.04 min; m/z=351.1 for [M+H]⁺.

Example 45: (2R)-3-(4-{[(tert-butoxy)carbonyl]amino}phenyl)-2-propanamidopropanoate) (12)

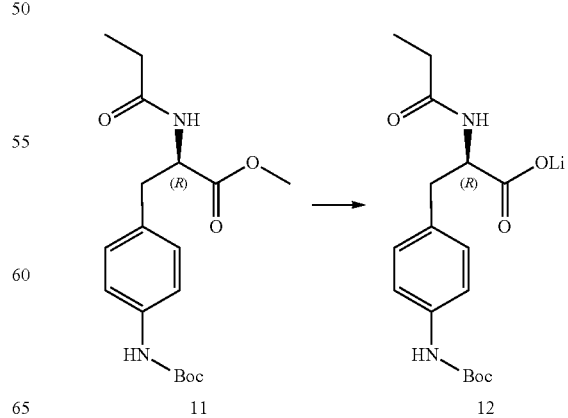

To a solution of 11 (15.5 g, 44.2 mmol, 1.0 eq.) in THF (150 mL) and MeOH (50 mL) was added 1M LiOH solution (53.1 mL, 53.1 mmol, 1.2 eq.). The resulting mixture was stirred at room temperature for 1 h and then concentrated to dryness to afford 12 as a white solid (15.1 g, 100%). $^1$H NMR (400 MHz, DMSO-d6) δ 9.12 (s, 1H), 7.22 (d, J=8.1 Hz, 2H), 6.95 (dd, J=7.3, 4.3 Hz, 3H), 3.87 (q, J=5.4 Hz, 1H), 2.97 (dd, J=13.1, 5.2 Hz, 1H), 2.83 (dd, J=13.1, 5.2 Hz, 1H), 2.01 (q, J=7.6 Hz, 2H), 1.46 (s, 9H), 0.94 (t, J=7.6 Hz, 3H). UPLC-MS (basic 2 min): Rt=0.77 min; m/z=337.0 for [M+H]$^+$.

Example 46: Tert-butyl N-{4-[(2R)-3-(4-benzylpiperazin-1-yl)-3-oxo-2-propanamidopropyl]phenyl}carbamate) (13)

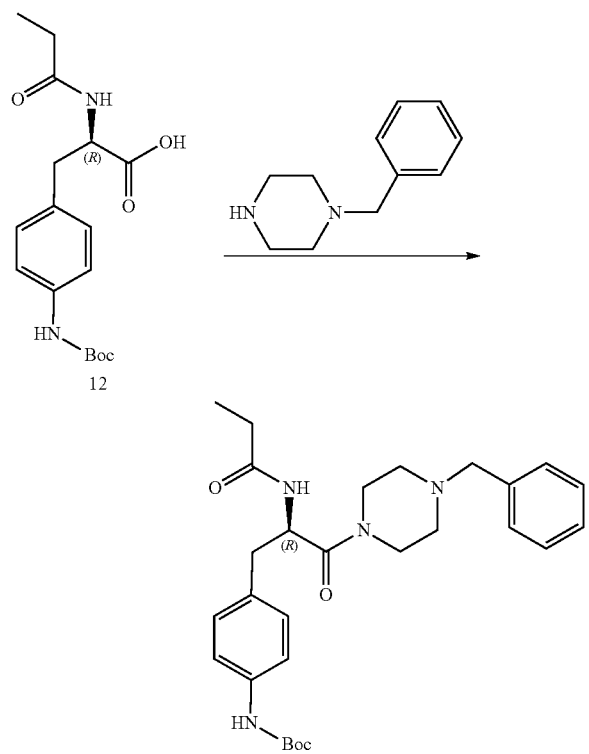

To a solution of 12 (5.1 g, 14.9 mmol, 1.0 eq.) in DMF (50 mL) was added HATU (8.5 g, 22.3 mmol, 1.5 eq.) and DIPEA (7.8 mL, 44.7 mmol, 3.0 eq). The resulting mixture was stirred at RT for 10 min. and then N-benzyl piperazine (3.1 mL, 17.9 mmol, 1.2 eq,) was added. The resulting mixture was stirred at RT under a N$_2$ atmosphere for 1 h. The mixture was diluted with aq. sat. NaHCO$_3$ solution (500 mL) and then extracted with EtOAc (2×500 mL). The organic layer was washed with ice cold brine (2×1 L), dried over Na$_2$SO$_4$ then concentrated to afford 13 as a brown solid (6.7 g, 91%). $^1$H NMR (400 MHz, DMSO-d6) δ 9.27 (s, 1H), 8.14 (d, J=8.3 Hz, 1H), 7.38-7.21 (m, 8H), 7.10-7.03 (m, 2H), 4.84 (q, J=7.6 Hz, 1H), 2.93-2.78 (m, 2H), 2.76-2.64 (m, 2H), 2.35-2.09 (m, 4H), 2.05 (q, J=7.6 Hz, 2H), 1.81 (s, 1H), 1.47 (s, 9H), 0.91 (t, J=7.6 Hz, 3H). UPLC-MS (basic 2 min): Rt=1.14 min; m/z=495.1 for [M+H]$^+$.

Example 47: N-[(2R)-3-(4-aminophenyl)-1-(4-benzylpiperazin-1-yl)-1-oxopropan-2-yl]propanamide (14)

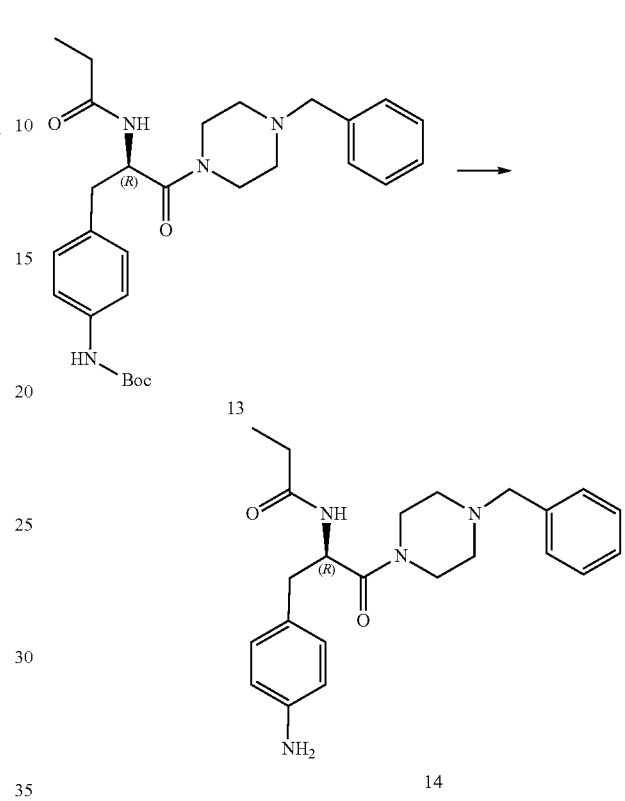

To a solution of 13 (3.70 g, 7.48 mmol, 1.0 eq.) in DCM (40 mL) was added TFA (7.5 mL) and the resulting mixture was stirred at RT for 24 h. The reaction mixture was concentrated to dryness and the residue was stirred in aq. sat. NaHCO$_3$ solution (10 mL) to obtain a precipitate which was filtered and washed with Et$_2$O to afford 14 as a flocculent yellow solid (2.30 g, 78%). The product was used in the next step without further purification. UPLC-MS (basic 2 min): Rt=0.91 min; m/z=395.1 for [M+H]$^+$.

Example 48: General Procedure C for the Synthesis of 16a-e

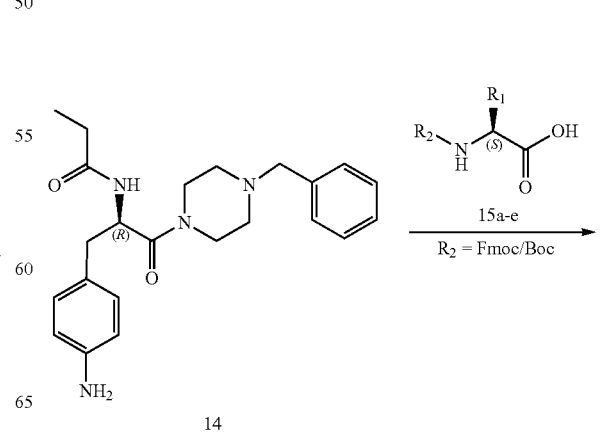

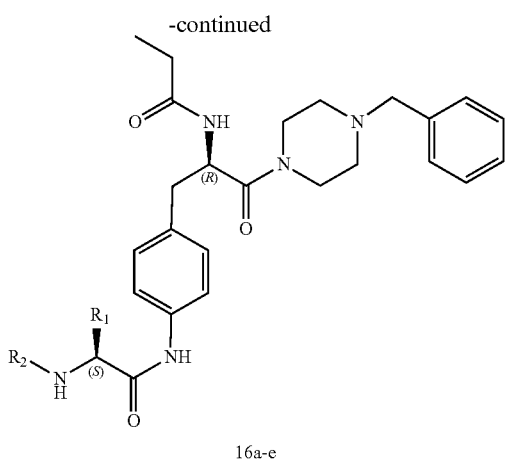

16a-e

To a solution of the required amino acid 15a-e (1.0-1.2 eq.) in DMF (0.05M) was added HATU (1.5 eq.) and DIPEA (3.0 eq.) and the resulting mixture was stirred at RT for 10 minutes. A solution of N-[(2R)-3-(4-aminophenyl)-1-(4-benzylpiperazin-1-yl)-1-oxopropan-2-yl]propanamide 14 (1.0 eq.) was added and the reaction mixture was stirred at RT for 1 h. The reaction mixture was concentrated to dryness to afford a residue which was purified via flash column chromatography to afford 16a-e.

Example 49: Tert-butyl N—[(S)-({4-[(2R)-3-(4-benzylpiperazin-1-yl)-3-oxo-2-propanamidopropyl]phenyl}carbamoyl)(cyclohexyl)methyl]carbamate (16a)

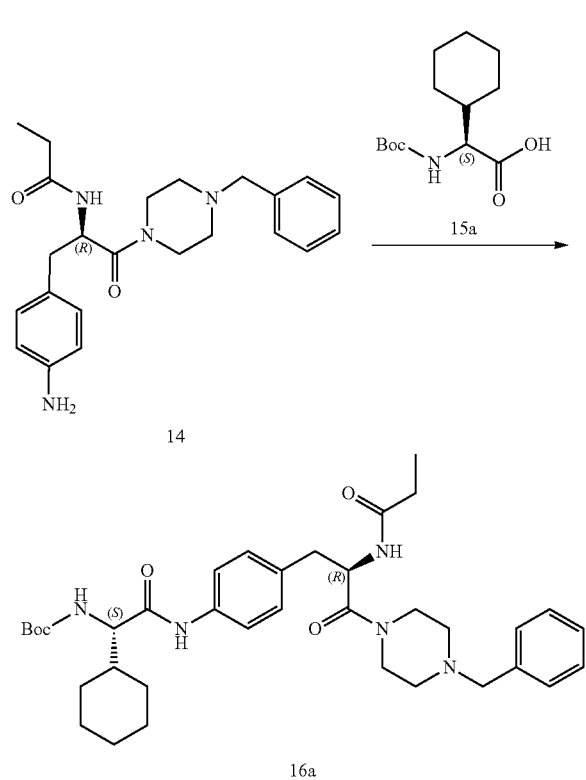

Following General Procedure $C_{1\text{-}14}$ (0.250 g, 0.634 mmol, 1.0 eq.) was reacted with (2S)-2-{[(tert-butoxy)carbonyl]amino}-2-cyclohexylacetic acid 15a (0.179 g, 0.697 mmol, 1.1 eq.), HATU (0.361 g, 0.951 mmol, 1.5 eq.) and DIPEA (0.33 mL, 1.90 mmol, 3.0 eq.) in DMF (5 mL) to afford, after flash column chromatography, 16a (0.550 g, 87%) as a white solid. UPLC-MS (basic 2 min): rt=1.21 min; m/z=634.5 for [M+H]$^+$.

Example 50: (9H-fluoren-9-yl)methyl N—[(S)-({4-[(2R)-3-(4-benzylpiperazin-1-yl)-3-oxo-2-propanamidopropyl]phenyl}carbamoyl)(4,4-difluorocyclohexyl)methyl]carbamate (16b)

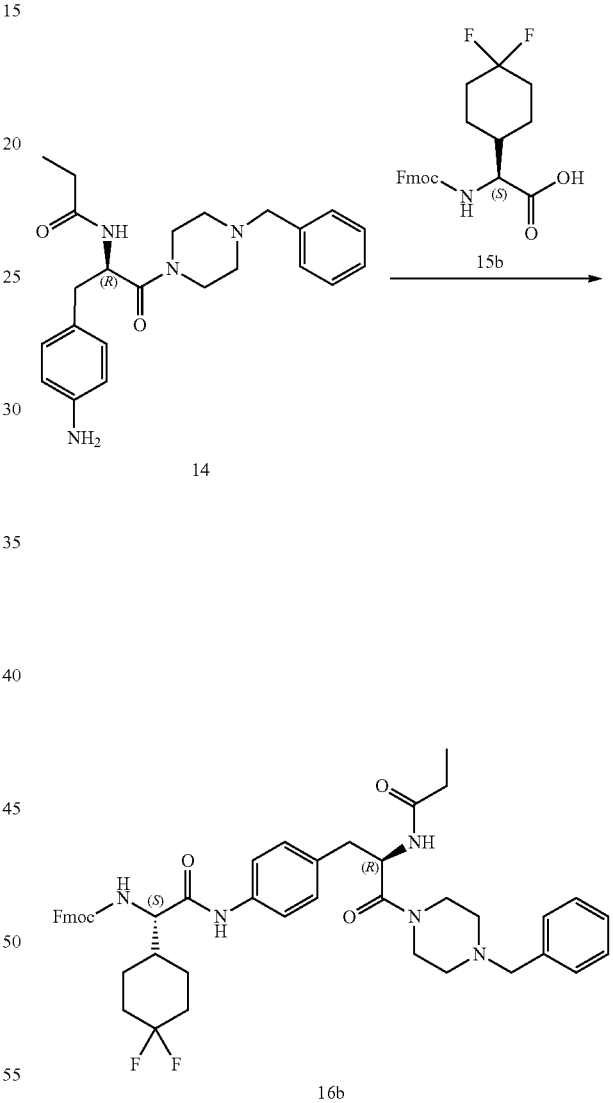

Following General Procedure $C_{1\text{-}14}$ (0.150 g, 0.380 mmol, 1.0 eq.) was reacted with (2S)-2-({[(4b,8a,9,9a-tetrahydro-4aH-fluoren-9-yl)methoxy]carbonyl}amino)-2-(4,4-difluorocyclohexyl)acetic acid 15b (0.160 g, 0.380 mmol, 1.0 eq.), HATU (0.217 g, 0.570 mmol, 1.5 eq.) and DIPEA (0.20 mL, 1.14 mmol, 3.0 eq.) in DMF (2.4 mL) to afford, after flash column chromatography, 16a (0.330 g, 99%) as a white solid. UPLC-MS (basic 2 min): rt=1.26 min; m/z=792.2 for [M+H]$^+$.

Example 51: Tert-butyl N—[(S)-({4-[(2R)-3-(4-benzylpiperazin-1-yl)-3-oxo-2-propanamidopropyl]phenyl}carbamoyl)(cycloheptyl)methyl]carbamate (16c)

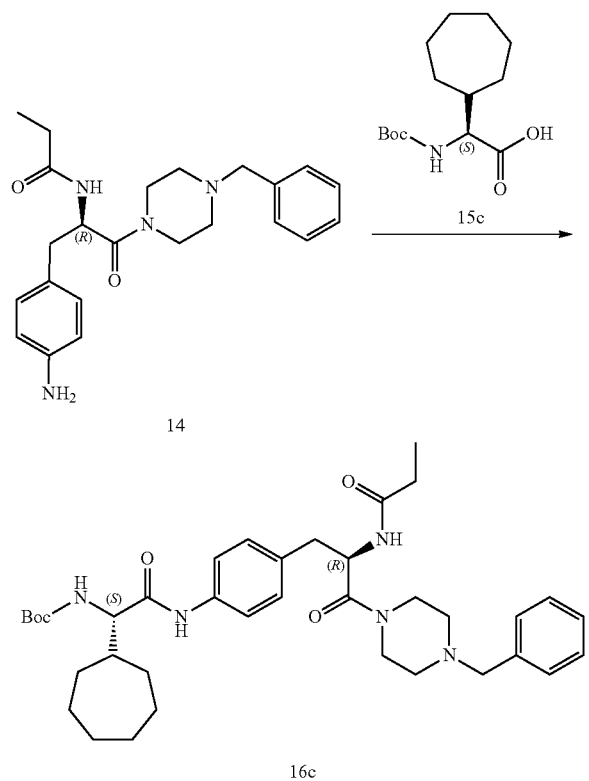

Following General Procedure $C_{1-14}$ (0.375 g, 0.950 mmol, 1.0 eq.) was reacted with (2S)-2-{[(tert-butoxy)carbonyl]amino}-2-cycloheptylacetic acid 15c (0.258 g, 0.950 mmol, 1.0 eq.), HATU (0.542 g, 1.42 mmol, 1.5 eq.) and DIPEA (0.50 mL, 2.85 mmol, 3.0 eq.) in DMF (5.2 mL) to afford, after flash column chromatography, 16c (0.570 g, 89%) as an orange solid. UPLC-MS (basic 2 min): rt=1.24 min; m/z=648.3 for [M+H]⁺.

Example 52: Tert-butyl N—[(S)-({4-[(2R)-3-(4-benzylpiperazin-1-yl)-3-oxo-2-propanamidopropyl]phenyl}carbamoyl)(2,3-dihydro-1H-inden-2-yl)methyl]carbamate (16d)

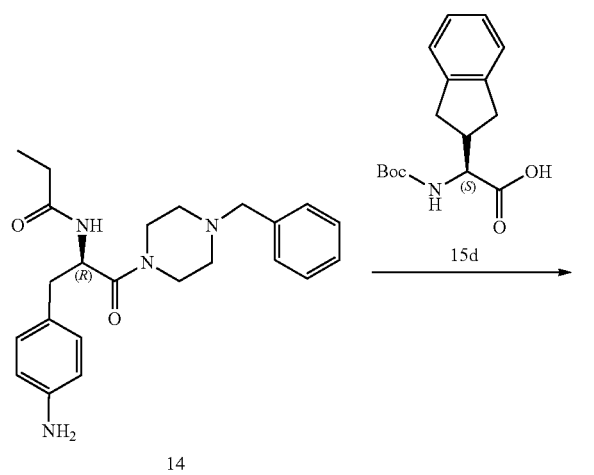

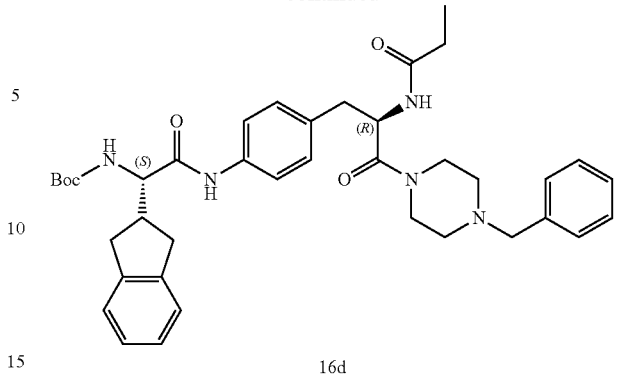

Following General Procedure $C_{1-14}$ (0.250 g, 0.634 mmol, 1.0 eq.) was reacted with (2S)-2-{[(tert-butoxy)carbonyl]amino}-2-(2,3-dihydro-1H-inden-2-yl)acetic acid 15d (0.185 g, 0.634 mmol, 1.0 eq.), HATU (0.361 g, 0.951 mmol, 1.5 eq.) and DIPEA (0.33 mL, 1.90 mmol, 3.0 eq.) in DMF (3.5 mL) to afford, after flash column chromatography, 16d (0.375 g, 89%) as an orange solid. UPLC-MS (basic 2 min): rt=1.17 min; m/z=668.3 for [M+H]⁺.

Example 53: (9H-fluoren-9-yl)methyl N—[(S)-({4-[(2R)-3-(4-benzylpiperazin-1-yl)-3-oxo-2-propanamidopropyl]phenyl}carbamoyl)(cyclopentyl)methyl]carbamate (16e)

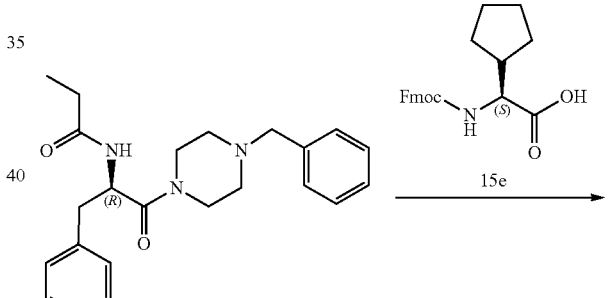

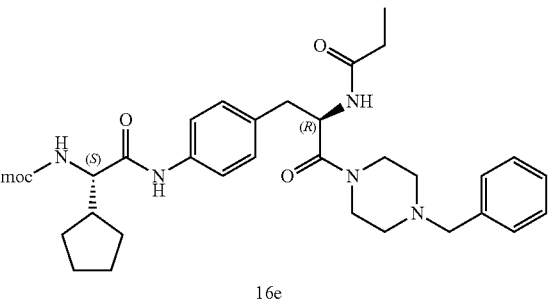

Following General Procedure $C_{1-14}$ (0.250 g, 0.634 mmol, 1.0 eq.) was reacted with (2S)-2-({[(4b, 8a,9,9a-tetrahydro-4aH-fluoren-9-yl)methoxy]carbonyl}amino)-2-cyclopentylacetic acid 15e (0.234 g, 0.634 mmol, 1.0 eq.), HATU (0.361 g, 0.951 mmol, 1.5 eq.) and DIPEA (0.33 mL, 1.90 mmol, 3.0 eq.) in DMF (3.5 mL) to afford, after flash column chromatography, 16e (0.335 g, 71%) as an orange solid. UPLC-MS (basic 2 min): rt=1.24 min; m/z=742.3 for [M+H]⁺.

Example 54: N-[(2R)-3-{4-[(2S)-2-amino-2-cyclohexylacetamido]phenyl}-1-(4-benzylpiperazin-1-yl)-1-oxopropan-2-yl]propanamide (17a)

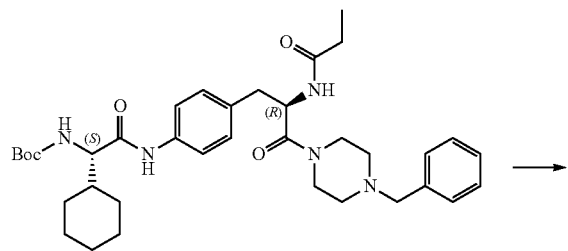

16a

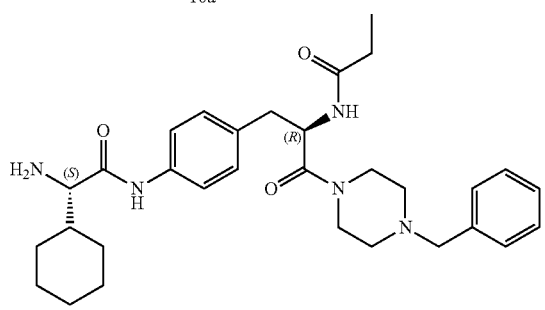

17a

To a solution of tert-butyl N—[(S)-({4-[(2R)-3-(4-benzylpiperazin-1-yl)-3-oxo-2-propanamidopropyl]phenyl}carbamoyl)(cyclohexyl)methyl]carbamate 16a (0.349 g, 0.550 mmol, 1.0 eq.) in DCM (1.8 mL) was added TFA (1.8 mL) and the resulting mixture was stirred at RT for 0.5 h. The reaction mixture was concentrated to dryness and the residue was stirred in aq. sat. K₂CO₃ solution (20 mL) to obtain a precipitate which was filtered to afford 17a as a white solid (0.271 g, 92%). UPLC-MS (basic 2 min): rt=1.10 min; m/z=534.4 for [M+H]⁺.

Example 55: N-[(2R)-3-{4-[(2S)-2-amino-2-(4,4-difluorocyclohexyl)acetamido]phenyl}-1-(4-benzylpiperazin-1-yl)-1-oxopropan-2-yl]propenamide (17b)

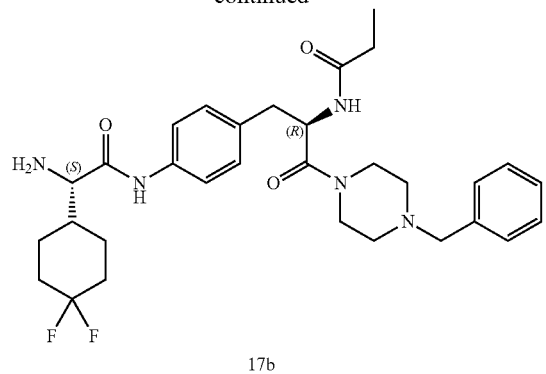

17b a solution of (9H-fluoren-9-yl)methyl N—[(S)-({4-[(2R)-3-(4-benzylpiperazin-1-yl)-3-oxo-2-propanamidopropyl]phenyl}carbamoyl)(4,4-difluorocyclohexyl)methyl]carbamate 16b (0.300 g, 0.379 mmol, 1.0 eq.) in DMF (4.2 mL) was added piperidine (0.75 mL, 7.58 mmol, 20.0 eq.) and the resulting mixture was stirred at RT for 3 h. The reaction mixture was concentrated to dryness and the residue dissolved in DCM (5.0 mL). Boc anhydride (0.291 g, 1.33 mmol, 3.5 eq.) and DIPEA (0.13 mL, 0.758 mmol, 2.0 eq.) were added and the resulting mixture was stirred at RT for 16 h. The reaction mixture was concentrated to dryness and then purified by flash column chromatography (Silica, 0-10% MeOH, DCM) to obtain the Boc-protected product. This was dissolved in DCM (12.5 mL) and then TFA (2.9 mL) was added. The resulting mixture was stirred at RT for 2 h and then concentrated to dryness to afford a residue which was purified by reverse phase column chromatography on a 120 g C18 cartridge eluting with a 5-95% H₂O:MeCN eluent (0.1% ammonia) to afford 17b as a white solid (0.050 g, 24%). UPLC-MS (basic 2 min): rt=1.15 min; m/z=570.2 for [M+H]⁺.

Example 56: N-[(2R)-3-{4-[(2S)-2-amino-2-cycloheptylacetamido]phenyl}-1-(4-benzylpiperazin-1-yl)-1-oxopropan-2-yl]propanamide; trifluoroacetic acid (17c)

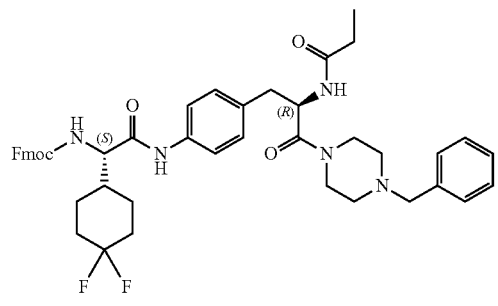

16b

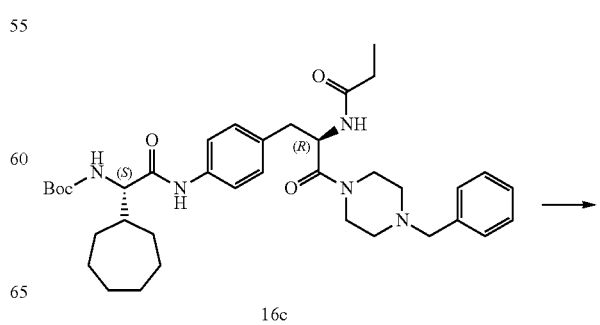

16c

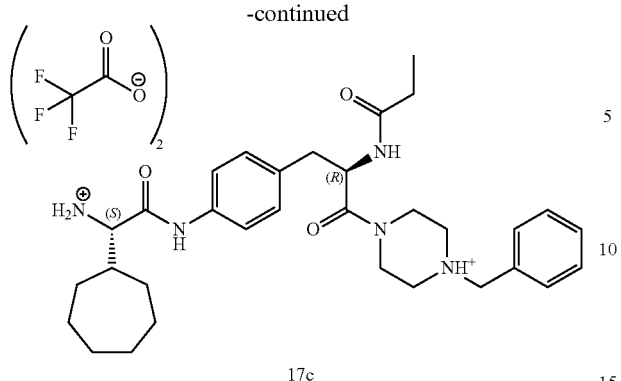

17c

To a solution of tert-butyl N—[(S)-({4-[(2R)-3-(4-benzylpiperazin-1-yl)-3-oxo-2-propanamidopropyl]phenyl}carbamoyl)(cycloheptyl)methyl]carbamate 16c (0.570 g, 0.880 mmol, 1.0 eq.) in DCM (30 mL) was added TFA (6 mL) and the resulting mixture was stirred at RT for 2 h. The reaction mixture was concentrated to dryness to afford 17c as a gummy orange solid (0.770 g, 100%). UPLC-MS (basic 2 min): rt=1.10 min; m/z=548.2 for [M+H]$^+$.

Example 57: N-[(2R)-3-{4-[(2S)-2-amino-2-(2,3-dihydro-1H-inden-2-yl)acetamido]phenyl}-1-(4-benzylpiperazin-1-yl)-1-oxopropan-2-yl]propanamide; trifluoroacetic acid (17d)

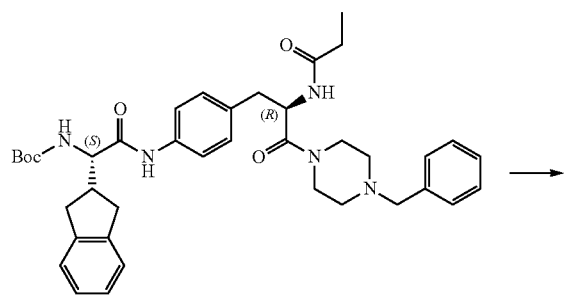

16d

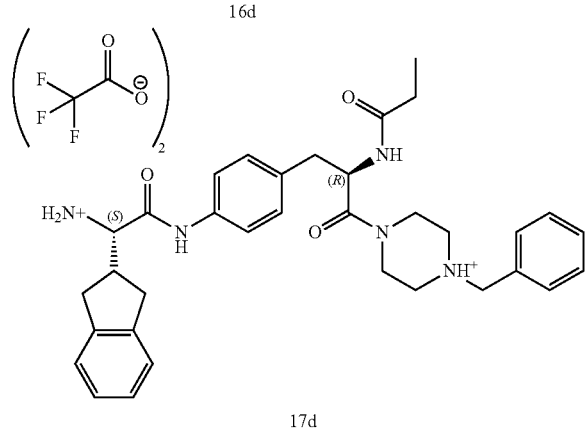

17d

To a solution of tert-butyl N—[(S)-({4-[(2R)-3-(4-benzylpiperazin-1-yl)-3-oxo-2-propanamidopropyl]phenyl}carbamoyl)(2,3-dihydro-1H-inden-2-yl)methyl]carbamate 16d (0.185 g, 0.277 mmol, 1.0 eq.) in DCM (10 mL) was added TFA (2 mL) and the resulting mixture was stirred at RT for 2 h. The reaction mixture was concentrated to dryness to afford 17d as a gummy orange solid (0.189 g, 100%). UPLC-MS (basic 2 min): rt=1.10 min; m/z=568.2 for [M+H]$^+$.

Example 58: N-[(2R)-3-{4-[(2S)-2-amino-2-cyclopentylacetamido]phenyl}-1-(4-benzylpiperazin-1-yl)-1-oxopropan-2-yl]propanamide; trifluoroacetic acid (17e)

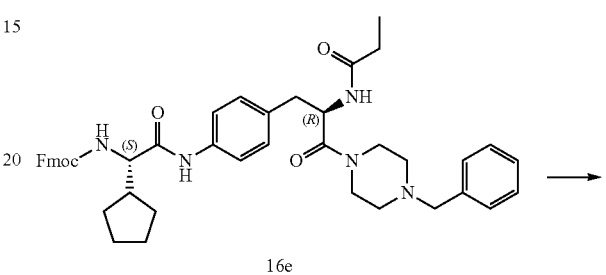

16e

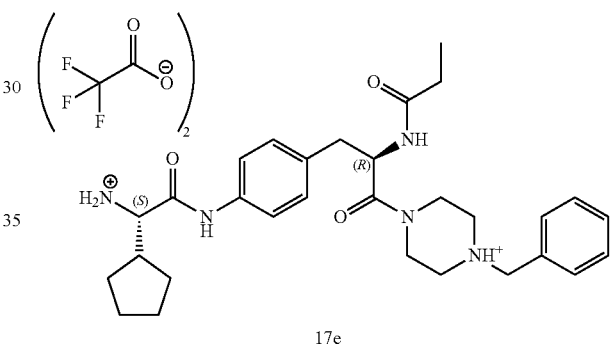

17e

To a solution of (9H-fluoren-9-yl)methyl N—[(S)-({4-[(2R)-3-(4-benzylpiperazin-1-yl)-3-oxo-2-propanamidopropyl]phenyl}carbamoyl)(cyclopentyl)methyl]carbamate 16e (0.320 g, 0.431 mmol, 1.0 eq.) in DMF (4.8 mL) was added piperidine (0.85 mL, 8.63 mmol, 20.0 eq.) and the resulting mixture was stirred at RT for 3 h. The reaction mixture was concentrated to dryness and the residue dissolved in DCM (5.0 mL). Boc anhydride (0.304 g, 1.39 mmol, 3.5 eq.) and DIPEA (0.15 mL, 0.863 mmol, 2.0 eq.) were added and the resulting mixture was stirred at RT for 16 h. The reaction mixture was concentrated to dryness and then purified by flash column chromatography (Silica, 0-10% MeOH, DCM) to obtain the Boc-protected product. This was dissolved in DCM (6.3 mL) and then TFA (2.9 mL) was added. The resulting mixture was stirred at RT for 1 h and then concentrated to dryness to afford 17e as a white solid (0.197 g, 99%). UPLC-MS (basic 2 min): rt=1.15 min; m/z=520.2 for [M+H]$^+$.

Example 59: General Procedure D for the Synthesis of 100, 126, 135, 139, 149, 152-156, 159 and 160

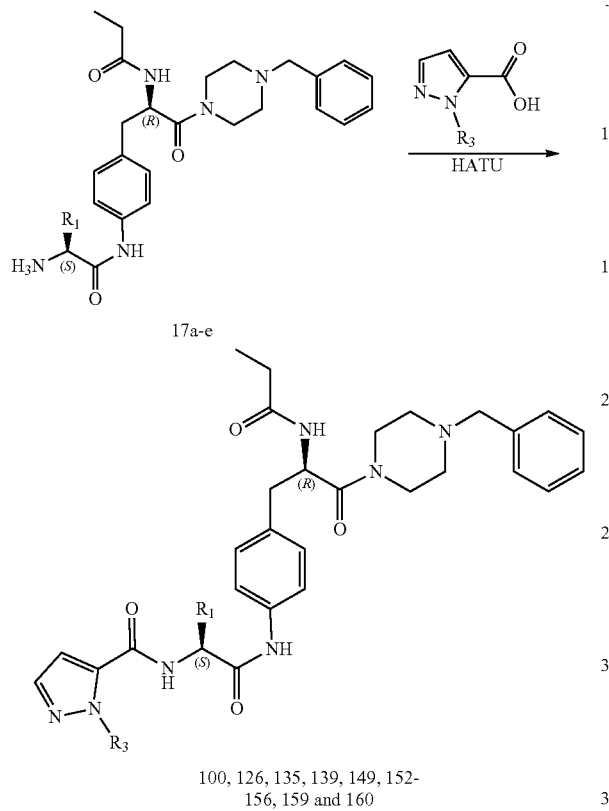

17a-e 100, 126, 135, 139, 149, 152-156, 159 and 160

To a solution of 5-substituted H-pyrazole-5-carboxylic acids (1.2 eq.) in DMF was added HATU (1.5 eq.) and DIPEA (4.0 eq) and then stirred at RT for 10 min. A solution of 17a-e (1.0 eq,) in DMF was added and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 100, 126, 135, 139, 149, 152-156, 159 and 160.

Example 60: N-[(2R)-1-(4-benzylpiperazin-1-yl)-3-{4-[(2S)-2-cyclohexyl-2-[(1-methyl-1H-pyrazol-5-yl)formamido]acetamido]phenyl}-1-oxopropan-2-yl]propanamide (100)

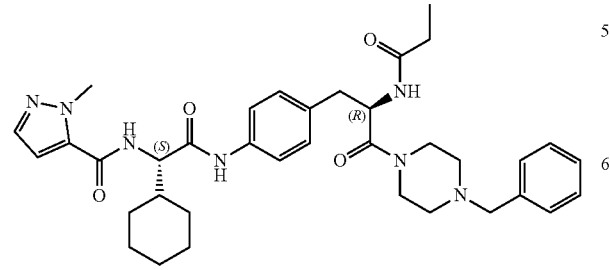

Following General Procedure D, 17a (0.103 g, 0.173 mmol, 1.0 eq.) was reacted with 1-methyl-1H-pyrazole-5-carboxylic acid (0.026 g, 0.208 mmol, 1.2 eq.), HATU (0.099 g, 0.260 mmol, 1.5 eq.) and DIPEA (0.09 mL, 0.520 mmol, 3.0 eq.) in DMF (3 mL) to afford, after reverse phase column chromatography, 100 (52.0 mg) as a white solid. ¹H NMR (400 MHz, DMSO-d6) δ 10.20 (d, J=2.7 Hz, 1H), 8.51 (d, J=8.3 Hz, 1H), 8.20 (d, J=8.2 Hz, 1H), 7.55 (dd, J=8.6, 2.0 Hz, 2H), 7.46 (t, J=1.7 Hz, 1H), 7.32-7.17 (m, 5H), 7.16-7.10 (m, 2H), 7.08 (dd, J=2.1, 1.2 Hz, 1H), 4.87 (q, J=7.8 Hz, 1H), 4.41 (t, J=8.5 Hz, 1H), 3.99 (d, J=1.3 Hz, 3H), 3.51 (s, 1H), 3.37 (s, 2H), 3.35-3.25 (m, 4H), 2.85 (dd, J=13.3, 7.6 Hz, 1H), 2.72 (dd, J=13.2, 7.2 Hz, 1H), 2.22 (d, J=16.1 Hz, 2H), 2.05 (q, J=7.6 Hz, 3H), 1.89-1.53 (m, 7H), 1.14 (s, 4H), 1.01 (t, J=12.0 Hz, 1H), 0.91 (t, J=7.6 Hz, 3H). UPLC-MS (basic 2 min): rt=1.08 min; m/z=642.4 for [M+H]⁺.

Example 61: N-[(2R)-1-(4-benzylpiperazin-1-yl)-3-{4-[(2S)-2-cycloheptyl-2-[(1-methyl-1H-pyrazol-5-yl)formamido]acetamido]phenyl}-1-oxopropan-2-yl]propanamide (126)

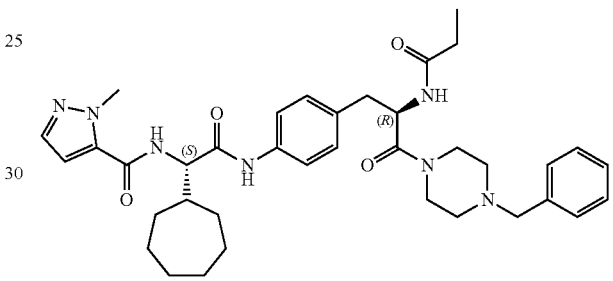

Following General Procedure D, 17c (0.064 g, 0.097 mmol, 1.0 eq.) was reacted with 1-methyl-1H-pyrazole-5-carboxylic acid (0.015 g, 0.116 mmol, 1.2 eq.), HATU (0.055 g, 0.145 mmol, 1.5 eq.) and DIPEA (0.067 mL, 0.387 mmol, 4.0 eq.) in DMF (0.5 mL) to afford, after reverse phase column chromatography, 126 (21.0 mg) as a white solid. UPLC-MS (basic 2 min): rt=1.16 min; m/z=656.5 for [M+H]⁺.

Example 62: N-[(2R)-1-(4-benzylpiperazin-1-yl)-3-{4-[(2S)-2-(2,3-dihydro-1H-inden-2-yl)-2-[(1-methyl-1H-pyrazol-5-yl)formamido]acetamido]phenyl}-1-oxopropan-2-yl]propanamide (135)

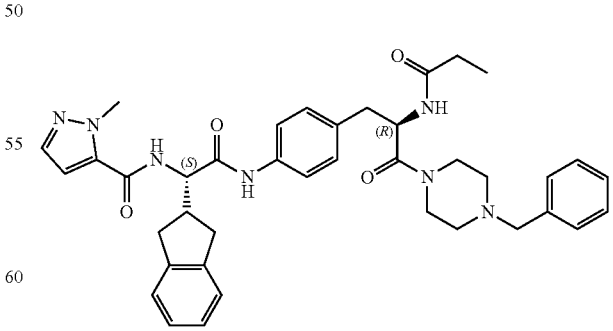

Following General Procedure D, 17d (0.062 g, 0.091 mmol, 1.0 eq.) was reacted with 1-methyl-1H-pyrazole-5-carboxylic acid (0.014 g, 0.109 mmol, 1.2 eq.), HATU (0.052 g, 0.136 mmol, 1.5 eq.) and DIPEA (0.063 mL, 0.364 mmol, 4.0 eq.) in DMF (0.5 mL) to afford, after reverse phase column chromatography, 135 (10.0 mg) as a white solid. UPLC-MS (basic 2 min): rt=1.09 min; m/z=676.4 for [M+H]⁺.

Example 63: N-[(2R)-1-(4-benzylpiperazin-1-yl)-3-{4-[(2S)-2-cyclopentyl-2-[(1-methyl-1H-pyrazol-5-yl)formamido]acetamido]phenyl}-1-oxopropan-2-yl]propanamide (139)

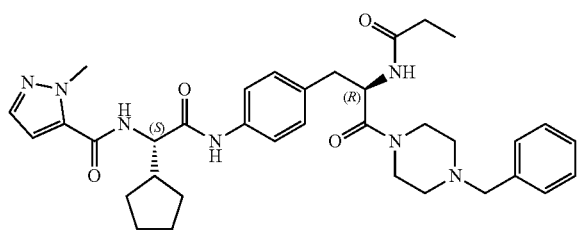

Following General Procedure D, 17e (0.040 g, 0.063 mmol, 1.0 eq.) was reacted with 1-methyl-1H-pyrazole-5-carboxylic acid (0.0096 g, 0.076 mmol, 1.2 eq.), HATU (0.036 g, 0.095 mmol, 1.5 eq.) and DIPEA (0.044 mL, 0.252 mmol, 4.0 eq.) in DMF (0.3 mL) to afford, after reverse phase column chromatography, 139 (26.0 mg) as a white solid. UPLC-MS (basic 2 min): rt=1.08 min; m/z=628.4 for [M+H]⁺.

Example 64: N—((S)-2-((4-((R)-3-(4-benzylpiperazin-1-yl)-3-oxo-2-propionamidopropyl)phenyl)amino)-1-cycloheptyl-2-oxoethyl)-1-isopropyl-1H-pyrazole-5-carboxamide (154)

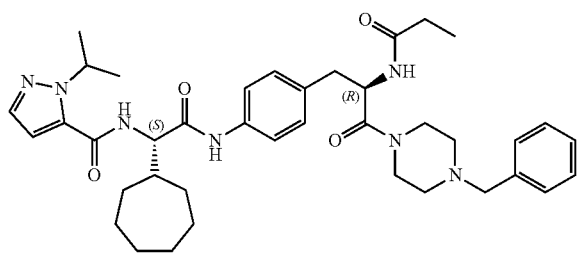

Following General Procedure D, 17c (0.064 g, 0.097 mmol, 1.0 eq.) was reacted with 2-isopropyl-2H-pyrazole-5-carboxylic acid (0.018 g, 0.116 mmol, 1.2 eq.), HATU (0.055 g, 0.145 mmol, 1.5 eq.) and DIPEA (0.067 mL, 0.387 mmol, 4.0 eq.) in DMF (0.5 mL) to afford, after reverse phase column chromatography, 154 (24.0 mg) as a white solid. UPLC-MS (basic 2 min): rt=1.23 min; m/z=684.5 for [M+H]⁺

Example 65: N—((S)-2-((4-((R)-3-(4-benzylpiperazin-1-yl)-3-oxo-2-propionamidopropyl)phenyl)amino)-1-cycloheptyl-2-oxoethyl)-1-ethyl-1H-pyrazole-5-carboxamide (149)

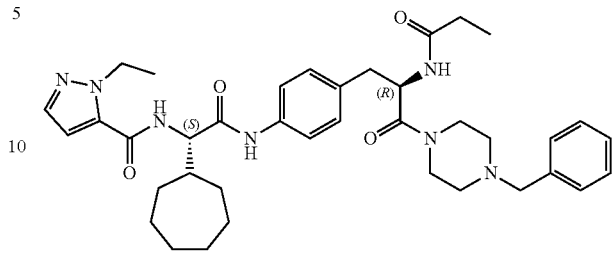

Following General Procedure D, 17c (0.064 g, 0.097 mmol, 1.0 eq.) was reacted with 2-ethyl-2H-pyrazole-5-carboxylic acid (0.016 g, 0.116 mmol, 1.2 eq.), HATU (0.055 g, 0.145 mmol, 1.5 eq.) and DIPEA (0.067 mL, 0.387 mmol, 4.0 eq.) in DMF (0.5 mL) to afford, after reverse phase column chromatography, 149 (24.0 mg) as a white solid. UPLC-MS (basic 2 min): rt=1.16 min; m/z=670.5 for [M+H]⁺.

Example 66: N—((S)-2-((4-((R)-3-(4-benzylpiperazin-1-yl)-3-oxo-2-propionamidopropyl)phenyl)amino)-1-(4,4-difluorocyclohexyl)-2-oxoethyl)-1-ethyl-1H-pyrazole-5-carboxamide (152)

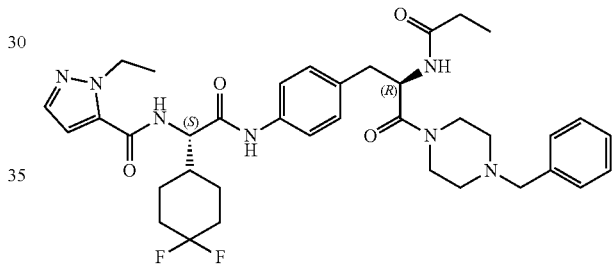

Following General Procedure D, 17b (0.020 g, 0.035 mmol, 1.0 eq.) was reacted with 2-ethyl-2H-pyrazole-5-carboxylic acid (0.006 g, 0.042 mmol, 1.2 eq.), HATU (0.020 g, 0.053 mmol, 1.5 eq.) and DIPEA (0.024 mL, 0.140 mmol, 4.0 eq.) in DMF (0.2 mL) to afford, after reverse phase column chromatography, 152 (8.0 mg) as a white solid. UPLC-MS (basic 2 min): rt=1.08 min; m/z=692.4 for [M+H]⁺.

Example 67: N—((S)-2-((4-((R)-3-(4-benzylpiperazin-1-yl)-3-oxo-2-propionamidopropyl)phenyl)amino)-1-(4,4-difluorocyclohexyl)-2-oxoethyl)-1-isopropyl-1H-pyrazole-5-carboxamide (155)

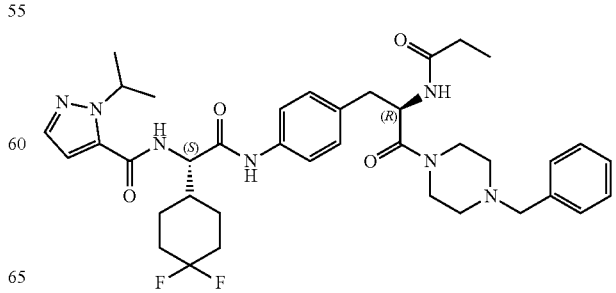

Following General Procedure D, 17b (0.025 g, 0.044 mmol, 1.0 eq.) was reacted with 2-isopropyl-2H-pyra-zole-5-carboxylic acid (0.008 g, 0.053 mmol, 1.2 eq.), HATU (0.025 g, 0.066 mmol, 1.5 eq.) and DIPEA (0.031 mL, 0.176 mmol, 4.0 eq.) in DMF (0.25 mL) to afford, after reverse phase column chromatography, 155 (29.0 mg) as a white solid. UPLC-MS (basic 2 min): rt=1.11 min; m/z=706.5 for [M+H]+.

Example 68: N—((S)-2-((4-((R)-3-(4-benzylpiper-azin-1-yl)-3-oxo-2-propionamidopropyl)phenyl)amino)-1-(2,3-dihydro-1H-inden-2-yl)-2-oxoethyl)-1-ethyl-1H-pyrazole-5-carboxamide (153)

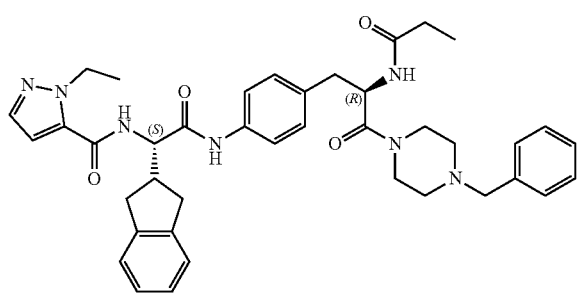

Following General Procedure D, 17d (0.062 g, 0.091 mmol, 1.0 eq.) was reacted with 2-ethyl-2H-pyrazole-5-carboxylic acid (0.015 g, 0.109 mmol, 1.2 eq.), HATU (0.052 g, 0.136 mmol, 1.5 eq.) and DIPEA (0.063 mL, 0.364 mmol, 4.0 eq.) in DMF (0.5 mL) to afford, after reverse phase column chromatography, 153 (11.0 mg) as a white solid. UPLC-MS (basic 2 min): rt=1.13 min; m/z=690.4 for [M+H]+.

Example 69: N—((S)-2-((4-((R)-3-(4-benzylpiper-azin-1-yl)-3-oxo-2-propionamidopropyl)phenyl)amino)-1-(2,3-dihydro-1H-inden-2-yl)-2-oxoethyl)-1-isopropyl-1H-pyrazole-5-carboxamide (156)

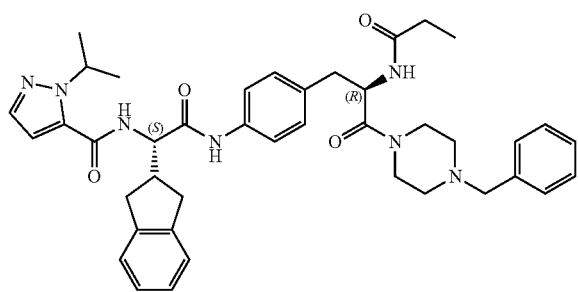

Following General Procedure D, 17d (0.062 g, 0.091 mmol, 1.0 eq.) was reacted with 2-isopropyl-2H-pyrazole-5-carboxylic acid (0.017 g, 0.109 mmol, 1.2 eq.), HATU (0.052 g, 0.136 mmol, 1.5 eq.) and DIPEA (0.063 mL, 0.364 mmol, 4.0 eq.) in DMF (0.5 mL) to afford, after reverse phase column chromatography, 156 (24.0 mg) as a white solid. UPLC-MS (basic 2 min): rt=1.21 min; m/z=704.5 for [M+H]+.

Example 70: N—((S)-2-((4-((R)-3-(4-benzylpiper-azin-1-yl)-3-oxo-2-propionamidopropyl)phenyl)amino)-1-cyclopentyl-2-oxoethyl)-1-ethyl-1H-pyra-zole-5-carboxamide (159)

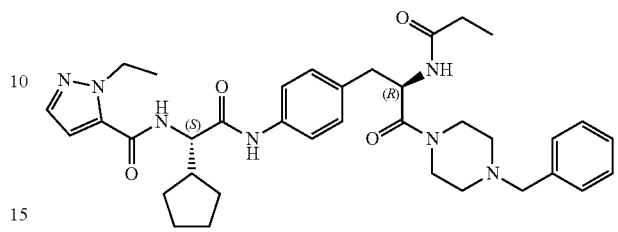

Following General Procedure D, 17e (0.040 g, 0.063 mmol, 1.0 eq.) was reacted with 2-ethyl-2H-pyrazole-5-carboxylic acid (0.011 g, 0.076 mmol, 1.2 eq.), HATU (0.036 g, 0.095 mmol, 1.5 eq.) and DIPEA (0.044 mL, 0.252 mmol, 4.0 eq.) in DMF (0.3 mL) to afford, after reverse phase column chromatography, 159 (12.0 mg) as a white solid. UPLC-MS (basic 2 min): rt=1.08 min; m/z=642.4 for [M+H]+.

Example 71: N—((S)-2-((4-((R)-3-(4-benzylpiper-azin-1-yl)-3-oxo-2-propionamidopropyl)phenyl)amino)-1-cyclopentyl-2-oxoethyl)-1-isopropyl-1H-pyrazole-5-carboxamide (160)

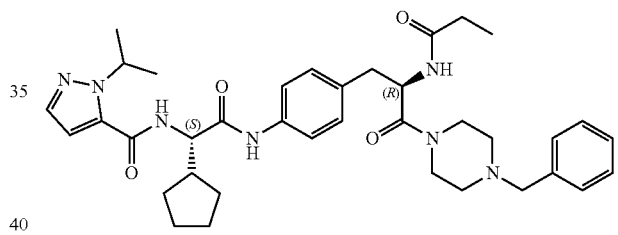

Following General Procedure D, 17e (0.040 g, 0.063 mmol, 1.0 eq.) was reacted with 2-isopropyl-2H-pyrazole-5-carboxylic acid (0.012 g, 0.076 mmol, 1.2 eq.), HATU (0.036 g, 0.095 mmol, 1.5 eq.) and DIPEA (0.044 mL, 0.252 mmol, 4.0 eq.) in DMF (0.3 mL) to afford, after reverse phase column chromatography, 160 (12.0 mg) as a white solid.

Example 72: Methyl (R)-2-((tert-butoxycarbonyl)amino)-3-(4-nitrophenyl)propanoate (20)

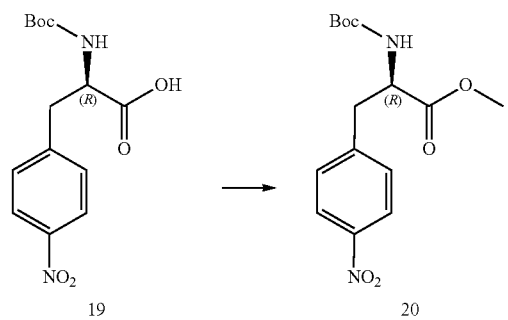

To a solution of (2R)-2-{[(tert-butoxy)carbonyl]amino}-3-(4-nitrophenyl)propanoic acid 19 (1.20 g, 3.87 mmol, 1.0 eq.) in DMF (10 mL) was added NaHCO₃ (0.650 g, 7.73 mmol, 2.0 eq.) and iodomethane (1.20 mL, 19.3 mmol, 5.0 eq) at 0° C. and the resulting mixture was stirred at RT for 18 h. The reaction mixture was poured onto ice-cold water (50 mL) and then extracted with EtOAc (2×20 mL). The combined organic phase was washed with ice-cold brine (2×50 mL) and then dried over sodium sulfate before filtering and concentrating to dryness to afford 20 as an off-white solid (1.095 g, 87%). $^1$H NMR (400 MHz, DMSO-d6) δ 8.17 (d, J=8.7 Hz, 2H), 7.54 (d, J=8.6 Hz, 2H), 7.41 (d, J=8.4 Hz, 1H), 4.28 (ddd, J=10.5, 8.5, 5.0 Hz, 1H), 3.64 (s, 3H), 3.17 (dd, J=13.7, 4.9 Hz, 1H), 2.99 (dd, J=13.6, 10.5 Hz, 1H), 1.31 (s, 9H). UPLC-MS (basic 2 min): Rt=1.11 min; m/z=325.0 for [M+H]$^+$.

Example 73: Methyl (R)-3-(4-aminophenyl)-2-((tert-butoxycarbonyl)amino)propanoate (21)

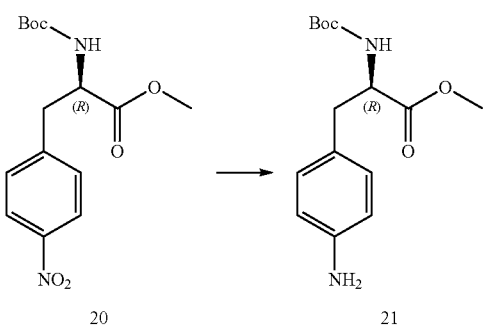

To a degassed solution of 20 (1.09 g, 3.36 mmol, 1.0 eq) in EtOH (34 mL) and THF (34 mL) was added Pd/C (0.072 g, 0.672 mmol, 0.20 eq). The mixture was degassed for another 20 minutes and then evacuated under vacuum before introducing a hydrogen balloon. The resulting mixture was stirred at RT for 4 h. The mixture was filtered through a pad of celite which was washed with THF (50 mL) and EtOH (50 mL). The solution was concentrated to dryness to afford 21 as a yellow oil (0.898 g, 91%). $^1$H NMR (400 MHz, DMSO-d6) δ 7.18 (d, J=7.9 Hz, 1H), 6.90-6.82 (m, 2H), 6.49-6.43 (m, 2H), 4.91 (s, 2H), 4.07-3.97 (m, 1H), 3.59 (s, 3H), 2.78 (dd, J=13.8, 5.4 Hz, 1H), 2.66 (dd, J=13.8, 9.5 Hz, 1H), 1.34 (s, 9H). UPLC-MS (basic 2 min): Rt=0.98 min; m/z=295.0 for [M+H]$^+$.

Example 74: Methyl (R)-3-(4-((S)-2-((((9H-fluoren-9-yl)methoxy)carbonyl)amino)-2-(4,4-difluorocyclohexyl)acetamido)phenyl)-2-((tert-butoxycarbonyl)amino)propanoate (22)

To a solution of 15b (0.100 g, 0.238 mmol, 1.0 eq.) in DMF (1.4 mL) was added HATU (0.136 g, 0.358 mmol, 1.5 eq.) and DIPEA (0.125 mL, 0.715 mmol, 3.0 eq.) and the resulting mixture was stirred at RT for 10 minutes. A solution of methyl (R)-3-(4-aminophenyl)-2-((tert-butoxycarbonyl)amino)propanoate 21 (0.070 g, 0.238 mmol, 1.0 eq.) in DMF (1 mL) was added and the reaction mixture was stirred at RT for 1 h. The reaction mixture was concentrated to dryness to afford a residue which was triturated with isohexane:EtOAc:MeCN (9:1:1, 2×5 mL) to afford 22 as a white solid (0.104 g, 63%). $^1$H NMR (400 MHz, DMSO-d6) δ 10.10 (s, 1H), 8.75 (d, J=4.2 Hz, 1H), 8.53 (d, J=8.4 Hz, 1H), 7.90 (d, J=7.6 Hz, 2H), 7.75 (t, J=7.8 Hz, 3H), 7.52 (d, J=7.7 Hz, 3H), 7.41 (s, 2H), 7.35-7.25 (m, 3H), 7.17 (d, J=8.0 Hz, 2H), 4.34-4.20 (m, 4H), 4.13-4.05 (m, 2H), 3.61 (s, 3H), 2.92 (dd, J=13.9, 8.6 Hz, 2H), 2.79 (s, 1H), 2.03 (s, 1H), 1.83 (s, 2H), 1.72 (s, 1H), 1.59 (s, 1H), 1.32 (s, 9H). UPLC-MS (basic 2 min): Rt=1.32 min; m/z=697.0 for [M+H]$^+$.

Example 75: Methyl (R)-3-(4-((S)-2-amino-2-(4,4-difluorocyclohexyl)acetamido)phenyl)-2-((tert-butoxycarbonyl)amino)propanoate (23)

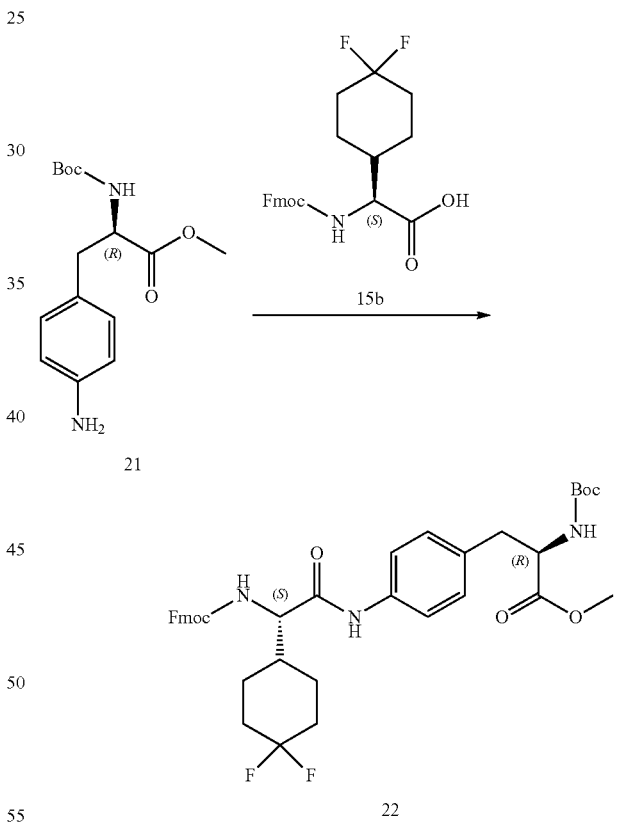

To a solution of methyl (R)-3-(4-((S)-2-((((9H-fluoren-9-yl)methoxy)carbonyl)amino)-2-(4,4-difluorocyclohexyl)acetamido)phenyl)-2-((tert-butoxycarbonyl)amino)propanoate 22 (0.296 g, 0.426 mmol, 1.0 eq.) in DMF (6.0 mL) was added piperidine (0.843 mL, 8.52 mmol, 20.0 eq.) and the resulting mixture was stirred at RT for 1 h. The solution was concentrated to dryness to afford 23 as a yellow oil (0.130 g, 65%) which was used in the next step without further purification. UPLC-MS (basic 2 min): Rt=1.07 min; m/z=470.2 for [M+H]$^+$.

Example 76: Methyl (R)-2-((tert-butoxycarbonyl)amino)-3-(4-((S)-2-(4,4-difluorocyclohexyl)-2-(1-methyl-1H-pyrazole-5-carboxamido)acetamido)phenyl)propanoate (24)

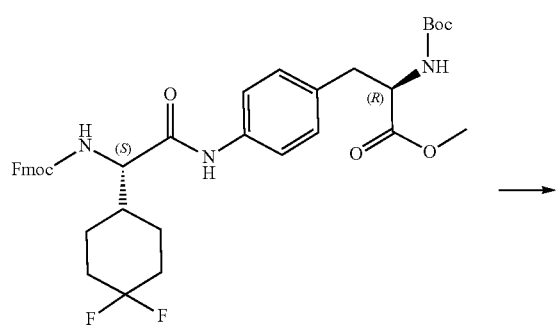

22

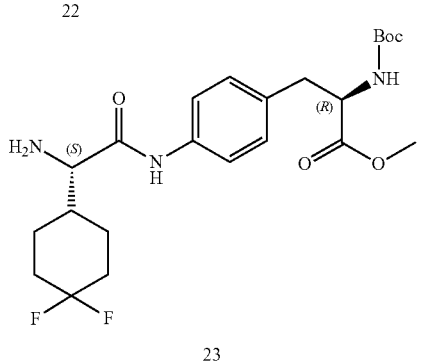

23

To a solution of 1-methyl-1H-pyrazole-5-carboxylic acid (0.033 g, 0.327 mmol, 1.2 eq.) in DMF (2 mL) was added HATU (0.124 g, 0.326 mmol, 1.5 eq.) and DIPEA (0.114 mL, 0.818 mmol, 3.0 eq) and then stirred at RT for 10 min. A solution of methyl (R)-3-(4-((S)-2-amino-2-(4,4-difluorocyclohexyl) acetamido)phenyl)-2-((tert-butoxycarbonyl) amino)propanoate 23 (0.128 g, 0.272 mmol, 1.0 eq,) in DMF was added and the resulting mixture was stirred at RT for 1 h. The mixture was concentrated to dryness to afford 24 (0.128 g, 100%) as an orange solid which was used in the next step without further purification. UPLC-MS (basic 2 min): Rt=1.10 min; m/z=578.3 for [M+H]⁺.

Example 77: (R)-2-((tert-butoxycarbonyl)amino)-3-(4-((S)-2-(4,4-difluorocyclohexyl)-2-(1-methyl-1H-pyrazole-5-carboxamido)acetamido)phenyl)propanoic acid (25)

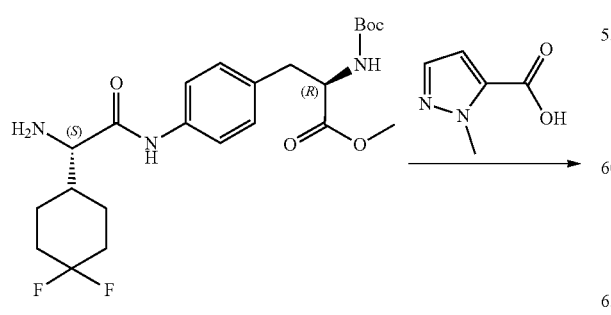

23

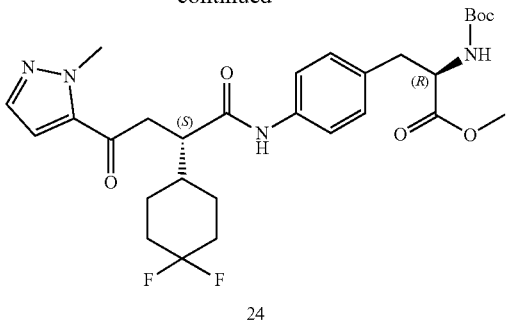

24

To a solution of methyl (R)-2-((tert-butoxycarbonyl)amino)-3-(4-((S)-2-(4,4-difluorocyclohexyl)-2-(1-methyl-1H-pyrazole-5-carboxamido)acetamido)phenyl)propanoate 24 (0.168 g, 0.242 mmol, 1.0 eq.) in THF (2.1 mL) and MeOH (0.7 mL) was added 1M LiOH solution (0.7 mL, 0.726 mmol, 3.0 eq.). The resulting mixture was stirred at room temperature for 1 h and then concentrated to dryness. The residue was suspended in water (400 mL) and then acidified with conc. HCl (pH=1.0). The resulting precipitate was filtered under vacuum to afford 25 as a white solid (0.137 g, 100%) which was used in the next step without further purification. UPLC-MS (basic 2 min): Rt=0.84 min; m/z=563.3 for [M+H]⁺.

Example 78: Tert-butyl ((R)-1-(4-benzylpiperazin-1-yl)-3-(4-((S)-2-(4,4-difluorocyclohexyl)-2-(1-methyl-1H-pyrazole-5-carboxamido)acetamido)phenyl)-1-oxopropan-2-yl)carbamate (26)

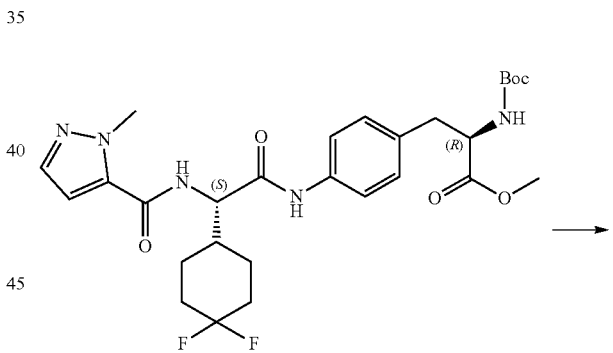

24

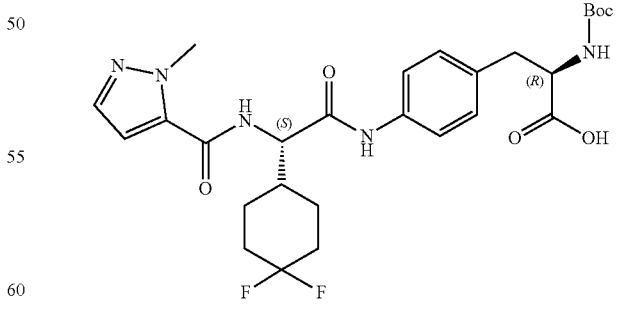

25

To a solution of (R)-2-((tert-butoxycarbonyl)amino)-3-(4-((S)-2-(4,4-difluorocyclohexyl)-2-(1-methyl-1H-pyrazole-5-carboxamido)acetamido)phenyl)propanoic acid 25 (0.0795 g, 0.140 mmol, 1.0 eq.) in DMF (1 mL) was added HATU (0.0772 g, 0.203 mmol, 1.5 eq.) and DIPEA (0.12 mL, 0.700 mmol, 5.0 eq). The resulting mixture was stirred at RT for 10 min. and then N-benzyl piperazine (0.048 g, 0.280 mmol, 2 eq,) was added. The resulting mixture was stirred at RT under a N₂ atmosphere for 1 h. The mixture was diluted with aq. sat. NaHCO₃ solution (5 mL) and then extracted with EtOAc (2×5 mL). The organic layer was washed with ice cold brine (5 mL), dried over Na₂SO₄ then concentrated to afford 26 as an orange solid (0.101 g, 100%) which was used in the next step without further purification. UPLC-MS (basic 2 min): Rt=1.14 min; m/z=722.4 for [M+H]⁺.

Example 79: (2S)—N-{4-[(2R)-2-amino-3-(4-benzylpiperazin-1-yl)-3-oxopropyl]phenyl}-2-(4,4-difluorocyclohexyl)-2-[(1-methyl-1H-pyrazol-5-yl)formamido]acetamide; trifluoroacetic acid (27)

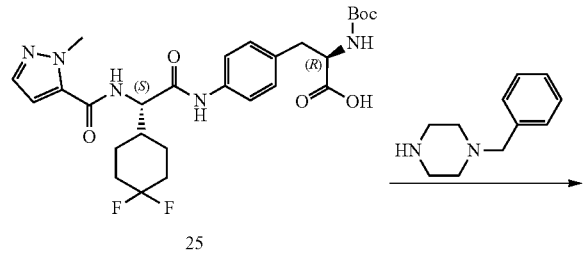

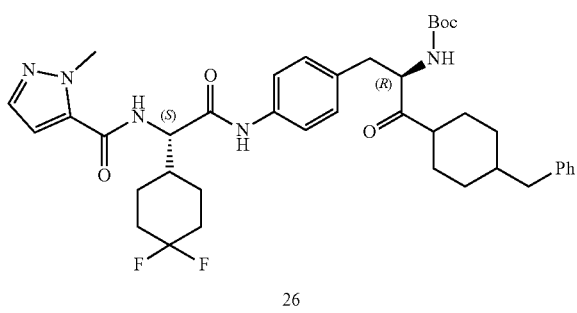

To a solution of tert-butyl ((R)-1-(4-benzylpiperazin-1-yl)-3-(4-((S)-2-(4,4-difluorocyclohexyl)-2-(1-methyl-1H-pyrazole-5-carboxamido)acetamido)phenyl)-1-oxopropan-2-yl)carbamate 26 (0.157 g, 0.217 mmol, 1.0 eq.) in DCM (0.78 mL) was added TFA (0.78 mL) and the resulting mixture was stirred at RT for 0.5 h. The reaction mixture was concentrated to dryness to afford 27 as a brown solid (0.160 g, 100%) which was used in the next step without further purification. UPLC-MS (basic 2 min): Rt=0.99 min; m/z=622.3 for [M+H]⁺.

Example 80: N-[(2R)-1-(4-benzylpiperazin-1-yl)-3-{4-[(2S)-2-(4,4-difluorocyclohexyl)-2-[(1-methyl-1H-pyrazol-5-yl)formamido]acetamido]phenyl}-1-oxopropan-2-yl]propanamide (131)

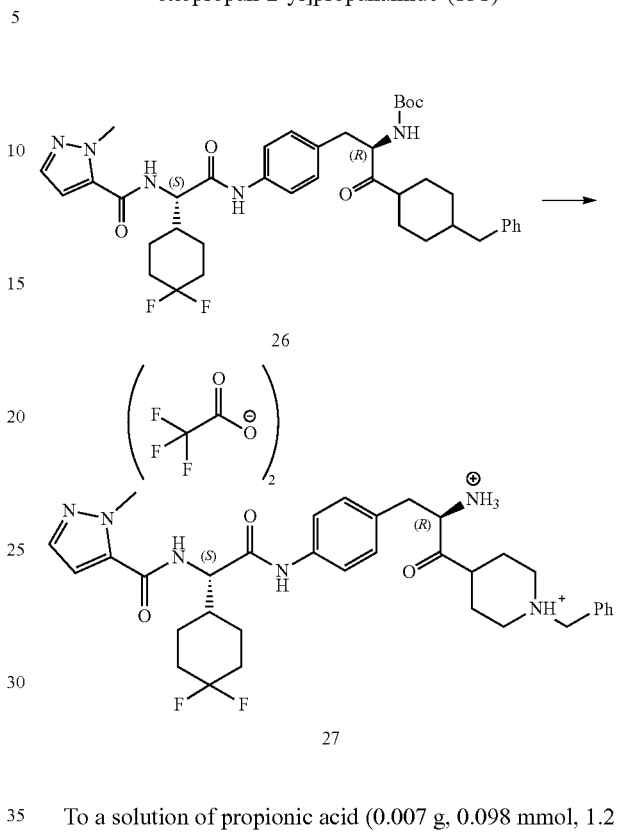

To a solution of propionic acid (0.007 g, 0.098 mmol, 1.2 eq.) in DMF (0.4 mL) was added HATU (0.0465 g, 0.122 mmol, 1.5 eq.) and DIPEA (0.057 mL, 0.326 mmol, 4.0 eq). The resulting mixture was stirred at RT for 10 min. and then a solution of (2S)—N-{4-[(2R)-2-amino-3-(4-benzylpiperazin-1-yl)-3-oxopropyl]phenyl}-2-(4,4-difluorocyclohexyl)-2-[(1-methyl-1H-pyrazol-5-yl)formamido]acetamide; trifluoroacetic acid 27 (0.060 g, 0.082 mmol, 1.0 eq,) in DMF (0.4 mL) was added. The resulting mixture was stirred at RT under a N₂ atmosphere for 1 h. The mixture was diluted with MeCN and purified via reverse phase column chromatography on a 120 g C18 cartridge eluting with a 5-95% H₂O:MeCN eluent (0.1% ammonia) to afford to afford 131 as a white solid (8.0 mg). ¹H NMR (400 MHz, DMSO-d6) δ 10.28 (s, 1H), 8.67 (d, J=8.4 Hz, 1H), 8.21 (d, J=8.2 Hz, 1H), 7.54 (d, J=8.1 Hz, 2H), 7.46 (d, J=2.1 Hz, 1H), 7.26 (dt, J=13.6, 7.1 Hz, 6H), 7.15 (d, J=8.2 Hz, 2H), 7.08 (d, J=2.1 Hz, 1H), 4.87 (q, J=7.8 Hz, 1H), 4.50 (t, J=8.7 Hz, 1H), 3.99 (s, 3H), 3.50 (s, 1H), 3.34 (d, J=4.8 Hz, 3H), 2.93-2.81 (m, 2H), 2.72 (dd, J=13.1, 7.3 Hz, 1H), 2.30-1.59 (m, 11H), 1.53-1.15 (m, 2H), 0.91 (t, J=7.6 Hz, 3H). UPLC-MS (basic 2 min): Rt=1.11 min; m/z=678.4 for [M+H]⁺.

Example 81: (R)-2-((tert-butoxycarbonyl)amino)-3-(4-((S)-2-cyclohexyl-2-(1-methyl-1H-pyrazole-5-carboxamido)acetamido)phenyl)propanoic acid (25-a)

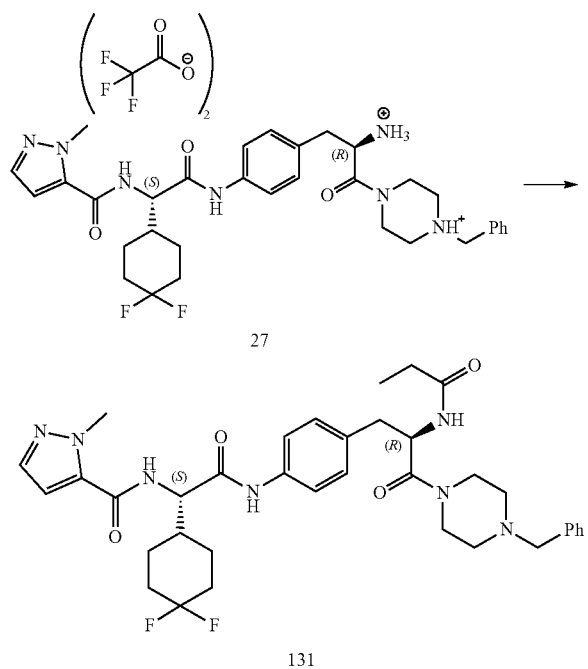

To a solution of methyl (2R)-2-{[(tert-butoxy)carbonyl]amino}-3-{4-[(2S)-2-cyclohexyl-2-[(1-methyl-1H-pyrazol-5-yl)formamido]acetamido]phenyl}propanoate 24-a made by a method analogous to compound 24 (4.20 g, 7.75 mmol, 1.0 eq.) in THF (50 mL) and MeOH (17.1 mL) was added 1M LiOH solution (17.1 mL, 17.1 mmol, 2.2 eq.). The resulting mixture was stirred at room temperature for 1 h and then concentrated to dryness. The residue was suspended in water (50 mL) and then acidified with conc. HCl (pH=1.0). The resulting precipitate was filtered under vacuum to afford 25-a as a white solid (2.38 g, 58%) which was used in the next step without further purification. UPLC-MS (basic 2 min): Rt=0.82 min; m/z=528.3 for [M+H]$^+$.

Example 82: Tert-butyl ((R)-1-(4-benzylpiperazin-1-yl)-3-(4-((S)-2-cyclohexyl-2-(1-methyl-1H-pyrazole-5-carboxamido)acetamido)phenyl)-1-oxopropan-2-yl)carbamate (26-a)

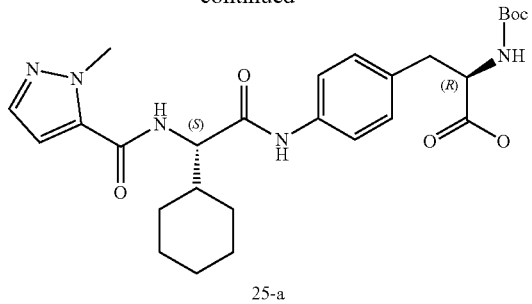

24-a

To a solution of (R)-2-((tert-butoxycarbonyl)amino)-3-(4-((S)-2-cyclohexyl-2-(1-methyl-1H-pyrazole-5-carboxamido)acetamido)phenyl)propanoic acid 25-a (0.400 g, 0.758 mmol, 1.0 eq.) in DMF (5 mL) was added HATU (0.432 g, 1.14 mmol, 1.5 eq.) and DIPEA (0.40 mL, 2.27 mmol, 3.0 eq). The resulting mixture was stirred at RT for 10 min. and then N-benzyl piperazine (0.160 g, 1.52 mmol, 1.2 eq,) was added. The resulting mixture was stirred at RT under a N$_2$ atmosphere for 1 h. The mixture was diluted with aq. sat. NaHCO$_3$ solution (5 mL) and then extracted with EtOAc (2×5 mL). The organic layer was washed with ice cold brine (5 mL), dried over Na$_2$SO$_4$ then concentrated to afford 26-a as an orange solid (0.467 g, 89%) which was used in the next step without further purification. UPLC-MS (basic 2 min): Rt=1.22 min; m/z=686.5 for [M+H]$^+$.

Example 83: (2S)—N-{4-[(2R)-2-amino-3-(4-benzylpiperazin-1-yl)-3-oxopropyl]phenyl}-2-cyclohexyl-2-[(1-methyl-1H-pyrazol-5-yl)formamido]acetamide; trifluoroacetic acid (27-a)

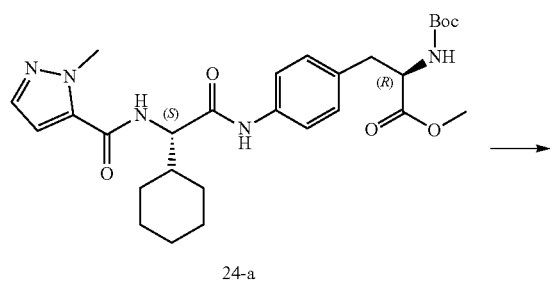

To a solution of tert-butyl ((R)-1-(4-benzylpiperazin-1-yl)-3-(4-((S)-2-cyclohexyl-2-(1-methyl-1H-pyrazole-5-carboxamido)acetamido)phenyl)-1-oxopropan-2-yl)carbamate 26-a (0.467 g, 0.680 mmol, 1.0 eq.) in DCM (5.0 mL) was added TFA (2.5 mL) and the resulting mixture was stirred at RT for 0.5 h. The reaction mixture was concentrated to dryness to afford 27-a as a brown solid (0.160 g, 100%) which was used in the next step without further purification. UPLC-MS (basic 2 min): Rt=1.05 min; m/z=586.2 for [M+H]$^+$.

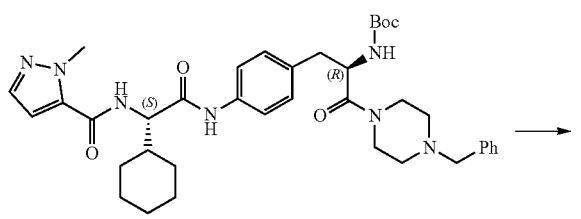

26-a

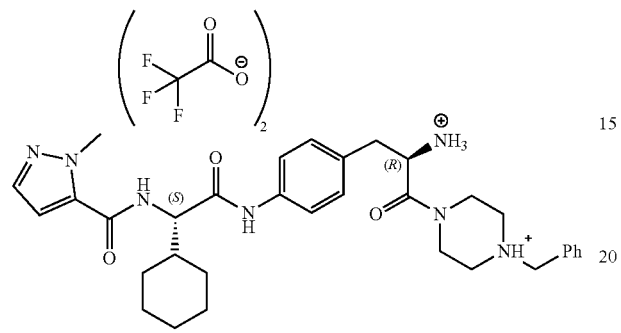

26-a

Example 84: N—((S)-2-((4-((R)-3-(4-benzylpiperazin-1-yl)-2-(3-cyclopropylureido)-3-oxopropyl)phenyl)amino)-1-cyclohexyl-2-oxoethyl)-1-methyl-1H-pyrazole-5-carboxamide (132)

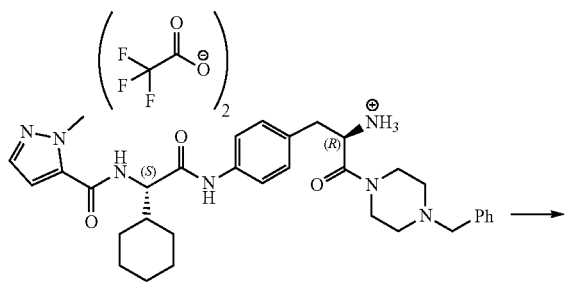

26-a

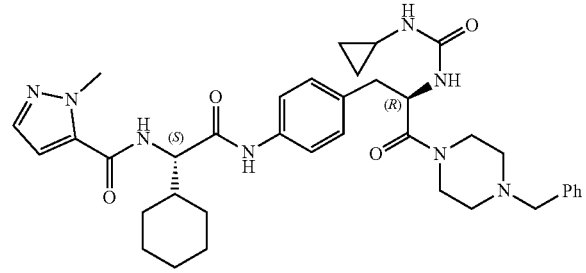

132

To a solution of (2S)—N-{4-[(2R)-2-amino-3-(4-benzylpiperazin-1-yl)-3-oxopropyl]phenyl}-2-cyclohexyl-2-[(1-methyl-1H-pyrazol-5-yl)formamido]acetamide; trifluoroacetic acid 27-a (0.238 g, 0.340 mmol, 1.0 eq.) in DCM (3.0 mL) were added isocyanatocyclopropane (0.031 g, 0.370 mmol, 1.1 eq.) and DIPEA (0.18 mL, 1.02 mmol, 3.0 eq.) at 0° C. and the resulting mixture was stirred at RT for 4 h. The reaction mixture was concentrated to dryness and the residue dissolved in EtOAc (20 mL). The solution was washed with aq. sat. NaHCO₃ solution (20 mL) and brine (20 mL) and then dried over anhydrous sodium sulfate before concentrating to dryness to afford 132 as an off-white solid (0.131 g, 58%). $^1$H NMR (400 MHz, DMSO-d$_6$) δ 10.19 (s, 1H), 8.49 (d, J=8.3 Hz, 1H), 7.57-7.43 (m, 3H), 7.30-7.22 (m, 4H), 7.10-7.07 (m, 2H), 6.30 (d, J=2.8 Hz, 1H), 6.02 (d, J=8.6 Hz, 1H), 4.79 (q, J=7.4 Hz, 1H), 4.42 (t, J=8.7 Hz, 1H), 3.99 (s, 3H), 3.55 (d, J=14.4 Hz, 1H), 3.37-3.24 (m, 7H) 2.80-2.66 (m, 2H), 2.40-2.21 (m, 3H), 2.09-1.58 (m, 8H), 1.24-1.11 (m, 4H), 1.05-0.99 (m, 1H), 0.53 (dt, J=6.7, 3.2 Hz, 2H), 0.27 (dt, J=6.1, 4.1 Hz, 2H). UPLC-MS (basic 2 min): Rt=1.07 min; m/z=669.5 for [M+H]⁺.

Example 85: N—((S)-2-((4-((R)-3-(4-benzylpiperazin-1-yl)-2-(3-cyclopropylureido)-3-oxopropyl)phenyl)amino)-1-(4,4-difluorocyclohexyl)-2-oxoethyl)-1-methyl-1H-pyrazole-5-carboxamide (145)

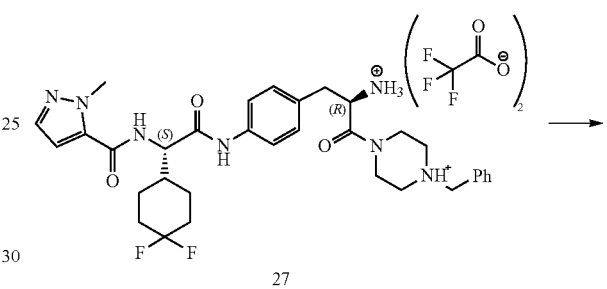

27

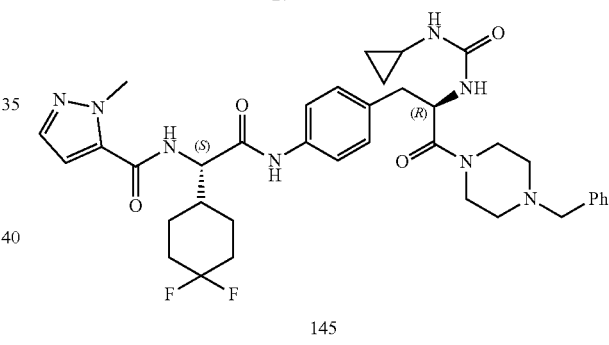

145

To a solution of (2S)—N-{4-[(2R)-2-amino-3-(4-benzylpiperazin-1-yl)-3-oxopropyl]phenyl}-2-(4,4-difluorocyclohexyl)-2-[(1-methyl-1H-pyrazol-5-yl)formamido]acetamide; trifluoroacetic acid 27 (0.101 g, 0.089 mmol, 1.0 eq.) in DCM (1.6 mL) were added isocyanatocyclopropane (0.015 g, 0.178 mmol, 2.0 eq.) and DIPEA (0.16 mL, 0.889 mmol, 10.0 eq.) at 0° C. and the resulting mixture was stirred at RT for 4 h. The reaction mixture was concentrated to dryness and the residue dissolved in EtOAc (20 mL). The solution was washed with aq. sat. NaHCO₃ solution (20 mL) and brine (20 mL) and then dried over anhydrous sodium sulfate before concentrating to dryness. The residue was purified by reverse phase column chromatography on a 120 g C18 cartridge eluting with a 5-95% H₂O:MeCN eluent (0.1% ammonia) to afford 145 as an off-white solid (10.8 mg, 17%). $^1$H NMR (400 MHz, DMSO-d$_6$) δ 10.25 (s, 1H), 8.63 (d, J=8.3 Hz, 1H), 7.55 (d, J=8.5 Hz, 2H), 7.46 (d, J=2.1 Hz, 1H), 7.34-7.18 (m, 5H), 7.13-7.03 (m, 3H), 6.29 (d, J=2.7 Hz, 1H), 6.02 (d, J=8.5 Hz, 1H), 4.79 (q, J=7.4 Hz, 1H), 4.51 (t, J=8.7 Hz, 1H), 3.99 (s, 3H), 3.54 (d, J=13.1 Hz, 1H), 3.26 (s, 2H), 3.37-3.30 (m, 4H), 2.93-2.65 (m, 3H), 2.40-2.21 (m, 3H), 2.08-1.65 (m, 8H), 1.49-1.25 (m, 2H), 0.54 (td, J=6.7, 4.4 Hz, 2H), 0.35-0.23 (m, 2H). UPLC-MS (basic 2 min): Rt=1.03 min; m/z=705.5 for [M+H]$^+$.

Example 86: Methyl (R)-2-amino-3-(4-cyanophenyl)propanoate hydrochloride (30)

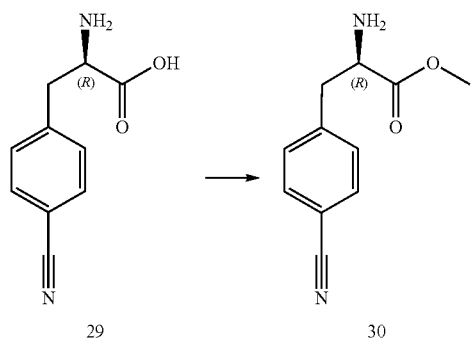

To a suspension of (2R)-2-amino-3-(4-cyanophenyl)propanoic acid) 29 (25.0 g, 131 mmol, 1.0 eq.) in MeOH (600 mL) was added thionyl chloride (47.9 mL, 657 mmol, 5.0 eq.) dropwise at 0° C. The resulting mixture was stirred at 0° C. for an hour and then allowed to warm to RT for 2 h. The solution was concentrated to dryness and the residue azeotroped with toluene to afford 30 as an off-white solid (29.1 g, 92%) which was used in the next step without further purification. $^1$H NMR (400 MHz, DMSO-d$_6$) δ 8.60 (br s, 3H), 7.89-7.80 (m, 2H), 7.50 (t, J=8.6 Hz, 2H), 4.39 (t, J=6.8 Hz, 1H), 3.69 (s, 3H), 3.24-3.19 (m, 2H). UPLC-MS (basic 2 min): Rt=0.82 min; m/z=205.1 for [M+H]$^+$.

Example 87: Methyl (R)-3-(4-cyanophenyl)-2-propionamidopropanoate (31)

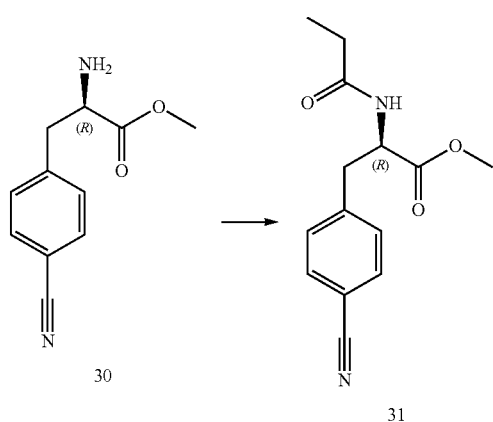

To a solution of propionic acid (7.1 mL, 95.2 mmol, 1.2 eq.) in DMF (200 mL) was added HATU (45.3 g, 119 mmol, 1.5 eq.) and DIPEA (27.6 mL, 159 mmol, 2.0 eq). The resulting mixture was stirred at RT for 10 min. and then a solution of methyl (R)-2-amino-3-(4-cyanophenyl)propanoate hydrochloride 31 (19.1 g, 79.4 mmol, 1.0 eq,) and DIPEA (27.6 mL, 159 mmol, 2.0 eq) in DMF (180.0 mL) was added. The resulting mixture was stirred at RT under a N$_2$ atmosphere for 1 h. The mixture was diluted with aq. sat. NaHCO$_3$ solution (2 L) and then extracted with EtOAc (2×500 mL). The organic layer was washed with ice cold brine (2×1 L), dried over Na$_2$SO$_4$ then concentrated to afford 31 as an orange oil (20.6 g, 100%). $^1$H NMR (400 MHz, DMSO-d$_6$) δ 8.29 (d, J=8.0 Hz, 1H), 7.82-7.71 (m, 2H), 7.50-7.40 (m, 2H), 4.52 (ddd, J=9.9, 8.0, 5.3 Hz, 1H), 3.62 (s, 3H), 3.13 (dd, J=13.7, 5.3 Hz, 1H), 3.07-2.87 (m, 1H), 2.04 (qd, J=7.5, 1.5 Hz, 2H), 0.89 (t, J=7.6 Hz, 3H) UPLC-MS (basic 2 min): Rt=0.86 min; m/z=261.0 for [M+H]$^+$ Example 88: Methyl (R)-3-(4-(((tert-butoxycarbonyl)amino)methyl)phenyl)-2-propionamidopropanoate (32)

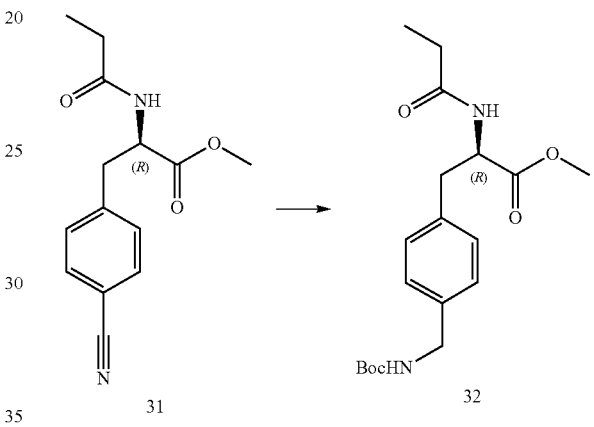

To a solution of methyl (R)-3-(4-cyanophenyl)-2-propionamidopropanoate 31 (6.30 g, 24.2 mmol, 1.0 eq.) in MeOH (484 mL) was added di-tert-butyl dicarbonate (10.6 g, 48.4 mmol, 2.0 eq.) and dichloronickel hexahydrate (0.575 g, 2.42 mmol, 0.1 eq) at −20° C. Sodium borohydride (6.41 g, 169 mmol, 7.0 eq.) was added portion wise over 10 min (exothermic and effervescent) whilst keeping the temperature at 0° C. The reaction mixture was stirred at 0° C. for 1 h and then allowed to warm to RT for another 1 h. The mixture was concentrated to dryness and then the residue redissolved in EtOAc (500 mL). The organic layer was washed with aq. sat. sodium bicarbonate solution (200 mL) and then dried over sodium sulfate before concentrating to dryness. The residue was purified by flash column chromatography (Silica, 0-100% EtOAc, isohexane) to afford 32 as a colorless oil which solidified to a white solid upon standing (5.50 g, 62%). $^1$H NMR (400 MHz, DMSO-d$_6$) δ 8.21 (d, J=7.8 Hz, 1H), 7.34 (t, J=6.3 Hz, 1H), 7.14 (s, 4H), 4.43 (ddd, J=9.4, 8.0, 5.5 Hz, 1H), 4.09 (dd, J=5.9, 4.3 Hz, 2H), 3.60 (s, 3H), 2.99 (dd, J=13.7, 5.6 Hz, 1H), 2.85 (dd, J=13.7, 9.3 Hz, 1H), 2.13-1.99 (m, 2H), 1.39 (s, 9H), 0.92 (t, J=7.6 Hz, 3H). UPLC-MS (basic 2 min): Rt=1.01 min; m/z=365.2 for [M+H]$^+$.

Example 89: (R)-3-(4-(((tert-butoxycarbonyl)amino)methyl)phenyl)-2-propionamidopropanoic acid (33)

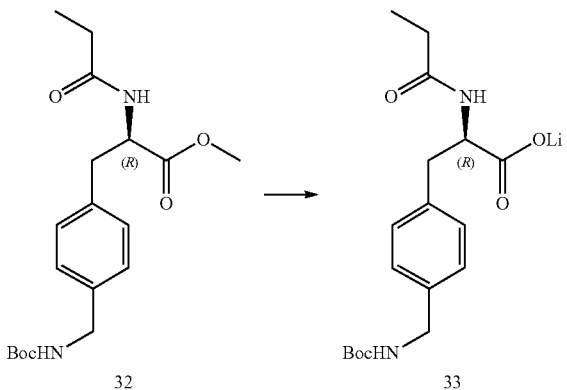

To a solution of methyl (R)-3-(4-(((tert-butoxycarbonyl)amino)methyl)phenyl)-2-propionamido propanoate 32 (5.5 g, 15.1 mmol, 1.0 eq.) in THF (60 mL) and MeOH (20 mL) was added 1M LiOH solution (18.1 mL, 18.1 mmol, 1.2 eq.). The resulting mixture was stirred at room temperature for 1 h and then concentrated to dryness to afford 33 as a white solid (5.38 g, 100%) which was used in the next step without further purification. UPLC-MS (basic 2 min): Rt=0.70 min; m/z=351.2 for [M+H]⁺.

Example 90: Tert-butyl (R)-(4-(3-(4-benzylpiperazin-1-yl)-3-oxo-2-propionamidopropyl)benzyl)carbamate (34)

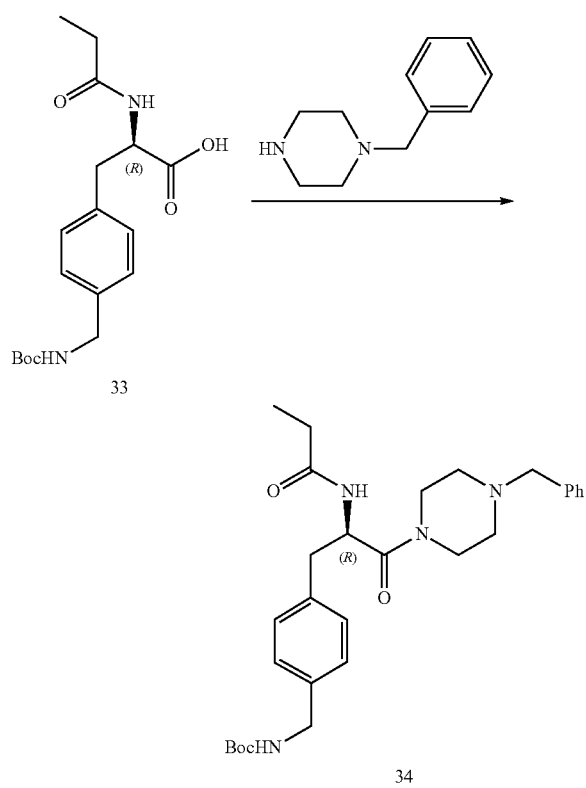

To a solution of (R)-3-(4-(((tert-butoxycarbonyl)amino)methyl)phenyl)-2-propionamidopropanoic acid 33 (4.50 g, 12.6 mmol, 1.0 eq.) in DMF (45 mL) was added HATU (7.20 g, 18.9 mmol, 1.5 eq.) and DIPEA (6.6 mL, 37.9 mmol, 3.0 eq). The resulting mixture was stirred at RT for 10 min. and then N-benzyl piperazine (2.45 g, 13.9 mmol, 1.1 eq,) was added. The resulting mixture was stirred at RT under a N₂ atmosphere for 1 h. The mixture was diluted with aq. sat. NaHCO₃ solution (500 mL) and then extracted with EtOAc (2×500 mL). The organic layer was washed with ice cold brine (2×1 L), dried over Na₂SO₄ then concentrated to afford 34 as an orange solid (5.27 g, 82%) which was used in the next step without further purification. UPLC-MS (basic 2 min): Rt=1.13 min; m/z=509.1 for [M+H]⁺.

Example 91: (R)—N-(3-(4-(aminomethyl)phenyl)-1-(4-benzylpiperazin-1-yl)-1-oxopropan-2-yl)propionamide (35)

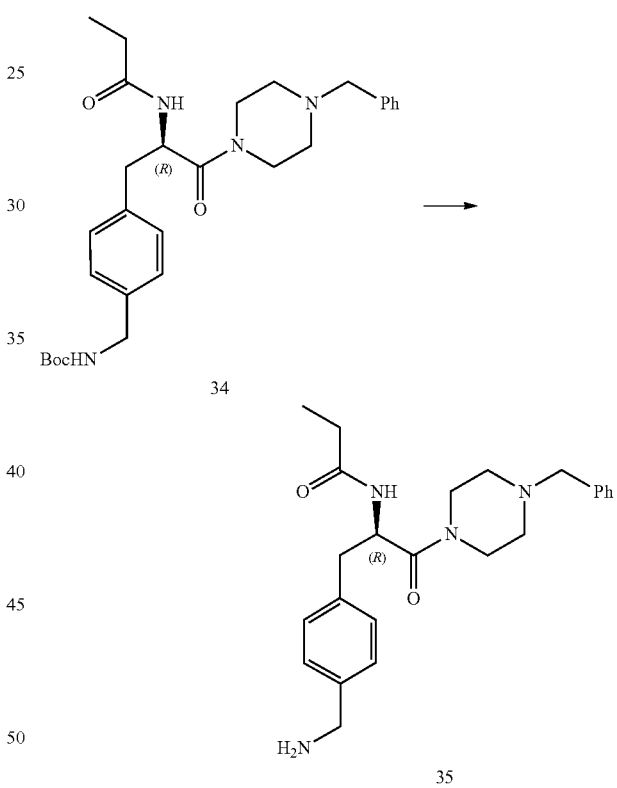

To a solution of tert-butyl (R)-(4-(3-(4-benzylpiperazin-1-yl)-3-oxo-2-propionamidopropyl)benzyl) carbamate 34 (1.00 g, 1.97 mmol, 1.0 eq.) in DCM (5.0 mL) was added TFA (5.0 mL) and the resulting mixture was stirred at RT for 2 h. The reaction mixture was concentrated to dryness and the residue dissolved in DCM (20 mL). A solution of potassium carbonate (1.5 g) in water (20 mL) was added and the mixture was stirred vigorously for 20 mins. The organic phase was dried over sodium sulfate before filtering and concentrating to dryness to afford 35 as a brown solid (0.654 g, 81%) which was used in the next step without further purification. UPLC-MS (basic 2 min): Rt=0.92 min; m/z=409.2 for [M+4]⁺.

Example 92: General Procedure E for the Synthesis of 36a-e

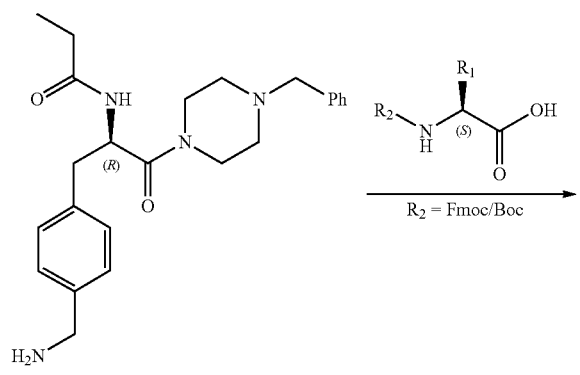

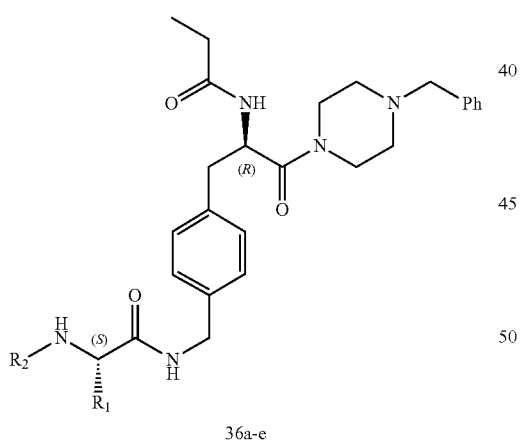

To a solution of the required amino acid (1.0-1.2 eq.) in DMF (0.05M) was added HATU (1.5 eq.) and DIPEA (3.0 eq.) and the resulting mixture was stirred at RT for 10 minutes. A solution of (R)—N-(3-(4-(aminomethyl)phenyl)-1-(4-benzylpiperazin-1-yl)-1-oxopropan-2-yl)propionamide 35 (1.0 eq.) was added and the reaction mixture was stirred at RT for 1 h. The reaction mixture was concentrated to dryness to afford a residue which was purified via flash column chromatography (Silica, 0-10% MeOH, DCM) to afford 36a-e.

Example 93: Tert-butyl ((S)-2-((4-((R)-3-(4-benzylpiperazin-1-yl)-3-oxo-2-propionamidopropyl)benzyl)amino)-1-cyclohexyl-2-oxoethyl)carbamate (36a)

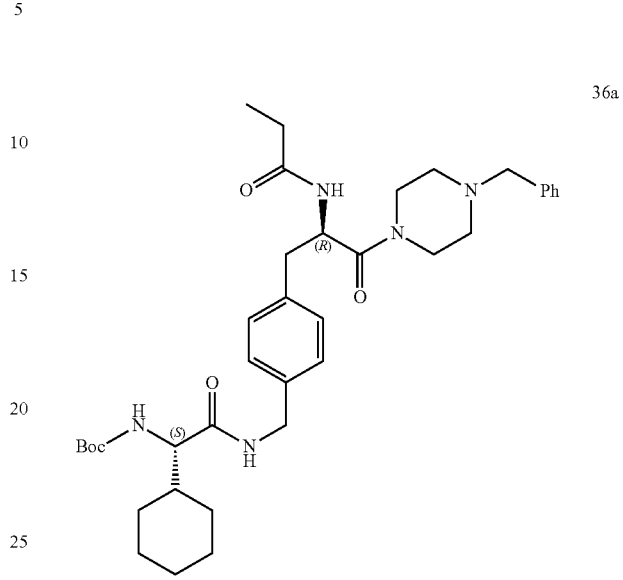

Following General Procedure E, 35 (0.300 g, 0.734 mmol, 1.0 eq.) was reacted with (2S)-2-{[(tert-butoxy)carbonyl]amino}-2-cyclohexylacetic acid 15a (0.189 g, 0.734 mmol, 1.0 eq.), HATU (0.419 g, 1.10 mmol, 1.5 eq.) and DIPEA (0.38 mL, 2.20 mmol, 3.0 eq.) in DMF (4 mL) to afford, after flash column chromatography, 36a (0.300 g, 63%) as a white solid. UPLC-MS (basic 2 min): rt=1.22 min; m/z=648.3 for [M+H]$^+$.

Example 94: (9H-fluoren-9-yl)methyl ((S)-2-((4-((R)-3-(4-benzylpiperazin-1-yl)-3-oxo-2-propionamidopropyl)benzyl)amino)-1-(4,4-difluorocyclohexyl)-2-oxoethyl)carbamate

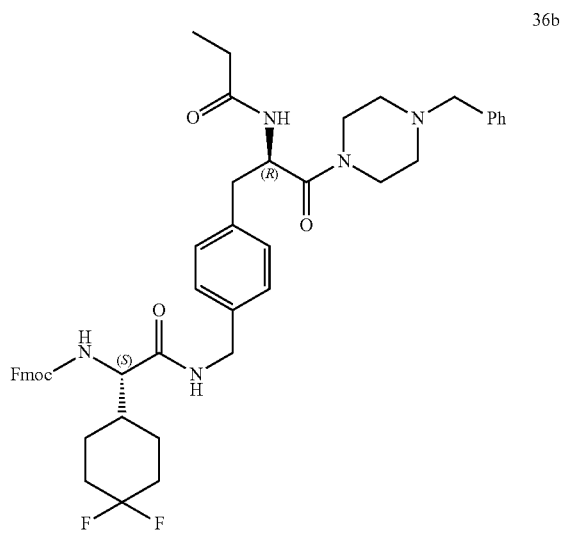

Following General Procedure E, 35 (0.300 g, 0.734 mmol, 1.0 eq.) was reacted with (2S)-2-({[(4b,8a,9,9a-tetrahydro- 4aH-fluoren-9-yl)methoxy]carbonyl}amino)-2-(4,4-difluorocyclohexyl)acetic acid 15b (0.308 g, 0.734 mmol, 1.0 eq.), HATU (0.419 g, 1.10 mmol, 1.5 eq.) and DIPEA (0.38 mL, 2.20 mmol, 3.0 eq.) in DMF (4 mL) to afford, after flash column chromatography, 36b (0.488 g, 82%) as a white solid. UPLC-MS (basic 2 min): rt=1.25 min; m/z=807.2 for [M+H]⁺.

Example 95: Tert-butyl ((S)-2-((4-((R)-3-(4-benzylpiperazin-1-yl)-3-oxo-2-propionamidopropyl)benzyl)amino)-1-cycloheptyl-2-oxoethyl)carbamate (36c)

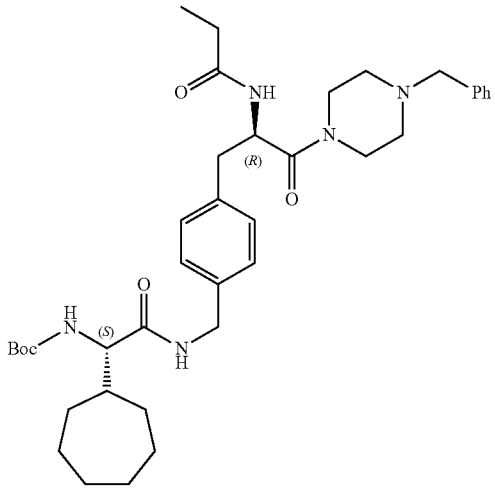

36c

Following General Procedure E, 35 (0.630 g, 1.54 mmol, 1.0 eq.) was reacted with (2S)-2-{[(tert-butoxy)carbonyl]amino}-2-cycloheptylacetic acid 15c (0.418 g, 1.54 mmol, 1.0 eq.), HATU (0.880 g, 2.31 mmol, 1.5 eq.) and DIPEA (0.81 mL, 4.63 mmol, 3.0 eq.) in DMF (3 mL) to afford, after flash column chromatography, 36c (0.637 g, 62%) as a white solid. UPLC-MS (basic 2 min): rt=1.23 min; m/z=662.3 for [M+H]⁺.

Example 96: Tert-butyl ((S)-2-((4-((R)-3-(4-benzylpiperazin-1-yl)-3-oxo-2-propionamidopropyl)benzyl)amino)-1-(2,3-dihydro-1H-inden-2-yl)-2-oxoethyl)carbamate (36d)

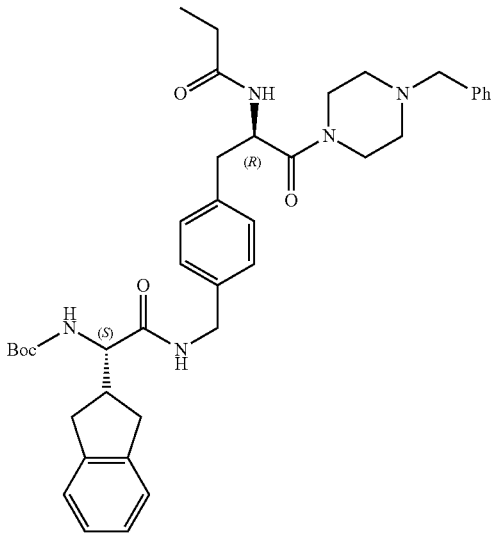

36d

Following General Procedure E, 35 (0.375 g, 0.917 mmol, 1.0 eq.) was reacted with (2S)-2-{[(tert-butoxy)carbonyl]amino}-2-(2,3-dihydro-1H-inden-2-yl)acetic acid 15d (0.267 g, 0.917 mmol, 1.0 eq.), HATU (0.523 g, 1.38 mmol, 1.5 eq.) and DIPEA (0.48 mL, 2.75 mmol, 3.0 eq.) in DMF (5 mL) to afford, after flash column chromatography, 36d (0.593 g, 95%) as a white solid. UPLC-MS (basic 2 min): rt=1.20 min; m/z=682.5 for [M+H]⁺.

Example 97: (9H-fluoren-9-yl)methyl ((S)-2-((4-((R)-3-(4-benzylpiperazin-1-yl)-3-oxo-2-propionamidopropyl)benzyl)amino)-1-cyclopentyl-2-oxoethyl)carbamate (36e)

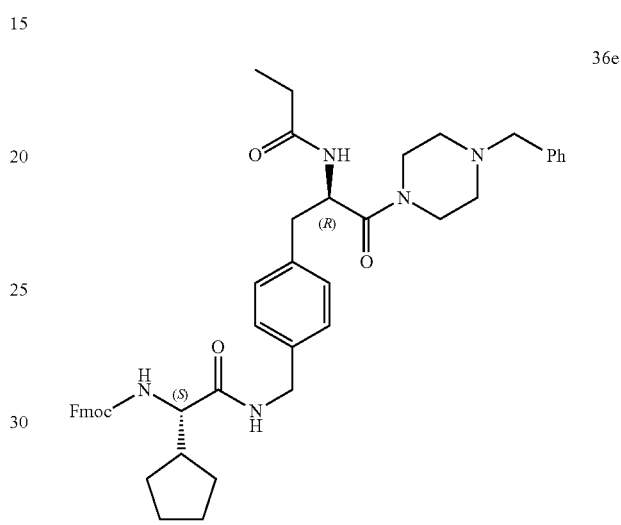

36e

Following General Procedure E, 35 (0.375 g, 0.375 mmol, 1.0 eq.) was reacted with (0.375 g, 0.917 mmol, 1.0 eq.) was reacted with (2S)-2-({[(4b,8a,9,9a-tetrahydro-4aH-fluoren-9-yl)methoxy]carbonyl}amino)-2-cyclopentylacetic acid 15e (0.339 g, 0.917 mmol, 1.0 eq.), HATU (0.523 g, 1.38 mmol, 1.5 eq.) and DIPEA (0.48 mL, 2.75 mmol, 3.0 eq.) in DMF (5 mL) to afford, after flash column chromatography, 36e (0.604 g, 87%) as a white solid. UPLC-MS (basic 2 min): rt=1.20 min; m/z=682.5 for [M+H]⁺.

Example 98: General Procedure F for the Synthesis of 37a/37c/37d

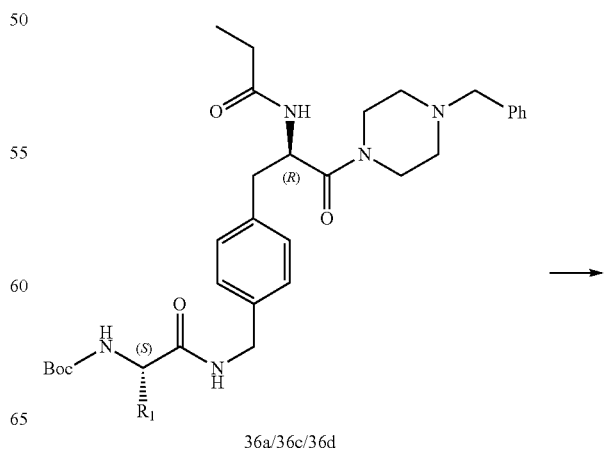

36a/36c/36d

-continued

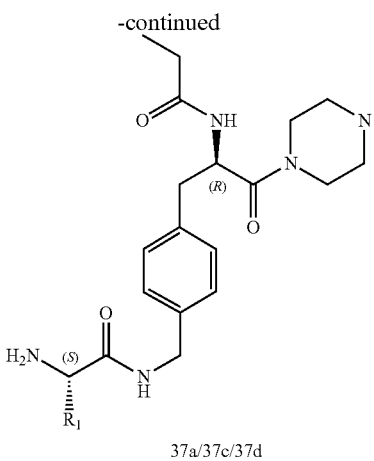

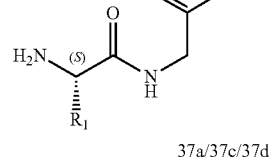

37a/37c/37d

To a solution of 36a/36c/36d (1.0 eq.) in DCM (5 volumes) was added TFA (5 volumes) and the resulting mixture was stirred at RT for 0.5 h. The reaction mixture was concentrated to dryness and the residue was stirred in aq. sat. K₂CO₃ solution (20 mL) to obtain a precipitate which was filtered to afford 37a/37c/37d.

Example 99: General Procedure G for the Synthesis of 37b/37e

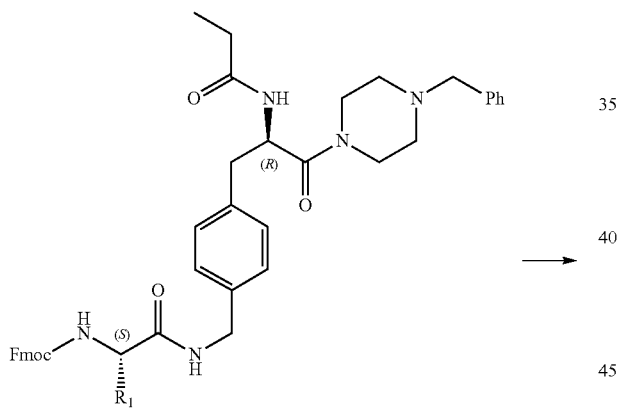

36b/36e

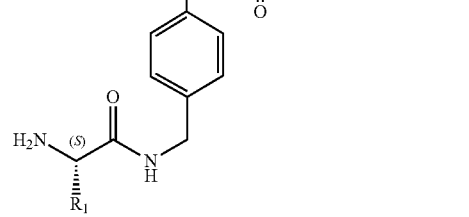

37b/37e

To a solution of 36b/36e (1.0 eq.) in DMF (10 volumes) was added Piperidine (2 volumes) and the resulting mixture was stirred at RT for 1 h. The reaction mixture was poured onto ice-cold brine and then extracted with EtOAc to remove impurities. The aqueous layer was extracted with 10% IPA/DCM and the organic layer was dried over sodium sulfate and then concentrated to dryness to afford 37b/37e.

Example 100: N—((R)-3-(4-(((S)-2-amino-2-cyclohexylacetamido)methyl)phenyl)-1-(4-benzylpiperazin-1-yl)-1-oxopropan-2-yl)propionamide (37a)

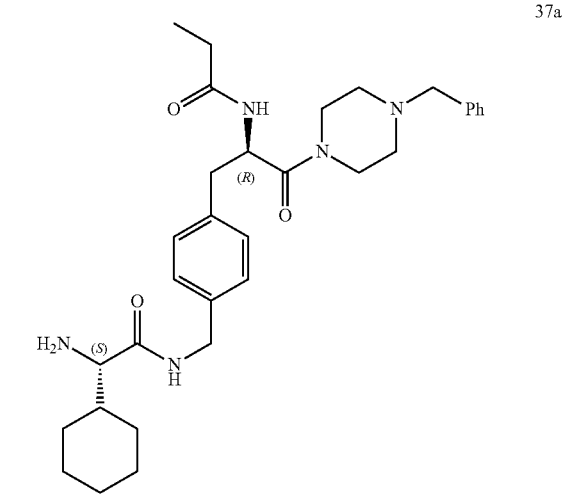

37a

Following General Procedure F, 36a (0.300 g, 0.463 mmol, 1.0 eq.) was reacted with TFA in DCM to afford 37a as an orange solid (0.070 g, 28%) which was used in the next step without further purification. UPLC-MS (basic 2 min): rt=1.04 min; m/z=548.4 for [M+H]⁺.

Example 101: N—((R)-3-(4-(((S)-2-amino-2-(4,4-difluorocyclohexyl)acetamido)methyl)phenyl)-1-(4-benzylpiperazin-1-yl)-1-oxopropan-2-yl)propionamide (37b)

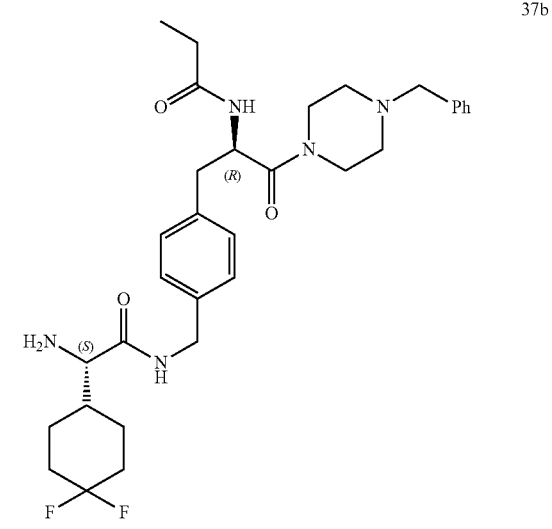

37b

Following General Procedure G, 36b (0.480 g, 0.593 mmol, 1.0 eq.) was reacted with piperidine in DMF to afford 37b as an off-white solid (0.220 g, 64%) which was used in the next step without further purification. UPLC-MS (basic 2 min): rt=1.00 min; m/z=584.4 for [M+H]+.

Example 102: N—((R)-3-(4-(((S)-2-amino-2-cycloheptylacetamido)methyl)phenyl)-1-(4-benzylpiperazin-1-yl)-1-oxopropan-2-yl)propionamide (37c)

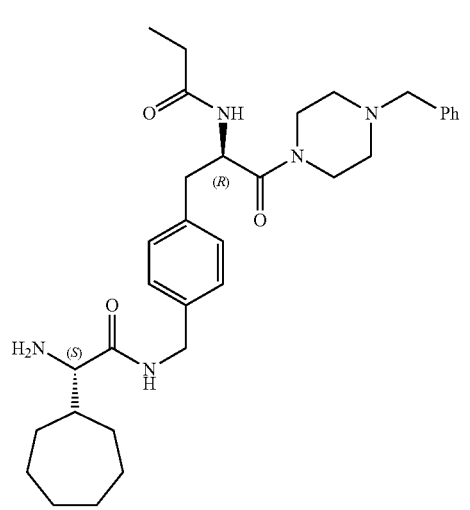

37c

Following General Procedure F, 36c (0.630 g, 0.952 mmol, 1.0 eq.) was reacted with TFA in DCM to afford 37c as a brown solid (0.533 g, 100%) which was used in the next step without further purification. UPLC-MS (basic 2 min): rt=1.07 min; m/z=562.4 for [M+H]+.

Example 103: N—((R)-3-(4-(((S)-2-amino-2-(2,3-dihydro-1H-inden-2-yl)acetamido)methyl)phenyl)-1-(4-benzylpiperazin-1-yl)-1-oxopropan-2-yl)propionamide (37d)

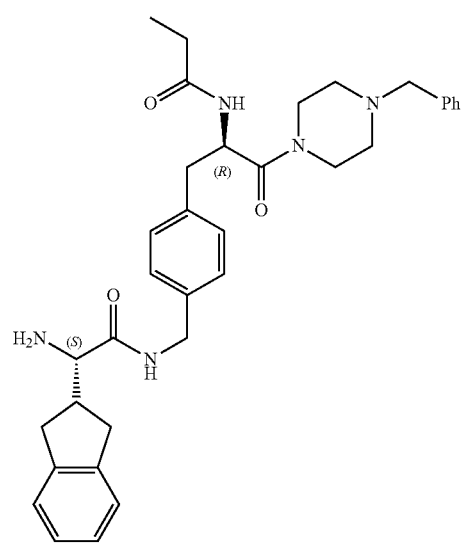

37d

Following General Procedure F, 36d (0.583 g, 0.855 mmol, 1.0 eq.) was reacted with TFA in DCM to afford 37d as a brown solid (0.420 g, 85%) which was used in the next step without further purification. UPLC-MS (basic 2 min): rt=1.04 min; m/z=582.2 for [M+H]+.

Example 104: N—((R)-3-(4-(((S)-2-amino-2-cyclopentylacetamido)methyl)phenyl)-1-(4-benzylpiperazin-1-yl)-1-oxopropan-2-yl)propionamide (37e)

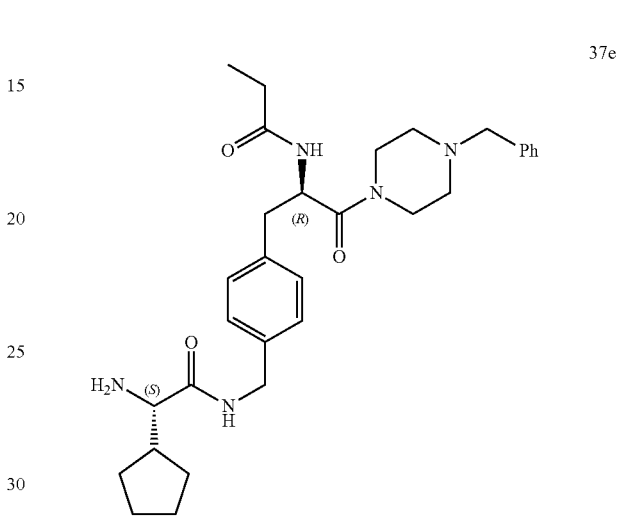

37e

Following General Procedure G, 36e (0.480 g, 0.593 mmol, 1.0 eq.) was reacted with piperidine in DMF to afford 37e as an off-white solid (0.200 g, 37%) which was used in the next step without further purification. UPLC-MS (basic 2 min): rt=0.99 min; m/z=534.4 for [M+H]+.

Example 105: General Procedure H for the Synthesis of 103, 129, 134, 136, 142, 150, 151, 157, 158, 161 and 164

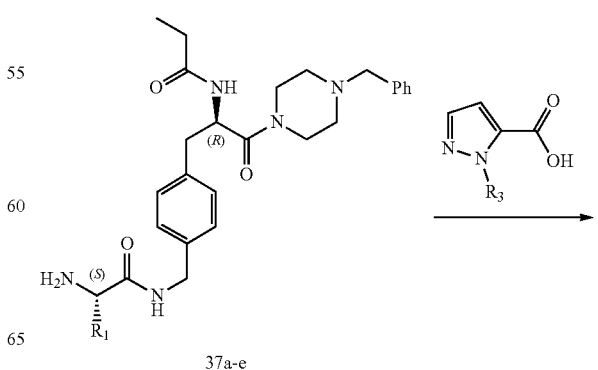

37a-e

-continued

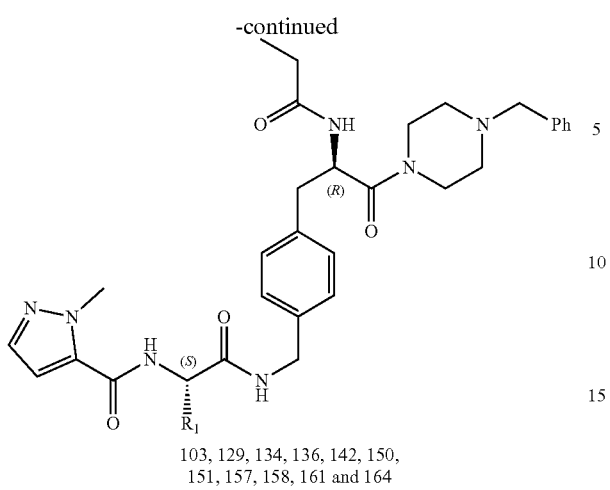

103, 129, 134, 136, 142, 150,
151, 157, 158, 161 and 164

To a solution of 1-methyl-1H-pyrazole-5-carboxylic acid (1.2 eq.) in DMF was added HATU (1.5 eq.) and DIPEA (4.0 eq) and then stirred at RT for 10 min. A solution of 37a-e (1.0 eq,) in DMF was added and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford 103, 129, 134, 136, 142, 150, 151, 157, 158, 161 and 164.

Example 106: N—((S)-2-((4-((R)-3-(4-benzylpiperazin-1-yl)-3-oxo-2-propionamidopropyl)benzyl)amino)-1-cyclohexyl-2-oxoethyl)-1-methyl-1H-pyrazole-5-carboxamide (103)

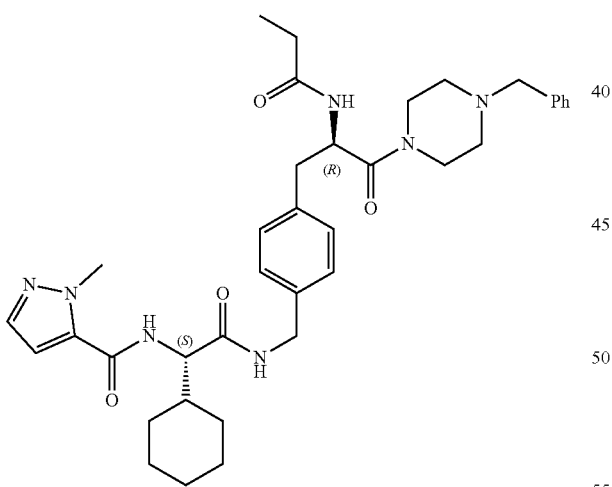

Following General Procedure H, 37a (0.070 g, 0.128 mmol, 1.0 eq.) was reacted with 1-methyl-1H-pyrazole-5-carboxylic acid (0.019 g, 0.153 mmol, 1.2 eq.), HATU (0.073 g, 0.192 mmol, 1.5 eq.) and DIPEA (0.089 mL, 0.511 mmol, 4.0 eq.) in DMF (0.6 mL) to afford, after reverse phase column chromatography, 103 (35.0 mg, 28%) as a white solid. $^1$H NMR (400 MHz, DMSO-$d_6$) δ 8.60 (td, J=6.0, 2.2 Hz, 1H), 8.35 (d, J=8.5 Hz, 1H), 8.20 (d, J=8.4 Hz, 1H), 7.45 (d, J=2.0 Hz, 1H), 7.35-7.21 (m, 5H), 7.15 (s, 3H), 7.02 (d, J=2.1 Hz, 1H), 4.87 (q, J=7.7 Hz, 1H), 4.34-4.25 (m, 3H), 4.03 (s, 3H), 3.38 (d, J=23.8 Hz, 3H), 2.88 (dd, J=13.4, 6.6 Hz, 1H), 2.72 (dd, J=13.4, 7.8 Hz, 1H), 2.21 (s, 3H), 2.03 (qd, J=7.4, 1.8 Hz, 3H), 1.88-1.49 (m, 6H), 1.25-0.93 (m, 6H), 0.89 (td, J=7.6, 2.3 Hz, 3H). UPLC-MS (basic 2 min): rt=1.08 min; m/z=656.4 for [M+H]$^+$.

Example 107: N—((S)-2-((4-((R)-3-(4-benzylpiperazin-1-yl)-3-oxo-2-propionamidopropyl)benzyl)amino)-1-(4,4-difluorocyclohexyl)-2-oxoethyl)-1-methyl-1H-pyrazole-5-carboxamide (134)

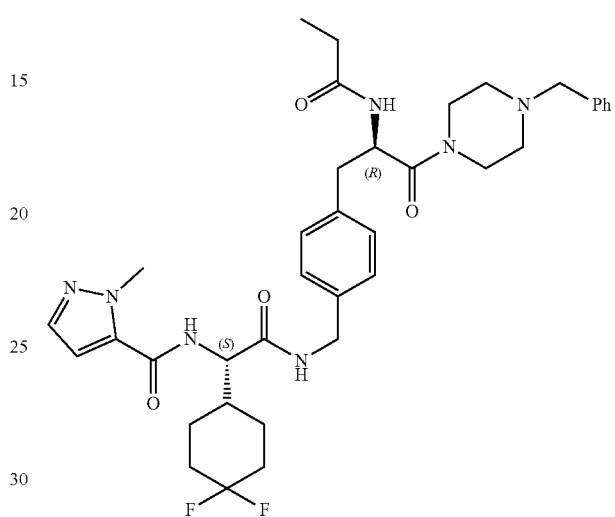

Following General Procedure H, 37b was reacted with 1-methyl-1H-pyrazole-5-carboxylic acid, HATU and DIPEA in DMF to afford, after reverse phase column chromatography, 134 (37.0 mg) as a white solid. UPLC-MS (basic 2 min): rt=1.04 min; m/z=692.4 for [M+H]$^+$.

Example 108: N—((S)-2-((4-((R)-3-(4-benzylpiperazin-1-yl)-3-oxo-2-propionamidopropyl)benzyl)amino)-1-cycloheptyl-2-oxoethyl)-1-methyl-1H-pyrazole-5-carboxamide (129)

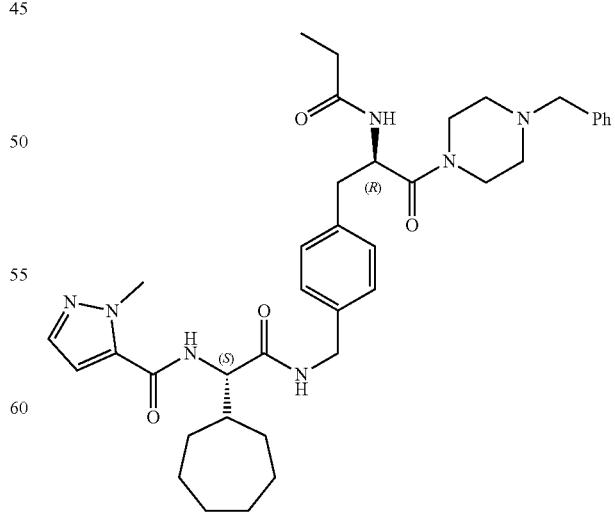

Following General Procedure H, 37c was reacted with 1-methyl-1H-pyrazole-5-carboxylic acid, HATU and Example 109: N—((S)-2-((4-((R)-3-(4-benzylpiperazin-1-yl)-3-oxo-2-propionamidopropyl)benzyl)amino)-1-(2,3-dihydro-1H-inden-2-yl)-2-oxoethyl)-1-methyl-1H-pyrazole-5-carboxamide (136)

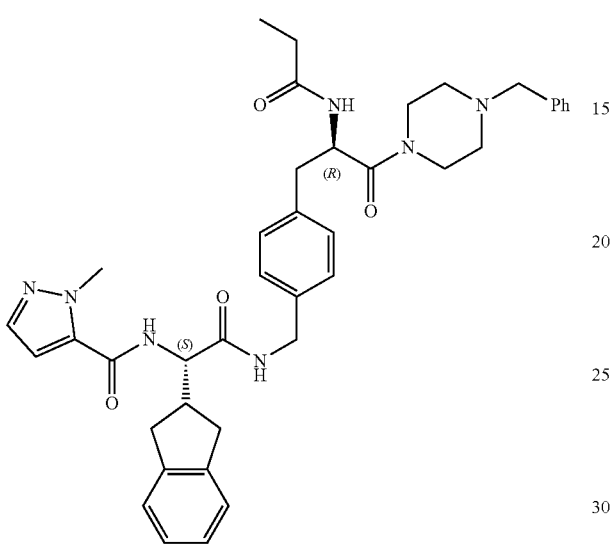

Following General Procedure H, 37d was reacted with 1-methyl-1H-pyrazole-5-carboxylic acid, HATU and DIPEA in DMF to afford, after reverse phase column chromatography, 136 (181.0 mg) as a white solid. UPLC-MS (basic 2 min): rt=1.10 min; m/z=690.2 for [M+H]$^+$.

Example 110: N—((S)-2-((4-((R)-3-(4-benzylpiperazin-1-yl)-3-oxo-2-propionamidopropyl)benzyl)amino)-1-cyclopentyl-2-oxoethyl)-1-methyl-1H-pyrazole-5-carboxamide (142)

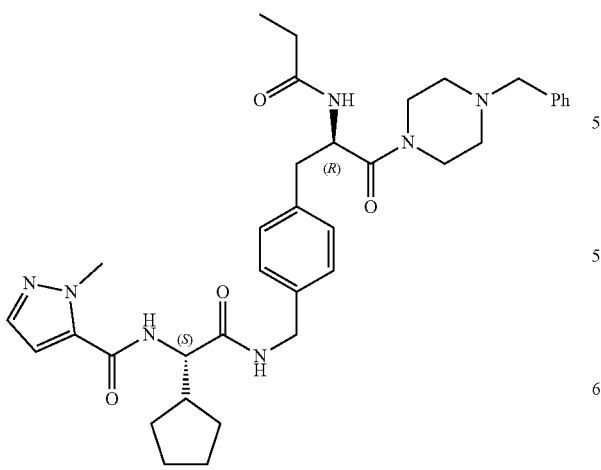

Following General Procedure H, 37e was reacted with 1-methyl-1H-pyrazole-5-carboxylic acid, HATU and DIPEA in DMF to afford, after reverse phase column chromatography, 142 (6.8 mg) as a white solid. UPLC-MS (basic 2 min): rt=1.10 min; m/z=642.4 for [M+H]$^+$.

Example 111: N—((S)-2-((4-((R)-3-(4-benzylpiperazin-1-yl)-3-oxo-2-propionamidopropyl)benzyl)amino)-1-cycloheptyl-2-oxoethyl)-1-isopropyl-1H-pyrazole-5-carboxamide (151)

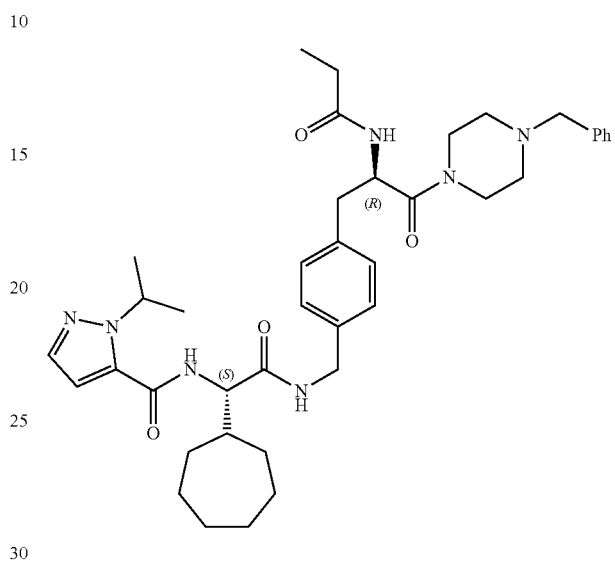

Following General Procedure H, 37c was reacted with 2-isopropyl-2H-pyrazole-5-carboxylic acid, HATU and DIPEA in DMF to afford, after reverse phase column chromatography, 151 (6.8 mg). UPLC-MS (basic 2 min): rt=1.34 min; m/z=698.4 for [M+H]$^+$.

Example 112: N—((S)-2-((4-((R)-3-(4-benzylpiperazin-1-yl)-3-oxo-2-propionamidopropyl)benzyl)amino)-1-cycloheptyl-2-oxoethyl)-1-ethyl-1H-pyrazole-5-carboxamide (157)

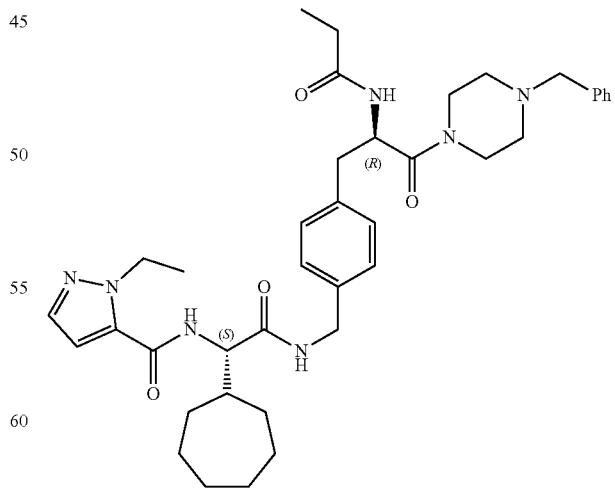

Following General Procedure H, 37c was reacted with 2-ethyl-2H-pyrazole-5-carboxylic acid, HATU and DIPEA in DMF to afford, after reverse phase column chromatography, 157 (70.0 mg) as a white solid. UPLC-MS (basic 2 min): rt=1.34 min; m/z=684.3 for [M+H]⁺.

Example 113: N—((S)-2-((4-((R)-3-(4-benzylpiperazin-1-yl)-3-oxo-2-propionamidopropyl)benzyl)amino)-1-(4,4-difluorocyclohexyl)-2-oxoethyl)-1-isopropyl-1H-pyrazole-5-carboxamide (158)

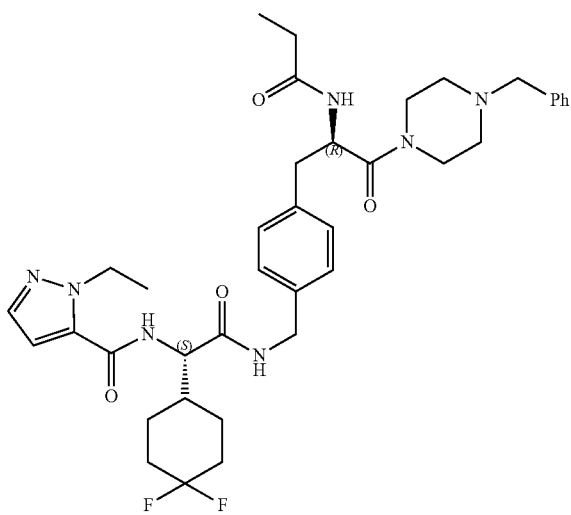

Following General Procedure H, 37b was reacted with 2-ethyl-2H-pyrazole-5-carboxylic acid, HATU and DIPEA in DMF to afford, after reverse phase column chromatography, 158 (70.0 mg) as a white solid. UPLC-MS (basic 2 min): rt=1.34 min; m/z=706.4 for [M+H]⁺.

Example 114: N—((S)-2-((4-((R)-3-(4-benzylpiperazin-1-yl)-3-oxo-2-propionamidopropyl)benzyl)amino)-1-(4,4-difluorocyclohexyl)-2-oxoethyl)-1-ethyl-1H-pyrazole-5-carboxamide (150)

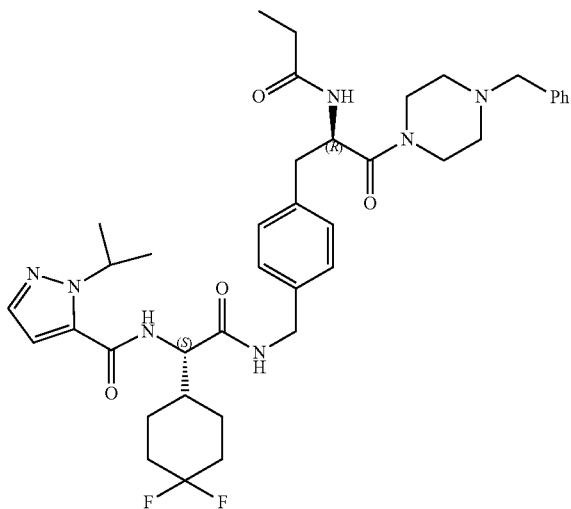

Following General Procedure H, 37b was reacted with 2-isopropyl-2H-pyrazole-5-carboxylic acid, HATU and DIPEA in DMF to afford, after reverse phase column chromatography, 150 (21.0 mg) as a white solid. UPLC-MS (basic 2 min): rt=1.11 min; m/z=720.5 for [M+H]⁺.

Example 115: N—((S)-2-((4-((R)-3-(4-benzylpiperazin-1-yl)-3-oxo-2-propionamidopropyl)benzyl)amino)-1-(2,3-dihydro-1H-inden-2-yl)-2-oxoethyl)-1-ethyl-1H-pyrazole-5-carboxamide (161)

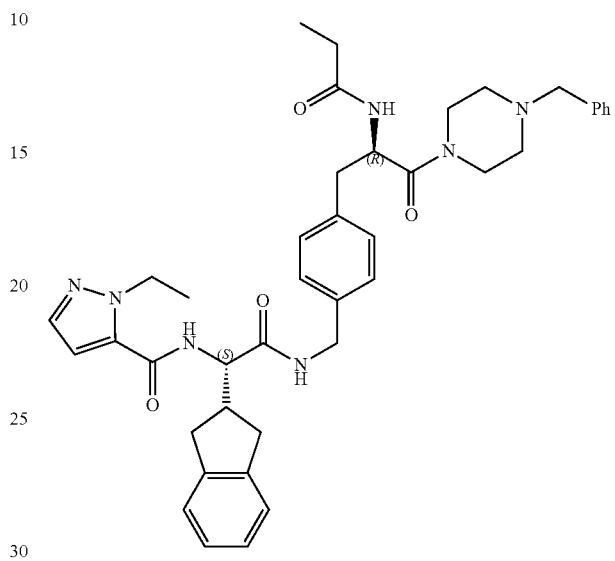

Following General Procedure H, 37d was reacted with 2-ethyl-2H-pyrazole-5-carboxylic acid, HATU and DIPEA in DMF to afford, after reverse phase column chromatography, 161 (27.0 mg) as a white solid. UPLC-MS (basic 2 min): rt=1.13 min; m/z=704.5 for [M+H]⁺.

Example 116: N—((S)-2-((4-((R)-3-(4-benzylpiperazin-1-yl)-3-oxo-2-propionamidopropyl)benzyl)amino)-1-(2,3-dihydro-1H-inden-2-yl)-2-oxoethyl)-1-isopropyl-1H-pyrazole-5-carboxamide (164)

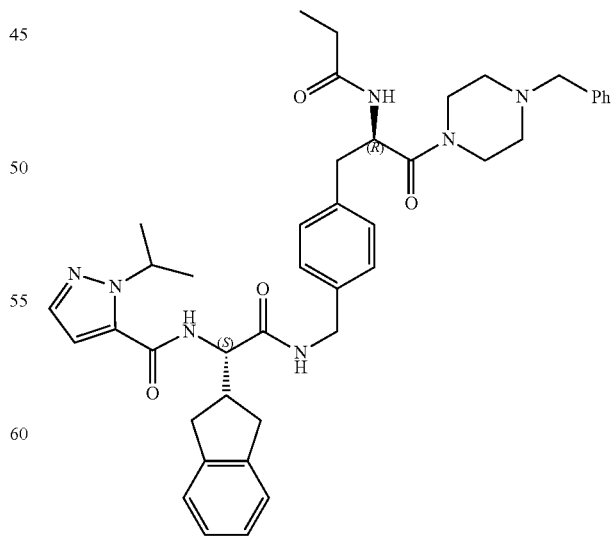

Following General Procedure H, 37d was reacted with 2-isopropyl-2H-pyrazole-5-carboxylic acid, HATU and DIPEA in DMF to afford, after reverse phase column chromatography, 164 (30.0 mg) as a white solid. UPLC-MS (basic 2 min): rt=1.16 min; m/z=718.5 for [M+H]$^+$.

Example 117: tert-butyl (R)-(4-(3-(4-methylpiperazin-1-yl)-3-oxo-2-propionamidopropyl)phenyl) carbamate (39)

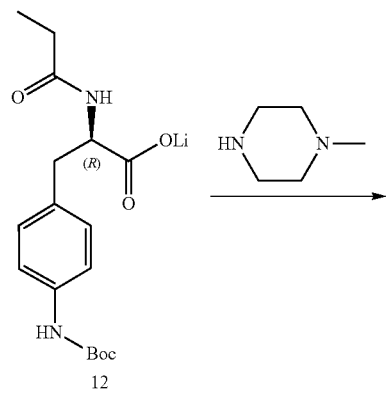

To a solution of lithium (2R)-3-(4-{[(tert-butoxy)carbonyl]amino}phenyl)-2-propanamidopropanoate) 12 (5.00 g, 14.6 mmol, 1.0 eq.) in DMF (50 mL) was added HATU (6.67 g, 17.5 mmol, 1.2 eq.) and DIPEA (6.4 mL, 36.5 mmol, 2.5 eq). The resulting mixture was stirred at RT for 10 min. and then N-methyl piperazine (1.54 g, 15.3 mmol, 1.05 eq,) was added. The resulting mixture was stirred at RT under a N$_2$ atmosphere for 1 h. The mixture was concentrated to dryness and the residue taken up in water (100 mL) and then extracted with DCM (2×100 mL). The organic layer was dried over sodium sulfate and concentrated which resulted to a precipitate. The solid was filtered to afford 39 as a white solid (4.30 g, 70%) which was used in the next step without further purification. UPLC-MS (basic 2 min): Rt=0.94 min; m/z=419.3 for [M+H]$^+$.

Example 118: (R)—N-(3-(4-aminophenyl)-1-(4-methylpiperazin-1-yl)-1-oxopropan-2-yl)propionamide (40)

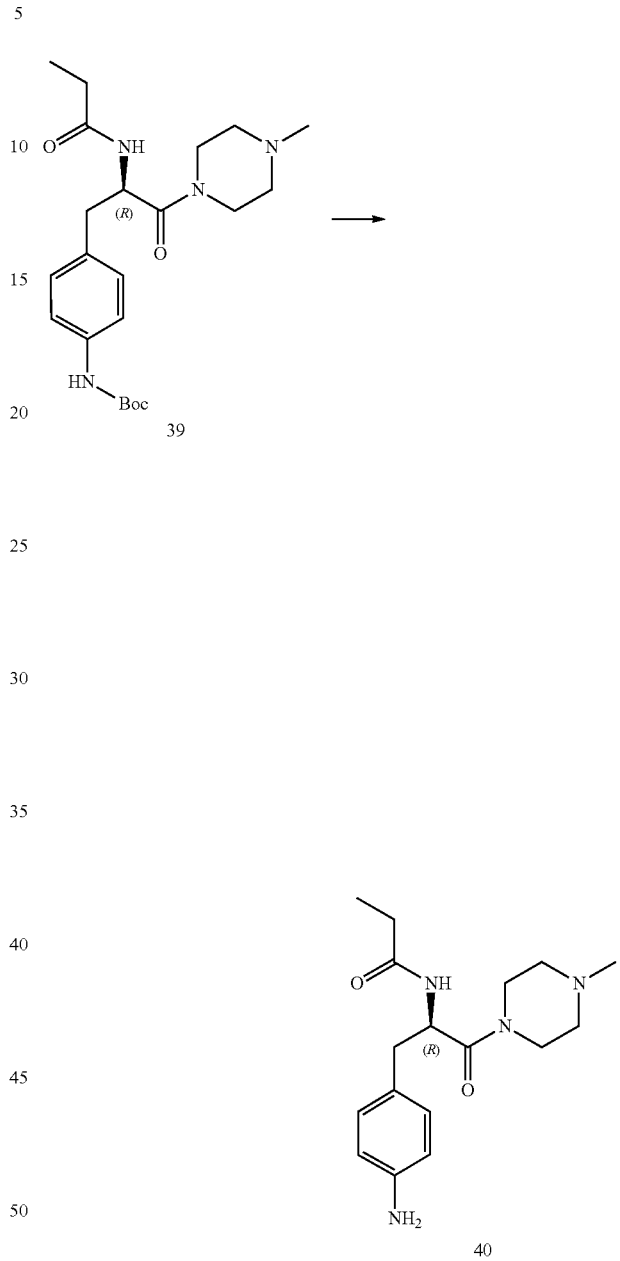

To a solution of tert-butyl (R)-(4-(3-(4-methylpiperazin-1-yl)-3-oxo-2-propionamidopropyl)phenyl) carbamate 40 (4.30 g, 10.3 mmol, 1.0 eq.) in DCM (125 mL) was added TFA (15 mL) and the resulting mixture was stirred at RT for 3 h. The reaction mixture was concentrated to dryness and the residue dissolved in DCM (20 mL). A solution of potassium carbonate (1.5 g) in water (20 mL) was added and the mixture was stirred vigorously for 20 mins. The organic phase was dried over sodium sulfate before filtering and concentrating to dryness to afford 35 as a white solid (1.50 g, 46%) which was used in the next step without further purification. UPLC-MS (basic 2 min): Rt=0.68 min; m/z=319.5 for [M+4]$^+$.

Example 119: tert-butyl ((S)-1-cycloheptyl-2-((4-((R)-3-(4-methylpiperazin-1-yl)-3-oxo-2-propionamidopropyl) phenyl)amino)-2-oxoethyl)carbamate (41)

Example 120: N—((R)-3-(4-((S)-2-amino-2-cycloheptylacetamido)phenyl)-1-(4-methylpiperazin-1-yl)-1-oxopropan-2-yl)propionamide (42)

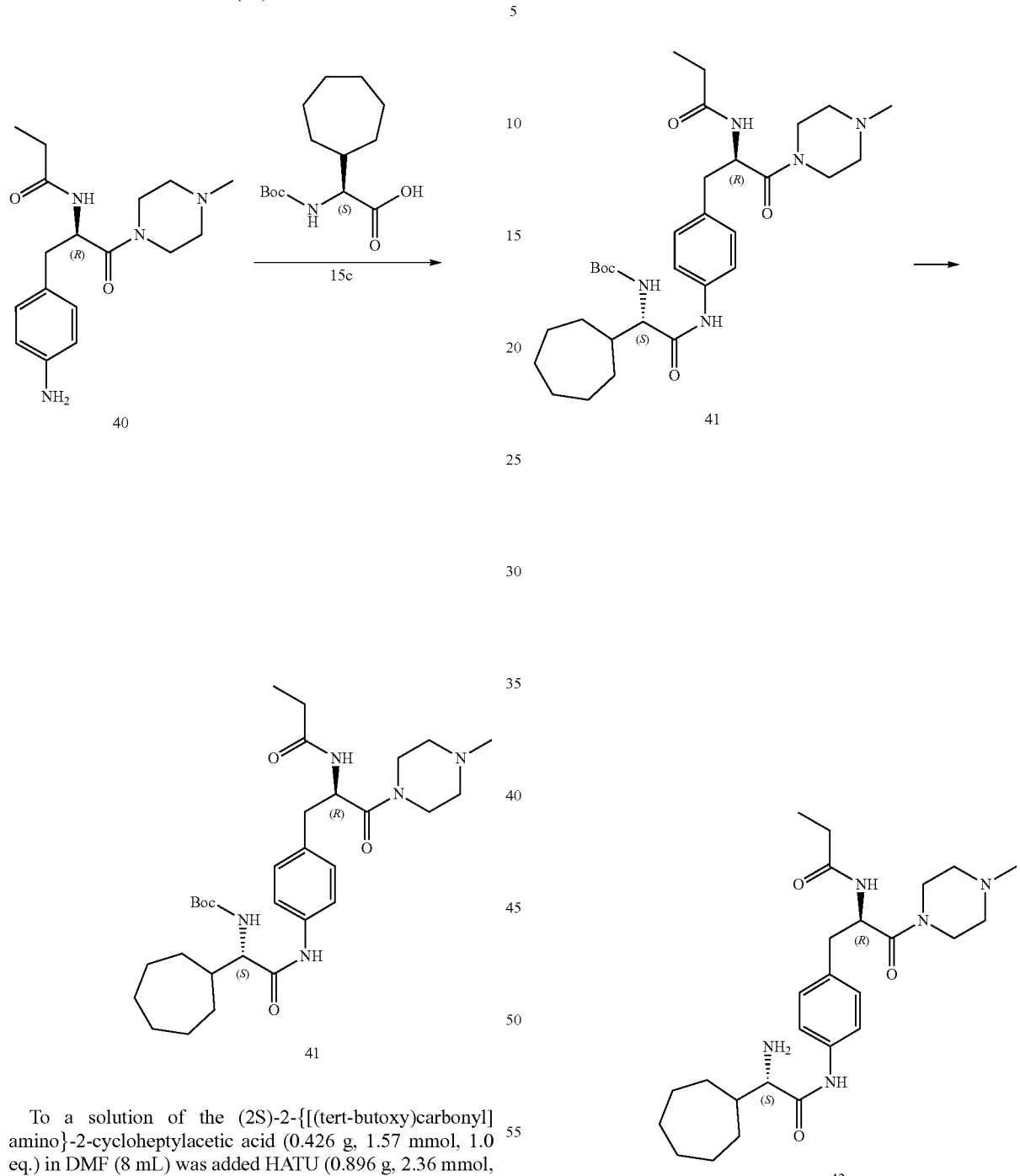

To a solution of the (2S)-2-{[(tert-butoxy)carbonyl]amino}-2-cycloheptylacetic acid (0.426 g, 1.57 mmol, 1.0 eq.) in DMF (8 mL) was added HATU (0.896 g, 2.36 mmol, 1.5 eq.) and DIPEA (0.82 mL, 4.71 mmol, 3.0 eq.) and the resulting mixture was stirred at RT for 10 minutes. A solution of (R)—N-(3-(4-aminophenyl)-1-(4-methylpiperazin-1-yl)-1-oxopropan-2-yl)propionamide 40 (0.500 g, 1.57 mmol, 1.0 eq.) was added and the reaction mixture was stirred at RT for 1 h. The reaction mixture was concentrated to dryness to afford 41 as an orange solid (0.650 g, 72%) which was used in the next step without further purification. UPLC-MS (basic 2 min): Rt=1.10 min; m/z=572.4 for [M+H]⁺

To a solution of 41 (0.225 g, 0.394 mmol, 1.0 eq.) in DCM (5 mL) was added TFA (0.75 mL) and the resulting mixture was stirred at RT for 3 h. The reaction mixture was concentrated to dryness to afford 42 as a brown gummy solid (0.230 g, 100%) which was used in the next step without further purification. UPLC-MS (basic 2 min): Rt=0.93 min; m/z=472.3 for [M+H]⁺.

Example 121: General Procedure I for the Synthesis of 163, 166 and 169

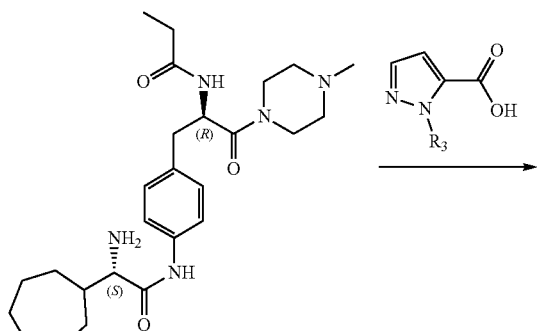

42

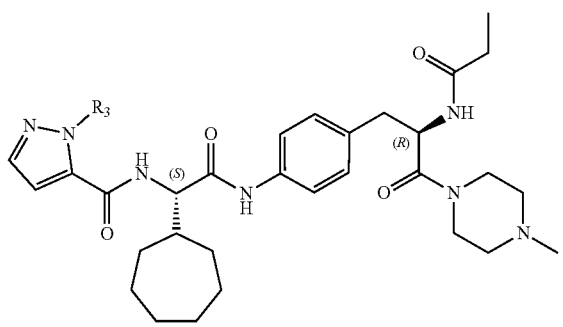

163, 166 and 169

To a solution of 1-methyl-1H-pyrazole-5-carboxylic acid (1.2 eq.) in DMF was added HATU (1.5 eq.) and DIPEA (4.0 eq) and then stirred at RT for 10 min. A solution of 42 (1.0 eq,) in DMF was added and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 163, 166 and 169.

Example 122: N—((S)-1-cycloheptyl-2-((4-((R)-3-(4-methylpiperazin-1-yl)-3-oxo-2-propionamidopropyl)phenyl)amino)-2-oxoethyl)-1-methyl-1H-pyrazole-5-carboxamide (163)

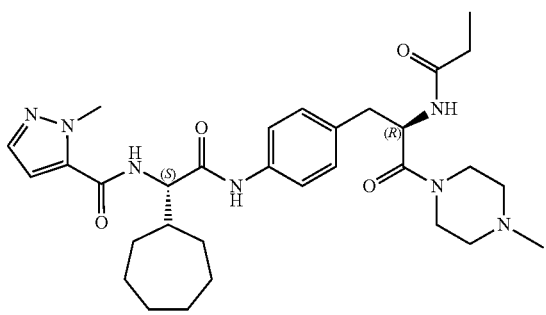

Following General Procedure I, 42 (0.080 g, 0.137 mmol, 1.0 eq.) was reacted with requisite 1-methyl-1H-pyrazole-5-carboxylic acid (0.021 g, 0.164 mmol, 1.2 eq.), HATU (0.078 g, 0.205 mmol, 1.5 eq.) and DIPEA (0.095 mL, 0.546 mmol, 4.0 eq.) in DMF (0.6 mL) to afford, after reverse phase column chromatography, 163 (45.0 mg, 57%) as a white solid. $^1$H NMR (400 MHz, DMSO-$d_6$) δ 8.22 (d, J=8.2 Hz, 1H), 7.53 (d, J=8.5 Hz, 2H), 7.46 (d, J=2.0 Hz, 1H), 7.30 (s, 1H), 7.17-7.10 (m, 2H), 7.07 (d, J=2.1 Hz, 1H), 6.71 (s, 1H), 4.86 (t, J=7.6 Hz, 1H), 4.46 (d, J=8.8 Hz, 1H), 4.03 (s, 3H), 3.35 (s, 4H), 2.86 (dd, J=13.3, 7.3 Hz, 1H), 2.77-2.67 (m, 1H), 2.25-1.95 (m, 7H), 1.91-1.25 (m, 9H), 0.91 (t, J=7.6 Hz, 3H). UPLC-MS (basic 2 min): rt=0.99 min; m/z=580.3 for [M+H]$^+$

Example 123: N—((S)-1-cycloheptyl-2-((4-((R)-3-(4-methylpiperazin-1-yl)-3-oxo-2-propionamidopropyl)phenyl)amino)-2-oxoethyl)-1-ethyl-1H-pyrazole-5-carboxamide (166)

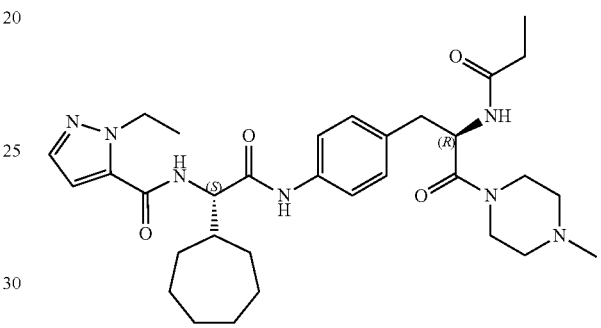

Following General Procedure I, 42 (0.080 g, 0.137 mmol, 1.0 eq.) was reacted with 2-ethyl-2H-pyrazole-5-carboxylic acid, HATU and DIPEA in DMF to afford, after reverse phase column chromatography, 166 (35.0 mg, 43%) as a white solid. UPLC-MS (basic 2 min): rt=1.02 min; m/z=594.3 for [M+H]$^+$.

Example 124: N—((S)-1-cycloheptyl-2-((4-((R)-3-(4-methylpiperazin-1-yl)-3-oxo-2-propionamidopropyl)phenyl)amino)-2-oxoethyl)-1-isopropyl-1H-pyrazole-5-carboxamide (169)

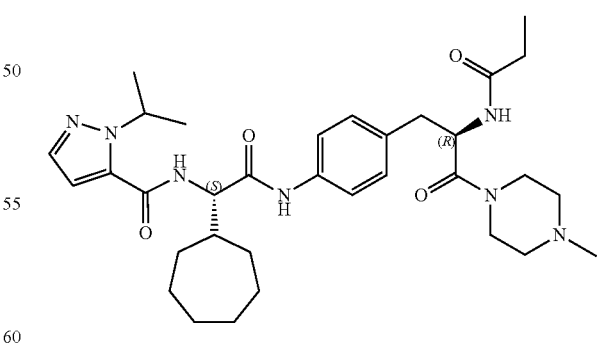

Following General Procedure I, 42 (0.080 g, 0.137 mmol, 1.0 eq.) was reacted with 2-isopropyl-2H-pyrazole-5-carboxylic acid, HATU and DIPEA in DMF to afford, after reverse phase column chromatography, 169 (25.0 mg, 30%) as a white solid. UPLC-MS (basic 2 min): rt=1.06 min; m/z=608.3 for [M+H]$^+$.

329

Example 125: tert-butyl (R)-(4-(3-(4-methylpiperazin-1-yl)-3-oxo-2-propionamidopropyl)benzyl)carbamate (44)

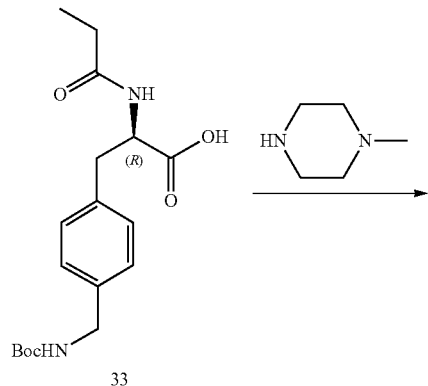

33

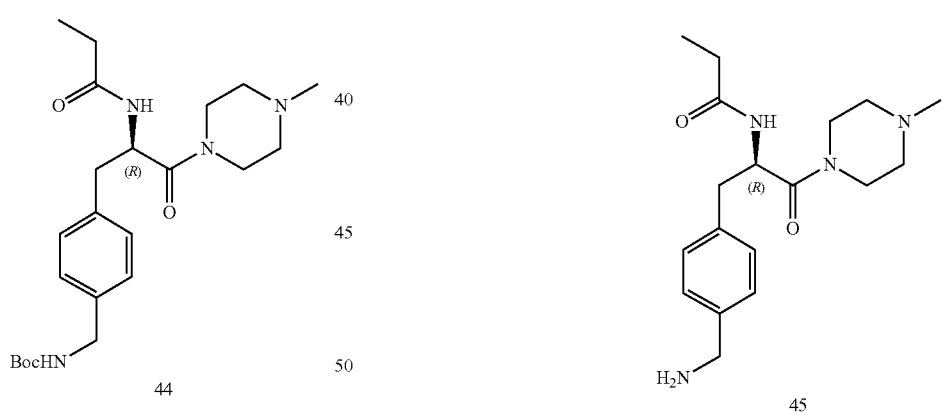

44

To a solution of (R)-3-(4-(((tert-butoxycarbonyl)amino)methyl)phenyl)-2-propionamidopropanoic acid 33 (5.38 g, 15.1 mmol, 1.0 eq.) in DMF (49 mL) was added HATU (8.61 g, 22.6 mmol, 1.5 eq.) and DIPEA (7.9 mL, 45.3 mmol, 3.0 eq). The resulting mixture was stirred at RT for 10 min. and then N-methyl piperazine (1.8 mL, 16.6 mmol, 1.1 eq,) was added. The resulting mixture was stirred at RT under a $N_2$ atmosphere for 1 h. The mixture was diluted with aq. sat. $NaHCO_3$ solution (500 mL) and then extracted with EtOAc (2×500 mL). The organic layer was washed with ice cold brine (2×1 L), dried over $Na_2SO_4$ then concentrated to afford 44 as an orange solid (3.72 g, 57%) which was used in the next step without further purification. UPLC-MS (basic 2 min): Rt=0.93 min; m/z=433.3 for [M+H]$^+$.

330

Example 126: (R)—N-(3-(4-(aminomethyl)phenyl)-1-(4-methylpiperazin-1-yl)-1-oxopropan-2-yl)propionamide (45)

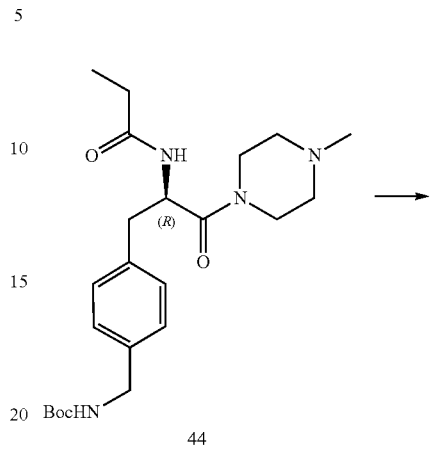

44

45

To a solution of tert-butyl (R)-(4-(3-(4-methylpiperazin-1-yl)-3-oxo-2-propionamidopropyl)benzyl)carbamate 44 (3.72 g, 8.60 mmol, 1.0 eq.) in DCM (37.0 mL) was added TFA (3.7 mL) and the resulting mixture was stirred at RT for 1 h. The reaction mixture was concentrated to dryness and the residue dissolved in DCM (20 mL). A solution of potassium carbonate (1.5 g) in water (20 mL) was added and the mixture was stirred vigorously for 20 mins. The organic phase was dried over sodium sulfate before filtering and concentrating to dryness to afford 45 as a brown solid (1.80 g, 63%) which was used in the next step without further purification. UPLC-MS (basic 2 min): Rt=0.69 min; m/z=333.2 for [M+H]$^+$.

Example 127: General Procedure J for the Synthesis of 46

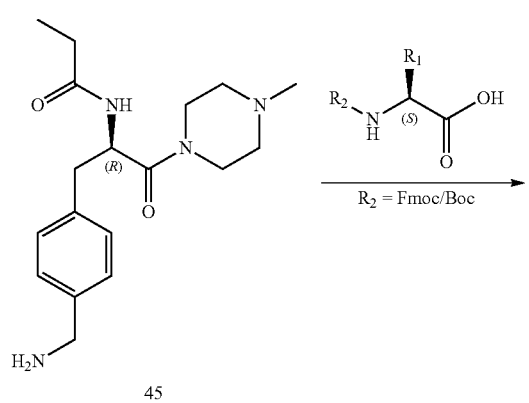

45

Example 128: tert-butyl ((S)-1-cycloheptyl-2-((4-((R)-3-(4-methylpiperazin-1-yl)-3-oxo-2-propionamidopropyl)benzyl)amino)-2-oxoethyl)carbamate (46)

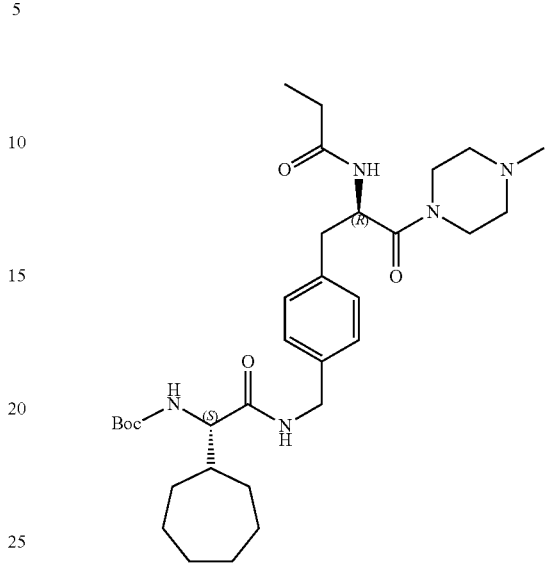

46

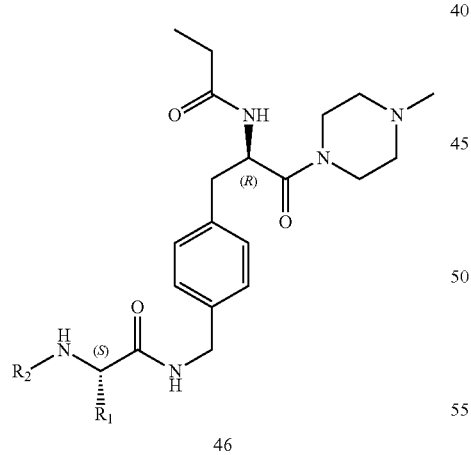

46

To a solution of the required amino acid (1.0-1.2 eq.) in DMF (0.05M) was added HATU (1.5 eq.) and DIPEA (3.0 eq.) and the resulting mixture was stirred at RT for 10 minutes. A solution of (R)—N-(3-(4-(aminomethyl)phenyl)-1-(4-methylpiperazin-1-yl)-1-oxopropan-2-yl)propionamide 45 (1.0 eq.) was added and the reaction mixture was stirred at RT for 1 h. The reaction mixture was concentrated to dryness to afford 46 which was used in the next step without further purification.

Following General Procedure J, 45 (0.350 g, 1.05 mmol, 1.0 eq.) was reacted with (2S)-2-{[(tert-butoxy)carbonyl]amino}-2-cycloheptylacetic acid (0.286 g, 1.05 mmol, 1.0 eq.), HATU (0.600 g, 1.58 mmol, 1.5 eq.) and DIPEA (0.55 mL, 3.16 mmol, 3.0 eq.) in DMF (3 mL) to afford 46 (0.537 g, 87%) as a white solid. UPLC-MS (basic 2 min): rt=1.09 min; m/z=586.4 for [M+H]$^+$.

Example 129: General Procedure K for the Synthesis of 47a-e

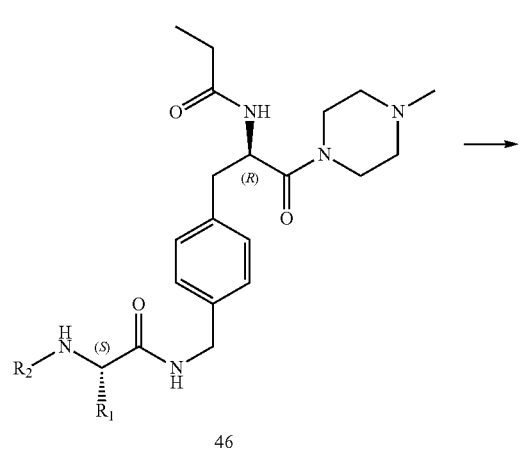

46

-continued

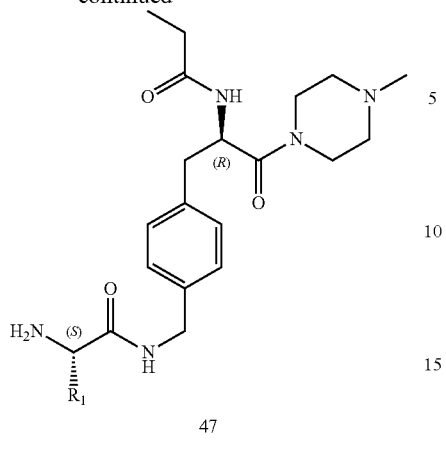

47

To a solution of 46 (1.0 eq.) in DCM (5 volumes) was added TFA (5 volumes) and the resulting mixture was stirred at RT for 0.5 h. The reaction mixture was concentrated to dryness to afford 47.

Example 130: (S)-1-cycloheptyl-2-((4-((R)-3-(4-methylpiperazin-1-yl)-3-oxo-2-propionamidopropyl)benzyl)amino)-2-oxoethan-1-aminium; trifluoroacetic acid (47)

Following General Procedure K, 46 (0.537 g, 0.917 mmol, 1.0 eq.) was reacted with TFA in DCM to afford 47 as a brown solid (0.540 g, 99%) which was used in the next step without further purification. UPLC-MS (basic 2 min): rt=0.91 min; m/z=486.3 for [M+H]$^+$.

Example 131: General Procedure L for the Synthesis of 162, 167 and 170

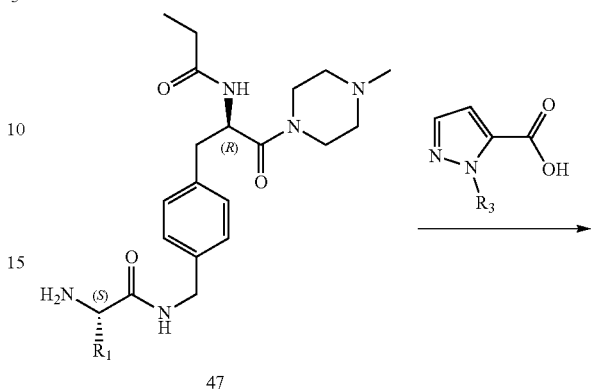

47

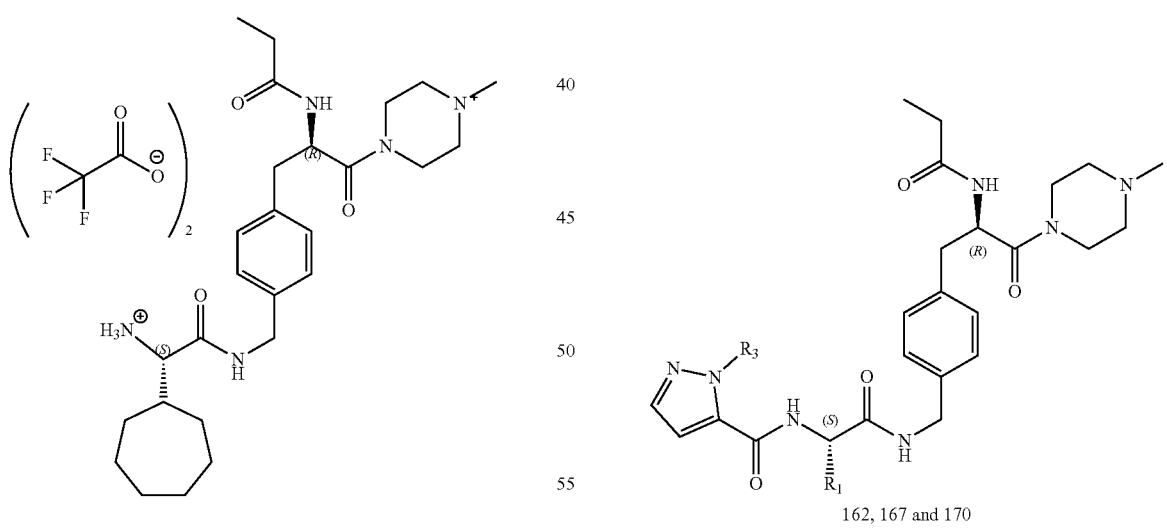

162, 167 and 170

To a solution of the required carboxylic acid (1.2 eq.) in DMF was added HATU (1.5 eq.) and DIPEA (4.0 eq) and then stirred at RT for 10 min. A solution of 47 (1.0 eq,) in DMF was added and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 162,167 and 170.

Example 132: N—((S)-1-cycloheptyl-2-((4-((R)-3-(4-methylpiperazin-1-yl)-3-oxo-2-propionamidopropyl)benzyl)amino)-2-oxoethyl)-1-methyl-1H-pyrazole-5-carboxamide (167)

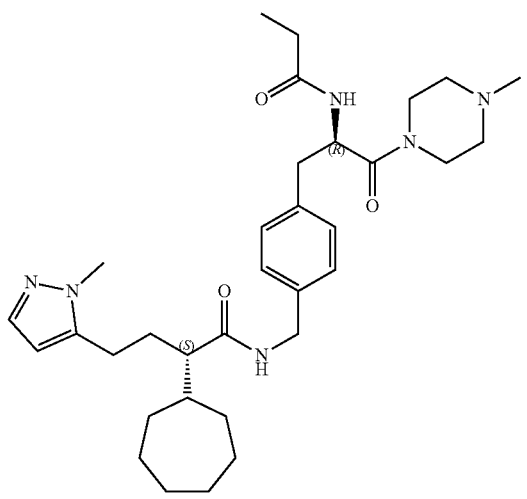

Following General Procedure L, 47 (0.180 g, 0.300 mmol, 1.0 eq.) was reacted with 1-methyl-1H-pyrazole-5-carboxylic acid (0.038 g, 0.300 mmol, 1.0 eq.), HATU (0.171 g, 0.450 mmol, 1.5 eq.) and DIPEA (0.314 mL, 1.8 mmol, 6.0 eq.) in DMF (3 mL) to afford, after reverse phase column chromatography, 167 (13.0 mg, 7%) as a white solid. UPLC-MS (basic 2 min): rt=0.98 min; m/z=594.3 for [M+H]$^+$.

Example 133: N—((S)-1-cycloheptyl-2-((4-((R)-3-(4-methylpiperazin-1-yl)-3-oxo-2-propionamidopropyl)benzyl)amino)-2-oxoethyl)-1-ethyl-1H-pyrazole-5-carboxamide (170)

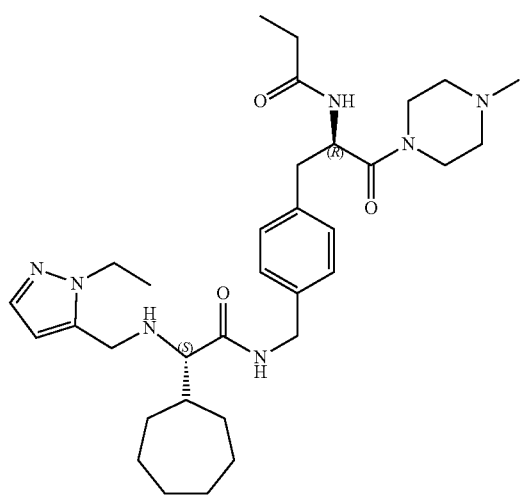

Following General Procedure L, 47 was reacted with 2-ethyl-2H-pyrazole-5-carboxylic acid, HATU and DIPEA in DMF to afford, after reverse phase column chromatography, 170 (5.0 mg, 8%) as a white solid. UPLC-MS (basic 2 min): rt=1.01 min; m/z=608.3 for [M+H]$^+$.

Example 134: N—((S)-1-cycloheptyl-2-((4-((R)-3-(4-methylpiperazin-1-yl)-3-oxo-2-propionamidopropyl)benzyl)amino)-2-oxoethyl)-1-isopropyl-1H-pyrazole-5-carboxamide (162)

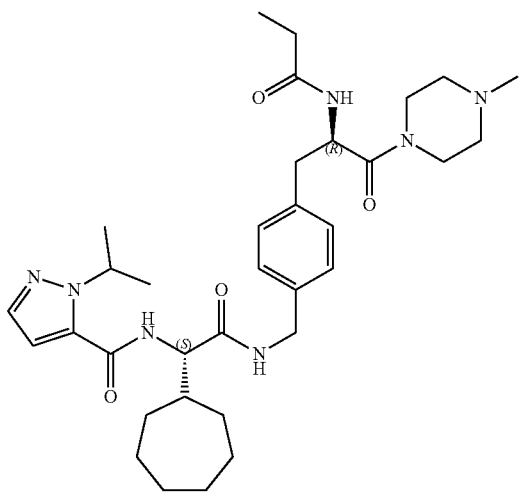

Following General Procedure L, 47 was reacted with 2-isopropyl-2H-pyrazole-5-carboxylic acid, HATU and DIPEA in DMF to afford, after reverse phase column chromatography, 162 (13.0 mg, 7%) as a white solid. UPLC-MS (basic 2 min): rt=1.05 min; m/z=622.3 for [M+H]$^+$.

Example 135: General Solid Phase Coupling Procedure

To a 1 eq of amine on solid phase, a solution of 3 eq of an acid (alpha-Fmoc protected amino acid or carboxylic acid), 3 eq of HATU, 6 eq of DIEA in DMF (final concentration 0.2-0.4M of the preactivated acid) was added and reacted for a minimum of 2 hours, unless otherwise noted. The resin was washed with DMF (5 times).

Example 136: General Solid Phase FMOC Deprotection Procedure

The Fmoc group was removed with 20% piperidine in DMF, 2+13 minutes, and the resin washed with DMF (6 times). The resin bound amine is ready to be modified with another coupling.

Example 137: Synthesis of Intermediate 48

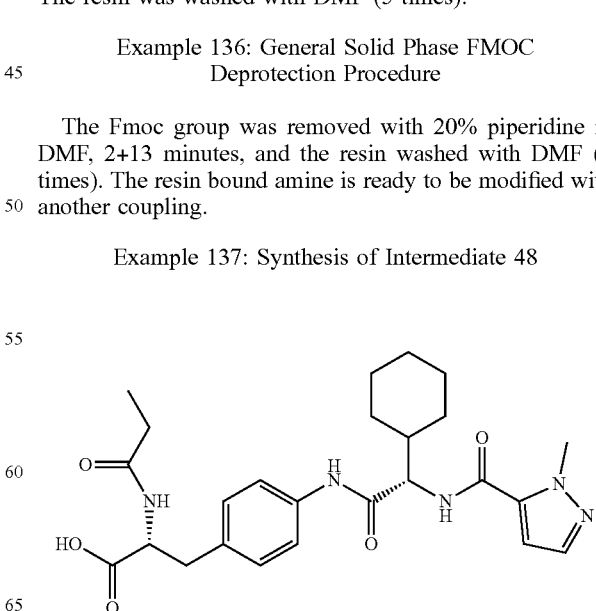

Wang resin 4 g, S=0.6 mmol/g was preloaded via HATU coupling of Fmoc-4'-nitro-R-phenyl alanine, 3 eq. rt, 6 h. 4 g of Wang resin (2.4 mmol) were split into two 50 mL syringes, 2 g resin each, swollen in DMF. Then 3.1 g (7.2 mmol=3 eq.) of Fmoc-4'-nitro-R-phenyl alanine, together with 2.75 g (7.2 mmol=3 eq.) of HATU was dissolved in 28 mL of DMF and then 2 mL (15 mmol=6 eq.) of DIEA and 150 ul of N-methylimidazole added, and shaken 2 min at rt. This solution of active ester was added to the resin in syringes (half each) and shaken another 6 h at rt. Then the resin was washed with DMF (5×2 min each) and used as is for the next step. The Fmoc group was deprotected by the procedure of Example 136, above. Measured substitution was 0.62 mmol/g.

Propionic acid was coupled using the procedure of Example 135, above. The Fmoc group was deprotected by the procedure of Example 136 above. Measured substitution 0.61 mmol/g.

Resin in the two syringes from previous steps was treated each 2× with 15 ml of 1M solution of dissolved $SnCl_2.2H_2O$ for total of 24 hours to reduce the nitro group. The resin was washed 6×DMF, then 2×DMF/DIEA and used as is for the next step. Fmoc-(S)-Cyclohexylglycine was coupled using the procedure of Example 135, above and the FMOC group was removed using the procedure of Example 136, above. 1-methyl-1H-pyrazole-5-carboxylic acid was coupled using the procedure of Example 135 above. The resin was washed with DMF (3×) and THE (4×) and dried in vacuo. The product was cleaved with 30% TFA/68% DCM/2% TIPS, rt, 3×1 h, and solution evaporated.

The crude product was purified using Gilson preparative HPLC, YMC column 250×50 plus 50×50 pre-column, Pack ODS-A, S-20 um, eluted with 60 mL/min gradient of water+0.1% TFA/acetonitrile, 0-100% in 22 min. Yield 625 mg (54%), MS m/z=484.3 Da.

Example 138: Synthesis of Intermediate 49

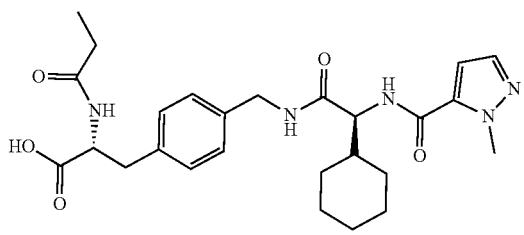 [SMILES: CCC(=O)N[C@H](Cc1ccc(CNC(=O)[C@@H](NC(=O)c2ccnn2C)C2CCCCC2)cc1)C(=O)O]

0.5 g of 2-Cl-Tritylchloride resin (declared substitution 1.7 mmol/g) was washed with dry DCM and a solution of 0.5 mmol (250 mg) of Fmoc-(D)Phe(4-$CH_2$—NH-Alloc) in 3 ml of dry DCM and 1 mmol DIEA were added. The reaction mixture was shaken for 45 min, the resin washed with DCM. The resin was capped with DCM/3 mmol HOAc/5 mmol DIEA for 10 minutes, washed with DCM and DMF. The Fmoc group was removed using the procedure of Example 136, above. Measured substitution 0.94 mmol/g. Propionic acid was coupled using the procedure of Example 135, above. The resin was washed with DMF and DCM and treated with 50 mg of $Pd(O)(PPh_3)_4$, 3 mmol dimethylbarbituric acid in 5 ml DCM, for 45 minutes. Repeated for another 45 minutes with fresh reagents. The resin was then washed with DCM, DCM/DMF/MeOH/DIEA (35/35/25/5), DMF.

Cyclohexylglycine was coupled using the procedure of Example 135, above and the FMOC group was removed using the procedure of Example 136, above. Measured substitution 0.76 mmol/g. 1-methyl-1H-pyrazole-5-carboxylic acid was coupled using the procedure of Example 135 above.

The resin was washed with DMF and DCM. The product was cleaved from the resin with trifluoroethanol/HOAc/DCM (2:2:6), 1 h and the cleaving solution was exchanged 4 times. After evaporation, the product was purified by RP HPLC, using YMC C8 30×100 column. Isolated yield 153 mg (66%, based on substitution 0.94 mmol/g).

Example 139: Synthesis of Compound 186 and Related Compounds

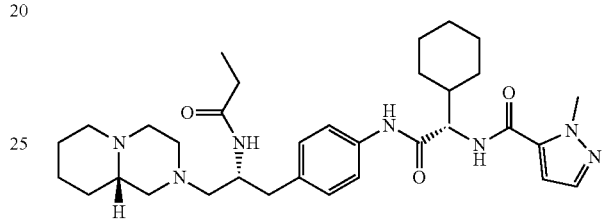

To a 20 mL scintillation vial was added the carboxylic acid intermediate 48 (15 mg, 0.031 mmol, 1 eq) DMF (0.5 mL), 1-hydroxybenzotriazole hydrate (14 mg, 0.09 mmol, 3 eq) and 1-(3-dimethylaminoproply)-3-ethylcarbodiimide hydrochloride (12 mg, 0.06 mmol 2 eq). The reaction mixture was stirred for 5 minutes when (S)-octahydro-1H-pyrido[1,2-A]pyrazine (9 mg, 0.06 mmol, 2 eq) was added. The reaction mixture was shaken at rt for 4 hours and then purified directly on a Beckman preparative system to provide 11.6 mg (0.019 mmol, 61%) of the desired compound. $M+H^+$: 606.3.

The compounds listed below in Table 2 were made by an analogous procedure to that described above and were characterized by mass spectroscopy.

TABLE 2

| Compound | $M + H^+$: |
|---|---|
| 172 | 613.1 |
| 174 | 642.1 |
| 175 | 628.3 |
| 176 | 648.2 |
| 177 | 642.1 |
| 178 | 566.3 |
| 185 | 654.3 |
| 188 | 606.1 |
| 189 | 592.1 |
| 191 | 618.5 |
| 192 | 592.1 |
| 193 | 620.5 |
| 194 | 606.5 |

Example 140: Synthesis of Compound 182 and Related Compound

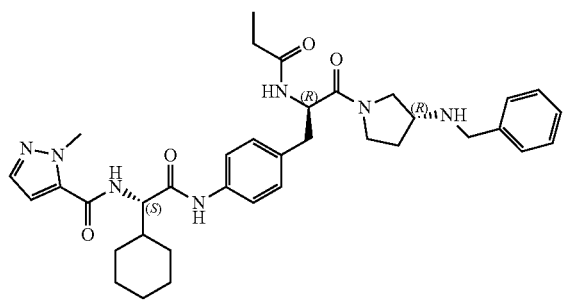

Intermediate 48 (25 mg, 0.0500 mmol), (3R)-(+)-3-(tert-butoxycarbonylamino)pyrrolidine (18.63 mg, 0.1000 mmol), 1-hydroxybenzotriazole hydrate (0.1 mmol, 13.5 mg) and DIC (0.1 mmol, 16 ul) were dissolved in 1 ml DMF and reacted overnight. The Boc protected intermediate was purified on Beckman instrument YMC C18 column 25×250, H₂O/ACN (0.1% HCOOH in H₂O, 0.1% HCOOH in ACN) to provide 18.7 mg (53% yield) of isolated. product.

Purified material was deprotected using TFA/DCM (1:1), 20 min, dried, dissolved in 1 ml solvent mixture (80% DCM/20% MeOH/2% AcOH) and benzaldehyde (3.4 mg, 0.0300 mmol) was added. The solution was shaken for 4 h and silica bound cyanoborohydride was added (120 mg, 1 mmol/g). The reaction mixture was shaken overnight, filtered, evaporated and purified on Beckman instrument YMC C18 column 25×250, H₂O/ACN (0.1% HCOOH in H20, 0.1% HCOOH in ACN). Purified overall yield of 182 was 9.3 mg (26.5% over all steps). M+H⁺: 642.1.

Compound 179 was made via an analogous procedure. M+H⁺: 642.1.

Example 141: Synthesis of Compound 184 and Related Compounds

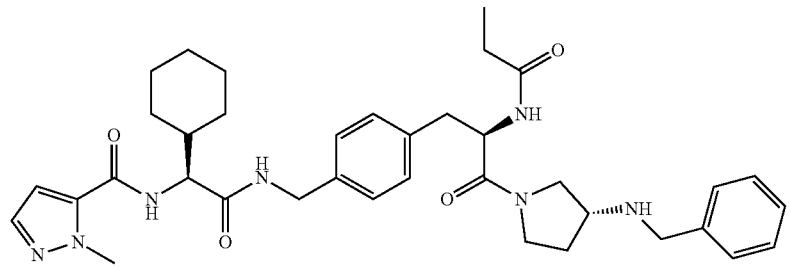 [SMILES: CCC(=O)N[C@H](Cc1ccc(CNC(=O)[C@@H](NC(=O)c2ccnn2C)C2CCCCC2)cc1)C(=O)N1CC[C@@H](NCc2ccccc2)C1]

Intermediate 49 (13.04 mg, 0.0700 mmol), 1-hydroxybenzotriazole (0.07 mmol, 10 mg) and DIC (0.07 mmol, 11 ul) was dissolved in 1 ml DMF and reacted overnight with a substituted amine. The Boc protected intermediate was purified on Beckman instrument YMC C18 column 25×250, H₂O/ACN (0.1% HCOOH in H₂0, 0.1% HCOOH in ACN). The purified material was deprotected with TFA/DCM (1:1) mixture for 20 min and dried to provide 12.8 mg (60%) of isolated product.

The dried material was dissolved in 1 ml solvent mixture (80% DCM/20% MeOH/2% AcOH) and benzaldehyde (2.12 mg, 0.0200 mmol) was added. The solution was shaken for 4 h and silica bound cyanoborohydride was added (200 mg, 1 mmol/g). The reaction mixture was shaken overnight, filtered, evaporated and purified on Beckman instrument YMC C18 column 25×250, H₂O/ACN (0.1% HCOOH in H₂O, 0.1% HCOOH in ACN). Purified overall yield of 184 was 4.9 mg (23%). M+H⁺: 656.4

Compound 183 was made via an analogous procedure. M+H⁺: 656.4

Example 142: Synthesis of Compound 181 and Related Compounds

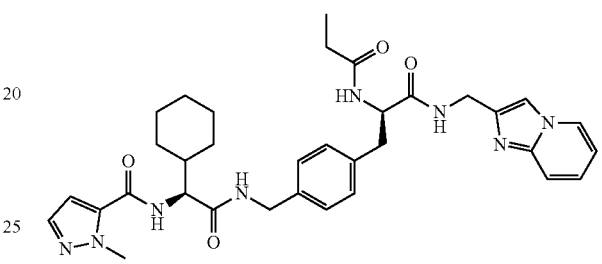

Intermediate 49 (12 mg, 0.024 mmol) was dissolved in DMF (1 ml), followed by addition of HOBt (9.8 mg, 0.072 mmol) and 1,3-diisopropylcarbodiimide (18 mg, 0.14 mmol). After shaking at RT for 10 min, imidazo[1,2-a]pyridin-2-ylmethanamine (11 mg, 0.072 mmol) was added. The resulting mixture was shaken at RT for 6 h and filtered. The filtrate was subjected to reversed phase HPLC and eluted with 5-100% ACN in H₂O with 0.1% formic acid to give the desired product as a white powder (10.6 mg, 70%). M+H⁺: 627.4.

The compounds listed below in Table 3 were made by an analogous procedure to that described above and were characterized by mass spectroscopy.

TABLE 3

| Compound | M + H⁺: |
|---|---|
| 173 | 642.4 |
| 180 | 662.3 |
| 187 | 656.1 |
| 190 | 656.5 |
| 195 | 634.5 |
| 196 | 668.5 |
| 197 | 620.4 |
| 198 | 620.5 |
| 199 | 606.3 |

TABLE 3-continued

| Compound | M + H⁺: |
|---|---|
| 200 | 632.5 |
| 201 | 606.3 |
| 202 | 620.6 |

Example 143: Synthesis of Intermediate 53

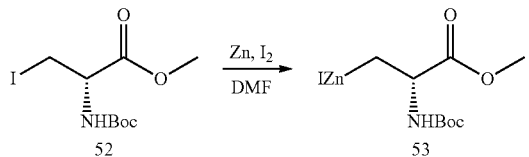

To a suspension of Zn (28.4 g, 434 mmol, 1.78 eq) in DMF (200 mL) was added I$_2$ (6.17 g, 24.3 mmol, 4.90 mL, 0.100 eq) at 20° C., then the mixture was stirred for 0.2 hr while the color changed from brown to grey. Then to the suspension was added compound 52 (80.0 g, 243 mmol, 1.00 eq) along with I$_2$ (6.17 g, 24.3 mmol, 4.90 mL, 0.100 eq) at 20.0° C. which was stirred at 20° C. for 2 hrs. The iodozinc compound 53 was not isolated.

Example 144: Synthesis of Intermediate 54

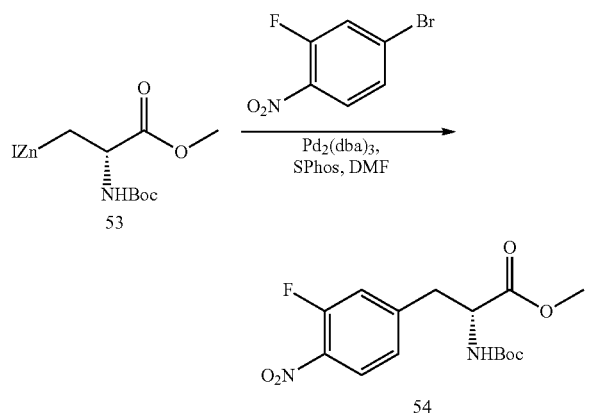

To compound 53 in DMF (200 mL) was added to a mixture of 3-fluoro, 4-nitro bromobenzene (53.5 g, 243 mmol, 1.00 eq), SPhos (5.99 g, 14.6 mmol, 0.060 eq) and Pd$_2$(dba)$_3$ (6.68 g, 7.29 mmol, 0.030 eq) in DMF (400 mL) at 20° C., which was then stirred at 65° C. under N$_2$ for 6 hrs. TLC (plate 1, Petroleum ether:Ethyl acetate=5:1, R$_f$=0.23) showed that some 3-fluoro, 4-nitro bromobenzene remained and one other major spot was formed. LCMS indicated the formation of desired product. The reaction mixture was concentrated under reduced pressure to remove most DMF, diluted with ethyl acetate (500 mL) and water (300 mL) and filtered and extracted with further ethyl acetate (200 mL (3×)). The combined organic layer was washed with water (300 mL) and brine (300 mL), dried over Na$_2$SO$_4$ and concentrated under reduced pressure to give a residue. The residue was purified by column (SiO$_2$, Petroleum ether:Ethyl acetate=1:0 to 10:1; plate 2, Petroleum ether:Ethyl acetate=5:1) to provide the desired product compound 54 (36.0 g, 105 mmol, 43.3% yield) as a yellow solid, which was used in the next step. LCMS: (M-99)⁺: 243.2.

Example 145: Synthesis of Intermediate 55


To a solution of compound 54 (36.0 g, 105 mmol, 1.00 eq) in THF (300 mL) was added a solution of LiOH H$_2$O (8.83 g, 210 mmol, 2.00 eq) in H$_2$O (300 mL), and the mixture was stirred at 20° C. for 12 hrs. LCMS indicated the presence of desired product. The reaction mixture was diluted with water (150 mL), then the pH of the solution was adjusted to 3 by 1 M HCl and extracted with ethyl acetate (200 mL (3×)), the combined organic layer was washed with brine (300 mL (2×)), dried over Na$_2$SO$_4$ and concentrated under reduced pressure to give a crude product compound 55 (36.8 g, crude) as a brown gum. LCMS: (M 99)⁺: 229.1.

Example 146: Synthesis of Intermediate 56

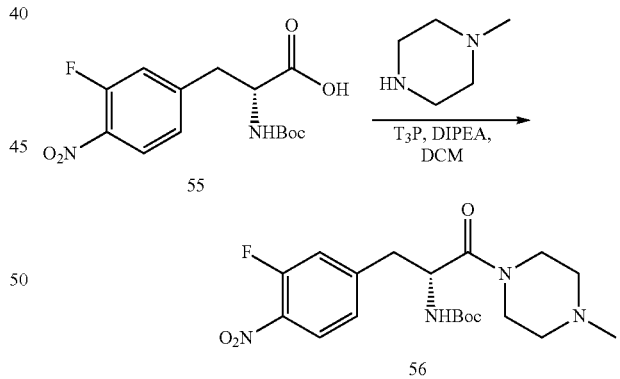

To a solution of compound 55 (36.8 g, 106 mmol, 1.00 eq) in DCM (350 mL) was added N-methyl piperidine (12.8 g, 127 mmol, 14.1 mL, 1.20 eq) followed with T$_3$P (81.0 g, 127 mmol, 75.7 mL, 50.0% purity, 1.20 eq) and DIEA (20.6 g, 159 mmol, 27.7 mL, 1.50 eq) at −20° C., then the mixture was stirred at −20° C. for 1.5 hrs. LCMS showed compound 55 was completely consumed and desired product was formed. The reaction mixture was diluted with sat. aq. NaHCO$_3$ (300 mL), the organic layer was washed with water (200 mL) and brine (200 mL), dried over Na$_2$SO$_4$ and concentrated under reduced pressure to give the crude product compound 56 (41.4 g, crude) as a yellow gum. A sample was obtained by prep-TLC (plate 1, DCM: MeOH=10:1, $R_f$=0.47) whose structure was confirmed by LCMS (M+H)$^+$: 411.3.

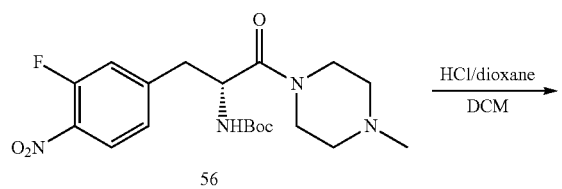

56

Example 147: Synthesis of Intermediate 57

To a solution of compound 56 (41.4 g, 101 mmol, 1.00 eq) in DCM (250 mL) was added HCl/dioxane (4.00 M, 250 mL, 9.93 eq) at 0° C. Then the mixture was warmed to 20° C. and stirred for 1 hr. LCMS showed compound 56 was completely consumed to provide desired product. The reaction mixture was concentrated under reduced pressure to give a crude product compound 57 (40.9 g, crude, 2HCl) as a yellow solid. LCMS: (M+1)$^+$: 311.3. H$^1$ NMR: (400 MHz, DMSO) δ 11.77-11.64 (m, 1H), 8.63-8.48 (m, 3H), 8.13 (t, J=8.0 Hz, 1H), 7.70-7.34 (m, 2H), 4.80-4.73 (m, 1H), 4.44-4.15 (m, 2H), 3.51-2.82 (m, 8H), 2.74 (s, 3H). F NMR: (376 MHz, DMSO) δ 119.31.

Example 148: Synthesis of Intermediate 58

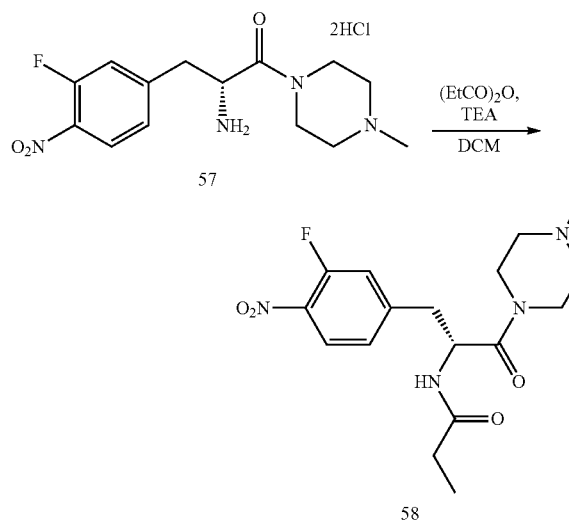

58

To a solution of compound 57 (40.9 g, 107 mmol, 1.00 eq, 2HCl) in DCM (400 mL) was added TEA (32.4 g, 320 mmol, 44.5 mL, 3.00 eq) and propanoyl propanoate (16.7 g, 128 mmol, 16.5 mL, 1.20 eq) at 0° C. in turn. Then the mixture was warmed to 20° C. and stirred for 2 hrs. LCMS indicated the formation of desired product. The reaction mixture was diluted with sat. aq. NaHCO$_3$ (100 mL) and extracted with further DCM (50.0 mL*2), the combined organic layer was washed with brine (50.0 mL), dried over Na$_2$SO$_4$ and concentrated under reduced pressure to give the desired product compound 58 (36.7 g, crude) as a yellow solid. LCMS: (M+1)$^+$: 367.3.

Example 149: Synthesis of Intermediate 59

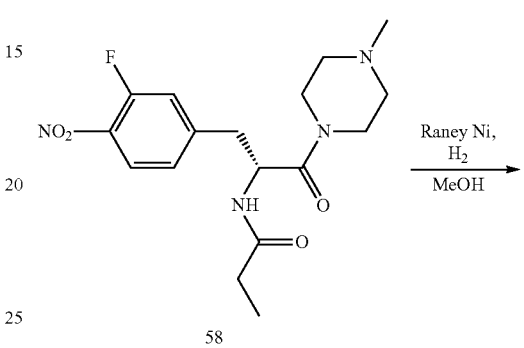

58

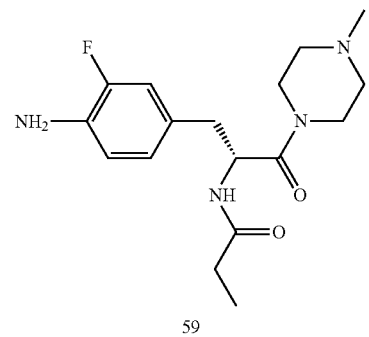

59

To a solution of compound 58 (35.7 g, 97.6 mmol, 1.00 eq) in MeOH (350 mL) was added Raney Ni (7.00 g, 119 mmol, 1.22 eq) under N$_2$ at 20° C., then the mixture was degassed and purged with H$_2$ (50 psi) and stirred for 4 hrs. LCMS indicated the presence of desired product. The reaction mixture was filtered and concentrated under reduced pressure to give a residue. The residue was purified by Reverse-MPLC (NH$_4$OH) on Xtimate C-18 (20/40 um, 120A) gel eluted with H$_2$O:MeCN (75:25) to get the desired product 59 (21.3 g, 61.3 mmol, 62.8% yield, 96.8% purity) as a yellow solid. LCMS: (M+1)$^+$: 337.3. H$^1$ NMR: (400 MHz, DMSO) δ 8.11 (d, J=8.4 Hz, 1H), 6.83-6.80 (m, 1H), 6.71-6.61 (m, 2H), 4.93 (s, 2H), 4.83-4.77 (m, 1H), 3.39-3.33 (m, 4H), 2.75-2.60 (m, 2H), 2.19-2.16 (m, 3H), 2.10 (s, 3H), 2.06 (q, J=7.6 Hz, 2H), 1.95-1.91 (m, 1H), 0.91 (t, J=7.2 Hz, 3H). F$^{19}$ NMR: (376 MHz, DMSO) δ 135.55.

Example 150: General Procedure M for the Synthesis of 61a-d

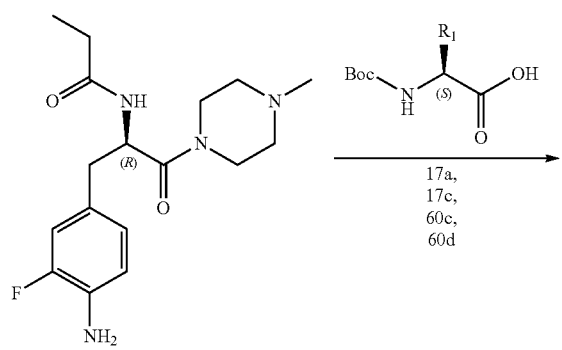

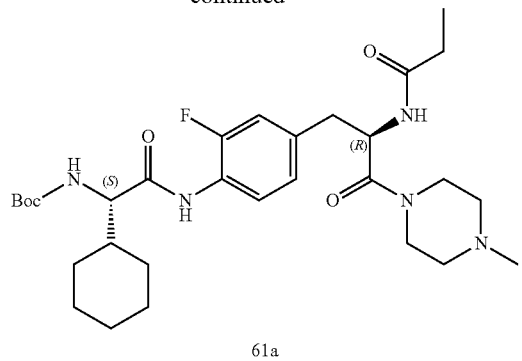

To a solution of N-[(2R)-3-(4-amino-3-fluorophenyl)-1-(4-methylpiperazin-1-yl)-1-oxopropan-2-yl]propanamide 59 (1.0 eq.) in DMF were added 17a, 17c, 60c, or 60d (1.2 eq.), DIPEA (4.0-8.0 eq.) and HATU (1.5-2.0 eq.) and the resulting mixture was stirred for 1 h. Aqueous saturated sodium bicarbonate solution was added and then extracted with EtOAc. The combined organic phase was washed with brine, dried over sodium sulfate then concentrated to afford 61a-d which was used in the next step without further purification.

Example 151: tert-butyl N—[(S)-cyclohexyl({2-fluoro-4-[(2R)-3-(4-methylpiperazin-1-yl)-3-oxo-2-propanamidopropyl]phenyl}carbamoyl)methyl]carbamate (61a)

Following General Procedure M, 59 (2.69 g, 8.00 mmol, 1.0 eq.) was reacted with (2S)-2-{[(tert-butoxy)carbonyl]amino}-2-cyclohexylacetic acid 17a (2.47 g, 9.60 mmol, 1.2 eq.), HATU (6.08 g, 16.0 mmol, 2.0 eq.) and DIPEA (5.6 mL, 32.0 mmol, 4.0 eq.) in DMF (27 mL) to afford, after aqueous work-up, 61a (4.41 g, 96% yield) as a yellow solid which was used in the next step without further purification. UPLC-MS (basic 2 min): rt=1.09 min; m/z=576.3 for [M+H]$^+$.

Example 152: tert-butyl N—[(S)-cycloheptyl({2-fluoro-4-[(2R)-3-(4-methylpiperazin-1-yl)-3-oxo-2-propanamidopropyl]phenyl}carbamoyl)methyl]carbamate (61b)

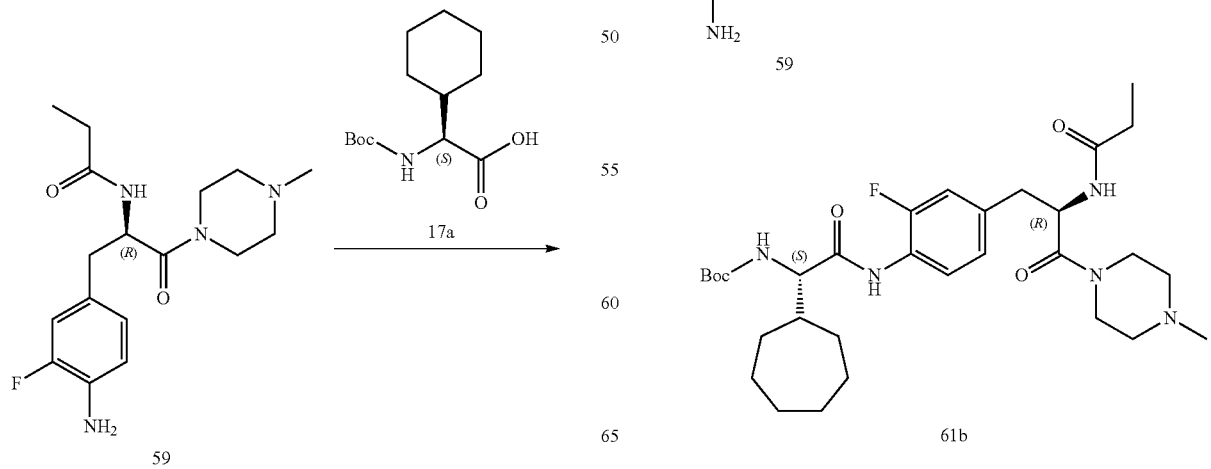

Following General Procedure M, 59 (0.200 g, 0.595 mmol, 1.0 eq.) was reacted with (2S)-2-{[(tert-butoxy)carbonyl]amino}-2-cycloheptylacetic acid) 17c (0.194 g, 0.713 mmol, 1.2 eq.), HATU (0.339 g, 0.892 mmol, 1.5 eq.) and DIPEA (0.83 mL, 4.76 mmol, 8.0 eq.) in DMF (2 mL) to afford, after aqueous work-up, 61b (0.140 g, 40% yield) as a yellow-orange gummy solid which was used in the next step without further purification. UPLC-MS (basic 2 min): rt=1.12 min; m/z=590.2 for [M+H]$^+$.

Example 153: tert-butyl N—[(S)-(4,4-difluorocyclohexyl)({2-fluoro-4-[(2R)-3-(4-methylpiperazin-1-yl)-3-oxo-2-propanamidopropyl]phenyl}carbamoyl)methyl]carbamate) (61c)

Example 154: tert-butyl N—[(S)-({2-fluoro-4-[(2R)-3-(4-methylpiperazin-1-yl)-3-oxo-2-propanamidopropyl]phenyl}carbamoyl)[(1r,4S)-4-methylcyclohexyl]methyl]carbamate) (61d)

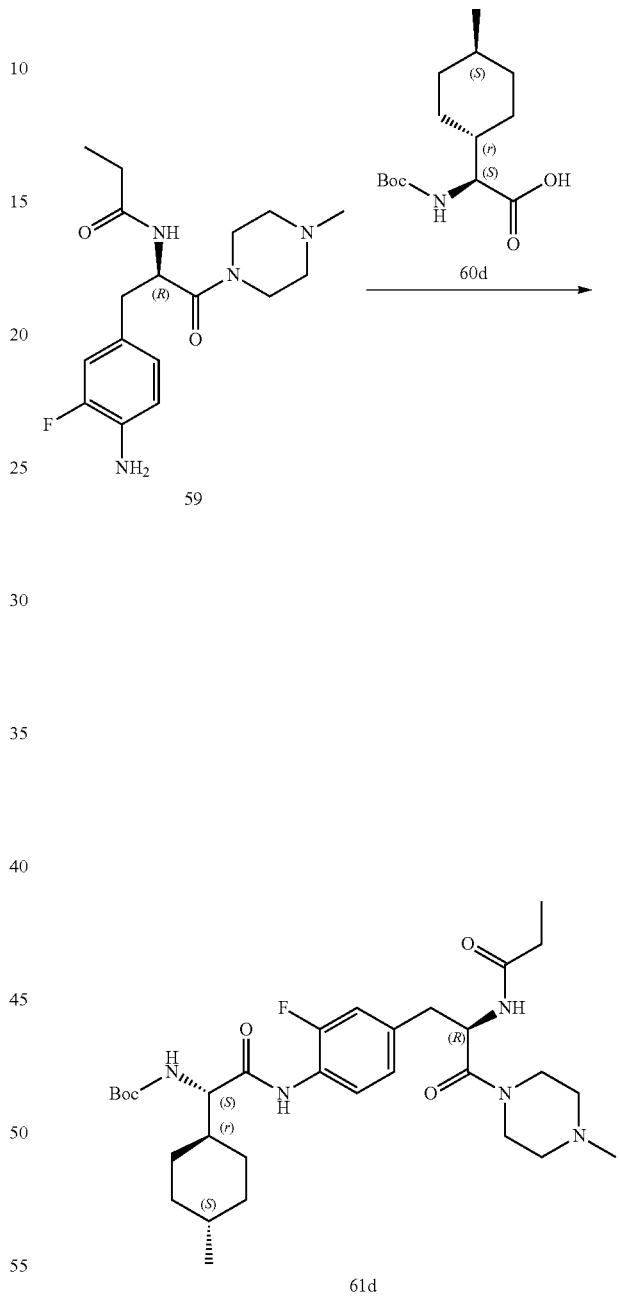

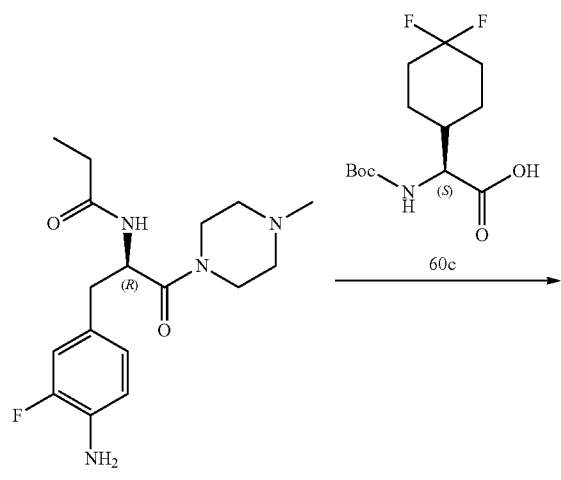

Following General Procedure M, 59 (0.300 g, 0.892 mmol, 1.0 eq.) was reacted with (2S)-2-{[(tert-butoxy)carbonyl]amino}-2-(4,4-difluorocyclohexyl)acetic acid) 60c (0.314 g, 1.07 mmol, 1.2 eq.), HATU (0.678 g, 1.78 mmol, 2.0 eq.) and DIPEA (1.2 mL, 7.13 mmol, 8.0 eq.) in DMF (6 mL) to afford, after aqueous work-up, 61c (0.284 g, 52% yield) as a yellow gummy solid which was used in the next step without further purification. UPLC-MS (basic 2 min): rt=1.04 min; m/z=612.3 for [M+H]$^+$.

Following General Procedure M, 59 (0.200 g, 0.595 mmol, 1.0 eq.) was reacted with (2S)-2-{[(tert-butoxy)carbonyl]amino}-2-[(1r,4S)-4-methylcyclohexyl]acetic acid) 60d (0.194 g, 0.713 mmol, 1.2 eq.), HATU (0.339 g, 0.892 mmol, 1.5 eq.) and DIPEA (0.83 mL, 4.76 mmol, 8.0 eq.) in DMF (2 mL) to afford, after aqueous work-up, 61d (0.184 g, 53% yield) as a yellow gummy solid which was used in the next step without further purification. UPLC-MS (basic 2 min): rt=1.14 min; m/z=590.2 for [M+H]$^+$.

Example 155: General Procedure N for the Synthesis of 62a-d

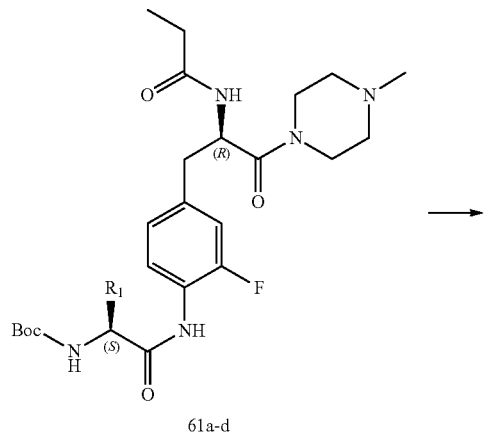

61a-d

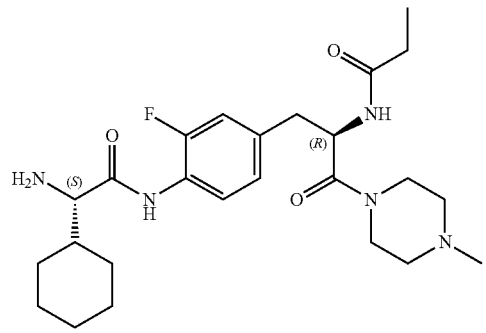

62a-d

To a solution of 61a-d (1.0 eq.) in DCM was added TFA and the resulting mixture was stirred at RT for 0.5 h. The reaction mixture was concentrated to dryness and the residue was stirred in aq. sat. $K_2CO_3$ solution and then extracted with DCM to afford 62a-d which was used in the next step without further purification.

Example 156: N-[(2R)-3-{4-[(2S)-2-amino-2-cyclohexylacetamido]-3-fluorophenyl}-1-(4-methylpiperazin-1-yl)-1-oxopropan-2-yl]propanamide (62a)

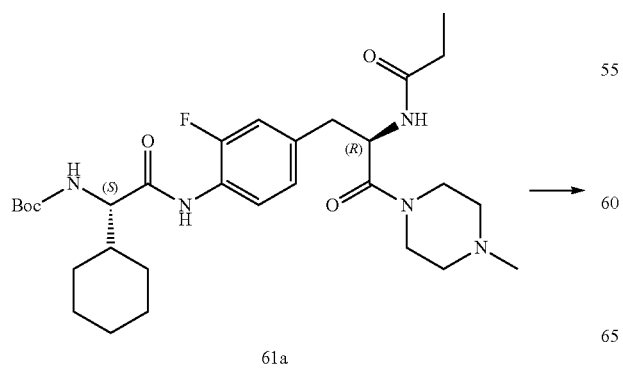

61a

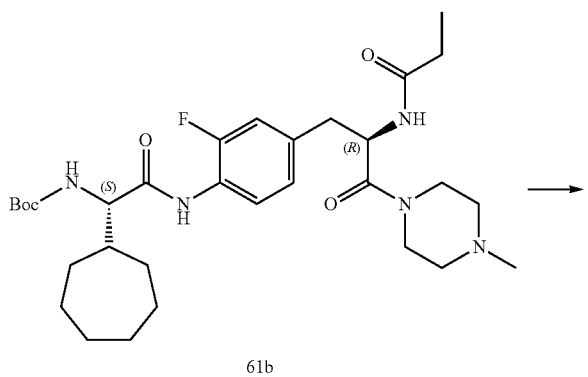

62a

Following General Procedure N, 61a (3.11 g, 5.40 mmol, 1.0 eq.) was reacted with TFA (10 mL) in DCM (10 mL) to afford, after aqueous work-up, 62a (2.54 g, 99% yield) as a yellow solid which was used in the next step without further purification. UPLC-MS (basic 2 min): rt=0.93 min; m/z=476.3 for $[M+H]^+$.

Example 157: N-[(2R)-3-{4-[(2S)-2-amino-2-cycloheptylacetamido]-3-fluorophenyl}-1-(4-methylpiperazin-1-yl)-1-oxopropan-2-yl]propanamide (62b)

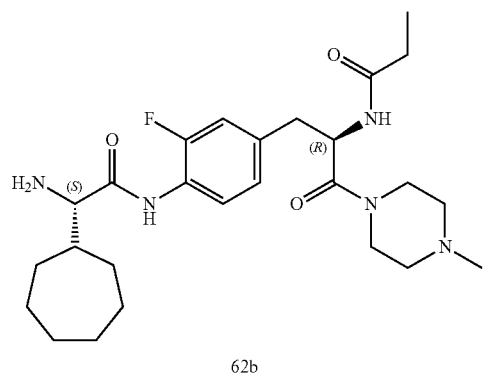

61b

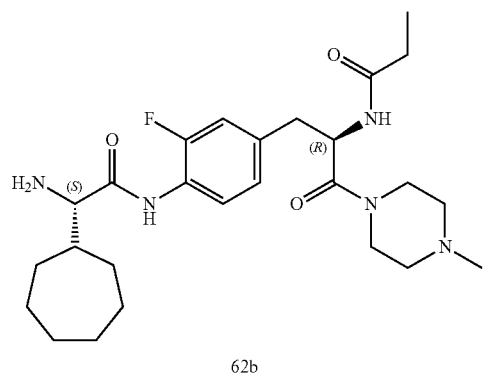

62b

Following General Procedure N, 61b (0.140 g, 0.237 mmol, 1.0 eq.) was reacted with TFA (1 mL) in DCM (2 mL) to afford, after aqueous work-up, 62b (0.084 g, 72% yield) as a yellow gummy solid which was used in the next step without further purification. UPLC-MS (basic 2 min): rt=0.99 min; m/z=490.3 for $[M+H]^+$.

Example 158: N-[(2R)-3-{4-[(2S)-2-amino-2-(4,4-difluorocyclohexyl)acetamido]-3-fluorophenyl}-1-(4-methylpiperazin-1-yl)-1-oxopropan-2-yl]propanamide) (62c)

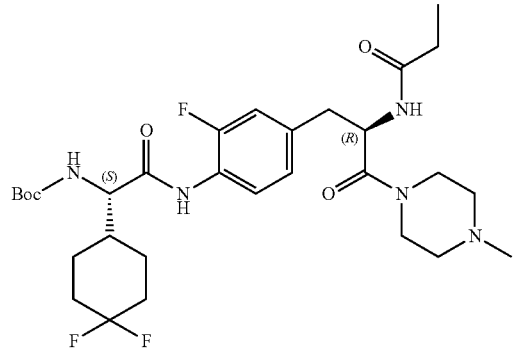

61c

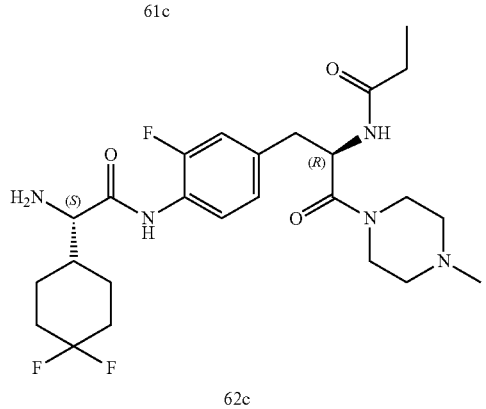

62c

Following General Procedure N, 61c (0.284 g, 0.464 mmol, 1.0 eq.) was reacted with TFA (2 mL) in DCM (4 mL) to afford, after aqueous work-up, 62c (0.190 g, 80% yield) as a yellow gummy solid which was used in the next step without further purification. UPLC-MS (basic 2 min): rt=0.88 min; m/z=512.2 for [M+H]$^+$.

Example 159: N-[(2R)-3-{4-[(2S)-2-amino-2-[(1R,4S)-4-methylcyclohexyl]acetamido]-3-fluorophenyl}-1-(4-methylpiperazin-1-yl)-1-oxopropan-2-yl]propanamide) (62d)

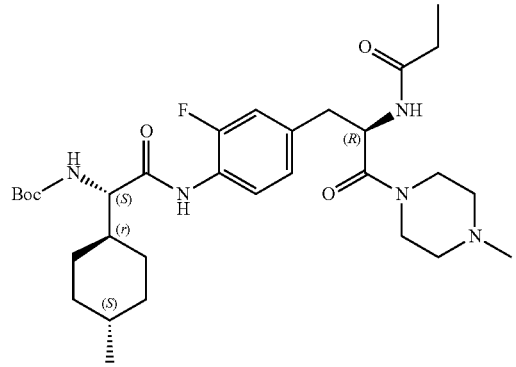

61d

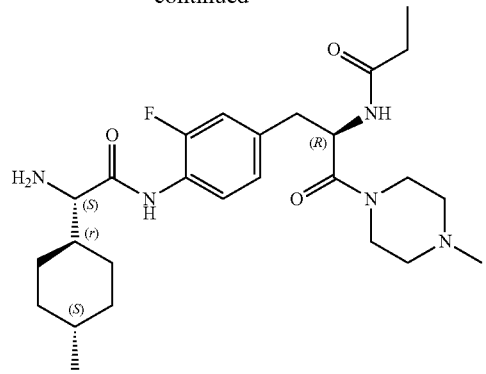

62d

Following General Procedure N, 61d (0.160 g, 0.271 mmol, 1.0 eq.) was reacted with TFA (1 mL) in DCM (2 mL) to afford, after aqueous work-up, 62d (0.090 g, 68% yield) as a yellow gummy solid which was used in the next step without further purification. UPLC-MS (basic 2 min): rt=0.99 min; m/z=490.3 for [M+H]$^+$.

Example 160: General Procedure 0 for the Synthesis of Compounds 203-216, 235-239 and 302

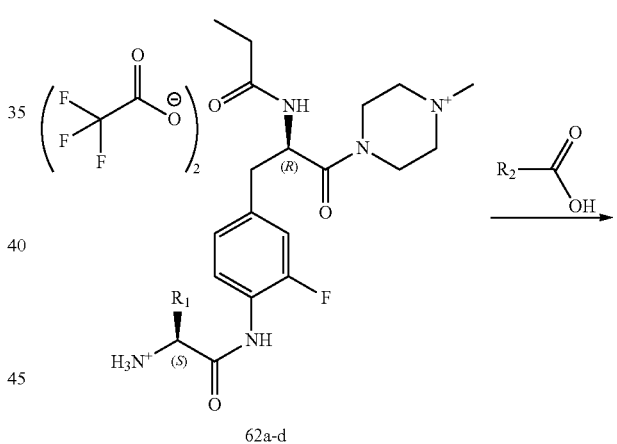

62a-d 203-216, 235-239 and 302

To a solution of 62a-d (1.0 eq.) in DMF were added the required carboxylic acid (1.2 eq.), DIPEA (3.0-8.0 eq.) and then HATU (1.5-2.0 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford compounds 203-216, 235-239 and 302.

Example 161: N-[(2R)-3-{4-[(2S)-2-cyclohexyl-2-[2,2-difluoro-2-(6-methoxypyridin-3-yl)acetamido]acetamido]-3-fluorophenyl}-1-(4-methylpiperazin-1-yl)-1-oxopropan-2-yl]propanamide (203)

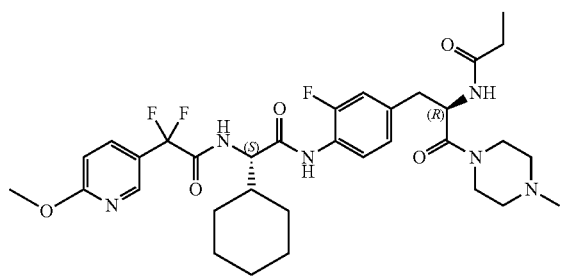

Following General Procedure O, 62a (0.050 g, 0.105 mmol, 1.0 eq.) was reacted with 2,2-difluoro-2-(6-methoxypyridin-3-yl)acetic acid (0.026 g, 0.208 mmol, 1.2 eq.), DIPEA (0.06 mL, 0.315 mmol, 3.0 eq.) and HATU (0.060 g, 0.158 mmol, 1.5 eq.) in DMF (1 mL) to afford, after reverse phase column chromatography, 203 (29.8 mg) as a white solid. ¹H NMR (400 MHz, DMSO-d₆) δ 9.93 (s, 1H), 9.05 (d, J=8.0 Hz, 1H), 8.42 (d, J=2.5 Hz, 1H), 8.23 (d, J=8.4 Hz, 1H), 7.92 (dd, J=8.8, 2.6 Hz, 1H), 7.66 (t, J=8.2 Hz, 1H), 7.10 (dd, J=11.8, 1.9 Hz, 1H), 7.04-6.94 (m, 2H), 4.90 (q, J=7.7 Hz, 1H), 4.42 (t, J=8.4 Hz, 1H), 3.90 (s, 3H), 3.41 (d, J=10.2 Hz, 4H), 2.89 (dd, J=13.4, 6.8 Hz, 1H), 2.75 (dd, J=13.3, 7.9 Hz, 1H), 2.21-2.14 (m, 2H), 2.11-2.00 (m, 6H), 1.94-1.82 (m, 2H), 1.66 (d, J=10.3 Hz, 3H), 1.58 (s, 2H), 1.12 (d, J=9.8 Hz, 4H), 0.90 (t, J=7.6 Hz, 4H). UPLC-MS (basic 2 min): rt=1.10 min; m/z=661.4 for [M+H]⁺.

Example 162: N-[(2R)-3-{4-[(2S)-2-cyclohexyl-2-(2,2-difluoro-2-phenylacetamido)acetamido]-3-fluorophenyl}-1-(4-methylpiperazin-1-yl)-1-oxopropan-2-yl]propanamide (204)

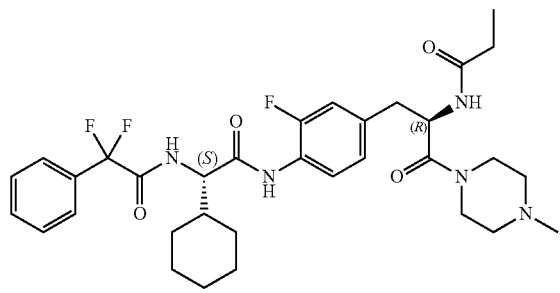

Following General Procedure O, 62a (0.080 g, 0.168 mmol, 1.0 eq.) was reacted with 2,2-difluoro-2-phenylacetic acid (0.035 g, 0.202 mmol, 1.2 eq.), DIPEA (0.23 mL, 1.35 mmol, 8.0 eq.) and HATU (0.096 g, 0.252 mmol, 1.5 eq.) in DMF (1 mL) to afford, after reverse phase column chromatography, 204 (38.0 mg) as a white solid. ¹H NMR (400 MHz, DMSO-d₆) δ 9.88 (s, 1H), 8.94 (d, J=8.3 Hz, 1H), 8.21 (d, J=8.5 Hz, 1H), 7.71-7.48 (m, 6H), 7.10 (dd, J=11.9, 1.8 Hz, 1H), 7.04-6.97 (m, 1H), 4.90 (q, J=7.8 Hz, 1H), 4.42 (t, J=8.5 Hz, 1H), 3.50-3.36 (m, 4H), 2.89 (dd, J=13.4, 6.8 Hz, 1H), 2.75 (dd, J=13.4, 7.9 Hz, 1H), 2.18 (d, J=11.5 Hz, 2H), 2.09 (s, 3H), 2.05 (q, J=7.6 Hz, 2H), 1.96-1.78 (m, 4H), 1.71-1.61 (m, 3H), 1.60-1.56 (m, 2H), 1.12 (q, J=19.2, 15.9 Hz, 4H), 0.91 (t, J=7.6 Hz, 3H). UPLC-MS (basic 2 min): rt=1.10 min; m/z=630.3 for [M+H]⁺.

Example 163: N-[(2R)-3-{4-[(2S)-2-cyclohexyl-2-[2,2-difluoro-2-(pyridin-3-yl)acetamido]acetamido]-3-fluorophenyl}-1-(4-methylpiperazin-1-yl)-1-oxopropan-2-yl]propanamide (205)

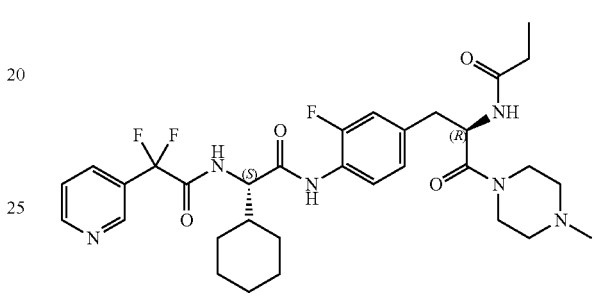

Following General Procedure O, 62a (0.050 g, 0.105 mmol, 1.0 eq.) was reacted with 2,2-difluoro-2-(pyridin-3-yl)acetic acid (0.020 g, 0.116 mmol, 1.1 eq.), DIPEA (0.06 mL, 0.315 mmol, 3.0 eq.) and HATU (0.060 g, 0.158 mmol, 1.5 eq.) in DMF (1 mL) to afford, after reverse phase column chromatography, 205 (16.0 mg) as a white solid. ¹H NMR (400 MHz, DMSO-d₆) δ 9.92 (s, 1H), 9.12 (d, J=8.2 Hz, 1H), 8.83 (d, J=2.3 Hz, 1H), 8.77 (dd, J=5.0, 1.6 Hz, 1H), 8.21 (d, J=8.5 Hz, 1H), 8.05 (dt, J=8.2, 2.1 Hz, 1H), 7.66 (t, J=8.2 Hz, 1H), 7.58 (dd, J=8.1, 4.8 Hz, 1H), 7.10 (dd, J=11.9, 1.8 Hz, 1H), 7.00 (dd, J=8.2, 1.9 Hz, 1H), 4.90 (q, J=7.8 Hz, 1H), 4.44 (t, J=8.5 Hz, 1H), 3.41 (dd, J=19.7, 9.5 Hz, 4H), 2.89 (dd, J=13.4, 6.8 Hz, 1H), 2.76 (dd, J=13.4, 7.9 Hz, 1H), 2.19 (dq, J=10.9, 6.8, 4.8 Hz, 2H), 2.11-2.00 (m, 5H), 1.95-1.89 (m, 1H), 1.85-1.88 (m, 2H), 1.65 (d, J=10.9 Hz, 3H), 1.58 (s, 2H), 1.17-1.11 (m, 4H), 0.89-0.94 (m, 4H). UPLC-MS (basic 2 min): rt=0.99 min; m/z=631.3 for [M+H]⁺.

Example 164: N-[(2R)-3-{4-[(2S)-2-cyclohexyl-2-[2,2-difluoro-2-(4-methoxyphenyl)acetamido] acetamido]-3-fluorophenyl}-1-(4-methylpiperazin-1-yl)-1-oxopropan-2-yl]propanamide (206)

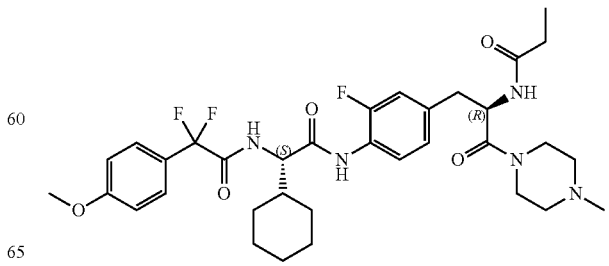

Following General Procedure O, 62a (0.050 g, 0.105 mmol, 1.0 eq.) was reacted with 2,2-difluoro-2-(4-methoxyphenyl)acetic acid (0.023 g, 0.116 mmol, 1.1 eq.), DIPEA (0.06 mL, 0.315 mmol, 3.0 eq.) and HATU (0.060 g, 0.158 mmol, 1.5 eq.) in DMF (1 mL) to afford, after reverse phase column chromatography, 206 (31.1 mg) as a white solid. $^1$H NMR (400 MHz, DMSO-d$_6$) δ 9.88 (s, 1H), 8.85 (d, J=8.3 Hz, 1H), 8.21 (d, J=8.5 Hz, 1H), 7.67 (t, J=8.3 Hz, 1H), 7.58-7.50 (m, 2H), 7.11 (dd, J=11.9, 1.8 Hz, 1H), 7.08-7.01 (m, 2H), 7.01 (dd, J=8.4, 1.9 Hz, 1H), 4.90 (q, J=7.8 Hz, 1H), 4.42 (t, J=8.5 Hz, 1H), 3.80 (s, 3H), 3.43 (s, 4H), 2.90 (dd, J=13.4, 6.8 Hz, 1H), 2.76 (dd, J=13.4, 7.9 Hz, 1H), 2.24 (s, 2H), 2.13 (s, 3H), 2.05 (q, J=7.5 Hz, 2H), 1.97 (s, 1H), 1.86 (d, J=10.3 Hz, 1H), 1.66 (s, 3H), 1.59 (s, 2H), 1.12 (s, 4H), 0.91 (t, J=7.6 Hz, 3H). UPLC-MS (basic 2 min): rt=1.11 min; m/z=660.3 for [M+H]$^+$.

Example 165: N-[(2R)-3-{4-[(2S)-2-cyclohexyl-2-[2,2-difluoro-2-(3-methoxyphenyl)acetamido] acetamido]-3-fluorophenyl}-1-(4-methylpiperazin-1-yl)-1-oxopropan-2-yl]propanamide (207)

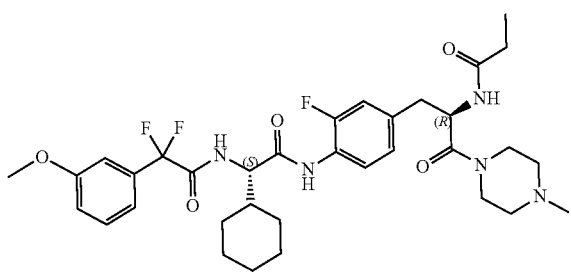

Following General Procedure O, 62a (0.050 g, 0.105 mmol, 1.0 eq.) was reacted with 2,2-difluoro-2-(3-methoxyphenyl)acetic acid (0.023 g, 0.208 mmol, 1.2 eq.), DIPEA (0.06 mL, 0.315 mmol, 3.0 eq.) and HATU (0.060 g, 0.158 mmol, 1.5 eq.) in DMF (1 mL) to afford, after reverse phase column chromatography, 207 (33.9 mg) as a white solid. $^1$H NMR (400 MHz, DMSO-d$_6$) δ 9.89 (s, 1H), 8.95 (d, J=8.3 Hz, 1H), 8.21 (d, J=8.4 Hz, 1H), 7.67 (t, J=8.3 Hz, 1H), 7.43 (t, J=8.1 Hz, 1H), 7.18 (dd, J=5.0, 2.9 Hz, 2H), 7.15-7.06 (m, 2H), 7.00 (dd, J=8.3, 1.9 Hz, 1H), 4.90 (q, J=7.8 Hz, 1H), 4.43 (t, J=8.5 Hz, 1H), 3.79 (s, 4H), 3.42-3.40 (m, 4H), 2.90 (dd, J=13.4, 6.8 Hz, 1H), 2.76 (dd, J=13.4, 7.9 Hz, 1H), 2.20-2.17 (dd, J=11.0, 5.7 Hz, 2H), 2.09-2.02 (m, 6H), 1.96-1.92-1.91 (m, 2H), 1.66-1.58 (m, 5H), 1.13-1.11 (m, 4H), 0.91 (t, J=7.6 Hz, 3H). UPLC-MS (basic 2 min): rt=1.12 min; m/z=660.4 for [M+H]$^+$.

Example 166: N-[(2R)-3-{4-[(2S)-2-cyclohexyl-2-[2,2-difluoro-2-(6-methylpyridin-3-yl)acetamido]acetamido]-3-fluorophenyl}-1-(4-methylpiperazin-1-yl)-1-oxopropan-2-yl]propanamide (208)

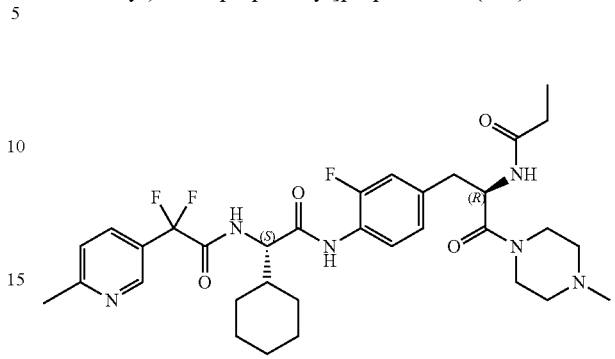

Following General Procedure O, 62a (0.050 g, 0.105 mmol, 1.0 eq.) was reacted with 2,2-difluoro-2-(6-methylpyridin-3-yl)acetic acid hydrochloride (0.026 g, 0.208 mmol, 1.2 eq.), DIPEA (0.06 mL, 0.315 mmol, 3.0 eq.) and HATU (0.060 g, 0.158 mmol, 1.5 eq.) in DMF (1 mL) to afford, after reverse phase column chromatography, 208 (51.0 mg) as a white solid. $^1$H NMR (400 MHz, DMSO-d$_6$) δ 9.91 (s, 1H), 9.06 (d, J=8.2 Hz, 1H), 8.70-8.65 (m, 1H), 8.21 (d, J=8.4 Hz, 1H), 7.91 (dd, J=8.3, 2.4 Hz, 1H), 7.66 (t, J=8.3 Hz, 1H), 7.42 (d, J=8.2 Hz, 1H), 7.10 (dd, J=11.9, 1.8 Hz, 1H), 7.00 (dd, J=8.3, 1.8 Hz, 1H), 4.90 (q, J=7.8 Hz, 1H), 4.43 (t, J=8.5 Hz, 1H), 3.41 (t, J=5.1 Hz, 4H), 2.89 (dd, J=13.4, 6.8 Hz, 1H), 2.76 (dd, J=13.4, 7.9 Hz, 1H), 2.53 (s, 3H), 2.19 (dd, J=11.1, 5.9 Hz, 2H), 2.11-2.00 (m, 5H), 1.95-1.82 (m, 2H), 1.69-1.49 (m, 5H), 1.23-1.13 (m, 4H), 0.99-0.95 (m, 1H), 0.91 (t, J=7.6 Hz, 3H). UPLC-MS (basic 2 min): rt=1.02 min; m/z=645.3 for [M+H]$^+$.

Example 167: N-[(2R)-3-{4-[(2S)-2-cyclohexyl-2-[2,2-difluoro-2-(5-methylpyridin-3-yl)acetamido]acetamido]-3-fluorophenyl}-1-(4-methylpiperazin-1-yl)-1-oxopropan-2-yl]propanamide) (209)

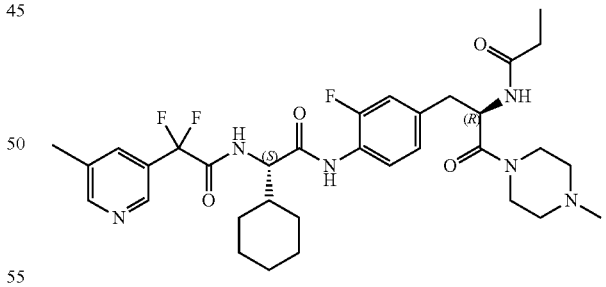

Following General Procedure O, 62a (0.050 g, 0.105 mmol, 1.0 eq.) was reacted with 2,2-difluoro-2-(5-methylpyridin-3-yl)acetic acid (0.024 g, 0.126 mmol, 1.2 eq.), DIPEA (0.06 mL, 0.421 mmol, 4.0 eq.) and HATU (0.060 g, 0.158 mmol, 1.5 eq.) in DMF (1 mL) to afford, after reverse phase column chromatography, 209 (24.0 mg) as a white solid. $^1$H NMR (400 MHz, DMSO-d$_6$) δ 9.85 (s, 1H), 8.73 (d, J=8.5 Hz, 1H), 8.47 (d, J=2.1 Hz, 1H), 8.21 (d, J=8.5 Hz, 1H), 7.82 (dd, J=8.1, 2.2 Hz, 1H), 7.68 (t, J=8.6 Hz, 2H), 7.11 (dd, J=11.8, 1.9 Hz, 1H), 7.01 (dd, J=8.3, 1.8 Hz, 1H), 4.90 (q, J=7.8 Hz, 1H), 4.47 (t, J=8.4 Hz, 1H), 3.41 (t, J=5.3

Hz, 4H), 2.89 (dd, J=13.4, 6.7 Hz, 1H), 2.75 (dd, J=13.4, 8.0 Hz, 1H), 2.36 (s, 3H), 2.19 (p, J=6.9, 6.0 Hz, 2H), 2.13-1.98 (m, 6H), 1.98-1.52 (m, 7H), 1.28-0.93 (m, 5H), 0.90 (t, J=7.6 Hz, 3H). UPLC-MS (basic 4 min): rt=1.74 min; m/z=645.4 for [M+H]$^+$.

Example 168: N-[(2R)-3-{4-[(2S)-2-cyclohexyl-2-[2,2-difluoro-2-(4-methylphenyl)acetamido]acetamido]-3-fluorophenyl}-1-(4-methylpiperazin-1-yl)-1-oxopropan-2-yl]propanamide (210)

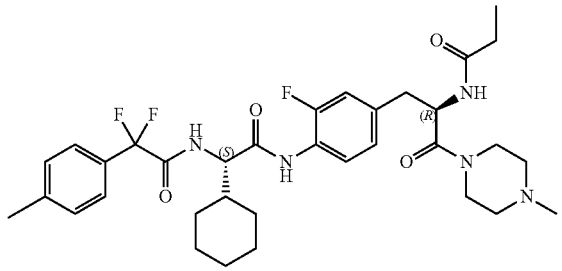

Following General Procedure O, 62a (0.060 g, 0.126 mmol, 1.0 eq.) was reacted with 2,2-difluoro-2-(4-methylphenyl)acetic acid (0.028 g, 0.151 mmol, 1.2 eq.), DIPEA (0.09 mL, 0.505 mmol, 4.0 eq.) and HATU (0.072 g, 0.189 mmol, 1.5 eq.) in DMF (1 mL) to afford, after reverse phase column chromatography, 210 (22.0 mg) as a white solid. $^1$H NMR (400 MHz, DMSO-d$_6$) δ 9.91 (s, 1H), 8.89 (d, J=8.2 Hz, 1H), 8.25 (d, J=8.0 Hz, 1H), 7.64 (s, 1H), 7.50 (d, J=8.1 Hz, 2H), 7.32 (d, J=8.0 Hz, 2H), 7.23-7.13 (m, 1H), 7.10-6.99 (m, 1H), 4.92 (d, J=7.6 Hz, 1H), 4.39 (t, J=8.4 Hz, 1H), 2.91 (dd, J=13.5, 6.2 Hz, 2H), 2.83-2.59 (m, 5H), 2.35 (s, 3H), 2.35-2.30 (m, 1H), 2.09 (s, 3H), 2.05 (t, J=7.5 Hz, 2H), 1.87 (d, J=10.7 Hz, 1H), 1.63 (d, J=35.0 Hz, 6H), 1.26-0.98 (m, 6H), 0.91 (t, J=7.6 Hz, 3H). UPLC-MS (basic 4 min): rt=1.35 min; m/z=644.4 for [M+H]$^+$.

Example 169: N-[(2R)-3-{4-[(2S)-2-[2-(4-chlorophenyl)-2,2-difluoroacetamido]-2-cyclohexylacetamido]-3-fluorophenyl}-1-(4-methylpiperazin-1-yl)-1-oxopropan-2-yl]propanamide (211)

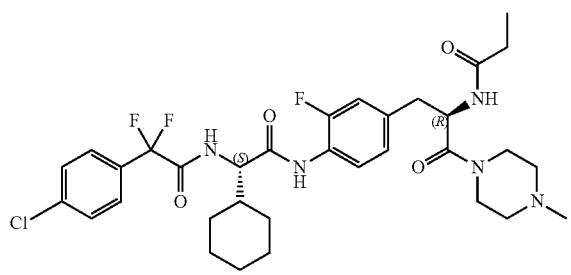

Following General Procedure O, 62a (0.060 g, 0.126 mmol, 1.0 eq.) was reacted with 2-(4-chlorophenyl)-2,2-difluoroacetic acid (0.031 g, 0.151 mmol, 1.2 eq.), DIPEA (0.09 mL, 0.505 mmol, 4.0 eq.) and HATU (0.072 g, 0.189 mmol, 1.5 eq.) in DMF (1 mL) to afford, after reverse phase column chromatography, 211 (18.0 mg) as a white solid. $^1$H NMR (400 MHz, DMSO-d$_6$) δ 9.92 (s, 1H), 9.66 (s, 1H), 9.01 (d, J=8.2 Hz, 1H), 8.25 (s, 1H), 7.69-7.58 (m, 4H), 7.23-7.14 (m, 1H), 7.10-7.00 (m, 1H), 4.92 (d, J=8.1 Hz, 1H), 4.40 (s, 1H), 3.29-2.53 (m, 10H), 2.09 (s, 3H), 2.05 (t, J=7.6 Hz, 2H), 1.88 (d, J=25.9 Hz, 1H), 1.75-1.43 (m, 5H), 1.24-1.04 (m, 5H), 0.91 (t, J=7.6 Hz, 3H). UPLC-MS (basic 4 min): rt=1.38 min; m/z=664.35 for [M+H]$^+$.

Example 170: N-[(2R)-3-{4-[(2S)-2-[2-(4-cyanophenyl)-2,2-difluoroacetamido]-2-cyclohexylacetamido]-3-fluorophenyl}-1-(4-methylpiperazin-1-yl)-1-oxopropan-2-yl]propanamide (212)

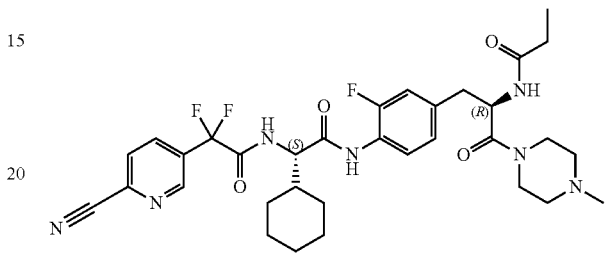

Following General Procedure O, 62a (0.060 g, 0.126 mmol, 1.0 eq.) was reacted with 2-(4-cyanophenyl)-2,2-difluoroacetic acid (0.030 g, 0.151 mmol, 1.2 eq.), DIPEA (0.09 mL, 0.505 mmol, 4.0 eq.) and HATU (0.072 g, 0.189 mmol, 1.5 eq.) to afford, after reverse phase column chromatography, 212 (35.0 mg) as a white solid. $^1$H NMR (400 MHz, DMSO-d$_6$) δ 9.90 (s, 1H), 9.12 (d, J=8.2 Hz, 1H), 8.21 (d, J=8.4 Hz, 1H), 8.04 (d, J=8.2 Hz, 2H), 7.83 (d, J=8.2 Hz, 2H), 7.65 (t, J=8.2 Hz, 1H), 7.10 (dd, J=11.8, 1.9 Hz, 1H), 7.00 (dd, J=8.1, 1.9 Hz, 1H), 4.90 (q, J=7.8 Hz, 1H), 4.42 (t, J=8.4 Hz, 1H), 3.40 (d, J=5.4 Hz, 4H), 2.89 (dd, J=13.3, 6.8 Hz, 1H), 2.75 (dd, J=13.4, 8.0 Hz, 1H), 2.18 (d, J=11.8 Hz, 2H), 2.08 (d, J=2.6 Hz, 4H), 2.05 (s, 3H), 1.96-1.79 (m, 2H), 1.72-1.50 (m, 5H), 1.22-1.01 (m, 4H), 0.91 (t, J=7.6 Hz, 3H). UPLC-MS (basic 4 min): rt=1.77 min; m/z=655.3 for [M+H]$^+$.

Example 171: N-[(2R)-3-{4-[(2S)-2-cyclohexyl-2-[2,2-difluoro-2-(1,3-thiazol-5-yl)acetamido]acetamido]-3-fluorophenyl}-1-(4-methylpiperazin-1-yl)-1-oxopropan-2-yl]propanamide (213)

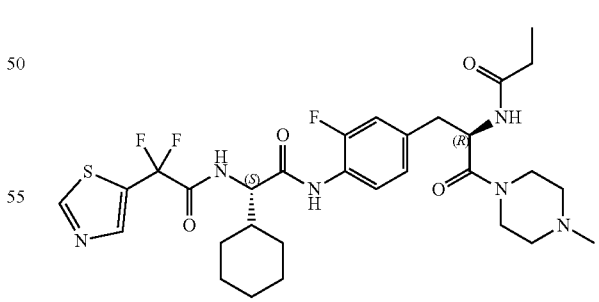

Following General Procedure O, 62a (0.060 g, 0.126 mmol, 1.0 eq.) was reacted with 2,2-difluoro-2-(1,3-thiazol-5-yl)acetic acid (0.030 g, 0.151 mmol, 1.2 eq.), DIPEA (0.09 mL, 0.505 mmol, 4.0 eq.) and HATU (0.072 g, 0.189 mmol, 1.5 eq.) to afford, after reverse phase column chromatography, 213 (21.0 mg) as a white solid. $^1$H NMR (400 MHz, DMSO-d$_6$) δ 10.01 (s, 1H), 9.95 (s, 1H), 9.64 (s, 1H), 9.35

(s, 1H), 9.22 (d, J=7.9 Hz, 1H), 8.26 (s, 1H), 7.69-7.59 (m, 1H), 7.17 (s, 1H), 7.04 (s, 1H), 4.93 (s, 1H), 4.44 (s, 1H), 2.94-2.71 (m, 8H), 2.09 (s, 3H), 2.05 (t, J=7.7 Hz, 2H), 1.88 (s, 2H), 1.66 (d, J=39.6 Hz, 5H), 1.15 (s, 4H), 0.91 (t, J=7.6 Hz, 3H). UPLC-MS (basic 4 min): rt=1.18 min; m/z=637.4 for [M+H]$^+$.

Example 172: N-[(2R)-3-{4-[(2S)-2-cycloheptyl-2-[2,2-difluoro-2-(6-methoxypyridin-3-yl)acetamido] acetamido]-3-fluorophenyl}-1-(4-methylpiperazin-1-yl)-1-oxopropan-2-yl]propanamide (214)

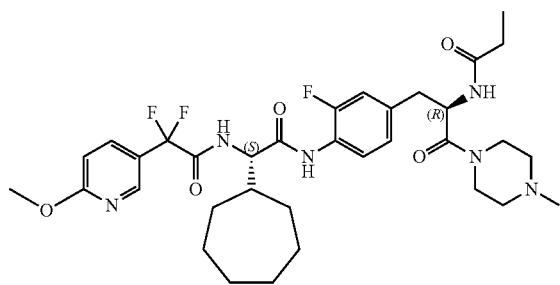

Following General Procedure O, 62b (0.084 g, 0.172 mmol, 1.0 eq.) was reacted with 2,2-difluoro-2-(6-methoxypyridin-3-yl)acetic acid (0.042 g, 0.206 mmol, 1.2 eq.), DIPEA (0.09 mL, 0.515 mmol, 3.0 eq.) and HATU (0.098 g, 0.257 mmol, 1.5 eq.) in DMF (1 mL) to afford, after reverse phase column chromatography, 214 (75.0 mg) as a white solid. $^1$H NMR (400 MHz, DMSO-d$_6$) δ 9.92 (s, 1H), 8.99 (d, J=8.4 Hz, 1H), 8.42 (s, 1H), 8.21 (d, J=8.5 Hz, 1H), 7.93 (dd, J=8.8, 2.6 Hz, 1H), 7.64 (t, J=8.2 Hz, 1H), 7.16-7.06 (m, 1H), 7.01 (d, J=8.4 Hz, 1H), 6.97 (d, J=8.7 Hz, 1H), 4.90 (q, J=7.8 Hz, 1H), 4.49 (t, J=8.3 Hz, 1H), 3.90 (s, 3H), 3.30 (s, 1H), 2.90 (dd, J=13.5, 6.9 Hz, 1H), 2.76 (dd, J=13.3, 7.8 Hz, 1H), 2.18 (d, J=11.6 Hz, 3H), 2.08 (d, J=4.9 Hz, 4H), 2.07-2.00 (m, 2H), 1.93 (s, 1H), 1.66-1.18 (m, 13H), 1.04 (d, J=6.1 Hz, 1H), 0.91 (t, J=7.6 Hz, 3H). UPLC-MS (basic 2 min): rt=1.12 min; m/z=675.3 for [M+H]$^+$.

Example 173: N-[(2R)-3-{4-[(2S)-2-[2,2-difluoro-2-(6-methoxypyridin-3-yl)acetamido]-2-(4,4-difluoro cyclohexyl)acetamido]-3-fluorophenyl}-1-(4-methylpiperazin-1-yl)-1-oxopropan-2-yl]propanamide (215)

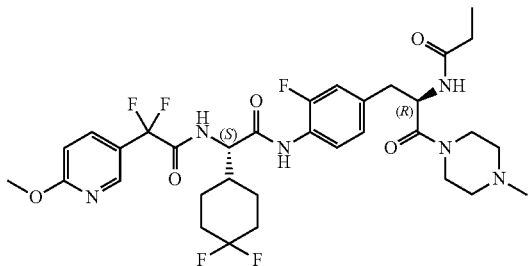

Following General Procedure O, 62c (0.190 g, 0.371 mmol, 1.0 eq.) was reacted with 2,2-difluoro-2-(6-methoxypyridin-3-yl)acetic acid (0.091 g, 0.446 mmol, 1.2 eq.), DIPEA (0.52 mL, 2.97 mmol, 8.0 eq.) and HATU (0.212 g, 0.557 mmol, 1.5 eq.) in DMF (2 mL) to afford, after reverse phase column chromatography, 215 (94.0 mg) as a white solid. $^1$H NMR (400 MHz, DMSO-d$_6$) δ 9.99 (s, 1H), 9.18 (d, J=8.0 Hz, 1H), 8.42 (s, 1H), 8.21 (d, J=8.5 Hz, 1H), 7.92 (dd, J=8.8, 2.6 Hz, 1H), 7.68 (t, J=8.2 Hz, 1H), 7.15-7.08 (m, 1H), 6.99 (dd, J=16.7, 9.0 Hz, 2H), 4.90 (q, J=7.7 Hz, 1H), 4.52 (t, J=8.4 Hz, 1H), 3.90 (s, 3H), 3.41 (t, J=6.4 Hz, 4H), 2.90 (dd, J=13.4, 6.7 Hz, 1H), 2.76 (dd, J=13.4, 7.9 Hz, 1H), 2.23-2.14 (m, 2H), 2.09 (s, 3H), 2.05 (q, J=7.5 Hz, 4H), 1.95 (dd, J=11.5, 5.4 Hz, 2H), 1.86-1.57 (m, 5H), 1.41 (d, J=12.6 Hz, 1H), 1.25 (d, J=11.9 Hz, 1H), 0.91 (t, J=7.6 Hz, 3H). UPLC-MS (basic 2 min): rt=1.04 min; m/z=697.3 for [M+H]$^+$.

Example 174: N-[(2R)-3-{4-[(2S)-2-[2,2-difluoro-2-(6-methoxypyridin-3-yl)acetamido]-2-[(1r,4S)-4-methylcyclohexyl]acetamido]-3-fluorophenyl}-1-(4-methylpiperazin-1-yl)-1-oxopropan-2-yl] propanamide (216)

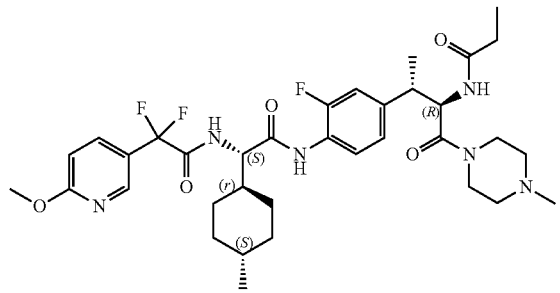

Following General Procedure O, 62d (0.090 g, 0.184 mmol, 1.0 eq.) was reacted with 2,2-difluoro-2-(6-methoxypyridin-3-yl)acetic acid (0.045 g, 0.221 mmol, 1.2 eq.), DIPEA (0.096 mL, 0.551 mmol, 3.0 eq.) and HATU (0.212 g, 0.557 mmol, 1.5 eq.) in DMF (1 mL) to afford, after reverse phase column chromatography, 216 (60.0 mg) as a white solid. 1H NMR (400 MHz, DMSO-d$_6$) δ 9.89 (s, 1H), 9.01 (d, J=8.2 Hz, 1H), 8.41 (d, J=2.5 Hz, 1H), 8.20 (d, J=8.5 Hz, 1H), 7.91 (dd, J=8.8, 2.5 Hz, 1H), 7.67 (td, J=8.2, 6.1 Hz, 1H), 7.09 (dd, J=11.8, 1.8 Hz, 1H), 6.99 (dd, J=8.2, 1.8 Hz, 1H), 6.96 (d, J=8.7 Hz, 1H), 4.89 (q, J=7.8 Hz, 1H), 4.40 (t, J=8.4 Hz, 1H), 3.89 (s, 3H), 3.41 (q, J=7.0, 5.3 Hz, 4H), 2.89 (dd, J=13.4, 6.8 Hz, 1H), 2.75 (dd, J=13.3, 7.8 Hz, 1H), 2.24-2.12 (m, 2H), 2.13-2.00 (m, 6H), 1.95-1.85 (m, 1H), 1.78 (d, J=10.7 Hz, 1H), 1.64 (d, J=12.3 Hz, 3H), 1.57 (d, J=12.6 Hz, 1H), 1.29-1.06 (m, 3H), 1.04 (d, J=6.1 Hz, 1H), 1.01-0.93 (m, 1H), 0.90 (t, J=7.6 Hz, 3H), 0.83 (d, J=6.4 Hz, 4H). UPLC-MS (basic 2 min): rt=1.13 min; m/z=675.3 for [M+H]$^+$.

Example 175: N-[(2R)-3-{4-[(2S)-2-cycloheptyl-2-[(1-ethyl-1H-pyrazol-5-yl)formamido]acetamido]-3-fluorophenyl}-1-(4-methylpiperazin-1-yl)-1-oxopropan-2-yl]propanamide (235)

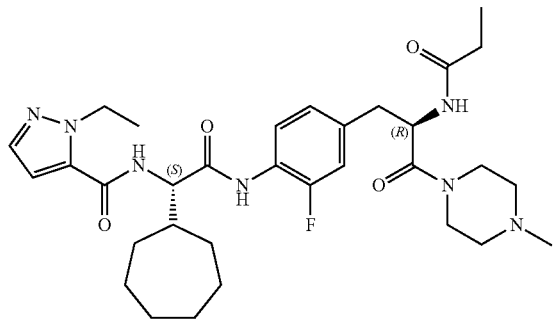

Compound 235 was synthesized by coupling 62b with the required carboxylic acid following general procedure O and purified using reverse phase column chromatography. 1H NMR (400 MHz, DMSO-d$_6$) δ 9.84 (s, 1H), 8.43 (d, J=8.6 Hz, 1H), 8.21 (d, J=8.4 Hz, 1H), 7.67 (t, J=8.2 Hz, 1H), 7.47 (d, J=2.0 Hz, 1H), 7.11 (d, J=11.9 Hz, 1H), 7.05-6.91 (m, 2H), 4.90 (q, J=7.7 Hz, 1H), 4.61 (t, J=8.4 Hz, 1H), 4.46 (q, J=7.1 Hz, 2H), 3.67-3.32 (m, 4H), 2.89 (dd, J=13.5, 6.7 Hz, 1H), 2.75 (dd, J=13.4, 8.0 Hz, 1H), 2.69 (s, 1H), 1.78-1.58 (m, 4H), 1.44 (dt, J=40.6, 9.6 Hz, 5H), 1.28 (t, J=7.1 Hz, 3H), 1.09 (t, J=7.0 Hz, 1H), 0.90 (t, J=7.6 Hz, 3H). UPLC-MS (basic 4 min): rt=1.70 min; m/z=612.4 for [M+H]$^+$.

Example 176: N-[(2R)-3-{4-[(2S)-2-cycloheptyl-2-[(3-ethyl-1,2-oxazol-4-yl)formamido]acetamido]-3-fluorophenyl}-1-(4-methylpiperazin-1-yl)-1-oxopropan-2-yl]propanamide (236)

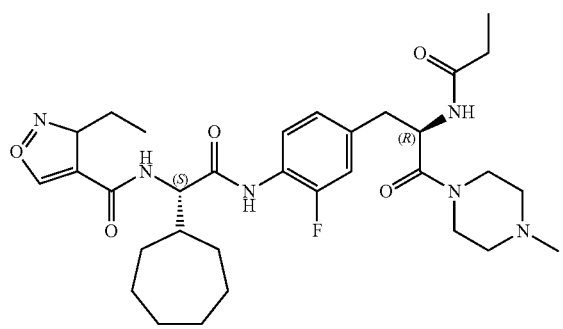

Compound 236 was synthesized by coupling 62b with the required carboxylic acid following general procedure O and purified using reverse phase column chromatography. $^1$H NMR (400 MHz, DMSO-d$_6$) δ 9.86 (s, 1H), 9.40 (s, 1H), 8.40 (d, J=8.6 Hz, 1H), 8.21 (d, J=8.5 Hz, 1H), 7.65 (t, J=8.2 Hz, 1H), 7.10 (dd, J=11.8, 1.9 Hz, 1H), 7.00 (dd, J=8.3, 1.8 Hz, 1H), 4.90 (q, J=7.7 Hz, 1H), 4.64 (t, J=8.2 Hz, 1H), 3.59-3.34 (m, 5H), 2.95-2.70 (m, 4H), 2.69 (s, 1H), 2.22 (s, 2H), 2.12 (s, 3H), 2.04 (q, J=7.6 Hz, 2H), 1.79-1.59 (m, 3H), 1.59-1.27 (m, 4H), 1.17 (t, J=7.5 Hz, 4H), 0.90 (t, J=7.6 Hz, 3H). UPLC-MS (basic 4 min): rt=1.74 min; m/z=613.4 for [M+H]$^+$.

Example 177: N-[(2R)-3-{4-[(2S)-2-cyclohexyl-2-[(1-propyl-1H-pyrazol-5-yl)formamido]acetamido]-3-fluorophenyl}-1-(4-methylpiperazin-1-yl)-1-oxopropan-2-yl]propanamide (237)

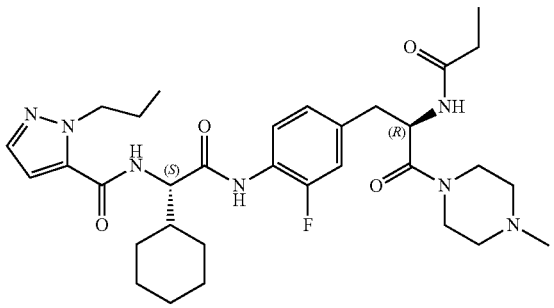

Compound 237 was synthesized by coupling 62a with the required carboxylic acid following general procedure O and purified using reverse phase column chromatography. $^1$H NMR (400 MHz, DMSO-d$_6$) δ 9.86 (s, 1H), 8.48 (d, J=8.3 Hz, 1H), 8.24 (d, J=8.4 Hz, 1H), 7.69 (t, J=8.2 Hz, 1H), 7.48 (d, J=2.0 Hz, 1H), 7.11 (d, J=12.1 Hz, 1H), 7.03-6.97 (m, 2H), 4.90 (q, J=7.8 Hz, 1H), 4.54 (t, J=8.5 Hz, 1H), 4.42 (t, J=7.1 Hz, 2H), 3.49-3.37 (m, 4H), 2.89 (dd, J=13.3, 6.7 Hz, 1H), 2.75 (dd, J=13.4, 8.0 Hz, 1H), 2.25-2.13 (m, 2H), 2.09 (s, 3H), 2.04 (q, J=7.6 Hz, 2H), 1.86 (ddd, J=44.1, 10.4, 5.2 Hz, 3H), 1.70 (q, J=7.3 Hz, 4H), 1.67-1.56 (m, 3H), 1.17 (dq, J=15.1, 8.4 Hz, 4H), 1.09-0.99 (m, 1H), 0.90 (t, J=7.6 Hz, 3H), 0.77 (t, J=7.4 Hz, 3H). UPLC-MS (basic 2 min): rt=1.04 min; m/z=612.3 for [M+H]$^+$.

Example 178: N-[(2R)-3-{4-[(2S)-2-cycloheptyl-2-{[1-(propan-2-yl)-1H-pyrazol-5-yl]formamido}acetamido]-3-fluorophenyl}-1-(4-methylpiperazin-1-yl)-1-oxopropan-2-yl]propanamide) (238)

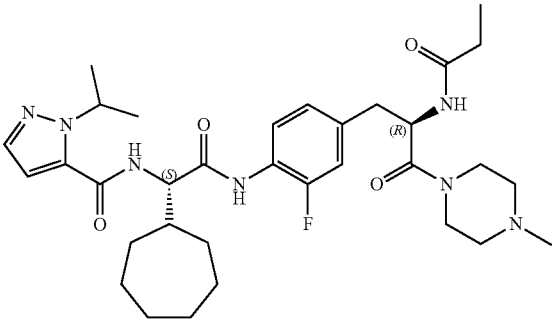

Compound 238 was synthesized by coupling 62b with the required carboxylic acid following general procedure O and purified using reverse phase column chromatography. $^1$H NMR (400 MHz, DMSO-d$_6$) δ 9.84 (s, 1H), 8.42 (d, J=8.6 Hz, 1H), 8.21 (d, J=8.5 Hz, 1H), 7.68 (t, J=8.3 Hz, 1H), 7.49 (d, J=1.9 Hz, 1H), 7.11 (dd, J=11.8, 1.9 Hz, 1H), 6.92 (d, J=2.0 Hz, 1H), 5.39 (h, J=6.6 Hz, 1H), 4.90 (q, J=7.8 Hz, 1H), 4.61 (t, J=8.4 Hz, 1H), 3.41 (t, J=5.1 Hz, 1H), 2.90 (dd, J=13.4, 6.7 Hz, 1H), 2.75 (dd, J=13.4, 8.0 Hz, 1H), 2.18 (dt, J=10.8, 5.1 Hz, 1H), 2.13-2.00 (m, 5H), 1.97-1.90 (m, 1H), 1.69 (q, J=11.7, 8.8 Hz, 4H), 1.53 (dd, J=14.2, 9.4 Hz, 2H), 1.45-1.27 (m, 8H), 0.91 (t, J=7.6 Hz, 3H). UPLC-MS (basic 2 min): rt=1.09 min; m/z=626.3 for [M+H]$^+$.

Example 179: N-[(2R)-3-{4-[(2S)-2-cyclohexyl-2-[(6-methoxy-1-benzofuran-3-yl)formamido]acetamido]-3-fluorophenyl}-1-(4-methylpiperazin-1-yl)-1-oxopropan-2-yl]propanamide (239)

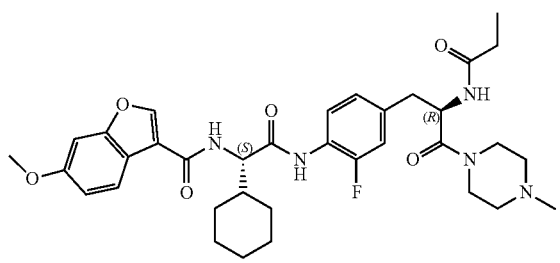

Compound 239 was synthesized by coupling 62a with the required carboxylic acid following general procedure O and purified using reverse phase column chromatography. $^1$H NMR (400 MHz, DMSO-d$_6$) δ 9.90 (s, 1H), 8.66 (s, 1H), 8.30 (d, J=8.4 Hz, 1H), 8.21 (d, J=8.4 Hz, 1H), 7.90 (d, J=8.6 Hz, 1H), 7.70 (t, J=8.3 Hz, 1H), 7.25 (d, J=2.2 Hz, 1H), 7.11 (dd, J=11.9, 1.8 Hz, 1H), 6.99 (ddd, J=13.8, 8.5, 2.0 Hz, 2H), 4.90 (q, J=7.8 Hz, 1H), 4.65 (t, J=8.3 Hz, 1H), 3.82 (s, 3H), 2.90 (dd, J=13.4, 6.8 Hz, 1H), 2.75 (dd, J=13.4, 8.0 Hz, 1H), 2.18 (dd, J=10.9, 5.5 Hz, 1H), 2.12-2.00 (m, 5H), 1.98-1.91 (m, 1H), 1.84 (d, J=10.8 Hz, 2H), 1.72 (s, 3H), 1.64 (s, 2H), 1.25-1.16 (m, 4H), 1.10 (t, J=12.0 Hz, 1H), 0.91 (t, J=7.6 Hz, 3H). UPLC-MS (basic 4 min): rt=1.83 min; m/z=650.3 for [M+H]$^+$.

Example 180: N-[(2R)-3-{4-[(2S)-2-cyclohexyl-2-[2,2-difluoro-2-(6-oxo-1,6-dihydropyridin-3-yl)acetamido]acetamido]-3-fluorophenyl}-1-(4-methylpiperazin-1-yl)-1-oxopropan-2-yl]propanamide (217)

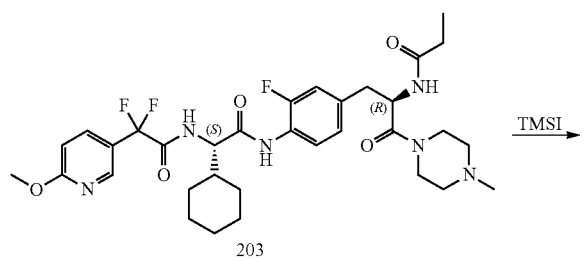

To a solution of 203 (0.063 g, 0.095 mmol, 1.0 eq.) in DCM (1.89 mL) was added iodotrimethylsilane (14 μL, 0.100 mmol, 1.05 eq.) and the resulting mixture was stirred at RT for 18 h. Methanol (0.2 mL) was added to the reaction mixture and then concentrated to dryness. The residue was purified via reverse phase column chromatography on a 120 g C18 cartridge eluting with a 5-95% H$_2$O:MeCN eluent (0.1% ammonia) to afford 217 (24.4 mg) as a white solid. 1H NMR (400 MHz, DMSO-d$_6$) δ 9.93 (s, 1H), 8.93 (d, J=7.6 Hz, 1H), 8.34 (s, 1H), 8.22 (d, J=8.5 Hz, 1H), 7.71-7.62 (m, 2H), 7.57 (dd, J=9.6, 2.8 Hz, 1H), 7.10 (dd, J=11.8, 1.8 Hz, 1H), 7.01 (dd, J=8.3, 1.8 Hz, 1H), 6.43 (d, J=9.6 Hz, 1H), 4.90 (q, J=7.9 Hz, 1H), 4.42 (s, 1H), 3.78 (dt, J=12.2, 6.1 Hz, 1H), 3.41 (t, J=5.3 Hz, 4H), 2.90 (dd, J=13.4, 6.8 Hz, 1H), 2.76 (dd, J=13.3, 8.0 Hz, 1H), 2.19 (dd, J=10.9, 5.9 Hz, 2H), 2.09 (s, 3H), 2.05 (q, J=7.6 Hz, 2H), 1.97-1.74 (m, 2H), 1.73-1.51 (m, 4H), 1.27-1.10 (m, 3H), 1.04 (d, J=6.1 Hz, 2H), 0.97 (t, J=11.4 Hz, 1H), 0.91 (t, J=7.6 Hz, 3H).

UPLC-MS (basic 2 min): rt=0.87 min; m/z=647.3 for [M+H]+

Example 181: General Procedure for Preparation of Intermediate 64

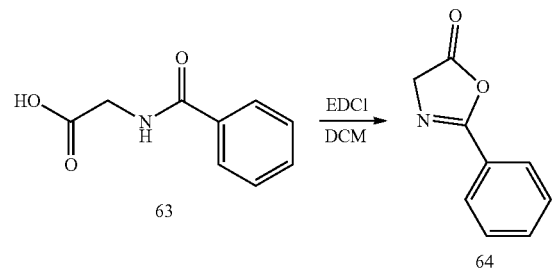 [SMILES: O=C(O)CNC(=O)c1ccccc1 ; O=C1CN=C(c2ccccc2)O1]

To a solution of compound 63 (140 g, 781 mmol, 1.00 eq) in DCM (1.50 L) was added EDCI (180 g, 937 mmol, 1.20 eq). The mixture was stirred at 25° C. for 5 hrs. TLC (Plate 1, petroleum ether:ethyl acetate=10:1) indicated compound 63 was completely consumed and one new spot was formed. The mixture was washed with brine (1.00 L*3), dried over Na$_2$SO$_4$, filtered and concentrated under reduced pressure to give a residue. Compound 64 (121 g, crude) was obtained as a yellow solid, whose structure was confirmed by LCMS and H$^1$ NMR. H$^1$ NMR (400 MHz, CDCl$_3$) δ 7.99 (d, J=8.8 Hz, 2H), 7.60-7.48 (m, 3H), 4.24 (s, 2H). LCMS: (M+H)$^+$: 162.1.

Example 182: General Procedure for Preparation of Intermediate 65

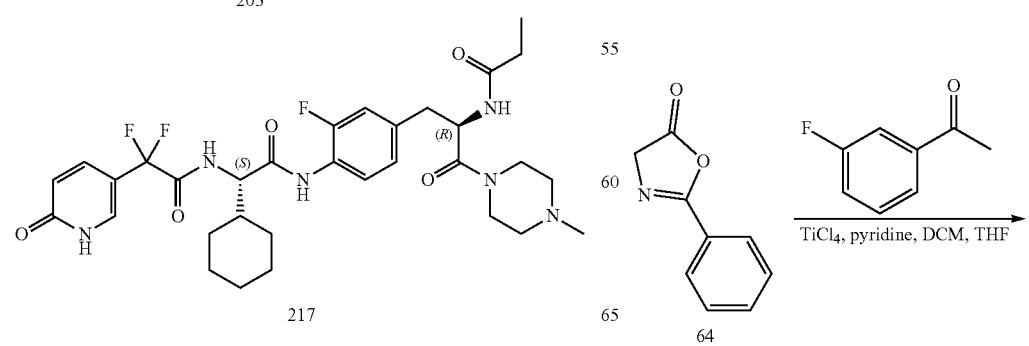

365
-continued

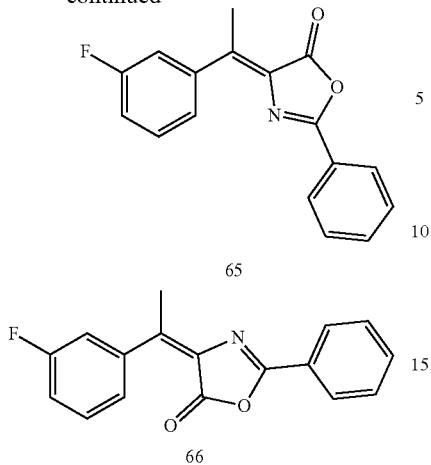

65

66

THF (1.70 L) was cooled to −10° C. and TiCl₄ (194 g, 1.02 mol, 1.50 eq) was added and the mixture stirred at −10° C. for 20 min. 3-Fluoroacet (94.3 g, 682 mmol, 83.4 mL, 1.00 eq) in THF (300 mL) was added and the mixture was stirred for another 10 min. Then compound 64 (121 g, 751 mmol, 1.10 eq) was added to the mixture and stirred for 30 min. To the mixture, pyridine (108 g, 1.37 mol, 110 mL, 2.00 eq) was added drop wise and the mixture was stirred at 25° C. for 12 hrs. TLC (Plate 1, petroleum ether:ethyl acetate=10:1) indicated compound 64 was consumed completely and four new spots were formed. The mixture was diluted with H₂O (1.00 L) and extracted with ethyl acetate (1.00 L*3). The combined organic layers were washed with brine (1.00 L*2), dried over Na₂SO₄, filtered and concentrated under reduced pressure to give a residue. The crude product was triturated with MeOH (500 mL) at 25° C. for 1 hr and filtered to get the cake. The cake was purified by re-crystallization from ethyl acetate (400 mL) at 60° C. to get the cake compound (65.0 g) as light yellow solid and the filtrate was concentrated under reduced pressure to give a yellow solid (80.0 g) which was purified by Prep-HPLC (column: Phenomenex luna C18 250*50 mm*10 um; mobile phase: [water (0.1% TFA)-ACN]; B %: 60%-85%, 20 min) to get compound 65 (35 g, P2) and compound 66 (33 g, P1). Compound 65 was obtained as a light yellow solid, whose structure was confirmed by LCMS, H¹ NMR and F¹⁹ NMR. H¹ NMR: (400 MHz, CDCl₃) [OBJ]δ δ 8.08 (d, J=7.2 Hz, 2H), 7.72-7.66 (m, 2H), 7.57 (t, J=7.2 Hz, 1H), 7.5-7.42 (m, 3H), 7.18-7.13 (m, 1H), 2.79 (s, 3H); F¹⁹ (400 MHz, CDCl₃ 112.9. LCMS: (M+H)⁺: 282.1.

Example 183: General Procedure for Preparation of Intermediate 67

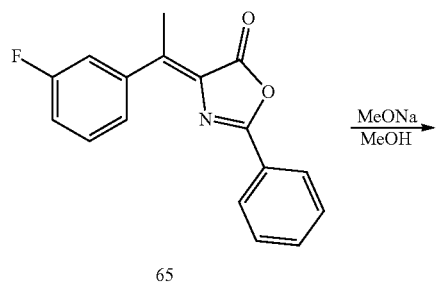

65

366
-continued

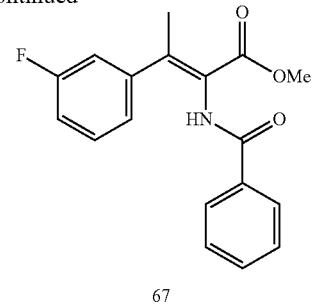

67

To a solution of compound 65 (65.0 g, 231 mmol, 1.00 eq) in MeOH (420 mL) was added NaOMe (624 mg, 11.5 mmol, 0.05 eq) in MeOH (30.0 mL) at 0° C. The mixture was stirred at 0° C. for 0.5 hr. TLC (Plate 1, petroleum ether: ethyl acetate=10:1) indicated compound 65 was completely consumed and one new spot was formed. The mixture was added to ice-cold water (600 mL), and extracted with ethyl acetate (1000 mL*2). The combined organic layers were washed with brine (700 mL), then dried over Na₂SO₄, filtered and concentrated under reduced pressure to give a residue. Compound 67 (70.0 g, 223 mmol, 96.7% yield) was obtained as a light yellow solid, whose structure was confirmed by LCMS, H¹ NMR and F¹⁹ NMR. H¹ NMR: EW17596-119-P1A1, (400 MHz, CDCl₃) δ 7.60 (d, J=7.2 Hz, 2H), 7.50 (t, J=7.2 Hz, 1H), 7.41-7.39 (m, 3H), 7.21 (s, 1H), 7.09 (d, J=7.2 Hz, 1H), 7.05-7.00 (m, 2H), 3.88 (s, 3H), 2.33 (s, 3H). F¹⁹ NMR: (400 MHz, CDCl₃) 111.3. LCMS: (M+H)⁺: 314.0.

Example 184: General Procedure for Preparation of Intermediate 69

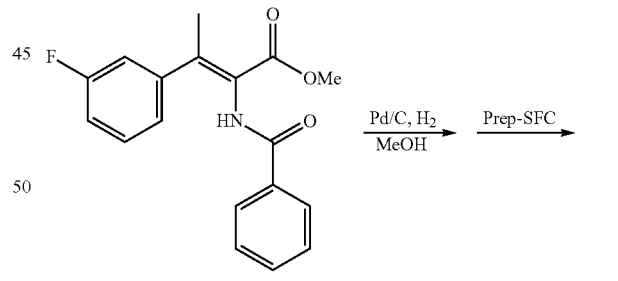

67

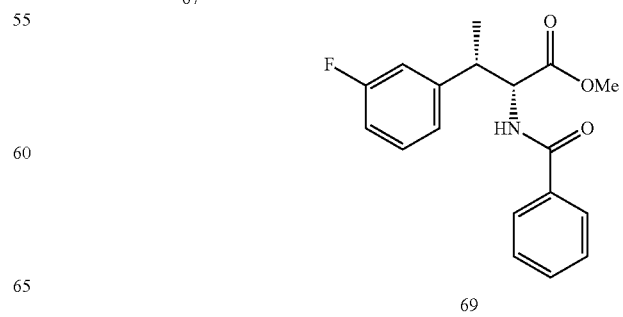

69

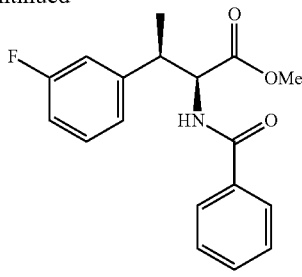

70

To a solution of compound 67 (70.0 g, 223 mmol, 1.00 eq) in MeOH (650 mL) was added Pd/C (20.0 g, 10.0% purity). The mixture was degassed and purged with H₂ for 3 times, and then the mixture was stirred at 50° C. for 12 hrs under H₂ atmosphere. TLC (Plate 1, petroleum ether:ethyl acetate=3:1) indicated compound 67 was completely consumed and one new spot was formed. The mixture was filtered and the filtrate was concentrated under reduced pressure to get a white solid. A mixture of compounds 69 and 70 (70.0 g, 222 mmol, 99.4% yield) was obtained as a white solid, whose structure was confirmed by LCMS ((M+H)⁺: 316.1). Compounds 69 and 70 were separated by SFC (column: DAICEL CHIRALPAK AD (250 mm*50 mm, 10 um); mobile phase: [Neu-EtOH]; B %: 25%-25%, 5.2 min; 920 min) to get peak 1 (34.5 g) and peak 2 (35.0 g). Compound 69 (34.5 g, 109 mmol, 49.3% yield) (Peak 1) was obtained as a white solid, whose structure was confirmed H¹ NMR and F¹⁹ NMR. H¹ NMR: (400 MHz, CDCl₃) δ 7.76 (d, J=7.2 Hz, 2H), 7.64 (t, J=7.2 Hz, 1H), 7.46 (t, J=7.2 Hz, 2H), 7.31-7.29 (m, 1H), 7.01-6.92 (m, 3H), 6.63 (d, J=8.4 Hz, 1H), 5.05-5.01 (m, 1H), 3.65 (s, 3H), 3.40-3.33 (m, 1H), 1.47 (d, J=7.2 Hz, 3H). F¹⁹ NMR: (400 MHz, CDCl₃) 112.1. Compound 70 (35.0 g, 111 mmol, 50.0% yield) (Peak 2) was obtained as a white solid.

Example 185: General Procedure for Preparation of Intermediate 71

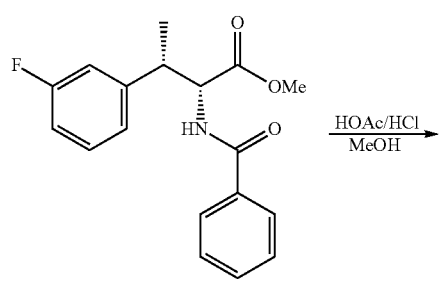

To a solution of compound 69 (17.0 g, 53.9 mmol, 1.00 eq) in HCl (3.00 M, 898 mL, 50.0 eq) was added HOAc (323 g, 5.39 mol, 308 mL, 100 eq). The mixture was stirred at 125° C. for 60 hrs. LC-MS showed compounds 69 was completely consumed and one main peak with the desired mass was detected. The mixture was concentrated under reduced pressure to give a white solid and the residue was washed with DCM (300 mL*2). Compound 71 (27.5 g, crude, HCl, 2 batches) was obtained as a white solid, whose structure was confirmed by H¹ NMR and F¹⁹ NMR. H¹ NMR: (400 MHz, DMSO) δ 13.7 (s, 1H), 8.39 (s, 3H), 7.42-7.36 (m, 1H), 7.18-7.09 (m, 3H), 4.09 (d, J=6.8 Hz, 1H), 3.40-3.36 (m, 1H), 1.37 (d, J=7.2 Hz, 3H). F¹⁹ NMR: (400 MHz, DMSO) 113.1.

Example 186: General Procedure for Preparation of Intermediates 72 and 73

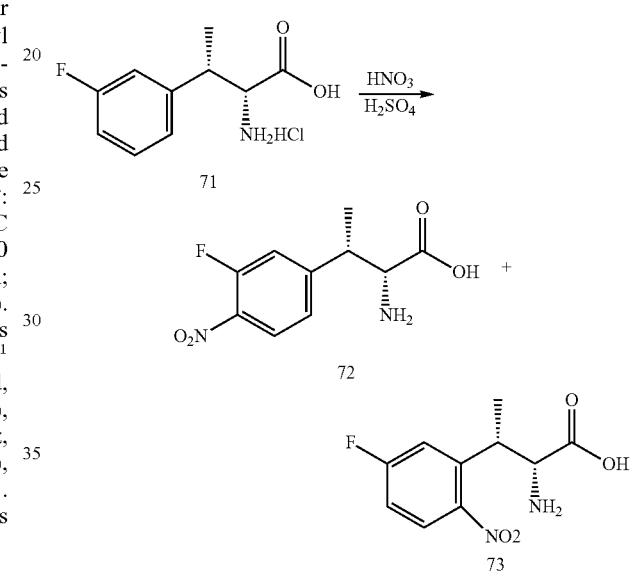

To a solution of compound 71 (15.5 g, 66.3 mmol, 1.00 eq, HCl) in H₂SO₄ (101 g, 1.03 mol, 55.0 mL, 15.6 eq) was added HNO3 (7.56 g, 81.6 mmol, 5.40 mL, 68.0% purity, 1.23 eq) at −20° C. and the mixture was stirred at 0° C. for 0.5 hr. HPLC indicated compound 71 was completely consumed. The mixture was added to crushed ice (500 mL) and Na₂CO₃ solid was added until the pH=8. Compounds 72 and 73 (16.1 g, crude) in H₂O (500 mL) was obtained as a yellow suspension which was used directly for next step.

Example 187: General Procedure for Preparation of Intermediate 74

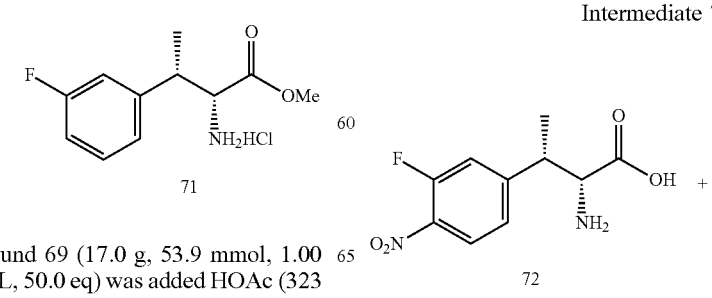

-continued

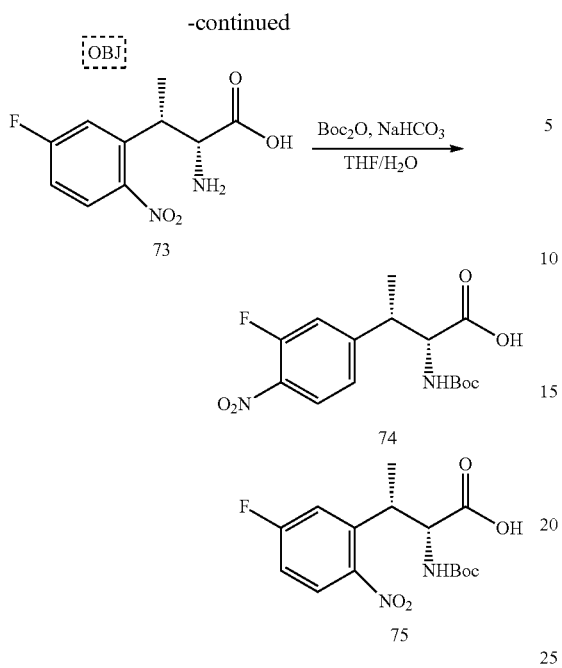

To compounds 72 and 73 (48.0 g, 198 mmol, 1.50 L H₂O, 1.00 eq) in THF (1.50 L) was added Boc₂O (86.5 g, 396 mmol, 91.1 mL, 2.00 eq), the mixture was degassed and purged with N₂ for 3 times and then stirred at 25° C. for 1 hrs under N₂ atmosphere. LCMS showed compounds 72 and 73 were consumed completely and one main peak with desired mass was detected. The mixture was extracted with ethyl acetate (700 mL*2) and the aqueous layer was discarded. The organic layers were washed with H₂O (300 mL*3) to provide an aqueous extract which was adjusted to by addition of 1M HCl until the pH. was 5 and extracted with ethyl acetate to provide crude compounds 74 and 75. The combined organic layers were washed with H₂O (500 mL*2), brine (500 mL) and dried over Na₂SO₄, filtered, concentrated under reduced pressure to give a residue. The residue was purified by SFC (column: REGIS (s,$) WHELK-01 (250 mm*50 mm, 10 um); mobile phase: [0.1% NH₃H₂O-MeOH]; B %: 20%-20%, 2.5 min; 1025 min) to provide peak 1 and peak 2. Peak 1 was concentrated under reduced pressure to give a yellow solid (compound 74, 45 g). Peak 2 was concentrated under reduced pressure to give a residue (P1). The residue (P1) was dissolved in H₂O (300 mL) and 0.05 M HCl was added until the pH=5, then extracted with ethyl acetate (300 mL*2). The combined organic layers were dried over Na₂SO₄ and concentrated under reduced pressure to give a residue. The residue was triturated with MTBE/PE (200 mL, V/V=1/1) at 25° C. for 1 hr and filtered to get a cake (10.2 g), the filtrate was concentrated under reduced pressure to get a yellow solid (compound 75, 7.00 g, crude). Compound 74 (was obtained as a yellow solid, whose structure was confirmed by H¹ NMR and F¹⁹ NMR. H¹ NMR: (400 MHz, DMSO) δ 12.7 (s, 1H), 8.09 (t, J=8.0 Hz, 1H), 7.50 (d, J=12.8 Hz, 1H), 7.32 (dd, J₂=12.0 Hz, J₂=8.4 Hz, 2H), 4.26 (t, J=7.8 Hz, 1H), 3.44-3.40 (m, 1H), 1.37-1.16 (m, 12H). F¹⁹ NMR: (400 MHz, DMSO) 119.7. Compound 74 (45.0 g, 125 mmol, 63.2% yield, NH₃) (Peak 1) was obtained as a yellow solid.

Example 188: tert-butyl N-[(2R,3S)-3-(3-fluoro-4-nitrophenyl)-1-(4-methylpiperazin-1-yl)-1-oxobutan-2-yl]carbamate (76)

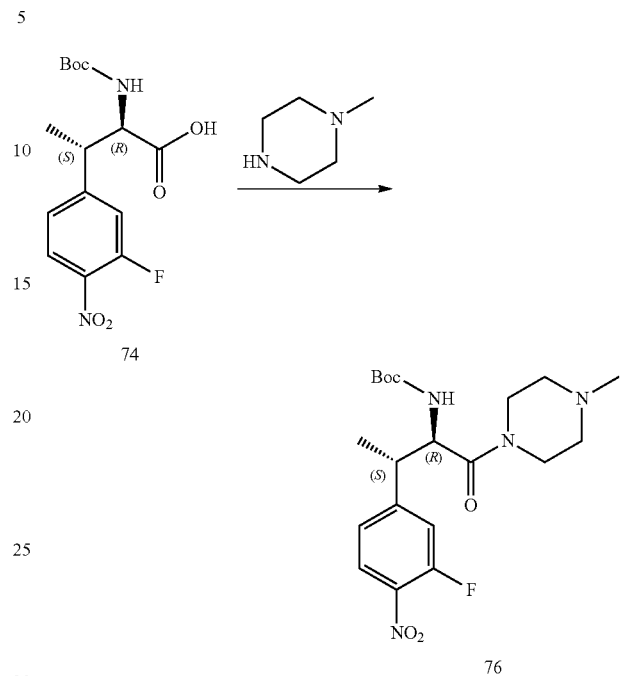

To a solution of 74 (1.13 g, 3.30 mmol, 1.0 eq.) in DMF (10 mL) was added N-methyl piperazine (0.44 mL, 3.96 mmol, 1.2 eq.), DIPEA (2.9 mL, 16.5 mmol, 5.0 eq) and HATU (1.88 g, 4.95 mmol, 1.5 eq.) and the resulting mixture was stirred at RT under a N₂ atmosphere for 1 h. The mixture was diluted with aq. sat. NaHCO₃ solution (600 mL) and then extracted with DCM (150 mL). The organic layer was washed with brine (200 mL), dried over Na₂SO₄ and then concentrated to afford 76 as an off-white solid (1.15 g, 82% yield) which was used in the next step without further purification. ¹H NMR (400 MHz, DMSO-d₆) δ 8.06 (t, J=8.2 Hz, 1H), 7.59-7.49 (m, 1H), 7.40-7.19 (m, 2H), 4.65 (t, J=9.0 Hz, 1H), 3.42 (s, 2H), 3.30-3.10 (m, 3H), 2.70 (s, 1H), 2.05 (s, 3H), 1.37 (s, 8H), 1.24 (d, J=6.9 Hz, 3H), 0.92-0.74 (m, 1H). UPLC-MS (basic 2 min): Rt=1.06 min; m/z=425.2 for [M+H]⁺.

Example 189: tert-butyl N-[(2R,3S)-3-(3-fluoro-4-nitrophenyl)-1-(4-methylpiperazin-1-yl)-1-oxobutan-2-yl]carbamate (77)

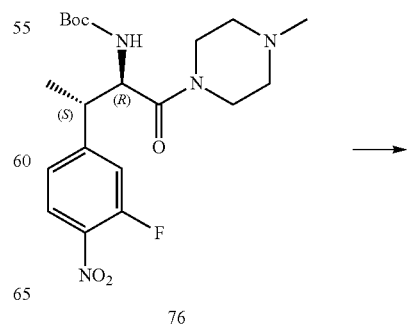

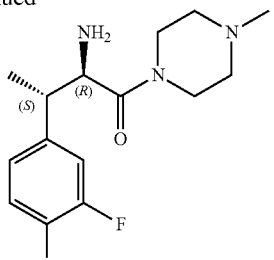

77

To a solution of 76 (0.683 g, 1.61 mmol, 1.0 eq.) in DCM (6 mL) was added TFA (3 mL) and the resulting mixture was stirred at RT for 1 h. The reaction mixture was concentrated to dryness and the residue was dissolved in DCM (15 mL), stirred in aq. sat. K₂CO₃ solution (2.5 g in 15 mL H₂O) and then extracted with DCM to afford 77 as a brown oil (0.458 g, 88% yield) which was used in the next step without further purification. ¹H NMR (400 MHz, DMSO-d₆) δ 8.06 (t, J=8.3 Hz, 1H), 7.52 (dd, J=13.0, 1.8 Hz, 1H), 7.31 (dd, J=8.5, 1.8 Hz, 1H), 3.83 (d, J=7.3 Hz, 1H), 3.45-3.34 (m, 3H), 3.21 (dd, J=11.4, 7.5 Hz, 1H), 2.96 (t, J=7.1 Hz, 1H), 2.35-2.13 (m, 2H), 2.07 (s, 3H), 1.78 (d, J=28.9 Hz, 4H), 1.26 (d, J=7.0 Hz, 3H), 1.11 (s, 1H). UPLC-MS (basic 2 min): Rt=0.85 min; m/z=325.2 for [M+H]⁺.

Example 190: N-[(2R,3S)-3-(3-fluoro-4-nitropheyl)-1-(4-methylpiperazin-1-yl)-1-oxobutan-2-yl]propanamide) (78)

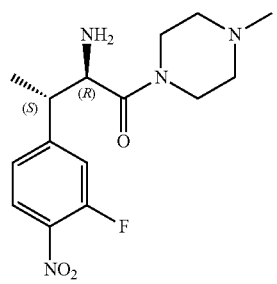

77

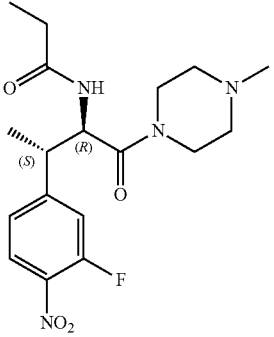

78

To a solution of 77 (0.458 g, 1.41 mmol, 1.0 eq.) in DMF (5.0 mL) were added propionic anhydride (0.22 mL, 1.69 mmol, 1.2 eq.) and DIPEA (0.74 mL, 4.24 mmol, 1.2 eq) and the resulting mixture was stirred at RT under a N₂ atmosphere for 1 h. The mixture was diluted with aq. sat. NaHCO₃ solution (100 mL) and then extracted with DCM (100 mL). The organic layer was washed with brine (100 mL), dried over Na₂SO₄ then concentrated to afford 78 as a dark yellow oil (0.425 g, 70% yield) which was used in the next step without further purification. ¹H NMR (400 MHz, DMSO-d₆) δ 8.34 (d, J=8.7 Hz, 1H), 8.07 (t, J=8.3 Hz, 1H), 7.55 (dd, J=12.7, 1.8 Hz, 1H), 7.31 (dd, J=8.5, 1.8 Hz, 1H), 4.99 (t, J=9.2 Hz, 1H), 3.48 (d, J=14.4 Hz, 1H), 3.31-3.20 (m, 1H), 3.14 (t, J=10.0 Hz, 1H), 2.21 (s, 1H), 2.16 (ddq, J=20.9, 14.8, 7.4 Hz, 2H), 1.70 (s, 2H), 1.24 (d, J=6.9 Hz, 3H), 0.99 (t, J=7.6 Hz, 3H). UPLC-MS (basic 2 min): Rt=0.90 min; m/z=381.2 for [M+H]⁺.

Example 191: N-[(2R,3S)-3-(4-amino-3-fluorophenyl)-1-(4-methylpiperazin-1-yl)-1-oxobutan-2-yl]propanamide) (79)

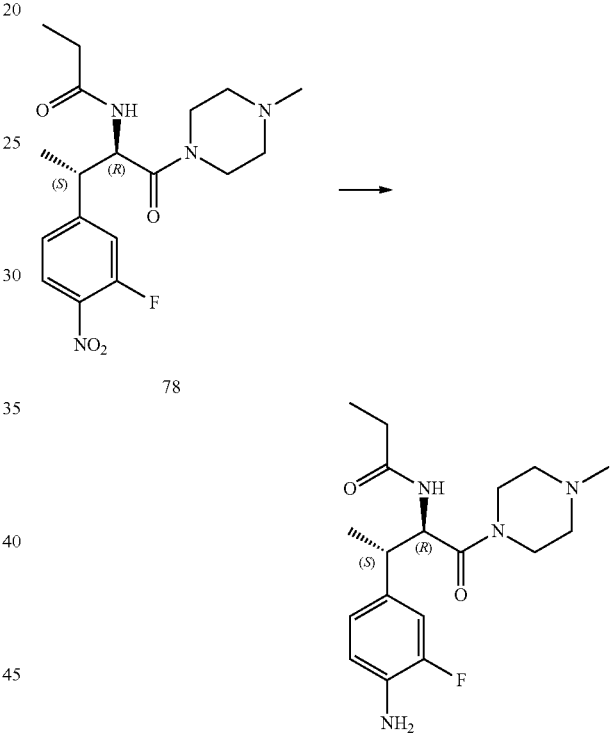

To a degassed solution of 78 (0.425 g, 1.12 mmol, 1.0 eq) in EtOH (10 mL) and THF (10 mL) was added Pd/C (0.050 g, 0.224 mmol, 0.20 eq). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness. The residue was triturated with DCM and iso-hexane to afford 79 as a light brown solid (0.354 g, 90% yield). ¹H NMR (400 MHz, DMSO-d₆) δ 8.18 (d, J=8.7 Hz, 1H), 6.82 (dd, J=12.8, 1.9 Hz, 1H), 6.75-6.58 (m, 2H), 4.94 (d, J=8.3 Hz, 1H), 4.76 (t, J=9.3 Hz, 1H), 3.27 (d, J=18.2 Hz, 3H), 3.18-3.03 (m, 1H), 2.94 (dd, J=9.8, 7.0 Hz, 1H), 2.13 (tt, J=15.0, 7.3 Hz, 4H), 1.77 (t, J=9.2 Hz, 1H), 1.59 (d, J=6.7 Hz, 1H), 1.15 (d, J=7.0 Hz, 3H), 0.98 (t, J=7.6 Hz, 3H). UPLC-MS (basic 2 min): Rt=0.79 min; m/z=351.2 for [M+H]⁺.

Example 192: General Procedure P for the Synthesis of 81a-d

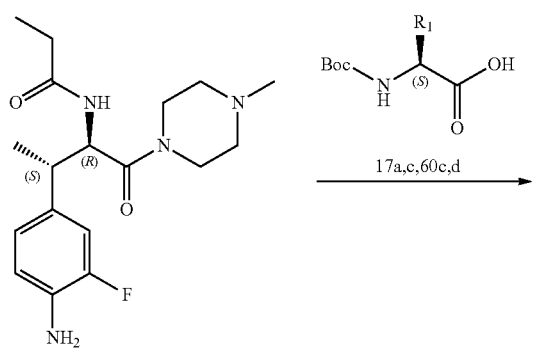

79

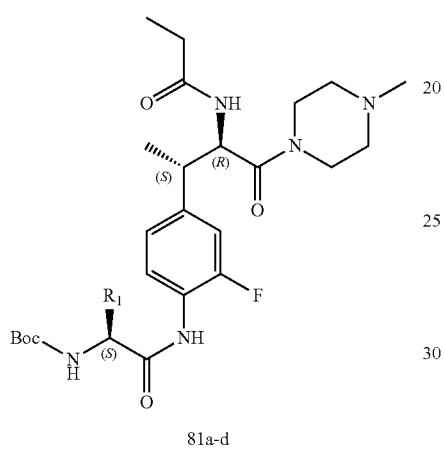

81a-d

To a solution of 79 (1.0 eq.) in DMF (0.1M) were added 17a,c,60c,d (1.2 eq.), DIPEA (4.0-8.0 eq.) and HATU (1.5-2.0 eq.) and the resulting mixture was stirred for 1 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 81a-c.

Example 193: tert-butyl N—[(S)-cyclohexyl({2-fluoro-4-[(2S,3R)-4-(4-methylpiperazin-1-yl)-4-oxo-3-propanamidobutan-2-yl]phenyl}carbamoyl)methyl]carbamate) (81a)

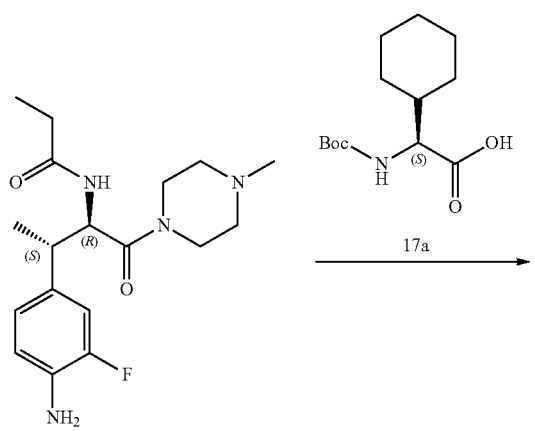

79

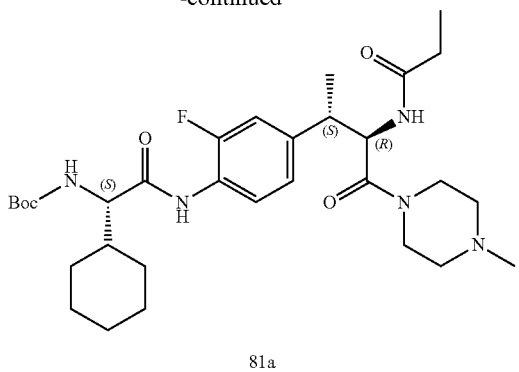

81a

Following General Procedure P, compound 79 (0.118 g, 0.337 mmol, 1.0 eq.) was reacted with (2S)-2-{[(tert-butoxy)carbonyl]amino}-2-cyclohexylacetic acid 17a (0.104 g, 0.404 mmol, 1.2 eq.), HATU (0.256 g, 0.673 mmol, 2.0 eq.) and DIPEA (0.47 mL, 2.69 mmol, 8.0 eq.) in DMF (5 mL) to afford, after flash column chromatography, 81a (0.136 g, 51% yield) as a brown solid. $^1$H NMR (400 MHz, DMSO-$d_6$) δ 9.62 (s, 1H), 8.27 (d, J=8.7 Hz, 1H), 7.74 (t, J=8.3 Hz, 1H), 7.11 (dd, J=12.1, 1.9 Hz, 1H), 7.01 (dd, J=8.3, 1.9 Hz, 1H), 6.86 (d, J=8.6 Hz, 1H), 4.86 (t, J=9.3 Hz, 1H), 4.07 (t, J=7.9 Hz, 1H), 3.44 (d, J=13.2 Hz, 2H), 3.15-3.01 (m, 2H), 2.25 (d, J=11.2 Hz, 2H), 2.25-2.09 (m, 2H), 2.05 (s, 3H), 1.68 (s, 5H), 1.58 (s, 4H), 1.38 (s, 11H), 1.20 (d, J=7.0 Hz, 3H), 1.11 (d, J=11.5 Hz, 3H), 0.99 (t, J=7.6 Hz, 3H). UPLC-MS (basic 2 min): rt=1.10 min; m/z=590.3 for [M+H]$^+$.

Example 194: tert-butyl N—[(S)-cycloheptyl({2-fluoro-4-[(2S,3R)-4-(4-methylpiperazin-1-yl)-4-oxo-3-propanamidobutan-2-yl]phenyl}carbamoyl)methyl]carbamate) (81b)

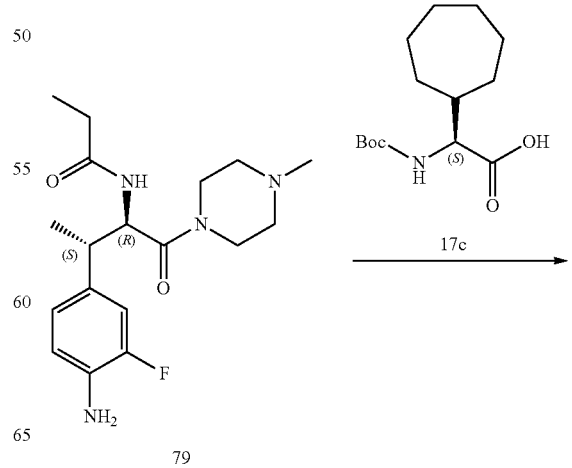

79

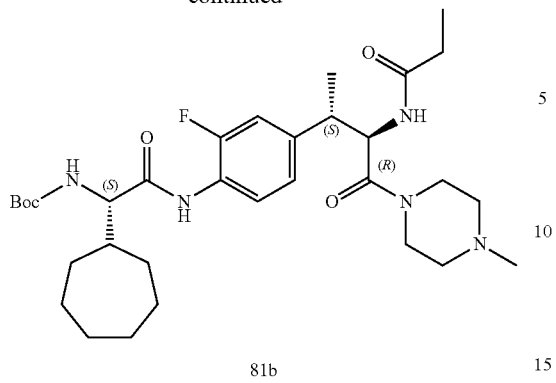

81b

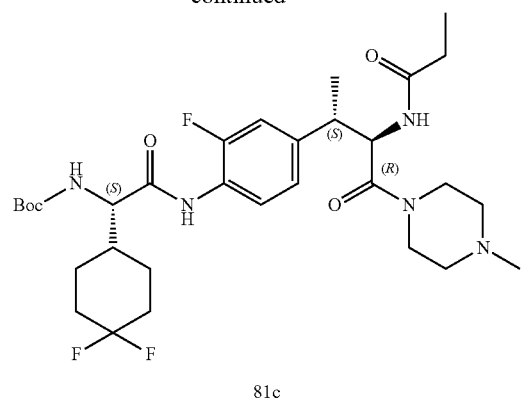

81c

Following General Procedure P, 79 (0.118 g, 0.337 mmol, 1.0 eq.) was reacted with (2S)-2-{[(tert-butoxy)carbonyl]amino}-2-cycloheptylacetic acid) 17c (0.110 g, 0.404 mmol, 1.2 eq.), HATU (0.256 g, 0.673 mmol, 2.0 eq.) and DIPEA (0.47 mL, 2.69 mmol, 8.0 eq.) in DMF (5 mL) to afford, after flash column chromatography, 81b (0.124 g, 61% yield) as a brown solid. $^1$H NMR (400 MHz, DMSO-$d_6$) δ 9.60 (s, 1H), 8.26 (d, J=8.7 Hz, 1H), 7.73 (t, J=8.3 Hz, 1H), 7.10 (dd, J=12.0, 1.9 Hz, 1H), 7.01 (dd, J=8.4, 1.9 Hz, 1H), 6.86 (d, J=8.7 Hz, 1H), 4.86 (t, J=9.3 Hz, 1H), 4.12 (t, J=8.0 Hz, 1H), 3.42 (d, J=13.0 Hz, 2H), 3.28 (d, J=17.0 Hz, 1H), 3.07 (dq, J=26.2, 10.1, 8.5 Hz, 2H), 2.26-2.05 (m, 4H), 2.01 (s, 3H), 1.70-1.44 (m, 7H), 1.38 (s, 10H), 1.20 (d, J=7.0 Hz, 3H), 0.99 (t, J=7.6 Hz, 3H). UPLC-MS (basic 2 min): rt=1.15 min; m/z=604.4 for [M+H]$^+$.

Following General Procedure P, 79 (0.118 g, 0.337 mmol, 1.0 eq.) was reacted with (2S)-2-{[(tert-butoxy)carbonyl]amino}-2-(4,4-difluorocyclohexyl)acetic acid) 60c (0.119 g, 0.404 mmol, 1.2 eq.), HATU (0.256 g, 0.673 mmol, 2.0 eq.) and DIPEA (0.47 mL, 2.69 mmol, 8.0 eq.) in DMF (5 mL) to afford, after flash column chromatography, 81c (0.104 g, 49% yield) as a brown solid. $^1$H NMR (400 MHz, DMSO-$d_6$) δ 9.73 (s, 1H), 8.26 (d, J=8.7 Hz, 1H), 7.75 (t, J=8.3 Hz, 1H), 7.12 (dd, J=12.1, 1.9 Hz, 1H), 7.07-6.98 (m, 2H), 4.87 (t, J=9.3 Hz, 1H), 4.20 (t, J=8.1 Hz, 1H), 3.16-3.01 (m, 1H), 3.07 (s, 1H), 2.25-2.06 (m, 4H), 2.01 (s, 4H), 1.78 (d, J=12.5 Hz, 3H), 1.65 (d, J=14.7 Hz, 4H), 1.55 (s, 1H), 1.39 (s, 9H), 1.20 (d, J=7.0 Hz, 3H), 0.99 (t, J=7.6 Hz, 3H). UPLC-MS (basic 2 min): rt=1.06 min; m/z=626.3 for [M+H]$^+$.

Example 195: tert-butyl N—[(S)-(4,4-difluorocyclohexyl)({2-fluoro-4-[(2S,3R)-4-(4-methylpiperazin-1-yl)-4-oxo-3-propanamidobutan-2-yl]phenyl}carbamoyl)methyl]carbamate) (81c)

Example 196: tert-butyl N—[(S)-({2-fluoro-4-[(2S,3R)-4-(4-methylpiperazin-1-yl)-4-oxo-3-propanamidobutan-2-yl]phenyl}carbamoyl)[(1r,4S)-4-methylcyclohexyl]methyl]carbamate) (81d)

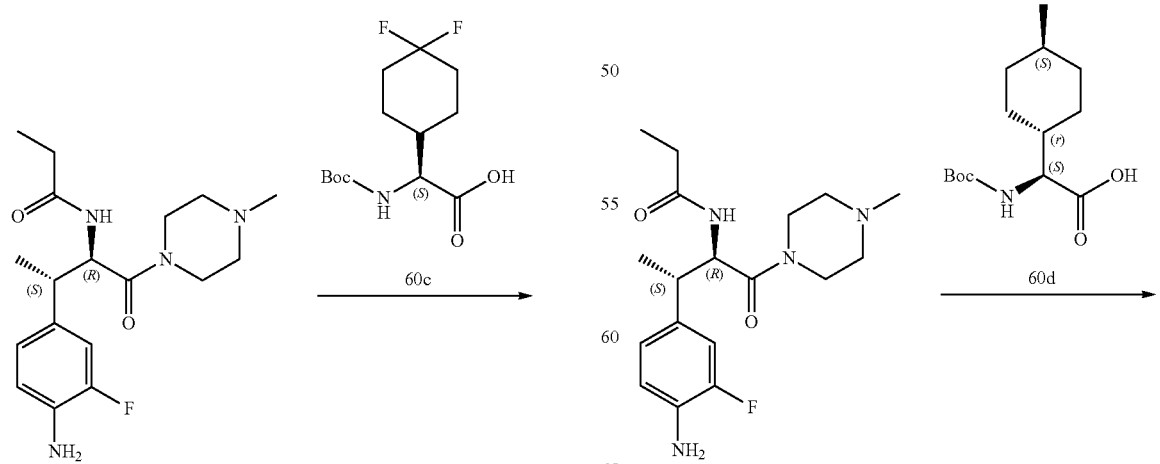

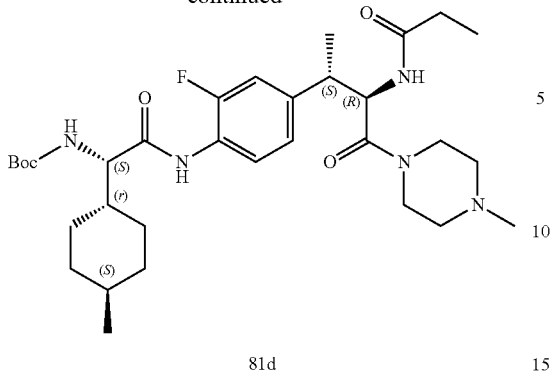

81d

Following General Procedure P, 79 (0.300 g, 0.856 mmol, 1.0 eq,) in DMF (3 mL) was reacted (2S)-2-{[(tert-butoxy)carbonyl]amino}-2-[(1r,4S)-4-methylcyclohexyl]acetic acid) (0.279 g, 1.03 mmol, 1.2 eq.), DIPEA (1.2 mL, 6.85 mmol, 8.0 eq.) and then HATU (0.488 g, 1.28 mmol, 1.5 eq.) and the resulting mixture was stirred at RT for 18 h. The combined organic phase was washed with brine, dried over sodium sulfate then concentrated to afford 81d which was used in the next step without further purification. $^1$H NMR (400 MHz, DMSO-$d_6$) δ 9.60 (s, 1H), 8.26 (d, J=8.8 Hz, 1H), 7.75 (t, J=8.3 Hz, 1H), 7.10 (d, J=12.0 Hz, 1H), 7.01 (d, J=8.4 Hz, 1H), 6.86 (d, J=8.7 Hz, 1H), 4.86 (t, J=9.3 Hz, 1H), 4.07 (d, J=8.1 Hz, 1H), 3.41 (s, 1H), 3.13-3.05 (m, 2H), 3.03 (s, 1H), 2.13 (ddq, J=22.3, 15.0, 7.4 Hz, 4H), 2.00 (s, 3H), 1.67 (d, J=12.6 Hz, 3H), 1.56 (d, J=14.4 Hz, 2H), 1.38 (s, 9H), 1.20 (d, J=7.0 Hz, 4H), 0.99 (t, J=7.6 Hz, 4H), 0.84 (d, J=6.5 Hz, 4H). UPLC-MS (2 min basic run) Rt=1.15 min. m/z=604.4 for [M+H]$^+$

Example 197: General Procedure Q for the Synthesis of 82a-d

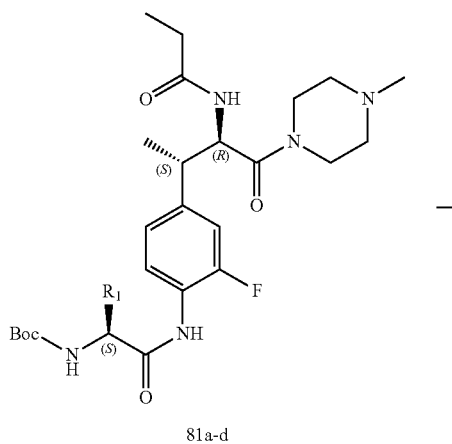

81a-d

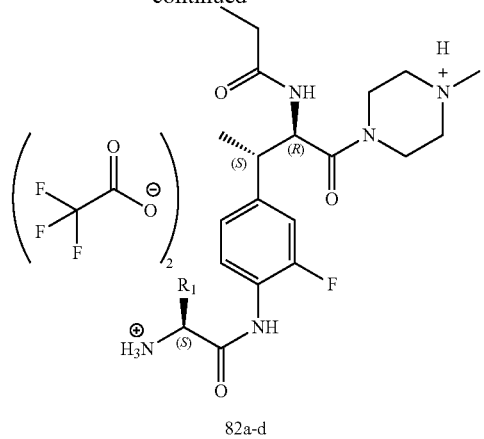

82a-d

To a solution of 81a-d (1.0 eq.) in DCM was added TFA (10 eq.) and the resulting mixture was stirred at RT for 0.5 h. The reaction mixture was concentrated to dryness to afford 82a-d which was used in the next step without further purification.

Example 198: (S)-cyclohexyl({2-fluoro-4-[(2S,3R)-4-(4-methylpiperazin-1-yl)-4-oxo-3-propanamidobutan-2-yl]phenyl}carbamoyl)methanaminium trifluoroacetate) (82a)

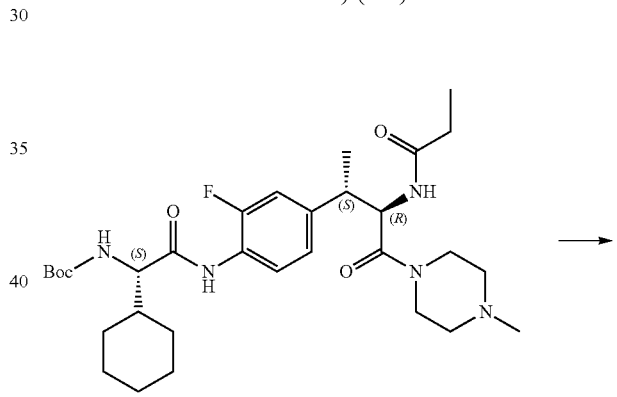

81a

82a

Following General Procedure Q, 81a (0.103 g, 0.175 mmol, 1.0 eq.) was reacted with TFA (2 mL) in DCM (2 mL) to afford, after concentration to dryness, 82a (0.106 g, 99% yield) as a brown oil which was used in the next step without further purification. UPLC-MS (basic 2 min): rt=0.96 min; m/z=490.3 for [M+H]$^+$.

Example 199: (S)-cycloheptyl({2-fluoro-4-[(2S,3R)-4-(4-methylpiperazin-1-yl)-4-oxo-3-propanamidobutan-2-yl]phenyl}carbamoyl)methanaminium trifluoroacetate) (82b)

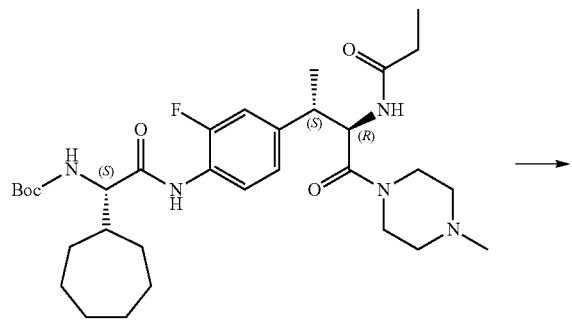

81b

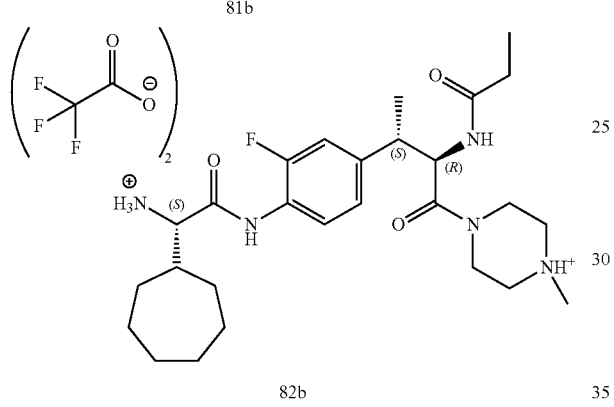

82b

Following General Procedure Q, 81b (0.140 g, 0.237 mmol, 1.0 eq.) was reacted with TFA (2 mL) in DCM (2 mL) to afford, after concentration to dryness, 82b (0.127 g, 99% yield) as a brown oil which was used in the next step without further purification. UPLC-MS (basic 2 min): rt=1.01 min; m/z=504.3 for [M+H]+.

Example 200: (S)-(4,4-difluorocyclohexyl)({2-fluoro-4-[(2S,3R)-4-(4-methylpiperazin-1-yl)-4-oxo-3-propanamidobutan-2-yl]phenyl}carbamoyl)methanaminium trifluoroacetate) (82c)

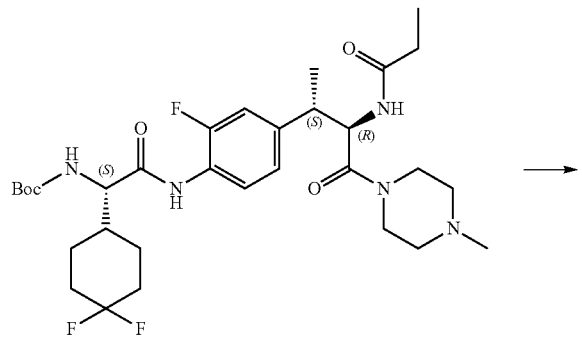

81c

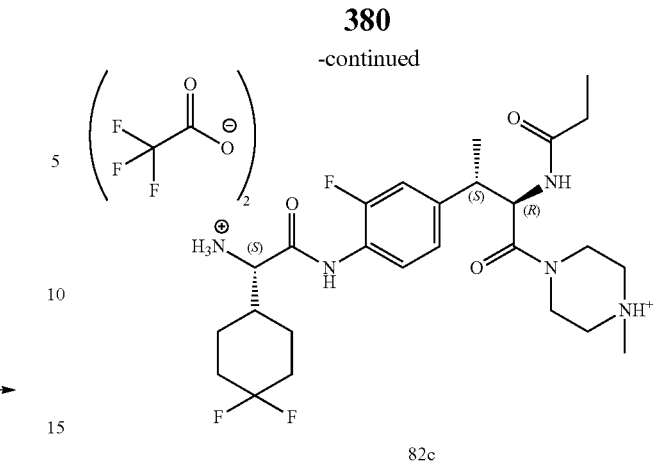

82c

Following General Procedure Q, 81c (0.104 g, 0.166 mmol, 1.0 eq.) was reacted with TFA (1 mL) in DCM (1 mL) to afford, after aqueous work-up, 82c (0.106 g, 99% yield) as a brown=0.91 min; m/z=526.3 for [M+H]+.

Example 201: 4-[(2R,3S)-3-{4-[(2S)-2-azaniumyl-2-[(1r,4S)-4-methylcyclohexyl]acetamido]-3-fluorophenyl}-2-propanamidobutanoyl]-1-methylpiperazin-1-ium ditrifluoroacetate) (82d)

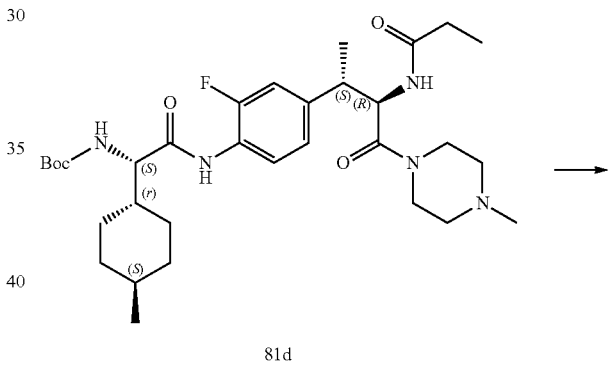

81d

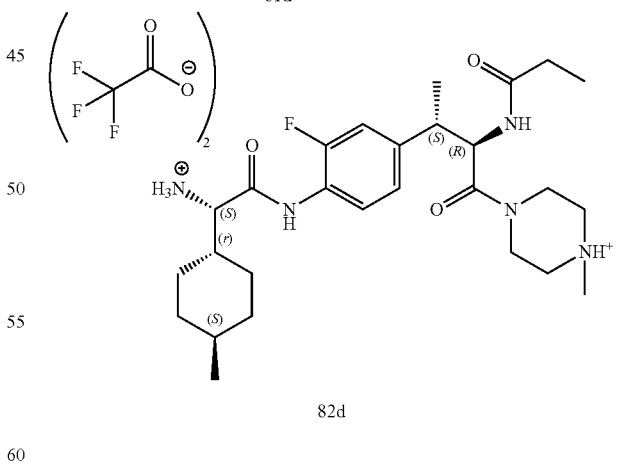

82d

Following General Procedure Q, 81d (0.280 g, 0.464 mmol, 1.0 eq.) in DCM (3 mL) was reacted with TFA (0.36 mL, 4.64 mmol, 10 eq.) and the resulting mixture was stirred at RT for 0.5 h. The reaction mixture was concentrated to dryness to afford 82d (0.340 g, 100%) as a brown gummy solid which was used in the next step without further purification.

Example 202: General Procedure R for the Synthesis of 218-220, 228-230, 233-234, 240-296, 389, 390, 393, 394, 397, 399, 404, 405, 418 and 419

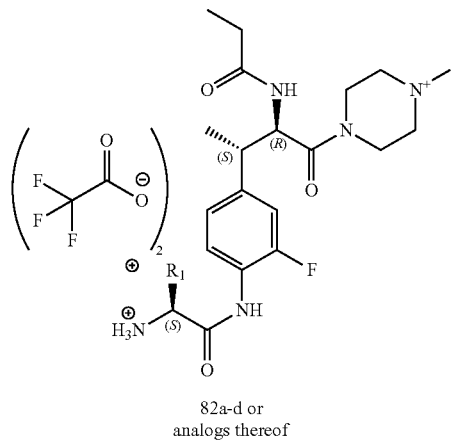

82a-d or analogs thereof

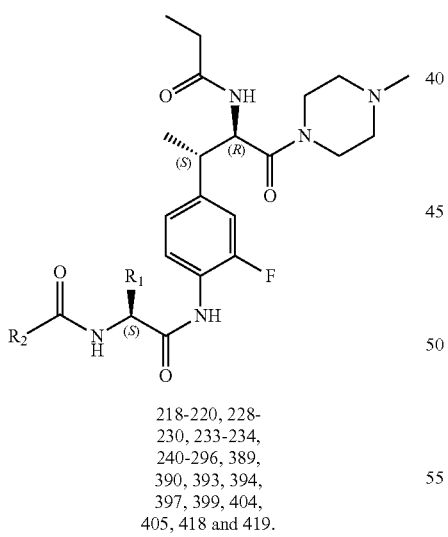

218-220, 228-230, 233-234, 240-296, 389, 390, 393, 394, 397, 399, 404, 405, 418 and 419.

To a solution of 82a-d thereof (1.0 eq,) in DMF were added the required carboxylic acid, DIPEA (8.0 eq.), HATU (1.5 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 218-220, 228-230, 233-234, 240-296, 389, 390, 393, 394, 397, 399, 404, 405, 418 and 419.

Example 203: N-[(2R,3S)-3-{4-[(2S)-2-cyclohexyl-2-[2,2-difluoro-2-(6-methoxypyridin-3-yl)acetamido] acetamido]-3-fluorophenyl}-1-(4-methylpiperazin-1-yl)-1-oxobutan-2-yl]propanamide) (218)

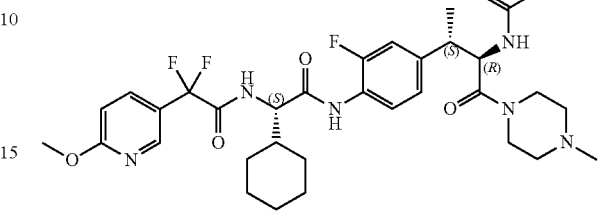

Following General Procedure R, 82a (0.065 g, 0.108 mmol, 1.0 eq.) was reacted with 2,2-difluoro-2-(6-methoxypyridin-3-yl)acetic acid (0.026 g, 0.129 mmol, 1.2 eq.), DIPEA (0.15 mL, 0.861 mmol, 8.0 eq.) and HATU (0.061 g, 0.162 mmol, 1.5 eq.) in DMF (1 mL) to afford, after reverse phase column chromatography, 218 (16.0 mg) as a white solid. $^1$H NMR (400 MHz, DMSO-$d_6$) δ 9.92 (s, 1H), 9.01 (d, J=8.2 Hz, 1H), 8.40 (d, J=2.5 Hz, 1H), 8.26 (d, J=8.7 Hz, 1H), 7.91 (dd, J=8.8, 2.5 Hz, 1H), 7.69 (t, J=8.3 Hz, 1H), 7.10 (dd, J=12.1, 1.9 Hz, 1H), 7.01 (dd, J=8.3, 1.9 Hz, 1H), 6.96 (d, J=8.8 Hz, 1H), 4.85 (t, J=9.3 Hz, 1H), 4.43 (t, J=8.5 Hz, 1H), 3.43 (d, J=12.2 Hz, 2H), 3.23 (t, J=10.5 Hz, 1H), 3.15-3.02 (m, 1H), 3.00 (t, J=10.5 Hz, 1H), 2.24-2.12 (m, 3H), 2.10 (dd, J=14.8, 7.5 Hz, 1H), 1.96 (s, 3H), 1.85 (d, J=10.3 Hz, 1H), 1.66 (d, J=10.5 Hz, 3H), 1.59 (s, 3H), 1.48 (t, J=9.7 Hz, 1H), 1.19 (d, J=7.0 Hz, 3H), 1.12 (d, J=9.1 Hz, 2H), 0.98 (t, J=7.6 Hz, 4H). UPLC-MS (basic 2 min): rt=1.10 min; m/z=675.3 for [M+H]⁺.

Example 204: N-[(2R,3S)-3-{4-[(2S)-2-cycloheptyl-2-[2,2-difluoro-2-(6-methoxypyridin-3-yl)acetamido] acetamido]-3-fluorophenyl}-1-(4-methylpiperazin-1-yl)-1-oxobutan-2-yl]propanamide) (219)

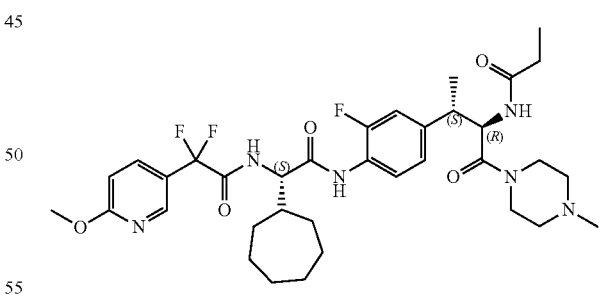

Following General Procedure R, 82b (0.072 g, 0.117 mmol, 1.0 eq.) was reacted with 2,2-difluoro-2-(6-methoxypyridin-3-yl)acetic acid (0.028 g, 0.140 mmol, 1.2 eq.), DIPEA (0.16 mL, 0.932 mmol, 8.0 eq.) and HATU (0.067 g, 0.175 mmol, 1.5 eq.) in DMF (1 mL) to afford, after reverse phase column chromatography, 219 (7.0 mg) as a white solid. $^1$H NMR (400 MHz, DMSO-$d_6$) δ 9.94 (s, 1H), 9.00 (d, J=8.5 Hz, 1H), 8.42 (d, J=2.5 Hz, 1H), 8.27 (d, J=8.7 Hz, 1H), 7.93 (dd, J=8.8, 2.6 Hz, 1H), 7.68 (t, J=8.3 Hz, 1H), 7.11 (dd, J=12.0, 1.9 Hz, 1H), 7.02 (dd, J=8.4, 1.9 Hz, 1H), 6.96 (d, J=8.7 Hz, 1H), 4.86 (t, J=9.3 Hz, 1H), 4.50 (t, J=8.5

Hz, 1H), 3.90 (s, 3H), 3.42 (s, 2H), 3.24 (t, J=9.8 Hz, 1H), 3.14-2.95 (m, 2H), 2.23-2.04 (m, 4H), 1.97 (s, 3H), 1.76-1.43 (m, 6H), 1.44-1.23 (m, 1H), 1.20 (d, J=7.0 Hz, 3H), 0.99 (t, J=7.6 Hz, 3H). UPLC-MS (basic 2 min): rt=1.29 min; m/z=689.4 for [M+H]$^+$.

Example 205: N-[(2R,3S)-3-{4-[(2S)-2-[2,2-difluoro-2-(4-methoxyphenyl)acetamido]-2-(4,4-difluorocyclo hexyl)acetamido]-3-fluorophenyl}-1-(4-methylpiperazin-1-yl)-1-oxobutan-2-yl]propanamide) (220)

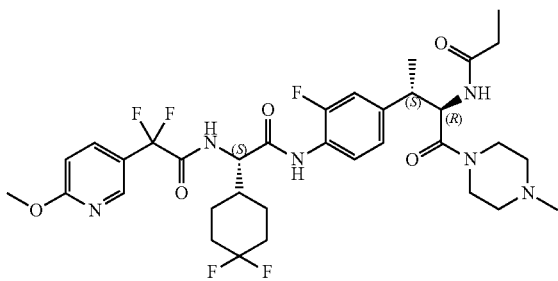

Following General Procedure R, 82c (0.053 g, 0.083 mmol, 1.0 eq.) was reacted with 2,2-difluoro-2-(6-methoxypyridin-3-yl)acetic acid (0.020 g, 0.100 mmol, 1.2 eq.), DIPEA (0.12 mL, 0.664 mmol, 8.0 eq.) and HATU (0.047 g, 0.125 mmol, 1.5 eq.) in DMF (1 mL) to afford, after reverse phase column chromatography, 220 (12.0 mg) as a white solid. $^1$H NMR (400 MHz, DMSO-d$_6$) δ 10.01 (s, 1H), 9.19 (d, J=7.9 Hz, 1H), 8.41 (d, J=2.5 Hz, 1H), 8.27 (d, J=8.7 Hz, 1H), 7.92 (dd, J=8.7, 2.6 Hz, 1H), 7.71 (t, J=8.3 Hz, 1H), 7.12 (dd, J=12.1, 1.9 Hz, 1H), 7.05-6.99 (m, 1H), 6.97 (d, J=8.7 Hz, 1H), 4.87 (t, J=9.3 Hz, 1H), 4.53 (t, J=8.5 Hz, 1H), 3.90 (s, 3H), 3.48-3.38 (m, 2H), 3.25 (d, J=20.0 Hz, 1H), 3.13-3.00 (m, 2H), 2.16 (ddd, J=15.0, 13.3, 7.5 Hz, 4H), 2.04 (dd, J=24.4, 9.0 Hz, 3H), 1.97 (s, 3H), 1.72 (dd, J=43.8, 13.0 Hz, 5H), 1.58-1.32 (m, 3H), 1.26 (s, 1H), 1.20 (d, J=7.0 Hz, 3H), 0.99 (t, J=7.6 Hz, 3H). UPLC-MS (basic 4 min): rt=1.71 min; m/z=711.3 for [M+H]$^+$.

Example 206: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]propanamide (229)

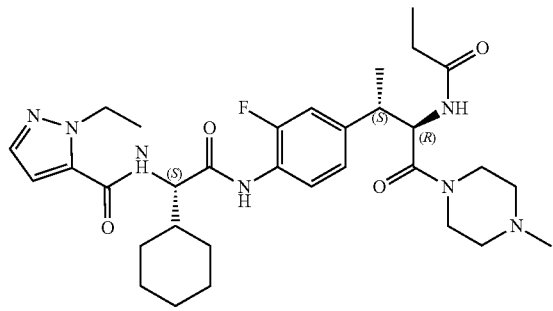

Following General Procedure R, 82a (0.065 g, 0.108 mmol, 1.0 eq.) was reacted with 1-ethyl-1H-pyrazole-5-carboxylic acid (0.018 g, 0.129 mmol, 1.2 eq.), DIPEA (0.15 mL, 0.861 mmol, 8.0 eq.) and HATU (0.061 g, 0.162 mmol, 1.5 eq.) in DMF (1 mL) to afford, after reverse phase column chromatography, 229 (18.0 mg) as a white solid. $^1$H NMR (400 MHz, DMSO-d$_6$) δ 9.85 (s, 1H), 8.43 (d, J=8.2 Hz, 1H), 8.25 (d, J=8.7 Hz, 1H), 7.73 (t, J=8.3 Hz, 1H), 7.47 (d, J=2.0 Hz, 1H), 7.14-7.06 (m, 1H), 7.04-6.96 (m, 2H), 4.86 (t, J=9.4 Hz, 1H), 4.55 (t, J=8.4 Hz, 1H), 4.46 (q, J=7.1 Hz, 2H), 3.31-3.20 (m, 1H), 3.09 (s, 1H), 3.07-2.97 (m, 1H), 2.13 (ddp, J=22.4, 15.1, 7.7 Hz, 3H), 1.98 (s, 3H), 1.80 (d, J=13.3 Hz, 1H), 1.70 (s, 2H), 1.64 (d, J=9.4 Hz, 2H), 1.51 (d, J=8.9 Hz, 1H), 1.31-1.17 (m, 7H), 1.16 (s, 4H), 0.98 (t, J=7.6 Hz, 3H). UPLC-MS (basic 2 min): rt=1.02 min; m/z=612.4 for [M+H]$^+$.

Example 207: N-[(2R,3S)-3-{4-[(2S)-2-[2-(3-cyanophenyl)-2,2-difluoroacetamido]-2-cyclohexyl acetamido]-3-fluorophenyl}-1-(4-methylpiperazin-1-yl)-1-oxobutan-2-yl]propanamide (230)

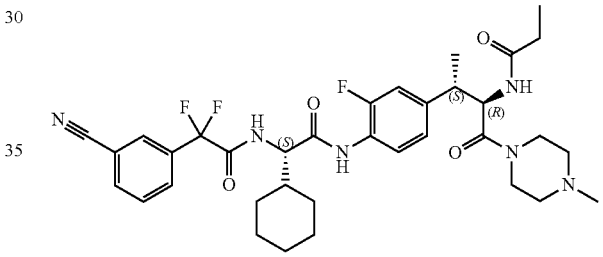

Following General Procedure R, 82a (0.138 g, 0.192 mmol, 1.0 eq.) was reacted with 2-(3-cyanophenyl)-2,2-difluoroacetic acid (0.046 g, 0.231 mmol, 1.2 eq.), DIPEA (0.27 mL, 1.54 mmol, 8.0 eq.) and HATU (0.110 g, 0.288 mmol, 1.5 eq.) in DMF (1 mL) to afford, after reverse phase column chromatography, 230 (35.7 mg) as a white solid. $^1$H NMR (400 MHz, DMSO-d$_6$) δ 9.93 (s, 1H), 9.08 (d, J=8.3 Hz, 1H), 8.26 (d, J=8.7 Hz, 1H), 8.14 (s, 1H), 8.07 (d, J=7.8 Hz, 1H), 7.95 (d, J=8.1 Hz, 1H), 7.77 (t, J=7.9 Hz, 1H), 7.70 (t, J=8.3 Hz, 1H), 7.10 (dd, J=12.2, 1.9 Hz, 1H), 7.01 (d, J=8.7 Hz, 1H), 4.86 (t, J=9.3 Hz, 1H), 4.44 (t, J=8.5 Hz, 1H), 3.42 (s, 2H), 3.24 (t, J=10.6 Hz, 1H), 3.05 (dt, J=33.7, 9.6 Hz, 2H), 2.25-2.04 (m, 2H), 2.09 (s, 3H), 1.96 (s, 3H), 1.85 (d, J=10.7 Hz, 1H), 1.73-1.56 (m, 7H), 1.50 (d, J=9.9 Hz, 1H), 1.26-1.09 (m, 7H), 1.06 (s, 1H), 0.99 (t, J=7.6 Hz, 3H), 0.92 (d, J=12.1 Hz, 1H). UPLC-MS (basic 4 min): rt=1.82 min; m/z=669.4 for [M+H]$^+$.

Example 208: N-[(2R,3S)-3-{4-[(2S)-2-cycloheptyl-2-[(1-ethyl-1H-pyrazol-5-yl)formamido]acetamido]-3-fluorophenyl}-1-(4-methylpiperazin-1-yl)-1-oxobutan-2-yl]propanamide (228)

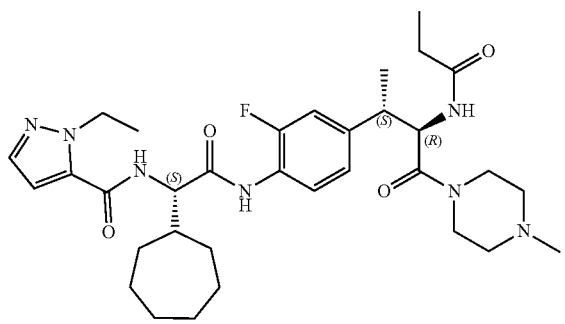

Following General Procedure R, 82b (0.110 g, 0.150 mmol, 1.0 eq.) was reacted with 1-ethyl-1H-pyrazole-5-carboxylic acid (0.025 g, 0.180 mmol, 1.2 eq.), DIPEA (0.21 mL, 1.20 mmol, 8.0 eq.) and HATU (0.086 g, 0.225 mmol, 1.5 eq.) in DMF (1 mL) to afford, after reverse phase column chromatography, 228 (18.1 mg) as a white solid. $^1$H NMR (400 MHz, DMSO-$d_6$) δ 9.87 (s, 1H), 8.44 (d, J=8.6 Hz, 1H), 8.26 (d, J=8.7 Hz, 1H), 7.72 (t, J=8.3 Hz, 1H), 7.47 (d, J=2.0 Hz, 1H), 7.11 (dd, J=12.1, 1.9 Hz, 1H), 7.05-6.96 (m, 2H), 4.86 (t, J=9.3 Hz, 1H), 4.62 (t, J=8.5 Hz, 1H), 4.47 (q, J=7.1 Hz, 2H), 3.42 (d, J=13.6 Hz, 2H), 3.26 (dd, J=19.0, 9.4 Hz, 2H), 3.14-2.99 (m, 1H), 2.19 (s, 1H), 2.16 (s, 1H), 2.19-2.04 (m, 2H), 1.98 (s, 3H), 1.72-1.62 (m, 5H), 1.51 (d, J=7.4 Hz, 6H), 1.40 (q, J=9.2, 8.2 Hz, 4H), 1.28 (t, J=7.1 Hz, 3H), 1.20 (d, J=7.0 Hz, 3H), 0.99 (t, J=7.6 Hz, 3H). UPLC-MS (basic 4 min): rt=1.74 min; m/z=626.4 for [M+H]$^+$.

Example 209: N-[(2R,3S)-3-{4-[(2S)-2-cycloheptyl-2-{[1-(propan-2-yl)-1H-pyrazol-5-yl]formamido}acetamido]-3-fluorophenyl}-1-(4-methylpiperazin-1-yl)-1-oxobutan-2-yl]propanamide (233)

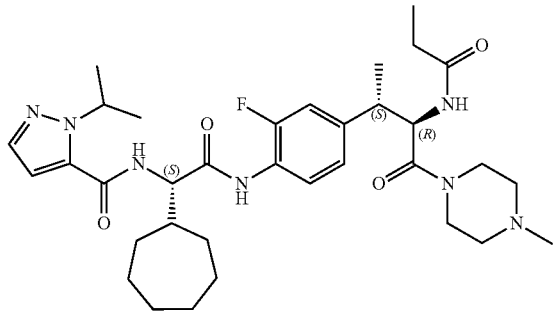

Following General Procedure R, 82b (0.230 g, 0.314 mmol, 1.0 eq.) was reacted with 1-(propan-2-yl)-1H-pyrazole-5-carboxylic acid (0.058 g, 0.377 mmol, 1.2 eq.), DIPEA (0.15 mL, 0.861 mmol, 8.0 eq.) and HATU (0.179 g, 0.471 mmol, 1.5 eq.) in DMF (2 mL) to afford, after reverse phase column chromatography, 233 (55.0 mg) as a white solid. $^1$H NMR (400 MHz, DMSO-$d_6$) δ 9.85 (s, 1H), 8.42 (d, J=8.5 Hz, 1H), 8.26 (d, J=8.7 Hz, 1H), 7.73 (t, J=8.3 Hz, 1H), 7.49 (d, J=2.0 Hz, 1H), 7.11 (d, J=12.5 Hz, 1H), 7.02 (d, J=8.6 Hz, 1H), 6.91 (d, J=2.0 Hz, 1H), 5.38 (p, J=6.6 Hz, 1H), 4.86 (t, J=9.3 Hz, 1H), 4.61 (t, J=8.4 Hz, 1H), 3.47-3.37 (m, 2H), 3.31-3.18 (m, 2H), 3.06 (dt, J=28.4, 9.1 Hz, 2H), 2.23-2.04 (m, 5H), 1.99 (s, 3H), 1.78-1.59 (m, 5H), 1.59-1.40 (m, 6H), 1.36 (dd, J=9.3, 6.6 Hz, 8H), 1.20 (d, J=7.0 Hz, 3H), 0.99 (t, J=7.6 Hz, 3H). UPLC-MS (basic 4 min): rt=1.82 min; m/z=640.5 for [M+H]$^+$.

Example 210: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-methylpiperazin-1-yl)-1-oxobutan-2-yl]propanamide) (234)

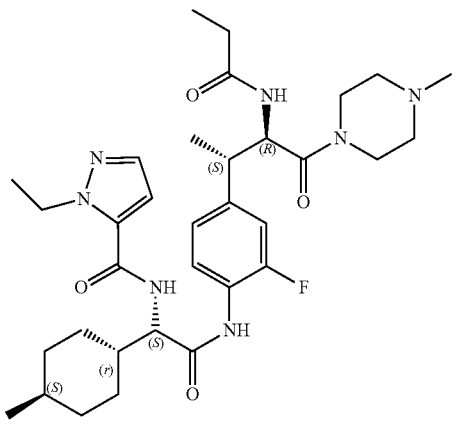

Following General Procedure R, 0.227 g, 0.310 mmol, 1.0 eq) of 82d in DMF (1 mL) were added 1-ethyl-1H-pyrazole-5-carboxylic acid (0.052 g, 0.372 mmol, 1.2 eq), DIPEA (0.43 mL, 2.482 mmol, 8.0 eq) and then HATU (0.177 g, 0.465 mmol, 1.5 eq.) and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 234 (0.025 g) as a white solid. $^1$H NMR (400 MHz, DMSO-$d_6$) δ 9.86 (s, 1H), 8.46 (d, J=8.3 Hz, 1H), 8.26 (d, J=8.7 Hz, 1H), 7.75 (t, J=8.3 Hz, 1H), 7.47 (d, J=2.1 Hz, 1H), 7.15-7.07 (m, 1H), 7.05-6.97 (m, 2H), 4.86 (t, J=9.4 Hz, 1H), 4.53 (t, J=8.4 Hz, 1H), 4.47 (q, J=7.2 Hz, 2H), 3.46-3.38 (m, 2H), 3.29-3.14 (m, 2H), 3.12-2.99 (m, 2H), 2.25-2.03 (m, 5H), 1.98 (s, 3H), 1.81 (ddt, J=15.0, 9.9, 5.6 Hz, 2H), 1.74-1.60 (m, 4H), 1.58-1.47 (m, 1H), 1.28 (t, J=7.1 Hz, 4H), 1.20 (d, J=7.0 Hz, 3H), 1.14-1.02 (m, 1H), 0.99 (t, J=7.6 Hz, 3H), 0.93-0.87 (m, 1H), 0.86 (d, J=6.5 Hz, 3H). UPLC-MS (basic 4 min): rt=1.76 min; m/z=626.4 for [M+H]$^+$.

Example 211: N-[(2R,3S)-3-{4-[(2S)-2-(4,4-difluorocyclohexyl)-2-[(1-ethyl-1H-pyrazol-5-yl)formamido] acetamido]-3-fluorophenyl}-1-(4-methylpiperazin-1-yl)-1-oxobutan-2-yl]propanamide) (240)

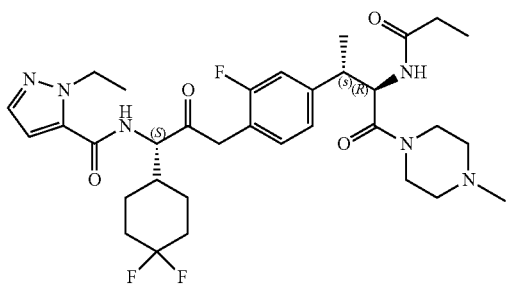

Compound 240 was synthesized by coupling 82c with the required carboxylic acid following General Procedure R and purified using reverse phase column chromatography. $^1$H NMR (400 MHz, DMSO-d$_6$) δ 9.96 (s, 1H), 8.59 (d, J=8.2 Hz, 1H), 8.26 (d, J=8.7 Hz, 1H), 7.75 (t, J=8.3 Hz, 1H), 7.48 (d, J=2.0 Hz, 1H), 7.13 (dd, J=12.1, 1.9 Hz, 1H), 7.05-6.98 (m, 2H), 4.87 (t, J=9.3 Hz, 1H), 4.67 (t, J=8.5 Hz, 1H), 4.47 (q, J=7.1 Hz, 2H), 3.40 (d, J=13.3 Hz, 2H), 3.26 (d, J=11.2 Hz, 1H), 3.16-3.01 (m, 2H), 2.14 (tq, J=22.4, 7.6 Hz, 7H), 1.99 (s, 3H), 1.85 (dd, J=28.9, 12.8 Hz, 2H), 1.78-1.64 (m, 3H), 1.51 (dd, J=23.3, 10.6 Hz, 2H), 1.43-1.32 (m, 1H), 1.28 (t, J=7.1 Hz, 3H), 1.20 (d, J=7.0 Hz, 3H), 0.99 (t, J=7.6 Hz, 3H). UPLC-MS (basic 4 min): rt=1.54 min; m/z=648.4 for [M+H].

Example 212: N-[(2R,3S)-3-{4-[(2S)-2-cycloheptyl-2-{[1-(propan-2-yl)-1H-pyrazol-5-yl]formamido}acetamido]-3-fluorophenyl}-1-(4-methylpiperazin-1-yl)-1-oxobutan-2-yl]propanamide (241)

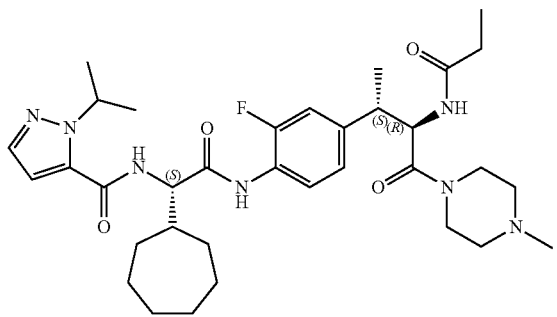

Compound 241 was synthesized by coupling 82b with the required carboxylic acid following General Procedure R and purified using reverse phase column chromatography. $^1$H NMR (400 MHz, DMSO-d$_6$) δ 9.85 (s, 1H), 8.42 (d, J=8.5 Hz, 1H), 8.26 (d, J=8.7 Hz, 1H), 7.73 (t, J=8.3 Hz, 1H), 7.49 (d, J=2.0 Hz, 1H), 7.11 (d, J=12.5 Hz, 1H), 7.02 (d, J=8.6 Hz, 1H), 6.91 (d, J=2.0 Hz, 1H), 5.38 (p, J=6.6 Hz, 1H), 4.86 (t, J=9.3 Hz, 1H), 4.61 (t, J=8.4 Hz, 1H), 3.47-3.37 (m, 2H), 3.31-3.18 (m, 2H), 3.06 (dt, J=28.4, 9.1 Hz, 2H), 2.23-2.04 (m, 5H), 1.99 (s, 3H), 1.78-1.59 (m, 5H), 1.59-1.40 (m, 6H), 1.36 (dd, J=9.3, 6.6 Hz, 8H), 1.20 (d, J=7.0 Hz, 3H), 0.99 (t, J=7.6 Hz, 3H). UPLC-MS (basic 4 min): rt=1.82 min; m/z=640.5 for [M+H]$^+$.

Example 213: N-[(2R,3S)-3-{4-[(2S)-2-cyclohexyl-2-(2-cyclopropyl-2,2-difluoroacetamido)acetamido]-3-fluorophenyl}-1-(4-methylpiperazin-1-yl)-1-oxobutan-2-yl]propanamide (242)

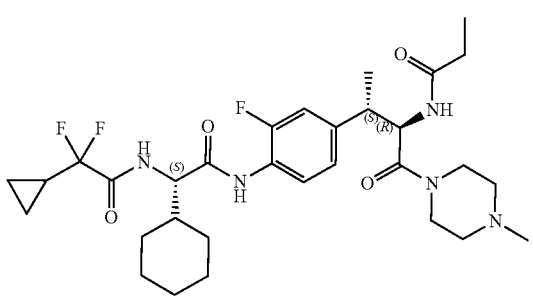

Compound 242 was synthesized by coupling 82a with the required carboxylic acid following General Procedure R and purified using reverse phase column chromatography. $^1$H NMR (400 MHz, DMSO-d$_6$) δ 9.89 (s, 1H), 8.52 (d, J=8.5 Hz, 1H), 8.27 (d, J=8.7 Hz, 1H), 7.72 (t, J=8.3 Hz, 1H), 7.11 (dd, J=12.1, 1.9 Hz, 1H), 7.02 (dd, J=8.4, 2.0 Hz, 1H), 4.87 (t, J=9.4 Hz, 1H), 4.44 (t, J=8.6 Hz, 1H), 3.44 (d, J=13.5 Hz, 2H), 3.30 (s, 2H), 3.15-3.05 (m, 1H), 3.03 (s, 2H), 2.25-2.05 (m, 3H), 2.02 (s, 3H), 1.83 (s, 1H), 1.78-1.43 (m, 8H), 1.18 (dd, J=22.1, 7.6 Hz, 6H), 0.99 (t, J=7.6 Hz, 4H), 0.70-0.58 (m, 4H). UPLC-MS (basic 4 min): rt=1.76 min; m/z=608.3 for [M+H]$^+$.

Example 214: N-[(2R,3S)-3-{4-[(2S)-2-cyclohexyl-2-[2,2-difluoro-2-(3-methoxyphenyl) acetamido]acetamido]-3-fluorophenyl}-1-(4-methylpiperazin-1-yl)-1-oxobutan-2-yl]propanamide (243)

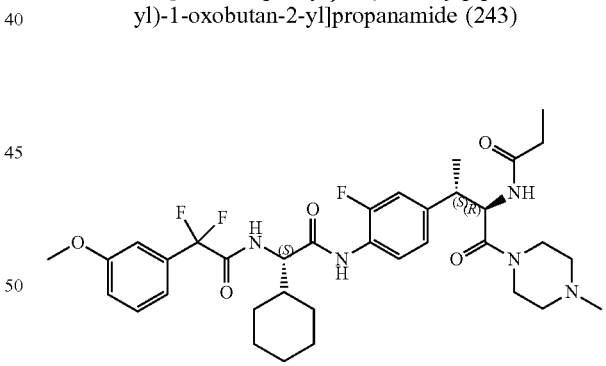

Compound 243 was synthesized by coupling 82a with the required carboxylic acid following General Procedure R and purified using reverse phase column chromatography. $^1$H NMR (400 MHz, DMSO-d$_6$) δ 9.91 (s, 1H), 8.95 (d, J=8.3 Hz, 1H), 8.27 (d, J=8.7 Hz, 1H), 7.71 (t, J=8.3 Hz, 1H), 7.43 (t, J=8.0 Hz, 1H), 7.21-7.16 (m, 2H), 7.14-7.07 (m, 2H), 7.05-6.98 (m, 1H), 4.86 (t, J=9.3 Hz, 1H), 4.44 (t, J=8.5 Hz, 1H), 3.79 (s, 3H), 3.42 (s, 2H), 3.29-3.20 (m, 1H), 3.14-3.03 (m, 1H), 3.02 (s, 1H), 2.25-2.04 (m, 5H), 1.97 (s, 3H), 1.86 (d, J=10.9 Hz, 1H), 1.65 (s, 5H), 1.58 (s, 2H), 1.50 (s, 1H), 1.16 (dd, J=34.1, 8.1 Hz, 7H), 0.99 (t, J=7.6 Hz, 3H), 0.91 (d, J=11.1 Hz, 1H). UPLC-MS (basic 4 min): rt=1.89 min; m/z=674.4 for [M+H]$^+$.

Example 215: N-[(2R,3S)-3-{4-[(2S)-2-[2-(2H-1,3-benzodioxol-5-yl)-2,2-difluoroacetamido]-2-cyclohexyl acetamido]-3-fluorophenyl}-1-(4-methylpiperazin-1-yl)-1-oxobutan-2-yl]propanamide (244)

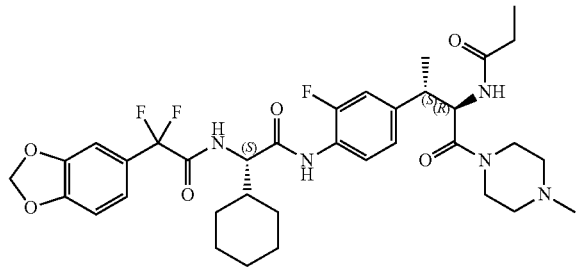

Compound 244 was synthesized by coupling 82a with the required carboxylic acid following General Procedure R and purified using reverse phase column chromatography. $^1$H NMR (400 MHz, DMSO-d$_6$) δ 9.90 (s, 1H), 8.87 (d, J=8.3 Hz, 1H), 8.27 (d, J=8.7 Hz, 1H), 7.71 (t, J=8.2 Hz, 1H), 7.17-7.07 (m, 3H), 7.02 (dd, J=8.2, 3.8 Hz, 2H), 6.10 (s, 2H), 4.86 (t, J=9.3 Hz, 1H), 4.42 (t, J=8.5 Hz, 1H), 3.24 (t, J=10.3 Hz, 1H), 3.14-2.97 (m, 2H), 2.25-2.04 (m, 4H), 1.97 (s, 3H), 1.85 (d, J=10.4 Hz, 1H), 1.66 (s, 5H), 1.59 (s, 3H), 1.51 (d, J=9.6 Hz, 1H), 1.20 (d, J=7.0 Hz, 3H), 1.15-1.09 (m, 5H), 0.99 (t, J=7.6 Hz, 4H). UPLC-MS (basic 4 min): rt=1.85 min; m/z=688.4 for [M+H]$^+$.

Example 216: N-[(2R,3S)-3-{4-[(2S)-2-cyclohexyl-2-[2,2-difluoro-2-(1H-indazol-5-yl)acetamido] acetamido]-3-fluorophenyl}-1-(4-methylpiperazin-1-yl)-1-oxobutan-2-yl]propanamide (245)

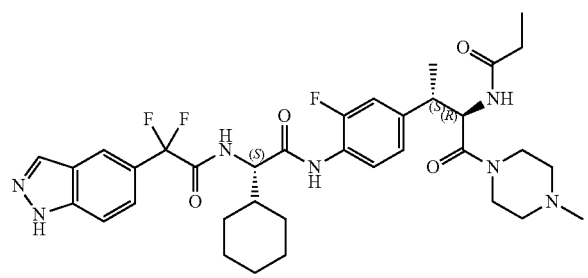

Compound 245 was synthesized by coupling 82a with the required carboxylic acid following General Procedure R and purified using reverse phase column chromatography. $^1$H NMR (400 MHz, DMSO-d$_6$) δ 13.34 (s, 1H), 9.89 (s, 1H), 8.91 (d, J=8.3 Hz, 1H), 8.26 (d, J=8.7 Hz, 1H), 8.21 (s, 1H), 8.06 (s, 1H), 7.71 (t, J=8.3 Hz, 1H), 7.66 (d, J=8.8 Hz, 1H), 7.56 (dd, J=8.8, 1.7 Hz, 1H), 7.11 (dd, J=12.1, 1.9 Hz, 1H), 7.01 (dd, J=8.3, 1.9 Hz, 1H), 4.86 (t, J=9.3 Hz, 1H), 4.44 (t, J=8.6 Hz, 1H), 3.42 (d, J=13.0 Hz, 2H), 3.23 (t, J=10.4 Hz, 1H), 3.15-3.04 (m, 1H), 3.01 (t, J=10.3 Hz, 1H), 2.17 (ddd, J=15.6, 10.5, 5.9 Hz, 3H), 2.09 (dd, J=14.9, 7.5 Hz, 1H), 1.94 (s, 3H), 1.86 (d, J=10.4 Hz, 1H), 1.63 (d, J=26.4 Hz, 5H), 1.48 (t, J=9.6 Hz, 1H), 1.20 (d, J=7.0 Hz, 3H), 1.12 (q, J=11.8, 11.1 Hz, 4H), 0.99 (t, J=7.6 Hz, 4H), 1.08-1.00 (m, 1H). m/z=684.4 for [M+H]$^+$.

Example 217: N-[(2R,3S)-3-{4-[(2S)-2-cyclohexyl-2-[2,2-difluoro-2-(5-methoxypyridin-3-yl)acetamido] acetamido]-3-fluorophenyl}-1-(4-methylpiperazin-1-yl)-1-oxobutan-2-yl]propanamide (246)

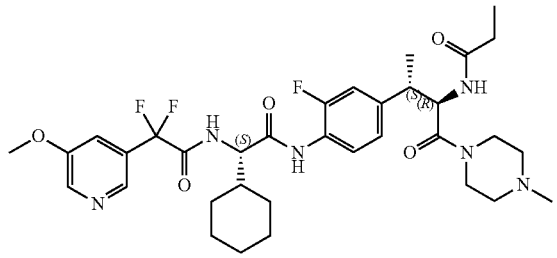

Compound 246 was synthesized by coupling 82a with the required carboxylic acid following General Procedure R and purified using reverse phase column chromatography. $^1$H NMR (400 MHZ, DMSO-d$_6$) δ 8.39 (d, J=3.2 Hz, 2H), 7.78 (t, J=8.2 Hz, 1H), 7.67-7.60 (m, 1H), 7.15-7.00 (m, 2H), 4.93 (d, J=10.4 Hz, 1H), 4.44 (d, J=8.8 Hz, 1H), 3.92 (s, 3H), 3.53 (d, J=13.9 Hz, 1H), 3.49-3.34 (m, 3H), 3.15 (dd, J=10.2, 6.7 Hz, 3H), 2.27 (dh, J=14.7, 7.4, 6.8 Hz, 5H), 2.07 (s, 3H), 1.86-1.64 (m, 7H), 1.57 (d, J=9.8 Hz, 1H), 1.33 (d, J=7.0 Hz, 3H), 1.31-1.16 (m, 4H), 1.13 (t, J=7.6 Hz, 4H), 1.08-1.00 (m, 1H). UPLC-MS (basic 4 min): rt=1.70 min; m/z 675.5 for [M+H]$^-$

Example 218: N-[(2R,3S)-3-{4-[(2S)-2-cyclohexyl-2-({furo[3,2-c]pyridin-3-yl}formamido)acetamido]-3-fluorophenyl}-1-(4-methylpiperazin-1-yl)-1-oxobutan-2-yl]propanamide (247)

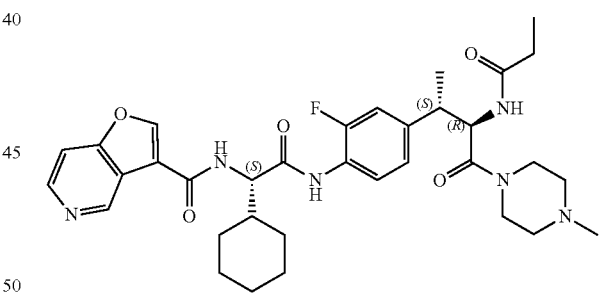

Compound 247 was synthesized by coupling 82a with the required carboxylic acid following General Procedure R and purified using reverse phase column chromatography. $^1$H NMR (400 MHz, Methanol-d$_4$) δ 9.29 (s, 1H), 8.59 (s, 1H), 8.50 (s, 1H), 7.85 (t, J=8.2 Hz, 1H), 7.68 (d, J=5.4 Hz, 1H), 7.19-6.98 (m, 2H), 4.94 (d, J=10.4 Hz, 1H), 4.65 (d, J=8.4 Hz, 1H), 3.50 (t, J=9.2 Hz, 1H), 3.42 (q, J=4.3, 3.8 Hz, 2H), 3.26-3.09 (m, 2H), 2.28 (qt, J=14.7, 7.3 Hz, 4H), 2.09 (s, 3H), 2.04-1.90 (m, 2H), 1.90-1.76 (m, 4H), 1.72 (d, J=11.0 Hz, 1H), 1.67-1.54 (m, 1H), 1.47-1.17 (m, 8H), 1.13 (t, J=7.6 Hz, 3H) UPLC-MS (basic 4 min): rt=1.56 min; m/z 635.4 for [M+H]$^+$.

391

Example 219: N-[(2R,3S)-3-{4-[(2S)-2-[(1-benzo-thiophen-3-yl)formamido]-2-cyclohexylacetamido]-3-fluorophenyl}-1-(4-methylpiperazin-1-yl)-1-oxobutan-2-yl]propanamide) (248)

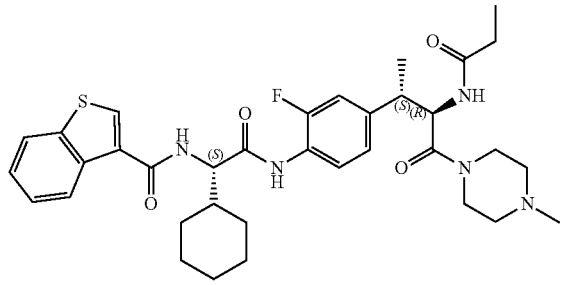

Compound 248 was synthesized by coupling 82a with the required carboxylic acid following General Procedure R and purified using reverse phase column chromatography. $^1$H NMR (400 MHz, Methanol-$d_4$) δ 8.40-8.31 (m, 1H), 8.25 (s, 1H), 7.99-7.90 (m, 1H), 7.86 (t, J=8.2 Hz, 1H), 7.49-7.36 (m, 2H), 7.19-7.03 (m, 2H), 4.94 (d, J=10.4 Hz, 1H), 4.63 (d, J=8.3 Hz, 1H), 3.53 (d, J=13.5 Hz, 1H), 3.49-3.34 (m, 2H), 3.25-3.04 (m, 2H), 2.27 (dh, J=14.7, 7.0 Hz, 4H), 2.06 (s, 3H), 1.97 (d, J=11.4 Hz, 2H), 1.82 (d, J=11.4 Hz, 4H), 1.71 (d, J=11.1 Hz, 1H), 1.60 (t, J=9.4 Hz, 1H), 1.34 (d, J=7.1 Hz, 4H), 1.31-1.18 (m, 3H), 1.13 (t, J=7.6 Hz, 3H). UPLC-MS (basic 4 min): rt=1.92 min; m/z=650.4 for [M+H]$^+$.

Example 220: N-[(2R,3S)-3-{4-[(2S)-2-cyclohexyl-2-({thieno[2,3-c]pyridin-3-yl}formamido)acetamido]-3-fluorophenyl}-1-(4-methylpiperazin-1-yl)-1-oxobutan-2-yl]propanamide (249)

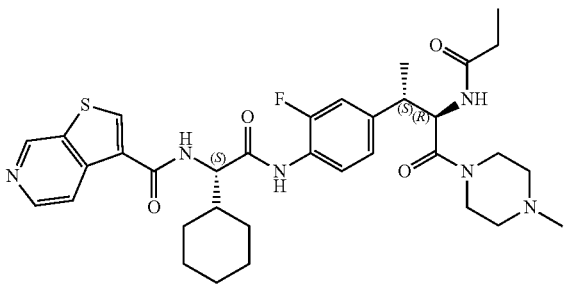

Compound 249 was synthesized by coupling 82a with the required carboxylic acid following General Procedure R and purified using reverse phase column chromatography. $^1$H NMR (400 MHz, Methanol-$d_4$) δ 9.19 (d, J=1.1 Hz, 1H), 8.69 (s, 1H), 8.49 (d, J=5.7 Hz, 1H), 8.35 (dd, J=5.7, 1.1 Hz, 1H), 7.86 (t, J=8.2 Hz, 1H), 7.24-7.04 (m, 2H), 4.95 (d, J=10.4 Hz, 1H), 4.65 (d, J=8.3 Hz, 1H), 3.58-3.47 (m, 1H), 3.42 (d, J=4.7 Hz, 2H), 3.26-3.05 (m, 2H), 2.41-2.18 (m, 5H), 2.08 (s, 3H), 1.98 (d, J=11.1 Hz, 2H), 1.91-1.77 (m, 4H), 1.68 (dd, J=28.3, 8.8 Hz, 2H), 1.34 (d, J=7.0 Hz, 4H), 1.31-1.17 (m, 4H), 1.13 (t, J=7.6 Hz, 3H). UPLC-MS (basic 4 min): rt=1.61 min; m/z=651.4 for [M+H]$^+$.

392

Example 221: N-[(2R,3S)-3-{4-[(2S)-2-cyclohexyl-2-({thieno[2,3-b]pyridin-3-yl}formamido)acetamido]-3-fluorophenyl}-1-(4-methylpiperazin-1-yl)-1-oxobutan-2-yl]propanamide) (250)

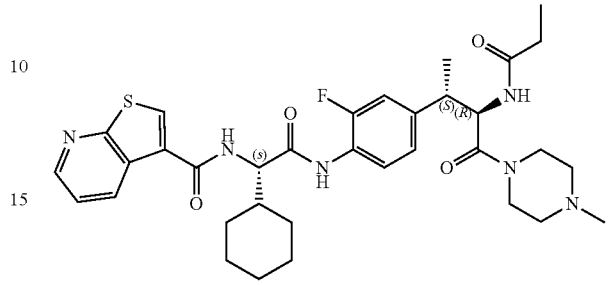

Compound 250 was synthesized by coupling 82a with the required carboxylic acid following General Procedure R and purified using reverse phase column chromatography. $^1$H NMR (400 MHz, Methanol-$d_4$) δ 8.76 (dt, J=8.2, 2.0 Hz, 1H), 8.58 (dd, J=4.6, 1.7 Hz, 1H), 8.46 (s, 1H), 7.81 (dt, J=31.8, 8.2 Hz, 1H), 7.50 (dd, J=8.2, 4.7 Hz, 1H), 7.19-7.00 (m, 2H), 5.01 (dd, J=51.7, 10.1 Hz, 1H), 4.63 (d, J=8.2 Hz, 1H), 3.92-3.36 (m, 4H), 3.16 (dd, J=10.3, 7.2 Hz, 2H), 2.54-2.15 (m, 5H), 2.09 (s, 3H), 2.05-1.92 (m, 2H), 1.83 (d, J=12.4 Hz, 3H), 1.77-1.57 (m, 1H), 1.43-1.18 (m, 8H), 1.13 (t, J=7.6 Hz, 3H). UPLC-MS (basic 4 min): rt=1.69 min; m/z=651.4 for [M+H]$^+$.

Example 222: N-[(2R,3S)-3-{4-[(2S)-2-cyclohexyl-2-[2,2-difluoro-2-(3-methanesulfonamidophenyl)acetamido]acetamido]-3-fluorophenyl}-1-(4-methylpiperazin-1-yl)-1-oxobutan-2-yl]propanamide (251)

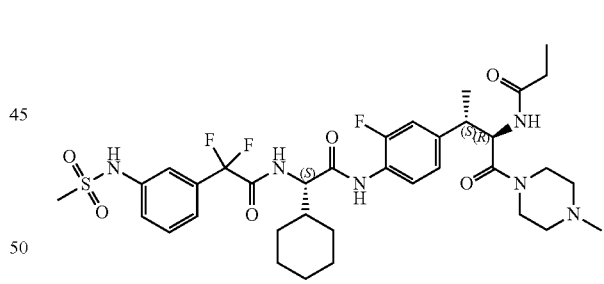

Compound 251 was synthesized by coupling 82a with the required carboxylic acid following General Procedure R and purified using reverse phase column chromatography. $^1$H NMR (400 MHz, DMSO-$d_6$) δ 10.05 (s, 1H), 9.90 (s, 1H), 8.95 (d, J=8.3 Hz, 1H), 8.26 (d, J=8.7 Hz, 1H), 7.71 (t, J=8.3 Hz, 1H), 7.49-7.43 (m, 2H), 7.38-7.27 (m, 2H), 7.10 (dd, J=12.1, 1.9 Hz, 1H), 7.02 (d, J=8.5 Hz, 1H), 4.86 (t, J=9.3 Hz, 1H), 4.42 (t, J=8.6 Hz, 1H), 3.42 (d, J=12.9 Hz, 2H), 3.30-3.16 (m, 2H), 3.15-3.01 (m, 2H), 2.99 (s, 3H), 2.13 (ddq, J=22.4, 15.1, 7.5 Hz, 4H), 1.98 (s, 3H), 1.88 (d, J=28.0 Hz, 1H), 1.66 (d, J=10.1 Hz, 3H), 1.54 (d, J=28.7 Hz, 3H), 1.20 (d, J=7.0 Hz, 3H), 1.11 (s, 4H), 0.99 (t, J=7.6 Hz, 3H), 0.90 (d, J=11.6 Hz, 1H). UPLC-MS (basic 4 min): rt=1.59 min; m/z=737.3 for [M+H]$^+$.

Example 223: N-[(2R,3S)-3-{4-[(2S)-2-cyclohexyl-2-(2-cyclohexyl-2,2-difluoroacetamido)acetamido]-3-fluorophenyl}-1-(4-methylpiperazin-1-yl)-1-oxobutan-2-yl]propanamide) (252)

Example 225: N-[(2R,3S)-3-{4-[(2S)-2-cyclohexyl-2-[(1-ethyl-1H-pyrrol-2-yl)formamido]acetamido]-3-fluorophenyl}-1-(4-methylpiperazin-1-yl)-1-oxobutan-2-yl]propanamide) (254)

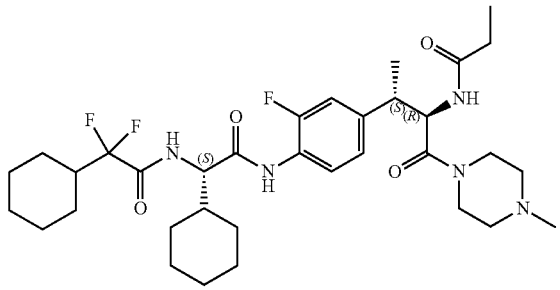

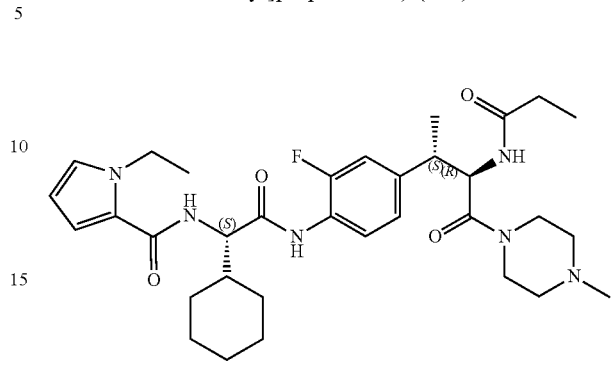

Compound 252 was synthesized by coupling 82a with the required carboxylic acid following General Procedure R and purified using reverse phase column chromatography. ¹H NMR (400 MHz, Methanol-d₄) δ 7.79 (t, J=8.2 Hz, 1H), 7.20-7.03 (m, 2H), 4.94 (d, J=10.4 Hz, 1H), 4.44 (d, J=8.6 Hz, 1H), 3.54 (d, J=13.6 Hz, 1H), 3.50-3.36 (m, 2H), 3.17 (dt, J=10.4, 6.9 Hz, 2H), 2.41-2.19 (m, 4H), 2.12 (s, 4H), 1.99-1.53 (m, 13H), 1.33 (d, J=7.0 Hz, 4H), 1.31-1.16 (m, 8H), 1.13 (t, J=7.6 Hz, 5H). UPLC-MS (basic 4 min): rt=2.06 min; m/z=650.4 for [M+H]⁺.

Compound 254 was synthesized by coupling 82a with the required carboxylic acid following General Procedure R and purified using reverse phase column chromatography. ¹H NMR (400 MHz, Methanol-d₄) δ 7.85 (t, J=8.2 Hz, 1H), 7.18-7.03 (m, 2H), 6.91 (dd, J=2.6, 1.7 Hz, 1H), 6.82 (dd, J=3.9, 1.7 Hz, 1H), 6.08 (dd, J=3.9, 2.6 Hz, 1H), 4.93 (d, J=10.5 Hz, 1H), 4.48 (d, J=8.3 Hz, 1H), 4.34 (q, J=7.1 Hz, 2H), 3.54 (d, J=13.8 Hz, 1H), 3.49-3.35 (m, 2H), 3.25-3.07 (m, 2H), 2.42-2.17 (m, 4H), 2.11 (s, 3H), 1.99-1.74 (m, 6H), 1.74-1.56 (m, 2H), 1.38-1.28 (m, 8H), 1.28-1.16 (m, 3H), 1.13 (t, J=7.6 Hz, 3H). UPLC-MS (basic 4 min): rt=1.71 min; m/z=611.4 for [M+H]⁺.

Example 224: N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]propanamide) (253)

Example 226: N-[(2R,3S)-3-{4-[(2S)-2-cyclohexyl-2-[(6-methoxy-1-benzofuran-3-yl)formamido]acetamido]-3-fluorophenyl}-1-(4-methylpiperazin-1-yl)-1-oxobutan-2-yl]propanamide) (255)

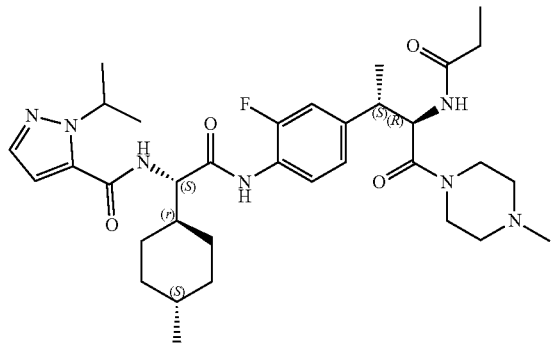

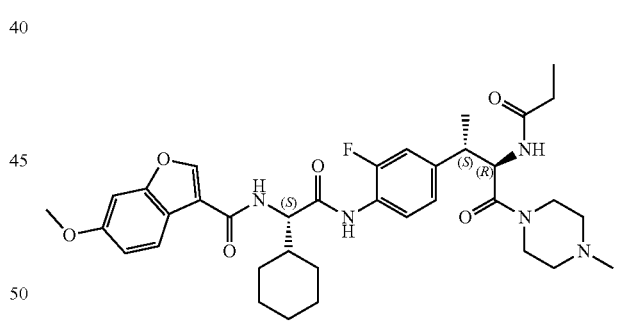

Compound 253 was synthesized by coupling 82d with the required carboxylic acid following General Procedure R and purified using reverse phase column chromatography. ¹H NMR (400 MHz, DMSO-d₆) δ 9.84 (s, 1H), 8.43 (d, J=8.2 Hz, 1H), 8.26 (d, J=8.7 Hz, 1H), 7.75 (t, J=8.3 Hz, 1H), 7.49 (d, J=2.0 Hz, 1H), 7.11 (dd, J=12.0, 1.9 Hz, 1H), 7.01 (dd, J=8.3, 2.0 Hz, 1H), 6.93 (d, J=2.0 Hz, 1H), 5.39 (p, J=6.6 Hz, 1H), 4.86 (t, J=9.4 Hz, 1H), 4.52 (t, J=8.3 Hz, 1H), 3.25 (t, J=10.2 Hz, 4H), 3.15-2.98 (m, 3H), 2.14 (tq, J=22.4, 7.6 Hz, 5H), 1.99 (s, 3H), 1.88-1.70 (m, 3H), 1.70-1.48 (m, 5H), 1.36 (dd, J=9.4, 6.6 Hz, 6H), 1.20 (d, J=7.0 Hz, 3H), 1.13-1.04 (m, 1H), 0.99 (t, J=7.6 Hz, 3H), 0.86 (d, J=6.5 Hz, 3H). UPLC-MS (basic 4 min): rt=1.85 min; m/z=640.4 for [M+H]⁺.

Compound 255 was synthesized by coupling 82a with the required carboxylic acid following General Procedure R and purified using reverse phase column chromatography. ¹H NMR (400 MHz, Methanol-d₄) δ 8.33 (s, 1H), 7.92-7.80 (m, 2H), 7.18-7.04 (m, 3H), 6.96 (dd, J=8.7, 2.3 Hz, 1H), 4.94 (d, J=10.4 Hz, 1H), 4.61 (d, J=8.2 Hz, 1H), 3.85 (s, 3H), 3.59-3.34 (m, 3H), 3.16 (dq, J=10.4, 6.9 Hz, 2H), 2.28 (qp, J=15.0, 7.2 Hz, 4H), 2.09 (s, 3H), 1.95 (d, J=6.4 Hz, 2H), 1.83 (t, J=11.6 Hz, 4H), 1.75-1.58 (m, 2H), 1.34 (d, J=7.1 Hz, 3H), 1.30-1.16 (m, 3H), 1.13 (t, J=7.6 Hz, 3H). UPLC-MS (basic 4 min): rt=1.57 min; m/z=664.4 for [M+H]⁺.

Example 227: N-[(2R,3S)-3-{4-[(2S)-2-cyclohexyl-2-[2,2-difluoro-2-(1H-indazol-6-yl)acetamido]acetamido]-3-fluorophenyl}-1-(4-methylpiperazin-1-yl)-1-oxobutan-2-yl]propanamide) (256)

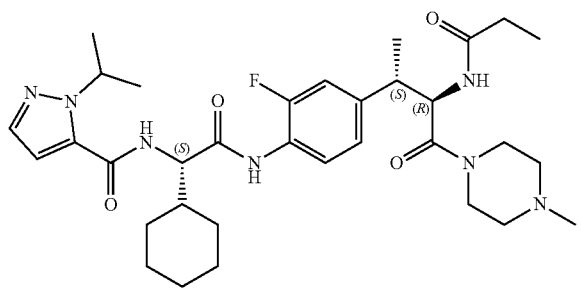

Compound 256 was synthesized by coupling 82a with the required carboxylic acid following General Procedure R and purified using reverse phase column chromatography. $^1$H NMR (400 MHz, Methanol-d$_4$) δ 7.83 (t, J=8.2 Hz, 1H), 7.50 (d, J=2.0 Hz, 1H), 7.17-7.04 (m, 2H), 6.78 (d, J=2.1 Hz, 1H), 5.38 (hept, J=6.6 Hz, 1H), 4.94 (d, J=10.4 Hz, 1H), 4.53 (d, J=8.4 Hz, 1H), 3.51 (d, J=14.2 Hz, 1H), 3.41 (d, J=5.5 Hz, 2H), 3.25-3.09 (m, 2H), 2.38-2.16 (m, 4H), 2.10 (s, 3H), 1.99-1.55 (m, 8H), 1.44 (dd, J=6.6, 4.2 Hz, 6H), 1.33 (d, J=7.0 Hz, 3H), 1.24 (dt, J=22.4, 11.5 Hz, 4H), 1.13 (t, J=7.6 Hz, 4H). UPLC-MS (basic 4 min): rt=1.71 min; m/z=626.4 for [M+H]$^+$.

Example 228: N-[(2R,3S)-3-{4-[(2S)-2-cycloheptyl-2-[(3-ethyl-1,2-oxazol-4-yl)formamido]acetamido]-3-fluorophenyl}-1-(4-methylpiperazin-1-yl)-1-oxobutan-2-yl]propanamide (257)

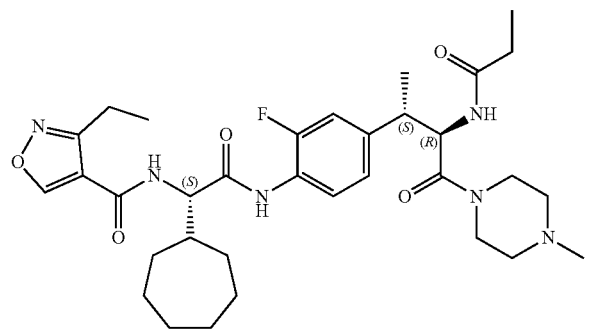

Compound 257 was synthesized by coupling 82b with the required carboxylic acid following General Procedure R and purified using reverse phase column chromatography. 1H NMR (400 MHz, DMSO-d$_6$) δ 9.89 (s, 1H), 9.40 (s, 1H), 8.42 (d, J=8.6 Hz, 1H), 8.26 (d, J=8.7 Hz, 1H), 7.70 (t, J=8.2 Hz, 1H), 7.11 (dd, J=12.0, 1.9 Hz, 1H), 7.04-6.99 (m, 1H), 4.87 (t, J=9.3 Hz, 1H), 4.65 (t, J=8.2 Hz, 1H), 3.41 (d, J=14.2 Hz, 3H), 3.25 (d, J=11.2 Hz, 1H), 3.18-2.99 (m, 2H), 2.90-2.77 (m, 2H), 2.23-2.08 (m, 4H), 1.99 (s, 3H), 1.79-1.60 (m, 5H), 1.59-1.31 (m, 9H), 1.27-1.14 (m, 6H), 0.99 (t, J=7.5 Hz, 3H). UPLC-MS (basic 4 min): rt=1.78 min; m/z=627.3 for [M+H]$^+$.

Example 229: N-[(2R,3S)-3-{4-[(2S)-2-cycloheptyl-2-[(6-methoxy-1-benzofuran-3-yl)formamido]acetamido]-3-fluorophenyl}-1-(4-methylpiperazin-1-yl)-1-oxobutan-2-yl]propanamide (258)

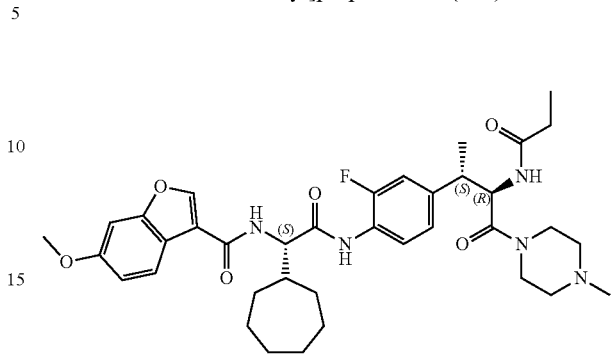

Compound 258 was synthesized by coupling 82b with the required carboxylic acid following General Procedure R and purified using reverse phase column chromatography. $^1$H NMR (400 MHz, DMSO-d$_6$) δ 9.93 (s, 1H), 8.66 (s, 1H), 8.34-8.23 (m, 2H), 7.89 (d, J=8.7 Hz, 1H), 7.72 (t, J=8.3 Hz, 1H), 7.25 (d, J=2.2 Hz, 1H), 7.14-7.09 (m, 1H), 7.03-7.00 (m, 1H), 6.99-6.95 (m, 1H), 4.86 (t, J=9.3 Hz, 1H), 4.73 (t, J=8.3 Hz, 1H), 3.82 (s, 3H), 3.41 (d, J=13.4 Hz, 2H), 3.25 (t, J=9.9 Hz, 1H), 3.11-2.97 (m, 2H), 2.23-2.03 (m, 5H), 1.98 (s, 3H), 1.83-1.32 (m, 14H), 1.20 (d, J=7.0 Hz, 3H), 0.99 (t, J=7.6 Hz, 3H). UPLC-MS (basic 4 min): rt=1.96 min; m/z=678.3 for [M+H]$^+$.

Example 230: N-[(2R,3S)-3-{4-[(2S)-2-[(1-benzothiophen-3-yl)formamido]-2-cycloheptylacetamido]-3-fluorophenyl}-1-(4-methylpiperazin-1-yl)-1-oxobutan-2-yl]propanamide (259)

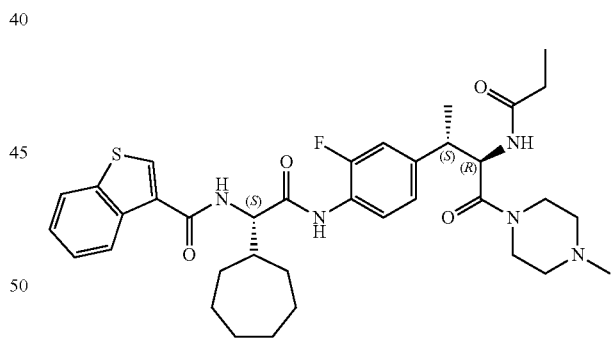

Compound 259 was synthesized by coupling 82b with the required carboxylic acid following General Procedure R and purified using reverse phase column chromatography. 1H NMR (400 MHz, DMSO-d$_6$) δ 9.90 (s, 1H), 8.51 (s, 1H), 8.47 (d, J=8.6 Hz, 1H), 8.44-8.39 (m, 1H), 8.27 (d, J=8.7 Hz, 1H), 8.07-8.02 (m, 1H), 7.74 (t, J=8.3 Hz, 1H), 7.49-7.39 (m, 2H), 7.15-7.07 (m, 1H), 7.02 (dd, J=8.3, 1.9 Hz, 1H), 4.87 (t, J=9.3 Hz, 1H), 4.72 (t, J=8.3 Hz, 1H), 3.42 (d, J=13.6 Hz, 2H), 3.25 (t, J=10.8 Hz, 1H), 3.16-2.97 (m, 2H), 2.24-2.04 (m, 5H), 1.98 (s, 3H), 1.85-1.62 (m, 5H), 1.61-1.37 (m, 9H), 1.20 (d, J=7.0 Hz, 3H), 0.99 (t, J=7.6 Hz, 3H). UPLC-MS (basic 4 min): rt=2.02 min; m/z=664.3 for [M+H]$^+$.

397

Example 231: N-[(2R,3S)-3-{4-[(2S)-2-[2-(3-cyanophenyl)-2,2-difluoroacetamido]-2-cycloheptyl acetamido]-3-fluorophenyl}-1-(4-methylpiperazin-1-yl)-1-oxobutan-2-yl]propanamide (260)

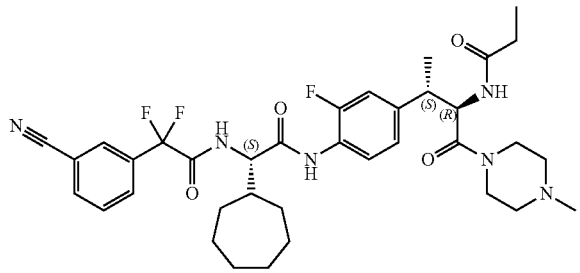

Compound 260 was synthesized by coupling 82b with the required carboxylic acid following General Procedure R and purified using reverse phase column chromatography. $^1$H NMR (400 MHz, DMSO-$d_6$) δ 9.95 (s, 1H), 9.08 (d, J=8.6 Hz, 1H), 8.27 (d, J=8.6 Hz, 1H), 8.18-8.13 (m, 1H), 8.10-8.03 (m, 1H), 8.00-7.93 (m, 1H), 7.81-7.63 (m, 2H), 7.14-6.98 (m, 2H), 4.93-4.79 (m, 1H), 4.58-4.45 (m, 1H), 3.47-3.38 (m, 2H), 3.28-3.19 (m, 1H), 3.14-2.95 (m, 2H), 2.26-1.90 (m, 8H), 1.68-1.57 (m, 3H), 1.56-1.44 (m, 5H), 1.40-1.37 (m, 2H), 1.34-1.23 (m, 4H), 1.20 (d, J=7.0 Hz, 3H), 0.99 (t, J=7.6 Hz, 3H) UPLC-MS (basic 4 min): rt=1.89 min; m/z=683.3 for [M+H]$^+$.

Example 232: N-[(2R,3S)-3-{4-[(2S)-2-[2-(5-cyanopyridin-3-yl)-2,2-difluoroacetamido]-2-cycloheptyl acetamido]-3-fluorophenyl}-1-(4-methylpiperazin-1-yl)-1-oxobutan-2-yl]propanamide (261)

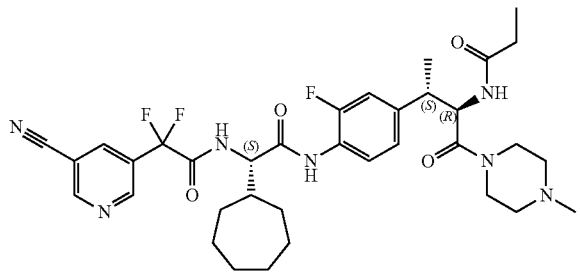

Compound 261 was synthesized by coupling 82b with the required carboxylic acid following General Procedure R and purified using reverse phase column chromatography. $^1$H NMR (400 MHz, DMSO-$d_6$) δ 10.00 (s, 1H), 9.25 (d, J=1.9 Hz, 1H), 9.18 (d, J=8.5 Hz, 1H), 9.10 (d, J=2.2 Hz, 1H), 8.69 (t, J=2.1 Hz, 1H), 8.28 (d, J=8.7 Hz, 1H), 7.68 (t, J=8.3 Hz, 1H), 7.11 (dd, J=12.0, 1.8 Hz, 1H), 7.07-6.96 (m, 1H), 4.90-4.80 (m, 1H), 4.51 (t, J=8.4 Hz, 1H), 3.24 (t, J=10.9 Hz, 1H), 3.14-2.97 (m, 2H), 2.23-2.03 (m, 5H), 1.98 (d, J=8.4 Hz, 3H), 1.76-1.15 (m, 16H), 0.99 (t, J=7.6 Hz, 3H). UPLC-MS (basic 4 min): rt=1.79 min; m/z=684.3 for [M+H]$^+$.

398

Example 233: N-[(2R,3S)-3-{4-[(2S)-2-cycloheptyl-2-[2,2-difluoro-2-(5-methoxypyridin-3-yl)acetamido] acetamido]-3-fluorophenyl}-1-(4-methylpiperazin-1-yl)-1-oxobutan-2-yl]propanamide (262)

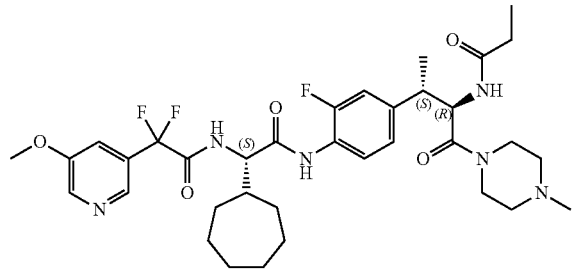

Compound 262 was synthesized by coupling 82b with the required carboxylic acid following General Procedure R and purified using reverse phase column chromatography. $^1$H NMR (400 MHz, DMSO-$d_6$) δ 9.96 (s, 1H), 9.10 (d, J=8.6 Hz, 1H), 8.48 (d, J=2.8 Hz, 1H), 8.40 (d, J=1.8 Hz, 1H), 8.27 (d, J=8.7 Hz, 1H), 7.71-7.63 (m, 2H), 7.14-7.08 (m, 1H), 7.04-7.00 (m, 1H), 4.86 (t, J=9.3 Hz, 1H), 4.51 (t, J=8.5 Hz, 1H), 3.88 (s, 3H), 3.43 (d, J=13.0 Hz, 2H), 3.24 (t, J=10.3 Hz, 1H), 3.12-2.96 (m, 2H), 2.27-2.03 (m, 5H), 1.97 (s, 3H), 1.69-1.24 (m, 13H), 1.22-1.17 (m, 4H), 0.99 (t, J=7.6 Hz, 3H). UPLC-MS (basic 4 min): rt=1.79 min; m/z=689.4 for [M+H]$^+$.

Example 234: N-[(2R,3S)-3-{4-[(2S)-2-[2-(3-cyanophenyl)-2,2-difluoroacetamido]-2-(4,4-difluoro cyclohexyl)acetamido]-3-fluorophenyl}-1-(4-methylpiperazin-1-yl)-1-oxobutan-2-yl]propanamide) (263)

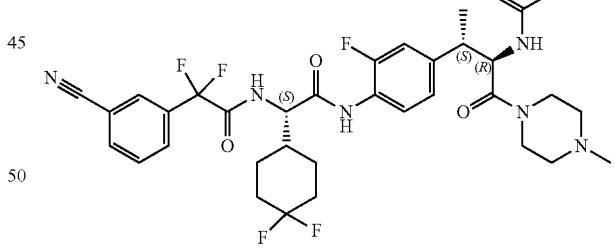

Compound 263 was synthesized by coupling 82c with the required carboxylic acid following General Procedure R and purified using reverse phase column chromatography. $^1$H NMR (400 MHz, DMSO-$d_6$) δ 9.99 (s, 1H), 9.24 (d, J=8.2 Hz, 1H), 8.26 (d, J=8.8 Hz, 1H), 8.13 (s, 1H), 8.06 (d, J=7.7 Hz, 1H), 7.94 (d, J=7.9 Hz, 1H), 7.73-7.78 (m, 1H), 7.70 (t, J=8.3 Hz, 1H), 7.09-7.14 (m, 1H), 7.01 (d, J=8.3 Hz, 1H), 4.85 (s, 1H), 4.53 (s, 1H), 3.36-3.45 (m, 2H), 3.20-3.28 (m, 1H), 2.98-3.14 (m, 2H), 2.05-2.22 (m, 4H), 1.96-2.05 (m, 3H), 1.95 (s, 3H), 1.59-1.84 (m, 5H), 1.45-1.55 (m, 1H), 1.31-1.45 (m, 1H), 1.21-1.29 (m, 1H), 1.17-1.21 (m, 3H), 0.98 (t, J=7.6 Hz, 3H). UPLC-MS (basic 4 min): rt=1.72 min; m/z=705.3 for [M+H]$^+$.

Example 235: N-[(2R,3S)-3-{4-[(2S)-2-[(3-ethyl-1,2-oxazol-4-yl)formamido]-2-[(1r,4S)-4-methylcyclohexyl] acetamido]-3-fluorophenyl}-1-(4-methylpiperazin-1-yl)-1-oxobutan-2-yl]propanamide) (264)

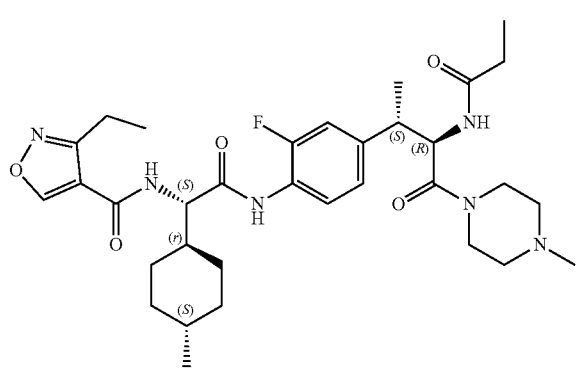

Compound 264 was synthesized by coupling 82d with the required amino acid following General Procedure R and purified using reverse phase column chromatography. ¹H NMR (400 MHz, DMSO-d$_6$) δ 9.86 (s, 1H), 9.39 (s, 1H), 8.42 (d, J=8.4 Hz, 1H), 8.22-8.29 (m, 1H), 7.72 (t, J=8.4 Hz, 1H), 7.09 (dd, J=12.0, 1.9 Hz, 1H), 7.01 (d, J=9.9 Hz, 1H), 4.81-4.90 (m, 1H), 4.53-4.60 (m, 1H), 3.36-3.45 (m, 3H), 3.20-3.27 (m, 1H), 3.00-3.12 (m, 2H), 2.80-2.87 (m, 2H), 2.04-2.24 (m, 4H), 1.98 (s, 3H), 1.76-1.85 (m, 1H), 1.65-1.73 (m, 3H), 1.59-1.65 (m, 1H), 1.49-1.57 (m, 1H), 1.21-1.35 (m, 2H), 1.14-1.21 (m, 6H), 1.02-1.13 (m, 1H), 0.98 (t, J=7.6 Hz, 3H), 0.77-0.93 (m, 5H). UPLC-MS (basic 4 min): rt=1.78 min; m/z=627.4 for [M+H]⁺.

Example 236: N-[(2R,3S)-3-{4-[(2S)-2-cycloheptyl-2-[2,2-difluoro-2-(5-methylthiophen-3-yl)acetamido]acetamido]-3-fluorophenyl}-1-(4-methylpiperazin-1-yl)-1-oxobutan-2-yl]propanamide (265)

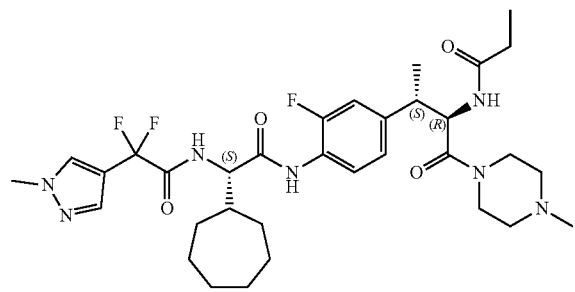

Compound 265 was synthesized by coupling 82b with the required amino acid following General Procedure R and purified using reverse phase column chromatography. ¹H NMR (400 MHz, DMSO-d$_6$) δ 9.91 (s, 1H), 8.80 (d, J=8.8 Hz, 1H), 8.27 (d, J=8.6 Hz, 1H), 7.74-7.64 (m, 2H), 7.12 (d, J=11.9 Hz, 1H), 7.01 (d, J=18.7 Hz, 2H), 4.86 (t, J=9.3 Hz, 1H), 4.49 (t, J=8.6 Hz, 1H), 3.50-3.38 (m, 2H), 3.14-2.95 (m, 3H), 2.26-2.04 (m, 4H), 2.01-1.96 (m, 3H), 1.71-1.58 (m, 5H), 1.56-1.44 (m, 5H), 1.43-1.28 (m, 5H), 1.23-1.19 (m, 3H), 0.99 (t, J=7.6 Hz, 3H). UPLC-MS (basic 4 min): rt=2.02 min; m/z=678.4 for [M+H]⁺.

Example 237: N-[(2R,3S)-3-{4-[(2S)-2-cycloheptyl-2-({4H,6H-furo[2,3-c]furan-3-yl}formamido) acetamido]-3-fluorophenyl}-1-(4-methylpiperazin-1-yl)-1-oxobutan-2-yl]propanamide (266)

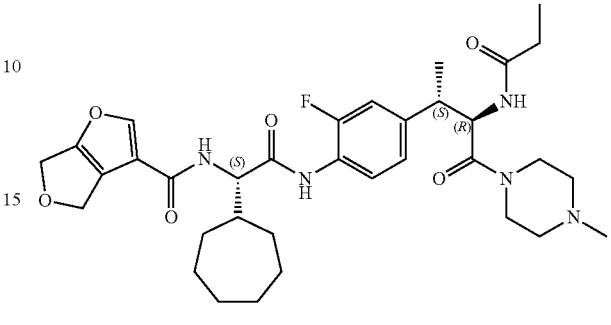

Compound 266 was synthesized by coupling 82b with the required amino acid following General Procedure R and purified using reverse phase column chromatography. ¹H NMR (400 MHz, DMSO-d$_6$) δ 9.91 (s, 1H), 8.80 (d, J=8.8 Hz, 1H), 8.27 (d, J=8.6 Hz, 1H), 7.74-7.64 (m, 2H), 7.12 (d, J=11.9 Hz, 1H), 7.01 (d, J=18.7 Hz, 2H), 4.86 (t, J=9.3 Hz, 1H), 4.49 (t, J=8.6 Hz, 1H), 3.50-3.38 (m, 2H), 3.14-2.95 (m, 3H), 2.26-2.04 (m, 4H), 2.01-1.96 (m, 3H), 1.71-1.58 (m, 5H), 1.56-1.44 (m, 5H), 1.43-1.28 (m, 5H), 1.23-1.19 (m, 3H), 0.99 (t, J=7.6 Hz, 3H). UPLC-MS (basic 4 min): rt=1.71 min; m/z=640.4 for [M+H]⁺.

Example 238: N-[(2R,3S)-3-{4-[(2S)-2-cycloheptyl-2-[2-(1-ethyl-1H-pyrazol-4-yl)-2,2-difluoroacetamido] acetamido]-3-fluorophenyl}-1-(4-methylpiperazin-1-yl)-1-oxobutan-2-yl]propanamide (267)

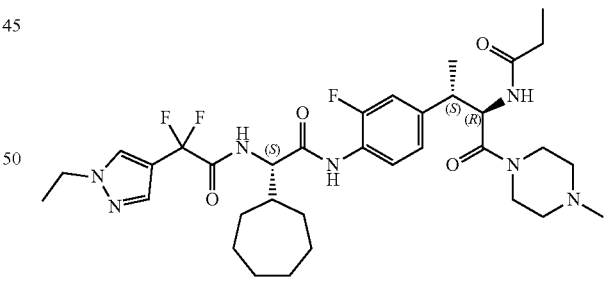

Compound 267 was synthesized by coupling 82b with the required amino acid following General Procedure R and purified using reverse phase column chromatography. ¹H NMR (400 MHz, DMSO-d$_6$) δ 9.89 (s, 1H), 8.71 (d, J=8.7 Hz, 1H), 8.24 (d, J=8.5 Hz, 1H), 8.09 (s, 1H), 7.74-7.63 (m, 2H), 7.11 (d, J=11.9 Hz, 1H), 7.02 (d, J=8.4 Hz, 1H), 4.86 (t, J=9.3 Hz, 1H), 4.50 (t, J=8.2 Hz, 1H), 4.18-4.11 (m, 2H), 3.41 (s, 3H), 3.13-2.98 (m, 4H), 2.23-2.04 (m, 7H), 1.98 (s, 3H), 1.67-1.46 (m, 11H), 1.39-1.33 (m, 3H), 1.20 (d, J=6.9 Hz, 3H), 1.06-0.93 (m, 3H). UPLC-MS (basic 4 min): rt=1.77 min; m/z=676.5 for [M+H]⁺.

Example 239: N-[(2R,3S)-3-{4-[(2S)-2-cycloheptyl-2-{[3-(propan-2-yl)-1,2-oxazol-4-yl]formamido}acetamido]-3-fluorophenyl}-1-(4-methylpiperazin-1-yl)-1-oxobutan-2-yl]propanamide (268)

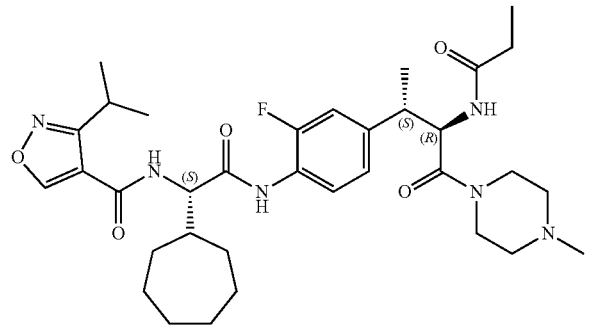

Compound 268 was synthesized by coupling 82b with the required amino acid following General Procedure R and purified using reverse phase column chromatography. $^1$H NMR (400 MHz, DMSO-d$_6$) δ 9.85 (s, 1H), 9.33 (d, J=2.3 Hz, 1H), 8.41 (d, J=8.5 Hz, 1H), 8.24 (d, J=8.6 Hz, 1H), 7.69 (t, J=8.1 Hz, 1H), 7.10 (d, J=11.9 Hz, 1H), 7.01 (d, J=8.4 Hz, 1H), 4.86 (t, J=9.2 Hz, 1H), 4.65 (t, J=8.1 Hz, 1H), 3.52-3.35 (m, 2H), 3.15-2.99 (m, 2H), 2.23-2.07 (m, 3H), 1.99 (d, J=2.3 Hz, 3H), 1.77-1.32 (m, 17H), 1.22 (qd, J=9.2, 8.2, 2.4 Hz, 11H), 1.05-0.95 (m, 3H). UPLC-MS (basic 4 min): rt=1.86 min; m/z=641.4 for [M+H]$^+$.

Example 240: N-[(2R,3S)-3-{4-[(2S)-2-cycloheptyl-2-[(3-cyclopropyl-1,2-oxazol-4-yl)formamido]acetamido]-3-fluorophenyl}-1-(4-methylpiperazin-1-yl)-1-oxobutan-2-yl]propanamide (269)

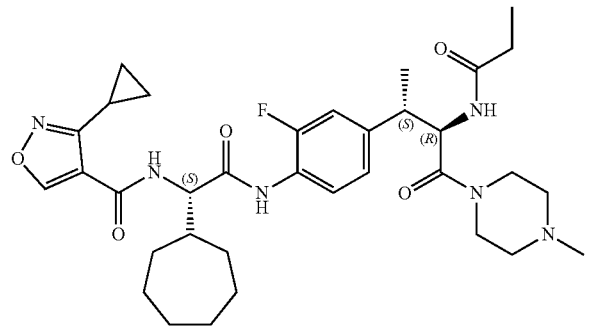

Compound 269 was synthesized by coupling 82b with the required amino acid following General Procedure R and purified using reverse phase column chromatography. $^1$H NMR (400 MHz, DMSO-d$_6$) δ 9.88 (s, 1H), 9.36 (d, J=1.6 Hz, 1H), 8.35 (d, J=8.6 Hz, 1H), 8.24 (d, J=8.7 Hz, 1H), 7.70 (t, J=8.2 Hz, 1H), 7.10 (d, J=11.9 Hz, 1H), 7.01 (d, J=8.4 Hz, 1H), 4.87 (t, J=9.3 Hz, 1H), 4.67 (t, J=7.9 Hz, 1H), 3.37 (d, J=12.5 Hz, 4H), 3.14-2.99 (m, 2H), 2.22-1.93 (m, 7H), 1.79-1.30 (m, 16H), 1.24-1.18 (m, 3H), 1.04-0.95 (m, 5H), 0.93-0.86 (m, 1H). UPLC-MS (basic 4 min): rt=1.80 min; m/z=639.4 for [M+H]$^+$.

Example 241: N-[(2R,3S)-3-{4-[(2S)-2-cycloheptyl-2-[(4-ethyl-1,2,5-oxadiazol-3-yl)formamido]acetamido]-3-fluorophenyl}-1-(4-methylpiperazin-1-yl)-1-oxobutan-2-yl]propanamide (270)

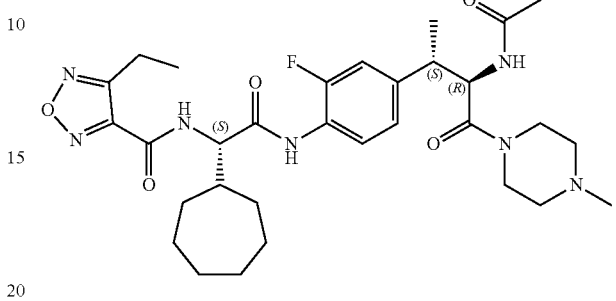

Compound 270 was synthesized by coupling 82b with the required amino acid following General Procedure R and purified using reverse phase column chromatography. $^1$H NMR (400 MHz, DMSO-d$_6$) δ 9.94 (s, 1H), 9.07 (d, J=8.6 Hz, 1H), 8.24 (d, J=8.8 Hz, 1H), 7.71 (t, J=8.2 Hz, 1H), 7.11 (dd, J=12.0, 1.9 Hz, 1H), 7.02 (dd, J=8.2, 1.9 Hz, 1H), 4.87 (dd, J=9.8, 8.8 Hz, 1H), 4.70 (t, J=8.0 Hz, 1H), 3.41 (d, J=13.7 Hz, 3H), 3.15-2.99 (m, 2H), 2.89 (q, J=7.5 Hz, 2H), 2.14 (tq, J=22.3, 7.4 Hz, 3H), 1.79-1.31 (m, 18H), 1.24 (t, J=7.5 Hz, 3H), 1.20 (d, J=7.1 Hz, 3H), 0.99 (t, J=7.6 Hz, 3H). UPLC-MS (basic 4 min): rt=1.95 min; m/z=628.4 for [M+H]$^+$.

Example 242: N-[(2R,3S)-3-{4-[(2S)-2-cycloheptyl-2-{[1-(cyclopropylmethyl)-1H-pyrazol-5-yl]formamido}acetamido]-3-fluorophenyl}-1-(4-methylpiperazin-1-yl)-1-oxobutan-2-yl]propanamide (271)

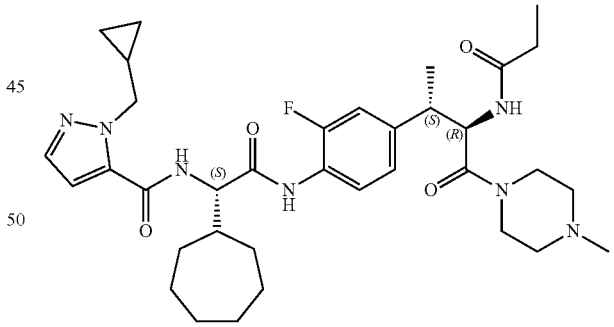

Compound 271 was synthesized by coupling 82b with the required amino acid following General Procedure R and purified using reverse phase column chromatography. $^1$H NMR (400 MHz, DMSO-d$_6$) δ 9.86 (s, 1H), 8.48 (d, J=8.5 Hz, 1H), 8.26 (d, J=8.7 Hz, 1H), 7.76-7.66 (m, 1H), 7.48 (d, J=1.8 Hz, 1H), 7.11 (d, J=11.9 Hz, 1H), 7.05-6.94 (m, 2H), 4.86 (t, J=9.3 Hz, 1H), 4.61 (t, J=8.5 Hz, 1H), 4.39-4.28 (m, 2H), 3.46-3.36 (m, 2H), 3.16-2.94 (m, 2H), 2.23-2.05 (m, 5H), 1.99 (s, 3H), 1.78-1.59 (m, 5H), 1.58-1.46 (m, 4H), 1.43-1.32 (m, 4H), 1.28-1.14 (m, 4H), 1.05-0.92 (m, 3H), 0.43-0.27 (m, 4H). UPLC-MS (basic 4 min): rt=1.84 min; m/z=652.3 for [M+H]$^+$.

Example 243: N-[(2R,3S)-3-{4-[(2S)-2-cycloheptyl-2-{[2-(propan-2-yl)furan-3-yl]formamido}acetamido]-3-fluorophenyl}-1-(4-methylpiperazin-1-yl)-1-oxobutan-2-yl]propanamide (272)

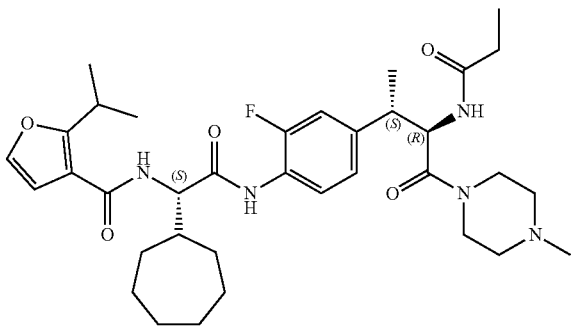

Compound 272 was synthesized by coupling 82b with the required amino acid following General Procedure R and purified using reverse phase column chromatography. 1H NMR (400 MHz, DMSO-$d_6$) δ 9.80 (s, 1H), 8.26 (d, J=8.7 Hz, 1H), 7.89 (d, J=8.5 Hz, 1H), 7.73 (t, J=8.2 Hz, 1H), 7.54 (d, J=2.0 Hz, 1H), 7.11 (d, J=12.0 Hz, 1H), 7.03-6.99 (m, 2H), 4.86 (t, J=9.4 Hz, 1H), 4.58 (d, J=8.5 Hz, 1H), 3.82-3.72 (m, 1H), 3.47-3.36 (m, 2H), 3.14-2.95 (m, 3H), 2.24-2.02 (m, 6H), 2.02-1.95 (m, 3H), 1.78-1.58 (m, 5H), 1.58-1.45 (m, 4H), 1.44-1.27 (m, 4H), 1.26-1.13 (m, 11H), 0.99 (t, J=7.6 Hz, 3H). UPLC-MS (basic 4 min): rt=2.02 min; m/z=640.5 for [M+H]$^+$.

Example 244: N-[(2R,3S)-3-{4-[(2S)-2-cycloheptyl-2-[(1-cyclopentyl-1H-pyrazol-5-yl)formamido]acetamido]-3-fluorophenyl}-1-(4-methylpiperazin-1-yl)-1-oxobutan-2-yl]propanamide (273)

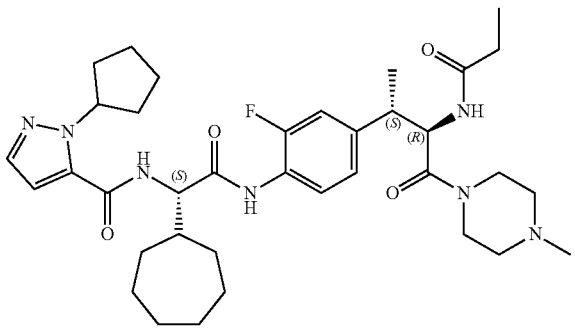

Compound 273 was synthesized by coupling 82b with the required amino acid following General Procedure R and purified using reverse phase column chromatography. $^1$H NMR (400 MHz, DMSO-$d_6$) δ 9.84 (s, 1H), 8.42 (d, J=8.3 Hz, 1H), 8.26 (d, J=8.8 Hz, 1H), 7.72 (t, J=8.3 Hz, 1H), 7.48 (d, J=1.9 Hz, 1H), 7.11 (d, J=12.1 Hz, 1H), 7.02 (d, J=8.4 Hz, 1H), 6.91 (d, J=2.0 Hz, 1H), 5.52 (t, J=7.5 Hz, 1H), 4.86 (t, J=9.5 Hz, 1H), 4.64-4.56 (m, 2H), 3.45-3.38 (m, 3H), 2.22-2.04 (m, 5H), 2.03-1.86 (m, 7H), 1.84-1.75 (m, 2H), 1.75-1.33 (m, 15H), 1.23-1.17 (m, 3H), 1.03-0.94 (m, 3H). UPLC-MS (basic 4 min): rt=1.98 min; m/z=666.5 for [M+H]$^+$.

Example 245: N-[(2R,3S)-3-{4-[(2S)-2-cycloheptyl-2-{[1-(propan-2-yl)-1H-pyrrol-2-yl]formamido}acetamido]-3-fluorophenyl}-1-(4-methylpiperazin-1-yl)-1-oxobutan-2-yl]propanamide (274)

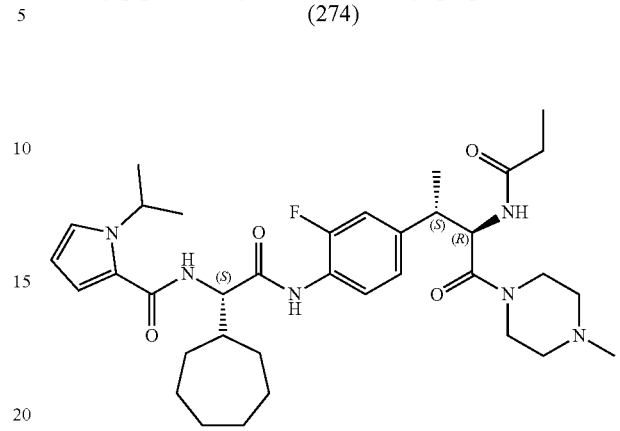

Compound 274 was synthesized by coupling 82b with the required amino acid following General Procedure R and purified using reverse phase column chromatography. 1H NMR (400 MHz, DMSO-$d_6$) δ 9.74 (s, 1H), 8.26 (d, J=8.7 Hz, 1H), 7.85 (d, J=8.8 Hz, 1H), 7.75 (t, J=8.3 Hz, 1H), 7.21-7.08 (m, 2H), 7.04-6.97 (m, 1H), 6.82 (dd, J=3.9, 1.7 Hz, 1H), 6.07 (t, J=3.3 Hz, 1H), 5.44-5.32 (m, 1H), 4.86 (t, J=9.3 Hz, 1H), 4.53 (t, J=8.z4 Hz, 1H), 3.45-3.36 (m, 2H), 3.28-3.18 (m, 1H), 3.15-2.98 (m, 2H), 2.24-2.04 (m, 5H), 1.77-1.60 (m, 5H), 1.59-1.27 (m, 17H), 1.25-1.17 (m, 3H), 1.03-0.95 (m, 3H). UPLC-MS (basic 4 min): rt=2.00 min; m/z=639.4 for [M+H]$^+$.

Example 246: N-[(2R,3S)-3-{4-[(2S)-2-cycloheptyl-2-[(1-ethyl-1H-pyrrol-2-yl)formamido]acetamido]-3-fluorophenyl}-1-(4-methylpiperazin-1-yl)-1-oxobutan-2-yl]propanamide (275)

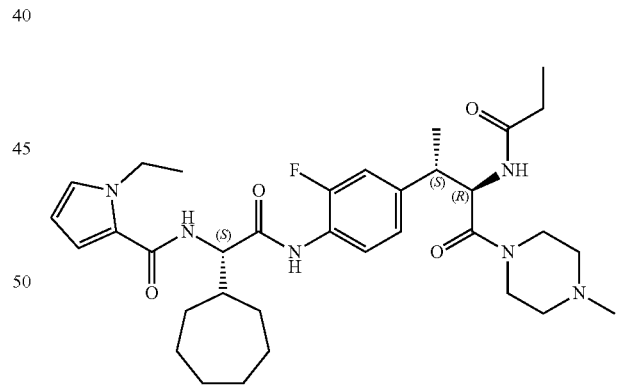

Compound 275 was synthesized by coupling 82b with the required amino acid following General Procedure R and purified using reverse phase column chromatography. $^1$H NMR (400 MHz, DMSO-$d_6$) δ 9.75 (s, 1H), 8.26 (d, J=8.7 Hz, 1H), 7.86 (d, J=8.8 Hz, 1H), 7.75 (t, J=8.3 Hz, 1H), 7.11 (d, J=12.1 Hz, 1H), 7.03-6.96 (m, 2H), 6.89 (d, J=3.6 Hz, 1H), 6.03 (t, J=3.3 Hz, 1H), 4.86 (t, J=9.2 Hz, 1H), 4.54 (t, J=8.5 Hz, 1H), 4.35-4.23 (m, 2H), 3.48-3.37 (m, 2H), 3.28-3.19 (m, 1H), 3.13-2.99 (m, 2H), 2.22-2.04 (m, 5H), 1.80-1.61 (m, 5H), 1.59-1.30 (m, 11H), 1.27-1.17 (m, 6H), 1.02-0.95 (m, 3H) UPLC-MS (basic 4 min): rt=1.92 min; m/z=625.4 for [M+H]$^+$.

Example 247: N-[(2R,3S)-3-{4-[(2S)-2-[2,2-difluoro-2-(5-methylthiophen-3-yl)acetamido]-2-[(1r,4S)-4-methylcyclohexyl]acetamido]-3-fluorophenyl}-1-(4-methylpiperazin-1-yl)-1-oxobutan-2-yl]propanamide (276)

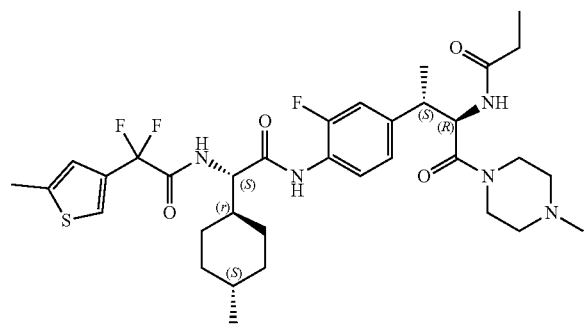

Compound 276 was synthesized by coupling 82d with the required amino acid following General Procedure R and purified using reverse phase column chromatography. ¹H NMR (400 MHz, DMSO-d₆) δ 9.89 (s, 1H), 8.83 (d, J=8.3 Hz, 1H), 8.26 (d, J=8.7 Hz, 1H), 7.72 (t, J=8.2 Hz, 1H), 7.66 (s, 1H), 7.11 (d, J=12.0 Hz, 1H), 7.02 (d, J=8.5 Hz, 1H), 6.98 (s, 1H), 4.86 (t, J=9.4 Hz, 1H), 4.41 (t, J=8.3 Hz, 1H), 3.49-3.37 (m, 2H), 3.14-2.96 (m, 3H), 2.45 (s, 3H), 2.23-2.04 (m, 5H), 1.89-1.75 (m, 1H), 1.75-1.56 (m, 5H), 1.55-1.46 (m, 1H), 1.30-1.11 (m, 7H), 0.99 (t, J=7.6 Hz, 4H), 0.90-0.76 (m, 5H). UPLC-MS (basic 4 min): rt=2.03 min; m/z=678.3 for [M+H]⁺.

Example 248: N-[(2R,3S)-3-{3-fluoro-4-[(2S)-2-({4H,6H-furo[2,3-c]furan-3-yl}formamido)-2-[(1r,4S)-4-methylcyclohexyl]acetamido]phenyl}-1-(4-methylpiperazin-1-yl)-1-oxobutan-2-yl]propanamide (277)

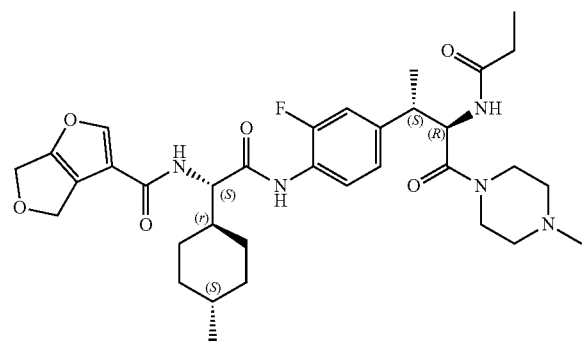

Compound 277 was synthesized by coupling 82d with the required amino acid following General Procedure R and purified using reverse phase column chromatography. ¹H NMR (400 MHz, DMSO-d₆) δ 9.85 (s, 1H), 8.40 (s, 1H), 8.26 (d, J=8.8 Hz, 1H), 8.17 (d, J=8.4 Hz, 1H), 7.72 (t, J=8.0 Hz, 1H), 7.10 (d, J=11.9 Hz, 1H), 7.01 (d, J=8.5 Hz, 1H), 4.92-4.79 (m, 3H), 4.74 (d, J=3.8 Hz, 2H), 4.53 (t, J=8.0 Hz, 1H), 3.45-3.35 (m, 2H), 3.14-3.00 (m, 2H), 2.23-2.06 (m, 5H), 1.99 (s, 3H), 1.84-1.76 (m, 1H), 1.73-1.63 (m, 5H), 1.62-1.48 (m, 1H), 1.32-1.14 (m, 6H), 0.99 (t, J=7.6 Hz, 3H), 0.86 (d, J=6.6 Hz, 5H). UPLC-MS (basic 4 min): rt=1.73 min; m/z=640.3 for [M+H]⁺.

Example 249: N-[(2R,3S)-3-{4-[(2S)-2-[(4-ethyl-1,2,5-oxadiazol-3-yl)formamido]-2-[(1r,4S)-4-methylcyclohexyl]acetamido]-3-fluorophenyl}-1-(4-methylpiperazin-1-yl)-1-oxobutan-2-yl]propanamide (278)

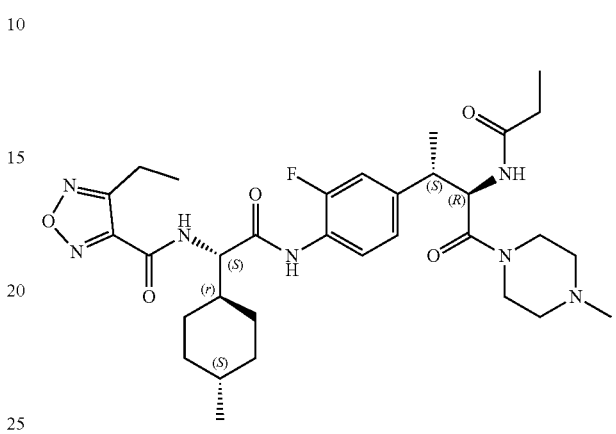

Compound 278 was synthesized by coupling 82d with the required amino acid following General Procedure R and purified using reverse phase column chromatography. ¹H NMR (400 MHz, DMSO-d₆) δ 9.95 (s, 1H), 9.11 (d, J=8.3 Hz, 1H), 8.27 (d, J=8.7 Hz, 1H), 7.74 (t, J=8.1 Hz, 1H), 7.12 (d, J=12.1 Hz, 1H), 7.03 (d, J=8.6 Hz, 1H), 4.87 (t, J=9.3 Hz, 1H), 4.64 (t, J=7.9 Hz, 1H), 3.46-3.37 (m, 2H), 3.18-2.99 (m, 2H), 2.95-2.84 (m, 2H), 2.23-2.04 (m, 6H), 1.85-1.75 (m, 2H), 1.72-1.59 (m, 5H), 1.58-1.48 (m, 1H), 1.37-1.16 (m, 9H), 0.99 (t, J=7.6 Hz, 3H), 0.86 (d, J=6.5 Hz, 6H). UPLC-MS (basic 4 min): rt=1.97 min; m/z=628.3 for [M+H]⁺.

Example 250: N-[(2R,3S)-3-{4-[(2S)-2-[(3-cyclopropyl-1,2-oxazol-4-yl)formamido]-2-[(1r,4S)-4-methyl cyclohexyl]acetamido]-3-fluorophenyl}-1-(4-methylpiperazin-1-yl)-1-oxobutan-2-yl]propanamide (279)

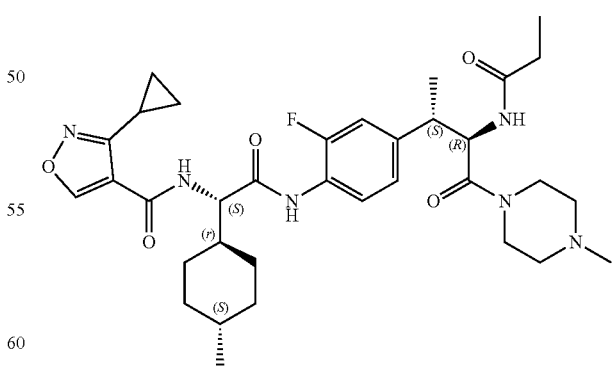

Compound 279 was synthesized by coupling 82d with the required amino acid following General Procedure R and purified using reverse phase column chromatography. ¹H NMR (400 MHz, DMSO-d₆) δ 9.89 (s, 1H), 9.37 (s, 1H), 8.39 (d, J=8.3 Hz, 1H), 8.26 (d, J=8.7 Hz, 1H), 7.73 (t, J=8.2

Hz, 1H), 7.14-7.08 (m, 1H), 7.02 (d, J=8.3 Hz, 1H), 4.87 (t, J=9.3 Hz, 1H), 4.59 (t, J=8.2 Hz, 1H), 3.50-3.37 (m, 2H), 3.18-2.99 (m, 2H), 2.47-2.40 (m, 1H), 2.22-2.03 (m, 4H), 1.87-1.78 (m, 1H), 1.78-1.60 (m, 5H), 1.60-1.50 (m, 1H), 1.35-1.16 (m, 6H), 1.03-0.95 (m, 5H), 0.92-0.79 (m, 8H). UPLC-MS (basic 4 min): rt=1.83 min; m/z=639.3 for [M+H]+.

Example 251: N-[(2R,3S)-3-{4-[(2S)-2-[(1-ethyl-1H-pyrrol-2-yl)formamido]-2-[(1r,4S)-4-methyl cyclohexyl]acetamido]-3-fluorophenyl}-1-(4-methylpiperazin-1-yl)-1-oxobutan-2-yl]propanamide (280)

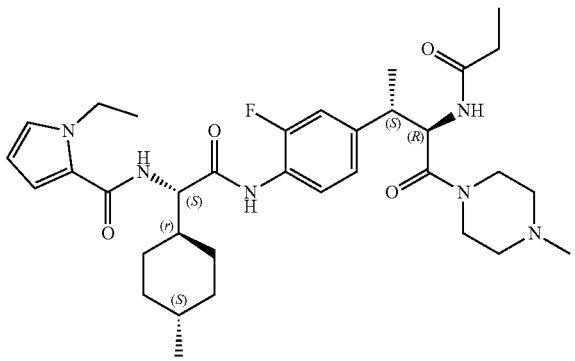

Compound 280 was synthesized by coupling 82d with the required amino acid following General Procedure R and purified using reverse phase column chromatography. 1H NMR (400 MHz, DMSO-d6) δ 9.74 (s, 1H), 8.26 (d, J=8.7 Hz, 1H), 7.88 (d, J=8.4 Hz, 1H), 7.77 (t, J=8.3 Hz, 1H), 7.10 (dd, J=12.2, 1.9 Hz, 1H), 7.03-6.95 (m, 2H), 6.90 (dd, J=3.9, 1.7 Hz, 1H), 6.03 (dd, J=3.9, 2.6 Hz, 1H), 4.86 (t, J=9.3 Hz, 1H), 4.46 (t, J=8.5 Hz, 1H), 4.34-4.23 (m, 2H), 3.45-3.36 (m, 2H), 3.27-2.97 (m, 3H), 2.23-2.04 (m, 5H), 1.87-1.73 (m, 2H), 1.74-1.57 (m, 5H), 1.57-1.47 (m, 1H), 1.28-1.14 (m, 8H), 0.99 (t, J=7.6 Hz, 3H), 0.86 (d, J=6.5 Hz, 5H). UPLC-MS (basic 4 min): rt=1.77 min; m/z=625.3 for [M+H]+.

Example 252: N-[(2R,3S)-3-{4-[(2S)-2-[2,2-difluoro-2-(5-methoxypyridin-3-yl)acetamido]-2-[(1r,4S)-4-methylcyclohexyl]acetamido]-3-fluorophenyl}-1-(4-methylpiperazin-1-yl)-1-oxobutan-2-yl]propanamide (281)

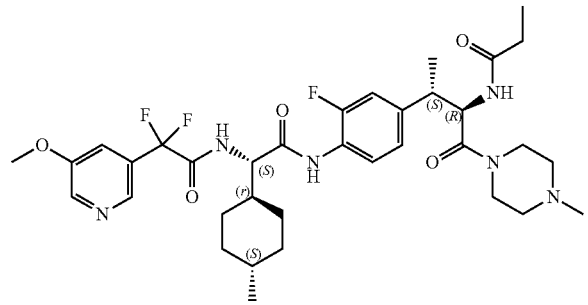

Compound 281 was synthesized by coupling 82d with the required amino acid following General Procedure R and purified using reverse phase column chromatography. 1H NMR (400 MHz, DMSO-d6) δ 9.94 (s, 1H), 9.12 (d, J=8.3 Hz, 1H), 8.48 (d, J=2.8 Hz, 1H), 8.40 (d, J=1.8 Hz, 1H), 8.26 (d, J=8.7 Hz, 1H), 7.71 (t, J=8.3 Hz, 1H), 7.65-7.61 (m, 1H), 7.11 (dd, J=12.0, 1.9 Hz, 1H), 7.01 (dd, J=8.4, 1.9 Hz, 1H), 4.86 (t, J=9.3 Hz, 1H), 4.43 (t, J=8.6 Hz, 1H), 3.88 (s, 3H), 3.51-3.39 (m, 2H), 3.29-3.21 (m, 1H), 3.15-2.97 (m, 2H), 2.26-2.05 (m, 4H), 1.97 (s, 3H), 1.84-1.75 (m, 1H), 1.70-1.55 (m, 5H), 1.53-1.45 (m, 1H), 1.27-1.10 (m, 6H), 1.06-0.96 (m, 4H), 0.89-0.78 (m, 5H). UPLC-MS (basic 4 min): rt=1.80 min; m/z=689.4 for [M+H]+.

Example 253: N-[(2R,3S)-3-{4-[(2S)-2-[2-(3-cyanophenyl)-2,2-difluoroacetamido]-2-[(1r,4S)-4-methyl cyclohexyl]acetamido]-3-fluorophenyl}-1-(4-methylpiperazin-1-yl)-1-oxobutan-2-yl]propanamide (282)

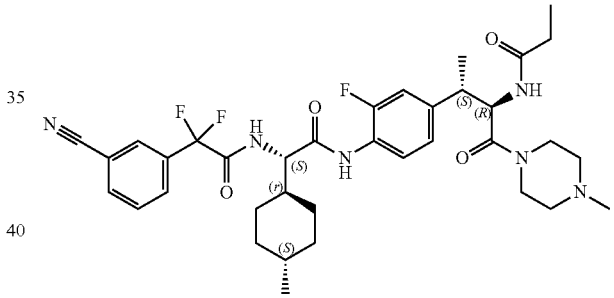

Compound 282 was synthesized by coupling 82d with the required amino acid following General Procedure R and purified using reverse phase column chromatography. 1H NMR (400 MHz, DMSO-d6) δ 9.91 (s, 1H), 9.08 (d, J=8.2 Hz, 1H), 8.26 (d, J=8.7 Hz, 1H), 8.14 (s, 1H), 8.07 (d, J=7.8 Hz, 1H), 7.95 (d, J=8.0 Hz, 1H), 7.77 (t, J=7.9 Hz, 1H), 7.71 (t, J=8.3 Hz, 1H), 7.10 (d, J=12.6 Hz, 1H), 7.01 (d, J=8.4 Hz, 1H), 4.86 (t, J=9.3 Hz, 1H), 4.42 (t, J=8.5 Hz, 1H), 3.48-3.38 (m, 2H), 3.27-3.19 (m, 1H), 3.15-2.95 (m, 2H), 2.28-2.11 (m, 4H), 1.96 (s, 3H), 1.83-1.72 (m, 1H), 1.69-1.54 (m, 5H), 1.52-1.43 (m, 1H), 1.20 (d, J=7.0 Hz, 3H), 1.16-1.04 (m, 1H), 0.99 (t, J=7.6 Hz, 4H), 0.84 (d, J=6.3 Hz, 5H). UPLC-MS (basic 4 min): rt=1.92 min; m/z=683.4 for [M+H]+.

Example 254: N-[(2R,3S)-3-{4-[(2S)-2-{[1-(cyclo-propylmethyl)-1H-pyrazol-5-yl]formamido}-2-[(1r,4S)-4-methylcyclohexyl]acetamido]-3-fluorophenyl}-1-(4-methylpiperazin-1-yl)-1-oxobutan-2-yl]propanamide (283)

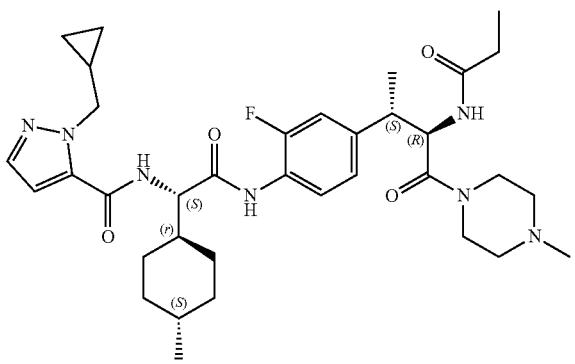

Compound 283 was synthesized by coupling 82d with the required amino acid following General Procedure R and purified using reverse phase column chromatography. 1H NMR (400 MHz, DMSO-$d_6$) δ 9.85 (s, 1H), 8.50 (d, J=8.3 Hz, 1H), 8.26 (d, J=8.7 Hz, 1H), 7.74 (t, J=8.2 Hz, 1H), 7.48 (d, J=2.0 Hz, 1H), 7.14-7.07 (m, 1H), 7.05-6.97 (m, 2H), 4.86 (t, J=9.3 Hz, 1H), 4.53 (t, J=8.4 Hz, 1H), 4.33 (d, J=7.1 Hz, 2H), 3.47-3.37 (m, 2H), 3.18-2.98 (m, 2H), 2.25-2.05 (m, 4H), 1.87-1.49 (m, 8H), 1.34-1.13 (m, 7H), 1.13-1.03 (m, 1H), 1.03-0.96 (m, 3H), 0.89-0.82 (m, 5H), 0.42-0.37 (m, 2H), 0.33-0.29 (m, 2H). UPLC-MS (basic 4 min): rt=1.87 min; m/z=652.3 for [M+H]$^+$.

Example 255: N-[(2R,3S)-3-{3-fluoro-4-[(2S)-2-{[3-(propan-2-yl)-1,2-oxazol-4-yl]}-2-[(1r,4S)-4-methylcyclohexyl]acetamido]phenyl}-1-(4-methylpiperazin-1-yl)-1-oxobutan-2-yl]propanamide (284)

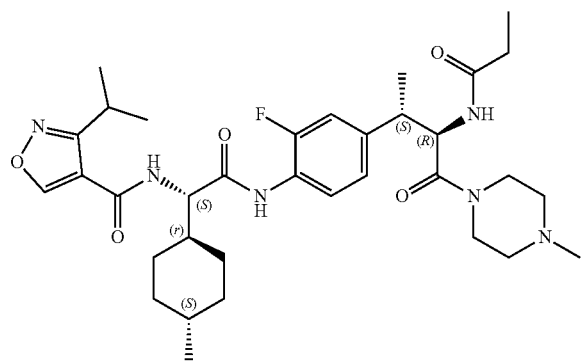

Compound 284 was synthesized by coupling 82d with the required amino acid following General Procedure R and purified using reverse phase column chromatography. 1H NMR (400 MHz, DMSO-$d_6$) δ 9.85 (s, 1H), 9.35 (s, 1H), 8.44 (d, J=8.3 Hz, 1H), 8.26 (d, J=8.7 Hz, 1H), 7.73 (t, J=8.3 Hz, 1H), 7.13-7.07 (m, 1H), 7.04-6.97 (m, 1H), 4.86 (t, J=9.3 Hz, 1H), 4.56 (t, J=8.2 Hz, 1H), 3.49-3.37 (m, 3H), 3.16-3.01 (m, 2H), 2.27-2.06 (m, 4H), 1.89-1.79 (m, 1H), 1.78-1.61 (m, 5H), 1.59-1.49 (m, 1H), 1.31-1.16 (m, 12H), 1.14-1.03 (m, 2H), 0.99 (t, J=7.6 Hz, 3H), 0.91-0.81 (m, 5H). UPLC-MS (basic 4 min): rt=1.90 min; m/z=641.3 for [M+H]$^+$.

Example 256: N-[(2R,3S)-3-{4-[(2S)-2-[2,2-difluoro-2-(6-methoxypyridin-3-yl)acetamido]-2-[4-(trifluoromethyl)cyclohexyl]acetamido]-3-fluorophenyl}-1-(4-methylpiperazin-1-yl)-1-oxobutan-2-yl]propanamide) (285)

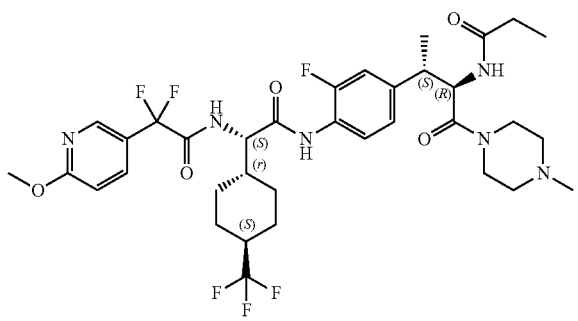

Compound 285 was synthesized by coupling the bis-TFA salt shown below, made by a procedure analogous to the synthesis of 82(a-d) with the required amino acid following General Procedure R and purified using reverse phase column chromatography.

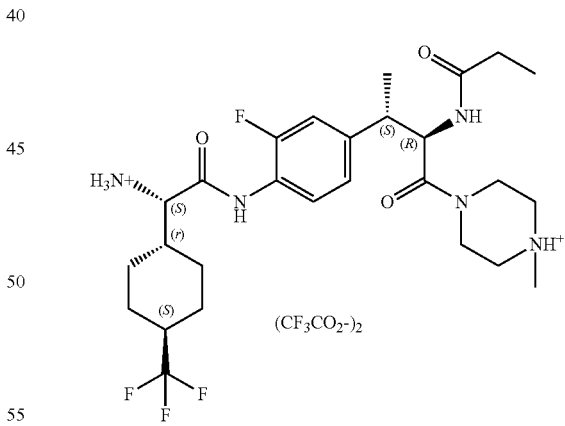

$^1$H NMR (400 MHz, DMSO-$d_6$) δ 9.97 (s, 1H), 9.08 (d, J=8.1 Hz, 1H), 8.42 (s, 1H), 8.27 (d, J=8.7 Hz, 1H), 7.92 (dd, J=8.8, 2.6 Hz, 1H), 7.71 (t, J=8.3 Hz, 1H), 7.12 (dd, J=12.1, 1.9 Hz, 1H), 6.99 (dd, J=17.4, 8.6 Hz, 2H), 4.86 (t, J=9.3 Hz, 1H), 4.45 (t, J=8.4 Hz, 1H), 3.90 (s, 3H), 3.42 (d, J=13.2 Hz, 2H), 3.28 (d, J=16.0 Hz, 2H), 3.14-2.99 (m, 2H), 2.14 (qq, J=14.9, 7.5 Hz, 2H), 1.97 (s, 3H), 1.84 (d, J=25.4 Hz, 4H), 1.67 (d, J=12.9 Hz, 2H), 1.52 (s, 1H), 1.20 (d, J=7.1 Hz, 5H), 1.09 (dd, J=24.2, 11.7 Hz, 1H), 0.99 (t, J=7.6 Hz, 3H). UPLC-MS (basic 4 min): rt=1.88 min; m/z=743.3 for [M+H]$^+$.

Example 257: N-[(2R,3S)-3-{4-[(2S)-2-[2-(3-cyano-phenyl)-2,2-difluoroacetamido]-2-[(1r,4S)-4-(trifluoro methyl)cyclohexyl]acetamido]-3-fluorophenyl}-1-(4-methylpiperazin-1-yl)-1-oxobutan-2-yl] propanamide) (286)

Example 258: N-[(2R,3S)-3-{4-[(2S)-2-[(1R)-2,3-dihydro-1H-inden-1-yl]-2-[(1-ethyl-1H-pyrazol-5-yl)formamido]acetamido]-3-fluorophenyl}-1-(4-methylpiperazin-1-yl)-1-oxobutan-2-yl]propanamide (287)

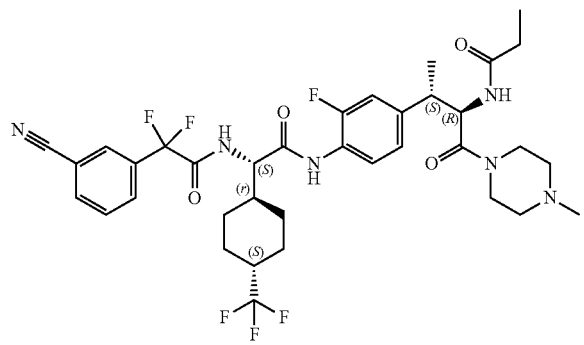

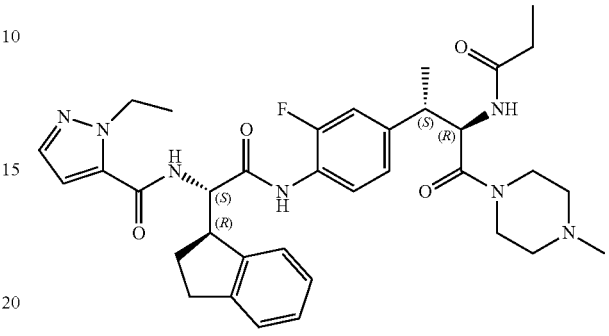

Compound 286 was synthesized by coupling the bis-TFA salt shown below, made by a procedure analogous to the synthesis of 82(a-d) with the required amino acid following General Procedure R and purified using reverse phase column chromatography.

Compound 287 was synthesized by coupling the bis-TFA salt shown below, made by a procedure analogous to the synthesis of 82(a-d) with the required amino acid following General Procedure R and purified using reverse phase column chromatography.

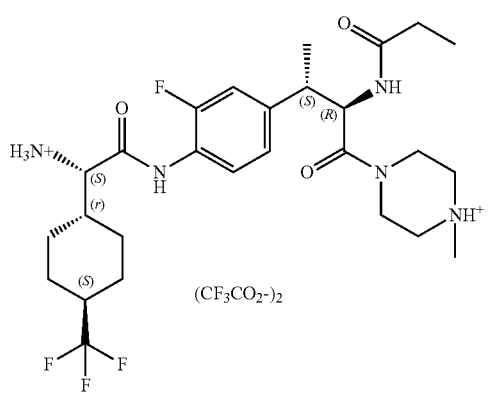

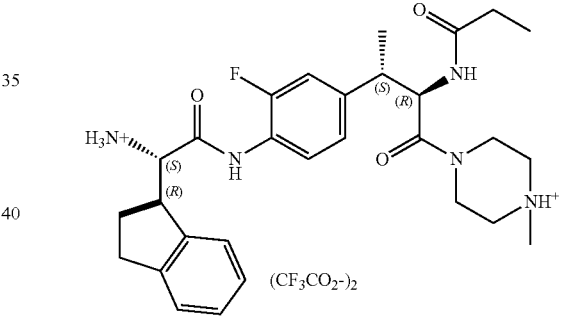

$^1$H NMR (400 MHz, DMSO-d$_6$) δ 9.96 (s, 2H), 9.14 (br d, J=8.1 Hz, 1H), 8.26 (d, J=8.7 Hz, 2H), 8.13 (s, 1H), 8.06 (d, J=7.8 Hz, 1H), 7.95 (d, J=8.2 Hz, 1H), 7.73-7.80 (m, 1H), 7.70 (t, J=8.3 Hz, 1H), 7.10 (br d, J=12.1 Hz, 1H), 7.00 (br d, J=8.6 Hz, 1H), 4.85 (s, 1H), 4.45 (s, 1H), 3.38 (br s, 2H), 3.20-3.28 (m, 1H), 2.97-3.14 (m, 2H), 2.05-2.23 (m, 5H), 1.95 (s, 3H), 1.80-1.90 (m, 3H), 1.61-1.77 (m, 3H), 1.45-1.56 (m, 1H), 1.19 (br d, J=7.0 Hz, 5H), 1.10-1.16 (m, 1H), 1.01-1.09 (m, 1H), 0.98 (t, J=7.6 Hz, 3H). UPLC-MS (basic 4 min): rt=1.87 min; m/z=737.3 for [M+H]$^+$ $^1$H NMR (400 MHz, DMSO-d$_6$) δ 10.01 (s, 1H), 8.96 (d, J=8.4 Hz, 1H), 8.26 (d, J=8.7 Hz, 1H), 7.73 (t, J=8.3 Hz, 1H), 7.50 (d, J=2.0 Hz, 1H), 7.38 (d, J=7.5 Hz, 1H), 7.24 (d, J=7.6 Hz, 1H), 7.13-7.17 (m, 1H), 7.12 (s, 1H), 7.07 (d, J=7.3 Hz, 1H), 7.00-7.05 (m, 2H), 4.87 (t, J=9.3 Hz, 1H), 4.73 (t, J=9.4 Hz, 1H), 4.42 (q, J=7.1 Hz, 2H), 3.65 (ddd, J=10.0, 7.8, 5.1 Hz, 1H), 3.40 (br d, J=13.7 Hz, 2H), 3.23-3.30 (m, 1H), 3.00-3.16 (m, 3H), 2.73-2.83 (m, 1H), 2.00-2.23 (m, 6H), 1.98 (s, 3H), 1.69 (br t, J=8.4 Hz, 1H), 1.51-1.62 (m, 1H), 1.17-1.26 (m, 6H), 0.99 (t, J=7.6 Hz, 3H). UPLC-MS (basic 4 min): rt=1.68 min; m/z=646.4 for [M+H]$^+$

413

Example 259: (2S,3R)-2-[(1-ethyl-1H-pyrazol-5-yl) formamido]-N-{2-fluoro-4-[(2S,3R)-4-(4-methyl piperazin-1-yl)-4-oxo-3-propanamidobutan-2-yl] phenyl}-3-phenylbutanamide) (288)

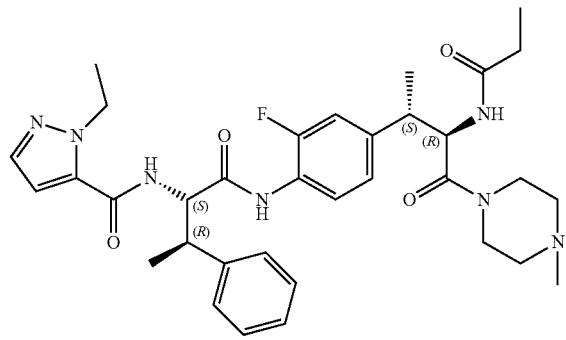

Compound 288 was synthesized by coupling the bis-TFA salt shown below, made by a procedure analogous to the synthesis of 82(a-d) with the required amino acid following General Procedure R and purified using reverse phase column chromatography.

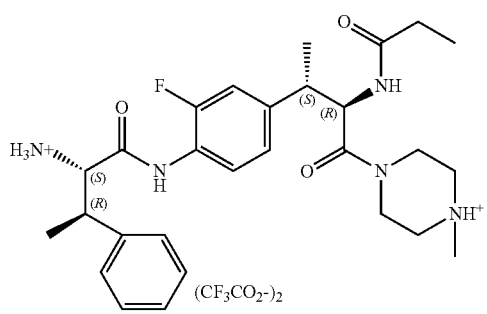

$^1$H NMR (400 MHz, DMSO-d$_6$) δ 10.13 (s, 1H), 8.54 (d, J=8.8 Hz, 1H), 8.27 (d, J=8.6 Hz, 1H), 7.81 (t, J=8.3 Hz, 1H), 7.40 (s, 1H), 7.38 (s, 1H), 7.37 (d, J=2.1 Hz, 1H), 7.27 (t, J=7.7 Hz, 2H), 7.16-7.19 (m, 1H), 7.15 (d, J=7.3 Hz, 1H), 7.01-7.06 (m, 1H), 6.65 (d, J=2.0 Hz, 1H), 4.98 (dd, J=10.4, 8.8 Hz, 1H), 4.87 (t, J=9.4 Hz, 1H), 4.21-4.32 (m, 2H), 3.38-3.48 (m, 2H), 3.22-3.28 (m, 2H), 3.08-3.16 (m, 1H), 2.99-3.07 (m, 1H), 2.03-2.25 (m, 4H), 1.98 (s, 3H), 1.59-1.76 (m, 1H), 1.46-1.59 (m, 1H), 1.28 (d, J=7.0 Hz, 3H), 1.21 (d, J=7.0 Hz, 3H), 1.11 (t, J=7.2 Hz, 3H), 0.99 (t, J=7.6 Hz, 3H). UPLC-MS (basic 4 min): rt=1.62 min; m/z=634.3 for [M+H]$^+$.

414

Example 260: (2S,3S)-2-[(1-ethyl-1H-pyrazol-5-yl) formamido]-N-{2-fluoro-4-[(2S,3R)-4-(4-methyl piperazin-1-yl)-4-oxo-3-propanamidobutan-2-yl] phenyl}-3-phenylbutanamide) (289)

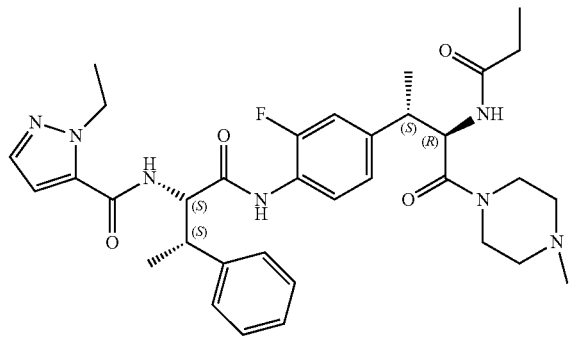

Compound 289 was synthesized by coupling the bis-TFA salt shown below, made by a procedure analogous to the synthesis of 82(a-d) with the required amino acid following General Procedure R and purified using reverse phase column chromatography.

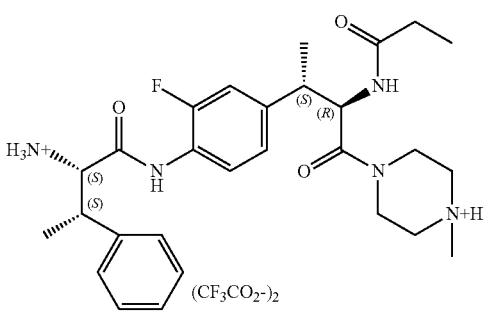

$^1$H NMR (400 MHz, DMSO-d$_6$) δ 10.13 (s, 1H), 8.54 (d, J=8.7 Hz, 1H), 8.27 (d, J=8.7 Hz, 1H), 7.81 (t, J=8.3 Hz, 1H), 7.40 (s, 1H), 7.36-7.38 (m, 2H), 7.27 (t, J=7.6 Hz, 2H), 7.16-7.19 (m, 1H), 7.15 (d, J=7.2 Hz, 1H), 7.04 (dd, J=8.4, 1.4 Hz, 1H), 6.65 (d, J=2.0 Hz, 1H), 4.98 (dd, J=10.4, 9.0 Hz, 1H), 4.87 (t, J=9.3 Hz, 1H), 4.20-4.33 (m, 2H), 3.43 (br d, J=13.3 Hz, 2H), 3.29 (s, 1H), 3.23-3.27 (m, 1H), 3.07-3.15 (m, 1H), 2.98-3.07 (m, 1H), 2.04-2.23 (m, 4H), 1.98 (s, 3H), 1.62-1.72 (m, 1H), 1.53 (br t, J=8.7 Hz, 1H), 1.28 (d, J=7.0 Hz, 3H), 1.21 (d, J=7.0 Hz, 3H), 1.11 (t, J=7.2 Hz, 3H), 0.99 (t, J=7.6 Hz, 3H) UPLC-MS (basic 4 min): rt=1.63 min; m/z=634.4 for [M+H]$^+$

Example 261: (2S,3S)-2-[2-(3-cyanophenyl)-2,2-difluoroacetamido]-N-{2-fluoro-4-[(2S,3R)-4-(4-methylpiperazin-1-yl)-4-oxo-3-propanamidobutan-2-yl]phenyl}-3-phenylbutanamide) (290)

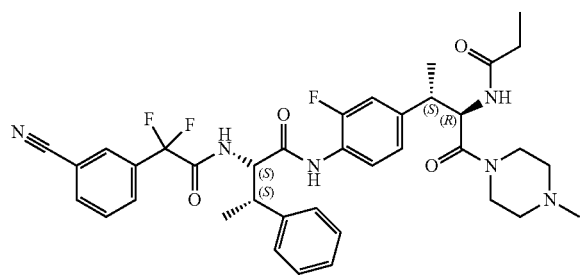

Compound 290 was synthesized by coupling the bis-TFA salt shown below, made by a procedure analogous to the synthesis of 82(a-d) with the required amino acid following General Procedure R and purified using reverse phase column chromatography.

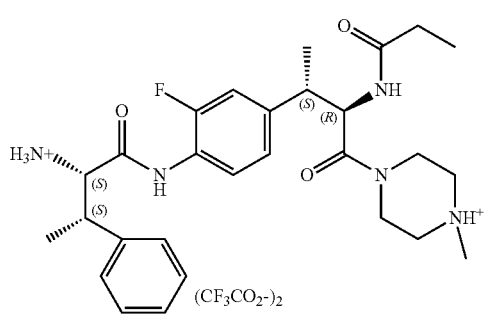

$^1$H NMR (400 MHz, DMSO-d$_6$) δ 10.23 (s, 1H), 9.24 (d, J=9.0 Hz, 1H), 8.27 (d, J=8.8 Hz, 1H), 7.96 (d, J=7.8 Hz, 1H), 7.79 (t, J=8.3 Hz, 1H), 7.67 (s, 1H), 7.56 (t, J=7.9 Hz, 1H), 7.43 (d, J=8.1 Hz, 1H), 7.24 (d, J=7.0 Hz, 2H), 7.02-7.19 (m, 5H), 4.91-4.99 (m, 1H), 4.83-4.91 (m, 1H), 3.38-3.50 (m, 2H), 3.20-3.29 (m, 2H), 3.11 (br dd, J=9.5, 7.0 Hz, 1H), 2.94-3.06 (m, 1H), 2.04-2.24 (m, 4H), 1.98 (s, 3H), 1.65 (br t, J=8.6 Hz, 1H), 1.44-1.54 (m, 1H), 1.14-1.26 (m, 6H), 0.99 (t, J=7.6 Hz, 3H). UPLC-MS (basic 4 min): rt=1.77 min; m/z=691.3 for [M+H]$^+$.

Example 262: (2S,3S)—N-{2-fluoro-4-[(2S,3R)-4-(4-methylpiperazin-1-yl)-4-oxo-3-propanamidobutan-2-yl]phenyl}-3-phenyl-2-{[1-(propan-2-yl)-1H-pyrazol-5-yl]formamido}butanamide) (291)

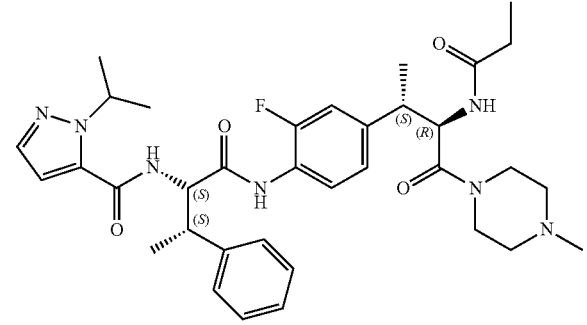

Compound 291 was synthesized by coupling the bis-TFA salt shown below, made by a procedure analogous to the synthesis of 82(a-d) with the required amino acid following General Procedure R and purified using reverse phase column chromatography.

$^1$H NMR (400 MHz, DMSO-d$_6$) δ 10.12 (s, 1H), 8.52 (d, J=8.8 Hz, 1H), 8.27 (d, J=8.7 Hz, 1H), 7.82 (t, J=8.4 Hz, 1H), 7.36-7.42 (m, 3H), 7.28 (t, J=7.6 Hz, 2H), 7.16-7.20 (m, 1H), 7.11-7.16 (m, 1H), 7.01-7.07 (m, 1H), 6.54 (d, J=2.0 Hz, 1H), 5.05 (dt, J=13.3, 6.7 Hz, 1H), 4.96 (dd, J=10.6, 8.7 Hz, 1H), 4.87 (t, J=9.5 Hz, 1H), 3.38-3.48 (m, 2H), 3.23-3.28 (m, 2H), 3.08-3.15 (m, 1H), 2.98-3.08 (m, 1H), 2.04-2.23 (m, 4H), 1.99 (s, 3H), 1.62-1.72 (m, 1H), 1.48-1.58 (m, 1H), 1.25-1.31 (m, 3H), 1.18-1.25 (m, 12H), 0.99 (t, J=7.6 Hz, 4H). UPLC-MS (basic 4 min): rt=1.70 min; m/z=648.4 for [M+H]$^+$.

Example 263: N-[(2R,3S)-3-{4-[(2S)-2-[2-(3-cyano-phenyl)-2,2-difluoroacetamido]-2-cyclopentyl acetamido]-3-fluorophenyl}-1-(4-methylpiperazin-1-yl)-1-oxobutan-2-yl]propanamide) (292)

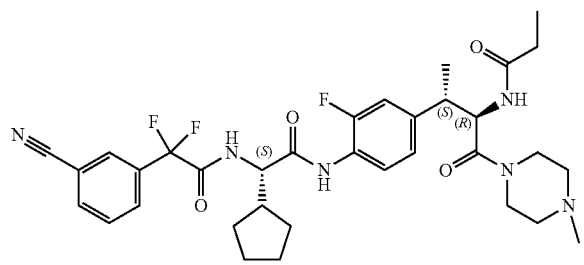

Compound 292 was synthesized by coupling the bis-TFA salt shown below, made by a procedure analogous to the synthesis of 82(a-d) with the required amino acid following General Procedure R and purified using reverse phase column chromatography.

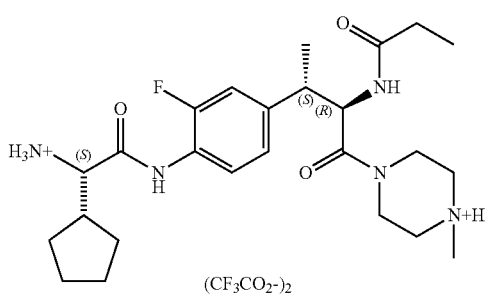

$^1$H NMR (400 MHz, DMSO-d$_6$) δ 9.91 (s, 1H), 9.22 (d, J=8.1 Hz, 1H), 8.25 (d, J=8.8 Hz, 1H), 8.13 (s, 1H), 8.06 (d, J=7.7 Hz, 1H), 7.95 (d, J=8.2 Hz, 1H), 7.76 (t, J=7.9 Hz, 1H), 7.66 (t, J=8.3 Hz, 1H), 7.10 (dd, J=12.0, 1.7 Hz, 1H), 7.00 (dd, J=8.4, 1.3 Hz, 1H), 4.85 (t, J=9.4 Hz, 1H), 4.44 (t, J=9.0 Hz, 1H), 3.35-3.46 (m, 2H), 3.20-3.28 (m, 2H), 2.99-3.13 (m, 2H), 2.27-2.38 (m, 1H), 2.03-2.24 (m, 4H), 1.96 (s, 3H), 1.61-1.72 (m, 2H), 1.52-1.61 (m, 3H), 1.41-1.52 (m, 3H), 1.32-1.41 (m, 1H), 1.16-1.24 (m, 3H), 1.05-1.16 (m, 1H), 0.98 (t, J=7.6 Hz, 3H). UPLC-MS (basic 4 min): rt=1.72 min; m/z=655.4 for [M+H]$^+$ Example 264: (2S,3S)-2-[(1-ethyl-1H-pyrazol-5-yl)formamido]-N-{2-fluoro-4-[(2S,3R)-4-(4-methylpiperazin-1-yl)-4-oxo-3-propanamidobutan-2-yl]phenyl}-3-phenylpentanamide) (293)

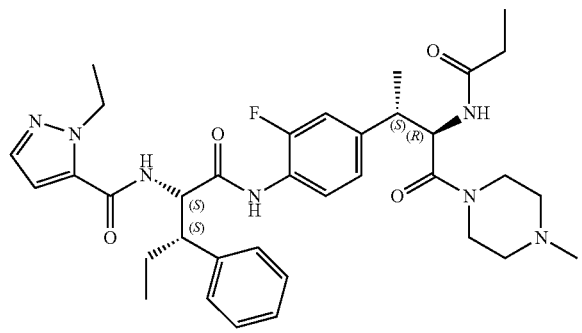

Compound 293 was synthesized by coupling the bis-TFA salt shown below, made by a procedure analogous to the synthesis of 82(a-d) with the required amino acid following General Procedure R and purified using reverse phase column chromatography.

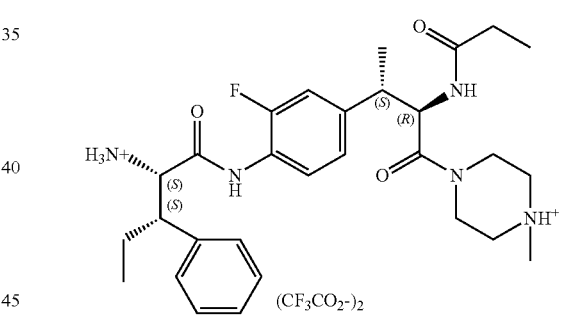

$^1$H NMR (400 MHz, DMSO-d$_6$) δ 7.86-7.93 (m, 1H), 7.36 (d, J=2.1 Hz, 1H), 7.31 (d, J=3.9 Hz, 4H), 7.19-7.25 (m, 1H), 7.13-7.18 (m, 1H), 7.11 (d, J=8.3 Hz, 1H), 6.40 (d, J=2.1 Hz, 1H), 5.03 (d, J=10.4 Hz, 1H), 4.96 (d, J=10.3 Hz, 1H), 4.19-4.38 (m, 2H), 3.51-3.59 (m, 1H), 3.46-3.51 (m, 1H), 3.43 (br t, J=5.0 Hz, 2H), 3.17-3.26 (m, 2H), 3.03-3.17 (m, 2H), 2.31-2.39 (m, 2H), 2.18-2.30 (m, 2H), 2.11 (s, 3H), 1.82-1.92 (m, 2H), 1.72 (s, 1H), 1.61-1.71 (m, 1H), 1.35 (d, J=7.1 Hz, 3H), 1.19 (t, J=7.2 Hz, 3H), 1.14 (t, J=7.6 Hz, 3H), 0.75 (s, 3H). UPLC-MS (basic 4 min): rt=1.70 min; m/z=648.4 for [M+H]$^+$.

419

Example 265: (2S,3S)-2-[(1-ethyl-1H-pyrazol-5-yl) formamido]-N-{2-fluoro-4-[(2S,3R)-4-(4-methyl piperazin-1-yl)-4-oxo-3-propanamidobutan-2-yl] phenyl}-3-(4-fluorophenyl)butanamide) (294)

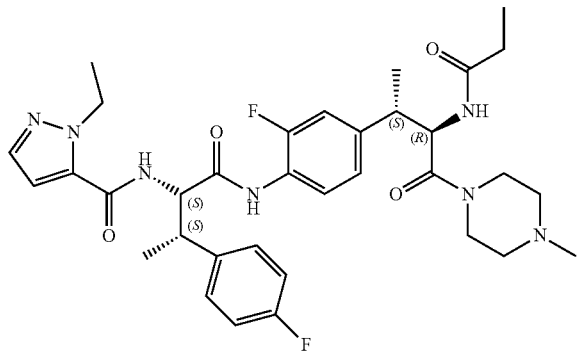

Compound 294 was synthesized by coupling the bis-TFA salt shown below, made by a procedure analogous to the synthesis of 82(a-d) with the required amino acid following General Procedure R and purified using reverse phase column chromatography.

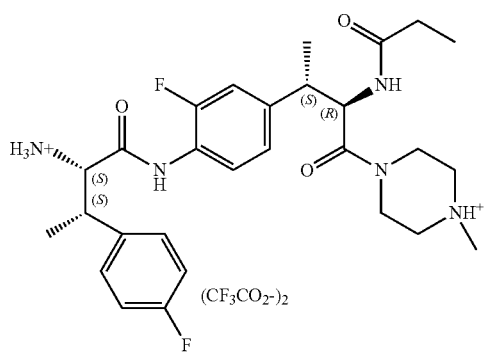

$^1$H NMR (400 MHz, DMSO-d$_6$) δ 10.13 (s, 1H), 8.56 (d, J=9.0 Hz, 1H), 8.27 (d, J=8.4 Hz, 1H), 7.81 (t, J=8.3 Hz, 1H), 7.39-7.44 (m, 2H), 7.38 (d, J=2.0 Hz, 1H), 7.13-7.19 (m, 1H), 7.06-7.13 (m, 2H), 7.01-7.06 (m, 1H), 6.68 (d, J=2.0 Hz, 1H), 4.96 (t, J=9.8 Hz, 1H), 4.83-4.91 (m, 1H), 4.19-4.36 (m, 2H), 3.37-3.48 (m, 2H), 3.21-3.28 (m, 1H), 3.07-3.15 (m, 1H), 2.97-3.07 (m, 1H), 2.07-2.24 (m, 4H), 1.90-2.06 (m, 3H), 1.60-1.75 (m, 1H), 1.45-1.60 (m, 1H), 1.27 (d, J=7.2 Hz, 3H), 1.17-1.25 (m, 4H), 1.11 (t, J=7.2 Hz, 3H), 0.99 (t, J=7.6 Hz, 3H). UPLC-MS (basic 4 min): rt=1.72 min; m/z=653.4 for [M+H]$^+$.

420

Example 266: N-[(2R,3S)-3-{4-[(2S)-2-[2,2-difluoro-2-(6-methoxypyridin-3-yl)acetamido]-2-[(1r,4S)-4-methylcyclohexyl]acetamido]-3-fluorophenyl}-1-(4-methylpiperazin-1-yl)-1-oxobutan-2-yl] propanamide (295)

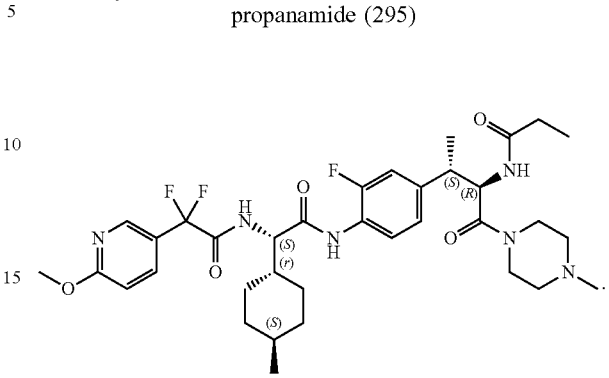

Compound 295 was synthesized by coupling 82d with the required amino acid following General Procedure R and purified using reverse phase column chromatography. $^1$H NMR (400 MHz, DMSO-d$_6$) δ 9.91 (s, 1H), 9.02 (d, J=8.2 Hz, 1H), 8.41 (d, J=2.5 Hz, 1H), 8.26 (d, J=8.7 Hz, 1H), 7.92 (dd, J=8.8, 2.6 Hz, 1H), 7.71 (t, J=8.3 Hz, 1H), 7.10 (dd, J=12.1, 1.9 Hz, 1H), 7.02 (dd, J=8.4, 1.9 Hz, 1H), 6.97 (d, J=8.7 Hz, 1H), 4.86 (t, J=9.4 Hz, 1H), 4.42 (t, J=8.4 Hz, 1H), 3.90 (s, 3H), 3.24 (t, J=10.7 Hz, 2H), 3.09 (dd, J=9.8, 6.9 Hz, 1H), 3.01 (t, J=10.6 Hz, 1H), 2.24-2.05 (m, 5H), 1.97 (s, 3H), 1.79 (d, J=10.5 Hz, 1H), 1.65 (q, J=13.3, 12.3 Hz, 5H), 1.56 (s, 1H), 1.49 (t, J=9.6 Hz, 1H), 1.20 (d, J=7.0 Hz, 3H), 1.17-1.09 (m, 1H), 0.99 (t, J=7.6 Hz, 4H), 0.84 (d, J=6.4 Hz, 4H), 0.82-0.79 (m, 1H) UPLC-MS (basic 4 min): rt=1.93 min; m/z=689.3 for [M+H]$^+$.

Example 267: N-[(2R,3S)-3-{4-[(2S)-2-(4,4-dimethylcyclohexyl)-2-[(1-ethyl-1H-pyrazol-5-yl)formamido] acetamido]-3-fluorophenyl}-1-(4-methylpiperazin-1-yl)-1-oxobutan-2-yl]propanamide) (296)

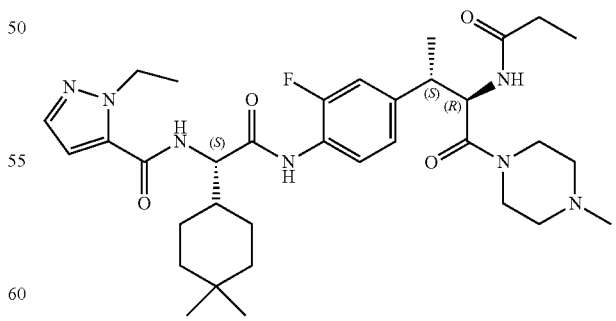

Compound 296 was synthesized by coupling the bis-TFA salt shown below, made by a procedure analogous to the synthesis of 82(a-d) with the required amino acid following General Procedure R and purified using reverse phase column chromatography.

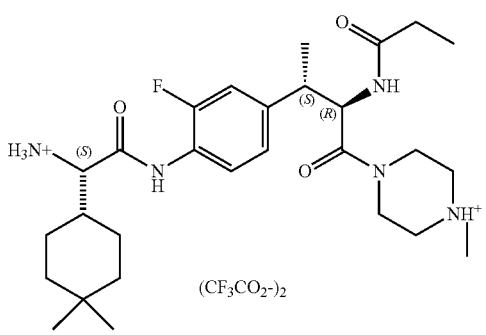

(CF₃CO₂⁻)₂

¹H NMR (400 MHz, DMSO-d₆) δ 9.85 (s, 1H), 8.47 (d, J=8.3 Hz, 1H), 8.25 (d, J=8.7 Hz, 1H), 7.71-7.77 (m, 1H), 7.47 (d, J=2.0 Hz, 1H), 7.10 (dd, J=12.1, 1.6 Hz, 1H), 7.01 (dd, J=8.4, 1.6 Hz, 1H), 6.97-6.99 (m, 1H), 4.85 (s, 1H), 4.59 (s, 1H), 4.46 (d, J=7.2 Hz, 2H), 3.36-3.46 (m, 2H), 3.19-3.28 (m, 1H), 3.06-3.14 (m, 1H), 2.97-3.06 (m, 1H), 2.03-2.23 (m, 4H), 1.98 (s, 3H), 1.70-1.83 (m, 1H), 1.58-1.69 (m, 2H), 1.47-1.56 (m, 1H), 1.33-1.46 (m, 4H), 1.25-1.30 (m, 3H), 1.21-1.25 (m, 1H), 1.19 (d, J=7.1 Hz, 3H), 1.05-1.16 (m, 2H), 0.98 (t, J=7.6 Hz, 3H), 0.88 (d, J=4.2 Hz, 6H). UPLC-MS (basic 4 min): rt=1.83 min; m/z=640.5 for [M+H]⁺.

Example 268: General Procedure for Preparation of Intermediate 84

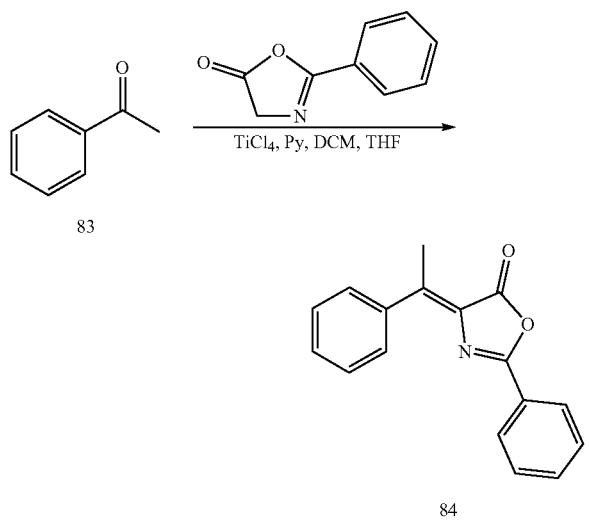

THF (150 mL) was chilled under N₂ to −10° C. A solution of TiCl₄ (23.7 g, 124 mmol, 13.7 mL, 1.50 eq) in DCM (30.0 mL) was added and stirred for 20 mins. To the stirring solution, compound 83 (10.0 g, 83.2 mmol, 9.71 mL, 1.00 eq) was added, the mixture was stirred for 10 mins, then the substituted benzene derivative compound (14.8 g, 91.6 mmol, 1.10 eq) was added and stirred for a further 30 mins. To this mixture, pyridine (13.2 g, 166 mmol, 13.4 mL, 2.00 eq) was added dropwise. The mixture was stirred for a further 5 hrs at 25° C. TLC (Petroleum ether:Ethyl acetate=10:1, plate 1, $R_f$ (R₁)=0.70, $R_f$ (P1)=0.75) showed compound 83 was completely consumed and a major new spot was generated. The mixture was added to saturated NH₄Cl (400 mL) and the aqueous was extracted with ethyl acetate (300 mL*2), the combined organic phases were washed with brine (200 mL*2), dried over Na₂SO₄ and concentrated under reduced pressure to give a residue. The residue was slurried with MeOH (50.0 mL). Compound 84 (7.80 g, 28.9 mmol, 34.7% yield, 97.6% purity) was obtained as a yellow solid, confirmed by LCMS and H¹ NMR. H¹ NMR: (400 MHz, CDCl₃) δ 8.08-8.06 (m, 2H), 7.89-7.87 (m, 2H), 7.49-7.47 (m, 1H), 7.46-7.43 (m, 5H), 2.80 (s, 3H). LCMS: Rt=1.06 mins, (M+H)⁺: 264.2.

Example 269: General Procedure for Preparation of Intermediate 85

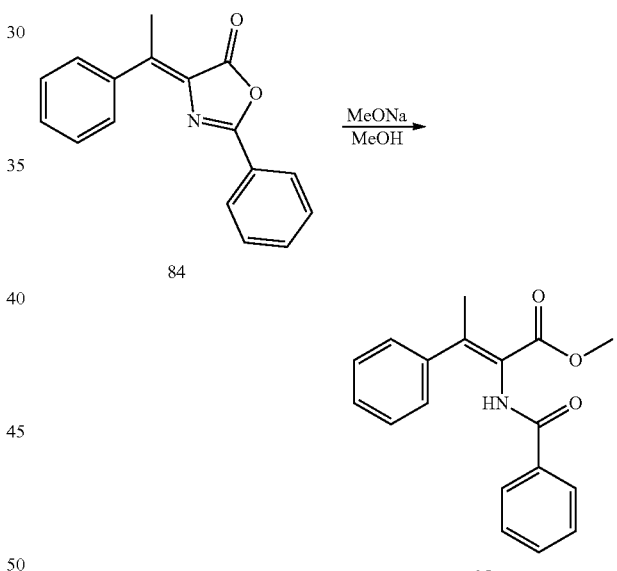

To a solution of CH₃ONa (365 mg, 6.76 mmol, 0.100 eq) in MeOH (350 mL) at 25° C. was added compound 84 (17.8 g, 67.6 mmol, 1.00 eq), then the mixture was stirred at 25° C. for 1 hr. TLC (Petroleum ether:Ethyl acetate=5:1, plate 1, $R_f$ (R1)=0.85, $R_f$ (P1)=0.15) showed compound 84 was completely consumed and a major new spot was generated. MeOH was removed in vacuo to give a residue. Cold water (50.0 mL) was added dropwise to the residue, which was filtered and the filter cake was collected as a white solid. Compound 85 (19.2 g, 65.0 mmol, 96.2% yield, 100% purity) was obtained as a white solid, confirmed by LCMS and H¹ NMR). H¹ NMR: (400 MHz, CDCl₃) δ 7.59-7.30 (m, 10H), 7.24 (brs, 1H), 3.88 (s, 3H), 2.33 (s, 3H). LCMS: Rt=0.894 mins, (M+H)⁺: 296.1

Example 270: General Procedure for Preparation of Intermediate 87

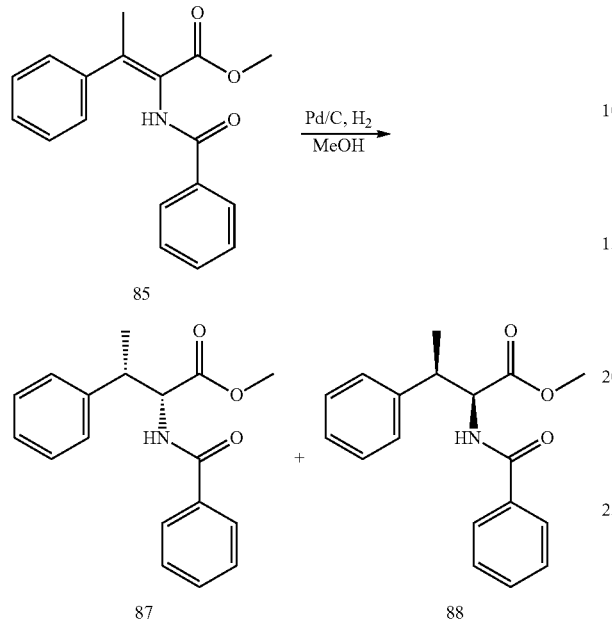

To a solution of compound 85 (19.2 g, 65.0 mmol, 990 uL, 1.00 eq) in MeOH (500 mL) was added Pd/C (4.00 g, 10.0% purity) and the reaction was stirred at 35° C. under H₂ (50 psi) for 12 hrs. TLC (Petroleum ether:Ethyl acetate=3:1, plate 1, $R_f$(R1)=0.20, $R_f$(P1)=0.25) showed compound 85 was consumed completely and a major new spot was generated. The mixture was filtered and the filtrate was concentrated in vacuum to give a residue. It was directly used for the next step without further purification. A mixture of compounds 87 and 88 (19.3 g, 64.9 mmol, 99.8% yield, 100% purity) was obtained as a white solid, confirmed by LCMS and H¹ NMR. H¹ NMR: (400 MHz, CDCl₃) δ 7.76-7.74 (m, 2H), 7.46-7.44 (m, 3H), 7.31-7.29 (m, 2H), 7.22-7.20 (m, 3H), 6.59 (d, J=8.4 Hz, 1H), 5.04-5.00 (m, 1H), 3.61 (s, 3H), 3.37-3.30 (m, 1H), 1.48 (d, J=7.2 Hz, 3H). LCMS: Rt=0.915 min, (M+H)+: 298.1.

Example 271: General Procedure for Preparation of Intermediate 87

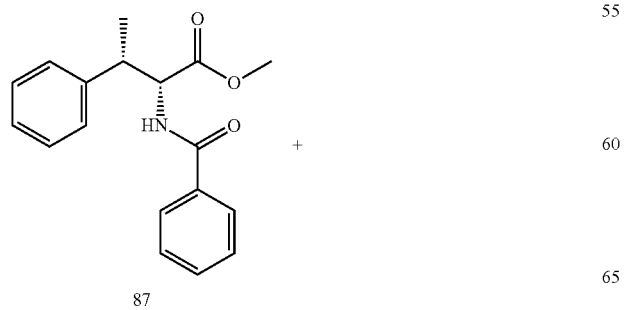

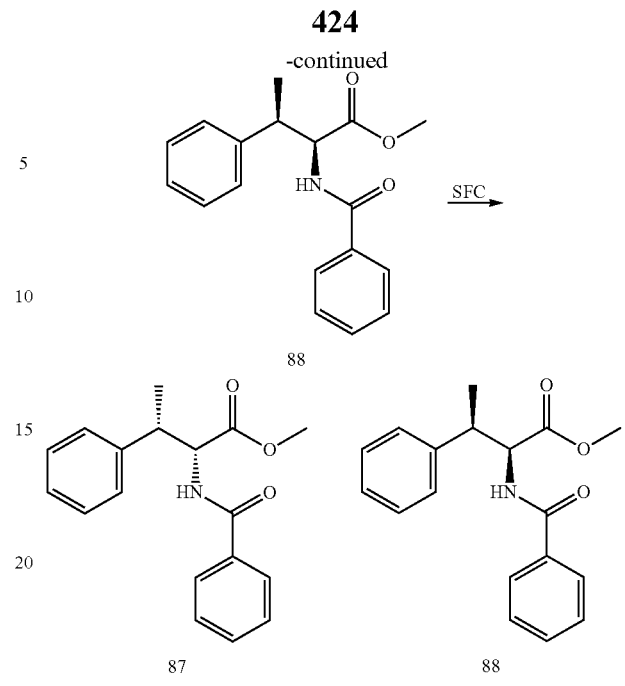

The mixture of compounds 87 and 88 was resolved by SFC (column: DAICEL CHIRALPAK AD (250 mm*30 mm, 10 um); mobile phase: [0.1% NH₃H₂O ETOH]; B %: 20%-20%, 3.4 min, 780 min) to get 2 products, compound 87 (9.45 g, 31.8 mmol, 49.0% yield, 100% purity) (H¹ NMR; (400 MHz, CDCl₃) δ 7.77-7.75 (m, 2H), 7.55-7.45 (m, 3H), 7.32-7.21 (m, 5H), 6.61 (d, J=8.4 Hz, 1H), 5.05-5.01 (m, 1H), 3.62 (s, 3H), 3.38-3.31 (m, 1H), 1.49 (d, J=7.2 Hz, 3H); LCMS (Rt=0.909 min, (M+1)+: 298.1)) as a white solid and compound 88 (9.57 g, 32.2 mmol, 49.6% yield, 100% purity) (H¹ NMR (400 MHz, CDCl₃) δ 7.77-7.75 (m, 2H), 7.53-7.45 (m, 3H), 7.32-7.21 (m, 5H), 6.62 (d, J=8.4 Hz, 1H), 5.05-5.01 (m, 1H), 3.62 (s, 3H), 3.36-3.33 (m, 1H), 1.49 (d, J=7.2 Hz, 3H); LCMS (Rt=0.920 min, (M+1)+: 298.1)) as a white solid.

Example 272: General Procedure for Preparation of Intermediate 89

To a solution of compound 87 (9.40 g, 31.6 mmol, 1.00 eq) in HCl (3 M, 527 mL, 50.0 eq) was added AcOH (190 g, 3.16 mol, 181 mL, 100 eq), then the mixture was stirred at 125° C. for 60 hrs. LCMS showed compound 87 was consumed. The solvent was removed in vacuum to provide a residue which was purified by slurrying with DCM (50.0 mL) to get the desired product compound 89 (6.21 g, 28.3 mmol, 89.7% yield, 98.4% purity, HCl) as a white solid, confirmed by $H^1$ NMR. $H^1$ NMR: (400 MHz, DMSO) δ 13.65 (brs, 1H), 8.49 (brs, 3H), 7.34-7.25 (m, 5H), 3.99 (d, J=4.0 Hz, 1H), 3.35-3.32 (m, 1H), 1.38 (d, J=7.2 Hz, 3H). LCMS: Rt=0.360 min, (M+1)$^+$: 180.1.

Example 273: General Procedure for Preparation of Intermediate 90

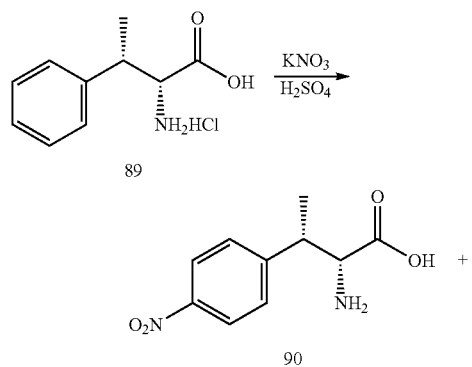

To a solution of compound 89 (5.21 g, 23.8 mmol, 1.00 eq, HCl) in $H_2SO_4$ (30.0 mL) was added $KNO_3$ (2.65 g, 26.2 mmol, 1.10 eq) at 0° C., then the mixture was warmed to 25° C. and stirred for 0.5 hr. LCMS showed the desired product was formed. HPLC showed there was one major peak formed. The reaction mixture was quenched with ice water (250 mL), then adjusted the pH of the solution to 9 with $Na_2CO_3$ solid to get the desired product compound 90 and 90A (5.33 g, 23.8 mmol, 100% yield) which was stored in water and used to next step directly. LCMS: Rt=0.533 min, (M+1)$^+$: 225.0.

Example 274: General Procedure for Preparation of Intermediate 91

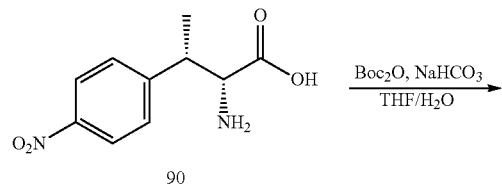

-continued

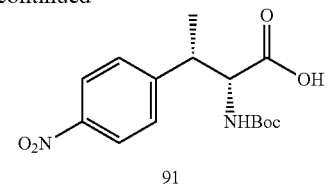

To a mixture of compound 90 and 90A (not shown) (5.33 g, 23.8 mmol, 1.00 eq) in water (250 mL) was added THF (40.0 mL), then $Boc_2O$ (7.78 g, 35.7 mmol, 8.19 mL, 1.50 eq) was added at 0° C. and warmed to 25° C. stirred for 2 hrs. LCMS indicated the desired product was formed. The reaction mixture was diluted with petroleum ether (100 mL), then adjusted the pH of the solution to 3 with 1 N HCl at 0° C. and extracted with ethyl acetate (100 mL*4), the combined organic layer was dried over $Na_2SO_4$ and concentrated under reduced pressure to give a residue. The residue was purified by SFC (column: DAICEL CHIRALPAK AD-H (250 mm*30 mm, 5um); mobile phase: [0.1% NH3H2O MEOH]; B %: 30%-30%, 3.2 min; 400 min) to get the desired product 91 (4.70 g, 14.5 mmol, 61.0% yield, 100% purity) ($H^1$ NMR (δ 12.63 (brs, 1H), 8.15 (d, J=8.8 Hz, 2H), 7.54 (d, J=8.8 Hz, 2H), 7.27 (d, J=9.2 Hz, 1H), 4.25-4.21 (m, 1H), 3.40-3.35 (m, 1H), 1.31-1.17 (m, 12H); LCMS: Rt=0.876 min, (M-99)$^+$: 225.2)) and LCMS as a light yellow solid.

Example 275: tert-butyl N-[(2R,3S)-1-(4-methylpiperazin-1-yl)-3-(4-nitrophenyl)-1-oxobutan-2-yl]carbamate) (92)

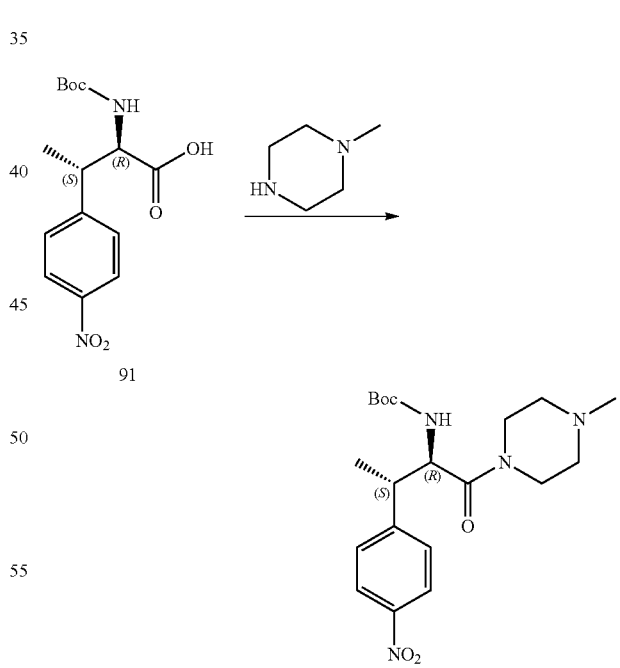

To a solution of 91 (0.600 g, 1.85 mmol, 1.0 eq.) in DMF (6 mL) was added N-methyl piperazine (0.25 mL, 2.22 mmol, 1.2 eq,), DIPEA (0.97 mL, 5.55 mmol, 3.0 eq) and HATU (1.06 g, 2.78 mmol, 1.5 eq.) and the resulting mixture was stirred at RT under a $N_2$ atmosphere for 1 h. The mixture was diluted with aq. sat. $NaHCO_3$ solution (20 mL) and then extracted with EtOAc (2×20 mL). The organic layer was washed with brine (50 mL), dried over Na$_2$SO$_4$ then concentrated to afford 92 as a yellow oil (0.684 g, 91%). $^1$H NMR (400 MHz, Chloroform-d) δ 8.12-8.05 (m, 2H), 7.38-7.30 (m, 2H), 5.32-5.23 (m, 1H), 4.67 (t, J=9.1 Hz, 1H), 3.51-3.39 (m, 1H), 3.39-3.28 (m, 2H), 3.16 (p, J=7.3 Hz, 1H), 3.06 (ddd, J=13.1, 7.1, 3.1 Hz, 1H), 2.85 (d, J=29.1 Hz, 2H), 2.10 (s, 3H), 2.02-1.95 (m, 1H), 1.81-1.72 (m, 1H), 1.35 (s, 9H), 1.31 (d, J=7.1 Hz, 3H). UPLC-MS (basic 2 min): Rt=1.06 min; m/z=407.2 for [M+H]$^+$.

Example 276: (2R,3S)-2-amino-1-(4-methylpiperazin-1-yl)-3-(4-nitrophenyl)butan-1-one) (93)

Example 277: N-[(2R,3S)-1-(4-methylpiperazin-1-yl)-3-(4-nitrophenyl)-1-oxobutan-2-yl]propanamide) (94)

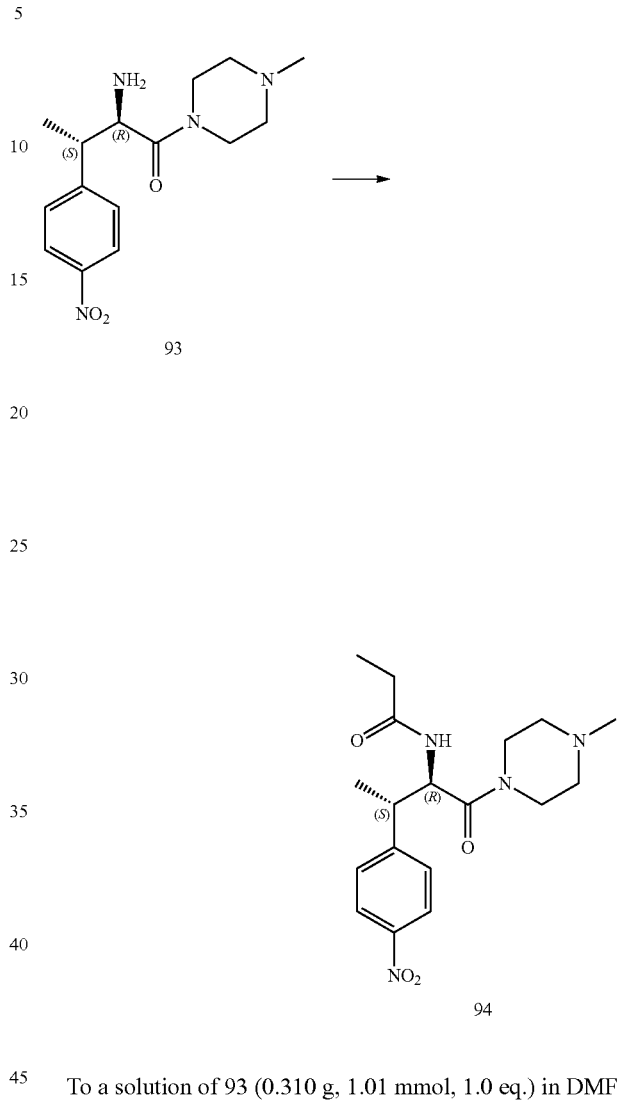

To a solution of 92 (0.684 g, 1.68 mmol, 1.0 eq.) in DCM (10 mL) was added TFA (5 mL) and the resulting mixture was stirred at RT for 1 h. The reaction mixture was concentrated to dryness and the residue was dissolved in DCM (10 mL), stirred in aq. sat. K$_2$CO$_3$ solution (1 g in 10 mL H$_2$O) and then extracted with DCM to afford 93 as a yellow gummy solid (0.316 g, 61% yield). $^1$H NMR (400 MHz, Chloroform-d) δ 8.13-8.05 (m, 2H), 7.41-7.33 (m, 2H), 5.23 (s, 1H), 3.67 (d, J=7.1 Hz, 1H), 3.45 (dd, J=6.7, 3.5 Hz, 2H), 3.29 (ddd, J=12.9, 7.3, 3.1 Hz, 1H), 3.09-2.97 (m, 2H), 2.25 (td, J=10.3, 9.7, 4.9 Hz, 2H), 2.12 (s, 3H), 2.03 (dt, J=11.3, 5.2 Hz, 1H), 1.80 (d, J=8.2 Hz, 1H), 1.32 (d, J=7.0 Hz, 3H). UPLC-MS (basic 2 min): Rt=0.83 min; m/z=307.2 for [M+H]$^+$.

To a solution of 93 (0.310 g, 1.01 mmol, 1.0 eq.) in DMF (3.0 mL) was added propionic anhydride (0.16 mL, 1.21 mmol, 1.2 eq.) and DIPEA (0.53 mL, 3.04 mmol, 3.0 eq) and the resulting mixture was stirred at RT under a N$_2$ atmosphere for 1 h. The mixture was diluted with aq. sat. NaHCO$_3$ solution (20 mL) and then extracted with EtOAc (2×20 mL). The organic layer was washed with brine (50 mL), dried over Na$_2$SO$_4$ and concentrated to afford 94 as a yellow oil (0.350 g, 95% yield) which was used in the next step without further purification. $^1$H NMR (400 MHz, Chloroform-d) δ 8.14-8.06 (m, 2H), 7.40-7.32 (m, 2H), 6.18 (d, J=9.2 Hz, 1H), 5.08 (t, J=9.3 Hz, 1H), 3.45-3.14 (m, 4H), 2.99 (ddd, J=13.4, 6.9, 3.1 Hz, 1H), 2.42 (q, J=7.4 Hz, 1H), 2.27-2.09 (m, 4H), 2.07 (s, 3H), 1.93 (ddd, J=11.2, 7.1, 3.5 Hz, 1H), 1.30 (d, J=7.1 Hz, 3H), 1.13-1.08 (m, 4H). UPLC-MS (basic 2 min): Rt=0.88 min; m/z=363.2 for [M+H]$^+$.

Example 278: N-[(2R,3S)-3-(4-aminophenyl)-1-(4-methylpiperazin-1-yl)-1-oxobutan-2-yl]propanamide)) (95)

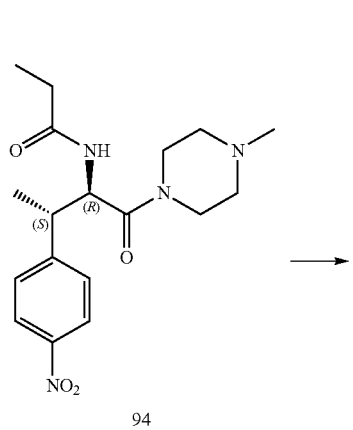
94

Example 279: General Procedure S for the Synthesis of 97a-b

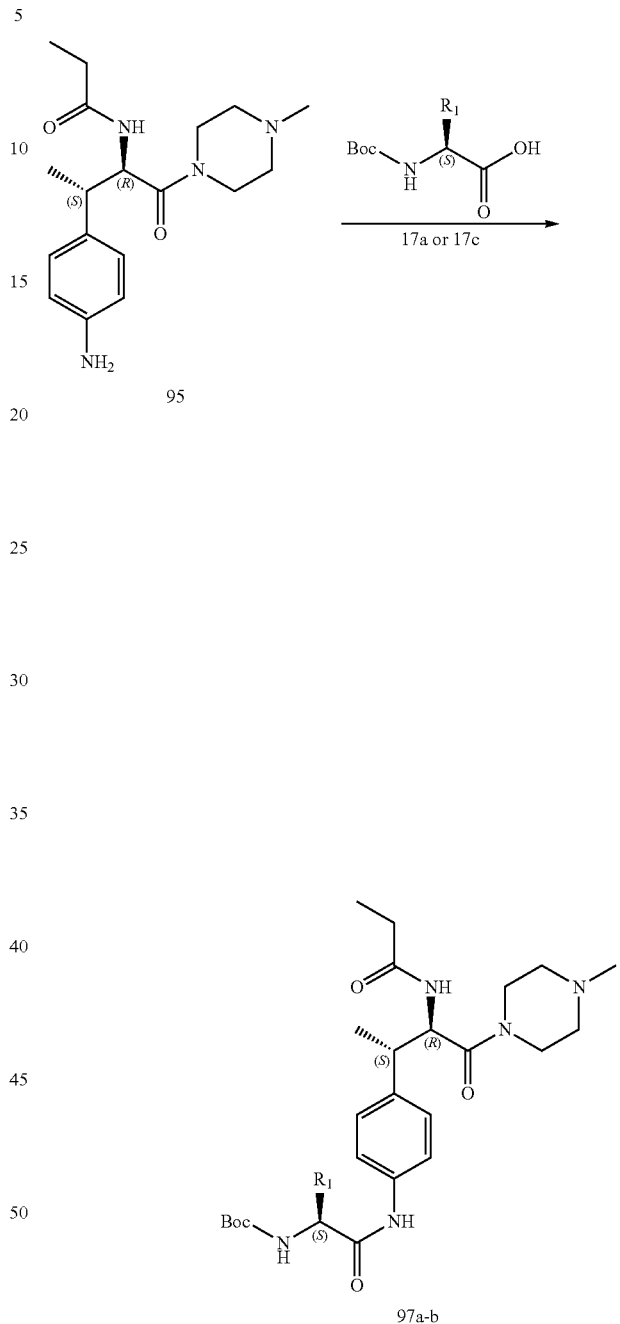

To a degassed solution of 94 (0.362 g, 1.00 mmol, 1.0 eq) in EtOH (10 mL) and THE (10 mL) was added Pd/C (0.020 g, 0.200 mmol, 0.20 eq). The mixture was degassed for another 20 minutes and then evacuated under vacuum before introducing a hydrogen balloon. The resulting mixture was stirred at RT for 6 h. The mixture was filtered through a pad of celite which was washed with EtOH (50 mL) and concentrated to dryness. The residue was triturated with DCM and iso-hexane to afford 95 as a yellow gummy solid (0.200 g, 60% yield) which was used in the next step without further purification. UPLC-MS (basic 2 min): Rt=0.75 min; m/z=333.2 for [M+H]$^+$.

To a solution of 95 (1.0 eq.) in DMF (0.1M) were added 17a or 17 c (1.2 eq.), DIPEA (4.0-8.0 eq.) and HATU (1.5-2.0 eq.) and the resulting mixture was stirred for 1 h. Aqueous saturated sodium bicarbonate solution was added and then extracted with EtOAc. The combined organic phase was washed with brine, dried over sodium sulfate then concentrated to dryness to afford 97a-b which was used in the next step without further purification.

Example 280: tert-butyl N—[(S)-cyclohexyl({4-[(2S,3R)-4-(4-methylpiperazin-1-yl)-4-oxo-3-propanamidobutan-2-yl]phenyl}carbamoyl)methyl]carbamate) (97a)

Example 281: tert-butyl N—[(S)-cycloheptyl({4-[(2S,3R)-4-(4-methylpiperazin-1-yl)-4-oxo-3-propanamidobutan-2-yl]phenyl}carbamoyl)methyl]carbamate) (97b)

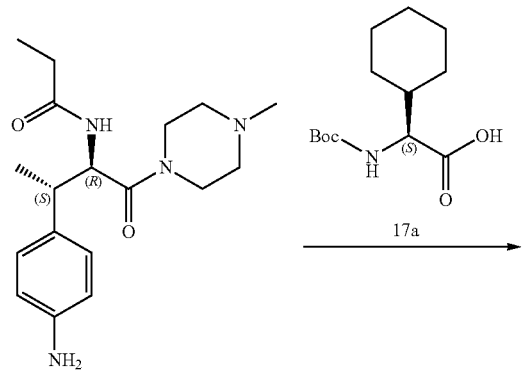 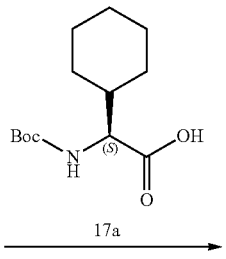 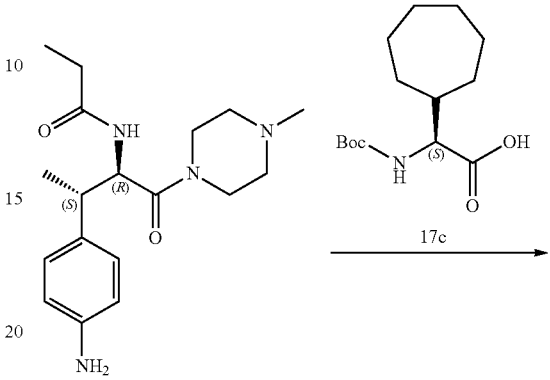

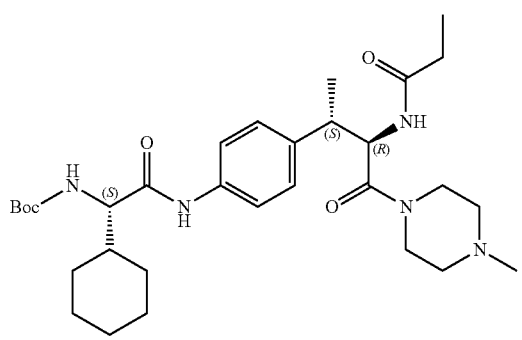

97a

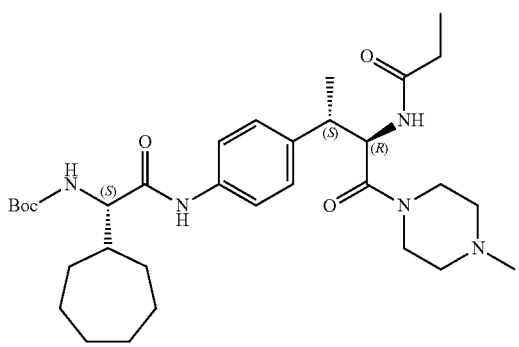

97b

Following General Procedure S, 95 (0.100 g, 0.301 mmol, 1.0 eq.) was reacted with (2S)-2-{[(tert-butoxy)carbonyl]amino}-2-cyclohexylacetic acid 17a (0.093 g, 0.361 mmol, 1.2 eq.), HATU (0.172 g, 0.451 mmol, 1.5 eq.) and DIPEA (0.16 mL, 0.902 mmol, 3.0 eq.) in DMF (1 mL) to afford, after aqueous work-up, 97a (0.065 g, 38% yield) as a yellow gummy solid which was used in the next step without further purification. UPLC-MS (basic 2 min): rt=1.08 min; m/z=572.3 for [M+H]$^+$.

Following General Procedure S, 95 (0.100 g, 0.301 mmol, 1.0 eq.) was reacted with (2S)-2-{[(tert-butoxy)carbonyl]amino}-2-cycloheptylacetic acid) 17c (0.098 g, 0.361 mmol, 1.2 eq.), HATU (0.172 g, 0.451 mmol, 1.5 eq.) and DIPEA (0.16 mL, 0.902 mmol, 3.0 eq.) in DMF (1 mL) to afford, after aqueous work-up, 97b (0.058 g, 33% yield) as a yellow gummy solid which was used in the next step without further purification. UPLC-MS (basic 2 min): rt=1.12 min; m/z=586.3 for [M+H]$^+$.

Example 282: General Procedure T for the Synthesis of 98a-b

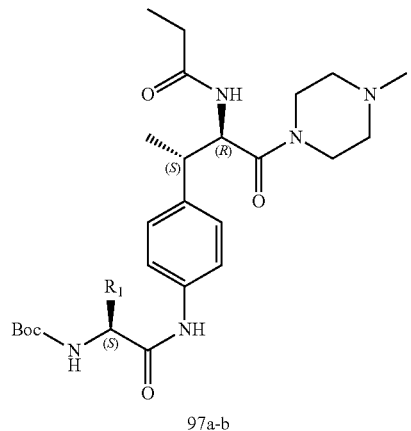

97a-b

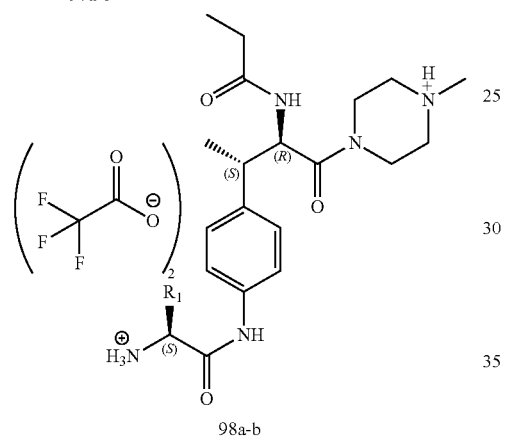

98a-b

To a solution of 97a-b (1.0 eq.) in DCM was added TFA and the resulting mixture was stirred at RT for 0.5 h. The reaction mixture was concentrated to dryness to afford 98a-b which was used in the next step without further purification.

Example 283: (S)-cyclohexyl({4-[(2S,3R)-4-(4-methylpiperazin-1-yl)-4-oxo-3-propanamidobutan-2-yl]phenyl}carbamoyl)methanaminium trifluoroacetate) (98a)

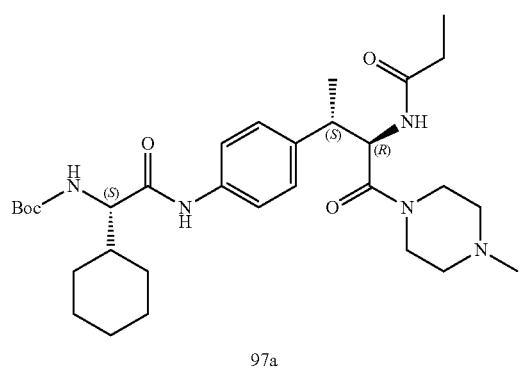

97a

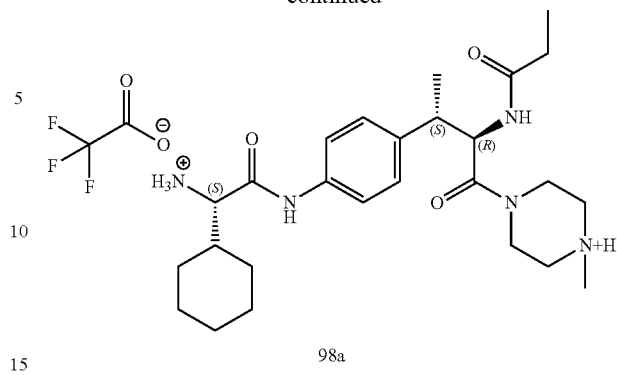

98a

Following General Procedure T, 97a (0.065 g, 0.114 mmol, 1.0 eq.) was reacted with TFA (0.5 mL) in DCM (1 mL) to afford, after concentration to dryness, 98a (0.066 g, 99% yield) as a brown oil which was used in the next step without further purification. UPLC-MS (basic 2 min): rt=0.91 min; m/z=472.3 for [M+H]⁺.

Example 284: (S)-cycloheptyl({4-[(2S,3R)-4-(4-methylpiperazin-1-yl)-4-oxo-3-propanamidobutan-2-yl]phenyl}carbamoyl)methanaminium trifluoroacetate) (98b)

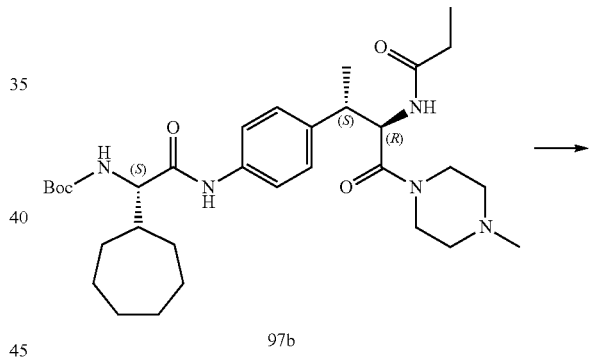

97b

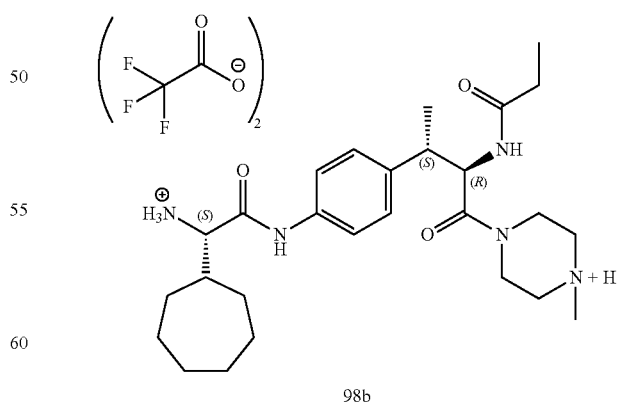

98b

Following General Procedure T, 97b (0.058 g, 0.099 mmol, 1.0 eq.) was reacted with TFA (0.5 mL) in DCM (1 285; m/z=486.3 for [M+H]⁺.

Example 285: General Procedure U for the Synthesis of 221, 222, 232 and 297-301

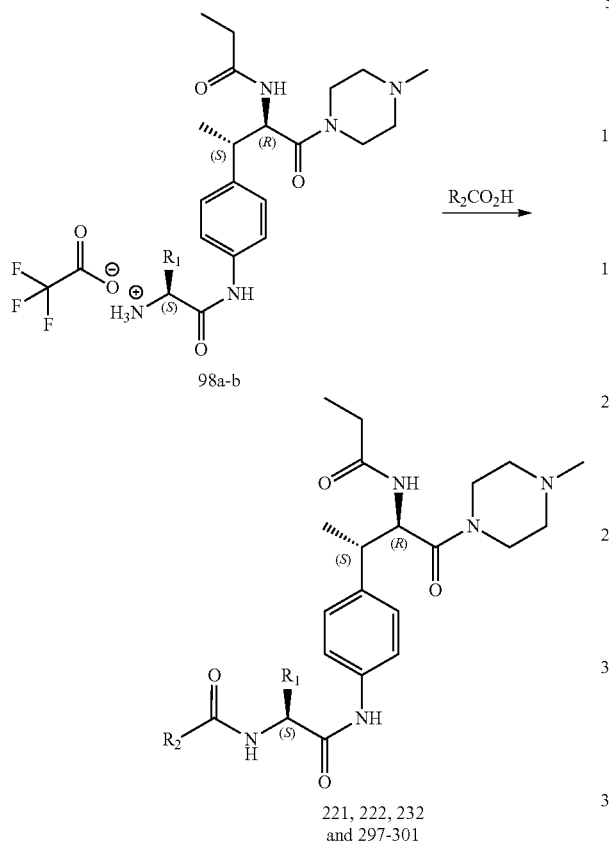

221, 222, 232 and 297-301

To a solution of 98a-b (1.0 eq.) in DMF were added the requisite carboxylic acid (1.2 eq.), DIPEA (8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford 221, 222, 232 and 297-301.

Example 286: N-[(2R,3S)-3-{4-[(2S)-2-cyclohexyl-2-[2,2-difluoro-2-(6-methoxypyridin-3-yl)acetamido]acetamido]phenyl}-1-(4-methylpiperazin-1-yl)-1-oxobutan-2-yl]propanamide) (221)

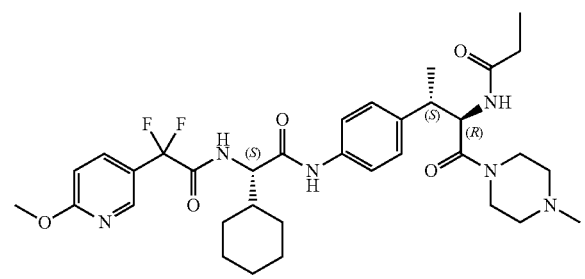

Following General Procedure U, 98a (0.067 g, 0.114 mmol, 1.0 eq.) was reacted with 2,2-difluoro-2-(6-methoxypyridin-3-yl)acetic acid (0.028 g, 0.137 mmol, 1.2 eq.), DIPEA (0.16 mL, 0.912 mmol, 8.0 eq.) and HATU (0.065 g, 0.171 mmol, 1.5 eq.) in DMF (1 mL) to afford, after reverse phase column chromatography, 221 (36.0 mg) as a white solid. $^1$H NMR (400 MHz, DMSO-$d_6$) δ 10.17 (s, 1H), 9.05 (d, J=8.2 Hz, 1H), 8.41 (s, 1H), 8.24 (d, J=8.7 Hz, 1H), 7.92 (dd, J=8.8, 2.6 Hz, 1H), 7.51 (d, J=8.5 Hz, 2H), 7.15 (d, J=8.5 Hz, 2H), 6.97 (d, J=8.7 Hz, 1H), 4.83 (t, J=9.5 Hz, 1H), 4.25 (t, J=8.6 Hz, 1H), 3.90 (s, 3H), 3.47 (d, J=13.7 Hz, 1H), 3.18 (d, J=10.5 Hz, 1H), 3.09-3.03 (m, 1H), 2.93 (d, J=11.4 Hz, 1H), 2.25-2.03 (m, 5H), 1.92 (s, 3H), 1.84 (s, 1H), 1.65 (d, J=9.8 Hz, 3H), 1.57 (d, J=13.9 Hz, 3H), 1.39-1.22 (m, 2H), 1.19 (d, J=7.0 Hz, 2H), 1.13 (d, J=20.2 Hz, 4H), 0.99 (t, J=7.6 Hz, 3H), 0.90 (d, J=11.9 Hz, 1H). UPLC-MS (basic 2 min): rt=1.08 min; m/z=657.3 for [M+H]$^+$.

Example 287: N-[(2R,3S)-3-{4-[(2S)-2-cycloheptyl-2-[2,2-difluoro-2-(6-methoxypyridin-3-yl)acetamido]acetamido]phenyl}-1-(4-methylpiperazin-1-yl)-1-oxobutan-2-yl]propanamide) (222)

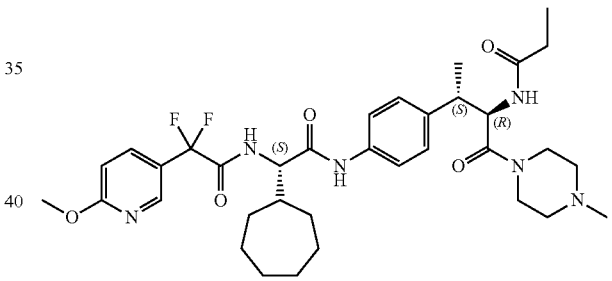

Following General Procedure U, 98b (0.059 g, 0.099 mmol, 1.0 eq.) was reacted with 2,2-difluoro-2-(6-methoxypyridin-3-yl)acetic acid (0.024 g, 0.119 mmol, 1.2 eq.), DIPEA (0.14 mL, 0.792 mmol, 8.0 eq.) and HATU (0.056 g, 0.175 mmol, 1.5 eq.) in DMF (1 mL) to afford, after reverse phase column chromatography, 222 (30.0 mg) as a white solid. $^1$H NMR (400 MHz, DMSO-$d_6$) δ 10.17 (s, 1H), 9.04 (d, J=8.4 Hz, 1H), 8.44-8.39 (m, 1H), 8.24 (d, J=8.7 Hz, 1H), 7.93 (dd, J=8.8, 2.5 Hz, 1H), 7.51 (d, J=8.5 Hz, 2H), 7.15 (d, J=8.6 Hz, 2H), 6.96 (d, J=8.7 Hz, 1H), 4.83 (t, J=9.5 Hz, 1H), 4.32 (t, J=8.6 Hz, 1H), 3.90 (s, 3H), 3.17 (t, J=10.5 Hz, 1H), 3.11-3.00 (m, 1H), 2.95 (t, J=10.0 Hz, 1H), 2.14 (ddp, J=22.2, 14.7, 7.4 Hz, 5H), 1.92 (s, 3H), 1.63-1.41 (m, 8H), 1.41-1.21 (m, 6H), 1.19 (d, J=7.0 Hz, 4H), 0.99 (t, J=7.6 Hz, 3H). UPLC-MS (basic 2 min): rt=1.12 min; m/z=671.3 for [M+H]$^+$.

Example 288: N-[(2R,3S)-3-{4-[(2S)-2-cycloheptyl-2-[(1-ethyl-1H-pyrazol-5-yl)formamido]acetamido]phenyl}-1-(4-methylpiperazin-1-yl)-1-oxobutan-2-yl]propanamide) (297)

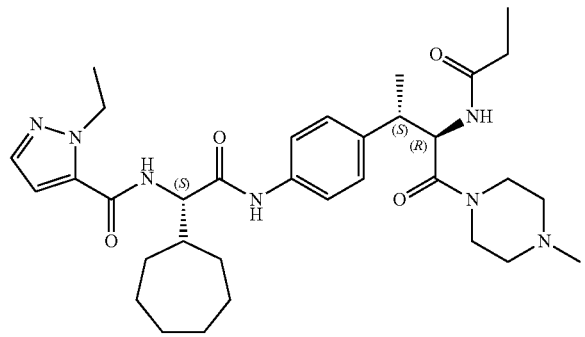

Compound 297 was synthesized by coupling 98b with the required amino acid following General Procedure U and purified using reverse phase column chromatography. ¹H NMR (400 MHZ, DMSO-d₆) δ 10.14 (s, 1H), 8.47 (d, J=8.5 Hz, 1H), 8.24 (d, J=8.7 Hz, 1H), 7.55 (d, J=8.4 Hz, 2H), 7.47 (d, J=2.0 Hz, 1H), 7.15 (d, J=8.5 Hz, 2H), 7.01 (d, J=2.1 Hz, 1H), 4.88-4.79 (m, 1H), 4.51-4.42 (m, 3H), 3.06 (dd, J=10.2, 7.1 Hz, 2H), 2.98 (d, J=9.8 Hz, 2H), 2.15 (ddq, J=22.5, 14.8, 7.5 Hz, 6H), 1.94 (s, 3H), 1.68-1.31 (m, 14H), 1.27 (t, J=7.2 Hz, 3H), 1.19 (d, J=7.0 Hz, 3H), 0.99 (t, J=7.6 Hz, 3H). UPLC-MS (basic 2 min): rt=1.04 min; m/z=608.4 for [M+H]⁻.

Example 289: N-[(2R,3S)-3-{4-[(2S)-2-cyclohexyl-2-[(3-ethyl-1,2-oxazol-4-yl)formamido]acetamido]phenyl}-1-(4-methylpiperazin-1-yl)-1-oxobutan-2-yl]propanamide) (298)

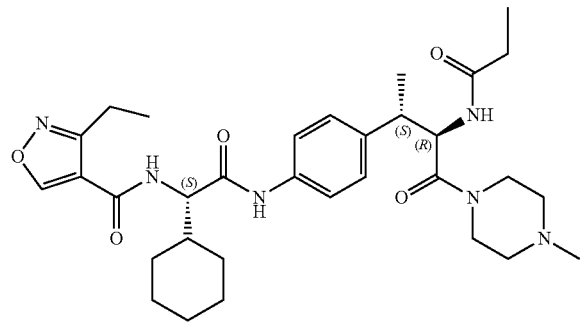

Compound 298 was synthesized by coupling 98a with the required amino acid following General Procedure U and purified using reverse phase column chromatography. ¹H NMR (400 MHZ, DMSO-d₆) 10.15 (s, 1H), 9.41 (s, 1H), 8.45 (d, J=8.3 Hz, 1H), 8.24 (d, J=8.7 Hz, 1H), 7.55 (d, J=8.4 Hz, 2H), 7.15 (d, J=8.4 Hz, 2H), 4.83 (t, J=9.5 Hz, 1H), 4.49-4.37 (m, 1H), 3.44 (d, J=11.6 Hz, 1H), 3.19 (t, J=10.6 Hz, 1H), 3.06 (dd, J=10.0, 7.1 Hz, 1H), 2.97 (t, J=10.6 Hz, 1H), 2.83 (q, J=7.4 Hz, 2H), 2.14 (qq, J=15.1, 7.6 Hz, 5H), 1.95 (s, 3H), 1.86-1.54 (m, 8H), 1.35 (dd, J=10.3, 6.6 Hz, 3H), 1.22-1.12 (m, 8H), 0.99 (t, J=7.6 Hz, 3H). UPLC-MS (basic 2 min): rt=1.02 min; m/z=595.4 for [M+H]⁺.

Example 290: N-[(2R,3S)-3-{4-[(2S)-2-[(1-ethyl-1H-pyrazol-5-yl) formamido]-2-[(1r,4S)-4-methyl-cyclohexyl]acetamido]phenyl}-1-(4-methylpiperazin-1-yl)-1-oxobutan-2-yl]propanamide) (299)

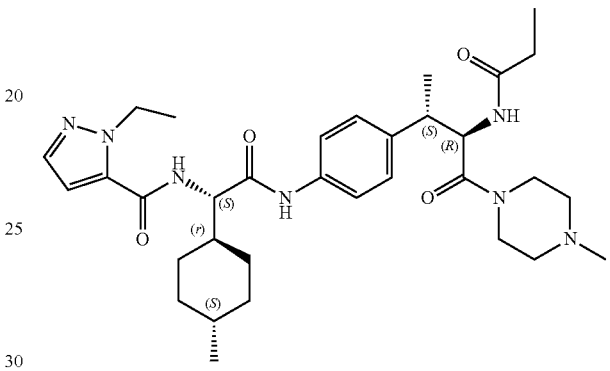

Compound 299 was synthesized by coupling the bis-TFA salt shown below, made by a procedure analogous to the synthesis of 98 (a-b) with the required amino acid following General Procedure U and purified using reverse phase column chromatography.

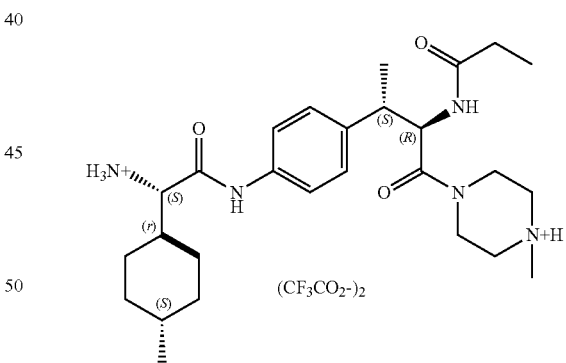

¹H NMR (400 MHZ, DMSO-d₆) δ 10.13 (s, 1H), 8.47 (d, J=8.2 Hz, 1H), 8.24 (d, J=8.7 Hz, 1H), 7.58-7.50 (m, 2H), 7.47 (d, J=2.0 Hz, 1H), 7.20-7.12 (m, 2H), 7.02 (d, J=2.1 Hz, 1H), 4.88-4.79 (m, 1H), 4.46 (q, J=7.1 Hz, 2H), 4.36 (t, J=8.5 Hz, 1H), 3.45 (d, J=12.9 Hz, 1H), 3.37 (s, 1H), 3.19 (t, J=10.2 Hz, 1H), 3.12-3.00 (m, 1H), 2.96 (t, J=9.7 Hz, 1H), 2.25-2.04 (m, 4H), 1.95 (s, 3H), 1.81 (dd, J=28.0, 12.1 Hz, 2H), 1.69 (d, J=13.5 Hz, 2H), 1.63-1.55 (m, 2H), 1.37 (t, J=9.7 Hz, 1H), 1.27 (t, J=7.2 Hz, 4H), 1.23-1.12 (m, 4H), 0.99 (t, J=7.6 Hz, 5H), 0.85 (d, J=6.4 Hz, 4H). UPLC-MS (basic 2 min): rt=1.05 min; m/z=608.5 for [M+H]⁺.

Example 291: N-[(2R,3S)-3-{4-[(2S)-2-[2-(3-cyano-phenyl)-2,2-difluoroacetamido]-2-cyclohexyl acet-amido]phenyl}-1-(4-methylpiperazin-1-yl)-1-oxobu-tan-2-yl]propanamide) (300)

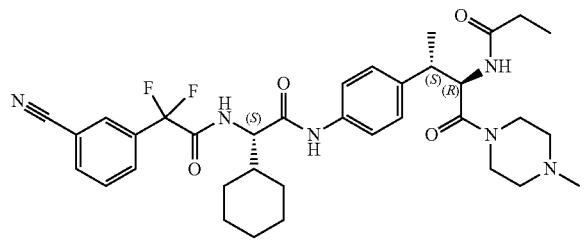

Compound 300 was synthesized by coupling 98a with the required amino acid following General Procedure U and purified using reverse phase column chromatography. ¹H NMR (400 MHZ, DMSO-d₆) δ 10.16 (s, 1H), 9.11 (d, J=8.2 Hz, 1H), 8.24 (d, J=8.7 Hz, 1H), 8.15 (s, 1H), 8.06 (d, J=7.7 Hz, 1H), 7.95 (d, J=8.1 Hz, 1H), 7.77 (t, J=7.9 Hz, 1H), 7.51 (d, J=8.4 Hz, 2H), 7.15 (d, J=8.4 Hz, 2H), 4.82 (t, J=9.5 Hz, 1H), 4.25 (t, J=8.6 Hz, 1H), 3.47 (d, J=13.2 Hz, 1H), 3.30 (s, 1H), 3.17 (t, J=10.7 Hz, 1H), 3.06 (dd, J=10.2, 7.0 Hz, 1H), 2.94 (t, J=10.3 Hz, 1H), 2.14 (ddp, J=22.5, 15.1, 7.6 Hz, 3H), 1.91 (s, 3H), 1.84 (d, J=11.1 Hz, 2H), 1.67-1.48 (m, 7H), 1.40-1.24 (m, 2H), 1.19 (d, J=7.0 Hz, 3H), 1.17-1.08 (m, 3H), 1.04 (d, J=11.9 Hz, 1H), 0.99 (t, J=7.6 Hz, 3H), 0.95-0.85 (m, 1H) UPLC-MS (basic 4 min): rt=1.77 min; m/z=651.4 for [M+H]⁺

Example 292: N-[(2R,3S)-3-{4-[(2S)-2-[2-(3-cyano-phenyl)-2,2-difluoroacetamido]-2-cyclohexyl acet-amido]phenyl}-1-(4-methylpiperazin-1-yl)-1-oxobu-tan-2-yl]-1,2,3-thiadiazole-5-carboxamide (301)

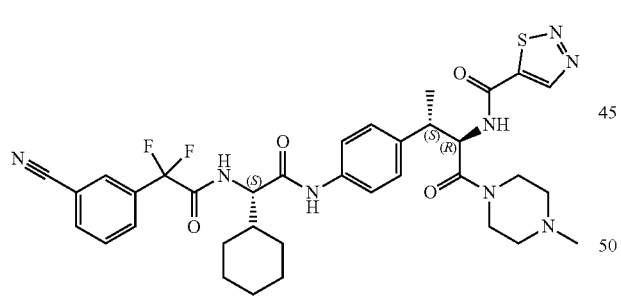

Compound 301 was synthesized by coupling 98a with the required amino acid following General Procedure U and purified using reverse phase column chromatography. ¹H NMR (400 MHZ, DMSO-d₆) δ 10.20 (s, 1H), 9.67 (d, J=8.2 Hz, 1H), 9.53 (s, 1H), 9.12 (d, J=8.3 Hz, 1H), 8.15 (s, 1H), 8.07 (d, J=7.7 Hz, 1H), 7.96 (d, J=8.0 Hz, 1H), 7.77 (t, J=7.9 Hz, 1H), 7.54 (d, J=8.5 Hz, 2H), 7.22 (d, J=8.4 Hz, 2H), 5.00 (dd, J=10.5, 8.3 Hz, 1H), 4.26 (t, J=8.6 Hz, 1H), 3.38 (s, 1H), 3.31-3.12 (m, 4H), 2.90 (t, J=10.6 Hz, 1H), 2.17 (t, J=12.4 Hz, 2H), 1.89 (s, 3H), 1.84 (s, 1H), 1.64 (d, J=10.5 Hz, 3H), 1.51 (q, J=10.4, 10.0 Hz, 3H), 1.31 (d, J=6.9 Hz, 3H), 1.20 (d, J=10.4 Hz, 1H), 1.14-1.06 (m, 3H), 0.93-0.85 (m, 1H). UPLC-MS (basic 4 min): rt=1.85 min; m/z=707.4 for [M+H]⁺.

Example 293: N-[(2R)-3-{4-[(2S)-2-[2-(3-cyano-phenyl)-2,2-difluoroacetamido]-2-cyclohexylacet-amido]-3-fluorophenyl}-1-(4-methylpiperazin-1-yl)-1-oxopropan-2-yl]propenamide (302)

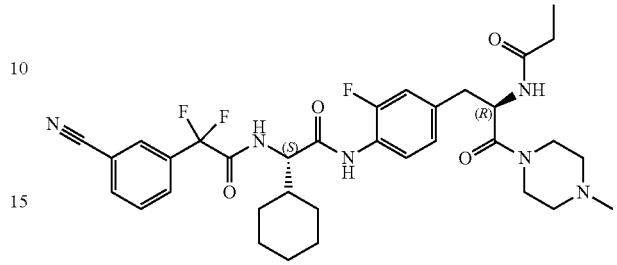

Compound 302 was synthesized by coupling 62a with the required amino acid following general procedure O and purified using reverse phase column chromatography. ¹H NMR (400 MHz, DMSO-d₆) δ 9.90 (s, 1H), 9.07 (d, J=8.3 Hz, 1H), 8.21 (d, J=8.4 Hz, 1H), 8.14 (d, J=1.8 Hz, 1H), 8.09-8.04 (m, 1H), 7.96 (dt, J=8.2, 1.5 Hz, 1H), 7.77 (t, J=7.9 Hz, 1H), 7.66 (t, J=8.2 Hz, 1H), 7.10 (dd, J=11.8, 1.9 Hz, 1H), 7.00 (dd, =8.3, 1.9 Hz, 1H), 4.90 (q, J=7.8 Hz, 1H), 4.43 (t, J=8.5 Hz, 1H), 3.42 (q, J=7.1, 5.5 Hz, 4H), 2.89 (dd, J=13.4, 6.8 Hz, 1H), 2.75 (dd, J=13.4, 7.9 Hz, 1H), 2.18 (d, J=11.4 Hz, 2H), 2.10-2.01 (m, 6H), 1.94-1.81 (m, 2H), 1.64 (s, 3H), 1.59 (d, J=10.5 Hz, 3H), 1.18-1.04 (m, 4H), 0.91 (t, J=7.6 Hz, 3H). UPLC-MS (basic 4 min): rt=1.77 min; m/z=655.3 for [M+H]⁺.

Example 294: General Procedure for Preparation of Intermediate 99

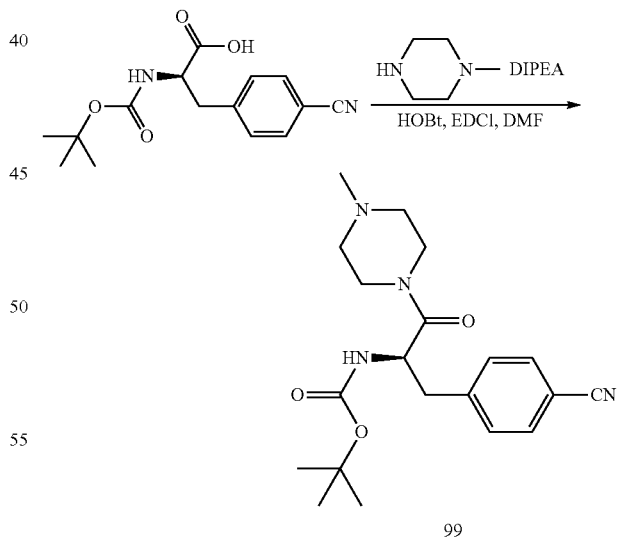

To a solution of the protected commercially available amino acid shown above (60.0 g, 206.6 mmol, 1.00 eq) in DMF (400.0 mL) was added HOBt (33.5 g, 248.0 mmol, 1.20 eq), EDCI (47.5 g, 248.0 mmol, 1.20 eq) and DIPEA (80.1 g, 620.0 mmol, 108.0 mL, 3.00 eq), then a solution of the cyclic diamine (24.8 g, 248.0 mmol, 27.5 mL, 1.20 eq) in DMF (200.0 mL) was added to the mixture at 0° C., the reaction was stirred at 10° C. for 12 hrs. TLC (DCM:MeOH=10:1) indicated the protected amino acid was consumed and a major new spot was generated. The reaction mixture was quenched with water (2000 mL) and the layers were separated. The aqueous layer was extracted with EtOAc (500.0 mL*4) and the combined organic layers were washed with saturated NH$_4$Cl (500.0 mL*4) and brine (500.0 mL*4), dried over Na$_2$SO$_4$, filtered and concentrated under reduced pressure to give a residue which was used directly for the next step without further purification. Compound 99 (61.5 g, 164.6 mmol, 79.6% yield, 99.7% purity) was obtained as a light yellow solid, confirmed by LCMS and H NMR (EW15716-5-P1H1). H$^1$ NMR: (400M CDCl$_3$) δ 7.58 7.56 (m, 2H), 7.30-7.28 (m, 2H), 5.39 (d, J=8.8 Hz, 1H), 4.84-4.82 (m, 1H), 3.61-3.59 (m, 1H), 3.53-3.52 (m, 1H), 3.47-3.46 (m, 1H), 3.21-3.20 (m, 1H), 3.07-3.03 (m, 1H), 2.98-2.94 (m, 1H), 2.34-2.26 (m, 3H), 2.23 (s, 3H), 2.00-1.99 (m, 1H), 1.38 (s, 9H). LCMS: EW15716-5-P1A1, (M+H)$^+$: 373.3.

Example 295: General Procedure for Preparation of Intermediate 1A

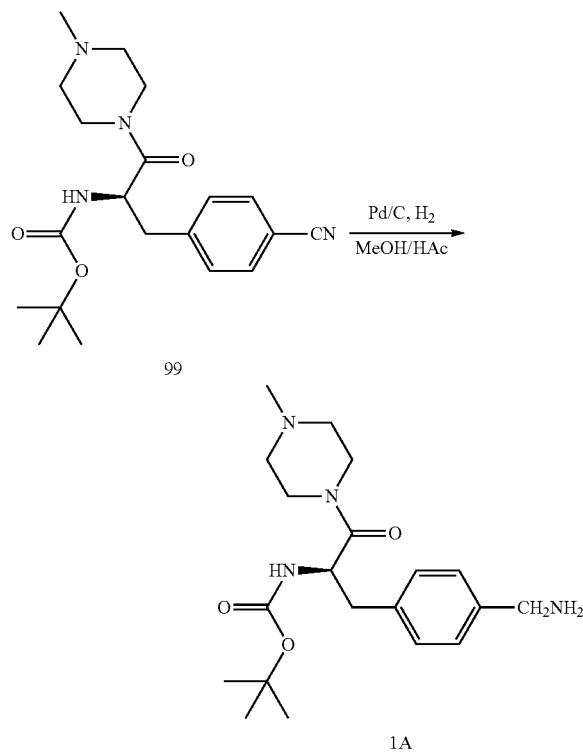

To a solution of compound 99 (15.0 g, 40.2 mmol, 1.00 eq) in MeOH (50.0 mL) and AcOH (50.0 mL) was added Pd/C (3.00 g, 10% purity), the mixture was stirred at 25° C. under H$_2$ (50 Psi) for 12 hrs. TLC (DCM:MeOH=10:1) indicated compound 99 was consumed and a major new spot was generated. The mixture was filtered under reduced pressure to give a residue which was purified by Prep-HPLC (column: Xbridge BEH C18, 250*50 mm, 10 um; mobile phase: [water (0.05% ammonia hydroxide v/v)-ACN]; B %: 10% 41%, 18.5 min). Compound 1A (10.7 g, 28.2 mmol, 70.2% yield, 99.5% purity) was obtained as a white solid, confirmed by LCMS and H$^1$ NMR (EW15716-8-P1H$_2$). H$^1$ NMR: (400M CDCl$_3$) δ 7.21 (d, J=8.0 Hz, 2H), 7.13 (d, J=8.0 Hz, 2H), 5.44 (d, J=8.4 Hz, 1H), 4.83-4.77 (m, 1H), 3.82 (s, 2H), 3.59-3.57 (m, 1H), 3.46-3.45 (m, 1H), 3.31-3.30 (m, 1H), 2.98-2.92 (m, 3H), 2.28-2.21 (m, 3H), 2.18 (s, 3H), 1.81-1.78 (m, 1H), 1.75 (s, 2H), 1.38 (s, 9H). LCMS: (M+H)$^+$: 377.3.

Example 296: Benzyl N—[(S)-[({4-[(2R)-2-{[(tert-butoxy)carbonyl]amino}-3-(4-methylpiperazin-1-yl)-3-oxopropyl] phenyl}methyl)carbamoyl](cyclohexyl)methyl]carbamate) (6A)

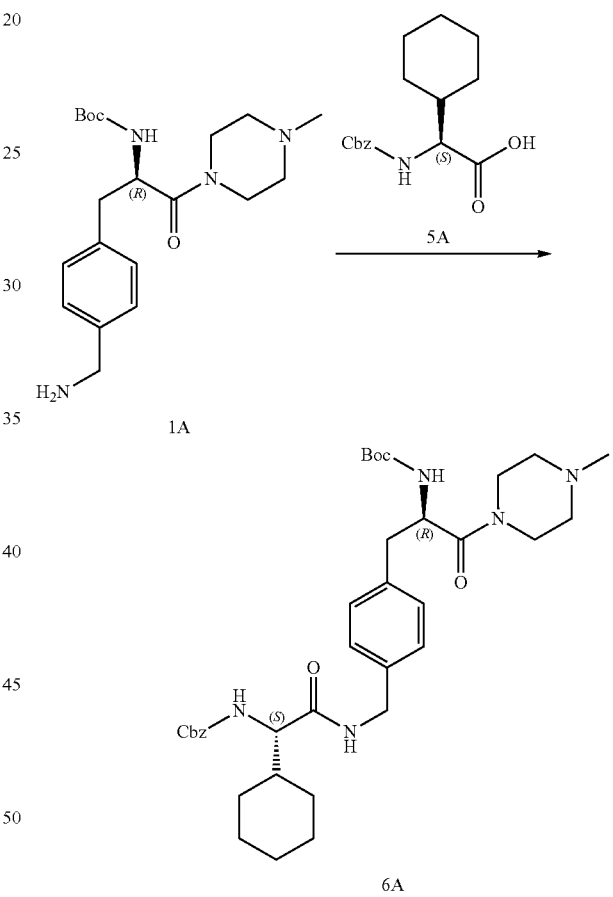

To a solution of 1A (0.500 g, 1.33 mmol, 1.0 eq.) in THF (6.0 mL) was added 5A (0.580 g, 1.99 mmol, 1.5 eq.), DIPEA (1.4 mL, 7.97 mmol, 6.0 eq.) and T3P (2.0 mL, 3.32 mmol, 50% in EtOAc, 2.0 eq.), the resulting mixture was stirred for 1 h, concentrated to dryness and the residue dissolved in DCM (20 mL). Aqueous saturated sodium bicarbonate solution was added and then extracted with DCM (2×20 mL). The combined organic phases was washed with brine, dried over sodium sulfate then concentrated to afford 6A as a brown solid (0.863 g, 100% yield) which was used in the next step without further purification. UPLC-MS (basic 4 min): rt=2.00 min; m/z=650.5 for [M+H]$^+$.

Example 297: Benzyl N—[(S)-[({4-[(2R)-2-amino-3-(4-methylpiperazin-1-yl)-3-oxopropyl]phenyl}methyl) carbamoyl](cyclohexyl)methyl]carbamate) (7A)

Example 298: Benzyl N—[(S)-cyclohexyl [({4-[(2R)-3-(4-methylpiperazin-1-yl)-3-oxo-2-[(1,2,3-thiadiazol-5-yl)formamido]propyl]phenyl}methyl)carbamoyl]methyl]carbamate) (8A)

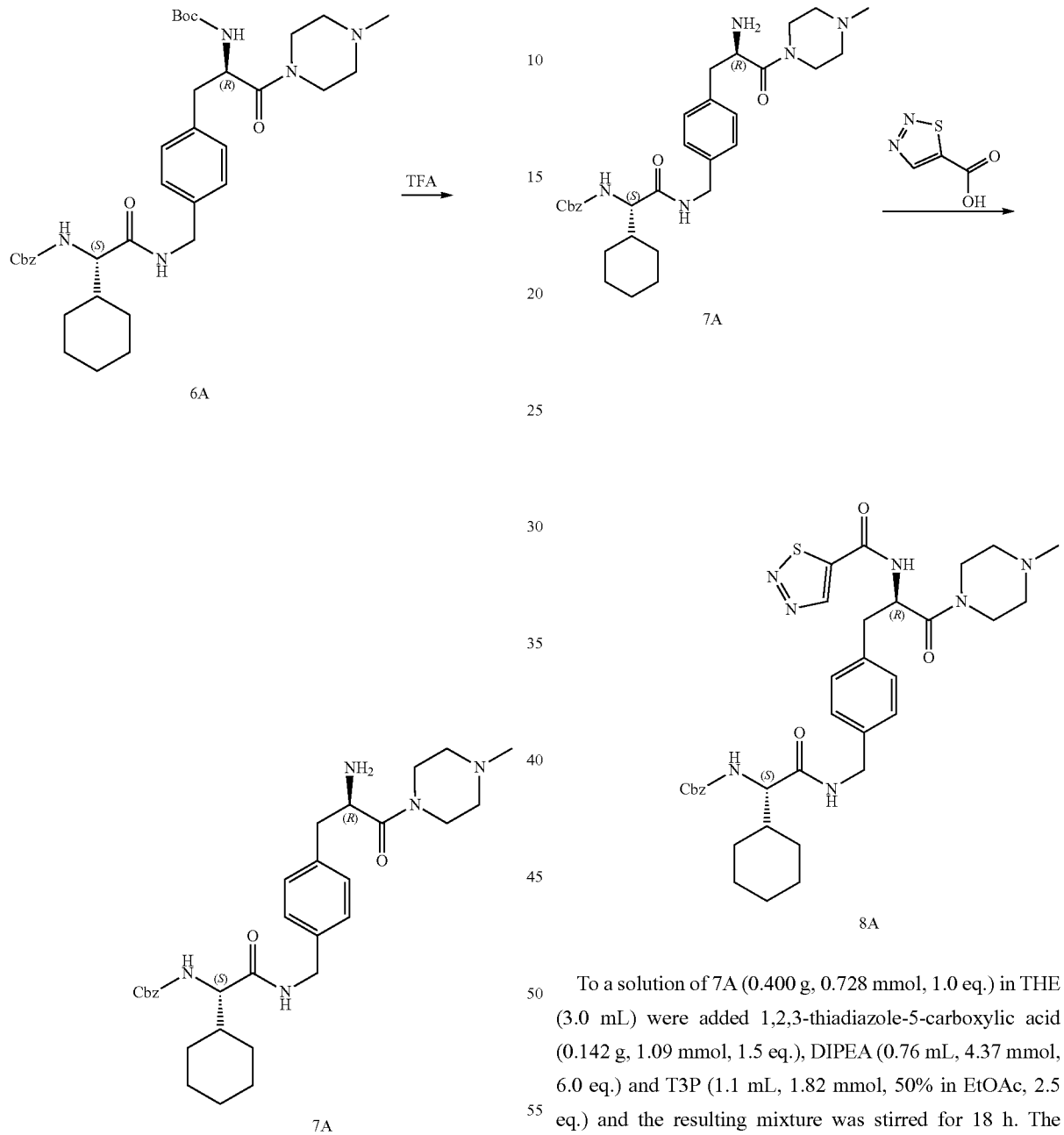

To a solution of 6A (0.863 g, 1.33 mmol, 1.0 eq.) in DCM (6.5 mL) was added TFA (2.4 mL) and the resulting mixture was stirred at RT for 1 h. The reaction mixture was concentrated to dryness and the residue was dissolved in DCM (10 mL), stirred in aq. sat. $K_2CO_3$ solution (1 g in 10 mL $H_2O$) and then extracted with DCM to afford 7A as a yellow gummy solid (0.400 g, 47% yield) which was used in the next step without further purification. UPLC-MS (basic 4 min): rt=1.40 min; m/z=550.4 for $[M+H]^+$.

To a solution of 7A (0.400 g, 0.728 mmol, 1.0 eq.) in THF (3.0 mL) were added 1,2,3-thiadiazole-5-carboxylic acid (0.142 g, 1.09 mmol, 1.5 eq.), DIPEA (0.76 mL, 4.37 mmol, 6.0 eq.) and T3P (1.1 mL, 1.82 mmol, 50% in EtOAc, 2.5 eq.) and the resulting mixture was stirred for 18 h. The mixture was concentrated to dryness and the residue was dissolved in DCM (20 mL). Aqueous saturated sodium bicarbonate solution was added and then extracted with DCM (2×20 mL). The combined organic phase was washed with brine, dried over sodium sulfate then concentrated to dryness. The residue was purified by reverse phase column chromatography (5-95% MeCN, water) to afford 8A as a white solid (0.100 g, 21%). $^1$H NMR (400 MHz, DMSO-$d_6$)

δ 9.59 (d, J=7.9 Hz, 1H), 9.42 (s, 1H), 8.39 (s, 1H), 7.45-6.99 (m, 10H), 5.02 (s, 3H), 4.23 (d, J=5.9 Hz, 2H), 3.87 (t, J=8.2 Hz, 1H), 3.58-3.15 (m, 9H), 3.15-2.86 (m, 2H), 2.14 (d, J=24.6 Hz, 7H), 1.98 (s, 1H), 1.88 (s, 2H), 1.76-1.41 (m, 8H), 1.22-0.71 (m, 8H). UPLC-MS (basic 4 min): rt=1.80 min; m/z=662.4 for [M+H]$^+$.

Example 299: N-[(2R)-3-(4-{[(2S)-2-amino-2-cyclohexylacetamido]methyl}phenyl)-1-(4-methylpiperazin-1-yl)-1-oxopropan-2-yl]-1,2,3-thiadiazole-5-carboxamide; trifluoroacetic acid) (9A)

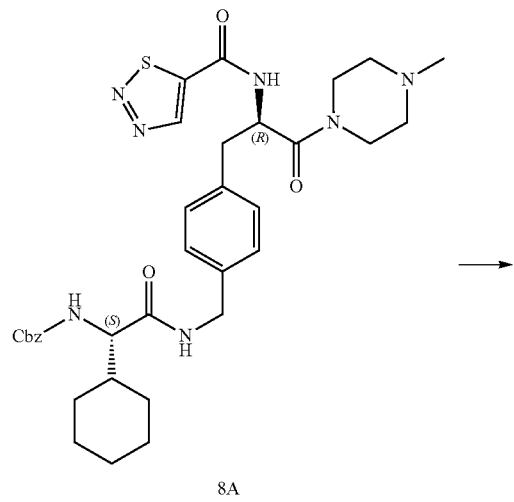

Compound 8A (0.080 g, 0.075 mmol, 1.0 eq.) was dissolved in TFA (2.0 mL) and the resulting mixture was stirred at 100° C. for 3 h. The reaction mixture was concentrated to dryness to afford 9A (0.079 g, 100%) as a brown gummy solid which was used in the next step without further purification. UPLC-MS (basic 4 min): rt=1.33 min; m/z=528.3 for [M+H]$^+$.

Example 300: N-[(2R)-3-(4-{[(2S)-2-cyclohexyl-2-[2,2-difluoro-2-(6-methoxypyridin-3-yl)acetamido]acetamido]methyl}phenyl)-1-(4-methylpiperazin-1-yl)-1-oxopropan-2-yl]-1,2,3-thiadiazole-5-carboxamide) (223)

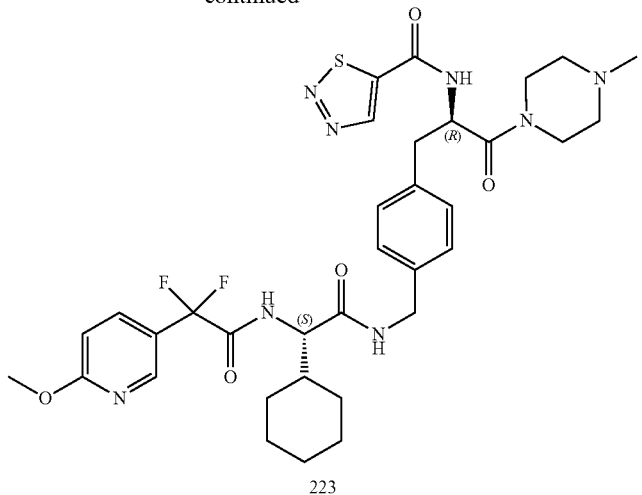

223

To a solution of 9A (0.065 g, 0.123 mmol, 1.0 eq,) in DMF (1 mL) were added 2,2-difluoro-2-(6-methoxypyridin-3-yl) acetic acid (0.030 g, 0.148 mmol, 1.2 eq.), DIPEA (0.26 mL, 1.48 mmol, 12.0 eq.) and then HATU (0.070 g, 0.185 mmol, 1.5 eq.) and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford 223 as a white solid (13.0 mg). $^1$H NMR (400 MHz, DMSO-$d_6$) δ 9.59 (s, 1H), 9.41 (s, 1H), 8.86 (d, J=8.4 Hz, 1H), 8.58 (t, J=5.9 Hz, 1H), 8.46-8.30 (m, 1H), 7.90 (dd, J=8.8, 2.6 Hz, 1H), 7.21 (d, J=8.0 Hz, 2H), 7.11 (d, J=7.9 Hz, 2H), 6.95 (d, J=8.7 Hz, 1H), 5.07 (t, J=7.4 Hz, 1H), 4.23 (d, J=5.6 Hz, 2H), 4.11 (q, J=8.6 Hz, 1H), 3.90 (s, 3H), 3.41 (d, J=24.5 Hz, 4H), 3.09-2.85 (m, 2H), 2.17 (q, J=6.8, 5.4 Hz, 4H), 2.10 (s, 3H), 1.76 (d, J=10.4 Hz, 1H), 1.60 (s, 4H), 1.47 (d, J=13.0 Hz, 1H), 1.19-0.99 (m, 2H), 0.99-0.73 (m, 2H). UPLC-MS (basic 4 min): rt=1.78 min; m/z=713.4 for [M+H]$^+$.

Example 301: tert-butyl N-[(2R,3S)-3-(4-amino-3-fluorophenyl)-1-(4-methylpiperazin-1-yl)-1-oxobutan-2-yl]carbamate) (10A)

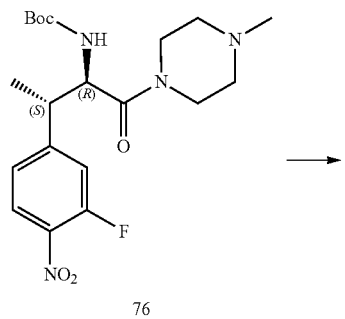

76

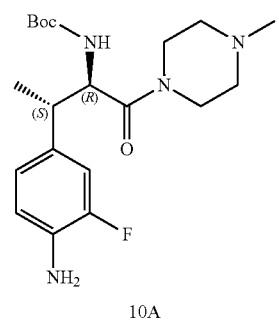

10A

To a degassed solution of 76 (0.457 g, 1.08 mmol, 1.0 eq) in THF (10 mL) was added Pd(OH)$_2$/C (0.150 g, 1.08 mmol, 1.0 eq.). The mixture was degassed for another 20 minutes and then evacuated under vacuum before introducing a hydrogen balloon. The resulting mixture was stirred at RT for 18 h, filtered through a pad of celite and concentrated to dryness to afford 10A as a light brown solid (0.414 g, 98% yield) which was used in the next step without further purification. $^1$H NMR (400 MHz, DMSO-$d_6$) δ 7.09 (d, J=8.7 Hz, 1H), 6.81 (d, J=12.7 Hz, 1H), 6.77-6.58 (m, 2H), 4.93 (s, 2H), 4.42 (t, J=9.2 Hz, 1H), 4.10 (q, J=5.2 Hz, 1H), 3.18 (d, J=5.0 Hz, 7H), 2.89 (q, J=8.0, 6.9 Hz, 1H), 2.70 (s, 1H), 2.14 (s, 2H), 2.05 (s, 3H), 1.82 (d, J=9.6 Hz, 1H), 1.65 (s, 1H), 1.37 (s, 9H), 1.16 (d, J=7.0 Hz, 3H). UPLC-MS (basic 2 min): Rt=0.96 min; m/z=395.3 for [M+H]$^+$.

Example 302: benzyl N—[(S)-({4-[(2S,3R)-3-{[(tert-butoxy)carbonyl]amino}-4-(4-methylpiperazin-1-yl)-4-oxobutan-2-yl]-2-fluorophenyl}carbamoyl)(cyclohexyl)methyl]carbamate (11A)

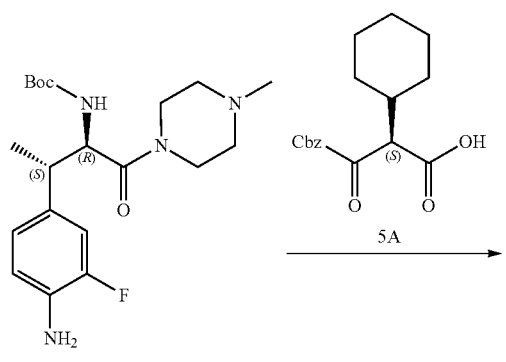

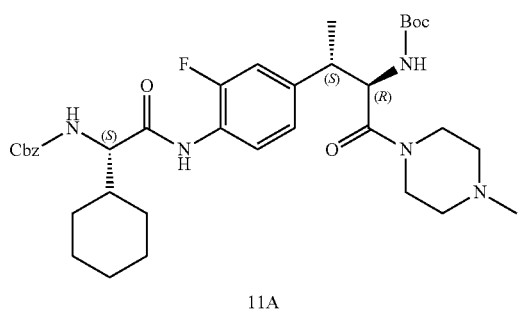

To a solution of 10A (0.200 g, 0.507 mmol, 1.0 eq.) in DMF (2 mL) were added 5A (0.177 g, 0.291 mmol, 1.2 eq.), DIPEA (0.5 mL, 2.87 mmol, 5.7 eq.) and HATU (0.739 g, 1.94 mmol, 3.8 eq.) and the resulting mixture was stirred for 18 h. More 5A (0.250 g, 0.858 mmol, 1.7 eq.) and COMU (0.217 g, 0.507 mmol, 1.0 eq.) were added and the reaction mixture stirred for 18 h. Aqueous saturated sodium bicarbonate solution was added and then extracted with EtOAc. The combined organic phases were washed with brine, dried over sodium sulfate and then concentrated to dryness. The residue was purified by flash column chromatography (Silica, 0-10% MeOH, DCM with 0.1% ammonia additive) to afford 11A as a yellow-orange solid (0.187 g, 55% yield). $^1$H NMR (400 MHz, DMSO-$d_6$) δ 9.72 (s, 1H), 7.72 (t, J=8.3 Hz, 1H), 7.44 (d, J=8.6 Hz, 1H), 7.41-7.26 (m, 4H), 7.22 (d, J=8.7 Hz, 1H), 7.10 (d, J=12.1 Hz, 1H), 7.00 (dd, J=8.3, 1.9 Hz, 1H), 5.03 (s, 2H), 4.53 (t, J=9.2 Hz, 1H), 4.18 (t, J=8.0 Hz, 1H), 3.20-2.93 (m, 3H), 2.19 (s, 3H), 2.03 (s, 4H), 1.86-1.46 (m, 10H), 1.38 (s, 10H), 1.29-0.84 (m, 11H). UPLC-MS (basic 2 min): Rt=1.23 min; m/z=668.5 for [M+H]$^+$.

Example 303: tert-butyl N-[(2R,3S)-3-{4-[(2S)-2-amino-2-cyclohexylacetamido]-3-fluorophenyl}-1-(4-methyl piperazin-1-yl)-1-oxobutan-2-yl]carbamate (12A)

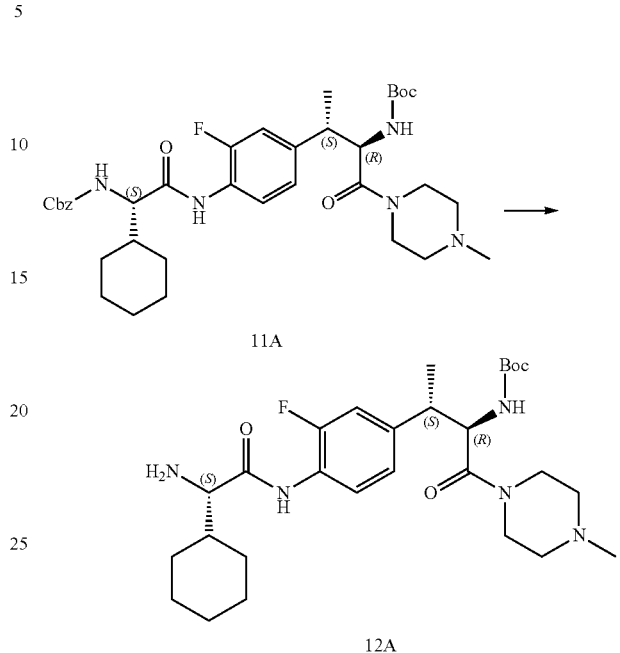

To a degassed solution of 11A (0.187 g, 0.280 mmol, 1.0 eq) in THF (10 mL) was added Pd(OH)$_2$/C (0.050 g, 0.356 mmol, 1.27 eq.). The mixture was degassed for another 20 minutes and then evacuated under vacuum before introducing a hydrogen balloon. The resulting mixture was stirred at RT for 2 h. The mixture was filtered through a pad of celite and the filtrate was concentrated to dryness to afford 12A as a brown oil (0.149 g, 100% yield) which was used in the next step without further purification. $^1$H NMR (400 MHz, DMSO-$d_6$) δ 7.98 (t, J=8.3 Hz, 1H), 7.21 (d, J=8.7 Hz, 1H), 7.14 (d, J=12.2 Hz, 1H), 6.98 (dd, J=8.6, 1.9 Hz, 1H), 4.52 (t, J=9.3 Hz, 1H), 4.09 (q, J=5.3 Hz, 0H), 3.23 (d, J=4.7 Hz, 1H), 3.18 (d, J=5.2 Hz, 1H), 3.14-2.81 (m, 4H), 2.18 (d, J=6.3 Hz, 3H), 2.01 (s, 4H), 1.84-1.45 (m, 10H), 1.38 (s, 12H), 1.16 (dd, J=42.9, 7.5 Hz, 9H). UPLC-MS (basic 2 min): Rt=1.11 min; m/z=534.4 for [M+H]$^+$.

Example 304: tert-butyl N-[(2R,3S)-3-{4-[(2S)-2-cyclohexyl-2-[2,2-difluoro-2-(6-methoxypyridin-3-yl)acetamido]acetamido]-3-fluorophenyl}-1-(4-methylpiperazin-1-yl)-1-oxobutan-2-yl]carbamate (13A)

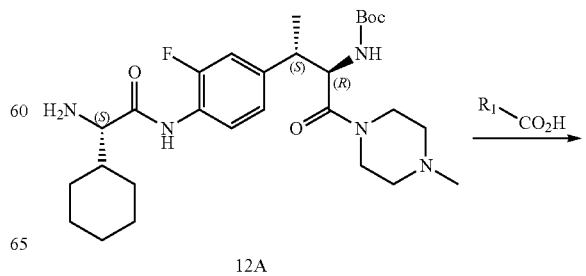

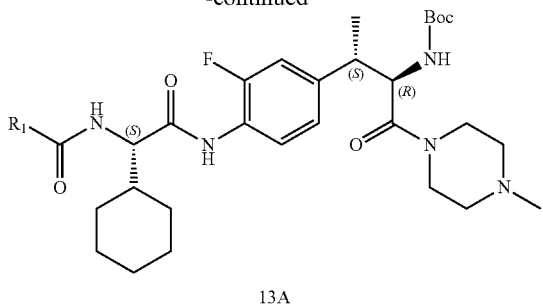

13A

A solution of 12A (0.158 g, 0.296 mmol, 1.0 eq,) in DMF (4 mL) was added 2-difluoro-2-(6-methoxypyridin-3-yl)acetic acid (1.2 eq.) (DIPEA (0.21 mL, 1.18 mmol, 4.0 eq.) and then HATU (0.220 g, 0.185 mmol, 1.5 eq.) and the resulting mixture was stirred at RT for 1 h. Aqueous saturated sodium bicarbonate solution was added and then extracted with EtOAc. The combined organic phase was washed with brine, dried over sodium sulfate then concentrated to dryness to afford 13A as a white solid (0.158 g, 74%) which was used in the next step without further purification. $^1$H NMR (400 MHz, DMSO-$d_6$) δ 9.92 (s, 1H), 9.02 (d, J=8.1 Hz, 1H), 8.41 (s, 1H), 7.92 (dd, J=8.7, 2.6 Hz, 1H), 7.69 (t, J=8.3 Hz, 1H), 7.22 (d, J=8.7 Hz, 1H), 7.10 (d, J=12.1 Hz, 1H), 6.98 (dd, J=12.3, 8.7 Hz, 2H), 4.52 (t, J=9.4 Hz, 1H), 4.43 (t, J=8.5 Hz, 1H), 4.04 (q, J=7.1 Hz, 1H), 3.95-3.80 (m, 5H), 3.07 (d, J=8.9 Hz, 3H), 2.18 (d, J=8.0 Hz, 2H), 1.99 (d, J=5.2 Hz, 4H), 1.84 (s, 1H), 1.77-1.47 (m, 8H), 1.37 (s, 12H), 1.29-1.01 (m, 12H), 1.00-0.73 (m, 1H). UPLC-MS (basic 2 min): Rt=1.23 min; m/z=719.3 for [M+H]$^+$.

Example 305: N—[(S)-({4-[(2S,3R)-3-amino-4-(4-methylpiperazin-1-yl)-4-oxobutan-2-yl]-2-fluorophenyl}carbamoyl)(cyclohexyl)methyl]-2,2-difluoro-2-(6-methoxypyridin-3-yl)acetamide (14A)

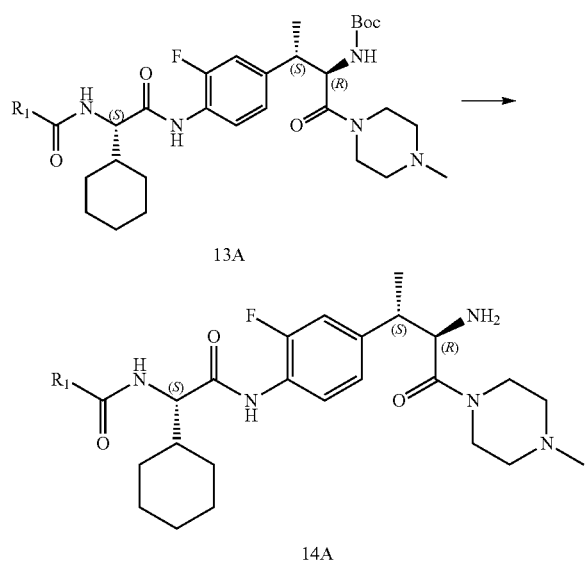

To a solution of 13A (0.158 g, 0.220 mmol, 1.0 eq.) in DCM (2 mL) was added TFA (2 mL) and the resulting mixture was stirred at RT for 2 h. The reaction mixture was concentrated to dryness and the residue was dissolved in DCM (10 mL), stirred in aq. sat. $K_2CO_3$ solution (1 g in 10 mL $H_2O$) and then extracted with DCM to afford 14A as an off-white solid (0.136 g, 100% yield) which was used in the next step without further purification. $^1$H NMR (400 MHz, DMSO-$d_6$) δ 10.15 (s, 1H), 9.07 (d, J=7.9 Hz, 1H), 8.41 (s, 1H), 7.93 (dd, J=8.8, 2.6 Hz, 1H), 7.60 (s, OH), 7.05 (s, 1H), 6.98 (d, J=8.7 Hz, 1H), 4.40 (s, 5H), 3.91 (s, 3H), 3.18 (s, 2H), 2.55 (s, 8H), 1.92 (d, J=33.9 Hz, 1H), 1.65 (d, J=34.5 Hz, 7H), 1.36 (s, 3H), 1.27-1.04 (m, 4H), 0.98 (t, J=11.5 Hz, 1H). UPLC-MS (basic 2 min): rt=1.06 min; m/z=619.3 for [M+H]$^+$.

Example 306: N-[(2R,3S)-3-{4-[(2S)-2-cyclohexyl-2-[2,2-difluoro-2-(6-methoxypyridin-3-yl)acetamido]acetamido]-3-fluorophenyl}-1-(4-methylpiperazin-1-yl)-1-oxobutan-2-yl]-1,2,3-thiadiazole-5-carboxamide) (224)

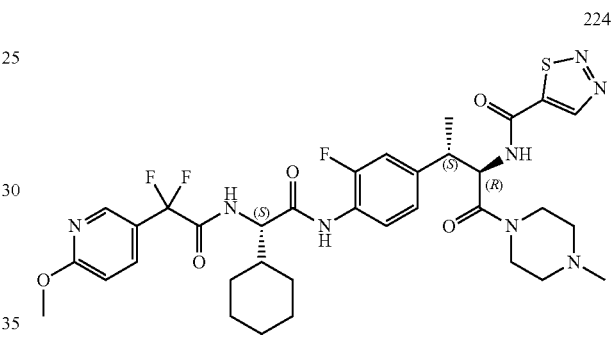

To a solution of 14A (0.150 g, 0.242 mmol, 1.0 eq.) in DMF (4.0 mL) was added 1,2,3-thiadiazole-5-carboxylic acid (0.038 g, 0.291 mmol, 1.2 eq.), DIPEA (0.25 mL, 1.44 mmol, 6.0 eq.) and HATU (0.138 g, 0.364 mmol, 1.5 eq.) and the resulting mixture was stirred for 18 h. Aqueous saturated sodium bicarbonate solution was added and then extracted with EtOAc. The combined organic phases were washed with brine, dried over sodium sulfate then concentrated to dryness. The residue was purified by Reverse Phase column chromatography on a 120 g C18 cartridge eluting with a 5-95% $H_2O$:MeCN eluent (0.1% ammonia) to afford 224 as a white solid (72.5 mg). $^1$H NMR (400 MHz, DMSO-$d_6$) δ 9.96 (s, 1H), 9.68 (d, J=8.1 Hz, 1H), 9.52 (s, 1H), 9.02 (d, J=8.2 Hz, 1H), 8.41 (s, 1H), 7.92 (dd, J=8.8, 2.5 Hz, 1H), 7.75 (t, J=8.3 Hz, 1H), 7.21 (d, J=11.8 Hz, 1H), 7.08 (d, J=8.5 Hz, 1H), 6.97 (d, J=8.7 Hz, 1H), 5.10-5.01 (m, 1H), 4.45 (t, J=8.5 Hz, 1H), 3.90 (s, 3H), 3.56 (d, J=52.6 Hz, 2H), 2.97 (d, J=11.2 Hz, 1H), 2.21 (s, 2H), 1.95 (s, 3H), 1.86 (s, 1H), 1.67 (d, J=10.4 Hz, 3H), 1.58 (s, 3H), 1.38 (s, OH), 1.34-1.20 (m, 7H), 1.13 (d, J=9.1 Hz, 2H), 0.95 (s, 2H). UPLC-MS (basic 4 min): rt=1.90 min; m/z=731.3 for [M+H]$^+$.

Example 307: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]-1,3-thiazole-5-carboxamide (303)

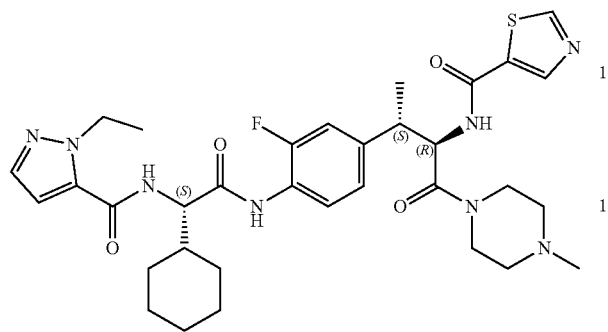

Following a synthetic scheme analogous to the preparation of 224 with coupling of a different carboxylic acids to the differentially protected amines 11A provided 303. $^1$H NMR (400 MHz, DMSO-d$_6$) δ 9.89 (s, 1H), 9.25 (d, J=0.6 Hz, 1H), 9.18 (d, J=8.3 Hz, 1H), 8.68 (d, J=0.7 Hz, 1H), 8.45 (d, J=8.3 Hz, 1H), 7.78 (t, J=8.3 Hz, 1H), 7.48 (d, J=2.0 Hz, 1H), 7.19 (dd, J=12.0, 1.9 Hz, 1H), 7.07 (d, J=8.4 Hz, 1H), 7.00 (d, J=2.1 Hz, 1H), 5.05-4.98 (m, 1H), 4.57 (t, J=8.5 Hz, 1H), 4.47 (q, J=7.1 Hz, 2H), 3.46 (d, J=13.1 Hz, 2H), 2.99 (t, J=10.4 Hz, 1H), 2.20-2.18 (m, 2H), 1.96 (s, 3H), 1.88-1.59 (m, 6H), 1.46-1.41 (m, 1H), 1.38-0.89 (m, 11H). UPLC-MS (basic 4 min): rt=1.66 min; m/z=667.5 for [M+H]$^+$.

Example 308: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]thiophene-2-carboxamide (304)

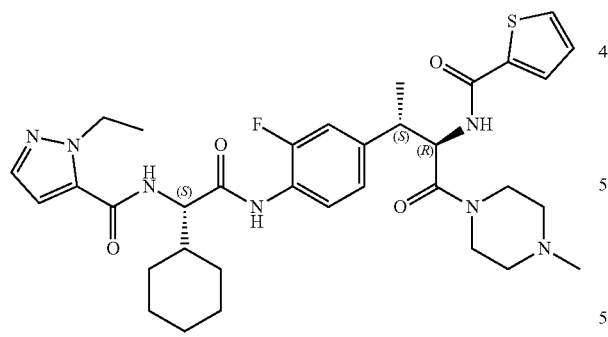

Following a synthetic scheme analogous to the preparation of 224 with coupling of a different carboxylic acids to the differentially protected amines 11A provided 304. $^1$H NMR (400 MHz, DMSO-d$_6$) δ 9.88 (s, 1H), 8.91 (d, J=8.3 Hz, 1H), 8.45 (d, J=8.3 Hz, 1H), 8.00 (dd, J=3.8, 1.2 Hz, 1H), 7.82-7.73 (m, 2H), 7.48 (d, J=2.1 Hz, 1H), 7.20-7.14 (m, 2H), 7.06 (d, J=8.4 Hz, 1H), 7.00 (d, J=2.1 Hz, 1H), 5.05-4.96 (m, 1H), 4.57 (t, J=8.4 Hz, 1H), 4.47 (q, J=7.1 Hz, 2H), 3.53-3.38 (m, 3H), 3.05-2.93 (m, 2H), 2.19 (dd, J=11.6, 5.1 Hz, 2H), 1.97 (s, 3H), 1.92-1.77 (m, 3H), 1.77-1.54 (m, 5H), 1.50-1.40 (m, 1H), 1.30-1.26 (m, 4H), 1.23-1.11 (m, 4H), 1.10-1.00 (m, 2H). UPLC-MS (basic 4 min): rt=1.81 min; m/z=666.3 for [M+H]$^+$ Example 309: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]-1,2-thiazole-4-carboxamide) (305)

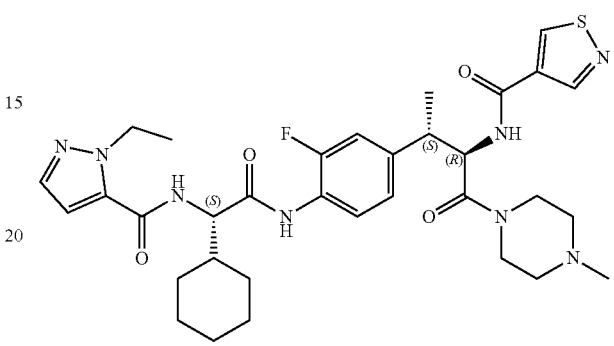

Following a synthetic scheme analogous to the preparation of 224 with coupling of a different carboxylic acids to the differentially protected amines 11A provided 305. $^1$H NMR (400 MHz, DMSO-d$_6$) δ 9.89 (s, 1H), 9.71 (s, 1H), 9.01 (d, J=8.3 Hz, 1H), 8.96 (s, 1H), 8.45 (d, J=8.3 Hz, 1H), 7.78 (t, J=8.3 Hz, 1H), 7.48 (d, J=2.0 Hz, 1H), 7.18 (dd, J=12.1, 1.9 Hz, 1H), 7.07 (dd, J=8.4, 1.9 Hz, 1H), 7.00 (d, J=2.0 Hz, 1H), 5.05 (dd, J=10.4, 8.3 Hz, 1H), 4.57 (t, J=8.4 Hz, 1H), 4.47 (q, J=7.1 Hz, 2H), 3.46 (d, J=12.9 Hz, 2H), 3.29 (d, J=6.8 Hz, 2H), 2.99 (t, J=10.1 Hz, 1H), 2.26-2.13 (m, 2H), 1.97 (s, 3H), 1.92-1.76 (m, 2H), 1.76-1.55 (m, 5H), 1.46 (t, J=9.0 Hz, 1H), 1.33-1.25 (m, 6H), 1.25-1.10 (m, 4H), 1.05 (q, J=11.3 Hz, 1H). UPLC-MS (basic 4 min): rt=1.69 min; m/z=667.5 for [M+H]$^+$.

Example 310: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]-1-methyl-1H-1,2,3-triazole-5-carboxamide) (306)

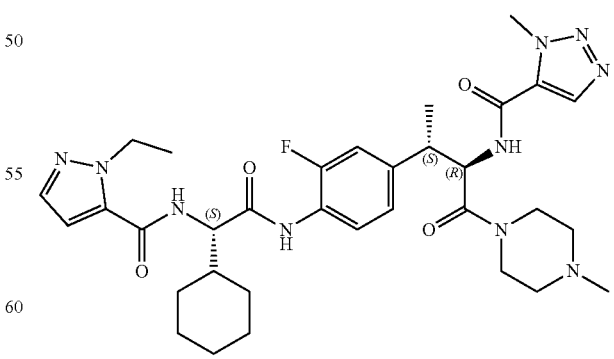

Following a synthetic scheme analogous to the preparation of 224 with coupling of a different carboxylic acids to the differentially protected amines 11A provided 306. $^1$H NMR (400 MHz, DMSO-d$_6$) δ 9.89 (s, 1H), 9.21 (d, J=8.3

Hz, 1H), 8.45 (d, J=8.3 Hz, 1H), 8.42 (s, 1H), 7.78 (t, J=8.3 Hz, 1H), 7.48 (d, J=2.1 Hz, 1H), 7.19 (dd, J=12.0, 1.9 Hz, 1H), 7.07 (dd, J=8.3, 1.9 Hz, 1H), 7.00 (d, J=2.1 Hz, 1H), 5.06 (dd, J=10.2, 8.3 Hz, 1H), 4.57 (t, J=8.4 Hz, 1H), 4.47 (q, J=7.1 Hz, 2H), 4.20 (s, 3H), 3.55-3.43 (m, 2H), 3.29 (dd, J=10.1, 6.7 Hz, 2H), 2.99 (t, J=10.3 Hz, 1H), 2.21 (dt, J=9.2, 3.3 Hz, 2H), 1.97 (s, 3H), 1.83 (dt, J=12.9, 5.8 Hz, 2H), 1.75-1.68 (m, 2H), 1.68-1.55 (m, 3H), 1.45 (dq, J=8.9, 5.7, 3.1 Hz, 1H), 1.32-1.26 (m, 6H), 1.19 (t, J=9.7 Hz, 4H), 1.05 (q, J=11.6 Hz, 1H). UPLC-MS (basic 4 min): rt=1.65 min; m/z=665.5 for [M+H]$^+$.

Example 311: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]-2-cyclopropylacetamide) (307)

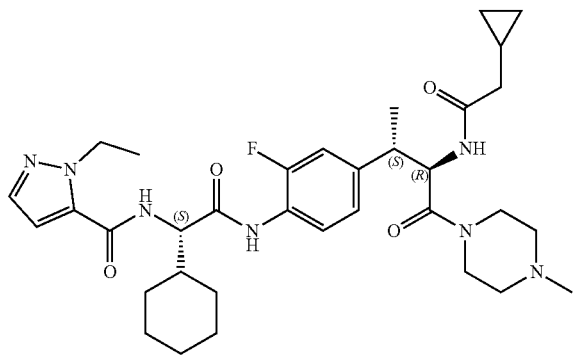

Following a synthetic scheme analogous to the preparation of 224 with coupling of a different carboxylic acids to the differentially protected amines 11A provided 307. $^1$H NMR (400 MHz, DMSO-d$_6$) δ 9.71 (s, 1H), 8.29 (d, J=8.3 Hz, 1H), 8.06 (d, J=8.8 Hz, 1H), 7.58 (t, J=8.3 Hz, 1H), 7.32 (d, J=2.1 Hz, 1H), 6.96 (dd, J=12.1, 1.9 Hz, 1H), 6.92-6.82 (m, 2H), 4.73 (t, J=9.3 Hz, 1H), 4.40 (t, J=8.5 Hz, 1H), 4.31 (q, J=7.1 Hz, 2H), 2.93 (dt, J=17.8, 10.3 Hz, 3H), 2.02 (d, J=3.0 Hz, 2H), 1.94-1.86 (m, 2H), 1.84 (s, 3H), 1.66 (d, J=13.1 Hz, 3H), 1.55 (s, 3H), 1.50 (d, J=12.3 Hz, 3H), 1.40 (d, J=8.3 Hz, 1H), 1.13 (t, J=7.1 Hz, 3H), 1.06 (d, J=7.0 Hz, 4H), 1.02 (d, J=8.4 Hz, 3H), 0.90 (t, J=11.7 Hz, 1H), 0.81 (ddd, J=12.7, 7.8, 5.2 Hz, 1H), 0.31-0.19 (m, 2H), −0.06 (s, 2H). UPLC-MS (basic 4 min): rt=1.75 min; m/z=638.5 for [M+H]$^+$.

Example 312: 2-(3-cyanophenyl)-N—[(S)-cyclohexyl({4-[(2S,3R)-3-(2-cyclopropylacetamido)-4-(4-methylpiperazin-1-yl)-4-oxobutan-2-yl]-2-fluorophenyl}carbamoyl)methyl]-2,2-difluoroacetamide) (308)

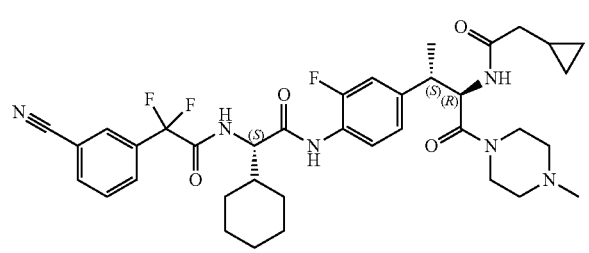

Following a synthetic scheme analogous to the preparation of 224 with coupling of a different carboxylic acids to the differentially protected amines 11A provided 308. $^1$H NMR (400 MHz, DMSO-d$_6$) δ 9.77 (s, 1H), 8.93 (d, J=8.3 Hz, 1H), 8.06 (d, J=8.8 Hz, 1H), 7.99 (d, J=1.7 Hz, 1H), 7.95-7.88 (m, 1H), 7.83-7.78 (m, 1H), 7.61 (t, J=7.8 Hz, 1H), 7.54 (t, J=8.3 Hz, 1H), 6.96 (dd, J=12.1, 1.9 Hz, 1H), 6.86 (dd, J=8.4, 1.9 Hz, 1H), 4.73 (t, J=9.3 Hz, 1H), 4.29 (t, J=8.5 Hz, 1H), 3.27 (d, J=13.3 Hz, 2H), 3.15-3.06 (m, 2H), 2.98-2.86 (m, 2H), 2.02 (s, 2H), 1.89 (dd, J=7.1, 5.0 Hz, 2H), 1.82 (s, 3H), 1.70 (d, J=10.8 Hz, 1H), 1.49 (s, 3H), 1.40 (t, J=11.1 Hz, 3H), 1.06 (d, J=7.0 Hz, 3H), 1.02-0.90 (m, 4H), 0.83-0.74 (m, 2H), 0.31-0.22 (m, 2H), −0.06 (s, 2H) UPLC-MS (basic 4 min): rt=1.90 min; m/z=695.4 for [M+H]$^+$ Example 313: N-[(2R,3S)-3-{4-[(2S)-2-cyclohexyl-2-[2,2-difluoro-2-(5-methoxypyridin-3-yl)acetamido]acetamido]-3-fluorophenyl}-1-(4-methylpiperazin-1-yl)-1-oxobutan-2-yl]-1,2,3-thiadiazole-5-carboxamide (309)

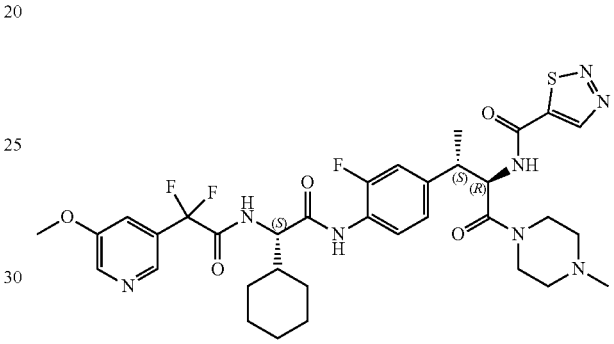

Following a synthetic scheme analogous to the preparation of 224 with coupling of a different carboxylic acids to the differentially protected amines 11A provided 309. $^1$H NMR (400 MHz, DMSO-d$_6$) δ 9.98 (s, 1H), 9.67 (d, J=7.8 Hz, 1H), 9.52 (s, 1H), 9.17-9.02 (m, 1H), 8.59-8.32 (m, 2H), 7.84-7.70 (m, 1H), 7.70-7.58 (m, 1H), 7.28-7.15 (m, 1H), 7.10-7.02 (m, 1H), 5.09-4.95 (m, 1H), 4.47 (t, J=8.6 Hz, 1H), 3.88 (s, 3H), 3.48 (s, 2H), 3.31-3.20 (m, 2H), 2.96 (t, J=10.4 Hz, 1H), 2.26-2.16 (m, 2H), 1.94 (s, 3H), 1.70-1.52 (m, 6H), 1.32 (d, J=6.9 Hz, 3H). UPLC-MS (basic 4 min): rt=1.76 min; m/z=731.3 for [M+H]$^+$.

Example 314: N-[(2R,3S)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxobutan-2-yl]-1,2,3-thiadiazole-5-carboxamide (310)

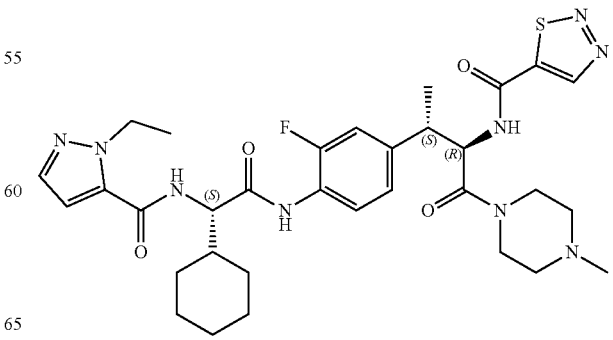

Following a synthetic scheme analogous to the preparation of 224 with coupling of a different carboxylic acids to the differentially protected amines 11A provided 310. $^1$H NMR (400 MHz, DMSO-d$_6$) δ 9.89 (s, 1H), 9.67 (d, J=7.7 Hz, 1H), 9.52 (s, 1H), 8.45 (d, J=8.3 Hz, 1H), 7.79 (t, J=8.3 Hz, 1H), 7.48 (d, J=2.0 Hz, 1H), 7.21 (dd, J=12.0, 1.9 Hz, 1H), 7.08 (dd, J=8.4, 1.9 Hz, 1H), 7.00 (d, J=2.0 Hz, 1H), 5.10-5.01 (m, 1H), 4.57 (t, J=8.4 Hz, 1H), 4.47 (q, J=7.1 Hz, 2H), 3.54-3.41 (m, 2H), 3.27 (dd, J=11.8, 4.9 Hz, 2H), 3.03-2.93 (m, 1H), 2.25-2.17 (m, 2H), 1.97 (s, 3H), 1.92-1.78 (m, 2H), 1.76-1.68 (m, 2H), 1.67-1.53 (m, 3H), 1.47-1.38 (m, 1H), 1.35-1.24 (m, 6H), 1.24-1.12 (m, 4H), 1.11-1.02 (m, 1H). UPLC-MS (basic 4 min): rt=1.76 min; m/z=668.4 for [M+H]$^+$ Example 315: N-[(2R,3S)-3-{4-[(2S)-2-[2-(3-cyanophenyl)-2,2-difluoroacetamido]-2-cyclohexyl acetamido]-3-fluorophenyl}-1-(4-methylpiperazin-1-yl)-1-oxobutan-2-yl]-1,2,3-thiadiazole-5-carboxamide (311)

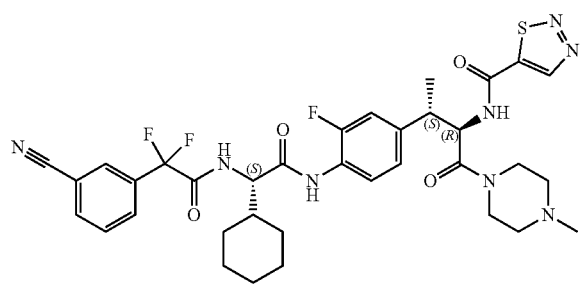

Following a synthetic scheme analogous to the preparation of 224 with coupling of a different carboxylic acids to the differentially protected amines 11A provided 311. $^1$H NMR (400 MHz, DMSO-d$_6$) δ 9.96 (s, 1H), 9.67 (d, J=8.2 Hz, 1H), 9.52 (s, 1H), 9.09 (d, J=8.3 Hz, 1H), 8.15 (d, J=1.8 Hz, 1H), 8.07 (dd, J=7.7, 1.7 Hz, 1H), 7.96 (dd, J=7.9, 1.6 Hz, 1H), 7.76 (q, J=8.2 Hz, 2H), 7.20 (dd, J=12.0, 1.9 Hz, 1H), 7.08 (dd, J=8.3, 1.9 Hz, 1H), 5.05 (dd, J=10.3, 8.2 Hz, 1H), 4.45 (t, J=8.5 Hz, 1H), 3.47 (d, J=13.1 Hz, 2H), 3.30-3.20 (m, 2H), 2.96 (t, J=10.7 Hz, 1H), 2.21 (d, J=11.2 Hz, 2H), 1.94 (s, 3H), 1.85 (d, J=10.8 Hz, 1H), 1.65 (s, 2H), 1.57 (q, J=11.5, 10.4 Hz, 4H), 1.38 (t, J=10.1 Hz, 1H), 1.31 (d, J=7.0 Hz, 3H), 1.14 (d, J=20.4 Hz, 4H), 0.92 (d, J=11.9 Hz, 1H) UPLC-MS (basic 4 min): rt=1.90 min; m/z=725.3 for [M+H]$^+$ Example 316: N-[(2R,3S)-3-{4-[(2S)-2-cyclohexyl-2-{[1-(propan-2-yl)-1H-pyrazol-5-yl]formamido}acetamido]-3-fluorophenyl}-1-(4-methylpiperazin-1-yl)-1-oxobutan-2-yl]-1,2,3-thiadiazole-5-carboxamide) (312)

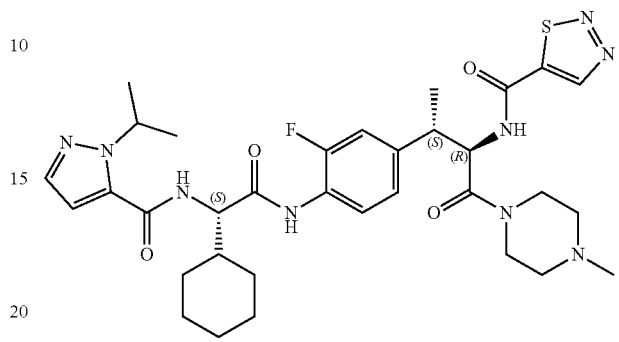

Following a synthetic scheme analogous to the preparation of 224 with coupling of a different carboxylic acids to the differentially protected amines 11A provided 312. $^1$H NMR (400 MHz, DMSO-d$_6$) δ 9.89 (s, 1H), 9.68 (d, J=8.2 Hz, 1H), 9.52 (s, 1H), 8.43 (d, J=8.3 Hz, 1H), 7.79 (t, J=8.3 Hz, 1H), 7.49 (d, J=2.0 Hz, 1H), 7.21 (dd, J=12.1, 1.9 Hz, 1H), 7.08 (d, J=8.5 Hz, 1H), 6.93 (d, J=2.0 Hz, 1H), 5.39 (p, J=6.6 Hz, 1H), 5.10-4.99 (m, 1H), 4.55 (t, J=8.4 Hz, 1H), 3.46 (s, 2H), 3.25 (d, J=13.5 Hz, 3H), 2.98 (t, J=10.4 Hz, 1H), 2.21 (d, J=11.3 Hz, 2H), 1.97 (s, 3H), 1.82 (d, J=13.8 Hz, 2H), 1.71 (s, 2H), 1.60 (dd, J=21.4, 10.6 Hz, 3H), 1.43 (d, J=9.4 Hz, 1H), 1.36 (dd, J=9.4, 6.6 Hz, 5H), 1.32 (d, J=6.9 Hz, 3H), 1.18 (d, J=8.7 Hz, 4H), 1.09-1.03 (m, 1H) UPLC-MS (basic 4 min): rt=1.60 min; m/z=682.3 for [M+H]$^+$.

Example 317: N-[(2R,3S)-3-{4-[(2S)-2-cycloheptyl-2-{[1-(propan-2-yl)-1H-pyrazol-5-yl]formamido}acetamido]phenyl}-1-(4-methylpiperazin-1-yl)-1-oxobutan-2-yl]-1,2,3-thiadiazole-5-carboxamide (231)

To a solution of 14B (0.101 g, 0.179 mmol, 1.0 eq.) in DMF (1.0 mL), which was made by reducing the nitro group of compound 91, acylating the aryl amine with CBZ-cycloheptylglycine, removing the CBZ group and acylating the alkyl amine with the depicted acid was added 1,2,3-thiadiazole-5-carboxylic acid (0.026 g, 0.197 mmol, 1.2 eq.), DIPEA (0.25 mL, 1.44 mmol, 8.0 eq.) and HATU (0.102 g, 0.268 mmol, 1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by reverse phase column chromatography on a 120 g C18 cartridge eluting with a 5-95% H$_2$O:MeCN eluent (0.1% ammonia) to afford 231 as a white solid (54.0 mg). $^1$H NMR (400 MHz, DMSO-d$_6$) δ 10.17 (s, 1H), 9.67 (d, J=8.0 Hz, 1H), 9.53 (s, 1H), 8.45 (d, J=8.5 Hz, 1H), 7.59 (d, J=8.5 Hz, 2H), 7.49 (d, J=2.0 Hz, 1H), 7.23 (d, J=8.6 Hz, 2H), 6.94 (d, J=2.0 Hz, 1H), 5.38 (p, J=6.6 Hz, 1H), 5.06-4.96 (m, 1H), 4.46 (t, J=8.5 Hz, 1H), 3.55-3.47 (m, 1H), 3.43-3.35 (m, 1H), 3.30-3.13 (m, 3H), 2.97-2.84 (m, 1H), 2.17 (dt, J=13.3, 5.9 Hz, 2H), 2.11-2.01 (m, 1H), 1.93 (s, 3H), 1.78-1.69 (m, 1H), 1.69-1.59 (m, 3H), 1.57-1.39 (m, 6H), 1.38-1.29 (m, 11H), 1.28-1.23 (m, 1H).

Example 318: (2S)-2-cyclohexyl-N-{4-[(2S,3R)-3-ethanesulfonamido-4-(4-methylpiperazin-1-yl)-4-oxobutan-2-yl]-2-fluorophenyl}-2-[(1-ethyl-1H-pyrazol-5-yl)formamido]acetamide (313)

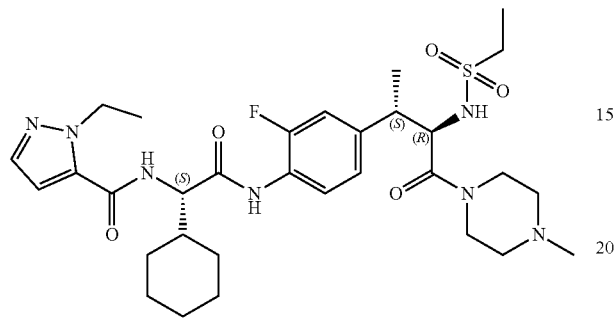

To a solution of 14A (1.0 eq.) in DMF (0.2 M) were added ethanesulfonyl chloride (1.1 eq.) and DIPEA (8.0 eq.) and the resulting mixture was stirred at RT for 24 h. The mixture was concentrated to dryness and the residue was purified via reverse phase column chromatography on a 120 g C18 cartridge eluting with a 5-95% H$_2$O:MeCN eluent (0.1% ammonia) to afford 313. $^1$H NMR (400 MHz, DMSO-d$_6$) δ 9.87 (s, 1H), 8.44 (d, J=8.3 Hz, 1H), 7.75 (t, J=8.2 Hz, 1H), 7.60 (d, J=9.0 Hz, 1H), 7.48 (d, J=2.0 Hz, 1H), 7.26-7.15 (m, 1H), 7.04-6.97 (m, 2H), 4.55 (d, J=8.5 Hz, 1H), 4.50-4.43 (m, 2H), 4.31 (t, J=9.3 Hz, 1H), 3.51-3.39 (m, 1H), 3.28-3.11 (m, 2H), 2.92 (m, 5H), 2.18 (s, 2H), 1.96 (s, 3H), 1.91-1.51 (m, 8H), 1.45-0.99 (m, 13H). UPLC-MS (basic 4 min): rt=1.70 min; m/z=648.3 for [M+H]$^+$.

Example 319: General Procedure Y

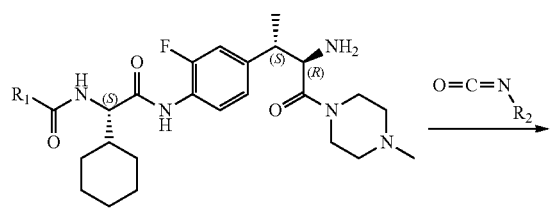

14A

To a solution of 14A (1.0 eq.) in DMF (0.1 M) were added the required isocyanate (1.2 eq.) and DIPEA (3.0-8.0 eq.) and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 314-318.

Example 320: (2S)-2-cyclohexyl-N-{4-[(2S,3R)-3-[(cyclopropylcarbamoyl)amino]-4-(4-methylpiperazin-1-yl)-4-oxobutan-2-yl]-2-fluorophenyl}-2-[(1-ethyl-1H-pyrazol-5-yl)formamido]acetamide (314)

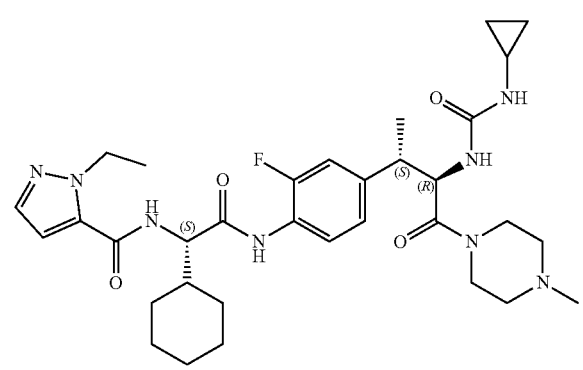

Compound 314 was prepared by General Procedure Y. $^1$H NMR (400 MHz, DMSO-d$_6$) δ 9.86 (s, 1H), 8.44 (d, J=8.3 Hz, 1H), 7.74 (t, J=8.3 Hz, 1H), 7.48 (d, J=2.0 Hz, 1H), 7.09 (dd, J=12.1, 1.9 Hz, 1H), 7.01 (dd, J=9.2, 2.0 Hz, 2H), 6.26 (d, J=2.8 Hz, 1H), 6.13 (d, J=9.3 Hz, 1H), 4.72 (t, J=9.1 Hz, 1H), 4.56 (t, J=8.5 Hz, 1H), 4.47 (q, J=7.1 Hz, 2H), 3.45 (d, J=12.9 Hz, 1H), 3.25 (s, 1H), 3.07 (t, J=10.4 Hz, 1H), 2.96 (q, J=7.4 Hz, 1H), 2.42 (dq, J=6.9, 3.3 Hz, 1H), 2.18 (s, 2H), 2.00 (s, 3H), 1.81 (d, J=13.7 Hz, 2H), 1.71 (s, 3H), 1.63 (s, 2H), 1.55 (d, J=9.8 Hz, 2H), 1.28 (t, J=7.2 Hz, 3H), 1.20 (d, J=7.0 Hz, 4H), 1.17 (s, 3H), 1.06 (t, J=11.8 Hz, 1H), 0.60-0.53 (m, 2H), 0.34-0.26 (m, 2H). UPLC-MS (basic 4 min): rt=1.65 min; m/z=639.4 for [M+H]$^+$.

Example 321: (2S)-2-cyclohexyl-N-{4-[(2S,3R)-3-[(cyclopropylcarbamoyl)amino]-4-(4-methylpiperazin-1-yl)-4-oxobutan-2-yl]-2-fluorophenyl}-2-{[1-(propan-2-yl)-1H-pyrazol-5-yl]formamido}acetamide (315)

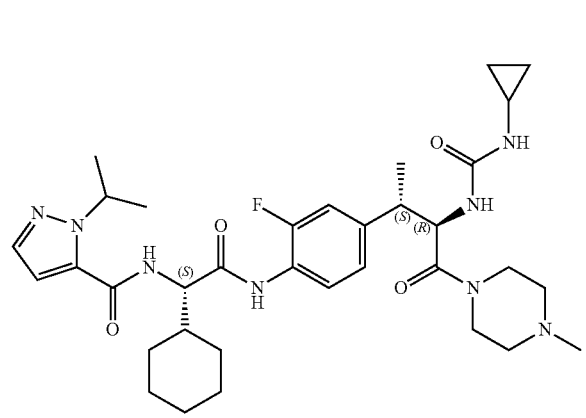

Compound 315 was prepared by General Procedure Y. ¹H NMR (400 MHz, DMSO-d₆) δ 9.85 (s, 1H), 8.42 (d, J=8.3 Hz, 1H), 7.75 (t, J=8.3 Hz, 1H), 7.49 (d, J=1.9 Hz, 1H), 7.10 (dd, J=12.2, 1.9 Hz, 1H), 7.01 (dd, J=8.3, 1.9 Hz, 1H), 6.93 (d, J=2.0 Hz, 1H), 6.26 (d, J=2.8 Hz, 1H), 6.13 (d, J=9.2 Hz, 1H), 5.38 (h, J=6.6 Hz, 1H), 4.72 (t, J=9.1 Hz, 1H), 4.55 (t, J=8.4 Hz, 1H), 3.52-3.42 (m, 2H), 3.42-3.34 (m, 1H), 3.27 (dd, J=19.0, 9.3 Hz, 1H), 3.10-3.02 (m, 1H), 2.96 (q, J=7.6 Hz, 1H), 2.42 (tt, J=6.8, 3.4 Hz, 1H), 2.19 (s, 2H), 2.00 (s, 3H), 1.81 (d, J=14.3 Hz, 2H), 1.71 (s, 2H), 1.63 (s, 1H), 1.54 (t, J=9.1 Hz, 1H), 1.36 (dd, J=9.2, 6.6 Hz, 6H), 1.20 (d, J=7.0 Hz, 5H), 1.17-1.13 (m, 2H), 1.06 (q, J=5.9, 4.8 Hz, 2H), 0.57 (td, J=6.8, 4.7 Hz, 2H), 0.34-0.25 (m, 2H). UPLC-MS (basic 4 min): rt=1.72 min; m/z=653.4 for [M+H]⁺

Example 322: 2-(3-cyanophenyl)-N—[(S)-cyclo-hexyl({4-[(2S,3R)-3-[(cyclopropylcarbamoyl) amino]-4-(4-methylpiperazin-1-yl)-4-oxobutan-2-yl]-2-fluorophenyl}carbamoyl)methyl]-2,2-difluoroacetamide) (316)

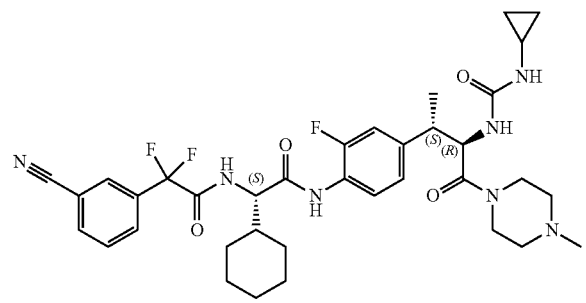

Compound 316 was prepared by General Procedure Y. ¹H NMR (400 MHz, DMSO-d₆) δ 9.92 (s, 1H), 9.08 (d, J=8.3 Hz, 1H), 8.14 (t, J=1.7 Hz, 1H), 8.12-8.03 (m, 1H), 7.96 (dd, J=8.2, 1.6 Hz, 1H), 7.73 (dt, J=26.0, 8.1 Hz, 2H), 7.09 (dd, J=12.1, 1.9 Hz, 1H), 7.01 (dd, J=8.3, 1.9 Hz, 1H), 6.26 (d, J=2.9 Hz, 1H), 6.13 (d, J=9.3 Hz, 1H), 4.71 (t, J=9.1 Hz, 1H), 4.45 (t, J=8.5 Hz, 1H), 3.51-3.41 (m, 1H), 3.24 (t, J=10.5 Hz, 1H), 3.05 (t, J=10.2 Hz, 1H), 2.96 (t, J=7.9 Hz, 1H), 2.42 (tq, J=6.9, 3.5 Hz, 1H), 2.18 (s, 2H), 1.98 (s, 3H), 1.85 (d, J=10.7 Hz, 1H), 1.67 (d, J=11.5 Hz, 4H), 1.60 (d, J=9.8 Hz, 3H), 1.49 (d, J=9.6 Hz, 1H), 1.20 (d, J=7.0 Hz, 3H), 1.16 (s, 1H), 1.14-1.04 (m, 3H), 0.92 (q, J=11.6 Hz, 1H), 0.61-0.53 (m, 2H), 0.36-0.27 (m, 2H). UPLC-MS (basic 4 min): rt=1.79 min; m/z=696.3 for [M+H]⁺

Example 323: 2-(3-cyanophenyl)-N—[(S)-cyclo-hexyl({2-fluoro-4-[(2S,3R)-3-[(methylcarbamoyl) amino]-4-(4-methylpiperazin-1-yl)-4-oxobutan-2-yl] phenyl}carbamoyl)methyl]-2,2-difluoroacetamide (317)

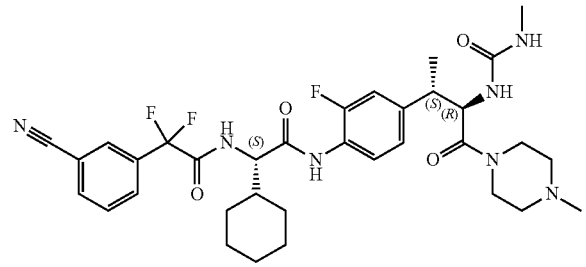

Compound 317 was prepared by General Procedure Y. ¹H NMR (400 MHz, DMSO-d₆) δ 9.92 (s, 1H), 9.08 (d, J=8.2 Hz, 1H), 8.14 (s, 1H), 8.07 (d, J=7.9 Hz, 1H), 7.95 (d, J=8.0 Hz, 1H), 7.77 (t, J=7.9 Hz, 1H), 7.70 (t, J=8.2 Hz, 1H), 7.09 (d, J=12.0 Hz, 1H), 7.01 (d, J=8.6 Hz, 1H), 6.30 (d, J=9.2 Hz, 1H), 5.87 (d, J=4.7 Hz, 1H), 4.70 (t, J=9.2 Hz, 1H), 4.44 (t, J=8.5 Hz, 1H), 3.52-3.34 (m, 3H), 3.27-3.17 (m, 1H), 3.08-2.87 (m, 2H), 2.25-2.14 (m, 2H), 1.97 (s, 3H), 1.90-1.80 (m, 1H), 1.74-1.38 (m, 8H), 1.30-1.01 (m, 9H), 1.02-0.85 (m, 1H). UPLC-MS (basic 4 min): rt=1.72 min; m/z=670.3 for [M+H]⁺

Example 324: 2-(3-cyanophenyl)-N—[(S)-({4-[(2S, 3R)-3-[(cyclobutylcarbamoyl)amino]-4-(4-methylpiperazin-1-yl)-4-oxobutan-2-yl]-2-fluorophenyl}carbamoyl)(cyclohexyl)methyl]-2,2-difluoroacetamide (318)

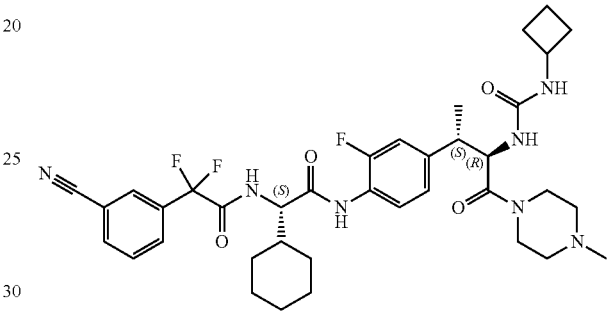

Compound 318 was prepared by General Procedure Y. ¹H NMR (400 MHz, DMSO-d₆) δ 9.92 (s, 1H), 9.08 (d, J=8.2 Hz, 1H), 8.14 (d, J=2.0 Hz, 1H), 8.07 (d, J=7.8 Hz, 1H), 7.95 (d, J=8.0 Hz, 1H), 7.77 (t, J=7.9 Hz, 1H), 7.70 (t, J=8.3 Hz, 1H), 7.12-7.05 (m, 1H), 7.03-6.97 (m, 1H), 6.29 (d, J=8.3 Hz, 1H), 6.15 (d, J=9.3 Hz, 1H), 4.67 (t, J=9.1 Hz, 1H), 4.44 (t, J=8.5 Hz, 1H), 4.02 (q, J=8.2 Hz, 1H), 3.46 (d, J=10.1 Hz, 1H), 3.37 (s, 1H), 3.26-3.14 (m, 2H), 3.06-2.98 (m, 1H), 2.97-2.89 (m, 1H), 2.25-2.06 (m, 4H), 1.97 (s, 3H), 1.85 (d, J=10.1 Hz, 1H), 1.78-1.69 (m, 2H), 1.64 (s, 3H), 1.62-1.52 (m, 4H), 1.49 (dd, J=13.3, 5.6 Hz, 2H), 1.19 (d, J=7.0 Hz, 3H), 1.08 (d, J=21.3 Hz, 3H), 0.92 (d, J=12.0 Hz, 1H). UPLC-MS (basic 4 min): rt=1.88 min; m/z=710.4 for [M+H]⁺

Example 325: General Procedure V for the Synthesis of 17Aa-b

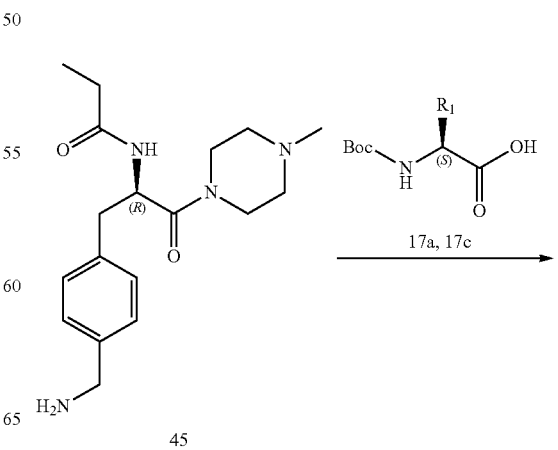

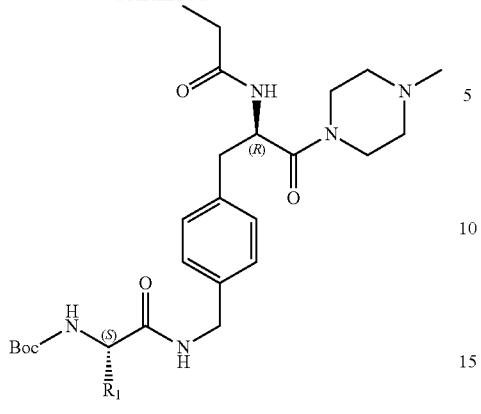

17Aa-b

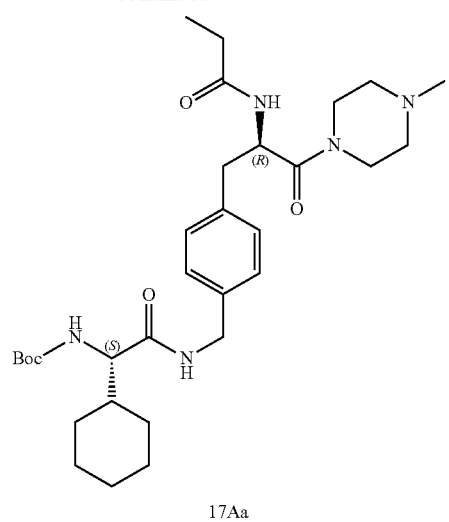

17Aa

To a solution of 45 (1.0 eq.) in THF were added 17a or 17c (1.5 eq.), DIPEA (5.0 eq.) and T3P (50% in EtOAc, 2.0 eq.) and the resulting mixture was stirred for 18 h. The mixture was concentrated to dryness and the residue dissolved in DCM. Aqueous saturated sodium bicarbonate solution was added and then extracted with DCM. The combined organic phase was washed with brine, dried over sodium sulfate then concentrated to afford 17Aa-b which was used in the next step without further purification.

Following General Procedure V, 45 (0.500 g, 1.31 mmol, 1.0 eq.) was reacted with (2S)-2-{[(tert-butoxy)carbonyl]amino}-2-cyclohexylacetic acid 17a (0.505 g, 1.96 mmol, 1.5 eq.), T3P (1.6 mL, 2.62 mmol, 50% in EtOAc, 2.0 eq.) and DIPEA (1.1 mL, 6.54 mmol, 5.0 eq.) in THF (6.0 mL) to afford, after aqueous work-up, 17Aa (0.747 g, 100% yield) as a yellow gummy solid which was used in the next step without further purification. UPLC-MS (basic 4 min): rt=1.68 min; m/z=572.4 for [M+H]⁺.

Example 326: tert-butyl N—[(S)-cyclohexyl[({4-[(2R)-3-(4-methylpiperazin-1-yl)-3-oxo-2-propanamidopropyl]phenyl}methyl)carbamoyl]methyl]carbamate) (17Aa)

Example 327: tert-butyl N—[(S)-cycloheptyl[({4-[(2R)-3-(4-methylpiperazin-1-yl)-3-oxo-2-propanamidopropyl]phenyl}methyl)carbamoyl]methyl]carbamate (17Ab)

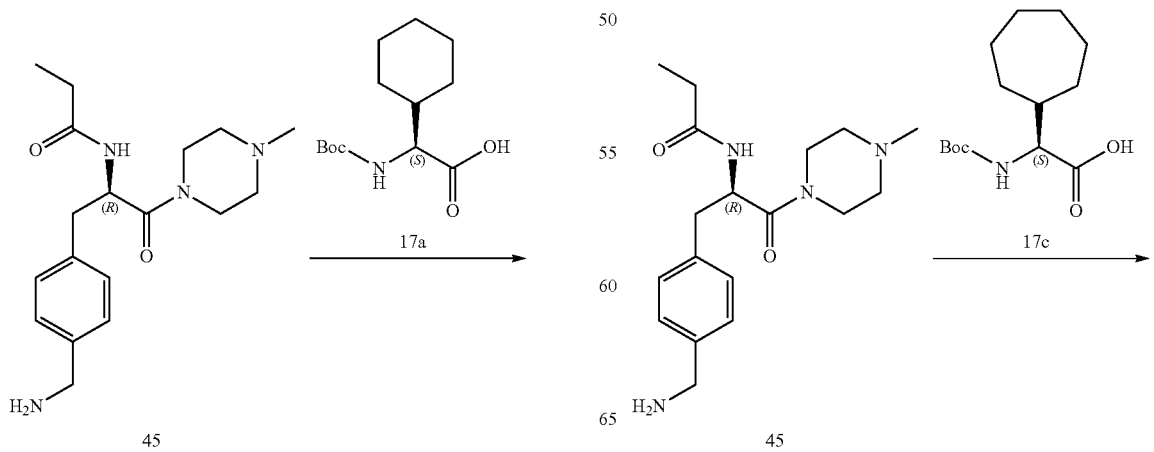

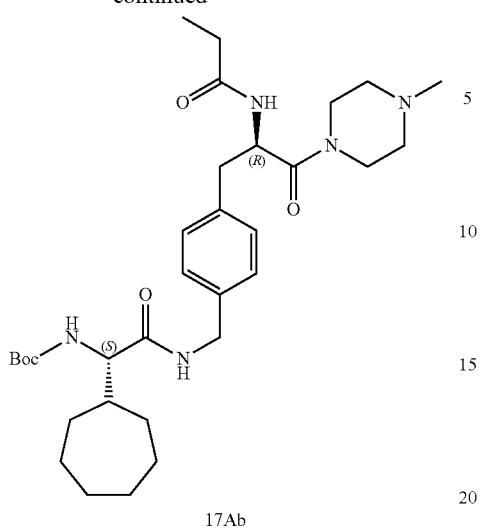

17Ab

Following General Procedure V, 45 (0.500 g, 1.31 mmol, 1.0 eq.) was reacted with (2S)-2-{[(tert-butoxy) carbonyl]amino}-2-cycloheptylacetic acid) 17c (0.533 g, 1.96 mmol, 1.5 eq.), T3P (1.6 mL, 2.62 mmol, 50% in EtOAc, 2.0 eq.) and DIPEA (1.1 mL, 6.54 mmol, 5.0 eq.) in THF (6.0 mL) to afford, after aqueous work-up, 17Ab (0.766 g, 100% yield) as a yellow gummy solid which was used in the next step without further purification. UPLC-MS (basic 4 min): rt=1.78 min; m/z=586.4 for [M+H]⁺.

Example 328: General Procedure W for the Synthesis of 18Aa-b

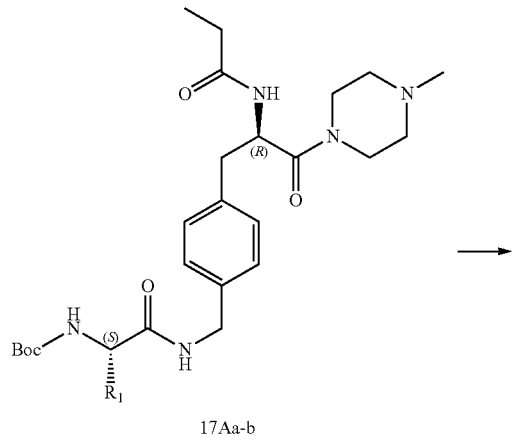

17Aa-b

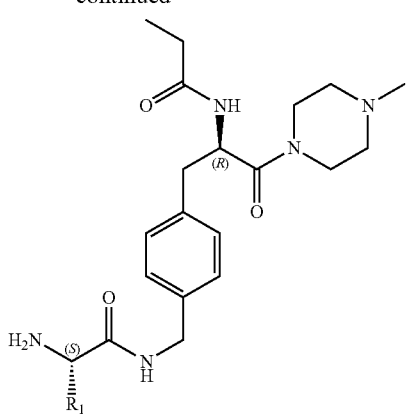

18Aa-b

To a solution of 17Aa-b (1.0 eq.) in DCM was added TFA and the resulting mixture was stirred at RT for 0.5 h. The reaction mixture was concentrated to dryness 8nd the residue was stirred in aq. sat. K₂CO₃ solution and then extracted with DCM to afford 18Aa-b.

Example 329: N-[(2R)-3-(4-{[(2S)-2-amino-2-cyclohexylacetamido]methyl}phenyl)-1-(4-methylpiperazin-1-yl)-1-oxopropan-2-yl]propanamide) (18Aa)

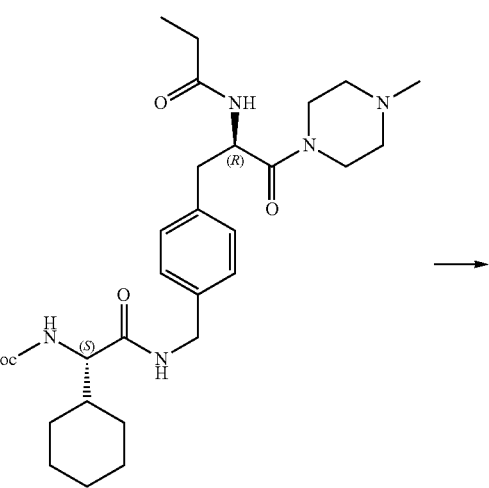

17Aa

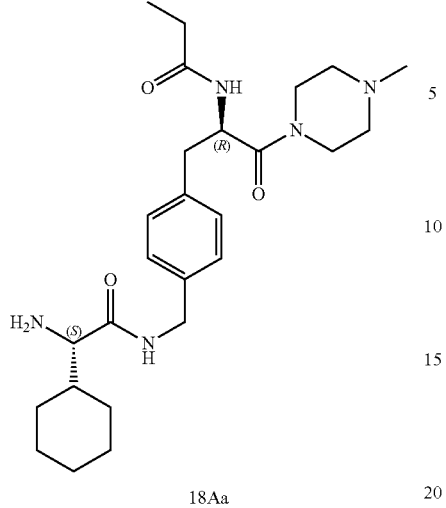

18Aa

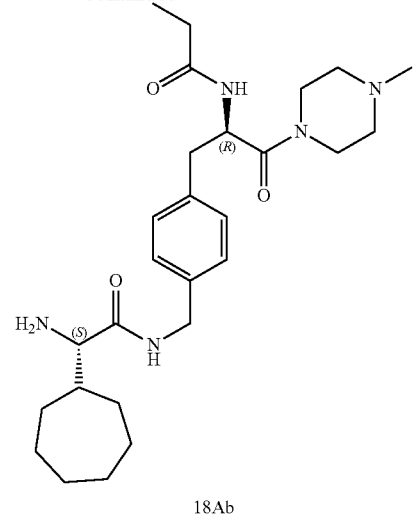

18Ab

Following General Procedure W, 17Aa (0.900 g, 1.57 mmol, 1.0 eq.) was reacted with TFA (2 mL) in DCM (6 mL) to afford, after aqueous work-up, 18Aa (0.095 g, 15% yield) as an off-white solid which was used in the next step without further purification. UPLC-MS (basic 4 min): rt=1.26 min; m/z=472.3 for [M+H]⁺.

Example 330: N-[(2R)-3-(4-{[(2S)-2-amino-2-cyclohexylacetamido]methyl}phenyl)-1-(4-methylpiperazin-1-yl)-1-oxopropan-2-yl]propanamide) (18Ab)

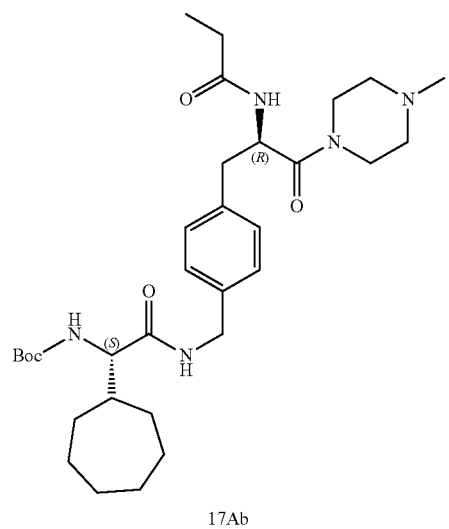

17Ab

Following General Procedure W, 17Ab (1.00 g, 1.71 mmol, 1.0 eq.) was reacted with TFA (2 mL) in DCM (6 mL) to afford, after aqueous work-up, 18Ab (0.100 g, 13% yield) as an off-white solid which was used in the next step without further purification. UPLC-MS (basic 4 min): rt=1.37 min; m/z=486.3 for [M+H]⁺.

Example 331: General Procedure X for the Synthesis of 225 and 226

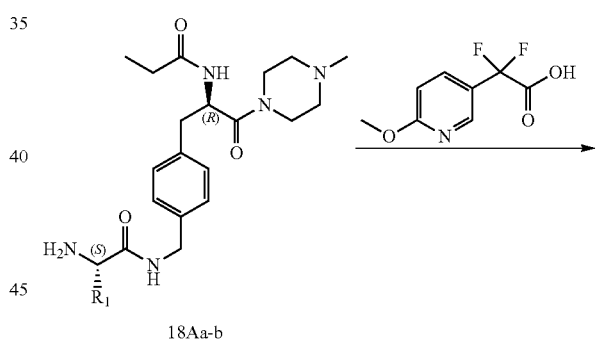

18Aa-b 225 and 226

To a solution of 18Aa-b (1.0 eq.) in DMF were added 2,2-difluoro-2-(6-methoxypyridin-3-yl)acetic acid (1.2 eq.), DIPEA (8.0 eq.) and then HATU (1.5 eq.) and the resulting mixture was stirred at RT for 1 h. The mixture was concen-

Example 332: N-[(2R)-3-(4-{[(2S)-2-cyclohexyl-2-[2,2-difluoro-2-(6-methoxypyridin-3-yl)acetamido]acetamido]methyl}phenyl)-1-(4-methylpiperazin-1-yl)-1-oxopropan-2-yl]propanamide) (225)

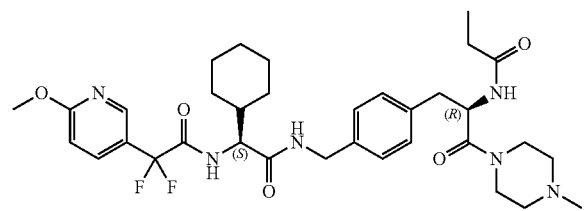

Following General Procedure W, 18Aa (0.095 g, 0.201 mmol, 1.0 eq.) was reacted with 2,2-difluoro-2-(6-methoxypyridin-3-yl)acetic acid (0.049 g, 0.242 mmol, 1.2 eq.), DIPEA (0.14 mL, 0.806 mmol, 4.0 eq.) and HATU (0.115 g, 0.302 mmol, 1.5 eq.) in DMF (1.5 mL) to afford, after reverse phase column chromatography, 225 (33.0 mg) as a white solid. $^1$H NMR (400 MHz, MeOH-d$_4$) δ 8.39 (dd, J=2.5, 1.1 Hz, 1H), 7.87 (dd, J=8.8, 2.6 Hz, 1H), 7.25-7.08 (m, 4H), 6.87 (dd, J=8.8, 0.8 Hz, 1H), 5.01 (dd, J=8.4, 6.9 Hz, 1H), 4.45-4.27 (m, 2H), 4.21 (d, J=8.9 Hz, 1H), 3.96 (s, 3H), 3.49 (dtd, J=20.8, 7.0, 3.7 Hz, 2H), 3.18 (ddd, J=13.3, 7.0, 3.0 Hz, 1H), 2.93 (qd, J=13.1, 7.7 Hz, 2H), 2.41-2.08 (m, 7H), 1.95-1.57 (m, 7H), 1.35-1.10 (m, 3H), 1.06 (t, J=7.6 Hz, 3H), 1.04-0.88 (m, 1H). UPLC-MS (basic 4 min): rt=1.71 min; m/z=657.5 for [M+H]$^+$.

Example 333: N-[(2R)-3-(4-{[(2S)-2-cycloheptyl-2-[2,2-difluoro-2-(6-methoxypyridin-3-yl)acetamido]acetamido]methyl}phenyl)-1-(4-methylpiperazin-1-yl)-1-oxopropan-2-yl]propanamide) (226)

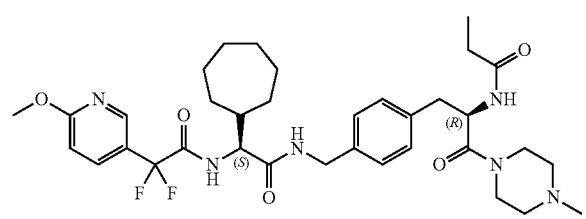

Following General Procedure X, 18Ab (0.090 g, 0.185 mmol, 1.0 eq.) was reacted with 2,2-difluoro-2-(6-methoxypyridin-3-yl)acetic acid (0.045 g, 0.222 mmol, 1.2 eq.), DIPEA (0.13 mL, 0.741 mmol, 4.0 eq.) and HATU (0.106 g, 0.278 mmol, 1.5 eq.) in DMF (1.5 mL) to afford, after reverse phase column chromatography, 226 (35.0 mg) as a white solid. $^1$H NMR (400 MHz, MeOH-d$_4$) δ 8.39 (dd, J=2.6, 1.1 Hz, 1H), 7.87 (dd, J=8.8, 2.6 Hz, 1H), 7.21-7.07 (m, 4H), 6.87 (dd, J=8.8, 0.8 Hz, 1H), 5.01 (dd, J=8.5, 6.9 Hz, 1H), 4.35 (s, 2H), 4.28 (d, J=8.7 Hz, 1H), 3.96 (s, 3H), 3.63-3.38 (m, 2H), 3.18 (ddd, J=13.3, 6.9, 2.9 Hz, 1H), 2.93 (qd, J=13.1, 7.7 Hz, 2H), 2.39-2.13 (m, 7H), 2.13-1.97 (m, 1H), 1.97-1.81 (m, 1H), 1.81-1.33 (m, 6H), 1.25 (tdd, J=14.0, 7.3, 3.4 Hz, 2H), 1.06 (t, J=7.6 Hz, 3H). UPLC-MS (basic 4 min): rt=1.80 min; m/z=671.5 for [M+H]$^+$.

Example 334: tert-butyl N-[(2R,3S)-1-(4-methylpiperazin-1-yl)-3-(4-nitrophenyl)-1-oxopentan-2-yl]carbamate) (20A)

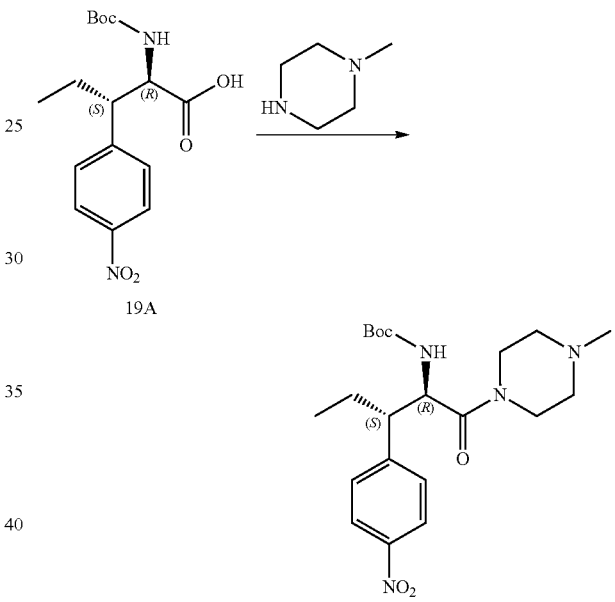

To a solution of 19A, (0.843 g, 2.49 mmol, 1.0 eq.) in DMF (7 mL) which was made as described in FIG. 21, was added N-methyl piperazine (0.33 mL, 2.99 mmol, 1.2 eq.), DIPEA (2.2 mL, 12.5 mmol, 5.0 eq) and HATU (1.42 g, 3.74 mmol, 1.5 eq.) and the resulting mixture was stirred at RT under a N$_2$ atmosphere for 1 h. The mixture was diluted with aq. sat. NaHCO$_3$ solution (50 mL) and then extracted with DCM (50 mL). The organic layer was washed with brine (200 mL), dried over Na$_2$SO$_4$ then concentrated. The residue was purified by flash column chromatography (Silica, 0-10% MeOH, DCM) to afford 20A as a yellow solid (0.932 g, 89% yield). $^1$H NMR (400 MHz, DMSO-d$_6$) δ 8.15 (d, J=8.6 Hz, 2H), 7.54-7.46 (m, 2H), 7.37 (d, J=8.8 Hz, 1H), 4.68 (t, J=9.5 Hz, 1H), 3.15 (s, 2H), 3.04 (t, J=10.6 Hz, 1H), 2.70 (s, 1H), 2.00 (s, 3H), 1.91-1.84 (m, 1H), 1.71 (d, J=7.0 Hz, 1H), 1.67 (s, 2H), 1.39 (s, 9H), 0.62 (t, J=7.3 Hz, 3H). UPLC-MS (basic 2 min): Rt=1.12 min; m/z=421.3 for [M+H]$^+$ Example 335: (2R,3S)-2-amino-1-(4-methylpiper-azin-1-yl)-3-(4-nitrophenyl)pentan-1-one) (21A)

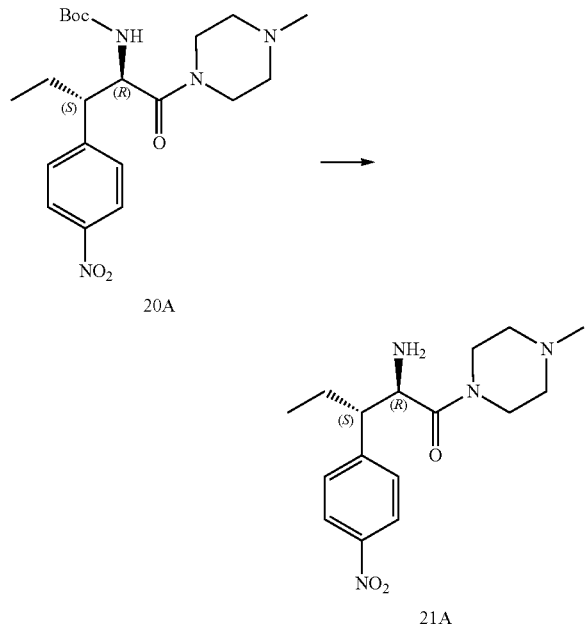

To a solution of 20A (0.932 g, 2.22 mmol, 1.0 eq.) in DCM (8 mL) was added TFA (4 mL) and the resulting mixture was stirred at RT for 20 min. The reaction mixture was concentrated to dryness and the residue was dissolved in DCM (25 mL), stirred in aq. sat. K$_2$CO$_3$ solution (4 g in 25 mL H$_2$O) and then extracted with DCM to afford 21A as an off-white solid (0.579 g, 82% yield) which was used in the next step without further purification. $^1$H NMR (400 MHz, DMSO-d$_6$) δ 8.18-8.10 (m, 2H), 7.54-7.46 (m, 2H), 3.81 (d, J=8.1 Hz, 1H), 2.76-2.66 (m, 1H), 2.18 (s, 1H), 2.25-2.04 (m, 2H), 2.02 (s, 3H), 1.79 (s, 2H), 1.62 (dq, J=11.6, 7.3 Hz, 2H), 0.64 (t, J=7.4 Hz, 3H). UPLC-MS (basic 2 min): Rt=0.88 min; m/z=320.2 for [M+H]$^+$.

Example 336: N-[(2R,3S)-1-(4-methylpiperazin-1-yl)-3-(4-nitrophenyl)-1-oxopentan-2-yl]propana-mide) (22A)

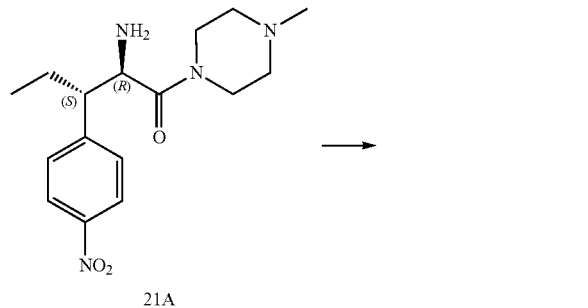

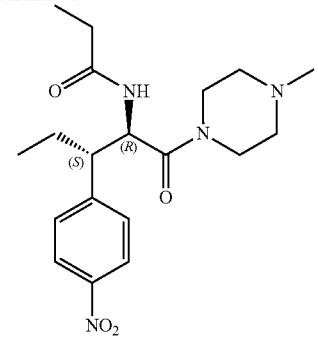

To a solution of 21A (0.579 g, 1.81 mmol, 1.0 eq.) in DMF (5.0 mL) were added propionic anhydride (0.28 mL, 2.17 mmol, 1.2 eq.) and DIPEA (0.94 mL, 5.42 mmol, 3.0 eq) and the resulting mixture was stirred at RT under a N$_2$ atmosphere for 1 h. The mixture was diluted with aq. sat. NaHCO$_3$ solution (100 mL) and then extracted with DCM (100 mL). The organic layer was washed with brine (100 mL), dried over Na$_2$SO$_4$ then concentrated to afford 22A as a yellow solid (0.612 g, 90% yield) which was used in the next step without further purification. $^1$H NMR (400 MHz, DMSO-d$_6$) δ 8.37 (d, J=8.8 Hz, 1H), 8.19-8.13 (m, 2H), 7.55-7.48 (m, 2H), 5.02 (dd, J=10.2, 8.8 Hz, 1H), 3.34 (d, J=14.5 Hz, 3H), 3.27-3.16 (m, 1H), 3.15-3.01 (m, 2H), 2.26-2.07 (m, 3H), 1.99 (s, 3H), 1.85 (ddd, J=13.8, 7.5, 3.5 Hz, 1H), 1.61 (q, J=7.4, 6.6 Hz, 3H), 1.00 (t, J=7.6 Hz, 3H), 0.63 (t, J=7.3 Hz, 3H). UPLC-MS (basic 2 min): Rt=0.94 min; m/z=377.2 for [M+H]$^+$.

Example 337: N-[(2R,3S)-3-(4-aminophenyl)-1-(4-methylpiperazin-1-yl)-1-oxopentan-2-yl]propana-mide) (23A)

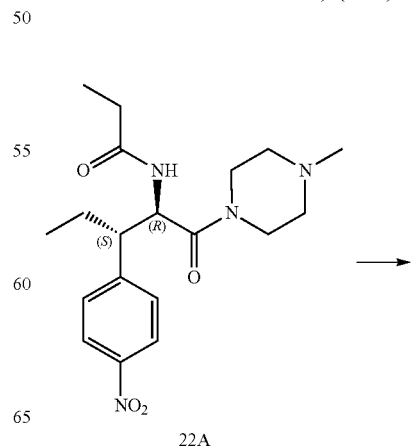

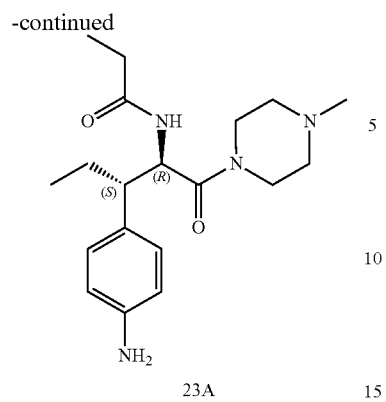

23A

To a degassed solution of 22A (0.612 g, 1.63 mmol, 1.0 eq) in EtOH (15 mL) and THF (15 mL) was added Pd/C (0.061 g, 0.573 mmol, 0.35 eq). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness. The residue was purified by reverse phase column chromatography 48 g C18 cartridge eluting with a 5-95% H$_2$O:MeCN eluent to afford 23A as an off-white solid (0.338 g, 60% yield). $^1$H NMR (400 MHz, DMSO-d$_6$) δ 8.15 (d, J=8.8 Hz, 1H), 6.83-6.77 (m, 2H), 6.51-6.43 (m, 2H), 4.81 (dd, J=10.4, 8.8 Hz, 1H), 3.21-3.10 (m, 2H), 2.66 (td, J=11.1, 3.4 Hz, 1H), 2.17 (dd, J=14.9, 7.6 Hz, 1H), 2.14-2.06 (m, 1H), 2.09-2.05 (m, 4H), 2.03 (s, 3H), 1.83-1.65 (m, 1H), 1.49-1.37 (m, 1H), 0.98 (t, J=7.6 Hz, 3H), 0.90-0.79 (m, 1H), 0.62 (t, J=7.3 Hz, 3H). UPLC-MS (basic 2 min): Rt=0.80 min; m/z=347.3 for [M+H]$^+$.

Example 338: tert-butyl N—[(S)-cycloheptyl({4-[(2R,3S)-1-(4-methylpiperazin-1-yl)-1-oxo-2-propanamidopentan-3-yl]phenyl}carbamoyl)methyl]carbamate) (25A)

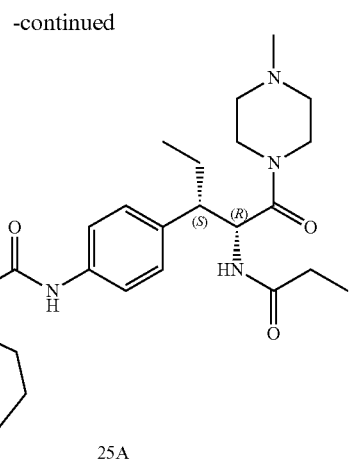

25A

To a solution of 23A (0.224 g, 0.647 mmol, 1.0 eq.) in DMF (5.0 mL) were added 17c (0.211 g, 0.776 mmol, 1.2 eq.), DIPEA (0.9 mL, 5.17 mmol, 8.0 eq.) and HATU (0.492 g, 1.29 mmol, 1.5 eq.) and the resulting mixture was stirred for 2 h. Aqueous saturated sodium bicarbonate solution (100 mL) was added and then extracted with DCM (50 mL). The combined organic phase was washed with brine (100 mL), dried over sodium sulfate then concentrated to dryness to afford 25A as a pale brown solid (0.223 g, 58% yield) which was used in the next step without further purification. $^1$H NMR (400 MHz, DMSO-d$_6$) δ 9.92 (s, 1H), 8.25 (d, J=8.7 Hz, 1H), 7.52 (d, J=8.2 Hz, 2H), 7.11 (d, J=8.5 Hz, 2H), 6.83 (d, J=8.8 Hz, 1H), 4.93-4.84 (m, 1H), 3.97 (t, J=8.3 Hz, 1H), 3.22 (d, J=10.0 Hz, 1H), 2.95 (s, 2H), 2.81 (s, 1H), 2.25-2.16 (m, 2H), 2.14 (s, OH), 2.17-2.03 (m, 2H), 1.99 (s, 3H), 1.64-1.57 (m, 2H), 1.48 (dt, J=17.5, 13.0 Hz, 2H), 1.38 (s, 9H), 1.35 (s, 8H), 1.31-1.20 (m, OH), 0.99 (t, J=7.6 Hz, 3H), 0.63 (t, J=7.3 Hz, 3H). UPLC-MS (basic 2 min): Rt=1.16 min; m/z=598.3 for [M+H]$^+$.

Example 339: N-[(2R,3S)-3-{4-[(2S)-2-amino-2-cycloheptylacetamido]phenyl}-1-(4-methylpiperazin-1-yl)-1-oxopentan-2-yl]propanamide) (26A)

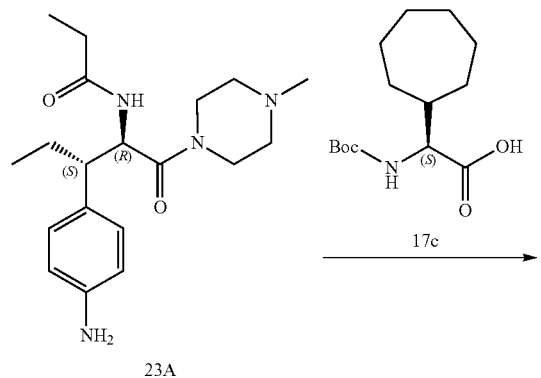

23A    17c

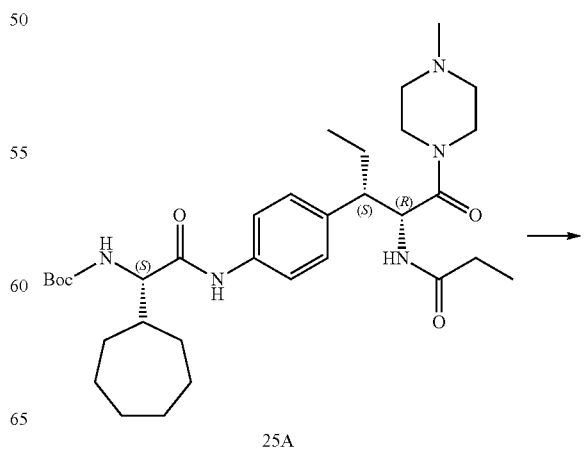

25A

-continued

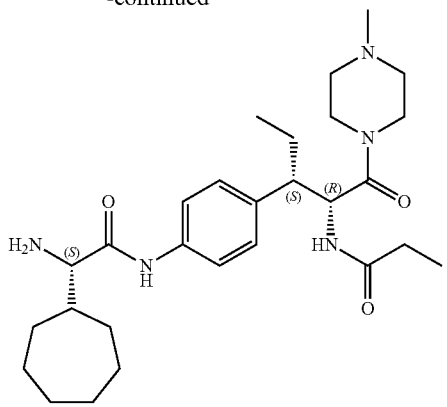

26A

To a solution of 25A (0.225 g, 0.375 mmol, 1.0 eq.) in DCM (3 mL) was added TFA (3 mL) and the resulting mixture was stirred at RT for 30 min. The reaction mixture was concentrated to dryness and the residue was dissolved in DCM (15 mL), stirred in aq. sat. $K_2CO_3$ solution (1 g in 15 mL $H_2O$) and then extracted with DCM to afford 26A as an off-white solid (0.356 g, 95% yield) which was used in the next step without further purification. $^1$H NMR (400 MHz, DMSO-$d_6$) δ 9.79 (s, 1H), 8.24 (d, J=8.7 Hz, 1H), 7.58-7.51 (m, 2H), 7.14-7.07 (m, 2H), 4.89 (dd, J=10.4, 8.8 Hz, 1H), 3.13 (d, J=5.4 Hz, 1H), 3.01 (t, J=10.1 Hz, 1H), 2.86-2.75 (m, 1H), 2.18 (dd, J=14.9, 7.6 Hz, 1H), 2.15-2.03 (m, 3H), 1.97 (s, 3H), 1.79 (s, 3H), 1.67-1.59 (m, 5H), 1.51 (d, J=7.9 Hz, 4H), 1.49-1.36 (m, 2H), 1.34-1.23 (m, 1H), 1.08-0.95 (m, 3H), 0.91-0.76 (m, 2H), 0.63 (t, J=7.3 Hz, 3H). UPLC-MS (basic 2 min): Rt=1.00 min; m/z=500.3 for [M+H]$^+$.

Example 340: N-[(2R,3S)-3-{4-[(2S)-2-cycloheptyl-2-[2,2-difluoro-2-(6-methoxypyridin-3-yl)acetamido]acetamido]phenyl}-1-(4-methylpiperazin-1-yl)-1-oxopentan-2-yl]propanamide) (227)

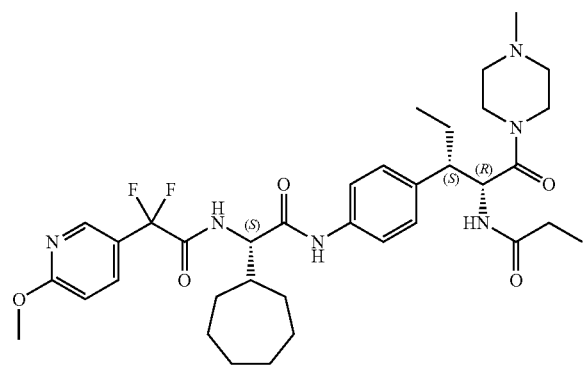

To a solution of 26A (0.089 g, 0.178 mmol, 1.0 eq,) in DMF (1.0 mL) was added 2,2-difluoro-2-(6-methoxypyridin-3-yl)acetic acid (0.043 g, 0.212 mmol, 1.2 eq.), DIPEA (0.25 mL, 1.43 mmol, 8.0 eq.) and then HATU (0.102 g, 0.267 mmol, 1.5 eq.) and the resulting mixture was stirred at RT for 4 h. The mixture was concentrated to dryness and the residue was purified via reverse phase column chromatography on a 120 g C18 cartridge eluting with a 5-95% $H_2O$:MeCN eluent (0.1% ammonia) to afford 227 (43.0 mg) as a white solid. $^1$H NMR (400 MHz, DMSO-$d_6$) δ 10.18 (s, 1H), 9.05 (d, J=8.5 Hz, 1H), 8.44-8.39 (m, 1H), 8.24 (d, J=8.7 Hz, 1H), 7.93 (dd, J=8.8, 2.6 Hz, 1H), 7.52 (d, J=8.3 Hz, 2H), 7.12 (d, J=8.4 Hz, 2H), 6.96 (d, J=8.7 Hz, 1H), 4.93-4.83 (m, 1H), 4.32 (t, J=8.6 Hz, 1H), 3.90 (s, 3H), 3.43 (d, J=14.0 Hz, 2H), 3.17 (t, J=10.9 Hz, 1H), 2.90 (t, J=10.2 Hz, 1H), 2.86-2.76 (m, 1H), 2.14 (qq, J=15.0, 7.6 Hz, 3H), 1.92 (s, 3H), 1.79 (s, 1H), 1.62-1.47 (m, 2H), 1.36 (dt, J=15.8, 9.3 Hz, 2H), 1.31-1.17 (m, 1H), 0.99 (t, J=7.6 Hz, 3H), 0.63 (t, J=7.3 Hz, 3H). UPLC-MS (basic 2 min): Rt=1.94 min; m/z=685.4 for [M+H]$^+$.

Example 341: N-[(2R,3S)-3-{4-[(2S)-2-cycloheptyl-2-[(1-ethyl-1H-pyrazol-5-yl)formamido]acetamido]phenyl}-1-(4-methylpiperazin-1-yl)-1-oxopentan-2-yl]propanamide) (319)

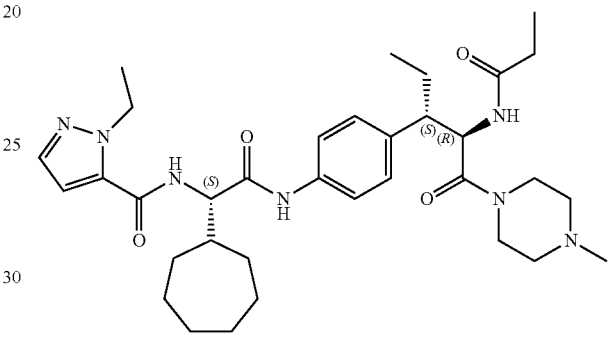

To a solution of 26A (0.089 g, 0.178 mmol, 1.0 eq,) in DMF (1.0 mL) was added pyrazolic acid (0.043 g, 0.212 mmol, 1.2 eq.), DIPEA (0.25 mL, 1.43 mmol, 8.0 eq.) and then HATU (0.102 g, 0.267 mmol, 1.5 eq.) and the resulting mixture was stirred at RT for 4 h. The mixture was concentrated to dryness and the residue was purified via reverse phase column chromatography on a 120 g C18 cartridge eluting with a 5-95% $H_2O$:MeCN eluent (0.1% ammonia) to afford 319. $^1$H NMR (400 MHz, DMSO-$d_6$) δ 10.15 (s, 1H), 8.48 (d, J=8.5 Hz, 1H), 8.24 (d, J=8.7 Hz, 1H), 7.56 (d, J=8.5 Hz, 2H), 7.47 (d, J=2.0 Hz, 1H), 7.12 (d, J=8.5 Hz, 2H), 7.01 (d, J=2.1 Hz, 1H), 4.93-4.84 (m, 1H), 4.51-4.41 (m, 3H), 3.19 (t, J=10.4 Hz, 1H), 2.92 (t, J=10.3 Hz, 1H), 2.87-2.76 (m, 1H), 2.14 (tq, J=14.9, 7.5 Hz, 3H), 1.94 (s, 3H), 1.76 (s, 1H), 1.65 (d, J=11.1 Hz, 2H), 1.52 (s, 4H), 1.50 (s, 1H), 1.41 (d, J=10.2 Hz, 5H), 1.38-1.31 (m, 2H), 1.27 (t, J=7.1 Hz, 3H), 0.99 (t, J=7.6 Hz, 3H), 0.63 (t, J=7.3 Hz, 3H). UPLC-MS (basic 2 min): rt=1.08 min; m/z=622.4 for [M+H]$^+$.

Example 342: Preparation of Intermediate 28A

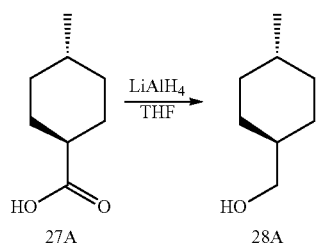

27A      28A

LiAlH$_4$ (33.3 g, 879 mmol, 1.00 eq) was added to THF (1000 mL) in portions at 0-15° C. under N$_2$. The mixture was stirred at 15° C. for 1 hr and compound 27A (125 g, 879 mmol, 1.00 eq) in THF (1000 mL) was added to the mixture drop-wise at 0° C. The mixture was stirred at 25° C. for 2 hrs. TLC indicated compound 27A was consumed completely and one new spot formed. The reaction mixture was cooled to 0° C. and successively added was H$_2$O (34.0 mL) drop-wise, 15% aq. NaOH (34.0 mL), H$_2$O (102 mL). The mixture was stirred at 25° C. for 30 min, dried over Na$_2$SO$_4$, filtered and concentrated to provide a residue. Compound 28A (110 g, 857 mmol, 97.6% yield) was obtained as yellow oil. The structure was confirmed by $^1$H NMR (400 MHz, CDCl$_3$): δ 3.44 (d, J=6.4 Hz, 2H), 1.79-1.71 (m, 4H), 1.43-1.26 (m, 2H), 0.97-0.87 (m, 7H).

Example 343: Preparation of Intermediate 29A

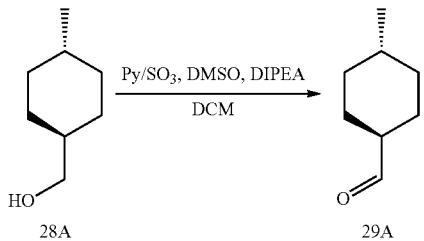

To a solution of compound 28A (90.0 g, 701 mmol, 1.00 eq) in DCM (450 mL) was added Py/SO$_3$ (223 gl, 1.40 mol, 2.00 eq), DMSO (164 g, 2.11 mol, 164 mL, 3.00 eq) and DIPEA (272 g, 2.11 mol, 366 mL, 3.00 eq) at 25° C. The mixture was stirred at 25° C. for 12 hrs. TLC (Petroleum ether:Ethyl acetate=3:1, R$_f$=0.40) showed the reaction was complete. The mixture was washed with aqueous saturated citric acid (400 mL*6 and brine (300 mL*4). The combined organic layers were dried over anhydrous Na$_2$SO$_4$ and used in the next step without further purification. Compound 29A (88.5 g, crude) in DCM (450 mL) was obtained as yellow liquid. The structure was confirmed by $^1$H NMR (400 MHz, CDCl$_3$): δ 9.61 (d, J=1.6 Hz, 1H), 2.18-2.11 (m, 1H), 1.98-1.94 (m, 2H), 1.83-1.78 (m, 2H), 1.30-1.22 (m, 2H), 1.02-0.89 (m, 6H).

Example 344: Preparation of Intermediate 30A

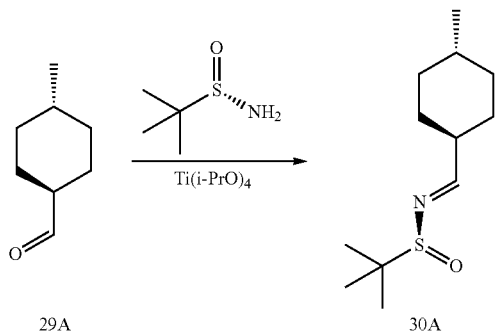

A mixture of compound 29A (88.5 g, 701 mmol, 1.00 eq) in DCM (450 mL) and the t-butylsulfonamide (85.1 g, 701 mmol, 1.00 eq), Ti(i-PrO)$_4$ (299 g, 1.05 mol, 310 mL, 1.50 eq) was stirred at 45° C. for 2 hrs. TLC indicated compound 29A was consumed completely. The reaction mixture was cooled to 0° C. and H$_2$O (500 mL) was added. The thick paste was filtered through a pad of celite and the cake was washed with DCM (1000 mL). The combined organic layers were dried over Na$_2$SO$_4$, filtered and concentrated under reduced pressure to give a yellow oil. The crude product (30.0 g) was purified by column chromatography (SiO$_2$, Petroleum ether:Ethyl acetate=100:1 to 1:1). Compound 30A (120 g, 523 mmol, 74.5% yield) was obtained as yellow oil. The structure was confirmed by LC-MS: (M+H)$^+$: 230.3 and $^1$H NMR, (400 MHz, CDCl$_3$): δ 7.93 (d, J=4.8 Hz, 1H), 2.36-2.33 (m, 1H), 1.90-1.86 (m, 2H), 1.78-1.74 (m, 2H), 1.31-1.23 (m, 3H), 1.15 (s, 9H), 1.02-0.93 (m, 2H), 0.88 (d, J=6.4 Hz, 3H) and SFC: 100%. chiral purity.

Example 345: Preparation of Intermediate 31A and Isomer 32A

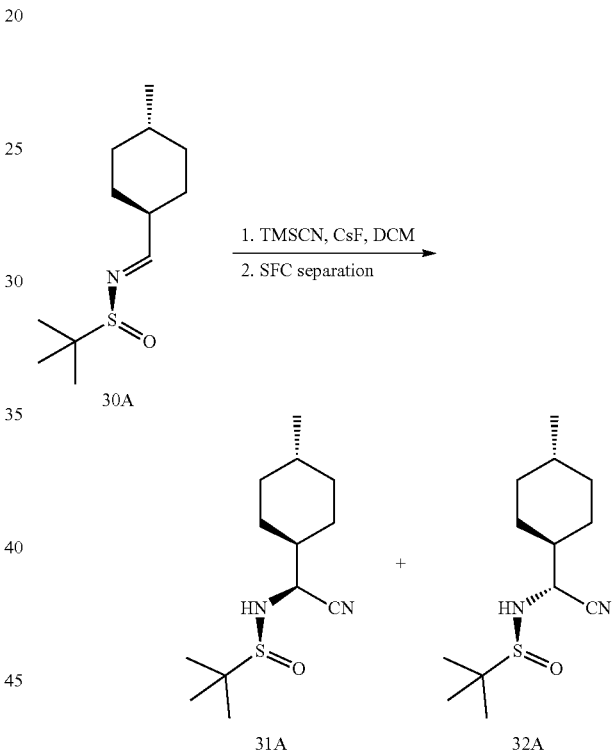

To a solution of compound 30A (120 g, 523 mmol, 1.00 eq) in DCM (1200 mL) was added TMSCN (103 g, 1.05 mol, 130 mL, 2.00 eq) and CsF (23.8 g, 156 mmol, 5.79 mL, 0.300 eq) at 25° C. and stirred at 25° C. for 12 hrs. The mixture was added to H$_2$O (1000 mL) and the organic phase separated. The water phase was extracted with DCM (500 mL*2) and the organic layer dried over Na$_2$SO$_4$, filtered and concentrated under reduced pressure to provide a residue. The crude product was purified by re-crystallization from ethyl acetate (300 mL) at 60° C. The crude product was confirmed by SFC and was separated by SFC (column: DAICEL CHIRALPAK AD (250 mm*50 mm, 10 um); mobile phase: [0.1% NH$_3$·H$_2$O MeOH]; B %: 65%-65%, 9.0 min; 162 min). Compound 31A (74.0 g, 288 mmol, 55.1% yield) was obtained as a white solid. The structure was confirmed by H NMR (EW18587-294-P1A), LC-MS (EW18587-294-P1A) and SFC (EW18587-294-PIA_C4). Compound 32A (7.00 g, 27.3 mmol, 5.22% yield) was obtained as a gray solid. The structure of 31A was confirmed by ¹H NMR 400 MHz, CDCl₃): δ 3.99-3.95 (m, 1H), 3.75 (d, J=8.4 Hz, 1H), 1.92-1.88 (m, 2H), 1.80-1.78 (m, 3H), 1.41-1.30 (m, 1H), 1.25 (s, 9H), 1.20-1.09 (m, 2H), 1.00-0.89 (m, 5H), LC-MS: (M+H)⁺: 257.3 and SFC: 100% chiral purity. The structure of 32A was confirmed by ¹H NMR (400 MHz, DMSO-d₆) δ 6.08 (d, J=7.6 Hz, 1H), 4.22-4.18 (m, 1H), 1.92-1.84 (m, 2H), 1.74-1.63 (m, 3H), 1.32-1.26 (m, 1H), 1.30-1.26 (m, 12H), 0.87-0.86 (m, 4H), (M+H)⁺: 257.3 and SFC: 100% chiral purity.

Example 346: Preparation of Intermediate 33A

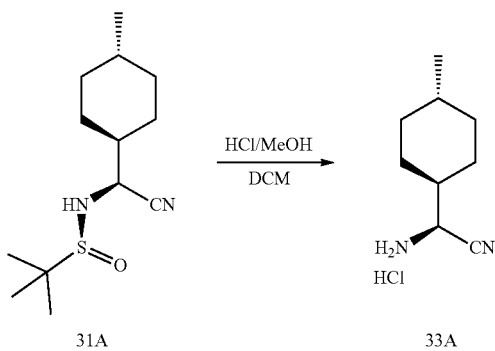 [SMILES: CC(C)(C)[S@](=O)N[C@H](C#N)[C@H]1CC[C@H](C)CC1 ; Cl ; C[C@H]1CC[C@H]([C@H](N)C#N)CC1]

To a solution of compound 31A (35.0 g, 136 mmol, 1.00 eq) in DCM (300 mL) was added HCl/MeOH (4 M, 200 mL, 5.86 eq) at 0° C. The mixture was stirred 25° C. for 3 hrs until TLC indicated compound 31A was completely consumed. The mixture was concentrated under reduced pressure to give a residue. The crude product was triturated with DCM (200 mL) at 25° C. for 30 min. Compound 33A (21.0 g, 111 mmol, 81.5% yield, HCl) was obtained as a white solid. The structure was confirmed by ¹H NMR (400 MHz, DMSO-d₆): δ 9.30 (s, 3H), 4.50 (d, J=6.4 Hz, 1H), 1.90-1.70 (m, 5H), 1.33-1.25 (m, 1H), 1.16-1.02 (m, 2H), 0.94-0.84 (m, 5H).

Example 347: Preparation of Intermediate 34A

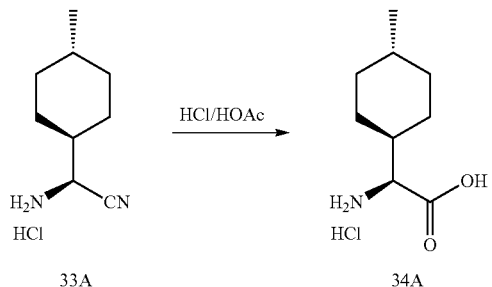

To a solution of compound 33A (21.0 g, 111 mmol, 1.00 eq, HCl) in HOAc (22.0 g, 367 mmol, 21.00 mL, 3.30 eq) was added HCl (6 M, 210 mL, 11.3 eq). The mixture was stirred 125° C. for 12 hrs. ¹H NMR detected the desired compound. The mixture was filtered and the cake was washed with DCM (200 mL) and concentrated to give the product 34A (20.0 g, 96.2 mmol, 86.5% yield, HCl) as a white solid. ¹H NMR (400 MHz, DMSO-d₆): δ 8.31-8.27 (m, 3H), 3.73 (brs, 1H), 1.75-1.59 (m, 5H), 1.28-1.24 (m, 2H), 1.10-1.07 (m, 1H), 0.90-0.78 (m, 5H); and LC-MS: (M+H)⁺: 172.1.

Example 348: Preparation of Intermediate 60d

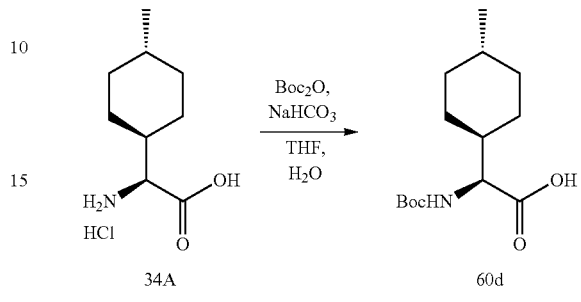

To a solution of compound 34A (20.0 g, 96.2 mmol, 1.00 eq, HCl) in THF (200 mL) and H₂O (100 mL) was added NaHCO₃ (40.4 g, 481 mmol, 18.7 mL, 5.00 eq) and Boc₂O (31.5 g, 144 mmol, 33.1 mL, 1.50 eq) at 0° C. The mixture was stirred at 25° C. for 2 hrs. LC-MS showed compound 34A was consumed completely and the desired mass was present. The mixture was filtered. The filtrate was extracted with MTBE (200 mL). The water phase was adjusted pH to 2 by 1 M HCl and extracted with ethyl acetate (100 mL*4), dried over Na₂SO₄, filtered and concentrated under reduced pressure to give a residue. The crude product was triturated with petroleum ether (100 mL) at 25° C. for 30 min. Compound 60d (17.0 g, 62.3 mmol, 64.7% yield, 99.5% purity) was obtained as a white solid. The structure was confirmed by ¹H NMR 400 MHz, DMSO-d₆): δ 6.40 (brs, 1H), 3.82 (t, J=6.0 Hz, 1H), 1.70-1.39 (m, 5H), 1.39 (s, 9H), 1.32-1.23 (m, 1H), 1.17-1.04 (m, 2H), 0.94-0.82 (m, 5H).

Example 349: Preparation of Intermediate 36A

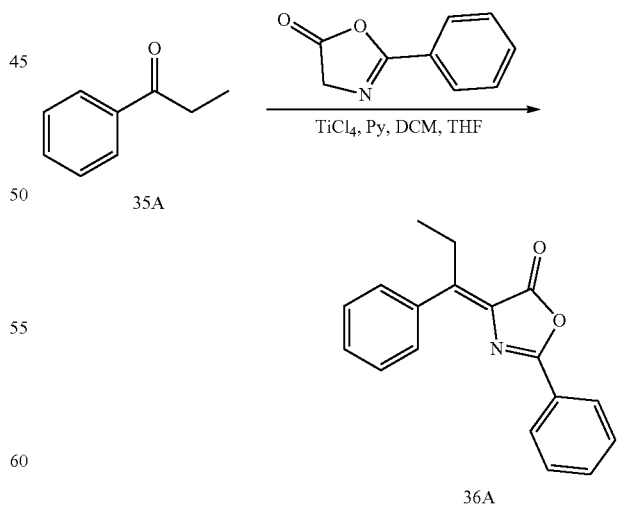

THF (150 mL) was chilled under N₂ to −10° C. A solution of TiCl₄ (21.2 g, 112 mmol, 1.50 eq) in DCM (30.0 mL) was added and stirred for 20 min. To the stirring solution, a solution of compound 35A (10.0 g, 74.5 mmol, 9.90 mL, 1.00 eq) in THF (30.0 mL) was added and the mixture was stirred for 10 min, then the imino lactone depicted above (18.0 g, 112 mmol, 1.50 eq) was added and stirred for a further 30 min. To this mixture, pyridine (11.8 g, 149 mmol, 12.0 mL, 2.00 eq) was added dropwise. The mixture was stirred for a further 5 hrs at 0° C. TLC (petroleum ether:ethyl acetate=10:1, plate 1, $R_f$ ($R_1$)=0.80, $R_f$ ($P_1$)=0.75) showed compound 35A was consumed completely and a major new spot was generated. Saturated $NH_4Cl$ (400 mL) was added and the aqueous layer was extracted with EtOAc (300 mL*2), the combined organic phase was washed with brine (200 mL*2), dried over $Na_2SO_4$, concentrated under reduced pressure to give a residue. The residue was purified by column with petroleum ether:ethyl acetate=50:1 ($SiO_2$, petroleum ether:ethyl acetate=10:1, plate 2, $R_f$ ($P_1$)=0.75). Compound 36A (16.6 g, 59.9 mmol, 80.3% yield) was obtained as a light yellow oil, confirmed by LCMS: (M+H)$^+$: 278.2 and $^1$H NMR δ 8.10-7.43 (10H), 3.30 (q, J=7.6 Hz, 2H), 1.17 (t, J=7.4 Hz, 3H).

Example 350: Preparation of Intermediate 37A

36A

37A

To a solution of $CH_3ONa$ (323 mg, 5.99 mmol, 0.100 eq) in MeOH (150 mL) at 25° C. was added compound 36A (16.6 g, 59.8 mmol, 1.00 eq), then the mixture was stirred at 25° C. for 2 hrs. TLC (petroleum ether:ethyl acetate=5:1, plate 1, $R_f$($R_1$)=0.75, $R_f$($P_1$)=0.20) showed compound 36A was consumed completely and a major new spot was generated. MeOH was removed in vacuo to give a residue. The residue was purified by column with petroleum ether: methyl tert-butyl ether=3:1 ($SiO_2$, petroleum ether:ethyl acetate=5:1, plate 2, $R_f$($P_1$)=0.20). Compound 37A (9.60 g, 30.3 mmol, 50.7% yield, 97.8% purity) was obtained as a white solid, confirmed by LCMS: (M+H)$^+$: 310.2 and H NMR: δ 7.55-7.27 (m, 10H), 7.14 (s, 1H), 3.89 (s, 3H), 2.64 (q, J=7.4 Hz, 2H), 1.02 (t, J=7.4 Hz, 3H Example 351: Preparation of Intermediate 38A and 39A

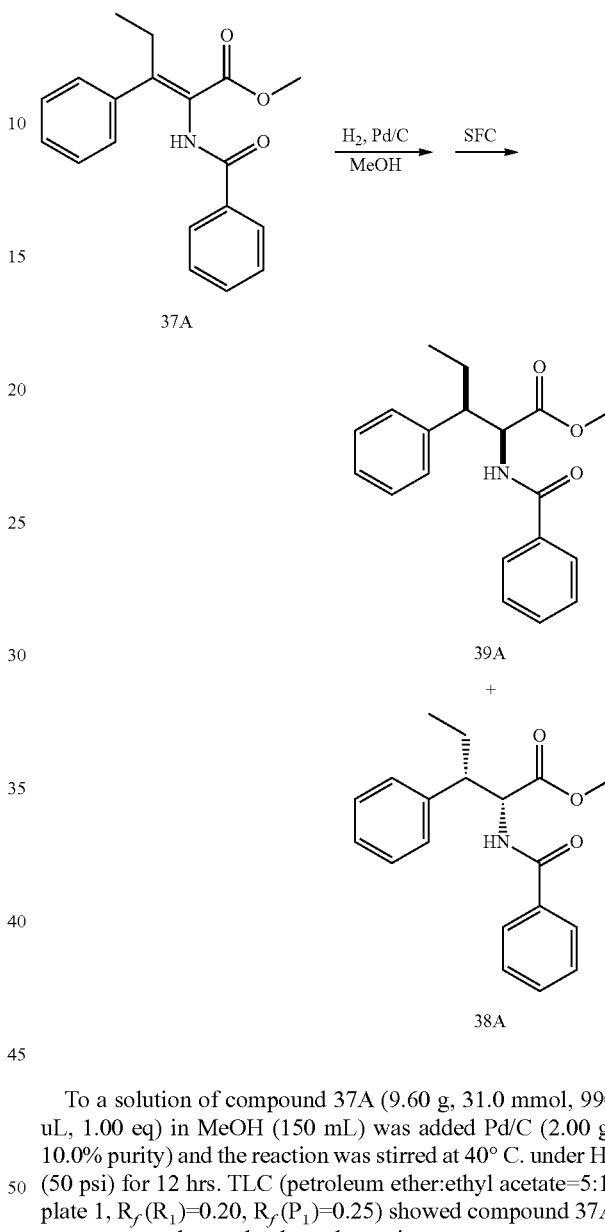

To a solution of compound 37A (9.60 g, 31.0 mmol, 990 uL, 1.00 eq) in MeOH (150 mL) was added Pd/C (2.00 g, 10.0% purity) and the reaction was stirred at 40° C. under $H_2$ (50 psi) for 12 hrs. TLC (petroleum ether:ethyl acetate=5:1, plate 1, $R_f$($R_1$)=0.20, $R_f$($P_1$)=0.25) showed compound 37A was consumed completely and a major new spot was generated. The mixture was filtered and the filtrate was concentrated in vacuum to give a residue, which was a mixture of stereoisomers 38A and 39A. It was directly used for the next step without further purification.

Compound 38A was purified by Prep-SFC (column: DAICEL CHIRALPAK AD-H (250 mm*30 mm, 5 um); mobile phase: [0.1% $NH_3H_2O$ MeOH]; B %: 25%-25%, 4 min; 520 min). Compound 38A (4.50 g, 14.4 mmol, 95.7% yield, 100% purity) was obtained as a white solid, confirmed by LCMS: (M+H)$^+$: 312.2; $^1$H NMR: 76-7.74 (m, 2H), 7.46-7.44 (m, 3H), 7.31-7.29 (m, 2H), 7.26-7.25 (m, 1H), 7.16-7.14 (m, 2H), 6.59 (d, J=8.0 Hz, 1H), 5.07-5.04 (m, 1H), 3.59 (s, 3H), 3.04-2.98 (m, 1H), 2.04-1.90 (m, 2H), 0.86 (t, J=7.4 Hz, 3H).

Example 352: Preparation of Intermediate 40A

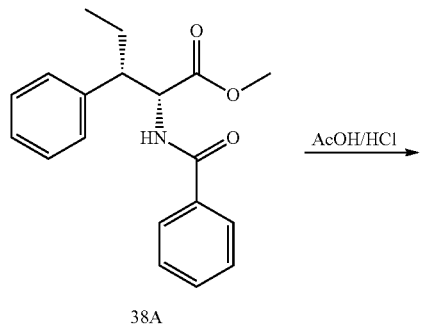

38A

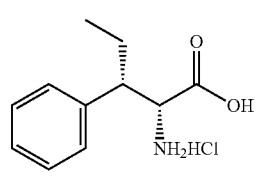

40A

A solution of compound 38A (4.50 g, 14.4 mmol, 1.00 eq) in HCl (3 M, 240 mL, 50.0 eq) and AcOH (86.8 g, 1.45 mol, 82.6 mL, 100 eq) was stirred at 125° C. for 60 hrs. TLC (dichloromethane:methanol=10:1, plate 1, $R_f$ (R$_1$)=0.95, $R_f$ (P$_1$)=0.00) showed compound 38A was consumed completely and a major new spot was generated. The mixture was evaporated under reduced pressure to give a residue. The residue was slurried with DCM (100 mL). Compound 40A (3.22 g, 14.0 mmol, 97.0% yield, 100% purity, HCl) was obtained as a white solid, confirmed by LCMS: (M+H)$^+$: 194.1 and H NMR: δ 8.53 (br s, 3H), 7.35-7.21 (m, 5H), 3.99 (d, J=6.4 Hz, 1H), 3.35-3.03 (m, 1H), 1.94-1.80 (m, 2H), 0.69 (t, J=7.2 Hz, 3H).

Example 353: Preparation of Intermediates 41A and 42A

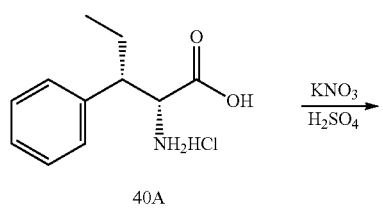

40A

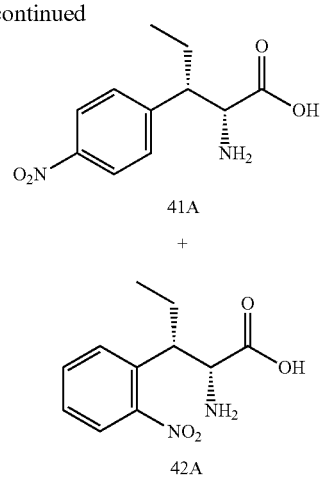

41A

+

42A

To a solution of compound 40A (1.60 g, 6.97 mmol, 1.00 eq, HCl) in H$_2$SO$_4$ (27.3 g, 278 mmol, 14.9 mL, 40.0 eq) was added KNO$_3$ (774 mg, 7.66 mmol, 1.10 eq) in portions at 0° C., the mixture was stirred at 25° C. for 2 hrs. LCMS (EW17597-90-P1D1) showed compound 40A was consumed completely and desired MS was detected. The mixture was slowly added to ice water (200 mL) and Na$_2$CO$_3$ (31.8 g, 300 mmol) was added to adjust pH=7-8. The solution was directly used for the next step. Compounds 41A and 42A (1.66 g, crude) was obtained as a light yellow solution.

Example 354: Preparation of Intermediate 19A

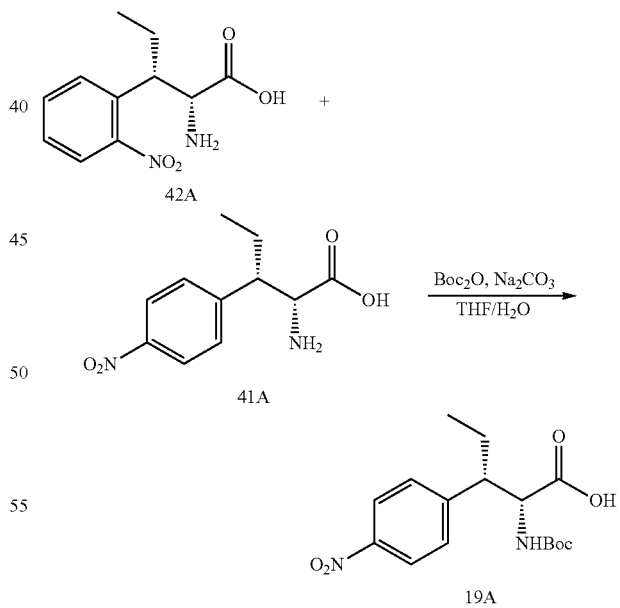

To a solution of compounds 41A and 42A (1.66 g, 6.97 mmol, 1.00 eq) in H$_2$O (200 mL) was added THF (150 mL), Na$_2$CO$_3$ (2.22 g, 20.9 mmol, 3.00 eq) and Boc$_2$O (2.28 g, 10.4 mmol, 2.40 mL, 1.50 eq), then the mixture was stirred at 25° C. for 4 hrs. LCMS EW17597-91-P1 D1) showed compounds 41A and 42A was consumed completely and desired MS was detected. THF was evaporated in vacuum and H₂O (100 mL) was added. The aqueous phase was acidified with 1 N HCl to adjust pH=5-6 and then extracted with EtOAc (150 mL*2), the combined organic phase was washed with brine (100 mL*2), dried over Na₂SO₄, filtered and concentrated under reduced pressure to give a residue. The residue was purified by Prep-SFC (column: DAICEL CHIRALPAK AD-H (250 mm*30 mm, 5 um); mobile phase: [0.1% NH₃H₂O MeOH]; B %: 25%-25%, 3.7 min; 740 min). Compound 19A (1.22 g, 3.58 mmol, 51.4% yield, 99.3% purity) was obtained as a light yellow solid, confirmed by LCMS: (M-99)⁺: 239.1 and ¹H NMR: (400 MHz, DMSO-d₆): δ 8.15-8.11 (m, 2H), 7.51-7.49 (m, 2H), 6.67 (br s, 1H), 4.26-4.22 (m, 1H), 3.16-3.11 (m, 1H), 1.83-1.75 (m, 2H), 1.36 (s, 9H), 0.71 (t, J=7.2 Hz, 3H).

Example 355: tert-butyl N-[(2R)-3-(4-amino-3-fluorophenyl)-1-(4-methylpiperazin-1-yl)-1-oxopropan-2-yl]carbamate) (43A)

Example 356: benzyl N—[(S)-({4-[(2R)-2-{[(tert-butoxy)carbonyl]amino}-3-(4-methylpiperazin-1-yl)-3-oxopropyl]-2-fluorophenyl}carbamoyl)(cyclohexyl)methyl]carbamate) (44A)

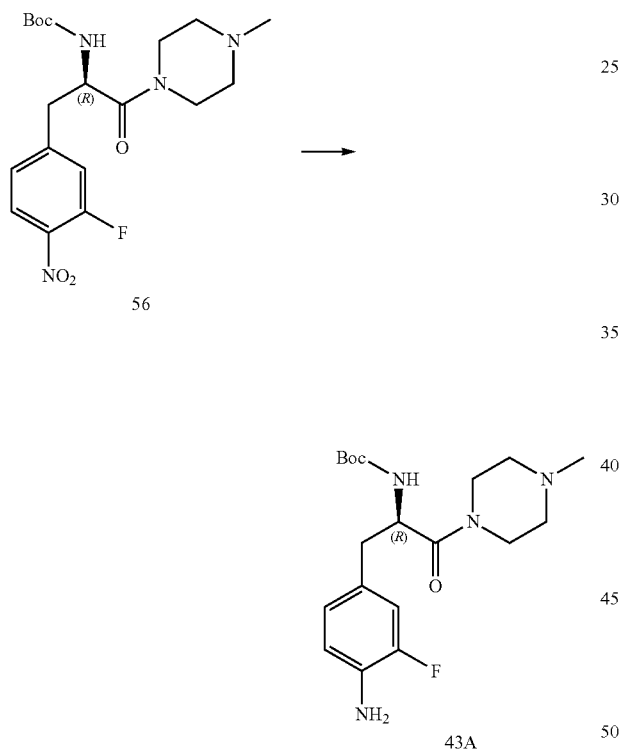

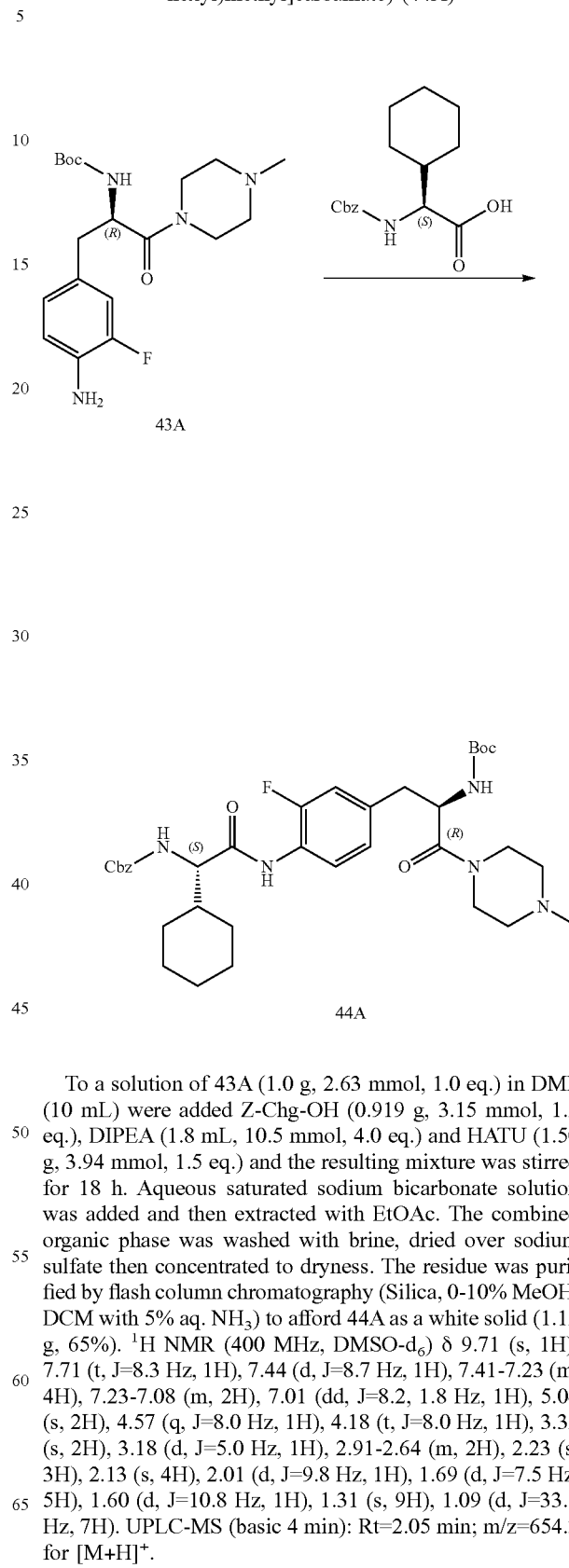

To a degassed solution of 56 (5.30 g, 12.9 mmol, 1.0 eq) in EtOH (50 mL) was added Pd/C (0.5 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 43A as a yellow oil (4.50 g, 91%). ¹H NMR (400 MHz, DMSO-d₆) δ 6.99 (d, J=8.4 Hz, 1H), 6.84 (dd, J=12.6, 1.8 Hz, 1H), 6.71 (dd, J=8.1, 1.9 Hz, 1H), 6.64 (dd, J=9.4, 8.0 Hz, 1H), 4.92 (s, 2H), 4.47 (q, J=7.7 Hz, 1H), 3.51-3.18 (m, 5H), 2.78-2.55 (m, 2H), 2.20 (td, J=8.2, 6.2, 3.3 Hz, 2H), 2.12 (s, 3H), 2.04-1.85 (m, 1H), 1.32 (s, 9H). UPLC-MS (basic 4 min): Rt=1.35 min; m/z=381.3 for [M+H]⁺.

To a solution of 43A (1.0 g, 2.63 mmol, 1.0 eq.) in DMF (10 mL) were added Z-Chg-OH (0.919 g, 3.15 mmol, 1.2 eq.), DIPEA (1.8 mL, 10.5 mmol, 4.0 eq.) and HATU (1.50 g, 3.94 mmol, 1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM with 5% aq. NH₃) to afford 44A as a white solid (1.12 g, 65%). ¹H NMR (400 MHz, DMSO-d₆) δ 9.71 (s, 1H), 7.71 (t, J=8.3 Hz, 1H), 7.44 (d, J=8.7 Hz, 1H), 7.41-7.23 (m, 4H), 7.23-7.08 (m, 2H), 7.01 (dd, J=8.2, 1.8 Hz, 1H), 5.04 (s, 2H), 4.57 (q, J=8.0 Hz, 1H), 4.18 (t, J=8.0 Hz, 1H), 3.32 (s, 2H), 3.18 (d, J=5.0 Hz, 1H), 2.91-2.64 (m, 2H), 2.23 (s, 3H), 2.13 (s, 4H), 2.01 (d, J=9.8 Hz, 1H), 1.69 (d, J=7.5 Hz, 5H), 1.60 (d, J=10.8 Hz, 1H), 1.31 (s, 9H), 1.09 (d, J=33.8 Hz, 7H). UPLC-MS (basic 4 min): Rt=2.05 min; m/z=654.3 for [M+H]⁺.

Example 357: tert-butyl N-[(2R)-3-{4-[(2S)-2-amino-2-cyclohexylacetamido]-3-fluorophenyl}-1-(4-methyl piperazin-1-yl)-1-oxopropan-2-yl]carbamate (45A)

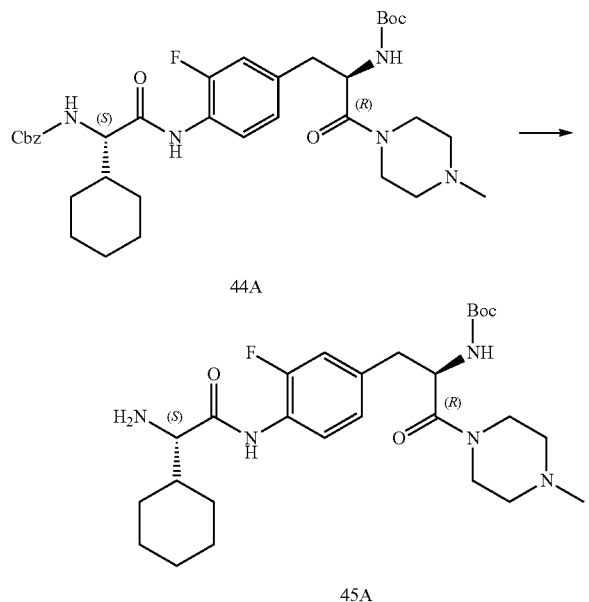

44A

45A

To a degassed solution of 44A (0.280 g, 0.428 mmol, 1.0 eq) in EtOH (50 mL) was added Pd(OH)$_2$ (0.150 g, 0.214 mmol, 0.5 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH (50 mL). The solution was concentrated to dryness to afford 45A as a yellow oil (0.217 g, 78%). $^1$H NMR (400 MHz, DMSO-d$_6$) δ 7.97 (t, J=8.3 Hz, 1H), 7.18 (d, J=9.5 Hz, 2H), 7.12 (d, J=9.0 Hz, 1H), 7.01 (d, J=8.7 Hz, 1H), 4.61-4.51 (m, 1H), 3.22 (d, J=4.6 Hz, 1H), 2.84 (dd, J=13.7, 6.5 Hz, 1H), 2.79-2.69 (m, 1H), 2.21 (s, 3H), 2.13 (d, J=11.3 Hz, 4H), 1.97 (s, 1H), 1.68 (d, J=13.3 Hz, 5H), 1.64-1.54 (m, 4H), 1.31 (s, 9H), 1.26 (s, 4H), 1.21 (s, 1H), 1.08 (dq, J=17.5, 11.6, 10.5 Hz, 4H), 0.91-0.76 (m, 2H). UPLC-MS (basic 2 min): Rt=1.08 min; m/z=520.3 for [M+H]$^+$.

Example 358: General Procedure Z

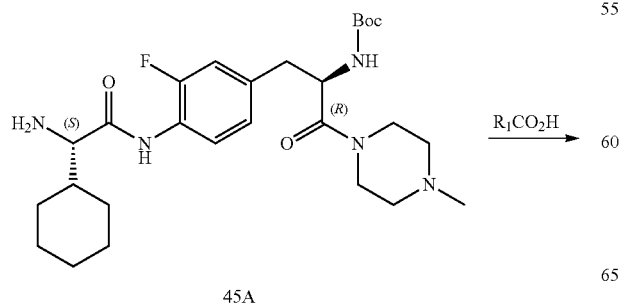

45A

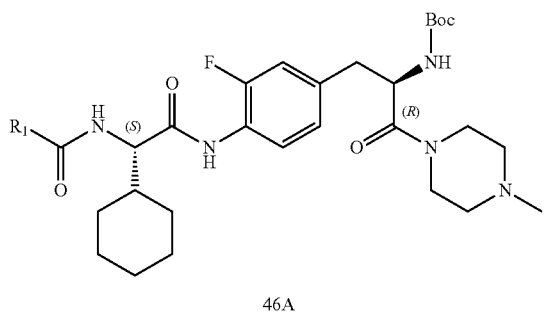

46A

To a solution of 45A (1.0 eq.) in DMF 0.10 mL) were added required carboxylic acid (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 46A.

Example 359: General Procedure AA

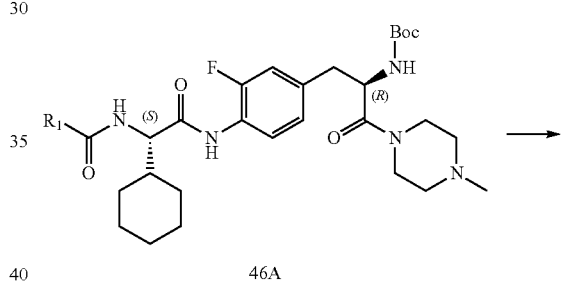

46A

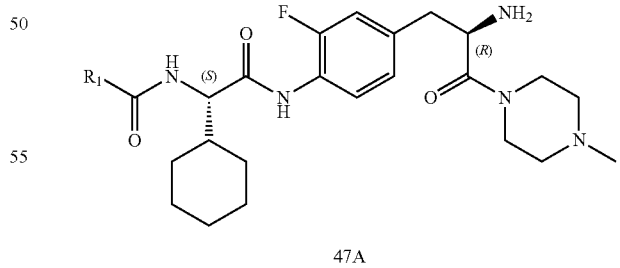

47A

To a solution of 46A (1.0 eq.) in DCM was added TFA and the resulting mixture was stirred at RT for 0.5 h. The reaction mixture was concentrated to dryness and the residue was stirred in aq. sat. K$_2$CO$_3$ solution and then extracted with DCM to afford 47A which was used in the next step without further purification.

Example 360: General Procedure AB

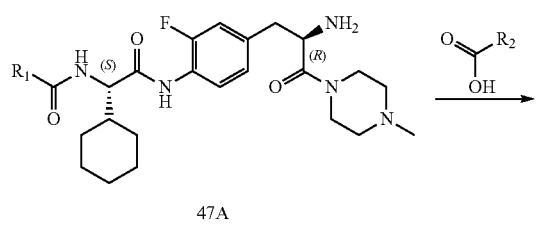

47A 320-324

To a solution of 47A (1.0 eq.) in DMF (0.1 M) were added the required carboxylic acid (1.2 eq.), DIPEA (3.0-8.0 eq.) and then HATU (1.5-2.0 eq.) and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford 320-324.

Example 361: N-[(2R)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxopropan-2-yl]-1-(1-methylpiperidin-4-yl)-1H-pyrazole-5-carboxamide (321)

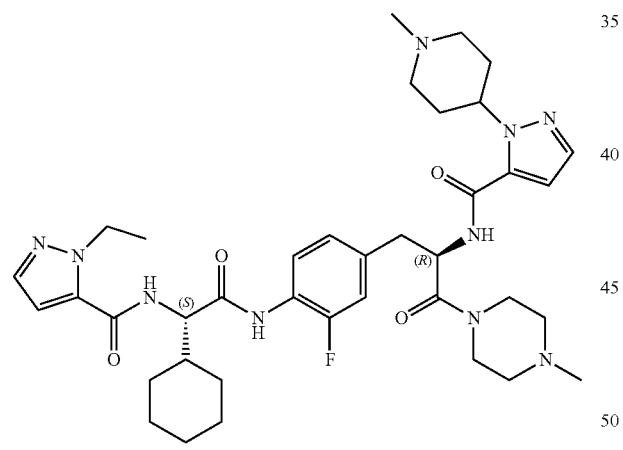

General Procedure AB provided 321. $^1$H NMR (400 MHz, DMSO-$d_6$) δ 9.84 (s, 1H), 8.79 (d, J=8.6 Hz, 1H), 8.42 (d, J=8.4 Hz, 1H), 7.70 (t, J=8.2 Hz, 1H), 7.47 (d, J=2.0 Hz, 2H), 7.18 (dd, J=12.1, 1.9 Hz, 1H), 7.06 (d, J=8.6 Hz, 1H), 7.00 (d, J=2.1 Hz, 1H), 6.84 (d, J=2.0 Hz, 1H), 5.16-5.05 (m, 1H), 4.56 (t, J=8.5 Hz, 1H), 4.47 (q, J=7.1 Hz, 2H), 3.51 (s, 2H), 3.47 (d, J=13.5 Hz, 1H), 2.99 (dd, J=13.6, 5.8 Hz, 1H), 2.92 (dd, J=13.6, 9.1 Hz, 1H), 2.81 (d, J=10.9 Hz, 1H), 2.76 (d, J=8.1 Hz, 1H), 2.20 (d, J=5.6 Hz, 3H), 2.12 (d, J=2.5 Hz, 7H), 2.00 (td, J=11.9, 3.7 Hz, 1H), 1.93-1.82 (m, 1H), 1.86 (s, 4H), 1.79 (d, J=12.4 Hz, 1H), 1.71 (s, 4H), 1.63 (s, 3H), 1.56 (s, 1H), 1.28 (t, J=7.1 Hz, 3H), 1.17 (s, 6H), 1.05 (dd, J=13.6, 9.3 Hz, 1H). UPLC-MS (basic 2 min): rt=1.03 min; m/z=733.4 for [M+H]$^+$.

Example 362: N-[(2R)-3-{4-[(2S)-2-cyclohexyl-2-[(1-ethyl-1H-pyrazol-5-yl)formamido]acetamido]-3-fluorophenyl}-1-(4-methylpiperazin-1-yl)-1-oxopropan-2-yl]-1,2,3-thiadiazole-5-carboxamide (322)

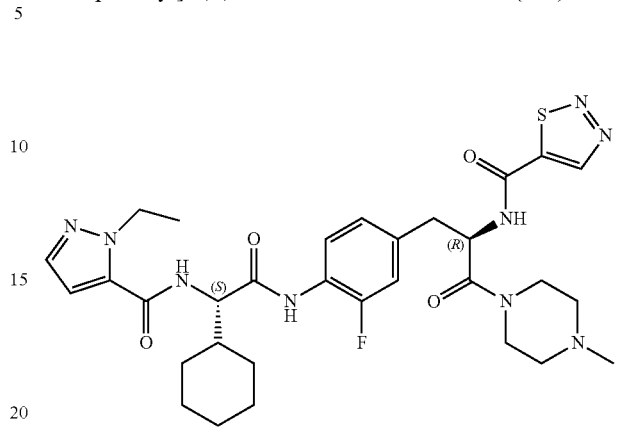

General Procedure AB provided 322. $^1$H NMR (400 MHz, MeOH-$d_4$) δ 9.19 (s, 1H), 7.82 (t, J=8.1 Hz, 1H), 7.49 (d, J=2.1 Hz, 1H), 7.20-7.03 (m, 2H), 6.85 (d, J=2.1 Hz, 1H), 5.23 (dd, J=8.5, 7.1 Hz, 1H), 4.64-4.35 (m, 3H), 3.74-3.40 (m, 4H), 3.22-3.00 (m, 2H), 2.43 (d, J=5.9 Hz, 2H), 2.21 (s, 4H), 1.97 (s, 1H), 1.90 (d, J=11.7 Hz, 3H), 1.79 (d, J=9.2 Hz, 4H), 1.70 (d, J=11.5 Hz, 1H), 1.37 (t, J=7.2 Hz, 3H), 1.23 (dp, J=33.6, 12.2 Hz, 3H). UPLC-MS (basic 4 min): rt=1.66 min; m/z=654.3 for [M+H]$^+$.

Example 363: N-[(2R)-3-{4-[(2S)-2-cyclohexyl-2-[2,2-difluoro-2-(6-methoxypyridin-3-yl)acetamido]acetamido]-3-fluorophenyl}-1-(4-methylpiperazin-1-yl)-1-oxopropan-2-yl]-1,2,3-thiadiazole-5-carboxamide (323)

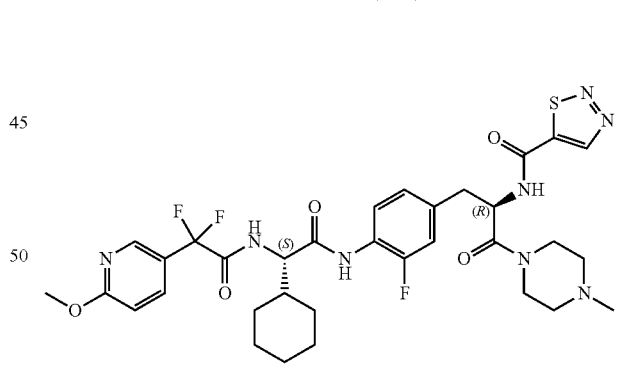

General Procedure AB provided 323. $^1$H NMR (400 MHz, MeOH-$d_4$) δ 9.19 (s, 1H), 8.40 (s, 1H), 7.89 (dd, J=8.8, 2.5 Hz, 1H), 7.77 (t, J=8.1 Hz, 1H), 7.17-7.05 (m, 2H), 6.87 (d, J=8.7 Hz, 1H), 5.26-5.18 (m, 1H), 4.43 (d, J=8.7 Hz, 1H), 3.95 (s, 3H), 3.64 (s, 1H), 3.50 (d, J=8.5 Hz, 2H), 3.45 (s, 2H), 3.18-3.03 (m, 2H), 2.80 (s, 2H), 2.37 (d, J=13.7 Hz, 2H), 2.16 (s, 3H), 2.13 (d, J=8.6 Hz, 1H), 1.90 (d, J=8.8 Hz, 1H), 1.81 (s, 1H), 1.72 (dd, J=30.3, 13.8 Hz, 5H), 1.32-1.22 (m, 3H), 1.18 (d, J=16.3 Hz, 2H), 1.08 (dd, J=26.8, 13.1 Hz, 1H). UPLC-MS (basic 2 min): rt=1.24 min; m/z=717.3 for [M+H]$^+$.

Example 364: N-[(2R)-3-{4-[(2S)-2-cyclohexyl-2-[2,2-difluoro-2-(5-methoxypyridin-3-yl)acetamido]acetamido]-3-fluorophenyl}-1-(4-methylpiperazin-1-yl)-1-oxopropan-2-yl]-1,2,3-thiadiazole-5-carboxamide (324)

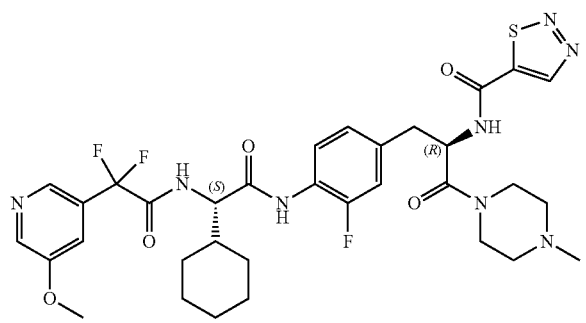

General Procedure AB provided 324. $^1$H NMR (400 MHz, MeOH-d$_4$) δ 9.19 (s, 1H), 8.39 (d, J=3.8 Hz, 2H), 7.77 (t, J=8.1 Hz, 1H), 7.64 (s, 1H), 7.10 (dd, J=19.8, 9.9 Hz, 2H), 5.22 (t, J=7.8 Hz, 2H), 4.43 (d, J=8.8 Hz, 1H), 3.92 (s, 2H), 3.63 (s, 2H), 3.47 (s, 4H), 3.17-3.02 (m, 3H), 2.38 (s, 2H), 2.16 (s, 3H), 1.89 (s, 2H), 1.86-1.63 (m, 5H), 1.32-1.00 (m, 6H). UPLC-MS (basic 4 min): rt=1.72 min; m/z=717.3 for [M+H]$^+$.

Example 365: 2S)-2-cyclohexyl-2-[(1-ethyl-1H-pyrazol-5-yl)formamido]-N-{2-fluoro-4-[(2R)-3-(4-methylpiperazin-1-yl)-3-oxo-2-({pyrido [3,4-d]pyrimidin-4-yl}amino)propyl]phenyl}acetamide) (320)

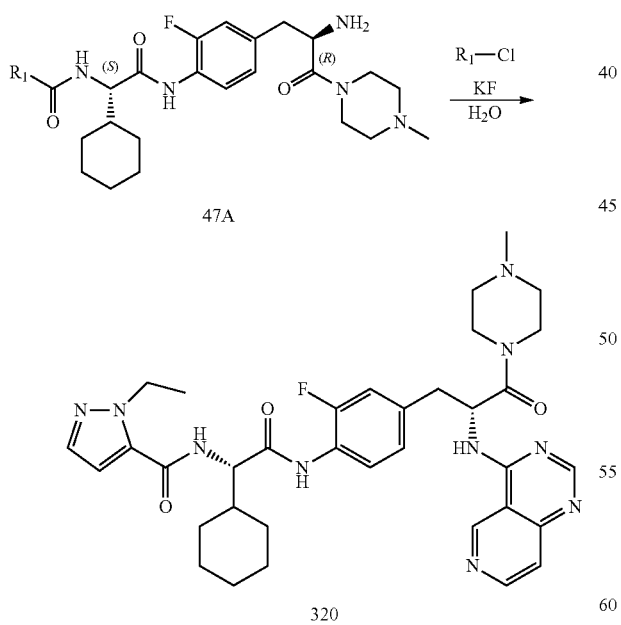

A suspension of 47A (1.0 eq,), the required aryl chloride (1.0 eq.) and potassium fluoride (5.0 eq.) in H$_2$O (0.1 M) was heated at 100 C via microwave irradiation for 5 minutes. The reaction mixture was cooled to RT and then directly purified via reverse phase column chromatography on a 120 g C18 cartridge eluting with a 5-95% H$_2$O:MeCN eluent (0.1% ammonia) to afford 320. $^1$H NMR (400 MHz, MeOH-d$_4$) δ 9.03 (s, 1H), 8.59 (s, 1H), 8.53 (d, J=5.7 Hz, 1H), 8.11 (dd, J=5.7, 0.9 Hz, 1H), 7.83 (t, J=8.1 Hz, 1H), 7.49 (d, J=2.1 Hz, 1H), 7.24-7.11 (m, 2H), 6.85 (d, J=2.1 Hz, 1H), 5.58 (t, J=7.8 Hz, 1H), 4.59-4.46 (m, 3H), 3.73-3.40 (m, 3H), 3.25 (d, J=7.7 Hz, 2H), 2.52-2.34 (m, 2H), 2.20 (s, 4H), 1.89 (d, J=11.5 Hz, 3H), 1.84-1.61 (m, 4H), 1.37 (t, J=7.2 Hz, 3H), 1.34-1.04 (m, 4H). UPLC-MS (basic 2 min): rt=1.60 min; m/z=671.5 for [M+H]$^+$.

Example 366: Preparation of (49A)

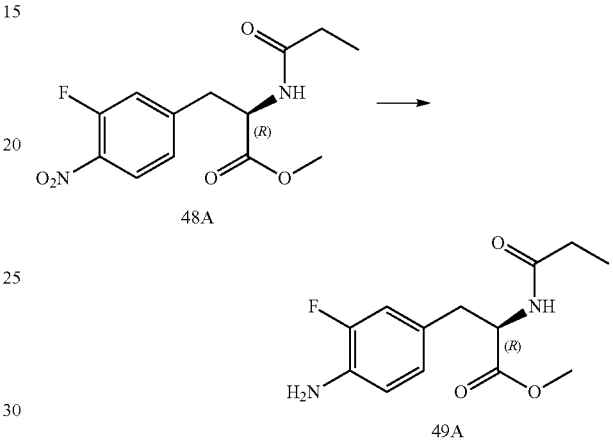

To a degassed solution of 48A prepared from by conventional methods (1.70 g, 5.70 mmol, 1.0 eq) in EtOH (30 mL) was added Pd/C (0.5 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 49A as a brown solid (1.33 g, 87%). $^1$H NMR (400 MHz, DMSO-d$_6$) δ 8.15 (d, J=7.8 Hz, 1H), 6.83 (dd, J=12.5, 1.7 Hz, 1H), 6.67-6.72 (m, 1H), 6.60-6.67 (m, 1H), 4.95 (s, 2H), 4.35 (ddd, J=9.3, 7.9, 5.6 Hz, 1H), 3.59 (s, 3H), 2.84 (dd, J=13.9, 5.6 Hz, 1H), 2.71 (dd, J=13.8, 9.3 Hz, 1H), 2.06 (q, J=7.6 Hz, 2H), 0.92 (t, J=7.6 Hz, 3H) UPLC-MS (basic 2 min): Rt=0.80 min; m/z=269.1 for [M+H]$^+$.

Example 367: methyl (2R)-3-{4-[(2S)-2-{[(tert-butoxy)carbonyl]amino}-2-cyclohexylacetamido]-3-fluorophenyl}-2-propanamidopropanoate) (50A)

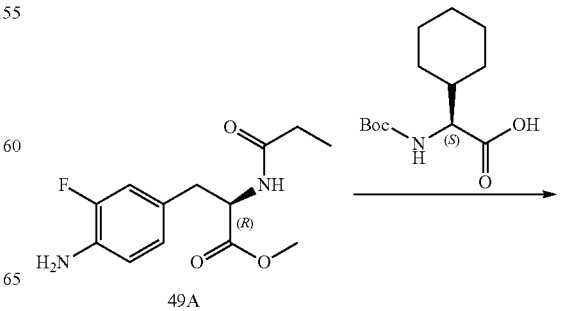

-continued

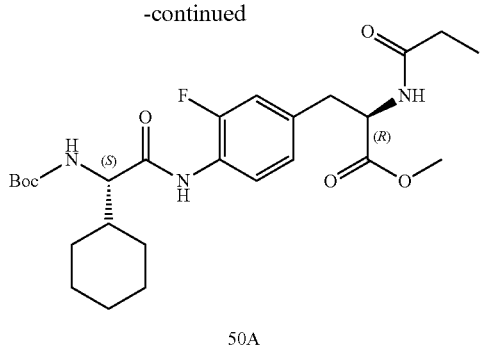

50A

To a solution of 49A (1.33 g, 4.96 mmol, 1.0 eq.) in DMF (25 mL) were added (2S)-2-{[(tert-butoxy)carbonyl]amino}-2-cyclohexylacetic acid (1.30 g, 5.05 mmol, 1.02 eq.), DIPEA (7.0 mL, 40.2 mmol, 8.0 eq.) and HATU (3.20 g, 8.42 mmol, 1.7 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 50A as a white solid (1.99 g, 79%). $^1$H NMR (400 MHz, DMSO-$d_6$) δ 9.61 (br s, 1H), 8.19-8.27 (m, 1H), 7.69 (t, J=8.3 Hz, 1H), 7.11 (br d, J=11.9 Hz, 1H), 6.99 (br d, J=7.9 Hz, 1H), 6.85 (br d, J=7.9 Hz, 1H), 4.40-4.50 (m, 1H), 3.85-4.12 (m, 1H), 3.61 (s, 3H), 2.96-3.05 (m, 1H), 2.87 (br dd, J=13.9, 4.3 Hz, 1H), 2.06 (d, J=7.6 Hz, 2H), 1.68 (br d, J=9.0 Hz, 3H), 1.51-1.63 (m, 2H), 1.38 (s, 11H), 0.98-1.19 (m, 6H), 0.91 (t, J=7.6 Hz, 3H). UPLC-MS (basic 2 min): Rt=1.17 min; m/z=508.4 for [M+H]$^+$.

Example 368: (S)-cyclohexyl({2-fluoro-4-[(2R)-3-methoxy-3-oxo-2-propanamidopropyl]phenyl}carbamoyl) methanaminium trifluoroacetate) (51A)

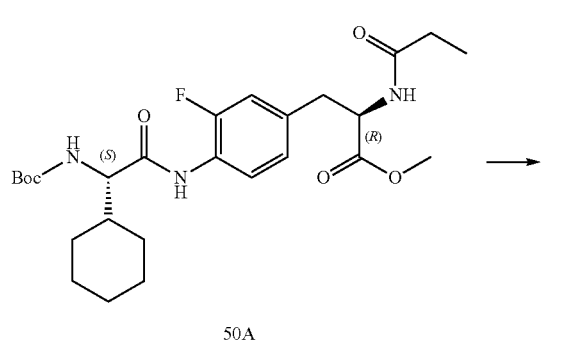

50A

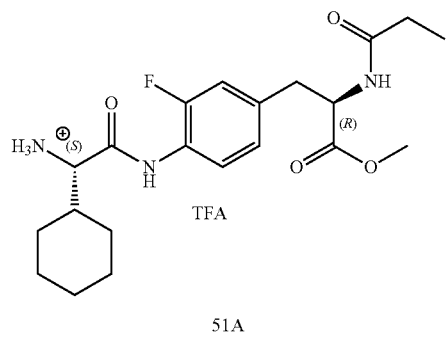

51A

To a solution of 50A (1.99 g, 3.92 mmol, 1.0 eq.) in DCM (24.0 mL) was added TFA (6.0 mL) and the resulting mixture was stirred at RT for 1 h. The reaction mixture was concentrated to dryness to afford 51A (1.43 g, 70%) which was used in the next step without further purification. $^1$H NMR (400 MHz, DMSO-$d_6$) δ 10.22 (s, 1H), 8.33 (br s, 1H), 8.20-8.27 (m, 3H), 7.70 (t, J=8.2 Hz, 1H), 7.18 (br d, J=12.0 Hz, 1H), 7.05 (br d, J=8.3 Hz, 1H), 4.41-4.54 (m, 4H), 3.88 (br s, 1H), 3.62 (s, 3H), 3.03 (br dd, J=13.6, 5.3 Hz, 1H), 2.82-2.92 (m, 1H), 2.06 (q, J=7.5 Hz, 2H), 1.71-1.82 (m, 3H), 1.57-1.70 (m, 2H), 1.01-1.21 (m, 6H), 0.91 (t, J=7.6 Hz, 3H). UPLC-MS (basic 2 min): rt=0.85 min; m/z=408.3 for [M+H]$^+$.

Example 369: methyl (2R)-3-{4-[(2S)-2-cyclohexyl-2-[(1-ethyl-1H-pyrazol-5-yl)formamido]acetamido]-3-fluorophenyl}-2-propanamidopropanoate) (51A)

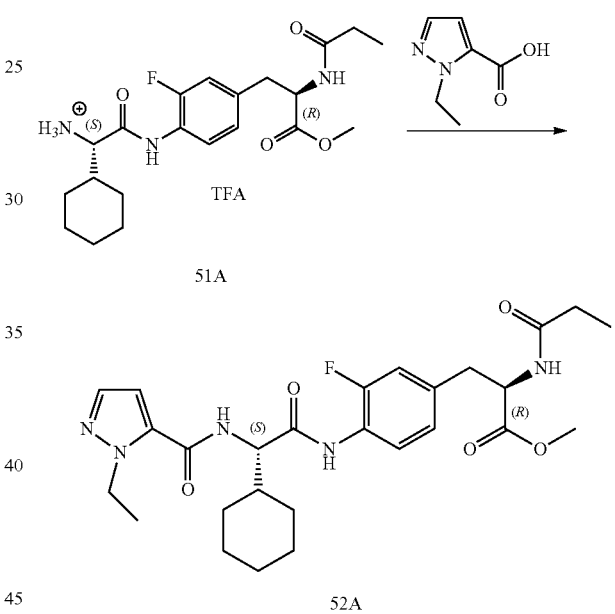

52A

To a solution of 51A (1.43 g, 2.74 mmol, 1.0 eq.) in DMF (25 mL) were added 1-ethyl-1H-pyrazole-5-carboxylic acid (0.388 g, 2.77 mmol, 1.01 eq,), DIPEA (4.0 mL, 23.0 mmol, 8.0 eq) and HATU (1.70 g, 4.47 mmol, 1.6 eq.) and the resulting mixture was stirred at RT for 1 h. The mixture was diluted with aq. sat. NaHCO$_3$ solution (30 mL) and then extracted with DCM (30 mL). The organic layer was washed with brine (30 mL), dried over Na$_2$SO$_4$ then concentrated to afford 52A as an off-white solid (1.00 g, 69% yield) which was used in the next step without further purification. $^1$H NMR (400 MHz, DMSO-$d_6$) δ 9.79-9.92 (m, 1H), 8.44 (br s, 1H), 8.22 (br d, J=7.8 Hz, 1H), 7.68 (br t, J=7.9 Hz, 1H), 7.47 (s, 1H), 7.12 (br d, J=11.6 Hz, 1H), 7.00 (br s, 2H), 4.50-4.57 (m, 1H), 4.40-4.50 (m, 3H), 3.61 (br s, 3H), 3.01 (br dd, J=13.3, 4.6 Hz, 1H), 2.81-2.89 (m, 1H), 2.01-2.10 (m, 2H), 1.77-1.90 (m, 2H), 1.67-1.77 (m, 2H), 1.58-1.67 (m, 2H), 1.00-1.19 (m, 8H), 0.91 (br t, J=7.4 Hz, 3H). UPLC-MS (basic 2 min): rt=1.07 min; m/z=530.3 for [M+H]$^+$.

Example 370: (2R)-3-{4-[(2S)-2-cyclohexyl-2-[(1-ethyl-1H-pyrazol-5-yl)formamido]acetamido]-3-fluorophenyl}-2-propanamidopropanoic acid) (53A)

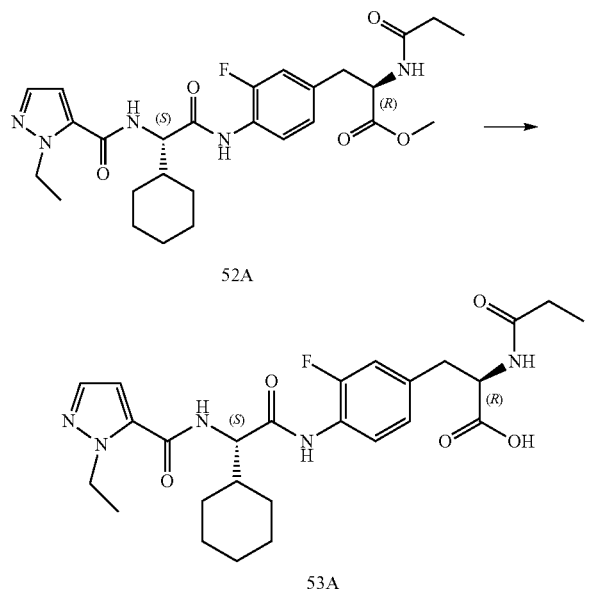

52A

53A

To a solution of 52A (1.00 g, 1.88 mmol, 1.0 eq.) in THF (20 mL) was added a solution of LiOH·H$_2$O (1.6 g, 38.1 mmol, 20.0 eq.) in H$_2$O (20 mL). The resulting mixture was stirred at RT for 1 h and then acidified with 1M aq. HCl solution. The resulting precipitate was filtered to afford 53A as a white solid (0.632 g, 65%). $^1$H NMR (400 MHz, DMSO-d$_6$) δ 11.95-13.58 (m, 1H), 9.85 (s, 1H), 8.44 (d, J=8.2 Hz, 1H), 7.95-8.13 (m, 1H), 7.61-7.71 (m, 1H), 7.47 (d, J=1.9 Hz, 1H), 7.10 (dd, J=11.7, 1.4 Hz, 1H), 6.95-7.04 (m, 2H), 4.53 (s, 1H), 4.43-4.50 (m, 2H), 4.34-4.42 (m, 1H), 2.98-3.07 (m, 1H), 2.82 (dd, J=13.9, 9.8 Hz, 1H), 2.05 (q, J=7.6 Hz, 2H), 1.76-1.91 (m, 2H), 1.67-1.75 (m, 2H), 1.55-1.66 (m, 2H), 1.24-1.31 (m, 3H), 1.10-1.23 (m, 4H), 0.98-1.09 (m, 1H), 0.91 (t, J=7.6 Hz, 3H). UPLC-MS (basic 2 min): rt=1.00 min; m/z=514.3 for [M−H]$^+$.

Example 371: General Procedure AC

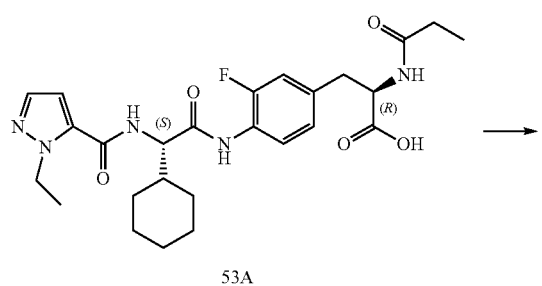

53A 325 and 382

To a solution of 53A (1.0 eq.) in DMF (0.1 M) were added the required amine (1.2 eq.), DIPEA (3.0-8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 325 and 382.

Example 372: N-[(2R)-3-{4-[(2S)-2-cyclohexyl-2-[2,2-difluoro-2-(6-methoxypyridin-3-yl)acetamido]acetamido]-3-fluorophenyl}-1-(4-methylpiperazin-1-yl)-1-oxopropan-2-yl]-1,2,3-thiadiazole-5-carboxamide) (325)

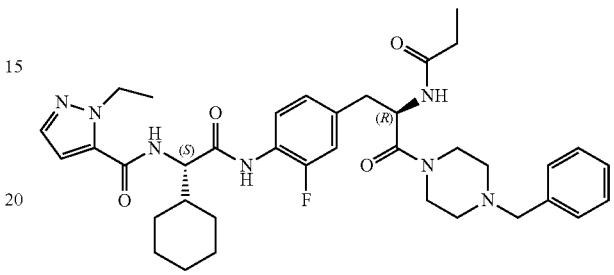

Using General Procedure AC provided 325. $^1$H NMR (400 MHz, DMSO-d$_6$) δ 9.87 (s, 1H), 8.44 (d, J=8.3 Hz, 1H), 8.20 (d, J=8.3 Hz, 1H), 7.69 (t, J=8.2 Hz, 1H), 7.47 (d, J=2.0 Hz, 1H), 7.34-7.20 (m, 5H), 7.11 (d, J=11.5 Hz, 1H), 7.03-6.97 (m, 2H), 4.90 (q, J=7.8 Hz, 1H), 4.56 (t, J=8.4 Hz, 1H), 4.46 (q, J=7.2 Hz, 2H), 3.52-3.39 (m, 4H), 2.89 (dd, J=13.4, 6.7 Hz, 1H), 2.75 (dd, J=13.3, 7.9 Hz, 1H), 2.32-2.21 (m, 2H), 2.18-2.08 (m, 1H), 2.04 (q, J=7.6 Hz, 2H), 1.97 (ddd, J=14.1, 6.8, 2.3 Hz, 1H), 1.85 (ddt, J=26.4, 14.4, 5.9 Hz, 3H), 1.77-1.57 (m, 4H), 1.27 (t, J=7.1 Hz, 3H), 1.24-0.96 (m, 6H), 0.90 (t, J=7.6 Hz, 3H). UPLC-MS (basic 4 min): rt=1.92 min; m/z=674.4 for [M+H]$^+$.

Example 373: N-[(2R)-3-{4-[(2S)-2-cyclohexyl-2-[(1-ethyl-1H-pyrazol-5-yl)formamido]acetamido]-3-fluorophenyl}-1-(4-hydroxy-4-methylpiperidin-1-yl)-1-oxopropan-2-yl]propanamide (382)

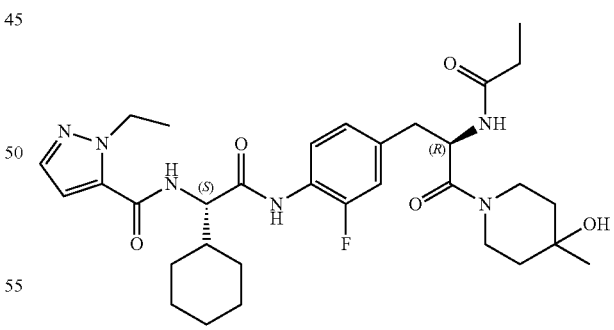

Using General Procedure AC provided 382. $^1$H NMR (400 MHz, DMSO-d$_6$) δ 9.48 (s, 1H), 8.10 (d, J=8.4 Hz, 1H), 7.79 (d, J=8.4 Hz, 1H), 7.68 (s, 1H), 7.45 (d, J=2.0 Hz, 1H), 7.06 (dd, J=11.9, 1.9 Hz, 1H), 6.99 (dd, J=8.2, 1.9 Hz, 1H), 6.92 (d, J=2.0 Hz, 1H), 4.96 (q, J=7.5 Hz, 1H), 4.56 (t, J=8.3 Hz, 1H), 4.48 (q, J=7.1 Hz, 2H), 4.04 (s, 1H), 3.37-3.06 (m, 2H), 3.00-2.89 (m, 2H), 2.79 (dd, J=13.5, 7.4 Hz, 1H), 2.08 (q, J=7.6 Hz, 2H), 1.98-1.86 (m, 1H), 1.85-1.58 (m, 5H), 1.41 (s, 3H), 1.32 (t, J=7.1 Hz, 4H), 1.27-1.02

(m, 9H), 0.95 (t, J=7.6 Hz, 3H). UPLC-MS (basic 4 min): rt=1.60 min; m/z=613.3 for [M+H]⁺.

Example 374: Preparation of 54A

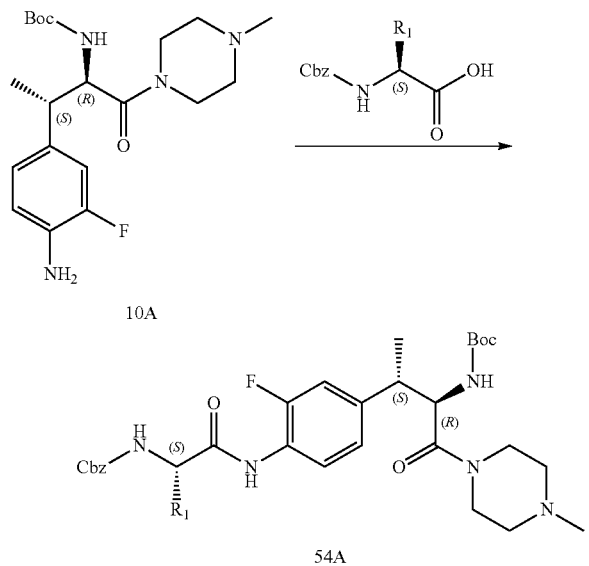

54A

To a solution of 54A (1.0 eq.) in DMF was added the Cbz protected glycine derivative (1.2 eq.), DIPEA (4.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate, then concentrated to dryness. The residue was purified by flash column chromatography (Silica, 0-10% MeOH, DCM with 5% aq. NH₃) to afford 54A.

Example 375: Preparation of 55A

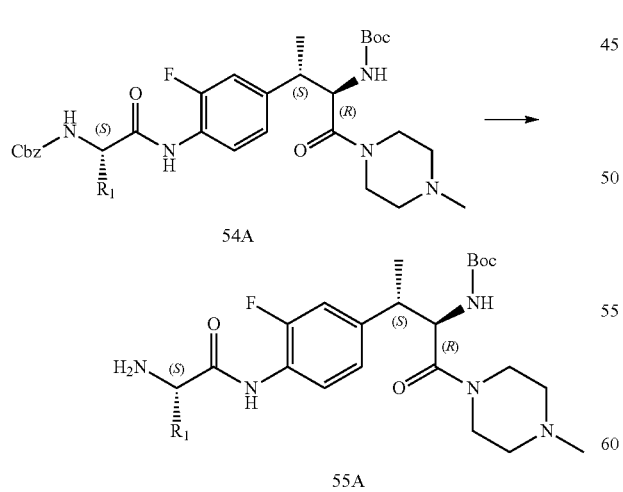

55A

To a degassed solution of 54A (1.0 eq) in EtOH was added Pd(OH)₂ (0.5 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH. The solution was concentrated to dryness to afford 55A.

Example 376: Preparation of 56A

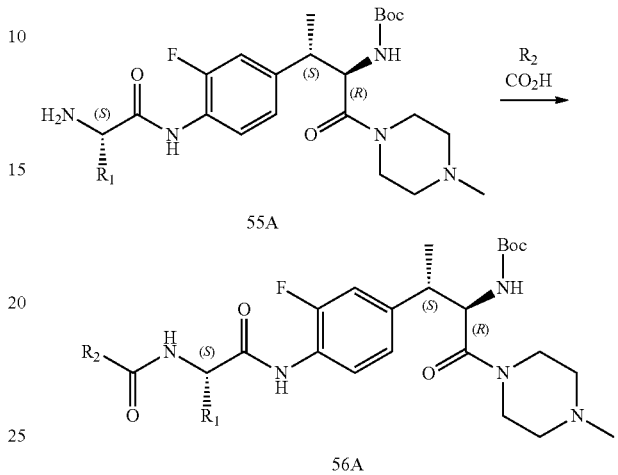

56A

To a solution of 55A (1.0 eq.) in DMF 0.10 mL) was added required carboxylic acid (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 56A.

Example 377: Preparation of 57A

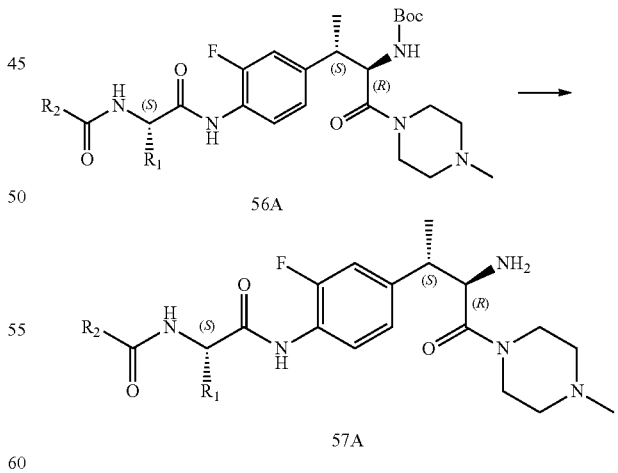

57A

To a solution of 56A (1.0 eq.) in DCM was added TFA and the resulting mixture was stirred at RT for 0.5 h. The reaction mixture was concentrated to dryness and the residue was stirred in aq. sat. K₂CO₃ solution and then extracted with DCM to afford 57A which was used in the next step without further purification.

Example 378: General Procedure AD

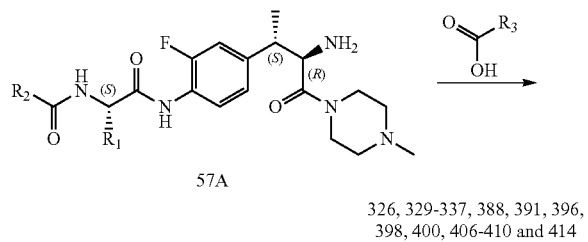

326, 329-337, 388, 391, 396, 398, 400, 406-410 and 414

To a solution of 57A (1.0 eq.) in DMF (0.1 M) were added the required carboxylic acid (1.2 eq.), DIPEA (3.0-8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 326, 329-337, 388, 391, 396, 398, 400, 406-410 and 414.

Example 379: General Procedure AE

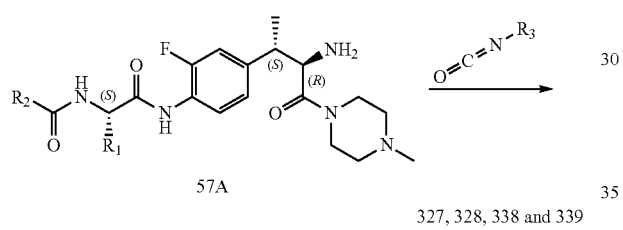

327, 328, 338 and 339

To a solution of 57A (1.0 eq.) in DMF (0.1 M) were added the required isocyanate (1.2 eq.) and DIPEA (3.0-8.0 eq.) and the resulting mixture was stirred at RT for 1 h. The mixture was concentrated to dryness and the residue was purified via reverse phase column chromatography on a 120 g C18 cartridge eluting with a 5-95% H$_2$O:MeCN eluent (0.1% ammonia) to afford 327, 328, 338 and 339.

Example 380: N-[(2R,3S)-3-{4-[(2S)-2-cycloheptyl-2-[2,2-difluoro-2-(6-methoxypyridin-3-yl)acetamido]acetamido]-3-fluorophenyl}-1-(4-methylpiperazin-1-yl)-1-oxobutan-2-yl]-1,2,3-thiadiazole-5-carboxamide) (331)

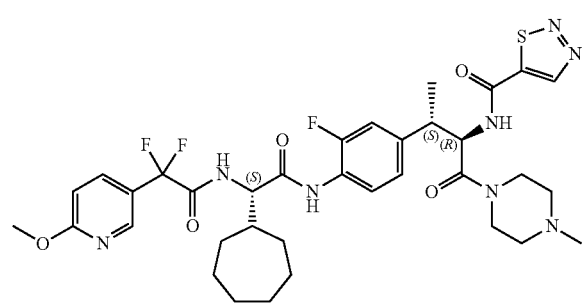

Compound 331 was made according to procedure AD. $^1$H NMR (400 MHz, DMSO-d$_6$) δ 9.97 (s, 1H), 9.86 (s, 1H), 9.67 (d, J=8.2 Hz, 1H), 9.52 (d, J=1.6 Hz, 1H), 9.46 (d, J=8.8 Hz, 1H), 9.26 (d, J=1.6 Hz, 1H), 9.00 (d, J=8.6 Hz, 1H), 8.95 (d, J=8.6 Hz, 1H), 8.42 (s, 1H), 7.92 (ddd, J=9.1, 6.5, 2.6 Hz, 2H), 7.73 (t, J=8.2 Hz, 1H), 7.56 (t, J=8.2 Hz, 1H), 7.34 (d, J=12.0 Hz, 1H), 7.21 (d, J=12.8 Hz, 1H), 7.16 (d, J=9.0 Hz, 1H), 7.08 (d, J=8.6 Hz, 1H), 7.01-6.91 (m, 2H), 6.53 (d, J=3.2 Hz, 1H), 5.22-5.09 (m, 1H), 5.09-4.97 (m, 1H), 4.51 (t, J=8.3 Hz, 1H), 4.44 (t, J=8.4 Hz, 1H), 3.79 (s, 1H), 3.64 (d, J=41.6 Hz, 1H), 3.46 (d, J=29.6 Hz, 3H), 2.96 (t, J=10.7 Hz, 1H), 2.38-2.25 (m, 3H), 2.21 (d, J=17.5 Hz, 3H), 2.08 (s, 1H), 1.56 (td, J=30.1, 23.9, 14.3 Hz, 16H), 1.44-1.27 (m, 4H), 1.23 (dd, J=13.4, 8.2 Hz, 2H). UPLC-MS (basic 4 min): rt=1.99 min; m/z=745.2 for [M+H]$^+$.

Example 381: N-[(2R,3S)-3-{4-[(2S)-2-cycloheptyl-2-{[1-(propan-2-yl)-1H-pyrazol-5-yl]formamido}acetamido]-3-fluorophenyl}-1-(4-methylpiperazin-1-yl)-1-oxobutan-2-yl]-1,2,3-thiadiazole-5-carboxamide (332)

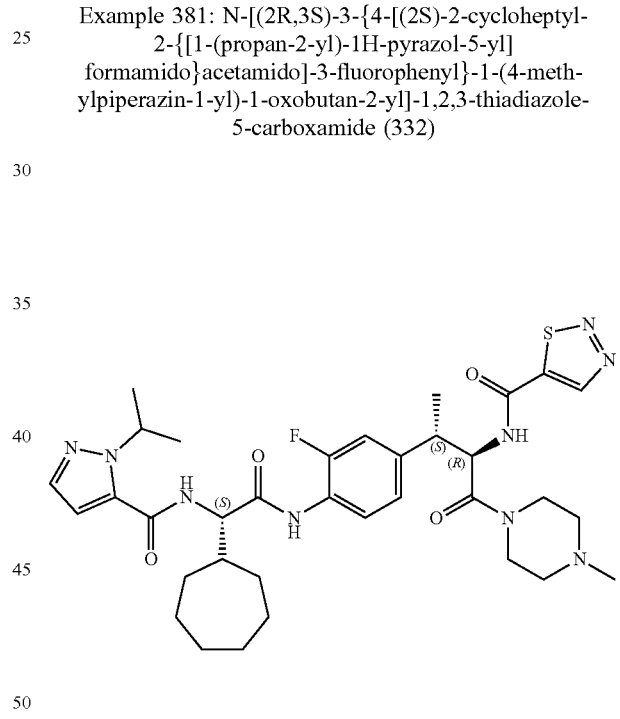

Compound 332 was made according to procedure AD. $^1$H NMR (400 MHz, DMSO-d$_6$) δ 9.88 (s, 1H), 9.67 (d, J=8.1 Hz, 1H), 9.52 (s, 1H), 8.43 (d, J=8.6 Hz, 1H), 7.77 (t, J=8.3 Hz, 1H), 7.49 (d, J=1.9 Hz, 1H), 7.21 (d, J=12.2 Hz, 1H), 7.10-7.04 (m, 1H), 6.91 (d, J=2.0 Hz, 1H), 5.39 (p, J=6.7 Hz, 1H), 5.10-4.99 (m, 1H), 4.62 (t, J=8.4 Hz, 1H), 3.47 (s, 2H), 3.29-3.21 (m, 2H), 2.98 (s, 1H), 2.21 (d, J=10.8 Hz, 2H), 2.15-2.05 (m, 1H), 1.97 (s, 3H), 1.76-1.62 (m, 4H), 1.59-1.46 (m, 4H), 1.44-1.28 (m, 15H). UPLC-MS (basic 4 min): rt=1.92 min; m/z=696.4 for [M+H]$^+$.

Example 382: N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]-1,2,3-thiadiazole-5-carboxamide (333)

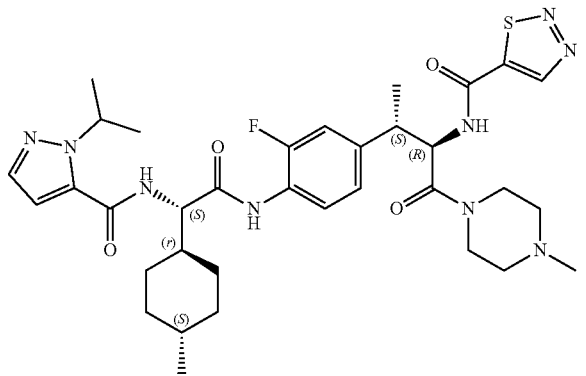

Compound 333 was made according to procedure AD. ¹H NMR (400 MHz, DMSO-d₆) δ 9.87 (s, 1H), 9.67 (d, J=8.1 Hz, 1H), 9.52 (s, 1H), 8.44 (d, J=8.3 Hz, 1H), 7.80 (t, J=8.3 Hz, 1H), 7.49 (d, J=2.0 Hz, 1H), 7.21 (dd, J=12.1, 1.9 Hz, 1H), 7.08 (d, J=7.7 Hz, 1H), 6.93 (d, J=2.0 Hz, 1H), 5.46-5.31 (m, 1H), 5.09-5.01 (m, 1H), 4.59-4.48 (m, 1H), 3.55-3.43 (m, 2H), 3.29-3.17 (m, 2H), 3.05-2.90 (m, 1H), 2.29-2.17 (m, 2H), 1.97 (s, 3H), 1.90-1.76 (m, 2H), 1.73-1.53 (m, 4H), 1.48-1.16 (m, 13H), 0.86 (d, J=6.5 Hz, 5H). UPLC-MS (basic 4 min): rt=1.93 min; m/z=696.5 for [M+H]⁺.

Example 383: N-[(2R,3S)-3-{4-[(2S)-2-cycloheptyl-2-[(3-ethyl-1,2-oxazol-4-yl)formamido]acetamido]-3-fluorophenyl}-1-(4-methylpiperazin-1-yl)-1-oxobutan-2-yl]-1,2,3-thiadiazole-5-carboxamide) (334)

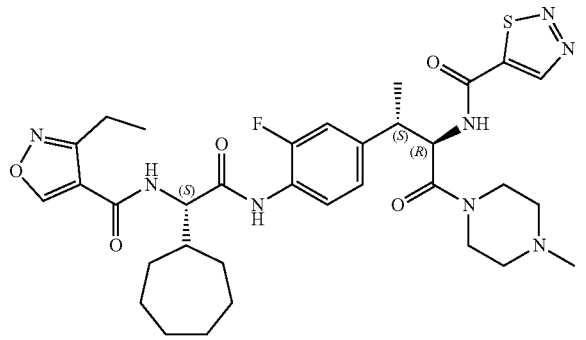

Compound 336 was made according to procedure AD. ¹H NMR (400 MHz, DMSO-d₆) δ 9.91 (s, 1H), 9.67 (d, J=8.2 Hz, 1H), 9.52 (s, 1H), 9.39 (d, J=8.5 Hz, 1H), 9.25 (s, 1H), 8.46-8.33 (m, 1H), 7.74 (t, J=8.2 Hz, 1H), 7.19 (dd, J=19.6, 10.2 Hz, 1H), 7.08 (d, J=8.3 Hz, 1H), 5.24-4.94 (m, 1H), 4.76-4.52 (m, 1H), 3.46 (s, 2H), 3.00 (s, 1H), 2.91-2.77 (m, 3H), 2.26 (d, J=58.0 Hz, 3H), 1.98 (s, 3H), 1.68 (d, J=18.2 Hz, 3H), 1.59-1.26 (m, 12H), 1.26-1.10 (m, 5H. UPLC-MS (basic 4 min): rt=1.85 min; m/z=683.3 for [M+H]⁺.

Example 384: N-[(2R,3S)-3-{4-[(2S)-2-[2-(5-cyano-pyridin-3-yl)-2,2-difluoroacetamido]-2-cycloheptyl acetamido]-3-fluorophenyl}-1-(4-methylpiperazin-1-yl)-1-oxobutan-2-yl]-1,2,3-thiadiazole-5-carboxamide) (335)

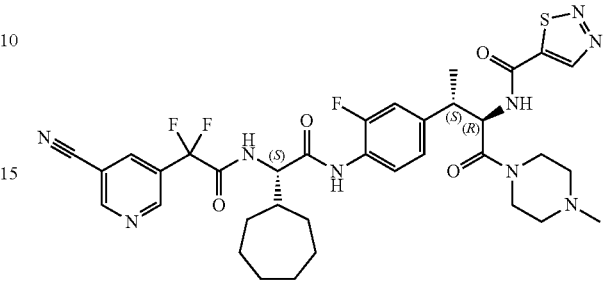

Compound 335 was made according to procedure AD. ¹H NMR (400 MHz, DMSO-d₆) δ 10.00 (s, 1H), 9.88 (s, 1H), 9.67 (d, J=7.9 Hz, 1H), 9.52 (s, 1H), 9.25 (d, J=3.9 Hz, 2H), 9.16 (s, 2H), 9.10 (s, 2H), 8.68 (d, J=3.5 Hz, 2H), 7.72 (s, 1H), 7.56 (s, 1H), 7.34 (d, J=11.6 Hz, 1H), 7.21 (d, J=11.8 Hz, 1H), 7.08 (d, J=8.4 Hz, 1H), 6.52 (s, 1H), 5.13 (s, 1H), 5.05 (s, 1H), 4.53 (s, 2H), 3.70 (d, J=83.4 Hz, 1H), 3.49 (s, 3H), 2.96 (s, 1H), 2.33 (s, 1H), 2.20 (d, J=14.7 Hz, 4H), 2.07 (s, 2H), 1.95 (s, 4H), 1.53 (s, 14H), 1.32 (d, J=6.5 Hz, 6H), 1.21 (d, J=7.2 Hz, 2H). UPLC-MS (basic 4 min): rt=1.87 min; m/z=740.3 for [M+H]⁺.

Example 385: N-[(2R,3S)-3-{4-[(2S)-2-[2-(3-cyano-phenyl)-2,2-difluoroacetamido]-2-[(1r,4S)-4-methyl cyclohexyl]acetamido]-3-fluorophenyl}-1-(4-methylpiperazin-1-yl)-1-oxobutan-2-yl]-1,2,3-thiadiazole-5-carboxamide) (336)

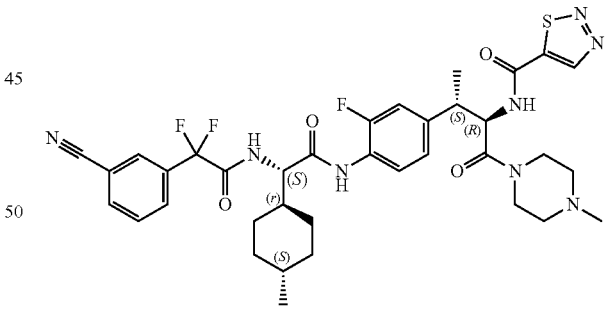

Compound 336 was made according to procedure AD. ¹H NMR (400 MHz, DMSO-d₆) δ 9.94 (s, 1H), 9.66 (br d, J=8.0 Hz, 1H), 9.51 (s, 1H), 9.09 (br d, J=8.4 Hz, 1H), 8.14 (s, 1H), 8.06 (d, J=7.7 Hz, 1H), 7.92-7.99 (m, 1H), 7.71-7.80 (m, 2H), 7.14-7.25 (m, 1H), 7.07 (br d, J=9.2 Hz, 1H), 4.98-5.10 (m, 1H), 4.38-4.47 (m, 1H), 3.44-3.52 (m, 2H), 2.90-3.00 (m, 1H), 2.15-2.25 (m, 2H), 1.93 (s, 3H), 1.71-1.84 (m, 1H), 1.59-1.69 (m, 3H), 1.48-1.58 (m, 2H), 1.34-1.42 (m, 1H), 1.27-1.34 (m, 3H), 1.17-1.27 (m, 3H), 1.05-1.17 (m, 1H), 0.89-1.04 (m, 1H), 0.84-0.89 (m, 1H), 0.83 (br d, J=6.4 Hz, 3H), 0.74-0.81 (m, 1H). UPLC-MS (basic 4 min): rt=2.00 min; m/z=739.3 for [M+H]⁺.

Example 386: N-[(2R,3S)-3-{4-[(2S)-2-cycloheptyl-2-[(1-ethyl-1H-pyrazol-5-yl)formamido]acetamido]-3-fluorophenyl}-1-(4-methylpiperazin-1-yl)-1-oxobutan-2-yl]-1,2,3-thiadiazole-5-carboxamide) (337)

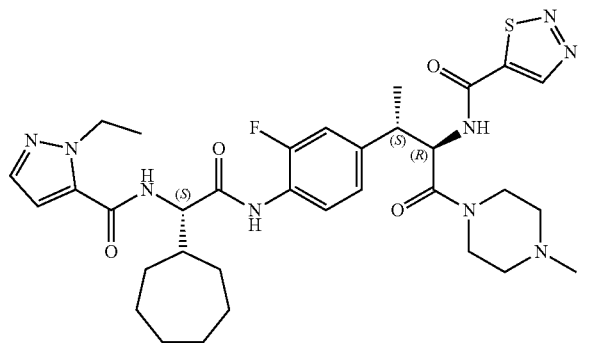

Compound 337 was made according to procedure AD. ¹H NMR (400 MHz, DMSO-d₆) δ 9.90 (s, 1H), 9.67 (d, J=8.1 Hz, 1H), 9.52 (s, 1H), 8.45 (d, J=8.5 Hz, 1H), 7.77 (t, J=8.2 Hz, 1H), 7.47 (dd, J=4.7, 2.0 Hz, 1H), 7.21 (d, J=11.4 Hz, 1H), 7.08 (d, J=8.4 Hz, 1H), 6.99 (d, J=2.0 Hz, 1H), 5.10-5.01 (m, 1H), 4.63 (t, J=8.5 Hz, 1H), 4.47 (q, J=7.1 Hz, 2H), 3.47 (s, 2H), 2.94 (d, J=33.4 Hz, 1H), 2.20 (d, J=14.7 Hz, 2H), 2.10 (s, 1H), 1.96 (s, 3H), 1.81-1.61 (m, 3H), 1.61-1.46 (m, 1H), 1.40 (d, J=10.3 Hz, 3H), 1.34-1.25 (m, 6H), 1.25-1.11 (m, 1H). UPLC-MS (basic 4 min): rt=1.82 min; m/z=682.4 for [M+H]⁺.

Example 387: (2S)-2-cycloheptyl-N-{4-[(2S,3R)-3-[(cyclopropylcarbamoyl)amino]-4-(4-methylpiperazin-1-yl)-4-oxobutan-2-yl]-2-fluorophenyl}-2-[(1-ethyl-1H-pyrazol-5-yl)formamido]acetamide) (338)

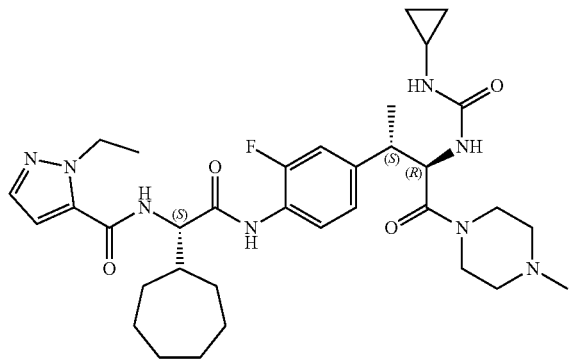

Compound 338 was made according to procedure AE. ¹H NMR (400 MHz, DMSO-d₆) δ 9.86 (s, 1H), 8.44 (d, J=8.6 Hz, 1H), 7.72 (t, J=8.3 Hz, 1H), 7.47 (d, J=2.0 Hz, 1H), 7.13-7.07 (m, 1H), 7.05-6.96 (m, 2H), 6.26 (d, J=2.9 Hz, 1H), 6.13 (d, J=9.2 Hz, 1H), 4.72 (t, J=9.2 Hz, 1H), 4.62 (t, J=8.4 Hz, 1H), 4.47 (q, J=7.1 Hz, 2H), 3.14-3.04 (m, 1H), 2.98 (d, J=8.2 Hz, 1H), 2.44-2.39 (m, 2H), 2.33 (t, 2H), 2.24-2.15 (m, 2H), 2.15-2.04 (m, 2H), 2.00 (s, 3H), 1.67 (d, J=21.7 Hz, 5H), 1.60-1.47 (m, 4H), 1.47-1.34 (m, 4H), 1.28 (t, J=7.1 Hz, 3H), 1.20 (d, J=7.0 Hz, 3H), 0.56 (td, J=6.8, 4.7 Hz, 2H), 0.35-0.27 (m, 2H). UPLC-MS (basic 4 min): rt=1.74 min; m/z=653.2 for [M+H]⁺.

Example 388: (2S)-2-cycloheptyl-N-{4-[(2S,3R)-3-[(cyclopropylcarbamoyl)amino]-4-(4-methylpiperazin-1-yl)-4-oxobutan-2-yl]-2-fluorophenyl}-2-{[1-(propan-2-yl)-1H-pyrazol-5-yl]formamido}acetamide) (339)

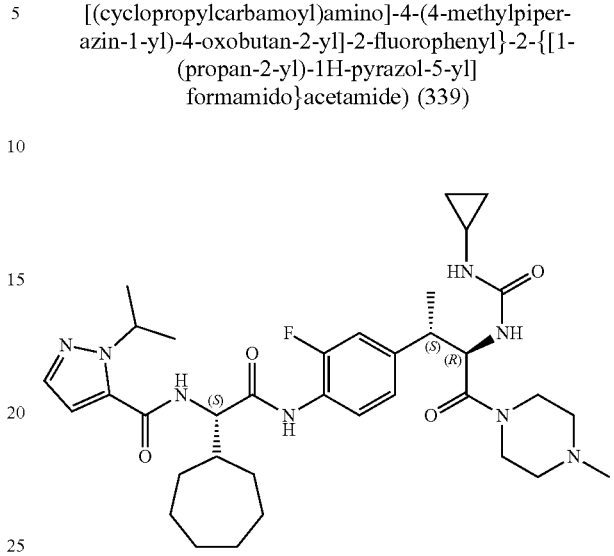

Compound 339 was made according to procedure AE. ¹H NMR (400 MHz, DMSO-d₆) δ 9.85 (s, 1H), 8.42 (d, J=8.5 Hz, 1H), 7.73 (t, J=8.3 Hz, 1H), 7.49 (d, J=2.0 Hz, 1H), 7.14-7.05 (m, 1H), 7.01 (d, J=7.8 Hz, 1H), 6.91 (d, J=2.1 Hz, 1H), 6.26 (s, 1H), 6.13 (d, J=9.1 Hz, 1H), 5.44-5.33 (m, 2H), 4.72 (t, J=9.1 Hz, 1H), 4.61 (t, J=8.4 Hz, 1H), 3.45 (s, 2H), 3.39 (s, 2H), 3.25 (s, 2H), 3.07 (s, 2H), 2.96 (d, J=8.1 Hz, 2H), 2.19 (s, 2H), 2.09 (s, 2H), 2.00 (s, 2H), 1.71 (s, 4H), 1.53 (s, 4H), 1.41 (s, 2H), 1.36 (dd, J=9.2, 6.6 Hz, 6H), 1.20 (d, J=7.0 Hz, 2H), 0.60-0.53 (m, 2H), 0.34-0.26 (m, 2H). UPLC-MS (basic 4 min): rt=1.83 min; m/z=667.5 for [M+H]⁺.

Example 389: N-[(2R,3S)-3-{4-[(2S)-2-cycloheptyl-2-[(1-ethyl-1H-pyrazol-5-yl)formamido]acetamido]-3-fluorophenyl}-1-(4-methylpiperazin-1-yl)-1-oxobutan-2-yl]-2-cyclopropylacetamide) (340)

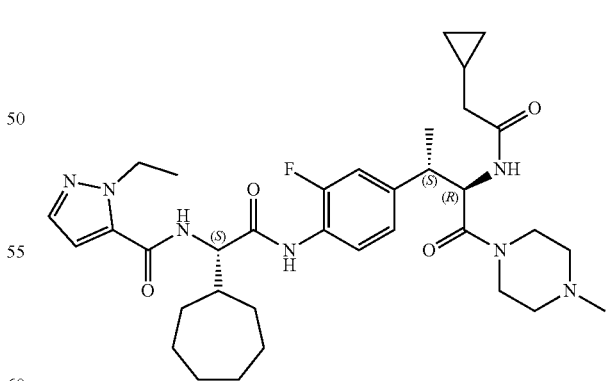

Compound 340 was made according to procedure AD. ¹H NMR (400 MHz, DMSO-d₆) δ 9.71 (s, 1H), 8.29 (d, J=8.8 Hz, 1H), 8.06 (d, J=8.8 Hz, 1H), 7.56 (t, J=8.3 Hz, 1H), 7.32 (d, J=2.1 Hz, 1H), 6.96 (d, J=11.8 Hz, 1H), 6.87 (d, J=8.3 Hz, 1H), 6.83 (d, J=2.1 Hz, 1H), 4.73 (t, J=9.4 Hz, 1H), 4.47 (t, J=8.5 Hz, 1H), 4.31 (q, J=7.1 Hz, 2H), 3.25 (s, 2H), 2.99-2.87 (m, 2H), 2.07-1.98 (m, 3H), 1.93, d, J=7.3 Hz, 2H), 1.89 (dd, J=7.1, 5.1 Hz, 2H), 1.84 (s, 3H), 1.63-1.46 (m, 5H), 1.46-1.30 (m, 5H), 1.30-1.17 (m, 5H), 1.13 (t, J=7.1 Hz, 3H), 1.06 (d, J=7.0 Hz, 3H), 0.80 (d, J=5.7 Hz, 1H), 0.29-0.22 (m, 2H). UPLC-MS (basic 4 min): rt=1.83 min; m/z=652.4 for [M+H]⁺.

Example 390: N-[(2R,3S)-3-{4-[(2S)-2-cycloheptyl-2-[(1-ethyl-1H-pyrazol-5-yl)formamido]acetamido]-3-fluorophenyl}-1-(4-methylpiperazin-1-yl)-1-oxobutan-2-yl]-1-fluorocyclopropane-1-carboxamide) (326)

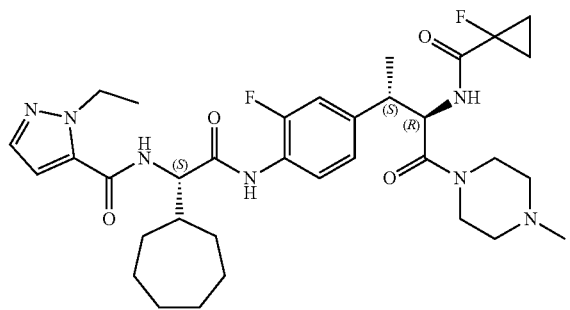

Compound 326 was made according to procedure AD. ¹H NMR (400 MHz, DMSO-d₆) δ 9.87 (s, 1H), 8.51 (d, J=8.4 Hz, 1H), 8.44 (d, J=8.6 Hz, 1H), 7.74 (t, J=8.2 Hz, 1H), 7.47 (d, J=2.0 Hz, 1H), 7.15 (d, J=11.3 Hz, 1H), 7.03 (d, J=8.6 Hz, 1H), 6.98 (d, J=2.1 Hz, 1H), 4.94-4.88 (m, 1H), 4.62 (t, J=8.5 Hz, 1H), 4.47 (q, J=7.2 Hz, 2H), 3.46-3.35 (m, 3H), 3.28-3.19 (m, 2H), 3.04-2.98 (m, 1H), 2.21-2.13 (m, 2H), 2.13-2.06 (m, 1H), 1.97 (s, 3H), 1.75-1.69 (m, 2H), 1.69-1.62 (m, 3H), 1.55-1.48 (m, 3H), 1.48-1.32 (m, 7H), 1.28 (t, J=7.1 Hz, 4H), 1.24 (d, J=7.0 Hz, 2H), 1.18 (dd, J=8.5, 3.7 Hz, 2H) UPLC-MS (basic 4 min): rt=1.87 min; m/z=656.4 for [M+H]⁺.

Example 391: (2S)-2-cycloheptyl-2-[(1-ethyl-1H-pyrazol-5-yl)formamido]-N-{2-fluoro-4-[(2S,3R)-4-(4-methylpiperazin-1-yl)-4-oxo-3-{[(propan-2-yl)carbamoyl]amino}butan-2-yl]phenyl}acetamide) (327)

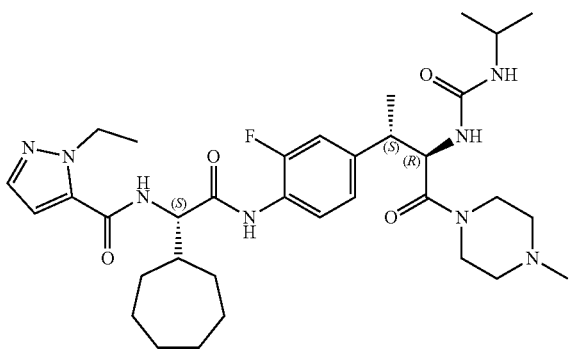

Compound 327 was made according to procedure AE. ¹H NMR (400 MHz, DMSO-d₆) δ 9.88 (s, 1H), 8.46 (d, J=8.5 Hz, 1H), 7.72 (t, J=8.3 Hz, 1H), 7.47 (d, J=2.0 Hz, 1H), 7.09 (dd, J=12.1, 2.0 Hz, 1H), 7.04-6.97 (m, 2H), 6.15 (d, J=9.3 Hz, 1H), 5.88 (d, J=7.7 Hz, 1H), 4.70 (t, J=9.1 Hz, 1H), 4.62 (t, J=8.5 Hz, 1H), 4.47 (q, J=7.2 Hz, 2H), 3.69-3.57 (m, 1H), 3.07 (s, 2H), 2.97-2.90 (m, 1H), 2.18 (s, 2H), 2.09 (s, 2H), 1.99 (s, 3H), 1.70 (dd, J=19.1, 11.7 Hz, 5H), 1.52 (s, 4H), 1.40 (d, J=12.0 Hz, 4H), 1.29 (d, J=7.1 Hz, 2H), 1.26 (t, J=3.4 Hz, 1H), 1.20 (d, J=7.0 Hz, 3H), 1.08 (d, J=6.6 Hz, 2H), 1.01 (dd, J=6.5, 1.8 Hz, 6H). UPLC-MS (basic 4 min): rt=1.78 min; m/z=655.5 for [M+H]⁺.

Example 392: (2S)-2-cycloheptyl-N-{2-fluoro-4-[(2S,3R)-4-(4-methylpiperazin-1-yl)-4-oxo-3-{[(propan-2-yl)carbamoyl]amino}butan-2-yl]phenyl}-2-{[1-(propan-2-yl)-1H-pyrazol-5-yl]formamido}acetamide) (328)

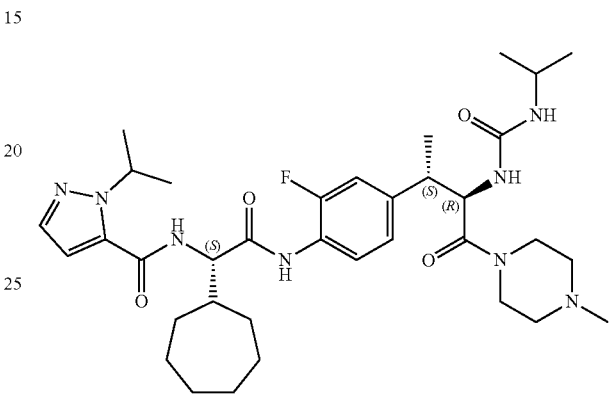

Compound 328 was made according to procedure AE. ¹H NMR (400 MHz, DMSO-d₆) δ 9.87 (s, 1H), 8.44 (d, J=8.6 Hz, 1H), 7.72 (t, J=8.3 Hz, 1H), 7.49 (d, J=2.0 Hz, 1H), 7.09 (d, J=12.0 Hz, 1H), 7.01 (d, J=8.6 Hz, 1H), 6.91 (d, J=2.0 Hz, 1H), 6.15 (d, J=9.4 Hz, 1H), 5.88 (d, J=7.7 Hz, 1H), 5.38 (p, J=6.7 Hz, 1H), 4.70 (t, J=9.1 Hz, 1H), 4.61 (t, J=8.5 Hz, 1H), 3.68-3.57 (m, 1H), 3.07 (s, 2H), 2.99-2.90 (m, 2H), 2.18 (s, 2H), 2.07 (d, J=11.6 Hz, 2H), 2.00 (s, 3H), 1.77-1.59 (m, 5H), 1.52 (s, 4H), 1.41 (s, 2H), 1.36 (dd, J=9.4, 6.6 Hz, 7H), 1.26 (d, J=6.7 Hz, 1H), 1.20 (d, J=7.0 Hz, 3H), 1.08 (d, J=6.6 Hz, 2H), 1.01 (dd, J=6.5, 1.8 Hz, 5H) UPLC-MS (basic 4 min): rt=1.87 min; m/z=669.5 for [M+H]⁺.

Example 393: 1-(cyclopropylmethyl)-N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]-1H-pyrazole-5-carboxamide (329)

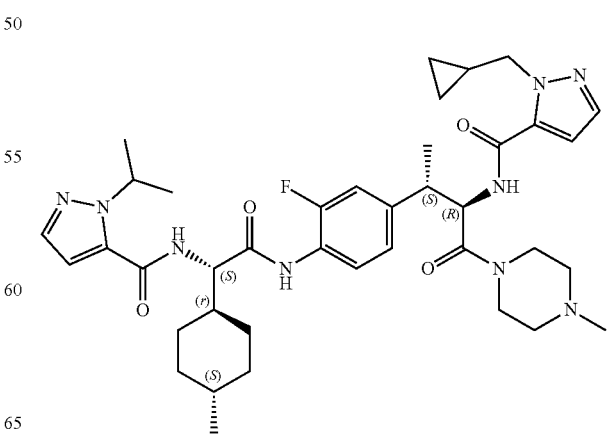

Compound 329 was made according to procedure AD. $^1$H NMR (400 MHz, DMSO-$d_6$) δ 9.86 (s, 1H), 8.89 (d, J=8.5 Hz, 1H), 8.43 (d, J=8.3 Hz, 1H), 7.77 (t, J=8.3 Hz, 1H), 7.49 (dd, J=2.1, 0.8 Hz, 2H), 7.18 (d, J=11.7 Hz, 1H), 7.09-6.99 (m, 2H), 6.93 (d, J=2.0 Hz, 1H), 5.39 (p, J=6.7 Hz, 1H), 5.10-4.99 (m, 1H), 4.53 (t, J=8.3 Hz, 2H), 4.45-4.25 (m, 2H), 3.54-3.36 (m, 3H), 3.17-3.03 (m, 1H), 2.27-2.12 (m, 2H), 1.88-1.51 (m, 8H), 1.40-1.33 (m, 7H), 1.33-1.16 (m, 7H), 1.13-1.01 (m, 1H), 0.95-0.79 (m, 6H), 0.45-0.36 (m, 2H), 0.33-0.26 (m, 2H). UPLC-MS (basic 4 min): rt=2.06 min; m/z=732.5 for [M+H]$^+$.

Example 394: N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]-1-(propan-2-yl)-1H-pyrazole-5-carboxamide (330)

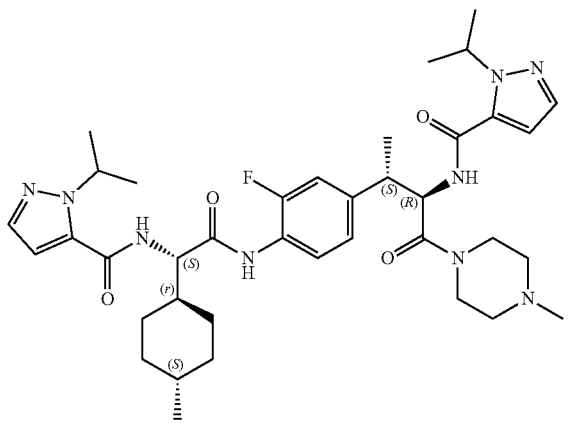

Compound 330 was made according to procedure AD. $^1$H NMR (400 MHz, DMSO-$d_6$) δ 9.86 (s, 1H), 8.83 (d, J=8.4 Hz, 1H), 8.44 (d, J=8.3 Hz, 1H), 7.78 (t, J=8.3 Hz, 1H), 7.50 (dd, J=3.5, 2.0 Hz, 2H), 7.22-7.14 (m, 1H), 7.06 (d, J=8.3 Hz, 1H), 6.97 (d, J=2.1 Hz, 1H), 6.93 (d, J=2.0 Hz, 1H), 5.44-5.34 (m, 2H), 5.07-4.99 (m, 1H), 4.53 (t, J=8.4 Hz, 1H), 3.44 (d, J=15.8 Hz, 2H), 3.07 (t, J=10.2 Hz, 1H), 2.22-2.15 (m, 2H), 1.99 (s, 3H), 1.87-1.75 (m, 2H), 1.73-1.61 (m, 4H), 1.59-1.48 (m, 1H), 1.43-1.33 (m, 13H), 1.33-1.22 (m, 5H), 1.18-1.01 (m, 1H), 0.93-0.80 (m, 6H). UPLC-MS (basic 4 min): rt=1.92 min; m/z=720.5 for [M+H]$^+$.

Example 395: Methyl (2R,3S)-3-(3-fluoro-4-nitrophenyl)-2-propanamidobutanoate) (59A)

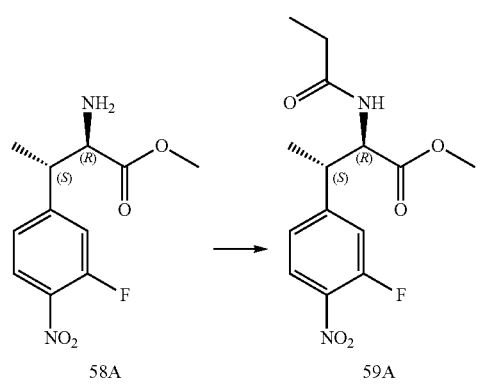

To a solution of 58A (0.970 g, 3.31 mmol, 1.0 eq.) in DMF (10 mL), which can be readily prepared from compound 74 by those of skill in the art, was added DIPEA (2.9 mL, 16.6 mmol, 5.0 eq.) and propionyl chloride (0.4 mL, 4.56 mmol, 1.4 eq.) and the resulting mixture was stirred at RT for 1 h. The mixture was concentrated to dryness and the residue was taken up in an aqueous NaHCO$_3$ solution and then extracted with EtOAc. The combined organic phase was washed with brine, dried over sodium sulfate then concentrated to dryness to afford 59A as a red solid. $^1$H NMR (400 MHz, DMSO-$d_6$) δ 8.32 (d, J=8.6 Hz, 1H), 8.09 (t, J=8.3 Hz, 1H), 7.53 (dd, J=12.8, 1.8 Hz, 1H), 7.33 (dd, J=8.6, 1.8 Hz, 1H), 4.64 (dd, J=8.7, 7.3 Hz, 1H), 3.51 (s, 3H), 2.14 (qd, J=7.5, 2.4 Hz, 2H), 1.27 (d, J=7.1 Hz, 3H), 0.94 (t, J=7.6 Hz, 3H). UPLC-MS (basic 2 min): Rt=0.97 min; m/z=313.1 for [M+H]$^+$.

Example 396: methyl (2R,3S)-3-(4-amino-3-fluorophenyl)-2-propanamidobutanoate) (60A)

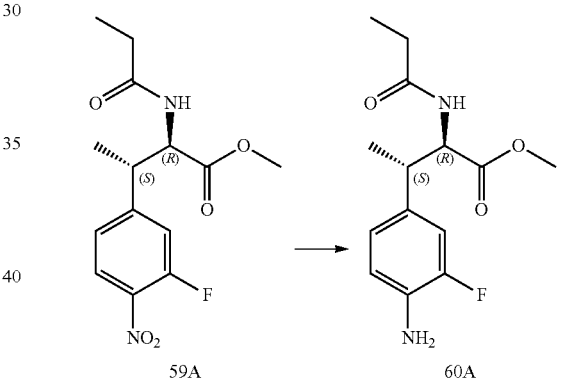

To a degassed solution of 59A (0.930 g, 2.98 mmol, 1.0 eq) in EtOH (10 mL) was added Pd(OH)$_2$/C (0.209 g 1.5 mmol, 0.5 eq.). The mixture was degassed for another 20 minutes and then evacuated under vacuum before introducing a hydrogen balloon. The resulting mixture was stirred at RT for 3 h. The mixture was filtered through a pad of celite which was washed with EtOH (50 mL). The solution was concentrated to dryness to afford 60A as a yellow solid (0.989 g, 99%). $^1$H NMR (400 MHz, DMSO-$d_6$) δ 8.23 (d, J=8.5 Hz, 1H), 7.03 (dd, J=26.1, 10.6 Hz, 2H), 6.90 (d, J=8.2 Hz, 1H), 4.45 (t, J=8.1 Hz, 1H), 3.45 (s, 16H), 3.20-3.05 (m, 1H), 2.14 (qd, J=7.5, 2.5 Hz, 2H), 1.33-1.12 (m, 4H), 0.95 (t, J=7.6 Hz, 3H). UPLC-MS (basic 2 min): Rt=0.86 min; m/z=283.1 for [M+H]$^+$.

Example 397: General Procedure AF

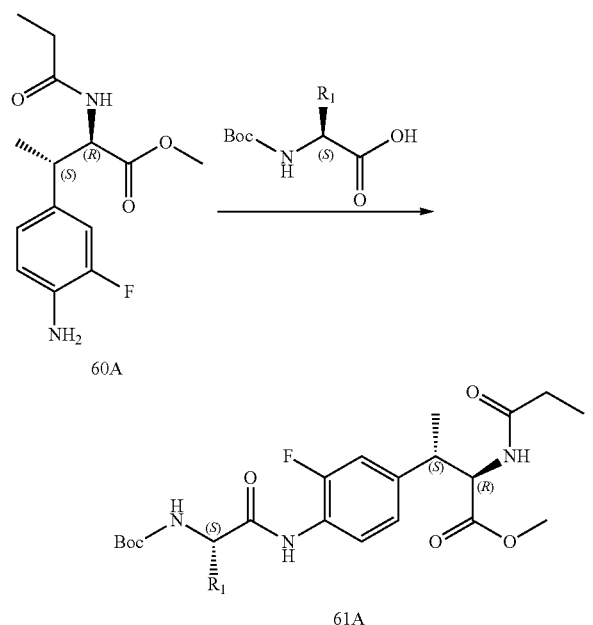

To a solution of 60A (1.0 eq.) in DMF were added required Boc protected glycine derivative (1.2 eq.), DIPEA (4.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM with 5% aq. NH$_3$) to afford 61A.

Example 398: General Procedure AG

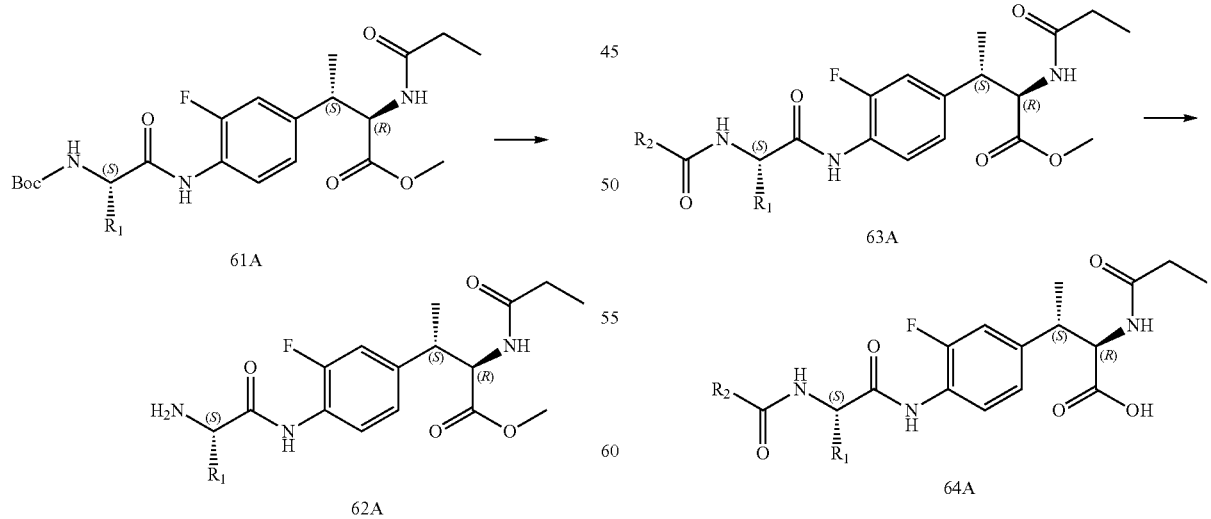

To a solution of 61A (1.0 eq.) in DCM was added TFA and the resulting mixture was stirred at RT for 0.5 h. The reaction mixture was concentrated to dryness and the residue was stirred in aq. sat. K$_2$CO$_3$ solution and then extracted with DCM to afford 62A which was used in the next step without further purification.

Example 399: General Procedure AH

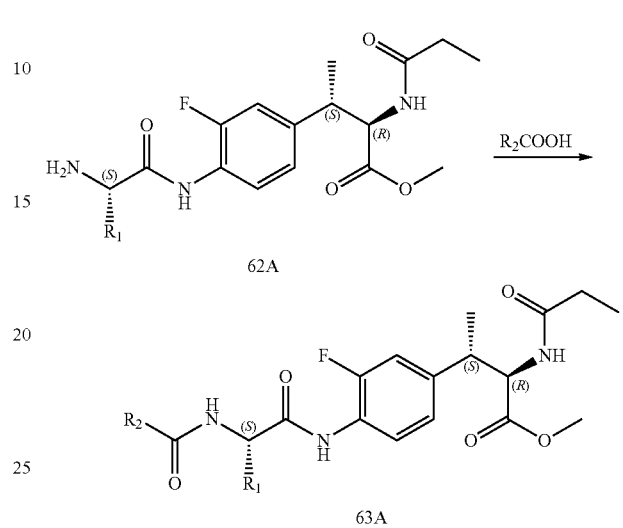

To a solution of 62A (1.0 eq.) in DMF 0.10 mL) were added required carboxylic acid (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 63A.

Example 398: General Procedure AI

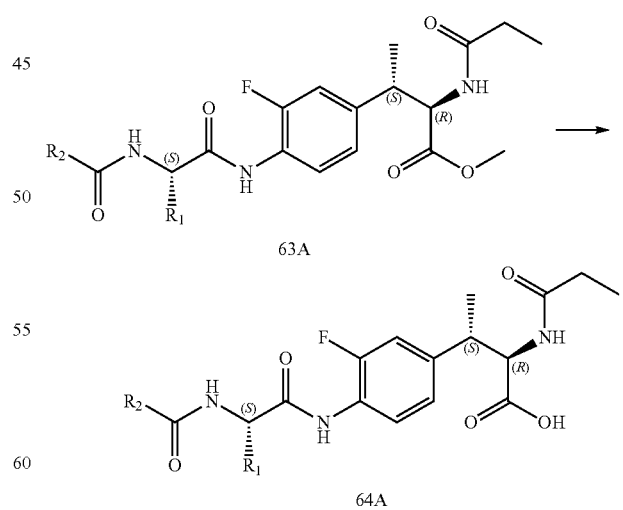

To a solution of 63A (1.0 eq.) in MeOH and THF was added a solution of 1M LiOH in H$_2$O (1.3 eq.) and the resulting mixture was stirred at RT for 0.5 h. The reaction mixture was concentrated to dryness and the residue was stirred in aq. sat. NaHCO₃ solution and then extracted with EtOAc. The aqueous layer was acidified with conc. HCl and the precipitate was filtered to afford 64A which was used in the next step without further purification.

Example 399: General Procedure AJ

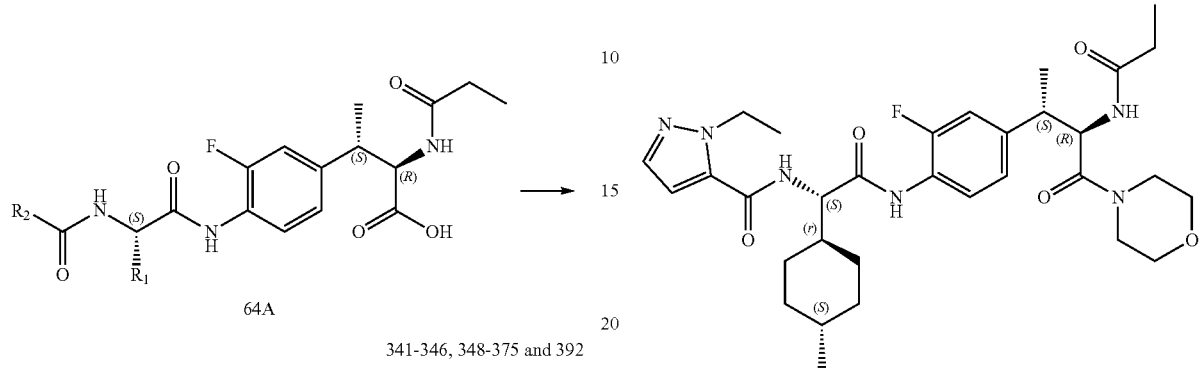

64A 341-346, 348-375 and 392

To a solution of 64A (1.0 eq,) in DMF (0.1 M) were added the required amine (1.2 eq.), DIPEA (3.0-8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 341-346, 348-375 and 392.

Example 400: N-[(2R,3S)-3-{4-[(2S)-2-[(1-ethyl-1H-pyrazol-5-yl)formamido]-2-[(1r,4S)-4-methyl cyclohexyl]acetamido]-3-fluorophenyl}-1-oxo-1-{4-[(pyridin-2-yl)methyl]piperazin-1-yl}butan-2-yl]propanamide (341)

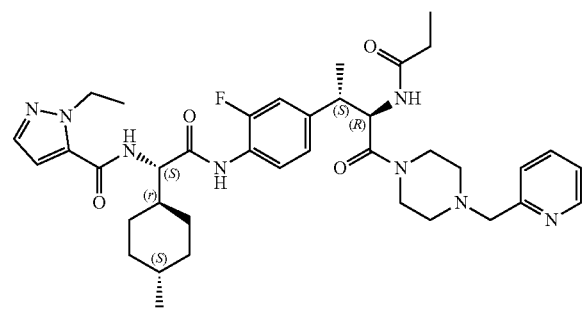

Following General Procedure AJ provided 341. ¹H NMR (400 MHz, Methanol-d₄) δ 8.58-8.41 (m, 1H), 7.90-7.69 (m, 2H), 7.61-7.22 (m, 4H), 7.18-7.01 (m, 2H), 6.85 (d, J=2.1 Hz, 1H), 5.01 (dd, J=50.2, 10.1 Hz, 1H), 4.61-4.39 (m, 3H), 3.71 (d, J=29.4 Hz, 2H), 3.56 (d, J=12.9 Hz, 1H), 3.52-3.34 (m, 3H), 3.28-3.07 (m, 2H), 2.98 (d, J=14.6 Hz, 3H), 2.78-2.49 (m, 1H), 2.49-2.33 (m, 1H), 2.33-2.17 (m, J=7.5 Hz, 1H), 2.09-1.61 (m, 4H), 1.44-1.07 (m, 11H), 1.04-0.79 (m, 6H). UPLC-MS (basic 4 min): rt=1.84 min; m/z=703.5 for [M+H]⁺.

Example 401: N-[(2R,3S)-3-{4-[(2S)-2-[(1-ethyl-1H-pyrazol-5-yl)formamido]-2-[(1r,4S)-4-methyl cyclohexyl]acetamido]-3-fluorophenyl}-1-(morpholin-4-yl)-1-oxobutan-2-yl]propanamide (342)

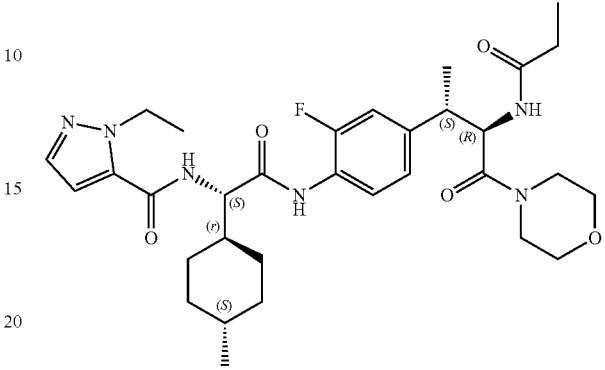

Following General Procedure AJ provided 342. ¹H NMR (400 MHz, Methanol-d₄) δ 7.76 (q, J=8.5 Hz, 1H), 7.48 (d, J=2.1 Hz, 1H), 7.19-6.98 (m, 2H), 6.86 (d, J=2.2 Hz, 1H), 4.98 (dd, J=50.6, 10.1 Hz, 1H), 4.52 (q, J=7.0 Hz, 3H), 3.89-3.55 (m, 2H), 3.48 (dtt, J=11.2, 7.6, 3.2 Hz, 3H), 3.24-3.07 (m, 2H), 3.07-2.93 (m, 2H), 2.34-2.20 (m, 2H), 2.04-1.83 (m, 2H), 1.78 (s, 3H), 1.43-1.29 (m, 6H), 1.29-1.16 (m, 2H), 1.13 (t, J=7.6 Hz, 3H), 1.07-0.94 (m, 2H), 0.94-0.80 (m, 4H). UPLC-MS (basic 4 min): rt=1.79 min; m/z=613.5 for [M+H]⁺.

Example 402: N-[(2R,3S)-3-{4-[(2S)-2-[(1-ethyl-1H-pyrazol-5-yl)formamido]-2-[(1r,4S)-4-methyl cyclohexyl]acetamido]-3-fluorophenyl}-1-(4-hydroxy-4-methylpiperidin-1-yl)-1-oxobutan-2-yl]propanamide (343)

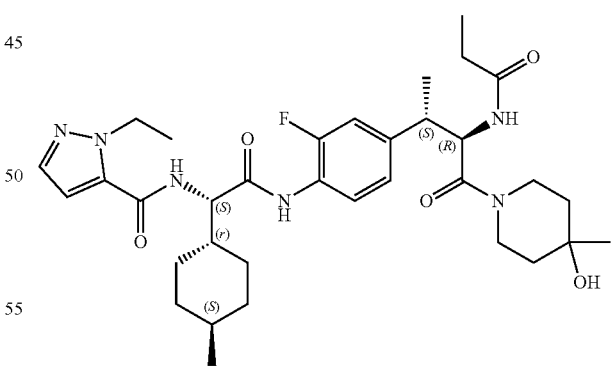

Following General Procedure AJ provided 343. ¹H NMR (400 MHz, Methanol-d₄) δ 7.81 (dt, J=69.6, 8.2 Hz, 1H), 7.49 (dd, J=2.1, 0.9 Hz, 1H), 7.17-7.02 (m, 2H), 6.85 (t, J=2.2 Hz, 1H), 5.13-4.94 (m, 1H), 4.61-4.44 (m, 3H), 3.91 (dd, J=60.2, 13.8 Hz, 1H), 3.77-3.40 (m, 1H), 3.27-2.77 (m, 4H), 2.39-2.17 (m, 1H), 2.08-1.56 (m, 6H), 1.55-1.09 (m, 15H), 1.09-0.44 (m, 8H). UPLC-MS (basic 4 min): rt=1.78 min; m/z=641.5 for [M+H]⁺.

Example 403: 2R,3S)—N-[(1S)-1-cyclopropyl-ethyl]-3-{4-[(2S)-2-[(1-ethyl-1H-pyrazol-5-yl)formamido]-2-[(1r,4S)-4-methylcyclohexyl]acetamido]-3-fluorophenyl}-2-propanamidobutanamide (344)

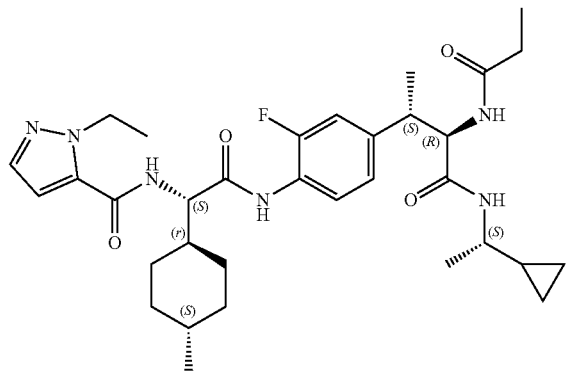

Following General Procedure AJ provided 344. $^1$H NMR (400 MHz, DMSO-d$_6$) δ 9.81 (s, 1H), 8.44 (d, J=8.7 Hz, 1H), 8.01 (dd, J=78.7, 8.8 Hz, 1H), 7.78-7.60 (m, 2H), 7.47 (d, J=2.0 Hz, 1H), 7.07 (dt, J=12.1, 2.4 Hz, 1H), 7.03-6.95 (m, 2H), 4.58-4.39 (m, 4H), 3.44 (q, J=6.8 Hz, 1H), 3.13-2.92 (m, 2H), 2.22-1.87 (m, 2H), 1.87-1.56 (m, 5H), 1.27 (t, J=7.1 Hz, 4H), 1.20-0.99 (m, 7H), 0.94 (t, J=7.6 Hz, 2H), 0.86 (d, J=6.4 Hz, 5H), 0.79-0.67 (m, 3H), 0.46--0.01 (m, 3H). UPLC-MS (basic 4 min): rt=2.10 min; m/z=611.5 for [M+H]$^+$.

Example 404: (2R,3S)—N-(cyclobutylmethyl)-3-{4-[(2S)-2-[(1-ethyl-1H-pyrazol-5-yl)formamido]-2-[(1r,4S)-4-methylcyclohexyl]acetamido]-3-fluorophenyl}-2-propanamidobutanamide (345)

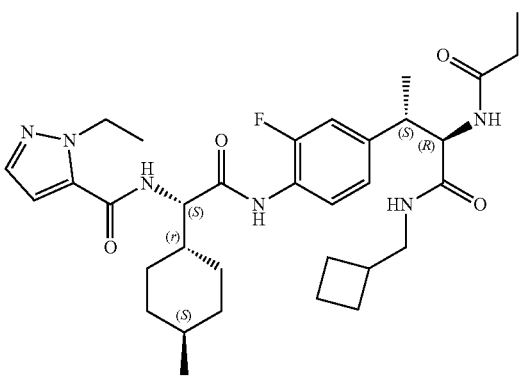

Following General Procedure AJ provided 345. $^1$H NMR (400 MHz, DMSO-d$_6$) δ 9.82 (s, 1H), 8.45 (d, J=8.3 Hz, 1H), 7.95 (d, J=9.2 Hz, 1H), 7.81 (t, J=5.8 Hz, 1H), 7.76-7.65 (m, 1H), 7.47 (d, J=2.0 Hz, 1H), 7.11-7.03 (m, 1H), 7.03-6.93 (m, 2H), 4.61-4.36 (m, 4H), 3.11-2.97 (m, 2H), 2.76 (ddd, J=12.8, 7.2, 4.9 Hz, 1H), 2.11 (qt, J=14.6, 7.4 Hz, 3H), 1.89-1.55 (m, 8H), 1.49-1.34 (m, 2H), 1.27 (t, J=7.2 Hz, 4H), 1.23 (s, 2H), 1.14 (d, J=7.1 Hz, 3H), 1.06 (d, J=12.8 Hz, 4H), 0.94 (t, J=7.6 Hz, 3H), 0.89 (d, J=14.4 Hz, 1H), 0.85 (d, J=6.5 Hz, 4H). UPLC-MS (basic 4 min): rt=1.97 min; m/z=611.5 for [M+H]$^+$.

Example 405: (2R,3S)-3-{4-[(2S)-2-[(1-ethyl-1H-pyrazol-5-yl)formamido]-2-[(1r,4S)-4-methyl cyclohexyl]acetamido]-3-fluorophenyl}-N-[(1-methylcyclopropyl)methyl]-2-propanamido butanamide (346)

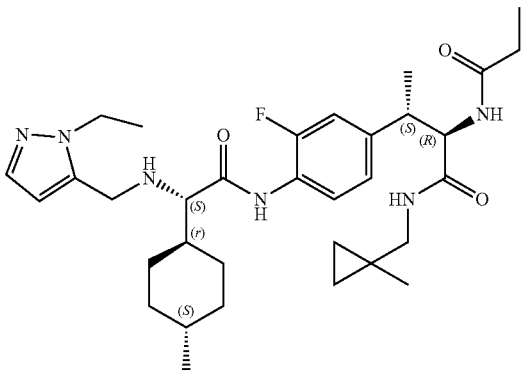

Following General Procedure AJ provided 346. $^1$H NMR (400 MHz, DMSO-d$_6$) δ 9.79 (s, 1H), 8.44 (d, J=8.2 Hz, 1H), 7.95 (d, J=9.2 Hz, 1H), 7.86 (t, J=5.9 Hz, 1H), 7.70 (t, J=8.3 Hz, 1H), 7.47 (d, J=2.0 Hz, 1H), 7.17-7.05 (m, 1H), 7.05-6.92 (m, 2H), 4.60-4.40 (m, 4H), 3.08 (p, J=6.9 Hz, 1H), 2.88 (dd, J=13.5, 6.6 Hz, 1H), 2.71 (dd, J=13.5, 5.1 Hz, 1H), 2.22-2.05 (m, J=7.4 Hz, 2H), 1.86-1.56 (m, 6H), 1.35-1.18 (m, 7H), 1.15 (d, J=7.1 Hz, 3H), 1.12-0.99 (m, 1H), 0.94 (t, J=7.6 Hz, 3H), 0.90-0.80 (m, 6H), 0.76 (s, 3H). UPLC-MS (basic 4 min): rt=1.95 min; m/z=611.5 for [M+H]$^+$.

Example 406: N-[(2R,3S)-3-{4-[(2S)-2-[2-(3-cyanophenyl)-2,2-difluoroacetamido]-2-cycloheptyl acetamido]-3-fluorophenyl}-1-(morpholin-4-yl)-1-oxobutan-2-yl]-1-(1-methylpiperidin-4-yl)-1H-pyrazole-5-carboxamide (347)

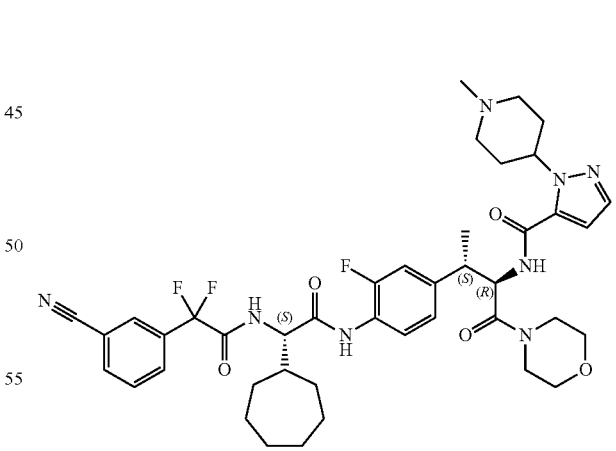

Following General Procedure AN provided 347. $^1$H NMR (400 MHz, DMSO-d$_6$) δ 9.94 (s, 1H), 9.08 (d, J=8.7 Hz, 1H), 8.17 (s, 1H), 8.07 (d, J=7.8 Hz, 1H), 7.96 (d, J=7.9 Hz, 1H), 7.76 (t, J=7.9 Hz, 1H), 7.59 (t, J=8.2 Hz, 1H), 7.27 (d, J=8.5 Hz, 1H), 7.14 (d, J=11.7 Hz, 1H), 7.01 (d, J=8.3 Hz, 1H), 4.62-4.24 (m, 2H), 3.46-3.37 (m, 3H), 3.26-3.19 (m, 2H), 3.17-3.00 (m, 3H), 1.64-1.13 (m, 24H). UPLC-MS (basic 4 min): rt=2.00 min; m/z=805.3 for [M+H]$^+$.

Example 407: N-[(2R,3S)-3-{4-[(2S)-2-cycloheptyl-2-[(1-ethyl-1H-pyrazol-5-yl)formamido]acetamido]-3-fluorophenyl}-1-oxo-1-{4-[(pyridin-2-yl)methyl]piperazin-1-yl}butan-2-yl]propanamide (348)

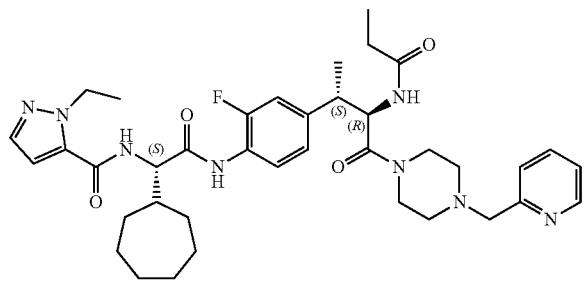

Following General Procedure AJ provided 348. $^1$H NMR (400 MHz, DMSO-d$_6$) δ 9.90 (s, 1H), 8.48-8.41 (m, 2H), 8.26 (d, J=8.7 Hz, 1H), 7.74-7.66 (m, 2H), 7.46 (d, J=2.0 Hz, 1H), 7.35 (dt, J=7.8, 1.1 Hz, 1H), 7.23 (ddd, J=7.5, 4.8, 1.2 Hz, 1H), 7.12 (dd, J=12.1, 1.9 Hz, 1H), 7.02 (dd, J=8.4, 1.9 Hz, 1H), 6.99 (d, J=2.0 Hz, 1H), 4.93-4.84 (m, 1H), 4.64 (t, J=8.4 Hz, 1H), 4.45 (q, J=7.2 Hz, 2H), 3.43 (d, J=6.1 Hz, 2H), 3.40-3.35 (m, 2H), 3.19-3.07 (m, 2H), 2.29 (ddt, J=23.3, 12.4, 3.1 Hz, 2H), 2.13 (tp, J=15.0, 7.5 Hz, 3H), 1.93-1.78 (m, 2H), 1.75-1.61 (m, 4H), 1.58-1.31 (m, 9H), 1.27 (t, J=7.1 Hz, 3H), 1.20 (d, J=7.0 Hz, 3H), 0.99 (t, J=7.6 Hz, 3H). UPLC-MS (basic 4 min): rt=1.84 min; m/z=703.4 for [M+H]$^+$.

Example 408: N-[(2R,3S)-3-{4-[(2S)-2-[2-(3-cyanophenyl)-2,2-difluoroacetamido]-2-cycloheptyl acetamido]-3-fluorophenyl}-1-(morpholin-4-yl)-1-oxobutan-2-yl]propanamide (349)

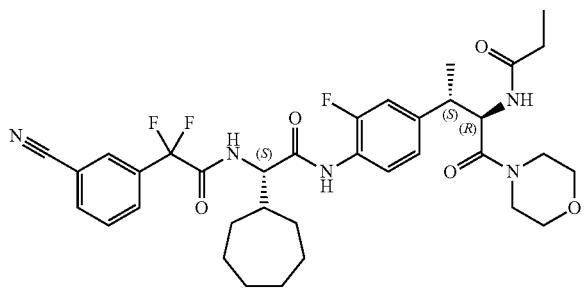

Following General Procedure AJ provided 349. $^1$H NMR (400 MHz, DMSO-d$_6$) δ 9.95 (s, 1H), 9.08 (d, J=8.5 Hz, 1H), 8.30 (d, J=8.6 Hz, 1H), 8.17 (s, 1H), 8.07 (d, J=7.7 Hz, 1H), 7.96 (d, J=8.0 Hz, 1H), 7.76 (t, J=7.9 Hz, 1H), 7.59 (dd, J=9.3, 7.2 Hz, 1H), 7.14 (dd, J=11.9, 1.9 Hz, 1H), 7.02 (dd, J=8.3, 1.9 Hz, 1H), 4.87 (t, J=9.2 Hz, 1H), 4.49 (t, J=8.5 Hz, 1H), 3.58-3.50 (m, 1H), 3.43-3.37 (m, 3H), 3.27-3.14 (m, 3H), 3.14-3.00 (m, 3H), 2.25-2.02 (m, 3H), 1.61-1.48 (m, 6H), 1.45-1.25 (m, 5H), 1.21 (d, J=7.1 Hz, 3H), 0.99 (t, J=7.6 Hz, 3H). UPLC-MS (basic 4 min): rt=1.94 min; m/z=670.3 for [M+H]$^+$.

Example 409: N-[(2R,3S)-3-{4-[(2S)-2-cycloheptyl-2-[(1-ethyl-1H-pyrazol-5-yl)formamido]acetamido]-3-fluorophenyl}-1-(4-hydroxy-4-methylpiperidin-1-yl)-1-oxobutan-2-yl]propanamide (350)

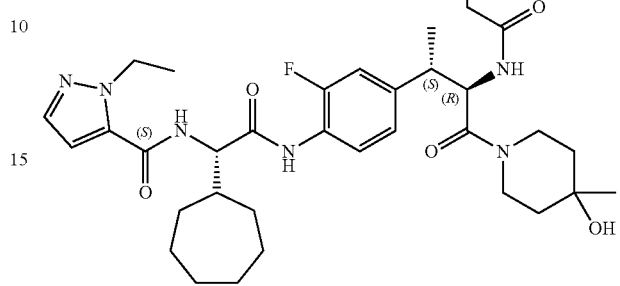

Following General Procedure AJ provided 350. $^1$H NMR (400 MHz, DMSO-d$_6$) δ 9.87 (s, 1H), 8.44 (d, J=8.6 Hz, 1H), 8.24 (d, J=9.0 Hz, 1H), 7.78 (t, J=8.3 Hz, 1H), 7.47 (dd, J=2.1, 1.0 Hz, 1H), 7.15-7.06 (m, 1H), 7.05-6.94 (m, 2H), 4.90 (dt, J=47.5, 9.4 Hz, 2H), 4.68-4.58 (m, 1H), 4.52-4.42 (m, 2H), 4.18 (s, 1H), 3.89-3.81 (m, 1H), 3.67-3.57 (m, 1H), 3.11 (dt, J=18.0, 9.4 Hz, 3H), 2.80-2.69 (m, 1H), 2.23-2.06 (m, 3H), 1.76-1.62 (m, 4H), 1.59-1.47 (m, 3H), 1.45-1.34 (m, 4H), 1.28 (t, J=7.1 Hz, 3H), 1.21 (d, J=7.1 Hz, 3H), 1.14 (dd, J=15.9, 6.1 Hz, 2H), 0.99 (t, J=7.6 Hz, 3H), 0.84 (s, 3H), 0.74-0.65 (m, 1H). UPLC-MS (basic 4 min): rt=1.76 min; m/z=641.4 for [M+H]$^+$.

Example 410: N-[(2R,3S)-3-{4-[(2S)-2-cycloheptyl-2-[(1-ethyl-1H-pyrazol-5-yl)formamido]acetamido]-3-fluorophenyl}-1-(morpholin-4-yl)-1-oxobutan-2-yl]propanamide (351)

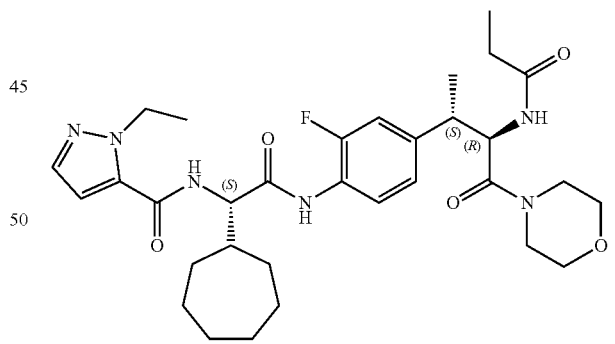

Following General Procedure AJ provided 351. $^1$H NMR (400 MHz, DMSO-d$_6$) δ 9.89 (s, 1H), 8.46 (d, J=8.7 Hz, 1H), 8.31 (d, J=8.6 Hz, 1H), 7.63 (t, J=8.2 Hz, 1H), 7.48 (d, J=2.0 Hz, 1H), 7.15 (dd, J=12.0, 1.7 Hz, 1H), 7.05-6.98 (m, 2H), 4.87 (t, J=9.3 Hz, 1H), 4.61 (t, J=8.3 Hz, 1H), 4.48 (q, J=7.0 Hz, 2H), 3.54 (ddd, J=12.4, 9.1, 4.4 Hz, 2H), 3.45-3.36 (m, 4H), 3.27-3.14 (m, 2H), 3.14-3.00 (m, 4H), 2.15 (dp, J=22.2, 7.4 Hz, 3H), 1.74-1.62 (m, 4H), 1.53 (ddd, J=17.2, 12.4, 6.9 Hz, 4H), 1.40 (dd, J=14.5, 5.5 Hz, 4H), 1.21 (d, J=7.0 Hz, 3H), 0.99 (t, J=7.6 Hz, 3H). UPLC-MS (basic 4 min): rt=1.78 min; m/z=613.4 for [M+H]$^+$.

Example 411: N-[(2R,3S)-3-{4-[(2S)-2-[2-(3-cyanophenyl)-2,2-difluoroacetamido]-2-cyclohexyl acetamido]-3-fluorophenyl}-1-(morpholin-4-yl)-1-oxobutan-2-yl]propanamide (352)

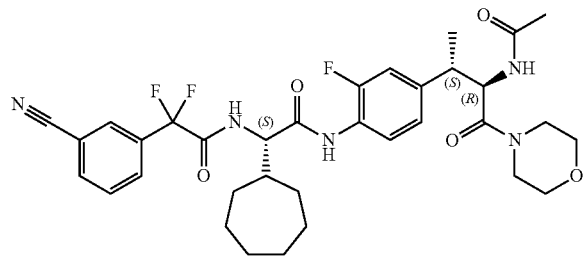

Following General Procedure AJ provided 352. $^1$H NMR (400 MHz, DMSO-d$_6$) δ 9.90 (s, 1H), 9.05 (d, J=8.2 Hz, 1H), 8.27 (d, J=8.6 Hz, 1H), 8.14 (s, 1H), 8.06 (d, J=7.9 Hz, 1H), 7.95 (d, J=8.2 Hz, 1H), 7.76 (t, J=7.8 Hz, 1H), 7.61 (t, J=8.2 Hz, 1H), 7.25-7.09 (m, 1H), 7.09-6.96 (m, 1H), 5.00-4.72 (m, 1H), 4.42 (t, J=8.5 Hz, 1H), 3.81-3.47 (m, 1H), 2.15 (ddt, J=20.7, 14.8, 7.4 Hz, 2H), 2.01-1.76 (m, 1H), 1.76-1.47 (m, 6H), 1.20 (d, J=7.0 Hz, 3H), 1.18-1.02 (m, 2H), 0.99 (t, J=7.6 Hz, 2H), 0.93 (d, J=11.9 Hz, 1H), 0.71 (t, J=7.6 Hz, 1H). UPLC-MS (basic 4 min): rt=1.82 min; m/z=656.3 for [M+H]$^+$.

Example 412: N-[(2R,3S)-3-{4-[(2S)-2-cycloheptyl-2-[(1-ethyl-1H-pyrazol-5-yl)formamido]acetamido]-3-fluorophenyl}-1-(1,1-dioxo-lib-thiomorpholin-4-yl)-1-oxobutan-2-yl]propanamide (353)

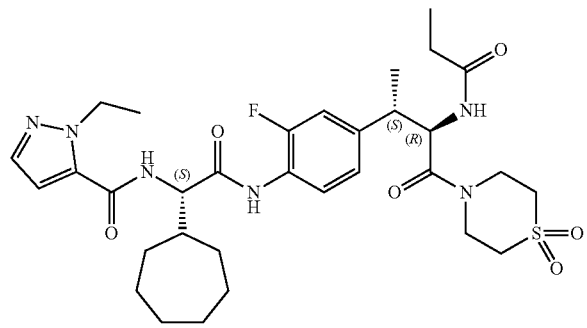

Following General Procedure AJ provided 353. $^1$H NMR (400 MHz, DMSO-d$_6$) δ 9.86 (s, 1H), 8.43 (d, J=8.6 Hz, 1H), 8.36 (d, J=8.2 Hz, 1H), 7.68 (t, J=8.2 Hz, 1H), 7.48 (d, J=2.1 Hz, 1H), 7.19 (dd, J=12.1, 1.9 Hz, 1H), 7.08-7.02 (m, 1H), 6.99 (d, J=2.1 Hz, 1H), 4.94 (t, J=8.8 Hz, 1H), 4.62 (t, J=8.5 Hz, 1H), 4.47 (q, J=7.1 Hz, 2H), 4.04-3.82 (m, 2H), 3.65 (ddd, J=15.5, 8.5, 2.4 Hz, 1H), 3.47-3.36 (m, 1H), 3.19-3.08 (m, 2H), 2.85 (tdd, J=35.9, 13.5, 5.9 Hz, 3H), 2.17 (qq, J=15.1, 7.5 Hz, 3H), 1.76-1.63 (m, 4H), 1.52 (dd, J=12.6, 5.4 Hz, 3H), 1.46-1.34 (m, 5H), 1.31-1.27 (m, 3H), 1.22 (d, J=7.0 Hz, 3H), 1.00 (t, J=7.6 Hz, 3H). UPLC-MS (basic 4 min): rt=1.78 min; m/z=661.3 for [M+H]$^+$.

Example 413: N-[(2R,3S)-3-{4-[(2S)-2-[2-(3-cyanophenyl)-2,2-difluoroacetamido]-2-cycloheptyl acetamido]-3-fluorophenyl}-1-(1,1-dioxo-lib-thiomorpholin-4-yl)-1-oxobutan-2-yl]propanamide (354)

Following General Procedure AJ provided 354. $^1$H NMR (400 MHz, Methanol-d$_4$) δ 8.04 (s, 1H), 7.93 (dd, J=19.2, 7.9 Hz, 2H), 7.71 (dq, J=14.7, 7.7, 7.1 Hz, 2H), 7.19-7.06 (m, 2H), 5.01 (dd, J=57.8, 10.0 Hz, 1H), 4.52 (d, J=8.2 Hz, 1H), 4.47-3.61 (m, 5H), 3.28-3.01 (m, 2H), 2.95 (t, J=11.5 Hz, 1H), 2.68 (dd, J=12.4, 9.1 Hz, 1H), 2.50 (d, J=11.9 Hz, 1H), 2.35-1.94 (m, 3H), 1.88-1.40 (m, 9H), 1.30 (dd, J=48.8, 7.0 Hz, 5H), 1.00 (dt, J=109.0, 7.6 Hz, 3H). UPLC-MS (basic 4 min): rt=1.93 min; m/z=718.5 for [M+H]$^+$.

Example 414: N-[(2R,3S)-3-{4-[(2S)-2-[2-(3-cyanophenyl)-2,2-difluoroacetamido]-2-cycloheptyl acetamido]-3-fluorophenyl}-1-(4-hydroxy-4-methylpiperidin-1-yl)-1-oxobutan-2-yl]propanamide (355)

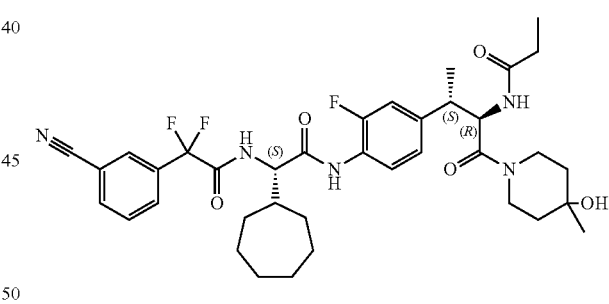

Following General Procedure AJ provided 355. H NMR (400 MHz, DMSO-d$_6$) δ 9.95 (d, J=11.0 Hz, 1H), 9.06 (d, J=8.4 Hz, 1H), 8.25 (d, J=9.0 Hz, 1H), 8.16 (s, 1H), 8.07 (d, J=7.8 Hz, 1H), 7.96 (d, J=8.2 Hz, 1H), 7.75 (q, J=8.1 Hz, 2H), 7.16-6.97 (m, 2H), 4.91 (dt, J=48.1, 9.4 Hz, 1H), 4.57-4.39 (m, 1H), 4.18 (s, 1H), 3.94-3.74 (m, 1H), 3.74-3.50 (m, 1H), 3.22-2.98 (m, 3H), 2.83-2.65 (m, 1H), 2.26-2.00 (m, 3H), 1.51 (dddd, J=29.2, 21.2, 16.8, 8.9 Hz, 8H), 1.40-1.28 (m, 4H), 1.21 (d, J=7.1 Hz, 3H), 1.17-1.13 (m, 2H), 0.99 (t, J=7.6 Hz, 3H), 0.83 (s, 3H), 0.70 (dd, J=7.7, 3.4 Hz, 1H). UPLC-MS (basic 4 min): rt=1.91 min; m/z=698.4 for [M+H]$^+$.

519

Example 415: N-[(2R,3S)-3-{4-[(2S)-2-cycloheptyl-2-[(1-ethyl-1H-pyrazol-5-yl)formamido]acetamido]-3-fluorophenyl}-1-[3-(dimethylamino)azetidin-1-yl]-1-oxobutan-2-yl]propanamide (356)

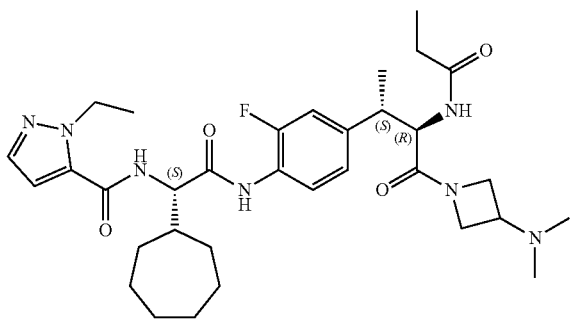

Following General Procedure AJ provided 356. $^1$H NMR (400 MHz, DMSO-d$_6$) δ 10.00-9.63 (m, 1H), 8.42 (t, J=8.2 Hz, 1H), 8.19-7.98 (m, 1H), 7.80-7.59 (m, 1H), 7.48-7.47 (m, 1H), 7.19-6.94 (m, 3H), 4.65-4.59 (m, 1H), 4.50-4.34 (m, 3H), 4.12-3.86 (m, 1H), 3.71-3.65 (m, 1H), 3.50-3.49 (m, 1H), 3.07-3.01 (m, 2H), 2.18-2.03 (m, 4H), 1.97 (s, 2H), 1.88 (s, 3H), 1.81-1.62 (m, 4H), 1.58-1.34 (m, 8H), 1.32-1.11 (m, 6H), 0.98 (t, J=7.6 Hz, 2H), 0.77-0.73 (m, 1H) UPLC-MS (basic 4 min): rt=1.74 min; m/z=626.4 for [M+H]$^+$.

Example 416: N-[(2R,3S)-3-{4-[(2S)-2-cycloheptyl-2-[(3-ethyl-1,2-oxazol-4-yl)formamido]acetamido]-3-fluorophenyl}-1-(4-hydroxy-4-methylpiperidin-1-yl)-1-oxobutan-2-yl]propanamide (357)

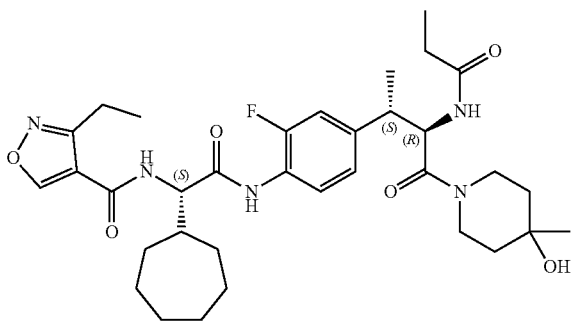

Following General Procedure AJ provided 357. $^1$H NMR (400 MHz, DMSO-d$_6$) δ 10.00-9.77 (m, 1H), 9.40 (d, J=5.3 Hz, 1H), 8.43 (d, J=8.5 Hz, 1H), 8.29-8.01 (m, 1H), 7.84-7.52 (m, 1H), 7.35-6.93 (m, 3H), 5.01-4.77 (m, 1H), 4.65 (q, J=7.9 Hz, 1H), 3.87-3.84 (m, 1H), 3.16-3.04 (m, 2H), 2.87-2.81 (m, 2H), 2.73-2.70 (m, 1H), 2.21-2.06 (m, 1H), 2.02-1.80 (m, 1H), 1.67-1.65 (m, 4H), 1.54-1.28 (m, 11H), 1.22-1.09 (m, 9H), 0.98 (td, J=7.5, 1.7 Hz, 2H), 0.83 (s, 1H), 0.70 (td, J=7.7, 2.9 Hz, 1H). UPLC-MS (basic 4 min): rt=1.78 min; m/z=642.4 for [M+H]$^+$.

520

Example 417: N-[(2R,3S)-3-{4-[(2S)-2-cyclohexyl-2-[(1-ethyl-1H-pyrazol-5-yl)formamido]acetamido]-3-fluorophenyl}-1-[4-(2-methoxyethyl)piperazin-1-yl]-1-oxobutan-2-yl]propanamide (358)

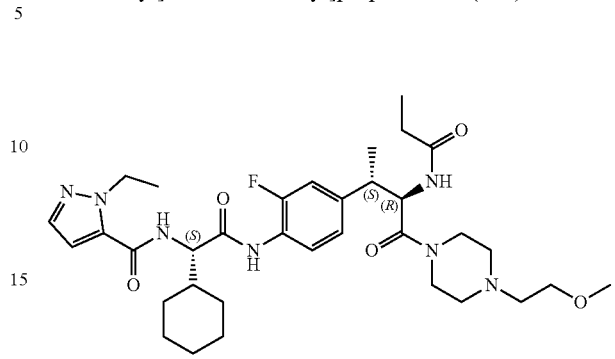

Following General Procedure AJ provided 358. $^1$H NMR (400 MHz, DMSO-d$_6$) δ 9.87 (s, 1H), 8.44 (d, J=8.3 Hz, 1H), 8.26 (d, J=8.7 Hz, 1H), 7.71 (t, J=8.3 Hz, 1H), 7.48 (d, J=2.0 Hz, 1H), 7.11 (dd, J=12.0, 1.9 Hz, 1H), 7.01 (dd, J=6.6, 2.0 Hz, 2H), 4.87 (t, J=9.3 Hz, 1H), 4.55 (t, J=8.4 Hz, 1H), 4.47 (q, J=7.1 Hz, 2H), 3.17 (s, 3H), 3.13-2.99 (m, 2H), 2.28 (t, J=5.7 Hz, 4H), 2.14 (qq, J=15.1, 7.6 Hz, 2H), 1.81 (d, J=11.3 Hz, 1H), 1.67 (d, J=28.0 Hz, 3H), 1.28 (t, J=7.1 Hz, 3H), 1.19 (t, J=8.0 Hz, 8H), 0.99 (t, J=7.6 Hz, 3H). UPLC-MS (basic 4 min): rt=1.69 min; m/z=656.4 for [M+H]$^+$.

Example 418: N-[(2R,3S)-3-{4-[(2S)-2-cyclohexyl-2-[(1-ethyl-1H-pyrazol-5-yl)formamido]acetamido]-3-fluorophenyl}-1-(morpholin-4-yl)-1-oxobutan-2-yl]propanamide (359)

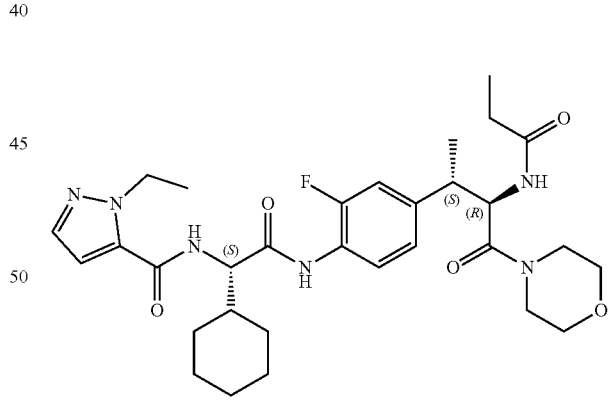

Following General Procedure AJ provided 359. $^1$H NMR (400 MHz, DMSO-d$_6$) δ 9.87 (s, 1H), 8.45 (d, J=8.3 Hz, 1H), 8.29 (d, J=8.5 Hz, 1H), 7.65 (t, J=8.3 Hz, 1H), 7.48 (d, J=2.1 Hz, 1H), 7.15 (d, J=11.0 Hz, 1H), 7.04-7.01 (m, 2H), 4.92-4.81 (m, 1H), 4.55 (t, J=8.5 Hz, 1H), 4.48 (q, J=7.1 Hz, 2H), 3.40 (dd, J=15.2, 5.4 Hz, 4H), 3.27-3.02 (m, 7H), 2.24-2.08 (m, 2H), 1.91-1.60 (m, 6H), 1.29 (t, J=7.2 Hz, 3H), 1.23-1.17 (m, 5H), 0.99 (t, J=7.6 Hz, 3H). UPLC-MS (basic 2 min): rt=1.05 min; m/z=599.3 for [M+H]$^+$.

Example 419: (2R,3S)-3-{4-[(2S)-2-cyclohexyl-2-[(1-ethyl-1H-pyrazol-5-yl)formamido]acetamido]-3-fluorophenyl}-N-(oxan-4-yl)-2-propanamidobutanamide (360)

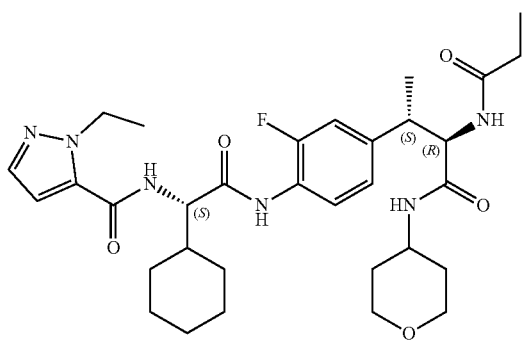

Following General Procedure AJ provided 360. $^1$H NMR (400 MHz, DMSO-d$_6$) δ 9.83 (s, 1H), 8.44 (d, J=8.4 Hz, 1H), 8.19 (s, 1H), 7.83 (d, J=9.1 Hz, 1H), 7.66 (d, J=8.4 Hz, 1H), 7.48 (d, J=2.1 Hz, 1H), 7.08 (d, J=11.2 Hz, 1H), 7.00 (d, J=2.1 Hz, 2H), 4.57-4.50 (m, 2H), 4.49-4.44 (m, 2H), 3.80 (dd, J=19.6, 10.1 Hz, 4H), 3.08-2.86 (m, 7H), 1.97-1.89 (m, 3H), 1.77-1.58 (m, 6H), 1.28 (t, J=7.2 Hz, 3H), 1.22-1.10 (m, 6H), 0.77 (t, J=7.6 Hz, 3H). UPLC-MS (basic 4 min): rt=1.65 min; m/z=613.3 for [M+H]$^+$.

Example 420: N-[(2R,3S)-3-{4-[(2S)-2-cyclohexyl-2-[(1-ethyl-1H-pyrazol-5-yl)formamido]acetamido]-3-fluorophenyl}-1-(1,1-dioxo-1ib-thiomorpholin-4-yl)-1-oxobutan-2-yl]propanamide (361)

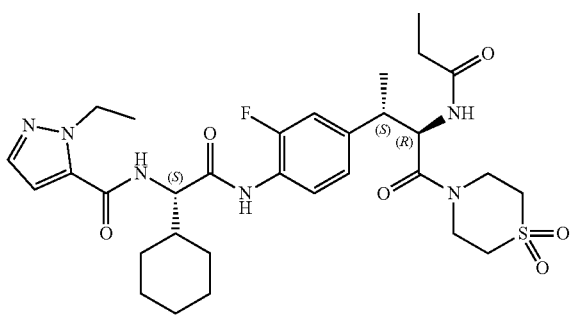

Following General Procedure AJ provided 361. NMR (400 MHz, DMSO-d$_6$) δ 9.86 (s, 1H), 8.43 (d, J=8.4 Hz, 1H), 8.36 (d, J=8.2 Hz, 1H), 7.68 (q, J=8.1 Hz, 1H), 7.48 (d, J=2.0 Hz, 1H), 7.24-7.17 (m, 1H), 7.04 (d, J=7.9 Hz, 1H), 7.00 (d, J=2.1 Hz, 1H), 4.93 (d, J=19.1 Hz, 1H), 4.60-4.52 (m, 1H), 4.52-4.42 (m, 2H), 3.21-2.91 (m, 6H), 2.25-2.08 (m, 2H), 1.96-1.77 (m, 3H), 1.77-1.56 (m, 4H), 1.28 (t, J=7.1 Hz, 3H), 1.22 (d, J=7.0 Hz, 3H), 1.20-1.12 (m, 4H), 1.00 (t, J=7.6 Hz, 3H). UPLC-MS (basic 2 min): rt=1.03 min; m/z=647.3 for [M+H]$^+$.

Example 421: N-[(2R,3S)-3-{4-[(2S)-2-cyclohexyl-2-[(1-ethyl-1H-pyrazol-5-yl)formamido]acetamido]-3-fluorophenyl}-1-oxo-1-[4-(propan-2-yl)piperazin-1-yl]butan-2-yl]propanamide (362)

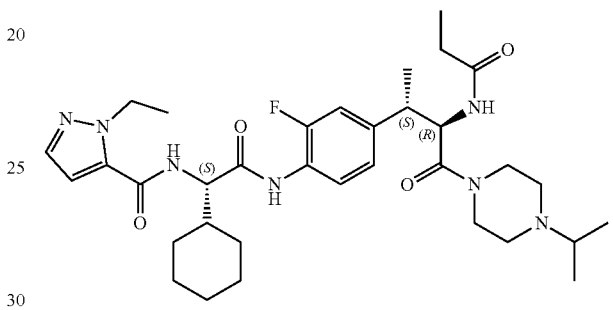

Following General Procedure AJ provided 362. $^1$H NMR (400 MHz, DMSO-d$_6$) δ 9.90 (d, J=8.8 Hz, 1H), 9.03 (d, J=8.3 Hz, 1H), 8.20 (t, J=9.7 Hz, 1H), 8.13 (s, 1H), 8.06 (d, J=7.8 Hz, 1H), 7.95 (d, J=8.3 Hz, 2H), 7.76 (td, J=8.1, 3.4 Hz, 2H), 7.59 (t, J=8.2 Hz, 1H), 7.29-6.91 (m, 2H), 4.96 (t, J=10.0 Hz, 1H), 4.84 (t, J=9.5 Hz, 1H), 4.54-4.34 (m, 2H), 3.85 (d, J=12.6 Hz, 1H), 3.61 (d, J=13.5 Hz, 1H), 3.10 (t, J=12.6 Hz, 2H), 2.31-2.02 (m, 2H), 1.96-1.77 (m, 2H), 1.62 (d, J=14.5 Hz, 6H), 1.30 (s, 1H), 1.25-1.03 (m, 5H), 0.99 (td, J=7.6, 1.7 Hz, 3H), 0.93 (s, 1H), 0.82 (s, 2H), 0.71 (td, J=7.6, 3.1 Hz, 1H), 0.43 (s, 1H). UPLC-MS (basic 4 min): rt=1.76 min; m/z=640.4 for [M+H]$^+$.

Example 422: N-[(2R,3S)-3-{4-[(2S)-2-[2-(3-cyanophenyl)-2,2-difluoroacetamido]-2-cyclohexyl acetamido]-3-fluorophenyl}-1-oxo-1-{4-[(pyridin-2-yl)methyl]piperazin-1-yl}butan-2-yl]propanamide (363)

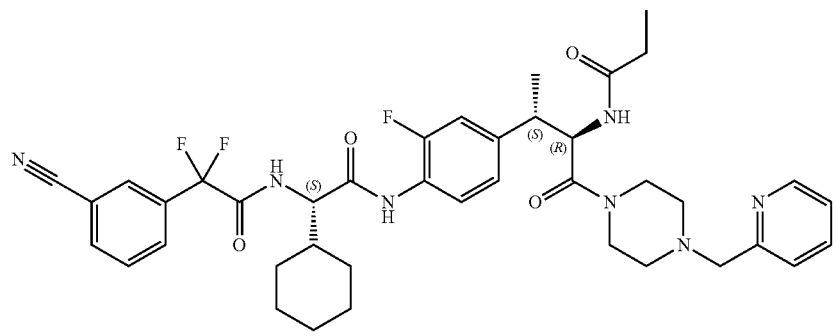

Following General Procedure AJ provided 363. ¹H NMR (400 MHz, DMSO-d₆) δ 9.97 (s, 1H), 9.11 (d, J=8.3 Hz, 1H), 8.53-8.43 (m, 1H), 8.28 (d, J=8.7 Hz, 1H), 8.15 (d, J=2.0 Hz, 1H), 8.05 (t, J=8.1 Hz, 2H), 7.95 (d, J=8.2 Hz, 1H), 7.82-7.56 (m, 4H), 7.39-7.32 (m, 1H), 7.30-7.18 (m, 1H), 7.11 (dd, J=12.0, 1.9 Hz, 1H), 7.02 (d, J=8.3 Hz, 1H), 4.88 (t, J=9.4 Hz, 1H), 4.50-4.38 (m, 1H), 3.11 (dd, J=17.0, 9.6 Hz, 1H), 2.31 (d, J=20.4 Hz, 2H), 2.14 (qq, J=15.1, 7.6 Hz, 2H), 1.99-1.73 (m, 3H), 1.61 (d, J=23.5 Hz, 8H), 1.19 (d, J=7.0 Hz, 3H), 1.16-1.01 (m, 3H), 0.98 (t, J=7.6 Hz, 3H), 0.92 (d, J=11.4 Hz, 1H), 0.70 (t, J=7.6 Hz, 1H). UPLC-MS (basic 4 min): rt=1.87 min; m/z=746.4 for [M+H]⁺.

Example 423: N-[(2R,3S)-3-{4-[(2S)-2-[2-(3-cyanophenyl)-2,2-difluoroacetamido]-2-cyclohexyl acetamido]-3-fluorophenyl}-1-(4-hydroxy-4-methylpiperidin-1-yl)-1-oxobutan-2-yl]propanamide (364)

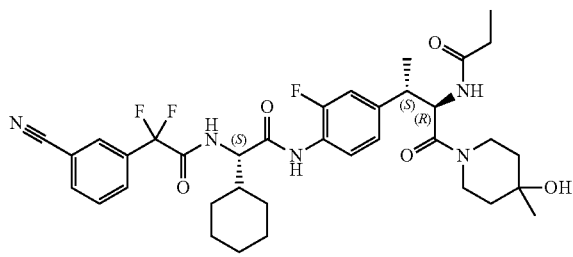

Following General Procedure AJ provided 364. ¹H NMR (400 MHz, DMSO-d₆) δ 9.90 (d, J=8.8 Hz, 1H), 9.03 (d, J=8.3 Hz, 1H), 8.20 (t, J=9.7 Hz, 1H), 8.13 (s, 1H), 8.06 (d, J=7.8 Hz, 1H), 7.95 (d, J=8.3 Hz, 2H), 7.76 (td, J=8.1, 3.4 Hz, 2H), 7.59 (t, J=8.2 Hz, 1H), 7.28-6.91 (m, 2H), 4.96 (t, J=10.0 Hz, 1H), 4.84 (t, J=9.5 Hz, 1H), 4.51-4.34 (m, 2H), 4.21 (s, 1H), 4.17 (s, 1H), 3.85 (d, J=12.6 Hz, 1H), 3.61 (d, J=13.5 Hz, 1H), 3.10 (t, J=12.6 Hz, 2H), 2.74 (d, J=11.1 Hz, 1H), 2.24-2.03 (m, 2H), 1.91-1.75 (m, 2H), 1.62 (d, J=14.5 Hz, 6H), 1.30 (s, 1H), 1.26-1.03 (m, 5H), 0.99 (td, J=7.6, 1.8 Hz, 3H), 0.93 (s, 2H), 0.82 (s, 2H), 0.71 (td, J=7.6, 3.1 Hz, 1H), 0.43 (s, 1H). UPLC-MS (basic 4 min): rt=1.81 min; m/z=684.4 for [M+H]⁺.

Example 424: N-[(2R,3S)-3-{4-[(2S)-2-[2-(3-cyanophenyl)-2,2-difluoroacetamido]-2-cyclohexyl acetamido]-3-fluorophenyl}-1-(1,1-dioxo-1λ⁶-thiomorpholin-4-yl)-1-oxobutan-2-yl]propanamide (365)

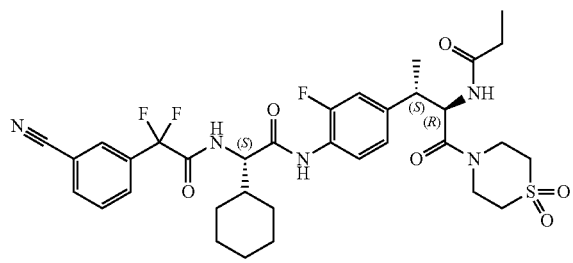

Following General Procedure AJ provided 365. ¹H NMR (400 MHz, DMSO-d₆) δ 9.92 (d, J=13.5 Hz, 1H), 9.09 (dd, J=8.3, 3.9 Hz, 1H), 8.38 (d, J=8.3 Hz, 1H), 8.15 (s, 1H), 8.13-8.04 (m, 1H), 7.96 (d, J=8.0 Hz, 1H), 7.77 (t, J=7.8 Hz, 1H), 7.64 (dt, J=17.1, 8.2 Hz, 1H), 7.28-7.15 (m, 1H), 7.06 (dd, J=18.7, 8.3 Hz, 1H), 4.94 (td, J=9.2, 4.1 Hz, 1H), 4.43 (td, J=8.5, 4.0 Hz, 1H), 4.30-3.54 (m, 3H), 3.29-2.96 (m, 2H), 2.96-2.62 (m, 1H), 2.30-2.02 (m, 1H), 2.02-1.77 (m, 1H), 1.62 (dd, J=23.0, 10.8 Hz, 6H), 1.30-1.18 (m, 2H), 1.18-1.03 (m, 3H), 1.00 (t, J=7.6 Hz, 2H), 0.97-0.83 (m, 1H), 0.72 (t, J=7.6 Hz, 1H). UPLC-MS (basic 4 min): rt=1.83 min; m/z=704.3 for [M+H]⁺.

Example 425: N-[(2R,3S)-1-(4-benzylpiperazin-1-yl)-3-{4-[(2S)-2-cyclohexyl-2-[(1-ethyl-1H-pyrazol-5-yl)formamido]acetamido]-3-fluorophenyl}-1-oxobutan-2-yl]propanamide (366)

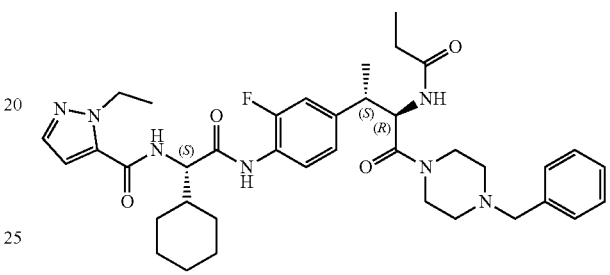

Following General Procedure AJ provided 366. ¹H NMR (400 MHz, DMSO-d₆) δ 9.93 (s, 1H), 8.26 (d, J=8.7 Hz, 1H), 7.74 (t, J=8.3 Hz, 1H), 7.47 (d, J=2.0 Hz, 1H), 7.30-7.17 (m, 5H), 7.01 (q, J=3.4, 2.9 Hz, 2H), 4.86 (t, J=9.3 Hz, 1H), 4.50-4.37 (m, 2H), 3.46 (s, 2H), 3.25 (d, J=5.4 Hz, 2H), 3.05 (dt, J=37.5, 8.5 Hz, 2H), 2.21 (d, J=7.6 Hz, 1H), 2.12 (ddt, J=22.4, 15.1, 7.5 Hz, 2H), 1.86 (dd, J=23.7, 11.5 Hz, 2H), 1.68 (d, J=10.7 Hz, 4H), 1.58 (d, J=30.2 Hz, 2H), 1.22 (dt, J=21.3, 7.2 Hz, 9H), 1.07 (t, J=12.1 Hz, 1H), 0.98 (t, J=7.6 Hz, 3H). UPLC-MS (basic 4 min): rt=1.96 min; m/z=688.5 for [M+H]⁺.

Example 426: N-[(2R,3S)-1-(4-benzylpiperazin-1-yl)-3-{4-[(2S)-2-[(1-ethyl-1H-pyrazol-5-yl)formamido]-2-[(1r,4S)-4-methylcyclohexyl]acetamido]-3-fluorophenyl}-1-oxobutan-2-yl]propanamide (367)

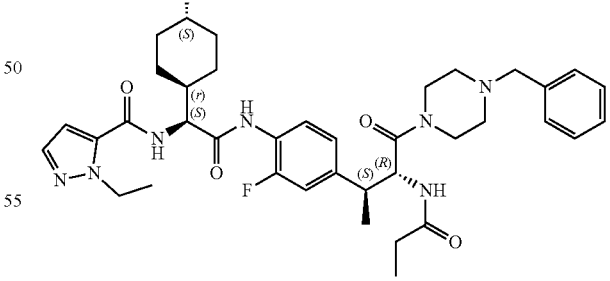

Following General Procedure AJ provided 367. ¹H NMR (400 MHz, DMSO-d₆) δ 9.91 (s, 1H), 8.46 (d, J=8.3 Hz, 1H), 8.26 (d, J=8.7 Hz, 1H), 7.75 (t, J=8.3 Hz, 1H), 7.47 (d, J=2.0 Hz, 1H), 7.27-7.18 (m, 5H), 7.04-6.98 (m, 2H), 4.86 (t, J=9.3 Hz, 1H), 4.58 (t, J=8.4 Hz, 1H), 4.48-4.41 (m, 2H), 3.49-3.44 (m, 2H), 3.29-3.20 (m, 3H), 3.11-3.07 (m, 1H), 3.03-2.97 (m, 1H), 2.28-2.08 (m, 4H), 1.89-1.78 (m, 2H), 1.71-1.65 (m, 4H), 1.57-1.47 (m, 1H), 1.35-1.20 (m, 8H), 0.98 (t, J=7.6 Hz, 3H), 0.91-0.82 (m, 5H). UPLC-MS (basic 4 min): rt=2.13 min; m/z=702.4 for [M+H]⁺.

Example 427: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-oxo-1-[4-(propan-2-yl)piperazin-1-yl]butan-2-yl]propanamide (368)

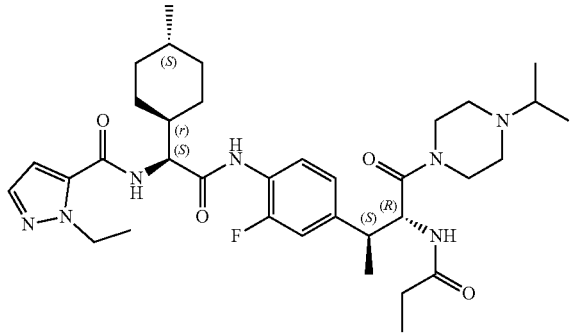

Following General Procedure AJ provided 368. H NMR (400 MHz, DMSO-d₆) δ 9.83 (s, 1H), 8.44 (d, J=8.5 Hz, 1H), 8.25 (d, J=8.7 Hz, 1H), 7.77 (t, J=8.3 Hz, 1H), 7.47 (d, J=2.0 Hz, 1H), 7.14-7.10 (m, 1H), 7.04-6.95 (m, 2H), 4.90-4.85 (m, 1H), 4.56-4.44 (m, 3H), 3.49-3.43 (m, 2H), 3.24-3.17 (m, 1H), 3.13-3.07 (m, 1H), 2.98-2.93 (m, 1H), 2.31-2.23 (m, 2H), 2.21-2.06 (m, 2H), 1.85-1.74 (m, 3H), 1.71-1.62 (m, 4H), 1.28 (t, J=7.1 Hz, 4H), 1.20 (d, J=7.0 Hz, 4H), 1.13-1.03 (m, 1H), 0.99 (t, J=7.6 Hz, 3H), 0.91-0.85 (m, 5H), 0.81-0.79 (m, 6H). UPLC-MS (basic 4 min): rt=1.99 min; m/z=654.5 for [M+H]⁺.

Example 428: N-[(2R,3S)-1-(4,4-difluoropiperidin-1-yl)-3-{4-[(2S)-2-[(1-ethyl-1H-pyrazol-5-yl) formamido]-2-[(1r,4S)-4-methylcyclohexyl]acetamido]-3-fluorophenyl}-1-oxobutan-2-yl]propanamide (369)

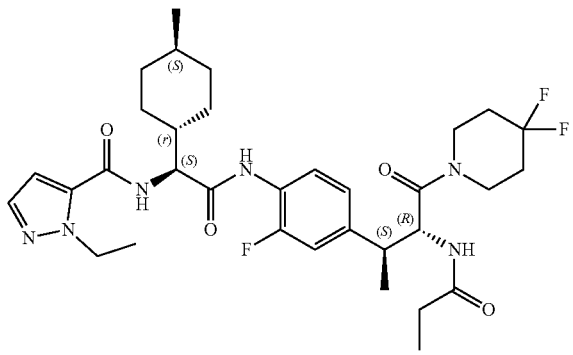

Following General Procedure AJ provided 369. ¹H NMR (400 MHz, DMSO-d₆) δ 9.84 (d, J=13.3 Hz, 1H), 8.46 (d, J=8.3 Hz, 1H), 8.33 (d, J=8.6 Hz, 1H), 8.07 (d, J=9.1 Hz, 0H), 7.72 (t, J=8.3 Hz, 0H), 7.65 (t, J=8.3 Hz, 0H), 7.52-7.43 (m, 1H), 7.22 (d, J=12.4 Hz, 0H), 7.15 (dd, J=12.1, 1.9 Hz, 1H), 7.06 (t, J=9.4 Hz, 1H), 7.00 (dd, J=3.0, 2.0 Hz, 1H), 4.94 (q, J=9.9, 9.5 Hz, 1H), 4.64-4.35 (m, 3H), 3.83 (s, 0H), 3.74 (d, J=8.4 Hz, 1H), 3.50 (s, 2H), 3.19-3.03 (m, 1H), 2.16 (qq, J=15.1, 7.5 Hz, 1H), 2.06-1.57 (m, 3H), 1.37-1.17 (m, 7H), 1.14 (d, J=7.0 Hz, 1H), 1.06 (d, J=12.5 Hz, 1H), 1.00 (t, J=7.6 Hz, 2H), 0.93-0.79 (m, 5H), 0.71 (t, J=7.6 Hz, 1H). UPLC-MS (basic 4 min): rt=1.94 min; m/z=647.3 for [M+H]⁺.

Example 429: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-methylpiperidin-1-yl)-1-oxobutan-2-yl]propanamide (370)

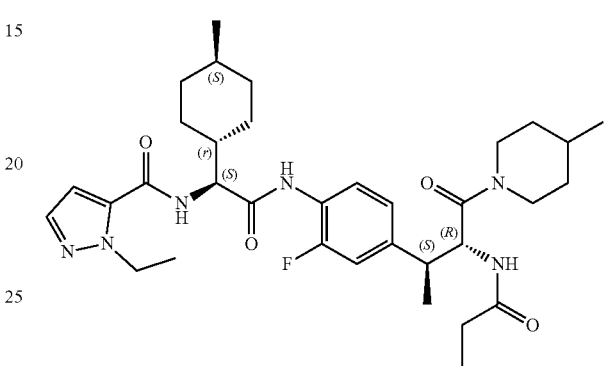

Following General Procedure AJ provided 370. ¹H NMR (400 MHz, DMSO-d₆) δ 9.89-9.77 (m, 1H), 8.45 (d, J=8.1 Hz, 1H), 8.24 (d, J=8.9 Hz, 1H), 7.99 (s, 0H), 7.84 (t, J=8.3 Hz, 1H), 7.63 (t, J=8.3 Hz, 0H), 7.47 (t, J=1.7 Hz, 1H), 7.21-6.92 (m, 2H), 5.03-4.74 (m, 1H), 4.63-4.34 (m, 2H), 4.17 (d, J=14.0 Hz, 1H), 3.91 (s, 1H), 3.23-3.05 (m, 1H), 3.05-2.56 (m, 1H), 2.40-2.24 (m, 1H), 2.24-1.99 (m, 1H), 1.95-1.74 (m, 2H), 1.70 (d, J=13.5 Hz, 3H), 1.46 (s, 0H), 1.41-1.18 (m, 6H), 1.18-1.02 (m, 2H), 0.99 (td, J=7.6, 4.5 Hz, 2H), 0.96-0.76 (m, 4H), 0.76-0.68 (m, 1H), 0.62 (d, J=6.0 Hz, 2H), 0.28 (s, 0H). UPLC-MS (basic 2 min): rt=1.20 min; m/z=625.4 for [M+H]⁺.

Example 430: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-oxo-1-(thiomorpholin-4-yl)butan-2-yl]propanamide (371)

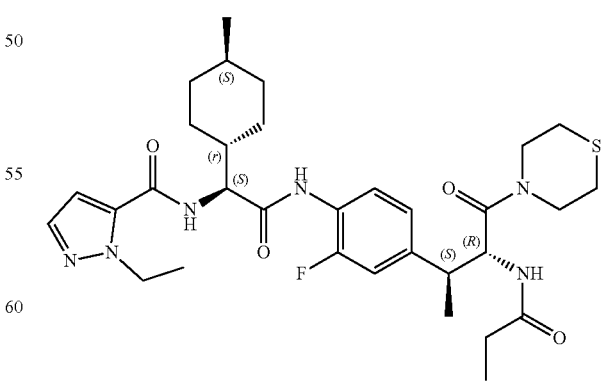

Following General Procedure AJ provided 371. ¹H NMR (400 MHz, DMSO-d₆) δ 9.84 (d, J=20.0 Hz, 1H), 8.45 (d, J=8.7 Hz, 1H), 8.32 (d, J=8.9 Hz, 1H), 8.07 (d, J=9.3 Hz, OH), 7.68 (dt, J=23.6, 8.3 Hz, 1H), 7.48 (d, J=2.0 Hz, 1H), 7.27-7.10 (m, 1H), 7.10-6.96 (m, 2H), 4.88 (q, J=9.3 Hz, 1H), 4.62-4.34 (m, 1H), 4.05-3.78 (m, 3H), 3.78-3.57 (m, 1H), 3.57-3.42 (m, 1H), 3.24-3.07 (m, 1H), 2.17 (ddq, J=22.2, 14.8, 7.6 Hz, 1H), 1.94-1.75 (m, 2H), 1.67 (t, J=17.3 Hz, 3H), 1.35-1.22 (m, 5H), 1.19 (d, J=7.0 Hz, 2H), 1.13 (d, J=6.9 Hz, 1H), 1.07 (d, J=12.3 Hz, 0H), 1.00 (t, J=7.6 Hz, 2H), 0.86 (d, J=6.5 Hz, 4H), 0.70 (t, J=7.6 Hz, 1H). UPLC-MS (basic 2 min): rt=1.15 min; m/z=629.4 for [M+H]$^+$.

Example 431: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-oxo-1-(4-phenoxypiperidin-1-yl)butan-2-yl]propanamide (372)

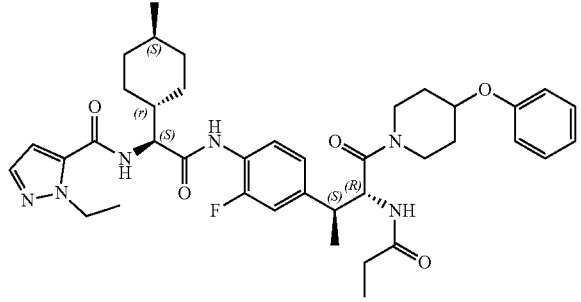

Following General Procedure AJ provided 372. $^1$H NMR (400 MHz, DMSO-d$_6$) δ 10.00-9.73 (m, 1H), 8.57-8.41 (m, 1H), 8.38-8.18 (m, 1H), 8.05 (dd, J=9.2, 3.5 Hz, 0H), 7.76 (t, J=8.3 Hz, 0H), 7.65 (td, J=8.3, 3.3 Hz, 1H), 7.48 (t, J=1.8 Hz, 1H), 7.40-7.18 (m, 3H), 7.14 (d, J=12.0 Hz, 1H), 7.09-6.80 (m, 6H), 4.93 (dt, J=13.5, 9.5 Hz, 1H), 4.76-4.31 (m, 4H), 4.13-3.92 (m, 1H), 3.23-2.98 (m, 1H), 2.30-2.03 (m, 2H), 2.02-1.74 (m, 3H), 1.67 (t, J=15.6 Hz, 3H), 1.60-1.36 (m, 1H), 1.27 (ddt, J=10.6, 6.9, 3.4 Hz, 5H), 1.20 (dt, J=7.1, 3.5 Hz, 2H), 1.17-1.03 (m, 1H), 1.00 (t, J=7.6 Hz, 2H), 0.85 (dt, J=8.1, 4.4 Hz, 4H), 0.71 (td, J=7.6, 2.7 Hz, 1H). UPLC-MS (basic 2 min): rt=1.25 min; m/z=703.4 for [M+H]$^+$.

Example 432: N-[(2R,3S)-1-{6,6-difluoro-2-azaspiro[3.3]heptan-2-yl}-3-{4-[(2S)-2-[(1-ethyl-1H-pyrazol-5-yl)formamido]-2-[(1r,4S)-4-methylcyclohexyl]acetamido]-3-fluorophenyl}-1-oxobutan-2-yl]propanamide (373)

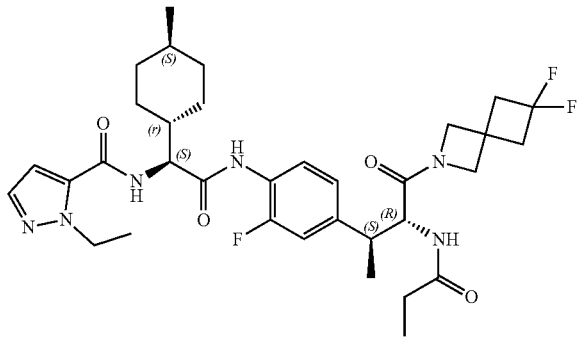

Following General Procedure AJ provided 373. $^1$H NMR (400 MHz, DMSO-d$_6$) δ 9.92 (s, 1H), 8.48 (d, J=8.1 Hz, 1H), 8.23 (d, J=8.6 Hz, 1H), 7.76 (t, J=8.3 Hz, 1H), 7.47 (d, J=2.0 Hz, 1H), 7.07 (dd, J=20.7, 10.1 Hz, 2H), 7.00 (d, J=2.1 Hz, 1H), 4.62-4.41 (m, 4H), 4.41-4.16 (m, 1H), 4.10 (d, J=9.0 Hz, 1H), 4.03-3.87 (m, 1H), 3.82 (d, J=10.2 Hz, 1H), 3.61 (t, J=6.6 Hz, 1H), 2.90-2.62 (m, 3H), 2.26-2.02 (m, 2H), 1.92-1.73 (m, 5H), 1.70 (d, J=15.1 Hz, 5H), 1.41-1.12 (m, 10H), 0.98 (t, J=7.6 Hz, 3H), 0.86 (d, J=6.4 Hz, 7H). UPLC-MS (basic 2 min): rt=1.15 min; m/z=659.4 for [M+H]$^+$.

Example 433: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-hydroxypiperidin-1-yl)-1-oxobutan-2-yl]propanamide (374)

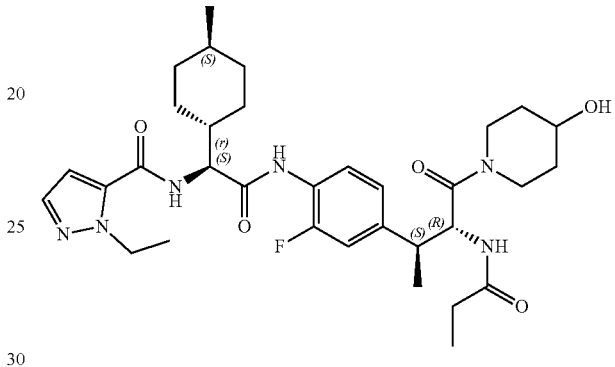

Following General Procedure AJ provided 374. $^1$H NMR (400 MHz, DMSO-d$_6$) δ 9.83 (t, J=11.8 Hz, 1H), 8.45 (dd, J=8.3, 3.6 Hz, 1H), 8.24 (dd, J=14.1, 8.9 Hz, 1H), 8.00 (t, J=9.0 Hz, 0H), 7.75-7.56 (m, 1H), 7.48 (d, J=2.0 Hz, 1H), 7.24-7.03 (m, 1H), 7.03-6.94 (m, 2H), 4.93 (q, J=9.5 Hz, 1H), 4.75 (dd, J=12.6, 4.1 Hz, 0H), 4.63 (d, J=4.0 Hz, 0H), 4.61-4.35 (m, 2H), 3.99 (s, OH), 3.58 (d, J=41.4 Hz, 2H), 3.24-3.07 (m, 1H), 3.07-2.78 (m, 1H), 2.26-2.02 (m, 1H), 1.94-1.46 (m, 6H), 1.38 (s, OH), 1.35-1.22 (m, 4H), 1.17 (d, J=7.0 Hz, 2H), 1.11 (q, J=7.3 Hz, 1H), 0.99 (q, J=7.4 Hz, 3H), 0.86 (d, J=6.4 Hz, 5H), 0.70 (td, J=7.6, 5.1 Hz, 1H). UPLC-MS (basic 2 min): rt=1.06 min; m/z=627.3 for [M+H]$^+$.

Example 434: N-[(2R,3S)-3-{4-[(2S)-2-[(1-cyclopentyl-1H-pyrazol-5-yl)formamido]-2-[(1r,4S)-4-methylcyclohexyl]acetamido]-3-fluorophenyl}-1-(4-methylpiperidin-1-yl)-1-oxobutan-2-yl]propanamide (375)

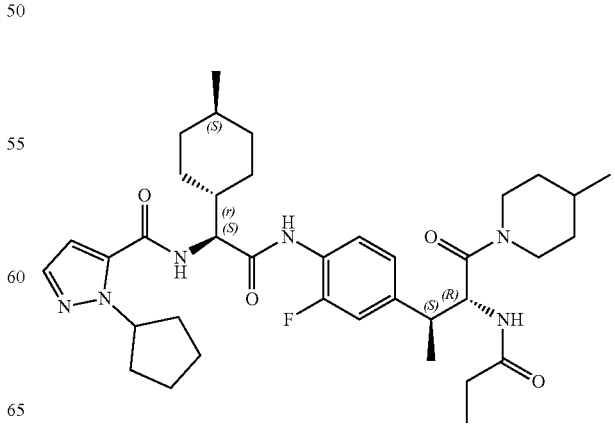

Following General Procedure AJ provided 375. ¹H NMR (400 MHz, DMSO-d₆) δ 9.82 (d, J=8.6 Hz, 1H), 8.42 (t, J=6.9 Hz, 1H), 8.23 (d, J=8.9 Hz, 1H), 7.74 (dt, J=80.2, 8.2 Hz, 1H), 7.47 (d, J=1.9 Hz, 1H), 7.15-6.86 (m, 3H), 5.51 (t, J=7.3 Hz, 1H), 4.88 (dt, J=41.2, 9.3 Hz, 1H), 4.51 (dt, J=14.7, 8.2 Hz, 1H), 4.15 (t, J=13.9 Hz, 1H), 3.91 (d, J=13.5 Hz, 1H), 3.21-3.04 (m, 1H), 2.83-2.54 (m, 1H), 2.29 (t, J=12.8 Hz, 1H), 2.23-2.05 (m, 2H), 2.05-1.39 (m, 14H), 1.38-0.94 (m, 11H), 0.94-0.75 (m, 7H), 0.62 (d, J=5.9 Hz, 2H), 0.16 (dd, J=97.5, 12.8 Hz, 1H). UPLC-MS (basic 4 min): rt=2.28 min; m/z=665.5 for [M+H]⁺.

Example 435: General Procedure AK

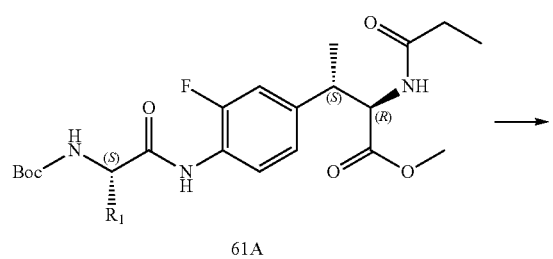

61A

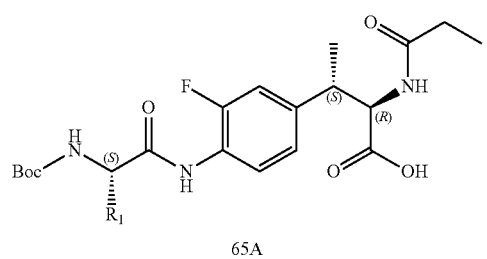

65A

To a solution of 61A (1.0 eq.) in MeOH and THF was added a solution of 1M LiOH in H₂O (1.3 eq.) and the resulting mixture was stirred at RT for 0.5 h. The reaction mixture was concentrated to dryness and the residue was stirred in aq. sat. NaHCO₃ solution and then extracted with EtOAc. The aqueous layer was acidified with conc. HCl and the precipitate was filtered to afford 65A which was used in the next step without further purification.

Example 436: General Procedure AL

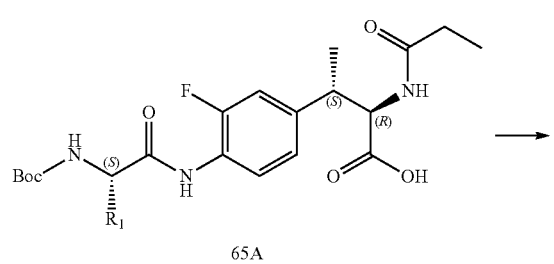

65A

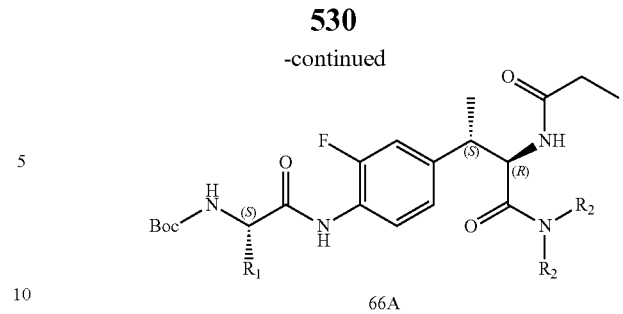

66A

To a solution of 65A (1.0 eq.) in DMF 0.10 mL) were added required amine (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 66A.

Example 437: General Procedure AM

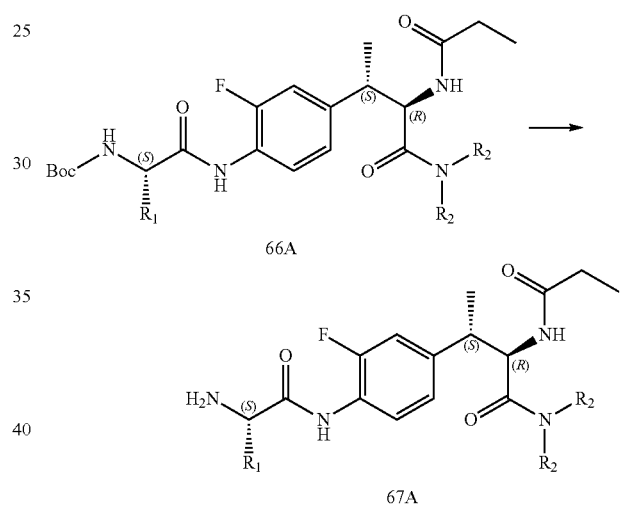

66A

67A

To a solution of 66A (1.0 eq.) in DCM was added TFA and the resulting mixture was stirred at RT for 0.5 h. The reaction mixture was concentrated to dryness and the residue was stirred in aq. sat. K₂CO₃ solution and then extracted with DCM to afford 67A which was used in the next step without further purification.

Example 438: General Procedure AN

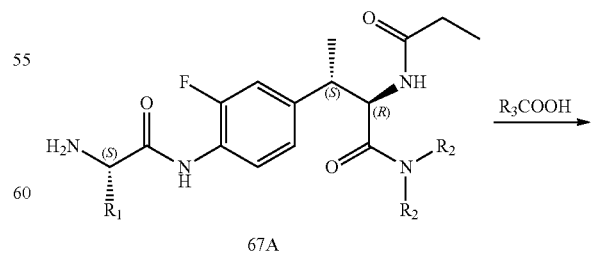

67A 347, 376-378 and 392

To a solution of 67A (1.0 eq,) in DMF (0.1 M) were added the required acid (1.2 eq.), DIPEA (3.0-8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 347, 376-378 and 392.

Example 439: N-[(2R,3S)-3-{4-[(2S)-2-[2,2-difluoro-2-(4-methyl-1,3-thiazol-2-yl)acetamido]-2-[(1r,4S)-4-methylcyclohexyl]acetamido]-3-fluorophenyl}-1-(4-hydroxy-4-methylpiperidin-1-yl)-1-oxobutan-2-yl]propanamide) (376)

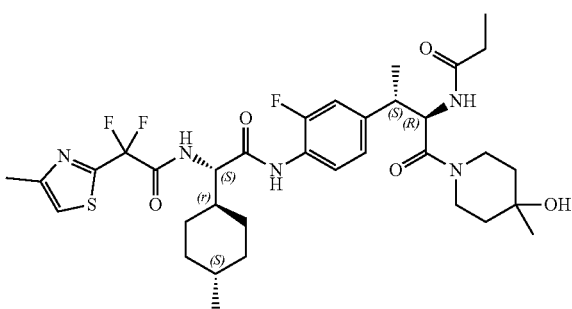

Following General Procedure AN provided 376. ¹H NMR (400 MHz, DMSO-d₆) δ 9.96-9.79 (m, 1H), 9.11-9.03 (m, 1H), 8.30-8.18 (m, 1H), 8.02-7.74 (m, 1H), 7.65 (t, J=1.2 Hz, 2H), 7.15-6.98 (m, 2H), 4.91 (dt, J=45.6, 9.4 Hz, 1H), 4.53-4.37 (m, 2H), 4.22 (d, J=19.2 Hz, 1H), 3.95-3.74 (m, 2H), 3.64 (dd, J=9.9, 6.5 Hz, 1H), 3.12 (d, J=10.6 Hz, 2H), 2.39 (dd, J=2.3, 1.0 Hz, 3H), 2.18 (dd, J=14.9, 7.6 Hz, 1H), 1.84-1.78 (m, 2H), 1.72-1.63 (m, 3H), 1.58 (dd, J=8.4, 3.7 Hz, 1H), 1.51-1.42 (m, 1H), 1.21 (d, J=7.0 Hz, 3H), 1.17-1.14 (m, 2H), 1.13-1.06 (m, 3H), 1.02-0.97 (m, 3H), 0.86-0.84 (m, 6H), 0.71 (td, J=7.6, 3.0 Hz, 1H) UPLC-MS (basic 4 min): rt=1.93 min; m/z=694.4 for [M+H]⁺.

Example 440: N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-hydroxy-4-methylpiperidin-1-yl)-1-oxobutan-2-yl]propanamide) (377)

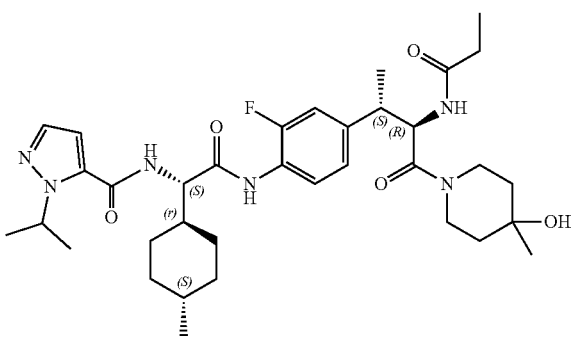

Following General Procedure AN provided 377. ¹H NMR (400 MHz, DMSO-d₆) δ 9.82 (d, J=20.6 Hz, 1H), 8.42 (d, J=8.3 Hz, 1H), 8.27-8.18 (m, 1H), 8.03-7.79 (m, 1H), 7.64 (t, J=7.0 Hz, 1H), 7.49 (d, J=2.0 Hz, 1H), 7.14-6.99 (m, 2H), 6.93 (dd, J=6.5, 2.0 Hz, 1H), 5.42-5.37 (m, 1H), 5.00-4.84 (m, 1H), 4.53 (t, J=8.2 Hz, 1H), 4.21 (d, J=18.2 Hz, 1H), 3.94-3.77 (m, 2H), 3.63 (dt, J=13.2, 6.0 Hz, 1H), 3.12 (dd, J=14.5, 5.8 Hz, 2H), 2.78-2.70 (m, 1H), 2.18 (dd, J=14.9, 7.5 Hz, 1H), 1.79 (dd, J=9.2, 3.9 Hz, 2H), 1.73-1.65 (m, 3H), 1.39-1.34 (m, 9H), 1.21 (d, J=7.1 Hz, 3H), 1.16 (d, J=8.0 Hz, 2H), 1.12 (d, J=4.9 Hz, 1H), 1.06 (s, 1H), 0.99 (td, J=7.6, 1.8 Hz, 3H), 0.87-0.84 (m, 6H), 0.73-0.69 (m, 1H). UPLC-MS (basic 4 min): rt=1.86 min; m/z=655.4 for [M+H]⁺.

Example 441: N-[(2R,3S)-3-{4-[(2S)-2-[2,2-difluoro-2-(1,3-thiazol-5-yl)acetamido]-2-[(1r,4S)-4-methylcyclohexyl]acetamido]-3-fluorophenyl}-1-(4-hydroxy-4-methylpiperidin-1-yl)-1-oxobutan-2-yl]propanamide) (378)

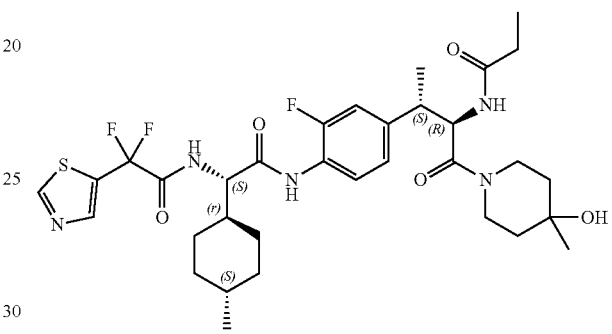

Following General Procedure AN provided 378. ¹H NMR (400 MHz, DMSO-d₆) δ 9.99-9.86 (m, 1H), 9.35 (d, J=0.8 Hz, 1H), 9.24-9.17 (m, 1H), 8.29-8.19 (m, 2H), 7.70 (dt, J=66.3, 8.2 Hz, 1H), 7.04 (td, J=19.6, 17.8, 10.2 Hz, 2H), 5.00-4.80 (m, 1H), 4.48-4.40 (m, 1H), 4.21 (d, J=22.2 Hz, 1H), 3.91-3.81 (m, 1H), 3.63 (dt, J=11.7, 6.1 Hz, 1H), 3.16-3.07 (m, 2H), 2.77-2.69 (m, 1H), 2.28-2.10 (m, 2H), 1.88-1.79 (m, 1H), 1.74 (s, 1H), 1.67 (td, J=11.3, 9.9, 5.6 Hz, 3H), 1.61-1.41 (m, 2H), 1.31 (dd, J=12.8, 7.5 Hz, 2H), 1.21 (d, J=7.1 Hz, 3H), 1.18-1.13 (m, 2H), 1.13-1.06 (m, 2H), 1.02-0.97 (m, 3H), 0.85 (d, J=7.4 Hz, 6H), 0.71 (td, J=7.6, 3.2 Hz, 1H). UPLC-MS (basic 4 min): rt=1.79 min; m/z=680.3 for [M+H]⁺.

Example 442: tert-butyl N-[(2R,3S)-3-(3-fluoro-4-nitrophenyl)-1-(morpholin-4-yl)-1-oxobutan-2-yl]carbamate 68A

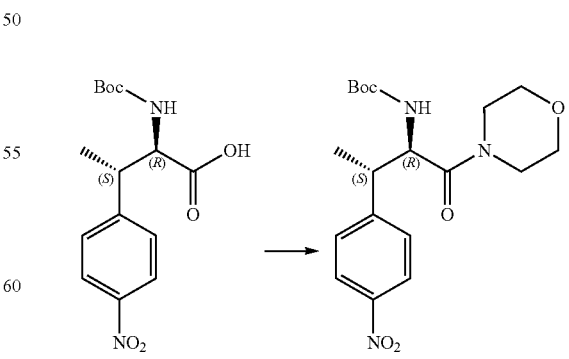

To a solution of 91 (0.420 g, 1.23 mmol, 1.0 eq.) in DMF (4.2 mL) was added morpholine (0.128 g, 1.47 mmol, 1.2 eq.), DIPEA (0.64 mL, 3.68 mmol, 3.0 eq.) and finally, HATU (0.700 g, 1.84 mmol, 1.50 eq.). The resulting mixture was stirred at RT under a N₂ atmosphere for 1 h. The mixture was diluted with aq. sat. NaHCO₃ solution (20 mL) and then extracted with EtOAc (2×20 mL). The organic layer was washed with ice cold brine (2×50 mL), dried over Na₂SO₄ then concentrated to afford 68A as a brown solid (0.457 g, 91%) which was used in the next step without further purification.

Example 443: tert-butyl N-[(2R,3S)-3-(4-amino-3-fluorophenyl)-1-(morpholin-4-yl)-1-oxobutan-2-yl] carbamate 69A

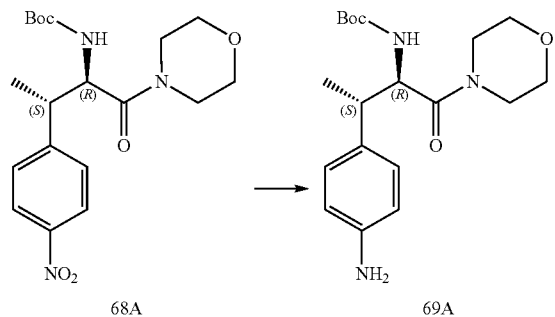

To a degassed solution of 68A (0.440 g, 1.07 mmol, 1.0 eq) in EtOH (12 mL) was added Pd/C (0.044 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 69A as a red solid (0.393 g, 96%) which was used in the next step without further purification.

Example 444: General Procedure AO

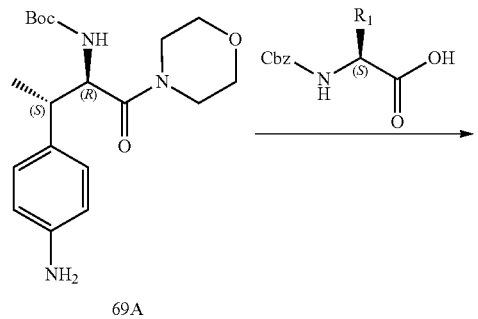

-continued

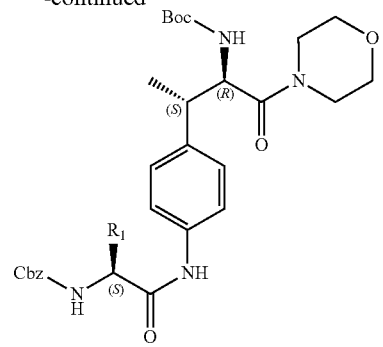

To a solution of 69A (0.393, 1.03 mmol, 1.0 eq.) in DMF were added the required Cbz protected glycine derivative (0.496 g, 1.6 mmol, 1.5 eq.), DIPEA (0.54 mL, 3.09 mmol, 3.0 eq.) and HATU (0.784 g, 2.06 mmol, 2.0 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified via reverse phase column chromatography on a 120 g C18 cartridge eluting with a 5-95% H₂O:MeCN eluent (0.1% ammonia) to afford 70A.

Example 445: General Procedure AP

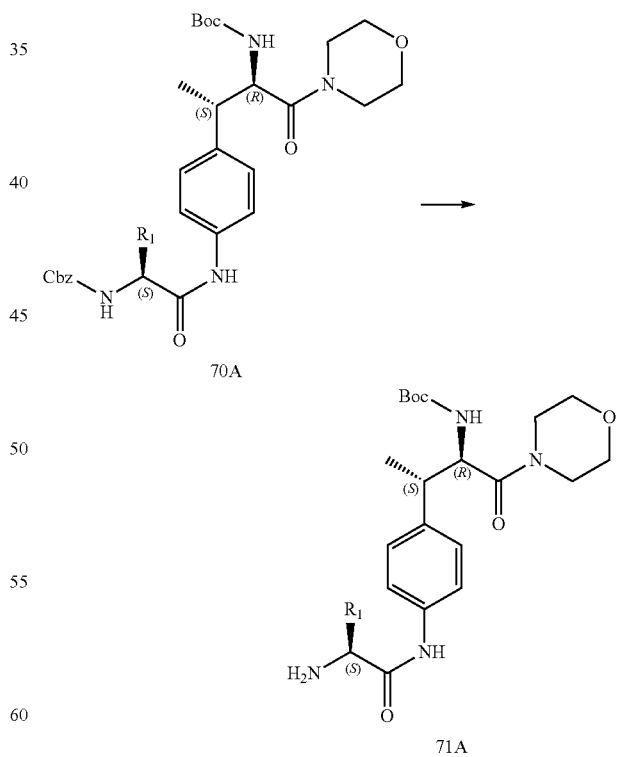

To a degassed solution of 70A (0.581 g, 0.869 mmol, 1.0 eq) in EtOH (8.8 mL) was added Pd/C (0.087 g). The mixture was degassed for another 20 minutes and then evacuated under vacuum before introducing a hydrogen balloon. The resulting mixture was stirred at RT for 18 h. The mixture was filtered through a pad of celite which was washed with EtOH (50 mL). The solution was concentrated to dryness to afford 71A which was used in the next step without further purification.

Example 446: General Procedure AQ

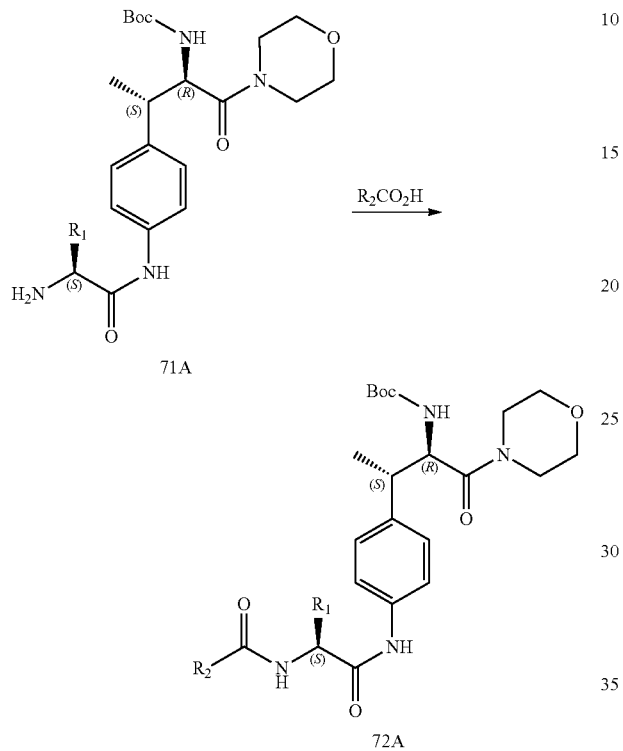

To a solution of 71A (1.0 eq.) in DMF 0.10 mL) was added required carboxylic acid (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified by flash column chromatography (Silica, 0-10% MeOH, DCM) to afford 72A.

Example 447: General Procedure AR

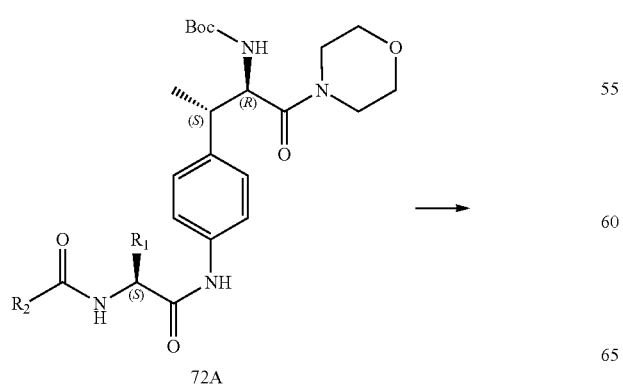

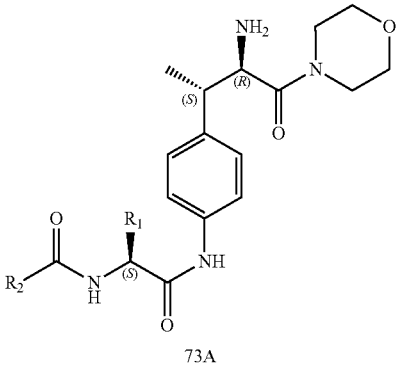

To a solution of 72A (1.0 eq.) in DCM was added TFA and the resulting mixture was stirred at RT for 0.5 h. The reaction mixture was concentrated to dryness and the residue was stirred in aq. sat. $K_2CO_3$ solution and then extracted with DCM to afford 73A which was used in the next step without further purification.

Example 448: General Procedure AS

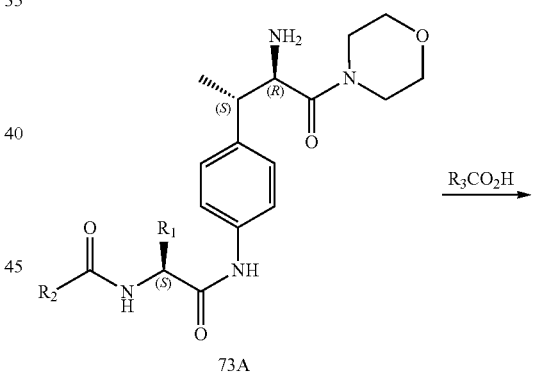

341-346, 348-375, 392, 411 and 412

To a solution of 73A (1.0 eq,) in DMF (0.1 M) was added the required acid (1.2 eq.), DIPEA (3.0-8.0 eq.) and then HATU (1.5 eq.) and the resulting mixture was stirred at RT for 1 h. The mixture was concentrated to dryness and the residue was purified via reverse phase column chromatography on a 120 g C18 cartridge eluting with a 5-95% $H_2O$:MeCN eluent (0.1% ammonia) to afford.

Example 449: N-[(2R,3S)-3-{4-[(2S)-2-[2,2-difluoro-2-(5-methoxypyridin-3-yl)acetamido]-2-[(1r,4S)-4-methylcyclohexyl]acetamido]-3-fluorophenyl}-1-(morpholin-4-yl)-1-oxobutan-2-yl] propanamide (379)

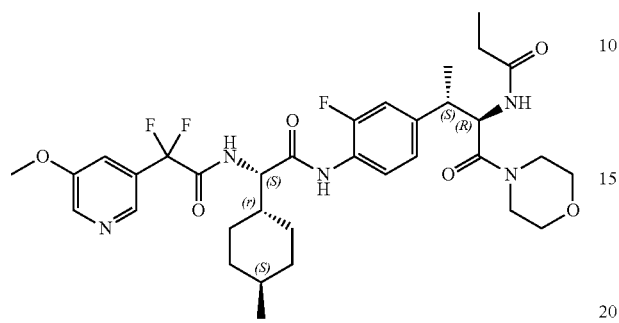

Following General Procedure AS provided 379. $^1$H NMR (400 MHz, DMSO-d$_6$) δ 9.94 (s, 1H), 9.12 (d, J=8.3 Hz, 1H), 8.48 (d, J=2.8 Hz, 1H), 8.40 (d, J=1.8 Hz, 1H), 8.26 (d, J=8.7 Hz, 1H), 7.71 (t, J=8.3 Hz, 1H), 7.65-7.61 (m, 1H), 7.11 (dd, J=12.0, 1.9 Hz, 1H), 7.01 (dd, J=8.4, 1.9 Hz, 1H), 4.86 (t, J=9.3 Hz, 1H), 4.43 (t, J=8.6 Hz, 1H), 3.88 (s, 3H), 3.51-3.39 (m, 2H), 3.29-3.21 (m, 1H), 3.15-2.97 (m, 2H), 2.26-2.05 (m, 4H), 1.97 (s, 3H), 1.84-1.75 (m, 1H), 1.70-1.55 (m, 5H), 1.53-1.45 (m, 1H), 1.27-1.10 (m, 6H), 1.06-0.96 (m, 4H), 0.89-0.78 (m, 5H) UPLC-MS (basic 4 min): rt=1.84 min; m/z=676.3 for [M+H]$^+$.

Example 450: N-[(2R,3S)-3-{4-[(2S)-2-[(1-cyclopentyl-1H-pyrazol-5-yl)formamido]-2-[(1r,4S)-4-methylcyclohexyl]acetamido]-3-fluorophenyl}-1-(morpholin-4-yl)-1-oxobutan-2-yl]-1-fluorocyclopropane-1-carboxamide (380)

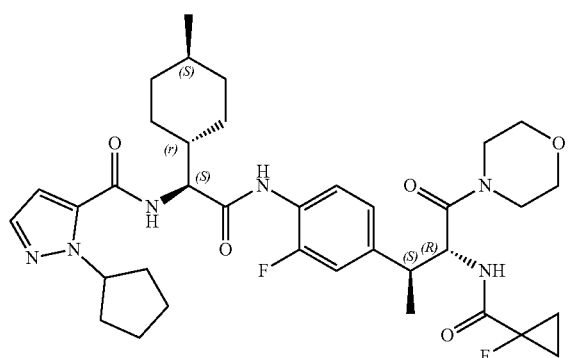

Following General Procedure AS provided 380. $^1$H NMR (400 MHz, DMSO-d$_6$) δ 9.86 (s, 1H), 8.56 (d, J=8.3 Hz, 1H), 8.44 (d, J=8.2 Hz, 1H), 7.68 (t, J=8.3 Hz, 1H), 7.48 (d, J=2.0 Hz, 1H), 7.18 (d, J=12.7 Hz, 1H), 7.04 (d, J=8.3 Hz, 1H), 6.94 (d, J=2.0 Hz, 1H), 5.53 (q, J=7.1 Hz, 1H), 4.97-4.86 (m, 1H), 4.52 (t, J=8.3 Hz, 1H), 3.39 (d, J=12.0 Hz, 3H), 3.27-2.91 (m, 4H), 2.05-1.54 (m, 14H), 1.38-1.12 (m, 10H), 0.86 (d, J=6.4 Hz, 6H). UPLC-MS (basic 4 min): rt=2.17 min; m/z=683.3 for [M+H]$^+$.

Example 451: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(morpholin-4-yl)-1-oxobutan-2-yl]-1,2,3-thiadiazole-5-carboxamide (381)

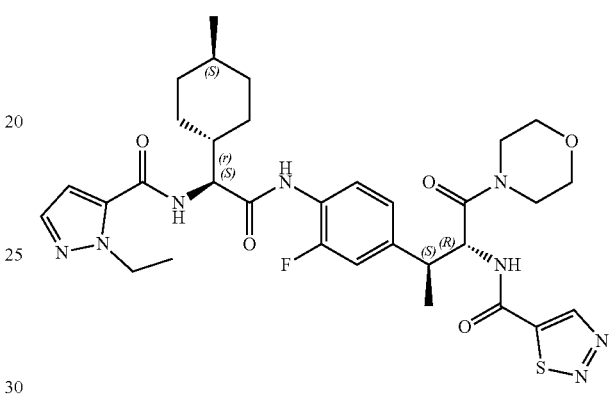

Following General Procedure AS provided 381. $^1$H NMR (400 MHz, DMSO-d$_6$) δ 9.90 (s, 1H), 9.69 (d, J=8.0 Hz, 1H), 9.52 (s, 1H), 8.46 (d, J=8.2 Hz, 1H), 7.69 (t, J=8.3 Hz, 1H), 7.48 (d, J=2.0 Hz, 1H), 7.25 (d, J=11.3 Hz, 1H), 7.08 (d, J=8.8 Hz, 1H), 7.01 (d, J=2.1 Hz, 1H), 5.11-5.02 (m, 1H), 4.57-4.43 (m, 4H), 3.42 (t, J=11.3 Hz, 4H), 3.05 (dd, J=40.7, 31.7 Hz, 4H), 1.87-1.60 (m, 6H), 1.35-1.23 (m, 11H), 0.87 (d, J=6.4 Hz, 6H). UPLC-MS (basic 4 min): rt=1.81 min; m/z=669.3 for [M+H]$^+$.

Example 452: benzyl N—[(S)-({4-[(2S,3R)-3-{[(tert-butoxy)carbonyl]amino}-4-(4-methylpiperazin-1-yl)-4-oxobutan-2-yl]-2-fluorophenyl}carbamoyl)(cycloheptyl)methyl]carbamate) 75B

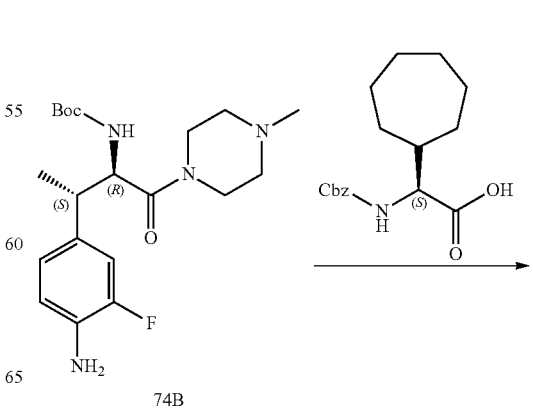

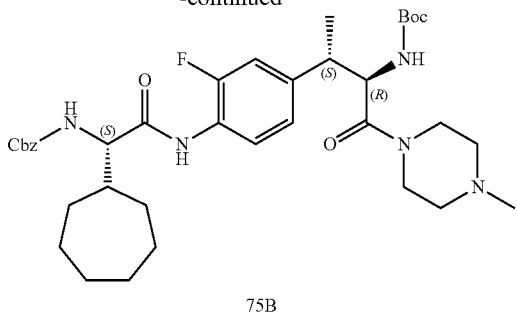

75B

To a solution of 74B (0.811 g, 2.06 mmol, 1.0 eq.) prepared by hydrogenation of 76 in DMF (3.0 mL) was added (2R)-2-{[(benzyloxy)carbonyl]amino}-2-cycloheptylacetic acid) (1.13 g, 3.69 mmol, 1.7 eq.), DIPEA (1.1 mL, 6.17 mmol, 3.0 eq.) and then HATU (1.56 g, 4.11 mmol, 2.0 eq.) and the resulting mixture was stirred at RT for 24 h. The mixture was directly purified via reverse phase column chromatography on a 120 g C18 cartridge eluting with a 5-95% H₂O:MeCN eluent (0.1% ammonia) to afford 75B (0.824 g, 59%) as a white solid. ¹H NMR (400 MHz, DMSO-d₆) δ 7.71 (t, J=8.2 Hz, 1H), 7.44 (d, J=8.8 Hz, 1H), 7.38-7.27 (m, 5H), 7.22 (d, J=8.7 Hz, 1H), 7.10 (d, J=12.1 Hz, 1H), 7.00 (dd, J=8.3, 1.9 Hz, 1H), 5.04 (s, 2H), 4.53 (t, J=9.3 Hz, 1H), 4.22 (t, J=8.0 Hz, 1H), 4.09 (q, J=5.3 Hz, 1H), 3.18 (d, J=5.2 Hz, 1H), 3.14-3.03 (m, 2H), 2.18 (s, 2H), 2.01 (s, 3H), 1.91 (s, 1H), 1.72 (t, J=7.9 Hz, 1H), 1.63 (d, J=11.2 Hz, 5H), 1.57-1.40 (m, 5H), 1.40-1.28 (m, 12H), 1.21 (d, J=6.7 Hz, 4H). UPLC-MS (basic 2 min): rt=1.27 min; m/z=682.4 for [M+H]⁺.

Example 453: tert-butyl N-[(2R,3S)-3-{4-[(2S)-2-amino-2-cycloheptylacetamido]-3-fluorophenyl}-1-(4-methylpiperazin-1-yl)-1-oxobutan-2-yl]carbamate) 76B

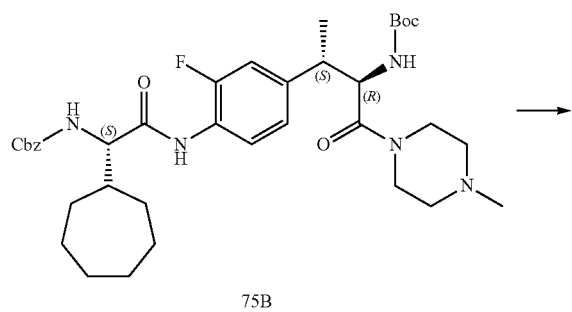

75B

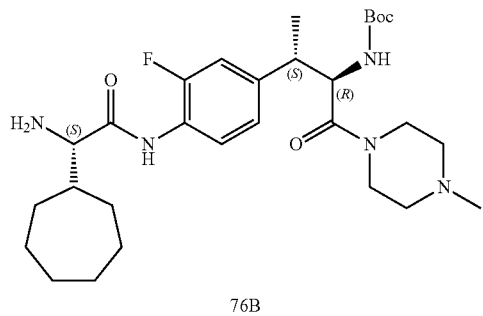

76B

To a degassed solution of 75B (0.824 g, 1.21 mmol, 1.0 eq) in EtOH (4 mL) and THF (4 mL) was added Pd/C (0.257 g, 0.242 mmol, 0.2 eq.). The mixture was degassed for another 20 minutes and then evacuated under vacuum before introducing a hydrogen balloon. The resulting mixture was stirred at RT for 1 h. The mixture was filtered through a pad of celite which was washed with EtOH (50 mL). The solution was concentrated to dryness to afford 76B as a yellow solid (0.656 g, 99%) which was used in the next step without further purification. ¹H NMR (400 MHz, DMSO-d₆) δ 7.98 (t, J=8.4 Hz, 1H), 7.21 (d, J=8.6 Hz, 1H), 7.17-7.11 (m, 1H), 6.99 (dd, J=8.4, 1.9 Hz, 1H), 4.52 (t, J=9.4 Hz, 1H), 4.35 (t, J=5.1 Hz, 1H), 3.45 (qd, J=7.0, 4.6 Hz, 2H), 3.15-2.97 (m, 3H), 2.25-2.12 (m, 2H), 2.06 (d, J=6.4 Hz, 1H), 2.01 (s, 2H), 1.97-1.89 (m, 1H), 1.73-1.59 (m, 4H), 1.59-1.47 (m, 5H), 1.47-1.40 (m, 4H), 1.38 (s, 9H), 1.25-1.18 (m, 4H), 1.06 (t, J=7.0 Hz, 3H). UPLC-MS (basic 2 min): rt=1.16 min; m/z=548.3 for [M+H]⁺.

Example 454: General Procedure AS

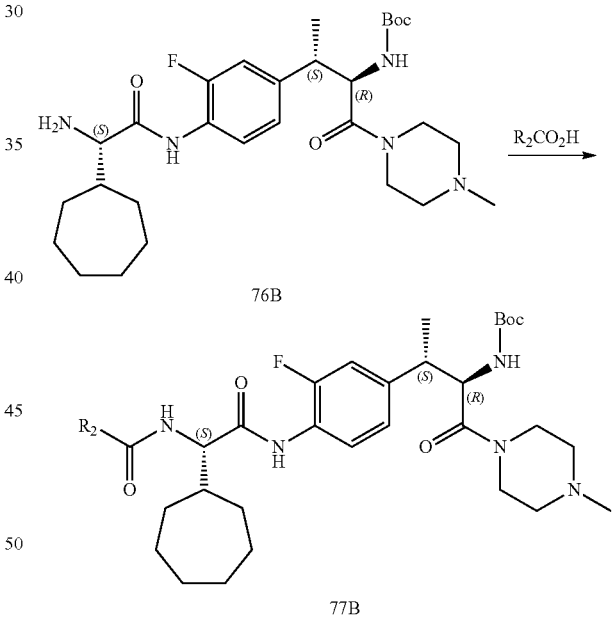

To a solution of 76B (1.0 eq.) in DMF (0.1 M) were added required carboxylic acid (1.2 eq.), DIPEA (3.0-8.0 eq.) and HATU (1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness. The residue was purified via reverse phase column chromatography on a 120 g C18 cartridge eluting with a 5-95% H₂O:MeCN eluent (0.1% ammonia) to afford 77B.

Example 455: General Procedure AT

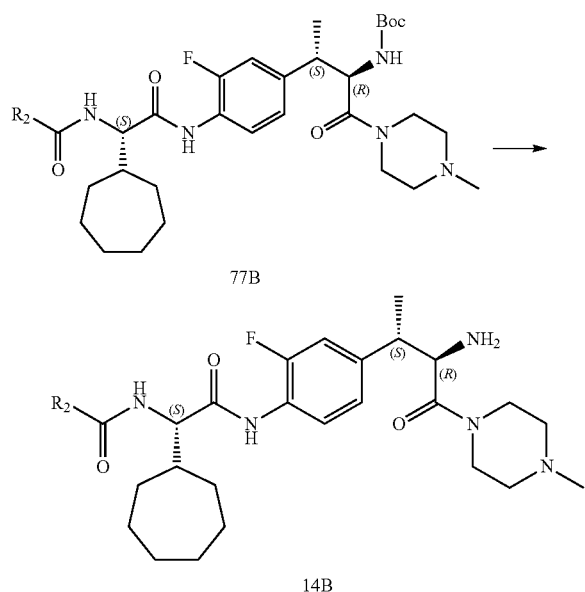

To a solution of 77B (1.0 eq.) in DCM was added TFA and the resulting mixture was stirred at RT for 0.5 h. The reaction mixture was concentrated to dryness and the residue was stirred in aq. sat. $K_2CO_3$ solution and then extracted with DCM to afford 14B which was used in the next step without further purification.

Example 456: Preparation of Intermediate 78B

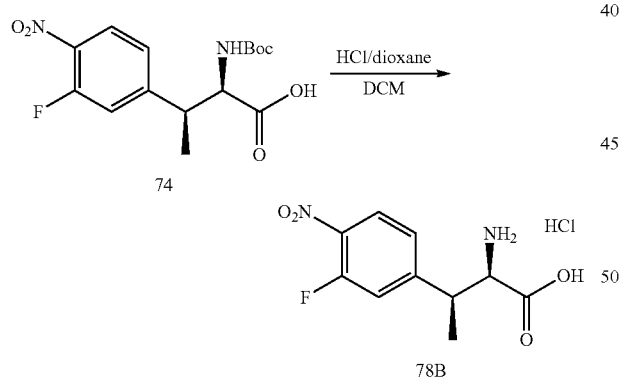

To a solution of 74 (500 mg, 1.46 mmol, 1.00 eq) in DCM (5.00 mL) was added HCl/dioxane (4 M, 5.00 mL, 13.6 eq) at 0° C. The mixture was stirred at 25° C. for 1 hr. LC-MS showed 74 was consumed completely and desired mass was detected. The reaction mixture was concentrated under reduced pressure to give a residue. Compound 78B (400 mg, 1.44 mmol, 98.2% yield, HCl) was obtained as white solid. LC-MS: (2M+1)⁻: 483.1, ¹H NMR: (400 MHz, DMSO-$d_6$) δ 8.50 (s, 2H), 8.15 (t, J=8.0 Hz, 1H), 7.59 (dd, $J_1$=1.6 Hz, $J_2$=12.8 Hz, 1H), 7.39 (dd, $J_1$=1.2 Hz, $J_2$=8.4 Hz, 1H), 4.21 (d, J=6.8 Hz, 1H), 3.57-3.51 (m, 1H), 1.40 (d, J=7.2 Hz, 3H).

Example 457: Preparation of Intermediate 79B

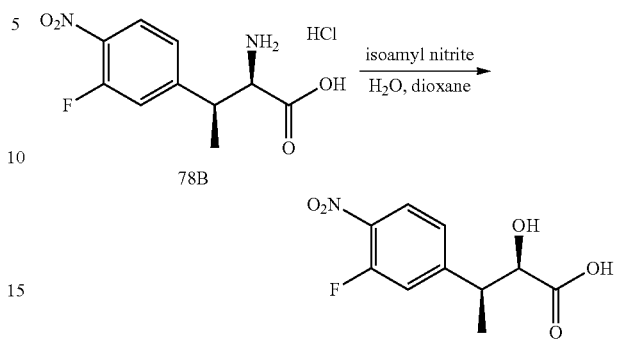

To a solution of compound 78B (400 mg, 1.44 mmol, 1.00 eq, HCl) in $H_2O$ (10.0 mL) and dioxane (10.0 mL) was added isoamyl nitrite (252 mg, 2.15 mmol, 289 uL, 1.50 eq) at 0° C. The mixture was stirred at 25° C. for 3 hrs. LC-MS showed that the desired mass was detected. The reaction mixture was added EtOAc (20.0 mL) and $H_2O$ (20.0 mL). The organic phase was separated, and the water phase was extracted with EtOAc (50.0 mL*2). The combined organic phase was dried over $Na_2SO_4$, filtered and concentrated under reduced pressure to give a residue. The residue was purified by Prep-HPLC (FA condition; column: Waters Atlantis T3 150*30 mm*5 um; mobile phase: [water (0.225% FA)-ACN]; B %: 18%-48%, 10 min). Compound 79B (180 mg, 740 umol, 51.5% yield) was obtained as yellow solid. ¹H NMR: (400 MHz, DMSO-$d_6$) δ 13.4-11.9 (m, 1H), 8.13-8.07 (m, 1H), 7.51 (dd, $J_1$=1.2 Hz, $J_2$=12.8 Hz, 1H), 7.37 (d, J=8.8 Hz, 1H), 4.12 (d, J=4.4 Hz, 1H), 3.28-3.25 (m, 1H), 1.21 (d, J=7.2 Hz, 3H).

Example 458: Preparation of Intermediate 80B

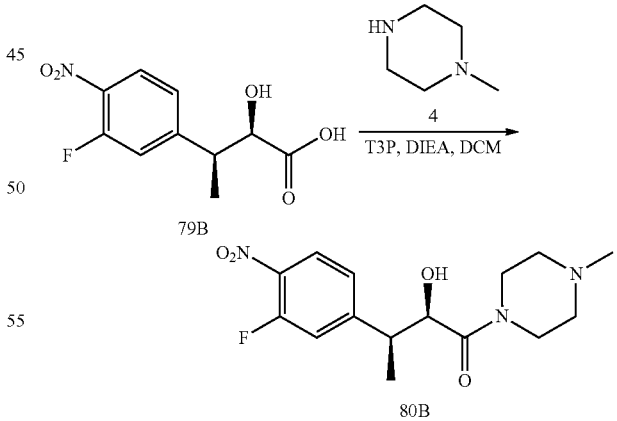

To a solution of compound 79B (160 mg, 657 umol, 1.00 eq) and compound 4 (98.8 mg, 986 umol, 109 uL, 1.50 eq) in DCM (5.00 mL) was added DIEA (425 mg, 3.29 mmol, 572 uL, 5.00 eq) and T3P (1.26 g, 1.97 mmol, 1.17 mL, 50.0% purity, 3.00 eq) at 0° C. The mixture was stirred at 25° C. for 12 hrs. TLC indicated compound 79B was consumed completely and many new spots formed. The reaction mixture was added EtOAc (20.0 mL) and H₂O (20.0 mL). The organic phase was separated, and the water phase was extracted with EtOAc (50.0 mL*2). The combined organic phase was dried over Na₂SO₄, filtered and concentrated under reduced pressure to give a residue. The residue was purified by Prep-TLC (SiO₂, DCM:MeOH=10:1, Plate 1: DCM:MeOH=10:1). Compound 80B (90.0 mg, 276 umol, 42.0% yield) was obtained as yellow oil. LC-MS: m/z=326.1, [M+H]⁺.

Example 459: Preparation of intermediate 81B

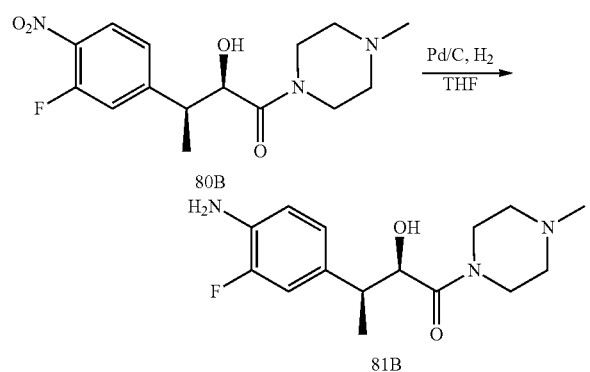

To a solution of compound 80B (80.0 mg, 245 umol, 1.00 eq) in THF (10.0 mL) was added Pd/C (5.00 mg, 10% purity) under N₂. The suspension was degassed under vacuum and purged with H₂ several times. The mixture was stirred under H₂ (15 psi) at 25° C. for 1 hr. LC-MS) showed desired mass was detected. The reaction mixture was filtered and concentrated under reduced pressure to give a residue. Compound 81B (60.0 mg, crude) was obtained as yellow oil. LC-MS: m/z=296.2, [M+H]⁺.

Example 460: Preparation of intermediate 82B

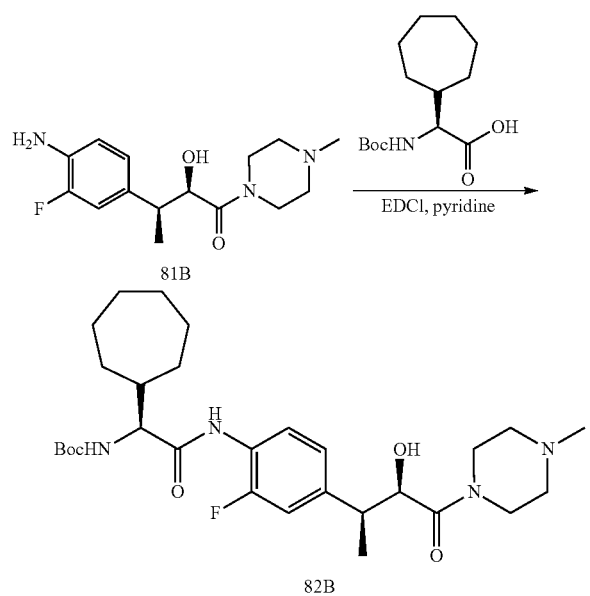

To a solution of compound 81B (60.0 mg, 203 umol, 1.00 eq) and the protected cycloheptylglycine (82.6 mg, 304 umol, 1.50 eq) in pyridine (10.0 mL) was added EDCI (77.8 mg, 406 umol, 2.00 eq). The mixture was stirred at 25° C. for 12 hrs. LC-MS showed desired mass detected. The reaction mixture was added H₂O (10.0 mL) and extracted with DCM (20.0 mL*2). The combined organic layers were washed with sat. aq NaHCO₃ (40.0 mL), dried over Na₂SO₄, filtered and concentrated under reduced pressure to give a residue. The residue was purified by Prep-TLC (SiO₂, DCM:MeOH=10:1, R$_f$=0.430). Compound 82B (35.0 mg, 63.7 umol, 31.4% yield) was obtained as white solid. LC-MS: m/z=549.5, [M+H]⁺; ¹H NMR: (400 MHz, CDCl₃) δ 8.21-8.17 (m, 2H), 7.12 (dd, J₁=1.2 Hz, J₂=10.4 Hz, 1H), 7.01 (d, J=8.4 Hz, 1H), 5.10 (d, J=8.4 Hz, 2H), 4.40 (d, J=4.8 Hz, 1H), 4.20-4.18 (m, 2H), 3.81-3.77 (m, 1H), 3.67-3.60 (m, 1H), 3.48-3.41 (m, 1H), 3.34-3.25 (m, 1H), 2.90-2.87 (m, 1H), 2.56-2.46 (m, 2H), 2.33 (s, 3H), 2.26-2.14 (m, 1H), 2.03-2.02 (m, 1H), 1.62-1.57 (m, 7H), 1.47 (s, 9H), 1.40-1.28 (m, 8H).

Example 461: Preparation of intermediate 83B

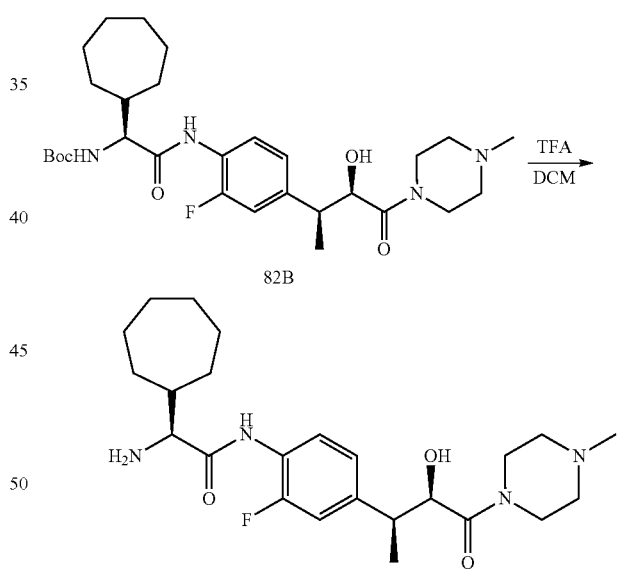

To a solution of compound 82B (30.0 mg, 54.6 umol, 1.00 eq) in DCM (4.00 mL) was added TFA (3.08 g, 27.0 mmol, 2.00 mL, 494 eq) at 0° C. The mixture was stirred at 25° C. for 2 hrs. LC-MS showed detection of the desired mass. The reaction mixture was diluted with H₂O (10.0 mL), and sat.aq NaHCO₃ was added to adjust pH to 9. The mixture was extracted with DCM (20.0 mL*2). The combined organic layers were dried over Na₂SO₄, filtered and concentrated under reduced pressure to give a residue. Compound 83B (20.0 mg, 44.5 umol, 81.5% yield) was obtained as yellow oil. LC-MS: m/z=449.4, [M+H]⁺.

Example 462: Preparation of compound 383

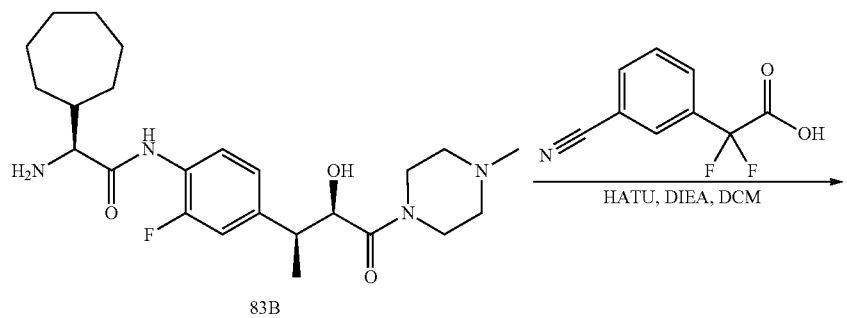

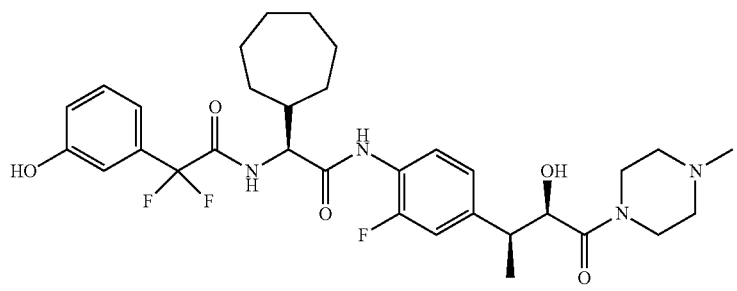

To a solution of compound 83B (13.1 mg, 66.8 umol, 1.50 eq) and HATU (50.8 mg, 133 umol, 3.00 eq) in DCM (5.00 mL) was added DIEA (28.8 mg, 222 umol, 38.8 uL, 5.00 eq). The mixture was stirred at 25° C. for 30 min. The carboxylic acid (20.0 mg, 44.5 umol, 1.00 eq) was added to the mixture and stirred at 25° C. for 12 hrs. LC-MS showed desired mass detected. The reaction mixture was diluted with $H_2O$ (10.0 mL), and sat.aq $NaHCO_3$ was added to adjust pH to 9. The mixture was extracted with DCM (20.0 mL*2). The combined organic layers were dried over $Na_2SO_4$, filtered and concentrated under reduced pressure to give a residue. The residue was purified by Prep-HPLC (basic condition, column: Waters Xbridge 150*25 mm*5 um; mobile phase: [water (0.05% ammonia hydroxide v/v)-ACN]; B %: 40%-70%, 10 min). Compound 383 (4.00 mg, 5.79 umol, 12.9% yield, 90.8% purity) was obtained as white solid. LC-MS: m/z=628.5, $[M+H]^+$; H NMR: (400 MHz, $CDCl_3$). δ 8.15-8.11 (m, 1H), 7.95 (s, 1H), 7.89 (d, J=8.0 Hz, 1H), 7.80 (d, J=7.6 Hz, 1H), 7.63-7.59 (m, 1H), 7.53 (s, 1H), 7.25-7.23 (m, 1H), 7.16 (dd, $J_1$=2.0 Hz, $J_2$=12.0 Hz, 1H), 7.06 (d, J=7.6 Hz, 1H), 4.48-4.43 (m, 2H), 3.78-3.75 (m, 2H), 3.58-3.52 (m, 1H), 3.42-3.37 (m, 1H), 3.29-3.21 (m, 1H), 2.92-2.87 (m, 1H), 2.39-2.29 (m, 7H), 2.15-2.08 (m, 1H), 1.85-1.65 (m, 4H), 1.53-1.27 (m, 8H), 1.30 (d, J=6.8 Hz, 3H).

Example 463: N-[(2R,3S)-3-{4-[(2S)-2-cycloheptyl-2-{[1-(propan-2-yl)-1H-pyrazol-5-yl]formamido}acetamido]phenyl}-1-(4-methylpiperazin-1-yl)-1-oxobutan-2-yl]propanamide) (232)

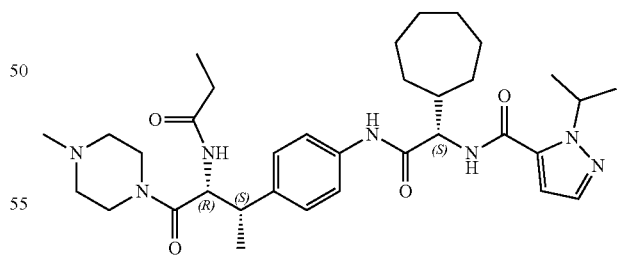

To a solution of (S)-cycloheptyl({4-[(2S,3R)-4-(4-methylpiperazin-1-yl)-4-oxo-3-propanamidobutan-2-yl]phenyl}carbamoyl)methanaminium trifluoroacetate) 82b (0.095 g, 0.158 mmol, 1.0 eq) in DMF (1 mL) were added 1-(propan-2-yl)-1H-pyrazole-5-carboxylic acid) (0.029 g, 0.190 mmol, 1.2 eq), DIPEA (0.221 mL, 1.27 mmol, 8.0 eq) and then HATU (0.090 g, 0.238 mmol, 1.5 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 232 (0.020 g) as a white solid. ¹H NMR (400 MHz, DMSO-d₆) δ 10.13 (s, 1H), 8.45 (d, J=8.5 Hz, 1H), 8.24 (d, J=8.7 Hz, 1H), 7.58-7.51 (m, 2H), 7.49 (d, J=2.0 Hz, 1H), 7.15 (d, J=8.5 Hz, 2H), 6.93 (d, J=2.0 Hz, 1H), 5.38 (p, J=6.6 Hz, 1H), 4.83 (t, J=9.5 Hz, 1H), 4.45 (t, J=8.5 Hz, 1H), 3.45 (d, J=12.8 Hz, 1H), 3.26-3.13 (m, 1H), 3.06 (dd, J=10.1, 6.9 Hz, 1H), 2.96 (t, J=10.0 Hz, 2H), 2.14 (qq, J=14.8, 7.4 Hz, 5H), 1.95 (s, 3H), 1.73 (d, J=8.2 Hz, 1H), 1.69-1.38 (m, 10H), 1.35 (dd, J=10.3, 6.6 Hz, 9H), 1.20 (d, J=7.0 Hz, 3H), 0.99 (t, J=7.6 Hz, 3H). UPLC-MS (basic 2 min): rt=1.08 min; m/z=622.5 for [M+H]⁺.

Example 464: Preparation of Intermediate 85B

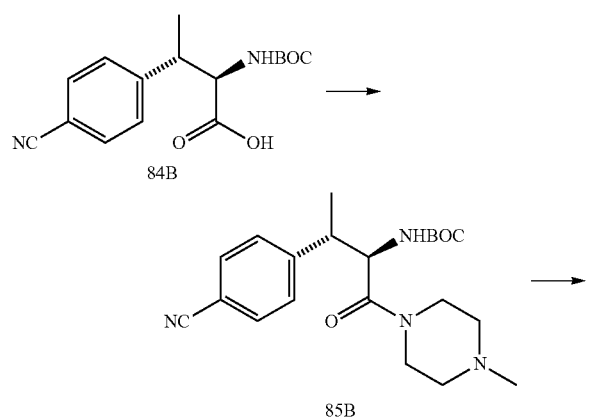

To a solution of compound 84B (600 mg, 1.97 mmol, 1.00 eq) in DCM (10.0 mL) was added N-methyl piperazine (240.00 mg, 2.40 mmol, 265.78 uL, 1.22 eq), DIEA (445.20 mg, 3.44 mmol, 600.00 uL, 1.75 eq) and T3P (1.51 g, 2.38 mmol, 1.41 mL, 50% purity, 1.21 eq) at −30° C. and the mixture was stirred at −30° C. for 4 hrs. TLC (Plate 1, DCM:MeOH=10:1, R_f=0.55) showed compound 84B was consumed and a new spot formed. The reaction mixture was diluted with DCM (50 mL) and washed with saturated aq. NaHCO₃ (15 mL), H₂O (15 mL) and brine (15 mL), then the organic layer was dried over anhydrous Na₂SO₄ and concentrated under reduced pressure to obtain the desired product, compound 85B (750 mg, 1.87 mmol, 95.0% yield, 96.5% purity). LCMS: [M+H]⁺: m/z=387.3; ¹H NMR: (400 MHz, CDCl₃) δ 7.60 (d, J=8.0 Hz, 2H), 7.36 (d, J=8.4 Hz, 2H), 5.33 (d, J=9.2 Hz, 1H), 4.12 (t, J=9.2 Hz, 1H), 3.47-3.42 (m, 3H), 3.19-3.13 (m, 2H), 2.32-2.23 (m, 2H), 2.19 (s, 3H), 2.05-2.00 (m, 1H), 1.77-1.69 (m, 1H), 1.43 (s, 9H), 1.36 (d, J=6.8 Hz, 3H), 1.04-0.86 (m, 2H)

Example 465: Preparation of Intermediate 86B

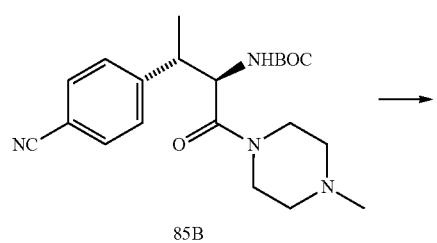

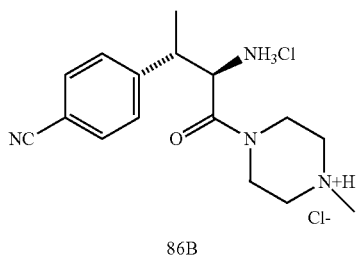

To a solution of compound 85B (650 mg, 1.62 mmol, 1.00 eq) in DCM (10 mL) and MeOH (5.00 mL) was added HCl/dioxane (4 M, 5.00 mL) at 0° C., then the mixture was stirred at 25° C. for 2 hrs. LCMS showed compound 85B was consumed completed and there was major peak with desired mass detected. The reaction mixture was concentrated under reduced pressure to get the crude product compound 86B (583 mg, crude, 2HCl) as a yellow solid.

Example 466: Preparation of Intermediate 87B

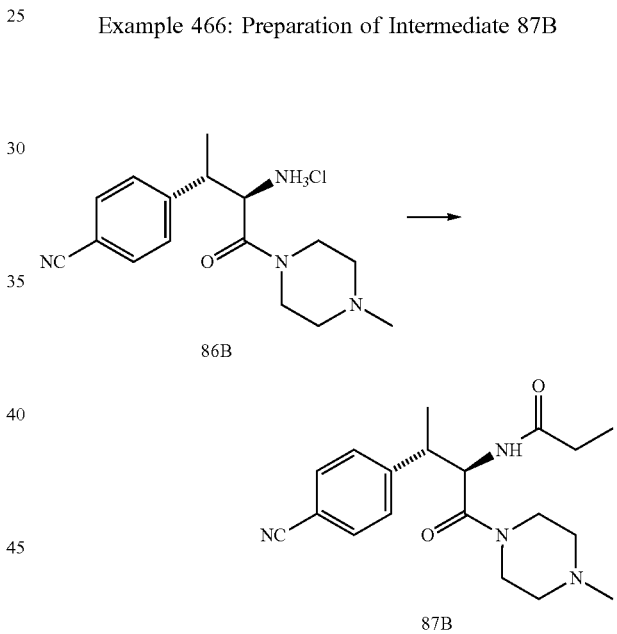

To a solution of compound 86B (583 mg, 1.62 mmol, 1.00 eq, 2HCl) in DCM (3 mL) was added TEA (727 mg, 7.18 mmol, 1.00 mL, 4.43 eq) at 0° C., then propanoyl propanoate (260 mg, 2.00 mmol, 257 uL, 1.23 eq) was added and the solution warmed to 20° C., and then stirred for 2 hrs. LCMS showed 86B was consumed and there was a major peak with desired mass detected. The reaction mixture was diluted with DCM (50 mL) and washed with saturated aq. NaHCO₃ (15 mL), H₂O (15 mL) and brine (15 mL), then the organic layer was dried over anhydrous Na₂SO₄ and concentrated under reduced pressure to give a residue. The residue was purified by Prep-TLC (Plate 1, DCM:MeOH=10:1) to get the desired product compound 87B (420 mg, 1.21 mmol, 74.6% yield, 98.7% purity). LCMS: [M+H]⁺: m/z=343.3.

Example 467: Preparation of Intermediate 88B

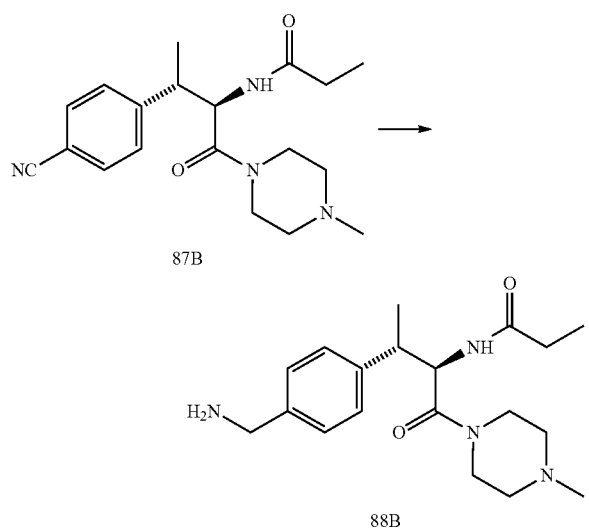

To a solution of compound 87B (420 mg, 1.21 mmol, 1.00 eq) in MeOH (50.0 mL) and NH$_3$·H$_2$O (9.10 g, 64.9 mmol, 10.0 mL, 25% purity, 53.6 eq) was added Raney-Ni (210 mg, 2.45 mmol, 2.02 eq) under N$_2$. The suspension was degassed under vacuum and purged with H$_2$ several times. The mixture was stirred under H$_2$ (50 psi) at 25° C. for 4 hours. LCMS and HPLC showed compound 87B was consumed completed and there was a major peak with desired mass detected. The reaction mixture was filtrated, the filtrate was concentrated under reduced pressure to get the desired product compound 88B (365 mg, 1.05 mmol, 87.0% yield) as a yellow solid. $^1$H NMR: (400 MHz, CDCl$_3$) δ 7.25-7.23 (m, 4H), 6.34 (d, J=8.4 Hz, 1H), 5.07 (t, J=9.2 Hz, 1H), 3.91 (br s, 1H), 3.46-3.32 (m, 3H), 3.11-3.07 (m, 1H), 2.90-2.85 (m, 1H), 2.29-2.24 (m, 5H), 2.13-1.97 (m, 6H), 1.62 (s, 1H), 1.35 (d, J=7.2 Hz, 3H), 1.18 (t, J=7.6 Hz, 1H)

Example 468: Preparation of Intermediate 89B

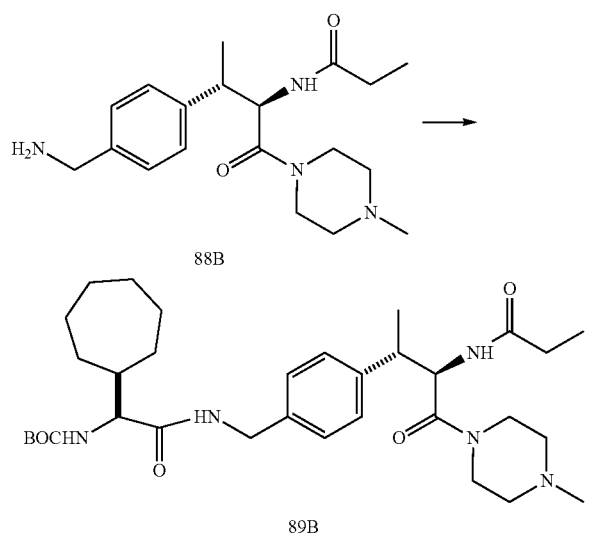

To a solution of compound 88B (150 mg, 433 umol, 1.00 eq) and BOC-cycloheptylglycine (180 mg, 663 umol, 1.53 eq) in DCM (10.0 mL) was added T3P (840 mg, 1.32 mmol, 785 uL, 50% purity, 3.05 eq) and DIEA (371 mg, 2.87 mmol, 0.50 mL, 6.63 eq) at 0° C., then the mixture was stirred at 20° C. for 2 hrs. LCMS showed that 88B was consumed and there was a major peak with the desired mass detected. The reaction mixture was diluted with saturated aq. NaHCO$_3$ (10 mL), the mixture was extracted with DCM (20 mL*3), then the organic layer was dried over anhydrous Na$_2$SO$_4$ and concentrated under reduced pressure to give a residue. The residue was purified by Prep-TLC (DCM:MeOH=10:1) to get the desired product compound 89B (220 mg, 356 umol, 82.3% yield, 97.1% purity) as a yellow solid. LCMS: [M+H]$^+$: m/z=600.5; $^1$H NMR: (400 MHz, CDCl$_3$) δ 7.21-7.17 (m, 4H), 6.84 (s, 1H), 6.61 (d, J=9.2 Hz, 1H), 5.35 (s, 1H), 5.02 (t, J=9.6 Hz, 1H), 4.41 (d, J=5.6 Hz, 2H), 3.98-3.92 (m, 1H), 3.67-3.60 (m, 1H), 3.35-3.01 (m, 1H), 3.12-3.01 (m, 2H), 2.62-2.58 (m, 1H), 2.32-2.26 (m, 4H), 2.18 (s, 3H), 2.14-1.90 (m, 4H), 1.74-1.56 (m, 10H), 1.52-1.45 (m, 15H), 1.35 (d, J=7.2 Hz, 4H), 1.18 (t, J=7.6 Hz, 3H).

Example 469: Preparation of Intermediate 90B

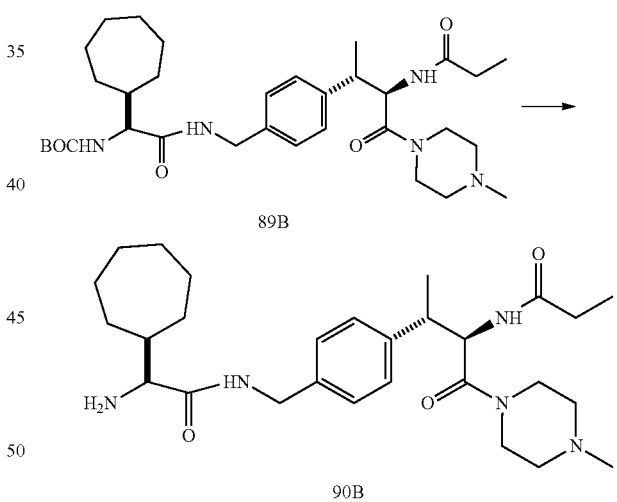

To a solution of compound 89B (80.0 mg, 130 umol, 1.00 eq) in DCM (1.00 mL) was added into TFA (308 mg, 2.70 mmol, 0.20 mL, 20.8 eq) at 25° C., then the mixture was stirred at 25° C. for 7 hrs. HPLC showed compound 89B was consumed and there was a major peak detected. The reaction mixture was concentrated under reduced pressure to give a residue. The residue was diluted with saturated aq. Na$_2$CO$_3$ (10 mL) and extracted with DCM (20 mL*3), the organic layer was dried over anhydrous Na$_2$SO$_4$ and concentrated under reduced pressure to get the crude product compound 90B (50.0 mg, crude). LCMS: [M+H]$^+$: m/z=500.4.

Example 470: Preparation of Compound 384

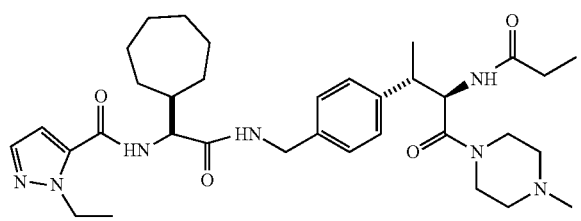

To a solution of the requisite carboxylic acid (30.0 mg, 214 umol, 2.14 eq) in DCM (2.00 mL) was added HATU (90.0 mg, 237 umol, 2.37 eq) and DIEA (92.8 mg, 718 umol, 125 uL, 7.17 eq). Then, the mixture was stirred for 30 min, a solution of compound 90B (50.0 mg, 100 umol, 1.00 eq) in DCM (2.00 mL) was added and the mixture stirred for 5 hrs at 25° C. LCMS showed the compound 90B was consumed and there was a major peak with the desired mass detected. The reaction mixture was diluted with DCM (20 mL) and washed with H$_2$O (10 mL) and saturated aq. Na$_2$CO$_3$, then the organic layer was dried over anhydrous Na$_2$SO$_4$ and concentrated under reduced pressure to give a residue. The residue was purified by Prep-TLC (DCM:MeOH=10:1) to get the desired product 384 (28.9 mg, 45.4 umol, 45.3% yield, 97.5% purity). LCMS: [M+H]$^+$: m/z=622.5; $^1$H NMR: (400 MHz, CDCl$_3$) δ 7.48 (s, 1H), 7.27-7.17 (m, 4H), 6.81 (d, J=8.4 Hz, 1H), 6.60-6.57 (m, 2H), 6.36 (d, J=9.2 Hz, 1H), 5.05 (t, J=9.6 Hz, 1H), 4.60-4.54 (m, 2H), 4.48-4.42 (m, 3H), 3.58-3.57 (m, 1H), 3.36-3.33 (m, 1H), 3.18-3.16 (m, 1H), 3.08-3.04 (m, 1H), 2.76-2.71 (m, 1H), 2.31-2.23 (m, 2H), 2.17 (s, 4H), 2.12-2.00 (m, 3H), 1.84-1.77 (m, 2H), 1.73-1.58 (m, 5H), 1.54-1.41 (m, 7H), 1.36-1.26 (m, 5H), 1.18 (t, J=7.6 Hz, 1H)

Example 471: Preparation of Compound 385

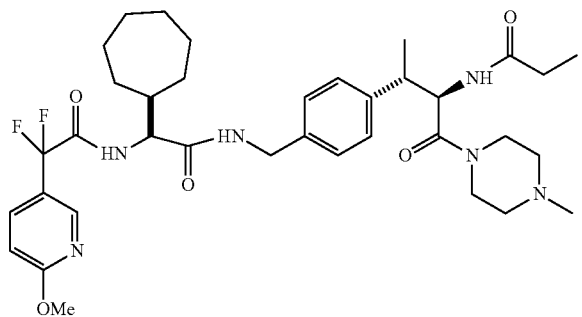

To a solution of the difluoro acid (40.0 mg, 197 umol, 2.19 eq) in DCM (2.00 mL) was added HATU (81.0 mg, 213 umol, 2.37 eq) and DIEA (74.2 mg, 574 umol, 0.100 mL, 6.38 eq), then the mixture was stirred for 30 min, a solution of compound 90B (45 mg, 90.06 umol, 1 eq) in DCM (2 mL) was added into the mixture, the mixture was stirred for 5 hrs at 25° C. LCMS showed a trace of compound 90B remained and there was desired product detected. The reaction mixture was diluted with DCM (20 mL) and washed with H$_2$O (10 mL) and saturated aq. Na$_2$CO$_3$ (10 mL), then the organic layer was dried over anhydrous Na$_2$SO$_4$ and concentrated under reduced pressure to give a residue. The residue was purified by Prep-TLC (DCM:MeOH=10:1) to get the desired product 385 (25.68 mg, 36.9 umol, 41.0% yield, 98.5% purity). LCMS: [M+H]$^+$: m/z=685.4; $^1$H NMR: (400 MHz, CDCl$_3$) δ 8.41 (d, J=1.6 Hz, 1H), 7.79 (dd, J1=2.4 Hz, J2=8.4 Hz, 1H), 7.30 (s, 1H), 7.21-7.16 (m, 4H), 6.81 (d, J=8.8 Hz, 1H) 6.56 (s, 1H), 6.31 (d, J=9.2 Hz, 1H) 5.03 (t, J=9.2 Hz, 1H), 4.42-4.31 (m, 3H), 3.98 (s, 3H), 3.63-3.58 (m, 1H), 3.36-3.34 (m, 1H), 3.15-3.02 (m, 2H), 2.71-2.67 (m, 1H), 2.29-2.23 (m, 2H), 2.18-2.11 (m, 5H), 2.08-1.99 (m, 2H), 1.80-1.39 (m, 11H), 1.34 (d, 7.2 Hz, 3H), 1.31-1.22 (m, 2H), 1.18 (t, J=7.6 Hz, 3H)

Example 472: Preparation of Compound 386

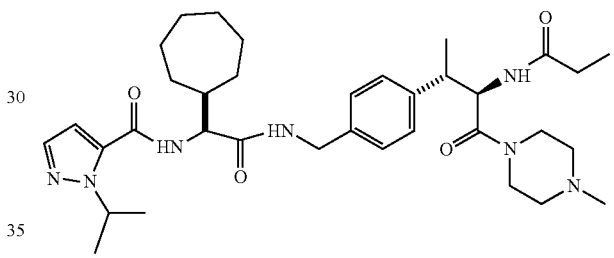

To a solution of the requisite acid (29.7 mg, 193 umol, 2.14 eq) in DCM (2.00 mL) was added HATU (81.0 mg, 213 umol, 2.37 eq) and DIEA (74.2 mg, 574 umol, 0.10 mL, 6.38 eq), then the mixture was stirred for 30 min, a solution of compound 90B (45 mg, 90.06 umol, 1 eq) in DCM (2 mL) was added into the mixture, the mixture was stirred for 2 hrs at 25° C. LCMS showed compound 90B was consumed completed and there was a major peak with desired product detected. The reaction mixture was diluted by DCM (20 mL) and washed by H$_2$O (10 mL) and saturated aq. Na$_2$CO$_3$ (10 mL), then the organic layer was dried over anhydrous Na$_2$SO$_4$ and concentrated under reduced pressure to give a residue. The residue was purified by Prep-TLC (DCM:MeOH=10:1) to get the desired product 386 (17.28 mg, 27.04 umol, 30.03% yield, 99.5% purity). LCMS: [M+H]$^+$: m/z=636.2; $^1$H NMR: (400 MHz, CDCl$_3$) δ 7.50 (d, J=2.0 Hz, 1H), 7.21-7.17 (m, 4H), 6.83-6.81 (m, 2H), 6.57 (d, J=2.0 Hz, 1H), 6.36 (d, J=9.2 Hz, 1H), 5.47-5.40 (m, 1H), 5.03 (t, J=9.2 Hz, 1H), 4.50-4.38 (m, 3H), 3.67-3.64 (m, 1H), 3.35-3.31 (m, 1H), 3.10-3.02 (m, 2H), 2.60-2.55 (m, 1H), 2.31-2.23 (m, 2H), 2.16-2.03 (m, 7H), 1.82-1.80 (m, 3H), 1.72-1.59 (m, 4H), 1.51-1.40 (m, 10H), 1.35-1.26 (m, 5H), 1.16 (t, J=7.6 Hz, 3H).

Example 473: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (388)

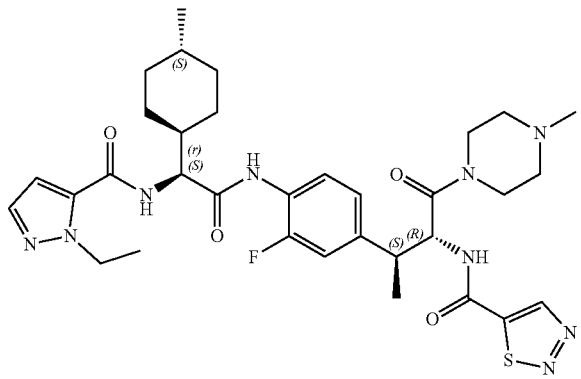

Compound 388 was synthesized by the procedure of FIG. 24. ¹H NMR (400 MHz, DMSO-d₆) δ 9.88 (s, 1H), 9.67 (d, J=8.1 Hz, 1H), 9.52 (s, 1H), 8.45 (d, J=8.3 Hz, 1H), 7.79 (t, J=8.3 Hz, 1H), 7.47 (d, J=2.1 Hz, 1H), 7.21 (dd, J=12.1, 1.9 Hz, 1H), 7.08 (dd, J=8.4, 1.9 Hz, 1H), 7.00 (d, J=2.1 Hz, 1H), 5.05 (dd, J=10.3, 8.2 Hz, 1H), 4.54 (t, J=8.4 Hz, 1H), 4.47 (q, J=7.1 Hz, 2H), 3.53-3.43 (m, 2H), 3.30-3.23 (m, 2H), 3.03-2.95 (m, 1H), 2.28-2.18 (m, 2H), 2.04-1.93 (m, 3H), 1.89-1.55 (m, 7H), 1.49-1.39 (m, 1H), 1.35-1.24 (m, 8H), 0.92-0.79 (m, 5H). UPLC-MS (basic 4 min): rt=1.85 min; m/z=682.5 for [M+H]⁺.

Example 474: 2S,3R)-3-(cyclohexyloxy)-2-[(1-ethyl-1H-pyrazol-5-yl)formamido]-N-{2-fluoro-4-[(2S,3R)-4-(4-methylpiperazin-1-yl)-4-oxo-3-propanamidobutan-2-yl]phenyl}butanamide) (389)

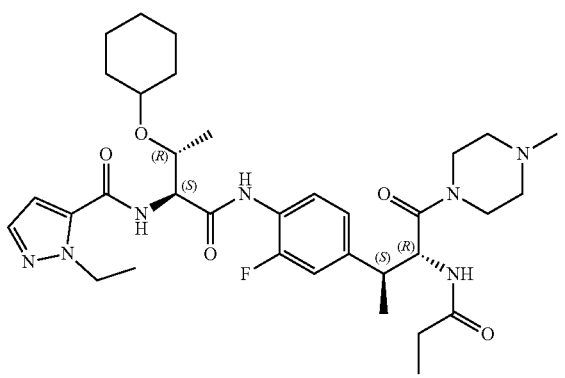

Compound 389 was synthesized by the procedure of FIG. 11. ¹H NMR (400 MHz, DMSO-d₆) δ 9.78 (s, 1H), 8.23-8.28 (m, 1H), 8.22 (br d, J=8.7 Hz, 1H), 7.67-7.77 (m, 1H), 7.49 (d, J=2.0 Hz, 1H), 7.13 (br d, J=12.1 Hz, 1H), 6.98-7.06 (m, 1H), 6.97 (d, J=2.0 Hz, 1H), 4.81-4.91 (m, 1H), 4.70-4.80 (m, 1H), 4.39-4.53 (m, 2H), 3.95-4.05 (m, 1H), 3.39-3.47 (m, 1H), 3.32-3.38 (m, 2H), 3.02-3.13 (m, 2H), 2.05-2.25 (m, 4H), 1.92-2.05 (m, 3H), 1.48-1.91 (m, 6H), 1.36-1.48 (m, 1H), 1.26-1.32 (m, 3H), 1.08-1.25 (m, 10H), 0.98 (br t, J=7.5 Hz, 3H). UPLC-MS (basic 4 min): rt=1.84 min; m/z=656.4 for [M+H]⁺.

Example 475: (2S,3S)-3-cyclohexyl-2-[(1-ethyl-1H-pyrazol-5-yl)formamido]-N-{2-fluoro-4-[(2S,3R)-4-(4-methylpiperazin-1-yl)-4-oxo-3-propanamidobutan-2-yl]phenyl}butanamide (390)

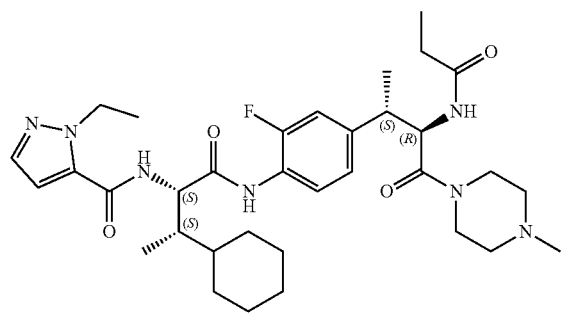

Compound 390 was synthesized by the procedure of FIG. 11. ¹H NMR (400 MHz, DMSO-d₆) δ 9.93 (s, 1H), 8.54-8.62 (m, 1H), 8.25 (d, J=8.7 Hz, 1H), 7.70 (t, J=8.3 Hz, 1H), 7.47 (d, J=2.1 Hz, 1H), 7.11 (dd, J=12.1, 1.8 Hz, 1H), 6.96-7.03 (m, 1H), 6.92 (d, J=2.1 Hz, 1H), 4.86 (t, J=9.4 Hz, 1H), 4.62-4.70 (m, 1H), 4.36-4.57 (m, 2H), 3.36-3.45 (m, 2H), 3.20-3.29 (m, 1H), 2.97-3.15 (m, 2H), 2.04-2.28 (m, 4H), 1.82-2.03 (m, 4H), 1.60-1.77 (m, 4H), 1.40-1.59 (m, 3H), 1.27 (t, J=7.1 Hz, 3H), 1.19 (d, J=7.0 Hz, 4H), 0.94-1.10 (m, 5H), 0.84 (d, J=7.0 Hz, 3H). UPLC-MS (basic 4 min): rt=1.84 min; m/z=640.4 for [M+H]⁺.

Example 476: N-[(2R,3S)-3-{4-[(2S)-2-[2-(3-cyanophenyl)-2,2-difluoroacetamido]-2-cycloheptyl acetamido]-3-fluorophenyl}-1-(4-methylpiperazin-1-yl)-1-oxobutan-2-yl]-1,2,3-thiadiazole-5-carboxamide (391)

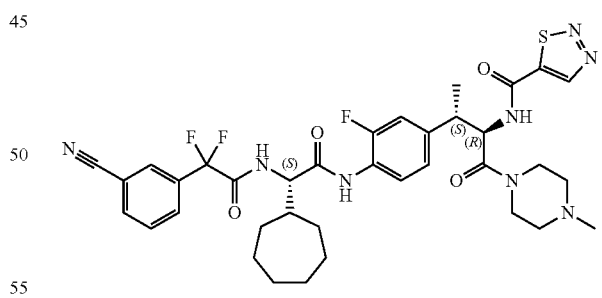

Compound 391 was synthesized by the procedure of FIG. 24. ¹H NMR (400 MHz, DMSO-d₆) δ 9.98 (s, 1H), 9.86 (s, OH), 9.67 (d, J=8.1 Hz, 1H), 9.52 (d, J=1.7 Hz, 1H), 9.46 (d, J=8.9 Hz, 0H), 9.26 (d, J=1.5 Hz, 0H), 9.08 (d, J=8.7 Hz, 1H), 9.03 (d, J=8.7 Hz, 0H), 8.16 (s, 2H), 8.06 (t, J=7.1 Hz, 2H), 7.95 (t, J=7.5 Hz, 2H), 7.75 (dt, J=15.8, 8.0 Hz, 3H), 7.56 (t, J=8.4 Hz, 0H), 7.34 (d, J=12.1 Hz, 0H), 7.19 (dd, J=19.3, 10.1 Hz, 1H), 7.08 (d, J=8.3 Hz, 1H), 6.53 (d, J=3.2 Hz, 1H), 5.20-5.09 (m, 1H), 5.09-4.99 (m, 1H), 4.51 (t, J=8.4 Hz, 1H), 4.43 (d, J=8.7 Hz, 0H), 3.75 (d, J=38.4 Hz, 0H), 3.45 (d, J=26.1 Hz, 3H), 2.98 (d, J=10.8 Hz, 1H), 2.33

(dd, J=3.9, 2.0 Hz, 1H), 2.20 (d, J=15.6 Hz, 3H), 2.08 (d, J=10.3 Hz, 2H), 1.95 (s, 4H), 1.55 (d, J=32.1 Hz, 16H), 1.44-1.27 (m, 6H), 1.23 (dd, J=19.4, 8.8 Hz, 3H). UPLC-MS (basic 4 min): rt=1.97 min; m/z=739.2 for [M+H]$^+$.

Example 477: N-[(2R,3S)-1-(1,1-dioxo-1λ$^6$-thiomorpholin-4-yl)-3-{4-[(2S)-2-[(1-ethyl-1H-pyrazol-5-yl)formamido]-2-[(1r,4S)-4-methylcyclohexyl]acetamido]-3-fluorophenyl}-1-oxobutan-2-yl]propenamide (392)

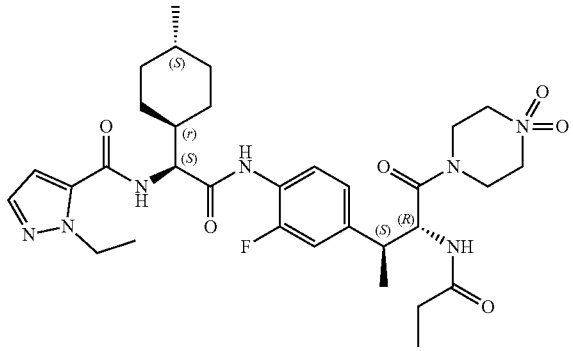

Compound 392 was synthesized by the procedure of FIG. 25. $^1$H NMR (400 MHz, DMSO-d$_6$) δ 9.84 (s, 1H), 8.43 (d, J=8.3 Hz, 1H), 8.36 (d, J=8.2 Hz, 1H), 7.70 (t, J=8.2 Hz, 1H), 7.47 (d, J=2.0 Hz, 1H), 7.18 (dd, J=12.1, 1.9 Hz, 1H), 7.10-7.01 (m, 1H), 6.99 (d, J=2.0 Hz, 1H), 4.93 (t, J=8.8 Hz, 1H), 4.58-4.37 (m, 3H), 4.05-3.78 (m, 2H), 3.75-3.55 (m, 1H), 3.41 (t, J=11.4 Hz, 1H), 3.22-3.05 (m, 2H), 2.97-2.60 (m, 3H), 2.16 (ddp, J=22.4, 15.0, 7.6 Hz, 2H), 1.81 (d, J=11.8 Hz, 2H), 1.67 (t, J=15.5 Hz, 3H), 1.27 (t, J=7.1 Hz, 4H), 1.21 (d, J=6.9 Hz, 4H), 1.17-1.03 (m, 1H), 1.00 (t, J=7.6 Hz, 3H), 0.85 (d, J=6.3 Hz, 5H). UPLC-MS (basic 4 min): rt=1.79 min; m/z=661.4 for [M+H]$^+$.

Example 478: (2S,3S)—N-{2-fluoro-4-[(2S,3R)-4-(4-methylpiperazin-1-yl)-4-oxo-3-propanamidobutan-2-yl]phenyl}-3-(4-fluorophenyl)-2-{[1-(propan-2-yl)-1H-pyrazol-5-yl]formamido}butanamide) (393)

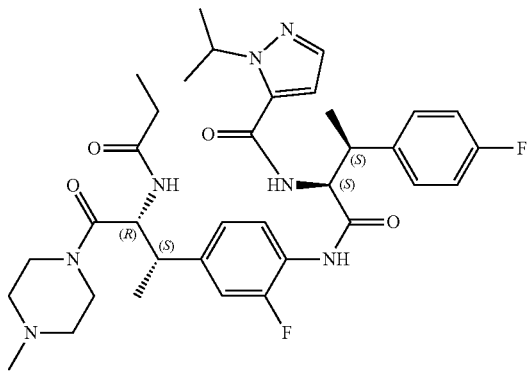

Compound 393 was synthesized by the procedure of FIG. 11. $^1$H NMR (400 MHz, DMSO-d$_6$) δ 10.12 (s, 1H), 8.55 (d, J=8.8 Hz, 1H), 8.23-8.30 (m, 1H), 7.82 (t, J=8.3 Hz, 1H), 7.35-7.44 (m, 3H), 7.07-7.19 (m, 3H), 7.04 (br d, J=9.8 Hz, 1H), 6.56 (d, J=2.0 Hz, 1H), 5.05 (quin, J=6.7 Hz, 1H), 4.91-5.00 (m, 1H), 4.84-4.91 (m, 1H), 3.38-3.48 (m, 2H), 3.28 (br s, 2H), 3.08-3.14 (m, 1H), 2.99-3.07 (m, 1H), 2.08-2.21 (m, 4H), 1.98 (s, 3H), 1.61-1.71 (m, 1H), 1.48-1.57 (m, 1H), 1.27 (d, J=7.1 Hz, 3H), 1.24 (d, J=6.6 Hz, 3H), 1.21-1.23 (m, 3H), 1.20 (d, J=3.2 Hz, 3H), 0.95-1.02 (m, 3H). UPLC-MS (basic 4 min): rt=1.72 min; m/z=666.4 for [M+H]$^+$.

Example 479: (2S,3S)-3-cyclohexyl-2-[[2,2-difluoro-2-(6-methoxy-3-pyridyl)acetyl]amino]-N-[2-fluoro-4-[(1S,2R)-1-methyl-3-(4-methylpiperazin-1-yl)-3-oxo-2-(propanoylamino)propyl]phenyl]butanamide (394)

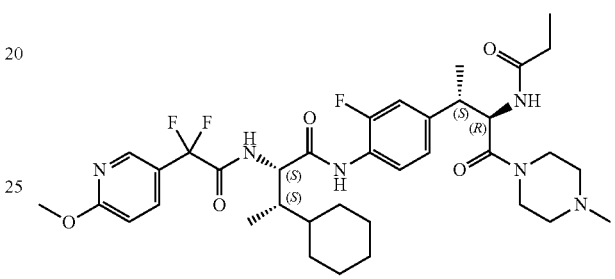

Compound 394 was synthesized by the procedure of FIG. 11. $^1$H NMR (400 MHz, DMSO-d$_6$) δ 10.02 (s, 1H), 9.16 (d, J=8.8 Hz, 1H), 8.46 (d, J=1.7 Hz, 1H), 8.26 (d, J=8.4 Hz, 1H), 7.93 (dd, J=8.9, 2.5 Hz, 1H), 7.67 (t, J=8.3 Hz, 1H), 7.08-7.15 (m, 1H), 6.99-7.03 (m, 1H), 6.97 (d, J=8.7 Hz, 1H), 4.80-4.92 (m, 1H), 4.47-4.59 (m, 1H), 3.89 (s, 3H), 3.36-3.48 (m, 2H), 3.20-3.28 (m, 1H), 3.06-3.14 (m, 1H), 2.97-3.06 (m, 1H), 1.76-2.25 (m, 6H), 1.26-1.70 (m, 6H), 1.20 (d, J=7.1 Hz, 3H), 1.08-1.13 (m, 1H), 1.01-1.08 (m, 1H), 0.98 (t, J=7.6 Hz, 3H), 0.68-0.96 (m, 4H), 0.46-0.67 (m, 1H) UPLC-MS (basic 4 min): rt=1.97 min; m/z=703.4 for [M+H]$^+$.

Example 480: N-[(2R,3S)-3-{4-[(2S)-2-[2,2-difluoro-2-(5-methoxypyridin-3-yl)acetamido]-2-[(1r,4S)-4-methylcyclohexyl]acetamido]-3-fluorophenyl}-1-(morpholin-4-yl)-1-oxobutan-2-yl]propanamide (395)

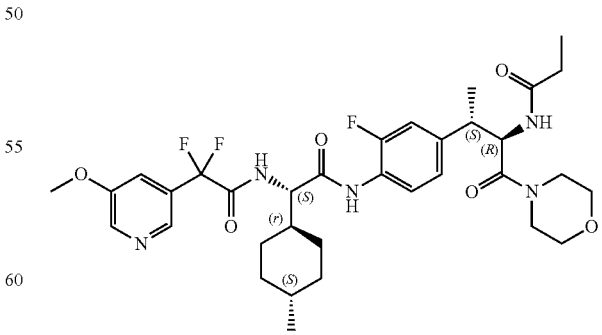

Compound 395 was synthesized by the procedure of FIG. 27. $^1$H NMR (400 MHZ, DMSO-d$_6$) δ 9.94 (s, 1H), 9.12 (d, J=8.3 Hz, 1H), 8.48 (d, J=2.8 Hz, 1H), 8.40 (d, J=1.8 Hz, 1H), 8.26 (d, J=8.7 Hz, 1H), 7.71 (t, J=8.3 Hz, 1H), 7.65-7.61 (m, 1H), 7.11 (dd, J=12.0, 1.9 Hz, 1H), 7.01 (dd, J=8.4, 1.9 Hz, 1H), 4.86 (t, J=9.3 Hz, 1H), 4.43 (t, J=8.6 Hz, 1H), 3.88 (s, 3H), 3.51-3.39 (m, 2H), 3.29-3.21 (m, 1H), 3.15-2.97 (m, 2H), 2.26-2.05 (m, 4H), 1.97 (s, 3H), 1.84-1.75 (m, 1H), 1.70-1.55 (m, 5H), 1.53-1.45 (m, 1H), 1.27-1.10 (m, 6H), 1.06-0.96 (m, 4H), 0.89-0.78 (m, 5H). UPLC-MS (basic 4 min): rt=1.84 min; m/z=676.3 for [M+H]$^+$.

Example 481: 2-cyclopropyl-N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-methylpiperazin-1-yl)-1-oxobutan-2-yl]acetamide) (396)

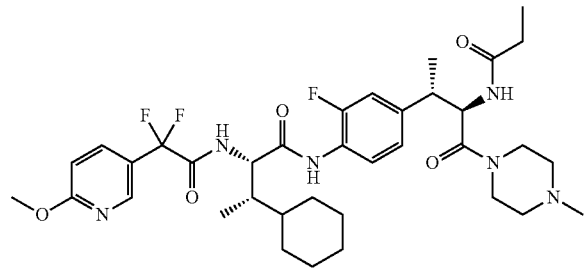

Compound 396 was synthesized by the procedure of FIG. 24. $^{1H}$ NMR (400 MHZ, DMSO-d$_6$) δ 9.70 (s, 1H), 8.30 (d, J=8.3 Hz, 1H), 8.06 (d, J=8.7 Hz, 1H), 7.59 (t, J=8.1 Hz, 1H), 7.32 (d, J=1.8 Hz, 1H), 6.96 (d, J=12.0 Hz, 1H), 6.91-6.81 (m, 2H), 4.74 (t, J=9.2 Hz, 1H), 4.38 (t, J=8.3 Hz, 1H), 4.31 (q, J=7.2 Hz, 2H), 3.25 (s, 2H), 3.01-2.82 (m, 2H), 2.07-1.99 (m, 2H), 1.93-1.87 (m, 2H), 1.84 (s, 3H), 1.74-1.60 (m, 2H), 1.58-1.46 (m, 5H), 1.46-1.38 (m, 1H), 1.18-1.10 (m, 5H), 1.07 (d, J=7.1 Hz, 4H), 0.96-0.88 (m, 1H), 0.84-0.78 (m, 1H), 0.71 (d, J=6.8 Hz, 6H), 0.30-0.21 (m, 2H), 0.03--0.08 (m, 2H) UPLC-MS (basic 4 min): rt=1.86 min; m/z=652.4 for [M+H]$^+$ Example 482: N-[(2R,3S)-3-{3-fluoro-4-[(2S)-2-{[3-(3-methyloxetan-3-yl)-1,2-oxazol-4-yl]formamido}-2-[(1r,4S)-4-methylcyclohexyl]acetamido]phenyl}-1-(4-methylpiperazin-1-yl)-1-oxobutan-2-yl]propenamide (397)

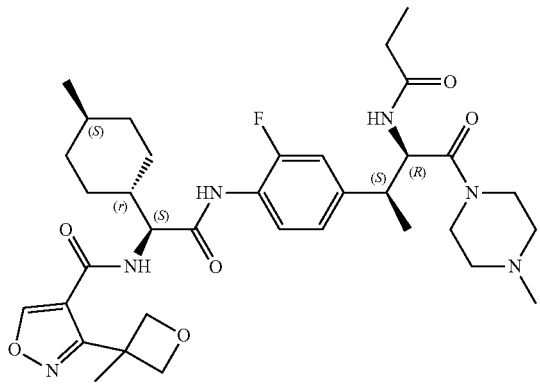

Compound 397 was synthesized by the procedure of FIG. 11. $^1$H NMR (400 MHz, DMSO-d$_6$) δ 9.87 (s, 1H), 9.50 (s, 1H), 8.57 (d, J=8.3 Hz, 1H), 8.26 (d, J=8.8 Hz, 1H), 7.71 (t, J=8.2 Hz, 1H), 7.11 (d, J=11.8 Hz, 1H), 7.05-6.97 (m, 1H), 4.90-4.83 (m, 4H), 4.55 (t, J=8.2 Hz, 1H), 4.48 (t, J=6.5 Hz, 2H), 3.45-3.36 (m, 2H), 3.15-2.99 (m, 3H), 2.23-2.06 (m, 4H), 1.99 (s, 3H), 1.86-1.78 (m, 1H), 1.74-1.61 (m, 8H), 1.59-1.50 (m, 1H), 1.33-1.14 (m, 6H), 1.13-1.03 (m, 1H), 1.02-0.97 (m, 3H), 0.89-0.82 (m, 5H) UPLC-MS (basic 4 min): rt=1.75 min; m/z=669.4 for [M+H]$^+$ Example 483: 1-cyclobutyl-N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]-1H-pyrazole-5-carboxamide (398)

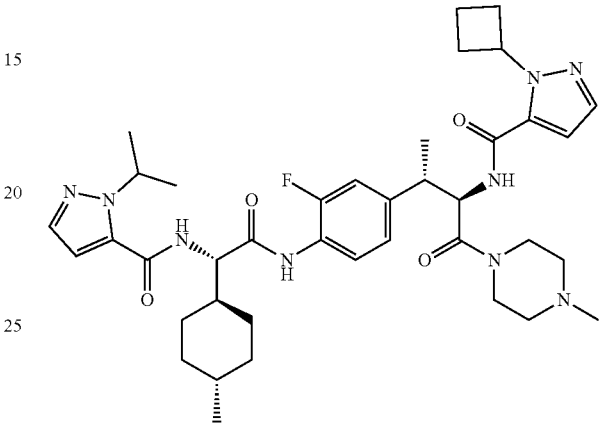

Compound 398 was synthesized by the procedure of FIG. 24. 1H NMR (DMSO-d$_6$) δ: 9.86 (s, 1H), 8.83 (d, J=8.4 Hz, 1H), 8.44 (d, J=8.2 Hz, 1H), 7.78 (t, J=8.3 Hz, 1H), 7.55 (d, J=2.0 Hz, 1H), 7.49 (d, J=2.0 Hz, 1H), 7.17 (d, J=12.0 Hz, 1H), 7.06 (d, J=8.5 Hz, 1H), 7.00 (d, J=1.9 Hz, 1H), 6.93 (d, J=2.0 Hz, 1H), 5.63-5.52 (m, 1H), 5.39 (p, J=6.3 Hz, 1H), 5.08-4.99 (m, 1H), 4.53 (t, J=8.4 Hz, 1H), 3.46 (s, 2H), 3.30 (s, 2H), 3.05 (s, 1H), 2.37-2.15 (m, 5H), 1.98 (d, J=9.2 Hz, 3H), 1.88-1.60 (m, 8H), 1.53 (s, 1H), 1.36 (dd, J=9.3, 6.6 Hz, 6H), 1.26 (d, J=7.1 Hz, 6H), 1.08 (d, J=12.6 Hz, 1H), 0.86 (d, J=6.6 Hz, 5H) UPLC-MS (acidic 4 min): rt=1.81 min; m/z=732.5 for [M+H]$^+$.

Example 484: 1-cyclopropyl-N-[(2R,3S)-3-{3-fluoro-4-[(2S)-2-{[1-(propan-2-yl)-1H-pyrazol-5-yl]formamido}-2-[(1r,4S)-4-methylcyclohexyl]acetamido]phenyl}-1-(4-methylpiperazin-1-yl)-1-oxobutan-2-yl]-1H-pyrazole-5-carboxamide (399)

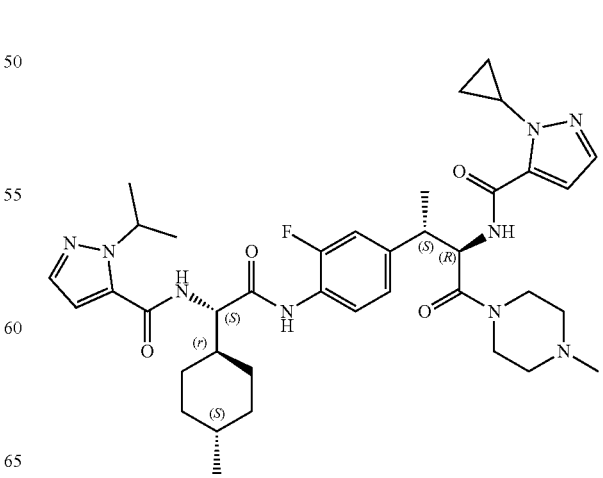

Compound 399 was synthesized by the procedure of FIG. 11. $^1$H NMR (400 MHz, DMSO-d$_6$) δ 9.87 (s, 1H), 8.85 (d, J=8.5 Hz, 1H), 8.44 (d, J=8.2 Hz, 1H), 7.78 (t, J=8.3 Hz, 1H), 7.46 (dd, J=28.6, 2.0 Hz, 2H), 7.18 (dd, J=12.0, 1.9 Hz, 1H), 7.07 (dd, J=8.3, 1.9 Hz, 1H), 6.95 (dd, J=18.9, 2.0 Hz, 2H), 5.39 (p, J=6.6 Hz, 1H), 5.06 (t, J=9.3 Hz, 1H), 4.53 (t, J=8.3 Hz, 1H), 4.47-4.38 (m, 1H), 3.47 (t, J=15.6 Hz, 2H), 3.11-3.02 (m, 1H), 2.24-2.16 (m, 3H), 1.99 (s, 3H), 1.89-1.76 (m, 2H), 1.74-1.60 (m, 4H), 1.57-1.47 (m, 1H), 1.43-1.33 (m, 7H), 1.33-1.17 (m, 5H), 1.06 (t, J=3.3 Hz, 3H), 0.96-0.82 (m, 7H) UPLC-MS (basic 4 min): rt=1.99 min; m/z=718.5 for [M+H]$^+$.

Example 485: N-[(2R,3S)-3-{4-[(2S)-2-[2,2-difluoro-2-(5-methoxypyridin-3-yl)acetamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (400)

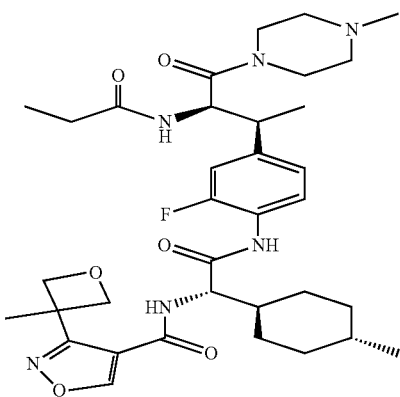

Compound 400 was synthesized by the procedure of FIG. 24. $^1$H NMR (400 MHz, DMSO-d$_6$) δ 9.96 (s, 1H), 9.67 (d, J=8.1 Hz, 1H), 9.51 (s, 1H), 9.12 (d, J=7.8 Hz, 1H), 8.46-8.48 (m, 1H), 8.39 (s, 1H), 7.71-7.78 (m, 1H), 7.63 (s, 1H), 7.20 (d, J=12.7 Hz, 1H), 7.07 (d, J=8.3 Hz, 1H), 4.99-5.09 (m, 1H), 4.44 (br t, J=7.5 Hz, 1H), 3.88 (s, 3H), 3.42-3.53 (m, 2H), 3.19-3.27 (m, 2H), 2.95 (br t, J=9.4 Hz, 1H), 2.16-2.24 (m, 2H), 1.94 (s, 3H), 1.72-1.84 (m, 1H), 1.60-1.71 (m, 3H), 1.49-1.59 (m, 2H), 1.38 (brt, J=9.3 Hz, 1H), 1.31 (d, J=6.8 Hz, 3H), 1.17-1.26 (m, 1H), 1.07-1.16 (m, 1H), 0.92-1.02 (m, 1H), 0.91 (br d, J=1.5 Hz, 1H), 0.83 (br d, J=6.4 Hz, 3H), 0.75-0.82 (m, 1H). UPLC-MS (basic 4 min): rt=1.89 min; m/z=745.3 for [M+H]$^+$.

Example 486: N-[(2R,3S)-3-{4-[(2S)-2-cycloheptyl-2-(2-cyclopropyl-2,2-difluoroacetamido)acetamido]-3-fluorophenyl}-1-(4-methylpiperazin-1-yl)-1-oxobutan-2-yl]propenamide (404)

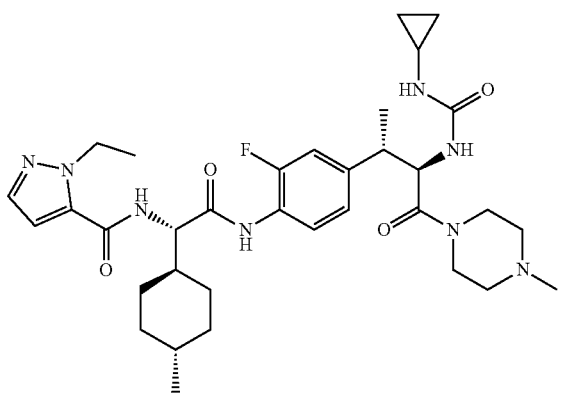 [SMILES: CCn1nccc1C(=O)N[C@H](C(=O)Nc1ccc([C@H](C)[C@@H](NC(=O)NC2CC2)C(=O)N2CCN(C)CC2)cc1F)[C@H]1CC[C@H](C)CC1]

Compound 404 was synthesized by the procedure of FIG. 11. $^1$H NMR (400 MHz, DMSO-d$_6$) δ 9.89 (s, 1H), 8.50 (d, J=8.7 Hz, 1H), 8.27 (d, J=8.7 Hz, 1H), 7.71 (t, J=8.3 Hz, 1H), 7.19-7.09 (m, 1H), 7.02 (d, J=8.4 Hz, 1H), 4.86 (t, J=9.3 Hz, 1H), 4.50 (t, J=8.5 Hz, 1H), 3.43 (d, J=12.2 Hz, 2H), 3.25 (t, J=10.5 Hz, 1H), 3.12-2.96 (m, 2H), 2.24-2.04 (m, 5H), 2.00 (s, 3H), 1.74-1.44 (m, 10H), 1.42-1.18 (m, 8H), 0.99 (t, J=7.6 Hz, 3H), 0.73-0.61 (m, 4H). UPLC-MS (basic 4 min): rt=1.87 min; m/z=622.4 for [M+H]$^+$.

Example 487: N-[(2R,3S)-3-{4-[(2S)-2-[2,2-difluoro-2-(2-methoxypyrimidin-5-yl)acetamido]-2-[(1r,4S)-4-methylcyclohexyl]acetamido]-3-fluorophenyl}-1-(4-methylpiperazin-1-yl)-1-oxobutan-2-yl]propenamide (405)

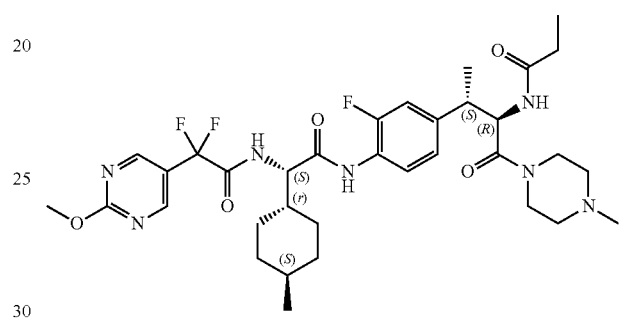

Compound 405 was synthesized by the procedure of FIG. 11. $^1$H NMR (400 MHz, DMSO-d$_6$) δ 9.94 (s, 1H), 9.13 (d, J=8.2 Hz, 1H), 8.86 (s, 2H), 8.26 (d, J=8.7 Hz, 1H), 7.70 (t, J=8.1 Hz, 1H), 7.11 (d, J=12.0 Hz, 1H), 7.02 (d, J=8.4 Hz, 1H), 4.86 (t, J=9.1 Hz, 1H), 4.44 (d, J=8.4 Hz, 1H), 3.99 (s, 3H), 3.47-3.38 (m, 2H), 3.28-3.20 (m, 1H), 3.13-2.97 (m, 3H), 2.21-2.11 (m, 4H), 1.97 (s, 3H), 1.84-1.75 (m, 1H), 1.72-1.54 (m, 6H), 1.53-1.42 (m, 1H), 1.31-1.11 (m, 5H), 0.99 (t, J=7.6 Hz, 4H), 0.84 (d, J=6.2 Hz, 5H) UPLC-MS (basic 4 min): rt=1.81 min; m/z=690.4 for [M+H]$^+$.

Example 488: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-methylpiperazin-1-yl)-1-oxobutan-2-yl]-1-fluorocyclopropane-1-carboxamide (406)

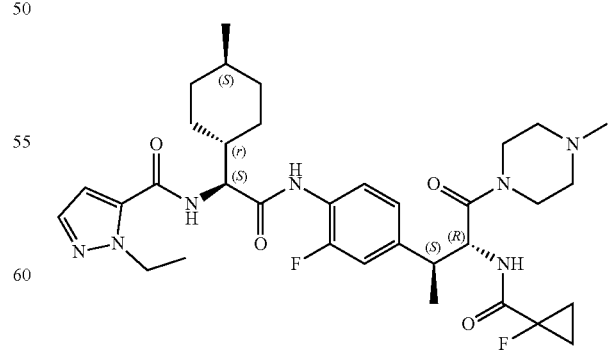

Compound 406 was synthesized by the procedure of FIG. 24. $^1$H NMR (400 MHz, DMSO-d$_6$) δ 9.86 (s, 1H), 8.51 (d, J=8.2 Hz, 1H), 8.45 (d, J=8.2 Hz, 1H), 7.77 (t, J=8.2 Hz, 1H), 7.47 (d, J=2.1 Hz, 1H), 7.14 (d, J=12.1 Hz, 1H), 7.06-6.97 (m, 2H), 4.90 (t, J=9.2 Hz, 1H), 4.54 (t, J=8.2 Hz, 1H), 4.47 (q, J=7.1 Hz, 2H), 3.49-3.35 (m, 2H), 3.26-3.18 (m, 1H), 3.06-2.96 (m, 1H), 2.23-2.12 (m, 2H), 1.97 (s, 3H), 1.87-1.75 (m, 2H), 1.73-1.59 (m, 4H), 1.49-1.40 (m, 1H), 1.37-1.13 (m, 15H), 1.10-1.04 (m, 1H), 0.86 (d, J=6.6 Hz, 5H. UPLC-MS (basic 4 min): rt=1.90 min; m/z=656.4 for [M+H]+.

Example 489: N-[(2R,3S)-3-{4-[(2S)-2-[2-(1-ethyl-1H-pyrazol-4-yl)-2,2-difluoroacetamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (407)

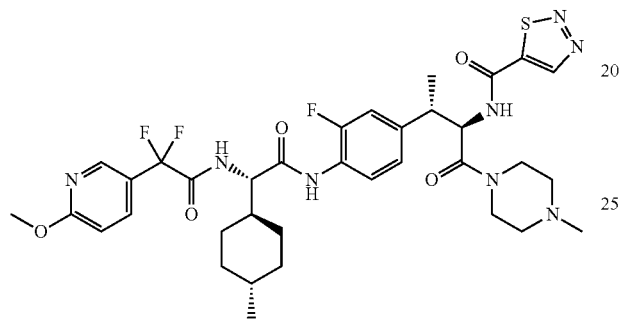

Compound 407 was synthesized by the procedure of FIG. 24. ¹H NMR (400 MHz, DMSO-d₆) δ 9.93 (s, 1H), 9.67 (d, J=8.1 Hz, 1H), 9.52 (s, 1H), 8.79 (d, J=8.3 Hz, 1H), 8.11 (s, 1H), 7.83-7.74 (m, 1H), 7.66 (s, 1H), 7.21 (dd, J=12.1, 1.9 Hz, 1H), 7.13-7.05 (m, 1H), 5.10-4.99 (m, 1H), 4.44 (t, J=8.3 Hz, 1H), 4.16 (q, J=7.3 Hz, 2H), 3.56-3.41 (m, 2H), 3.31-3.21 (m, 3H), 2.97 (ddd, J=13.2, 8.9, 2.5 Hz, 1H), 2.26-2.17 (m, 2H), 1.96 (s, 3H), 1.83-1.55 (m, 6H), 1.46-1.39 (m, 1H), 1.36 (t, J=7.2 Hz, 3H), 1.32 (d, J=6.9 Hz, 3H), 1.28-1.20 (m, 1H), 1.20-1.11 (m, 1H), 0.99 (q, J=12.1 Hz, 1H), 0.85 (d, J=6.3 Hz, 3H), 0.83-0.77 (m, 1H). UPLC-MS (basic 4 min): rt=1.88 min; m/z=733.2 for [M+H]+.

Example 490: N-[(2R,3S)-3-{4-[(2S)-2-[(4-ethyl-1,2,5-oxadiazol-3-yl)formamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (408)

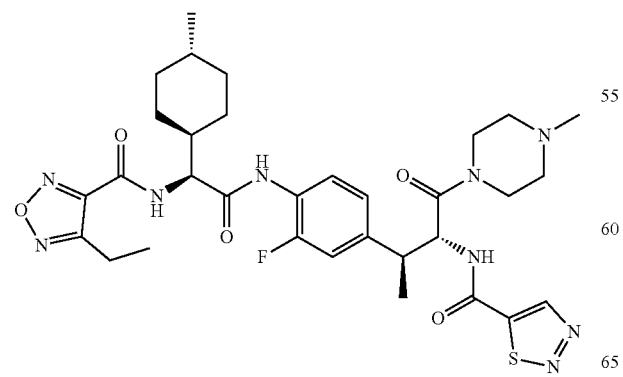

Compound 408 was synthesized by the procedure of FIG. 24. ¹H NMR (400 MHz, DMSO-d₆) δ 9.99 (s, 1H), 9.68 (d, J=7.8 Hz, 1H), 9.52 (s, 1H), 9.12 (d, J=8.3 Hz, 1H), 7.79 (t, J=8.2 Hz, 1H), 7.22 (dd, J=12.0, 1.9 Hz, 1H), 7.09 (dd, J=8.8, 1.8 Hz, 1H), 5.10-5.01 (m, 1H), 4.65 (t, J=7.8 Hz, 1H), 3.51-3.43 (m, 2H), 3.28 (d, J=10.6 Hz, 4H), 2.99 (dt, J=10.5, 6.5 Hz, 1H), 2.90 (q, J=7.5 Hz, 2H), 2.22 (dd, J=7.6, 3.5 Hz, 2H), 1.98 (s, 3H), 1.85-1.74 (m, 2H), 1.69 (d, J=13.6 Hz, 3H), 1.58 (t, J=10.4 Hz, 1H), 1.43 (t, J=10.1 Hz, 1H), 1.32 (d, J=6.9 Hz, 3H), 1.24 (t, J=7.5 Hz, 3H), 1.21-1.01 (m, 2H), 0.95-0.87 (m, 1H), 0.86 (d, J=6.5 Hz, 3H). UPLC-MS (basic 4 min): rt=2.06 min; m/z=684.3 for [M+H]+.

Example 491: N-[(2R,3S)-3-{4-[(2S)-2-[(3-ethyl-furan-2-yl)formamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (409)

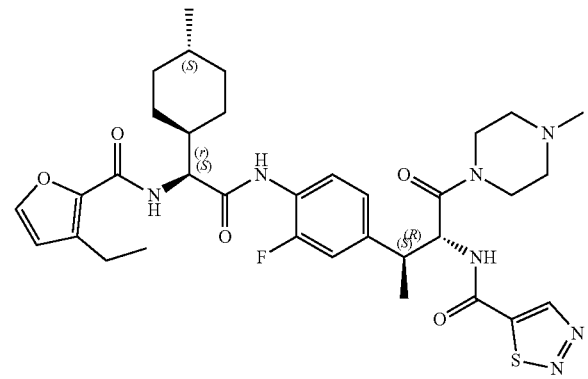

Compound 409 was synthesized by the procedure of FIG. 24. ¹H NMR (400 MHz, DMSO-d₆) δ 9.91 (s, 1H), 9.67 (d, J=6.7 Hz, 1H), 9.52 (s, 1H), 7.79 (t, J=8.3 Hz, 1H), 7.76-7.72 (m, 2H), 7.25-7.17 (m, 1H), 7.11-7.04 (m, 1H), 6.61 (d, J=1.8 Hz, 1H), 5.05 (td, J=7.4, 2.4 Hz, 1H), 4.56 (t, J=8.2 Hz, 1H), 3.48-3.44 (m, 1H), 3.32-3.21 (m, 4H), 3.03-2.93 (m, 1H), 2.77 (q, J=7.5 Hz, 2H), 2.25-2.17 (m, 2H), 1.96 (s, 3H), 1.82-1.73 (m, 2H), 1.68 (dt, J=10.8, 6.9 Hz, 3H), 1.57 (h, J=4.0 Hz, 1H), 1.42 (dt, J=9.6, 4.2 Hz, 1H), 1.31 (d, J=6.9 Hz, 3H), 1.28-1.24 (m, 1H), 1.22-1.15 (m, 1H), 1.12 (t, J=7.5 Hz, 3H), 1.02 (t, J=12.2 Hz, 1H), 0.94-0.87 (m, 1H), 0.85 (d, J=6.3 Hz, 3H). UPLC-MS (basic 4 min): rt=2.07 min; m/z=682.3 for [M+H]+.

Example 492: N-[(2R,3S)-3-{4-[(2S)-2-[(1-ethyl-1H-1,2,4-triazol-5-yl)formamido]-2-[(1r,4S)-4-methylcyclohexyl]acetamido]-3-fluorophenyl}-1-(4-methyl piperazin-1-yl)-1-oxobutan-2-yl]-1,2,3-thiadiazole-5-carboxamide (410)

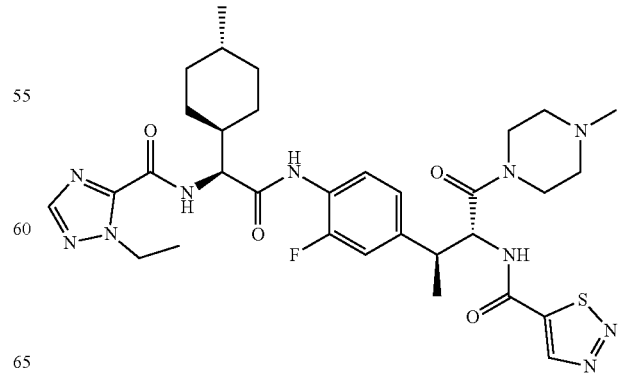

Compound 410 was synthesized by the procedure of FIG. 24. ¹H NMR (400 MHz, DMSO-d₆) δ 10.02 (s, 1H), 9.67 (s, 1H), 9.51 (s, 1H), 8.45 (d, J=8.8 Hz, 1H), 8.11 (s, 1H), 7.79 (t, J=8.3 Hz, 1H), 7.26-7.19 (m, 1H), 7.12-7.05 (m, 1H), 5.05 (d, J=10.1 Hz, 1H), 4.68-4.58 (m, 2H), 4.56 (d, J=7.2 Hz, 1H), 3.50-3.42 (m, 2H), 3.27 (dd, J=14.9, 7.2 Hz, 3H), 2.99 (dt, J=10.6, 5.8 Hz, 1H), 2.21 (dd, J=7.7, 3.4 Hz, 2H), 1.97 (s, 3H), 1.79 (ddd, J=24.9, 11.3, 7.7 Hz, 2H), 1.72-1.64 (m, 3H), 1.62-1.54 (m, 1H), 1.47-1.39 (m, 1H), 1.36 (t, J=7.2 Hz, 3H), 1.32 (d, J=6.9 Hz, 3H), 1.29-1.14 (m, 2H), 1.05 (q, J=12.3 Hz, 1H), 0.93-0.87 (m, 1H), 0.85 (d, J=6.4 Hz, 3H). UPLC-MS (basic 4 min): rt=1.88 min; m/z=683.3 for [M+H]+

Example 493: N-[(2R,3S)-3-{4-[(2S)-2-[(3-ethyl-1,2-oxazol-4-yl)formamido]-2-[(1r,4S)-4-methylcyclohexyl]acetamido]-3-fluorophenyl}-1-(4-methylpiperazin-1-yl)-1-oxobutan-2-yl]-1,2,3-thiadiazole-5-carboxamide (414)

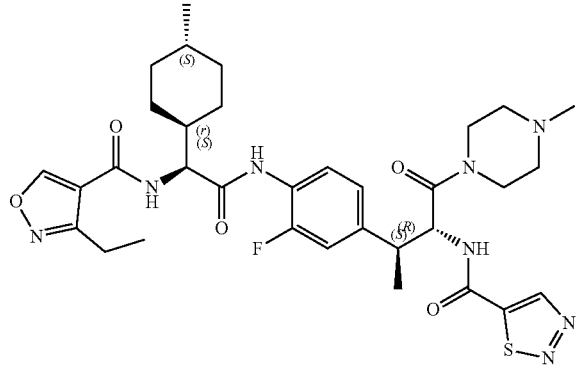

Compound 414 was synthesized by the procedure of FIG. 24. ¹H NMR (400 MHz, DMSO-d₆) δ 9.90 (s, 1H), 9.67 (dd, J=8.2 Hz, 1H), 9.51 (s, 1H), 9.40 (s, 1H), 8.43 (d, J=8.4 Hz, 1H), 7.77 (t, J=8.3 Hz, 1H), 7.20 (d, J=12.0, 1.8 Hz, 1H), 7.07 (dd, J=8.3, 1.4 Hz, 1H), 5.05 (dd, J=10.0, 8.4 Hz, 1H), 4.57 (t, J=8.2 Hz, 1H), 3.38-3.51 (m, 2H), 3.20-3.29 (m, 2H), 2.99 (br t, J=9.2 Hz, 1H), 2.83 (d, J=7.5 Hz, 2H), 2.15-2.25 (m, 2H), 1.96 (s, 3H), 1.81 (br d, J=11.8 Hz, 1H), 1.54-1.77 (m, 5H), 1.43 (br t, J=9.2 Hz, 1H), 1.31 (d, J=6.9 Hz, 3H), 1.26 (br d, J=3.8 Hz, 1H), 1.19-1.24 (m, 1H), 1.13-1.19 (m, 3H), 1.01-1.13 (m, 1H), 0.90 (br s, 1H), 0.85 (d, J=6.5 Hz, 3H), 0.81 (br d, J=3.1 Hz, 1H). UPLC-MS (basic 4 min): rt=1.88 min; m/z=683.4 for [M+H]⁺.

Example 494: N-[(2R,3S)-3-{4-[(2S)-2-cycloheptyl-2-[2,2-difluoro-2-(2-methoxypyrimidin-5-yl)acetamido]acetamido]-3-fluorophenyl}-1-(4-methylpiperazin-1-yl)-1-oxobutan-2-yl]propenamide (418)

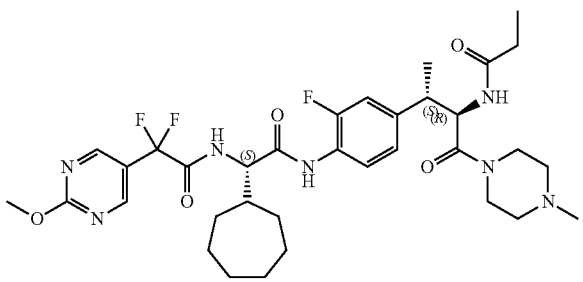

Compound 418 was synthesized by the procedure of FIG. 11. ¹H NMR (400 MHz, DMSO-d₆) δ 9.96 (s, 1H), 9.11 (d, J=8.4 Hz, 1H), 8.87 (s, 2H), 8.27 (d, J=8.6 Hz, 1H), 7.68 (t, J=8.3 Hz, 1H), 7.11 (d, J=11.7 Hz, 1H), 7.02 (d, J=8.4 Hz, 1H), 4.86 (t, J=9.3 Hz, 1H), 4.52 (t, J=8.2 Hz, 1H), 3.99 (s, 3H), 3.49-3.39 (m, 3H), 3.14-2.95 (m, 3H), 2.23-2.14 (m, 4H), 1.97 (s, 3H), 1.67-1.54 (m, 7H), 1.48 (s, 4H), 1.41-1.30 (m, 4H), 1.20 (d, J=7.0 Hz, 4H), 0.99 (t, J=7.6 Hz, 3H). UPLC-MS (basic 4 min): rt=1.79 min; m/z=690.4 for [M+H]⁺.

Example 495: N-[(2R,3S)-3-{4-[(2S)-2-(2-cyclohexyl-2,2-difluoroacetamido)-2-[(1r,4S)-4-methylcyclohexyl]acetamido]-3-fluorophenyl}-1-(4-methylpiperazin-1-yl)-1-oxobutan-2-yl]propenamide (419)

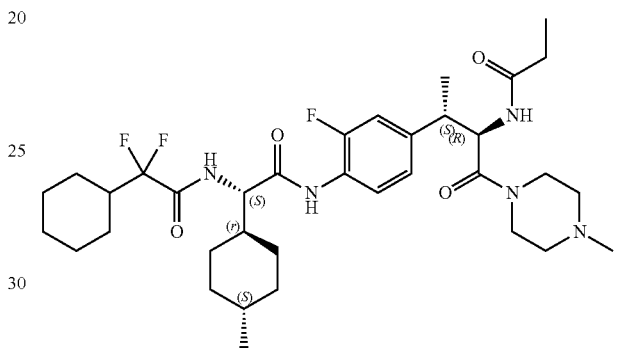

Compound 419 was synthesized by the procedure of FIG. 11. ¹H NMR (400 MHz, DMSO-d₆) δ 9.84 (s, 1H), 8.55 (d, J=8.3 Hz, 1H), 8.26 (d, J=8.7 Hz, 1H), 7.72 (t, J=8.3 Hz, 1H), 7.11 (d, J=11.6 Hz, 1H), 7.02 (d, J=8.4 Hz, 1H), 4.86 (t, J=9.3 Hz, 1H), 4.39 (t, J=8.5 Hz, 1H), 3.50-3.39 (m, 2H), 3.29-3.19 (m, 1H), 3.17-2.98 (m, 2H), 2.23-2.11 (m, 4H), 2.00 (s, 3H), 1.83-1.42 (m, 14H), 1.34-1.05 (m, 10H), 0.99 (t, J=7.6 Hz, 4H), 0.85 (d, J=6.5 Hz, 4H). UPLC-MS (basic 4 min): rt=2.17 min; m/z=664.4 for [M+H]⁺

Example 496: tert-Butyl N-[(2R,3S)-3-(4-aminophenyl)-1-(4-methylpiperazin-1-yl)-1-oxobutan-2-yl]carbamate (91B)

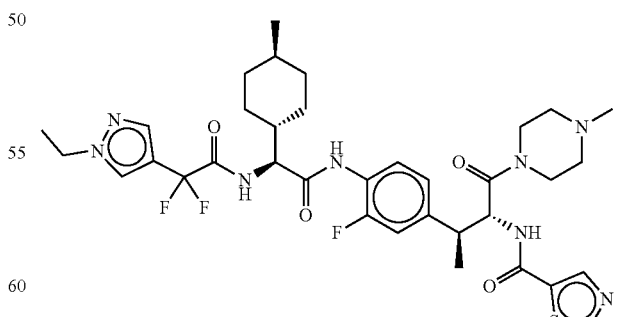

To a degassed solution of 92 (0.680 g, 1.67 mmol, 1.0 eq) in EtOH (7 mL) and THF (7 mL) was added Pd/C (0.7 g). The mixture was degassed for another 20 minutes and then evacuated under vacuum before introducing a hydrogen balloon. The resulting mixture was stirred at RT for 6 h. The mixture was filtered through a pad of celite which was washed with EtOH (50 mL). The solution was concentrated to dryness to afford 91B as an off-white solid (0.525 g, 83%) which was used in the next step without further purification. $^1$H NMR (400 MHz, DMSO-$d_6$) δ 9.72 (s, 1H), 7.77-7.62 (m, 1H), 7.44 (d, J=8.7 Hz, 1H), 7.39-7.26 (m, 8H), 7.22 (d, J=8.7 Hz, 1H), 7.10 (dd, J=12.0, 1.9 Hz, 1H), 7.00 (dd, J=8.4, 1.9 Hz, 1H), 5.04 (s, 3H), 4.53 (t, J=9.2 Hz, 1H), 4.18 (q, J=7.6, 1H), 3.13-3.05 (m, 2H), 2.20-2.15 (m, 2H), 2.01 (s, 3H), 1.77-1.65 (m, 7H), 1.59-1.53 (m, 4H), 1.38 (s, 9H), 1.34 (s, 1H), 1.26-1.15 (m, 4H), 1.19-1.08 (m, 6H), 1.05 (t, J=11.7 Hz, 1H). UPLC-MS (basic 2 min): Rt=0.94 min; m/z=377.3 for [M+H]$^+$ Example 497: benzyl N—[(S)-({4-[(2S,3R)-3-{[(tert-butoxy)carbonyl]amino}-4-(4-methylpiperazin-1-yl)-4-oxobutan-2-yl]phenyl}carbamoyl)(cyclohexyl)methyl]carbamate (92B)

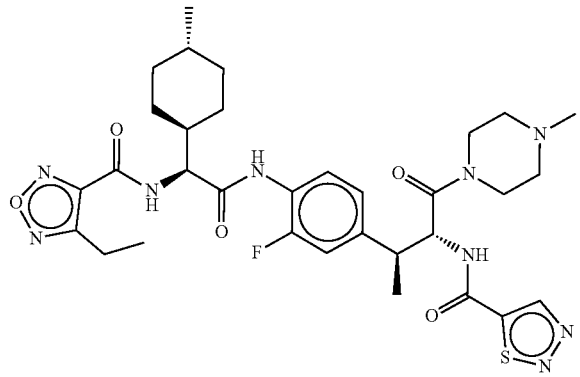

To a solution of 91B (0.125 g, 0.332 mmol, 1.0 eq.) in DMF (1 mL) were added Z-Chg-OH (0.106 g, 0.364 mmol, 1.1 eq.), DIPEA (0.17 mL, 0.996 mmol, 3.0 eq.) and HATU (0.189 g, 0.498 mmol, 1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness to afford 92B as an orange solid (0.199 g, 92%) which was used in the next step without further purification. UPLC-MS (basic 2 min): Rt=1.21 min; m/z=650.3 for [M+H]+

Example 498: tert-Butyl N-[(2R,3S)-3-{4-[(2S)-2-amino-2-cyclohexylacetamido]phenyl}-1-(4-methylpiperazin-1-yl)-1-oxobutan-2-yl]carbamate (93B)

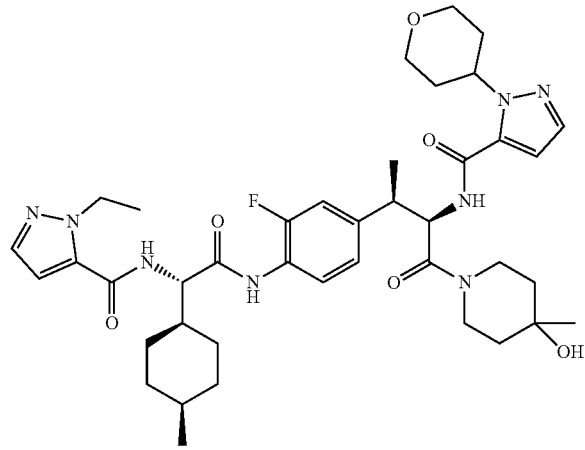 [SMILES: CCn1nccc1C(=O)N[C@H](C(=O)Nc1ccc([C@@H](C)[C@@H](NC(=O)c2ccnn2C2CCOCC2)C(=O)N2CCC(C)(O)CC2)cc1F)[C@H]1CC[C@@H](C)CC1]

To a degassed solution of 92B (0.199 g, 0.306 mmol, 1.0 eq) in EtOH (8 mL) and THF (2 mL) was added Pd(OH)$_2$ (0.020 g, 0.142 mmol, 0.5 eq.). The mixture was degassed for another 20 minutes and then evacuated under vacuum before introducing a hydrogen balloon. The resulting mixture was stirred at RT for 4 h. The mixture was filtered through a pad of celite which was washed with EtOH (50 mL). The solution was concentrated to dryness to afford 93B as an off-white solid (0.154 g, 98%) which was used in the next step without further purification. $^1$H NMR (400 MHz, DMSO-$d_6$) δ 9.79 (s, 1H), 7.53 (d, J=8.2 Hz, 2H), 7.15 (dd, J=16.1, 8.7 Hz, 3H), 4.49 (t, J=9.4 Hz, 1H), 3.10 (dd, J=5.6, 2.9 Hz, 2H), 2.14-2.10 (m, 2H), 1.99 (s, 3H), 1.68 (d, J=10.0 Hz, 4H), 1.60 (d, J=10.4 Hz, 2H), 1.53 (s, 2H), 1.38 (s, 9H), 1.34 (s, 2H), 1.19 (dd, J=17.7, 5.9 Hz, 7H), 1.13-1.07 (m, 2H), 1.07-0.96 (m, 2H). UPLC-MS (basic 2 min): Rt=1.06 min; m/z=516.3 for [M+H]+

Example 499: tert-Butyl N-[(2R,3S)-3-{4-[(2S)-2-cyclohexyl-2-[(1-ethyl-1H-pyrazol-5-yl)formamido]acetamido]phenyl}-1-(4-methylpiperazin-1-yl)-1-oxobutan-2-yl]carbamate (94B)

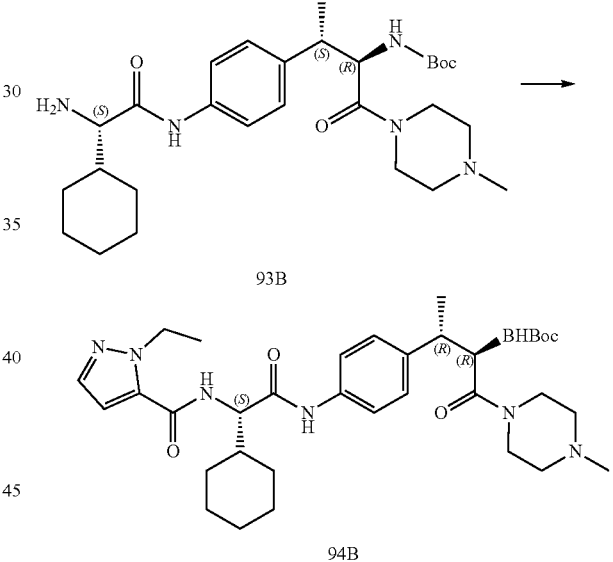

To a solution of 93B (0.150 g, 0.291 mmol, 1.0 eq.) in DMF (1 mL) were added required carboxylic acid (0.045 g, 0.320 mmol, 1.0 eq.), DIPEA (0.15 mmol, 0.873 mmol, 3.0 eq.) and HATU (0.166 g, 0.436 mmol, 1.5 eq.) and the resulting mixture was stirred for 18 h. Aqueous saturated sodium bicarbonate solution was added and then extracted with EtOAc. The combined organic phase was washed with brine, dried over sodium sulfate then concentrated to dryness to afford 94B (0.143 g, 77% yield) as a yellow solid which was used in the next step without further purification. $^1$H NMR (DMSO-$d_6$) δ: 10.13 (s, 1H), 8.45 (d, J=8.2 Hz, 1H), 7.54 (d, J=8.2 Hz, 2H), 7.48 (dd, J=4.4, 2.0 Hz, 1H), 7.16 (dd, J=13.8, 8.6 Hz, 3H), 7.00 (dd, J=13.7, 2.1 Hz, 1H), 4.53-4.34 (m, 4H), 3.30 (s, 5H), 3.02 (d, J=8.7 Hz, 2H), 2.70 (s, 1H), 2.14 (s, 1H), 1.96 (s, 2H), 1.82 (d, J=12.2 Hz, 2H), 1.69 (s, 2H), 1.61 (s, 2H), 1.38 (s, 7H), 1.36-1.18 (m, 11H), 1.15 (s, 3H), 1.01 (d, J=12.5 Hz, 1H). UPLC-MS (basic 2 min): Rt=1.13 min; m/z=638.4 for [M+H]$^+$.

Example 500: (2S)—N-{4-[(2S,3R)-3-Amino-4-(4-methylpiperazin-1-yl)-4-oxobutan-2-yl]phenyl}-2-cyclohexyl-2-[(1-ethyl-1H-pyrazol-5-yl)formamido]acetamide (95B)

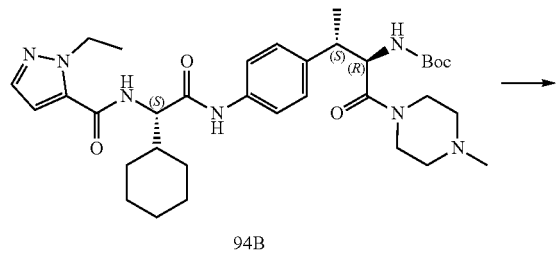

94B

-continued

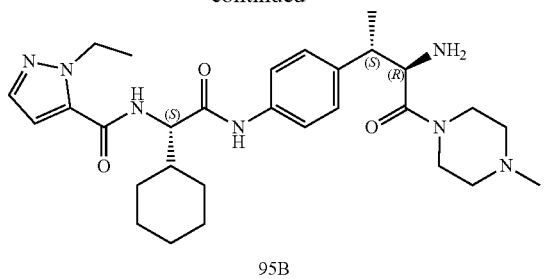

95B

To a solution of 94B (0.142 g, 0.223 mmol, 1.0 eq.) in DCM (0.5 mL) was added TFA (0.5 mL) and the resulting mixture was stirred at RT for 0.5 h. The reaction mixture was concentrated to dryness and the residue was stirred in aq. sat. K₂CO₃ solution and then extracted with DCM to afford 95B (0.062 g, 51% yield) which was used in the next step without further purification. ¹H NMR (DMSO-d₆) δ: 10.11 (s, 1H), 8.45 (d, J=8.2 Hz, 1H), 7.55-7.50 (m, 2H), 7.47 (d, J=2.0 Hz, 1H), 7.18-7.11 (m, 2H), 7.02 (d, J=2.1 Hz, 1H), 4.46 (q, J=7.2 Hz, 2H), 4.39 (t, J=8.6 Hz, 1H), 3.66 (d, J=7.9 Hz, 1H), 3.50 (d, J=13.0 Hz, 1H), 3.23-3.14 (m, 3H), 3.06 (t, J=9.4 Hz, 1H), 2.73 (p, J=7.1 Hz, 1H), 2.24-2.11 (m, 2H), 1.99 (s, 3H), 1.72 (ddd, J=56.4, 33.4, 11.7 Hz, 8H), 1.45 (d, J=6.7 Hz, 1H), 1.28-1.11 (m, 10H), 1.01 (q, J=11.7 Hz, 1H). UPLC-MS (basic 2 min): Rt=0.94 min; m/z=538.2 for [M+H]⁺.

Example 501: (2S)-2-cyclohexyl-N-{4-[(2S,3R)-3-[(cyclopropylcarbamoyl)amino]-4-(4-methylpiperazin-1-yl)-4-oxobutan-2-yl]phenyl}-2-[(1-ethyl-1H-pyrazol-5-yl)formamido]acetamide (402)

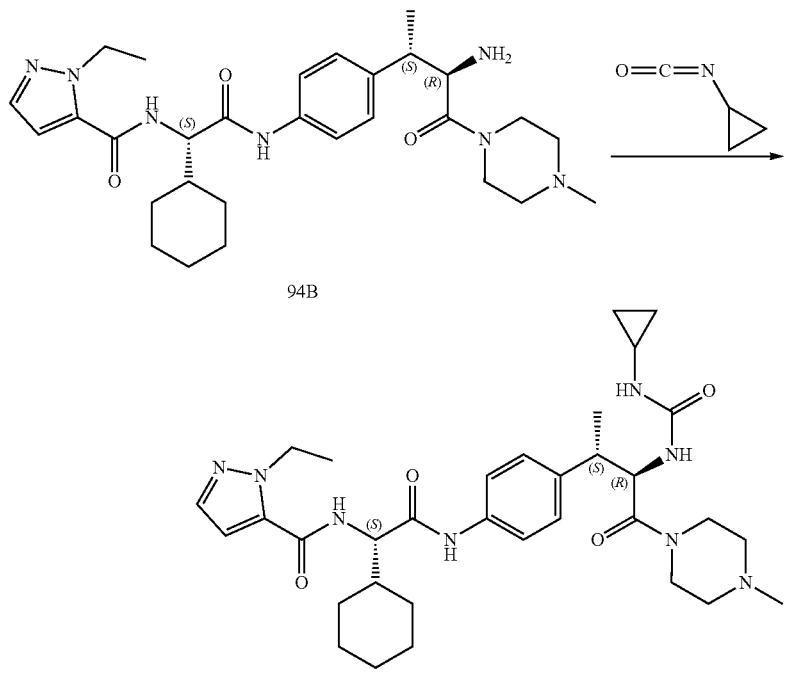

To a solution of 95B (0.062 g, 0.115 mmol, 1.0 eq.) in DMF (0.4 mL) were added isocyanate (0.011 g, 0.138 mmol, 1.2 eq.) and DIPEA (0.06 mL, 0.346 mmol, 3.0 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 402. ¹H NMR (400 MHz, DMSO-d₆) δ 10.14 (s, 1H), 8.46 (d, J=8.2 Hz, 1H), 7.58-7.51 (m, 2H), 7.47 (d, J=2.0 Hz, 1H), 7.18-7.11 (m, 2H), 7.02 (d, J=2.1 Hz, 1H), 6.25 (d, J=2.9 Hz, 1H), 6.10 (d, J=9.3 Hz, 1H), 4.68 (t, J=9.3 Hz, 1H), 4.46 (q, J=7.1 Hz, 2H), 4.39 (t, J=8.6 Hz, 1H), 3.48 (d, J=13.3 Hz, 1H), 3.28-3.29 (m, 1H), 3.18 (d, J=4.7 Hz, 1H), 3.01-2.88 (m, 2H), 2.42 (tt, J=6.9, 3.5 Hz, 1H), 2.16 (t, J=14.6 Hz, 2H), 1.96 (s, 3H), 1.82 (d, J=11.9 Hz, 2H), 1.69 (s, 2H), 1.62 (d, J=11.1 Hz, 3H), 1.36 (t, J=9.5 Hz, 196BH), 1.27 (t, J=7.1 Hz, 3H), 1.20 (d, J=7.0 Hz, 4H), 1.15 (s, 3H), 1.02 (t, J=11.9 Hz, 1H), 0.57 (td, J=6.9, 4.7 Hz, 2H), 0.34-0.27 (m, 2H). UPLC-MS (basic 4 min): rt=1.59 min; m/z=621.3 for [M+H]⁺.

Example 502: Lithium(1+) (2R,3S)-2-{[(tert-butoxy)carbonyl]amino}-3-{4-[(2S)-2-[(1-ethyl-1H-pyrazol-5-yl)formamido]-2-[(1r,4S)-4-methylcyclohexyl]acetamido]-3-fluorophenyl}butanoate) (97B)

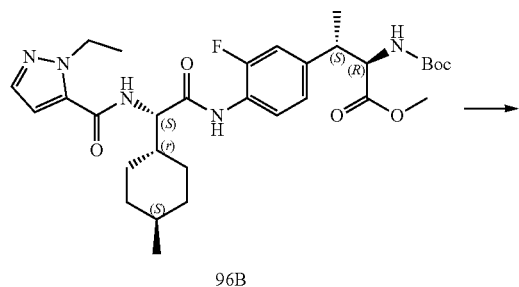

96B

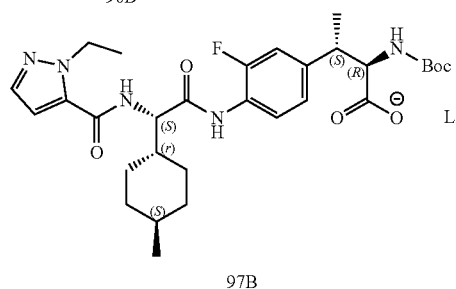

97B

To a solution of 96B (0.284 g, 0.472 mmol, 1.0 eq.) in THF (5 mL) was added a solution of LiOH (0.022 g, 0.519 mmol, 1.1 eq.) in H₂O (5 mL) and the resulting mixture was stirred at RT for 0.5 h. The reaction mixture was concentrated to dryness to afford 97B (0.280 g, 99%) as a white solid which was used in the next step without further purification. ¹H NMR (400 MHz, DMSO-d₆) δ 9.80 (s, 1H), 8.51 (d, J=8.4 Hz, 1H), 7.64-7.53 (m, 1H), 7.45 (dd, J=9.8, 2.0 Hz, 1H), 7.10-6.85 (m, 4H), 5.75 (d, J=7.2 Hz, 1H), 4.47 (p, J=8.2, 7.1 Hz, 4H), 3.64 (dd, J=7.5, 3.6 Hz, 1H), 1.90-1.56 (m, 8H), 1.38-1.29 (m, 11H), 1.29-0.99 (m, 10H), 0.99-0.76 (m, 8H). UPLC-MS (acidic 4 min): rt=1.99 min; m/z=586.4 for [M+H]⁺.

Example 503: tert-butyl N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-hydroxy-4-methylpiperidin-1-yl)-1-oxobutan-2-yl] carbamate) (98B)

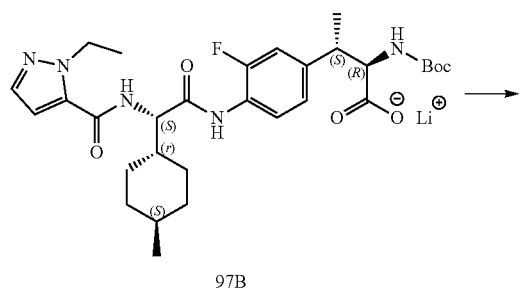

97B

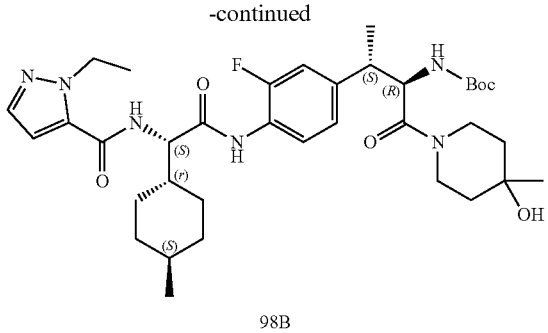

98B

To a solution of 97B (0.350 g, 0.472 mmol, 1.0 eq,) in DMF (5 mL) were added 4-methylpiperidin-4-ol (0.060 g, 0.519 mmol, 1.1 eq.), DIPEA (0.41 mL, 2.36 mmol, 5.0 eq.) and then HATU (0.215 g, 0.566 mmol, 1.2 eq.) and the resulting mixture was stirred at RT for 1 h. The mixture was concentrated to dryness and the residue was purified via reverse phase column chromatography on a 40 g C18 cartridge eluting with a 5-95% H₂O:MeCN eluent (0.1% ammonia) to afford 98B (0.140 g, 43%) as an orange solid. ¹H NMR (400 MHz, DMSO-d₆) δ 9.84 (s, 1H), 8.44 (d, J=8.4 Hz, 1H), 7.82-7.59 (m, 1H), 7.46 (d, J=2.0 Hz, 1H), 7.25-7.03 (m, 4H), 7.03-6.93 (m, 2H), 4.68-4.40 (m, 5H), 4.26-4.14 (m, 1H), 3.69 (d, J=101.3 Hz, 1H), 3.10 (dd, J=23.6, 12.0 Hz, 3H), 2.74 (s, 1H), 1.92-1.44 (m, 9H), 1.36 (d, J=3.0 Hz, 15H), 1.31-1.08 (m, 9H), 1.06 (s, 3H), 0.99-0.76 (m, 10H). UPLC-MS (basic 4 min): rt=2.04 min; m/z=685.5 for [M+H]⁺.

Example 504: (2S)—N-{4-[(2S,3R)-3-amino-4-(4-hydroxy-4-methylpiperidin-1-yl)-4-oxobutan-2-yl]-2-fluorophenyl}-2-[(1-ethyl-1H-pyrazol-5-yl)formamido]-2-[(1r,4S)-4-methylcyclohexyl]acetamide) (99B)

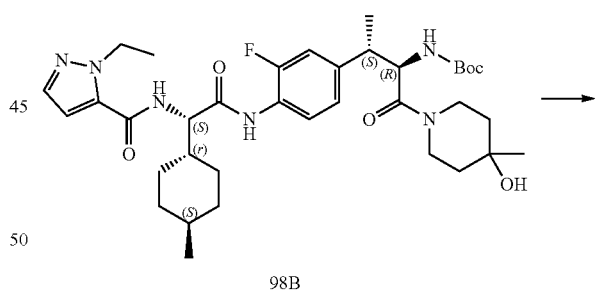

98B

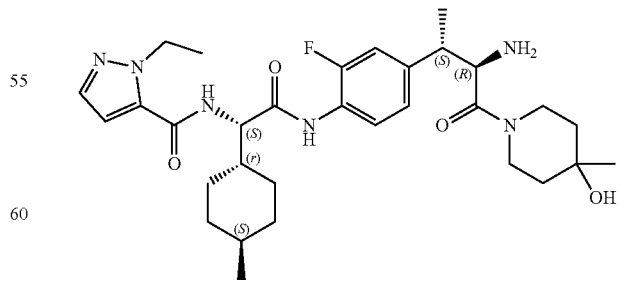

99B

To a solution of 98B (0.140 g, 0.204 mmol, 1.0 eq.) in DCM (1.4 mL) was added TFA (0.6 mL) and the resulting mixture was stirred at RT for 0.5 h. The reaction mixture was concentrated to dryness and the residue was stirred in aq. sat. K₂CO₃ solution and then extracted with DCM to afford 99B (0.090 g, 75%) as a white solid which was used in the next step without further purification. ¹H NMR (400 MHz, DMSO-d₆) δ 9.86 (d, J=10.0 Hz, 1H), 8.49 (t, J=9.7 Hz, 1H), 7.68 (dt, J=54.1, 8.3 Hz, 1H), 7.47 (d, J=2.0 Hz, 1H), 7.14 (dd, J=39.4, 12.1 Hz, 1H), 7.06-6.92 (m, 2H), 4.59-4.38 (m, 3H), 4.24 (d, J=31.3 Hz, 1H), 3.91 (t, J=14.8 Hz, 1H), 3.72 (dd, J=41.9, 7.1 Hz, 1H), 3.61-3.39 (m, 1H), 3.11 (t, J=12.5 Hz, 1H), 2.96-2.69 (m, 2H), 1.89-1.51 (m, 8H), 1.36 (d, J=12.6 Hz, 1H), 1.27 (ddd, J=10.7, 7.4, 4.9 Hz, 6H), 1.17 (q, J=6.5, 6.0 Hz, 3H), 1.12-0.96 (m, 1H), 0.96-0.41 (m, 8H). UPLC-MS (basic 4 min): rt=1.67 min; m/z=585.5 for [M+H]⁺.

Example 506: N-[(2R,3S)-3-{4-[(2S)-2-[(1-ethyl-1H-pyrazol-5-yl)formamido]-2-[(1r,4S)-4-methylcyclohexyl]acetamido]-3-fluorophenyl}-1-(4-hydroxy-4-methylpiperidin-1-yl)-1-oxobutan-2-yl]-1-(oxan-4-yl)-1H-pyrazole-5-carboxamide (417)

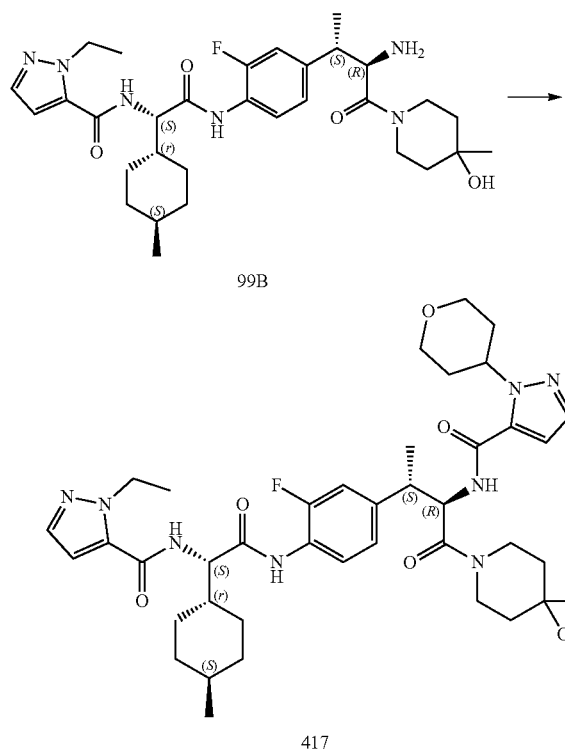

To a solution of 99B (0.045 g, 0.077 mmol, 1.0 eq.) in DMF (1 mL) were added the required carboxylic acid (0.017 g, 0.0785 mmol, 1.1 eq.), DIPEA (0.067 mL, 0.385 mmol, 5.0 eq.) and then HATU (0.035 g, 0.092 mmol, 1.2 eq.) and the resulting mixture was stirred at RT for 1 h. The mixture was concentrated to dryness and the residue was purified via reverse phase column chromatography on a 120 g C18 cartridge eluting with a 5-95% H₂O:MeCN eluent (0.1% ammonia) to afford 417 (0.031 g) as a white solid. ¹H NMR (400 MHz, DMSO-d₆) δ 9.86 (d, J=7.4 Hz, 1H), 8.84 (dd, J=9.1, 3.2 Hz, 1H), 8.44 (d, J=8.3 Hz, 1H), 7.74 (dt, J=67.7, 8.2 Hz, 1H), 7.52 (d, J=2.0 Hz, 1H), 7.47 (d, J=2.0 Hz, 1H), 7.16 (t, J=11.5 Hz, 1H), 7.11-6.91 (m, 3H), 5.35-5.11 (m, 1H), 5.04 (t, J=9.4 Hz, 1H), 4.59-4.38 (m, 3H), 4.21 (d, J=17.0 Hz, 1H), 4.03-3.62 (m, 4H), 3.47-3.33 (m, 3H), 3.22-2.96 (m, 1H), 2.81-2.68 (m, 1H), 2.04 (dtt, J=23.7, 12.3, 6.3 Hz, 2H), 1.88-1.57 (m, 7H), 1.40-1.12 (m, 11H), 1.05 (d, J=18.3 Hz, 2H), 0.86 (d, J=7.2 Hz, 7H), 0.58 (dt, J=104.1, 11.0 Hz, 1H). UPLC-MS (basic 4 min): rt=1.87 min; m/z=763.5 for [M+H]⁺.

Example 507: Preparation of 100B

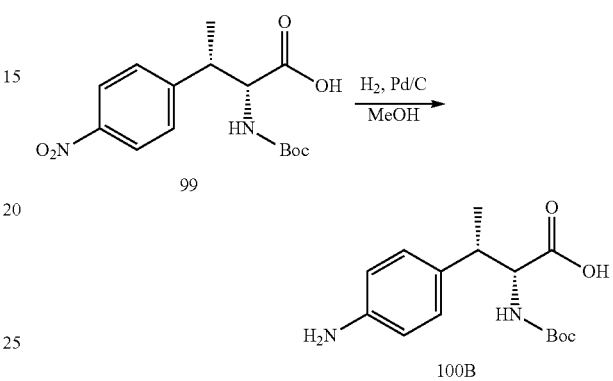

To a solution of 99B (2.30 g, 7.09 mmol, 1.00 eq) in MeOH (20 mL) was added Raney Ni (2.30 g, 39.2 mmol, 5.53 eq), the mixture was then stirred under H₂ (30 Psi) at 25° C. for 12 hrs. LCMS showed the reactant was consumed completely and the main peak was desired product. The mixture was filtered and the filtrate was concentrated to give compound 100B (2.00 g, 6.79 mmol, 95.8% yield) as white solid, which was used in next step directly.

Example 508: Preparation of 84B

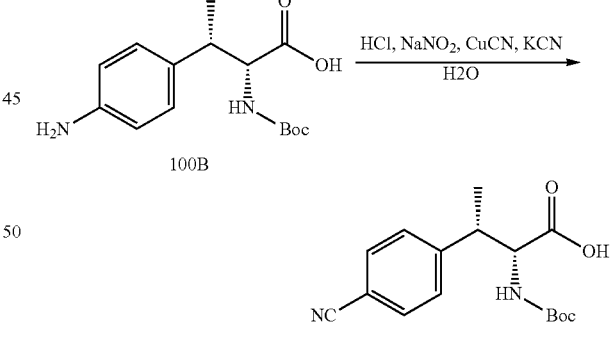

A suspension of compound 100B (2.00 g, 6.79 mmol, 1.00 eq) in HCl (1.50 M, 10.0 mL, 2.21 eq) was stirred at 0° C., then NaNO₂ (938 mg, 13.6 mmol, 2.00 eq) in H₂O (3.00 mL) was added drop wise at 0° C. The mixture was stirred at 0° C. for 0.5 hr. The mixture was carefully neutralized with solid Na₂CO₃ to pH=8 and noted as solution 1. CuCN (1.83 g, 20.4 mmol, 4.45 mL, 3.00 eq) and KCN (2.21 g, 33.9 mmol, 1.46 mL, 5.00 eq) in H₂O (10.0 mL) was warmed to 65° C. The solution 1 was added drop wise at 65° C. After the addition the mixture was stirred at 65° C. for 1 hrs. LCMS: ET27305-6-P1H showed compound 1 was consumed completely. The reaction was acidified to pH=5, extracted with EtOAc (10.0 mL*3), the combined organic layer was dried over $Na_2SO_4$, concentrated to give a yellow solid (HPLC: ET27305-6-P1A1). The residue was purified by reversed-phase HPLC (0.1% FA condition) to give 84B (0.700 g, 2.24 mmol, 33.0% yield, 97.6% purity) as white solid. $^1$H NMR: (400 MHz, DMSO-$d_6$) δ 12.57 (s, 1H), 7.75 (d, J=8.0 Hz, 2H), 7.46 (d, J=8.0 Hz, 2H), 7.22 (d, J=4.0 Hz, 1H), 4.28-4.10 (m, 1H), 3.33-3.32 (m, 1H), 1.46-1.10 (m, 12H).

Example 509: IL-17A/IL-17RA ELISA-Based Interaction Assay

This assay determines the extent to which the interaction between IL-17A/A and IL-17RA is disrupted by small molecule inhibitors. An Fc fusion of soluble portion of IL-17RA (IL-17RA-Fc, R&D Systems #177-IR-100) was immobilized on an Immulon ELISA plate (Fisher #14245153). The plate was then blocked, compound inhibitors were serially diluted in DMSO, and the compound titration and IL-17A-biotin (R&D Systems #BT7955-025) were added to the plate sequentially. SA-HRP was then allowed to bind to the remaining IL-17A-biotin, and the plate was developed using TMB buffer (Fisher #NC9247813), then quenched with stop solution (Fisher #NC0213329) and read at $A_{450}$.

Blocking solution (50 mM Tris-HCl, pH 7.5, 150 mM NaCl, 0.05% Tween-20 [Fisher #50843297], 2% BSA) was used as a diluent at every step except immobilization, compound serial dilution, and development. Immobilization was conducted in TBS (50 mM Tris-HCl, pH 7.5, 150 mM NaCl), and the plate was incubated overnight at 4° C. Every other step except development (5 min.) was 1 hr. long, at RT (22° C.).

The resulting inhibition curve was then analyzed using Graphpad Prism 7.0, and $IC_{50}$ measurements were determined using a 4-parameter nonlinear fit. Compounds 100-103, 106, 109-125, 127, 130, 132, 133, 137, 140, 141, 144, 147, 148, 172-175, 177, 179, 180-192, 194-196, 198, 199, 201-203, 219, 228-230, 234-236, 239, 242, 245, 321, 322, and 366, have an $IC_{50}$ measurement of less than 10 μM in this assay.

Example 510: IL-17A/A HEK-Blue Cell Assay

The HEK-Blue IL-17A reporter cell line (Fisher #NC1408637) was used for cell-based IL-17A/A inhibition assays. Cells were grown and prepared for assays according to the manufacturer's instructions. This cell line consists of HEK 293 cells that were designed to expressed IL-17RA, IL-17RC, and the ActI adapter molecule, the combination of which, when stimulated by IL-17A/A activates a NFκB promoter and drives expression of a recombinant Secreted Alkaline Phosphatase (SEAP) geneprotein. Media from the cells is then added to a development reagent (Quanti-Blue Substrate, Fisher #NC9711613), and read at $A_{630}$.

Compounds were titrated in DMSO and added to the cells immediately before adding IL-17A/A (Genscript #Z03228). The cells, compound, and IL-17A/A were then incubated for 20 hours before media was removed for SEAP analysis. The resulting inhibition curve was then analyzed using Graphpad Prism 7.0, and $IC_{50}$ values were determined using a 4-parameter nonlinear fit. DMSO was added to a universal final concentration of 0.1% to optimize background. Compounds 100, 101, 103, 126, 128, 129, 131, 132, 134, 137, 139, 140, 145, 149-152, 154-164, 166, 167, 169-172, 203-208, 210, 211, 213-224, 227-378, 380-400, 402, 404-410, 414, and 417-419 have an IC50 measurement of less than 10 μM in this assay.

Example 511: IL-17A/F HEK-Blue Cell Assay

The HEK-Blue IL-17A reporter cell line (Fisher #NC1408637) was used for cell-based IL-17A/F inhibition assays. Cells were grown and prepared for assays according to the manufacturer's instructions. This cell line consists of HEK 293 cells that were designed to expressed IL-17RA, IL-17RC, and the ActI adapter molecule, the combination of which, when stimulated by IL-17A/F, activates a NFκB promoter and drives expression of a recombinant Secreted Alkaline Phosphatase (SEAP) geneprotein. Media from the cells is then added to a development reagent (Quanti-Blue Substrate, Fisher #NC9711613), and read at $A_{630}$.

Compounds were titrated in DMSO and added to the cells immediately before adding IL-17A/F (custom from R&D systems, untagged IL-17A/F+BSA as a carrier protein). The cells, compound, and IL-17A/F were then incubated for 20 hours before media was removed for SEAP analysis. The resulting inhibition curve was then analyzed using Graphpad Prism 7.0, and IC50 values were determined using a 4-parameter nonlinear fit. DMSO was added to a universal final concentration of 0.1% to optimize background. Compounds 103, 129, 134, 149, 151, 154, 157, 158, 163, 166, 169, 170, 214, 216, 224, 228-231, 233-238, 241, 283-285, 320, 322, 348, 350, 355, 399 and 404 have an IC50 measurement of less than 10 μM in this assay.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating psoriasis, psoriatic arthritis, or ankylosing spondylitis in a patient comprising administering to the patient in need thereof a therapeutically effective amount of a compound of Formula (I):

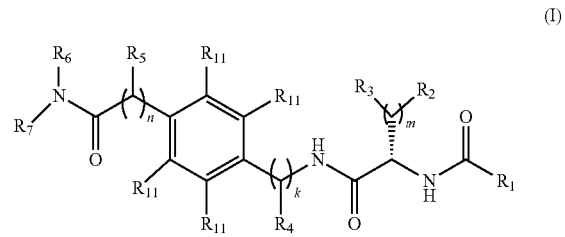

or a pharmaceutically acceptable salt, solvate, or hydrate thereof wherein:

$R_1$ is alkyl, substituted alkyl, aryl, substituted aryl, heteroaryl, substituted heteroaryl, arylalkyl, substituted arylalkyl, heteroarylalkyl, substituted heteroarylalkyl —$OR_8$ or —$NR_9R_{10}$;

$R_2$ is alkyl, substituted alkyl, cycloheteroalkyl, substituted cycloheteroalkyl, aryl, substituted aryl, fused cycloalkylaryl, substituted fused cycloalkylaryl, heteroaryl, or substituted heteroaryl;

each $R_3$ is independently hydrogen, ($C_1$-$C_7$) alkyl, ($C_1$-$C_7$) substituted alkyl or —$OR_{32}$;

m is 0, 1 or 2;

each $R_4$ is independently hydrogen, ($C_1$-$C_7$) alkyl, or ($C_1$-$C_7$) substituted alkyl;

k is 1;

each $R_5$ is hydrogen or —$NR_{14}C(O)R_{15}$;

$R_6$ is hydrogen or alkyl; $R_7$ is cycloheteroalkyl, substituted cycloheteroalkyl, —$(CHR_{16})_oR_{17}$ or —$(CHR_{18})_p$ $R_{19}$ or $R_6$ and $R_7$ taken together with the nitrogen atom to which they are attached form piperazine, substituted piperazine, cycloheteroalkyl or substituted cycloheteroalkyl,

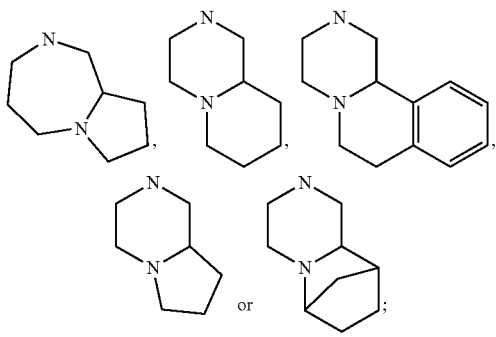

$R_8$ is ($C_1$-$C_7$) alkyl, ($C_1$-$C_7$) substituted alkyl, aryl, substituted aryl, heteroaryl or substituted heteroaryl;

each $R_{11}$ is hydrogen;

n is 1, 2, or 3;

o is 1, 2 or 3;

p is 1, 2 or 3;

each $R_{16}$ is independently hydrogen, ($C_1$-$C_7$) alkyl or ($C_1$-$C_7$) substituted alkyl;

$R_{17}$ is

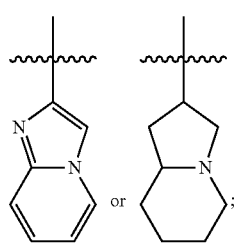

each $R_{18}$ is independently hydrogen, ($C_1$-$C_7$) alkyl or ($C_1$-$C_7$) substituted alkyl;

$R_{19}$ is —$NR_{27}R_{28}$;

$R_{27}$ and $R_{28}$ together with the nitrogen atom to which they are attached form a cycloheteroalkyl or substituted cycloheteroalkyl ring or

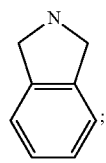

and $R_9$, $R_{10}$, $R_{14}$, $R_{15}$, and $R_{32}$ are independently hydrogen, alkyl, substituted alkyl, heteroalkyl, substituted heteroalkyl, aryl, substituted aryl, heteroaryl or substituted heteroaryl; or $R_9$ and $R_{10}$ together with atom to which they are attached form a cycloalkyl, substituted cycloalkyl, cycloheteroalkyl or substituted cycloheteroalkyl ring.

2. The method of claim 1, wherein $R_1$ is phenyl, substituted phenyl, phenylalkyl, substituted phenylalkyl, heteroaryl, substituted heteroaryl, heteroarylalkyl, substituted heteroarylalkyl or —$OR_8$.

3. The method of claim 1, wherein $R_1$ is phenyl, substituted phenyl, 5-membered heteroaryl, or substituted 5-membered heteroaryl.

4. The method of claim 1, wherein $R_1$ is substituted phenyl, oxadiazole, substituted oxadiazole, pyrazole, substituted pyrazole, thiophene, substituted thiophene, furan, substituted furan, thiazole, substituted thiazole, pyrrole, substituted pyrrole, oxazole, substituted oxazole, isoxazole, substituted isoxazole, thiadiazole, substituted thiadiazole, tetrazole or substituted tetrazole, triazole or substituted triazole.

5. The method of claim 1, wherein $R_1$ is

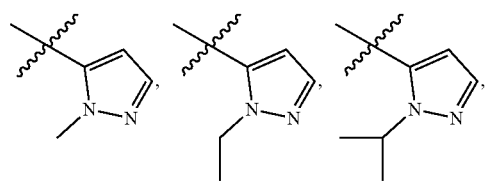

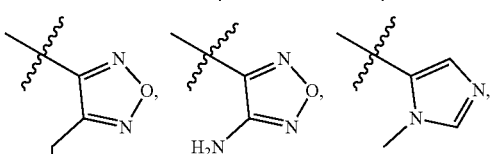

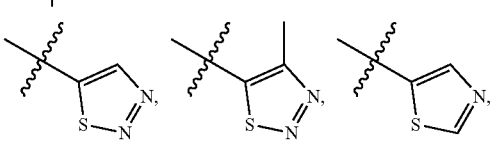

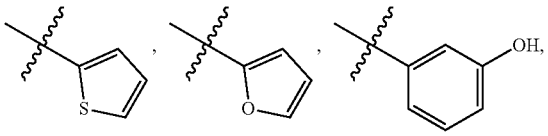

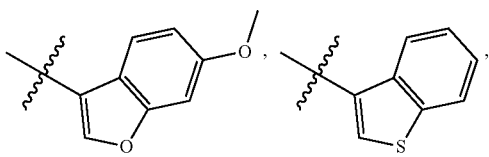

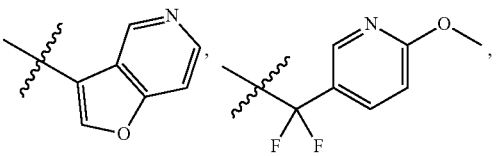

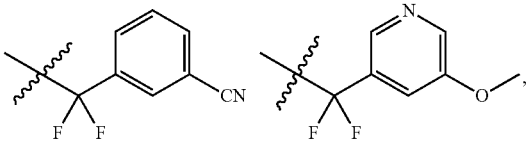

-continued

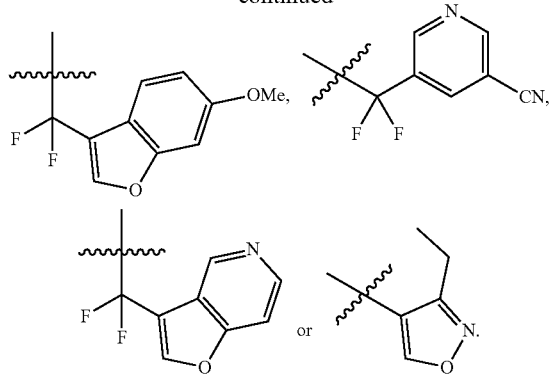

or

6. The method of claim 1, wherein $R_2$ is cycloalkyl, substituted alkyl, aryl, substituted aryl, heteroaryl, substituted heteroaryl, 1-indanyl, 2-indanyl, 1-tetrahydronapthyl, 2-tetrahydronapthyl or 4-methylcyclohexyl.

7. The method of claim 1, wherein $R_2$ is cyclohexyl, cycloheptyl, cyclooctyl, cyclopentyl, 1-indanyl, 2-indanyl, 1-tetrahydronapthyl, 2-tetrahyronapthyl, 4-methylcyclohexyl, —CH($R_3$)phenyl or when m is 1 or greater, phenyl, substituted phenyl, o-chlorophenyl or p-fluorophenyl.

8. The method of claim 1, wherein m is 0.

9. The method of claim 1, wherein each $R_3$ is independently hydrogen, ($C_1$-$C_4$) alkyl or —$OR_{32}$.

10. The method of claim 1, wherein each $R_4$ is independently hydrogen, or ($C_1$-$C_4$) alkyl.

11. The method of claim 1, wherein $R_7$ is cycloheteroalkyl, substituted cycloheteroalkyl, —(CHR$_{16}$)$_o$R$_{17}$ or —(CHR$_{18}$)$_p$R$_{19}$.

12. The method of claim 1, wherein each $R_{16}$ is independently hydrogen or ($C_1$-$C_4$) alkyl or each $R_{18}$ is independently hydrogen or ($C_1$-$C_4$) alkyl.

13. The method of claim 1, wherein $R_6$ and $R_7$ taken together with the nitrogen atom to which they are attached form a cycloheteroalkyl, substituted cycloheteroalkyl ring,

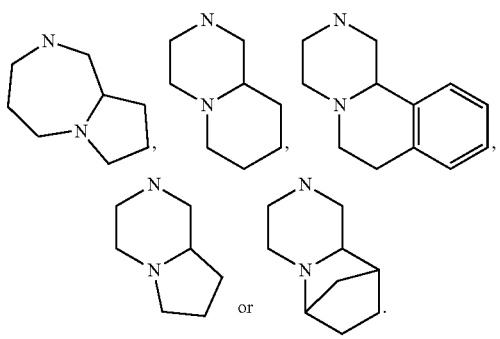

14. The method of claim 1, wherein $R_8$ is ($C_1$-$C_4$) alkyl, aryl or heteroaryl.

15. The method of claim 1, wherein $R_{27}$ and $R_{28}$ together with the nitrogen atom to which they are attached form a cycloheteroalkyl or substituted cycloheteroalkyl ring.

16. The method of claim 1, wherein $R_9$, $R_{10}$, $R_{14}$, and $R_{15}$, are each independently hydrogen, alkyl, heteroalkyl, aryl or heteroaryl.

17. The method of claim 1, wherein the patient in need thereof comprises a psoriasis patient.

18. The method of claim 1, wherein the patient in need thereof comprises an ankylosing spondylitis patient.

19. The method of claim 1, wherein the patient in need thereof comprises a psoriatic arthritis patient.

20. The method of claim 1, wherein the administering of the compound of Formula (I) or the pharmaceutically acceptable salt, solvate, or hydrate thereof, further comprises a pharmaceutically acceptable vehicle.

* * * * *